(12) United States Patent
Wang et al.

(10) Patent No.: US 8,222,253 B2
(45) Date of Patent: Jul. 17, 2012

(54) PEPTIDE AND SMALL MOLECULE AGONISTS OF EPHA AND THEIR USES

(75) Inventors: Bingchen Wang, Strongsville, OH (US); Eugene Myshkin, Cleveland, OH (US); Hui Miao, Rocky River, OH (US)

(73) Assignee: Case Western Reserve University, Cleveland, OH (US)

( * ) Notice: Subject to any disclaimer, the term of this patent is extended or adjusted under 35 U.S.C. 154(b) by 601 days.

(21) Appl. No.: 11/577,770

(22) PCT Filed: Oct. 21, 2005

(86) PCT No.: PCT/US2005/037687
§ 371 (c)(1),
(2), (4) Date: Apr. 23, 2007

(87) PCT Pub. No.: WO2006/052409
PCT Pub. Date: May 18, 2006

(65) Prior Publication Data
US 2009/0247540 A1     Oct. 1, 2009

Related U.S. Application Data

(60) Provisional application No. 60/621,041, filed on Oct. 23, 2004.

(51) Int. Cl.
*A61K 31/497* (2006.01)
(52) U.S. Cl. .................................. 514/252.17
(58) Field of Classification Search .............. 514/252.17
See application file for complete search history.

(56) References Cited

FOREIGN PATENT DOCUMENTS
JP            10-101579 A    *    4/1998

OTHER PUBLICATIONS

Kyprianou et al. (Cancer Research 2000; 60: 4550-4555).*
Fox et al. (Biochemical and Biophysical Research Communications 2006; 342: 1263-1272).*
Keledjian et al., The journal of Uroloy, 2003;169:1150-1156.*
Cheng et al., Molecular Cancer Research, 2002;1:2-11.*
Machine English Translation of JP10-101579A.*

* cited by examiner

*Primary Examiner* — San-Ming Hui
(74) *Attorney, Agent, or Firm* — Tarolli, Sundheim, Covell & Tummino LLP

(57) ABSTRACT

Methods and compositions for activating an EphA receptor can be used for identifying therapeutic agents for cancer.

2 Claims, 56 Drawing Sheets

```
EP2           ¹YSCCLNLYTPWPLC-DCVEEWA
                 : :  : | | :   |   :    |
Ephrin-A1        KFQRFTPFTLGKEFKEGHSY Ephrin-B2        KFQEFSPNLWGLEFQKNKDY
                 :      : |  | : :  : |
EP1           ¹RRCVWSTNVYSMEPALFCAA
```

Step 3: Generate spheres to fill the active site

Step 4: Matching and Scoring

Step 1: Start with crystal coordinates of target receptor

Step 2: Generate molecular surface for receptor

DOBUTAMINE anti-PY99 anti-EphA2 no treatment
0.2ug/ml eA1-Fc
Fc control
0.2mM
1 mM
5 mM

IP

LABETALOL

DOXAZOSIN

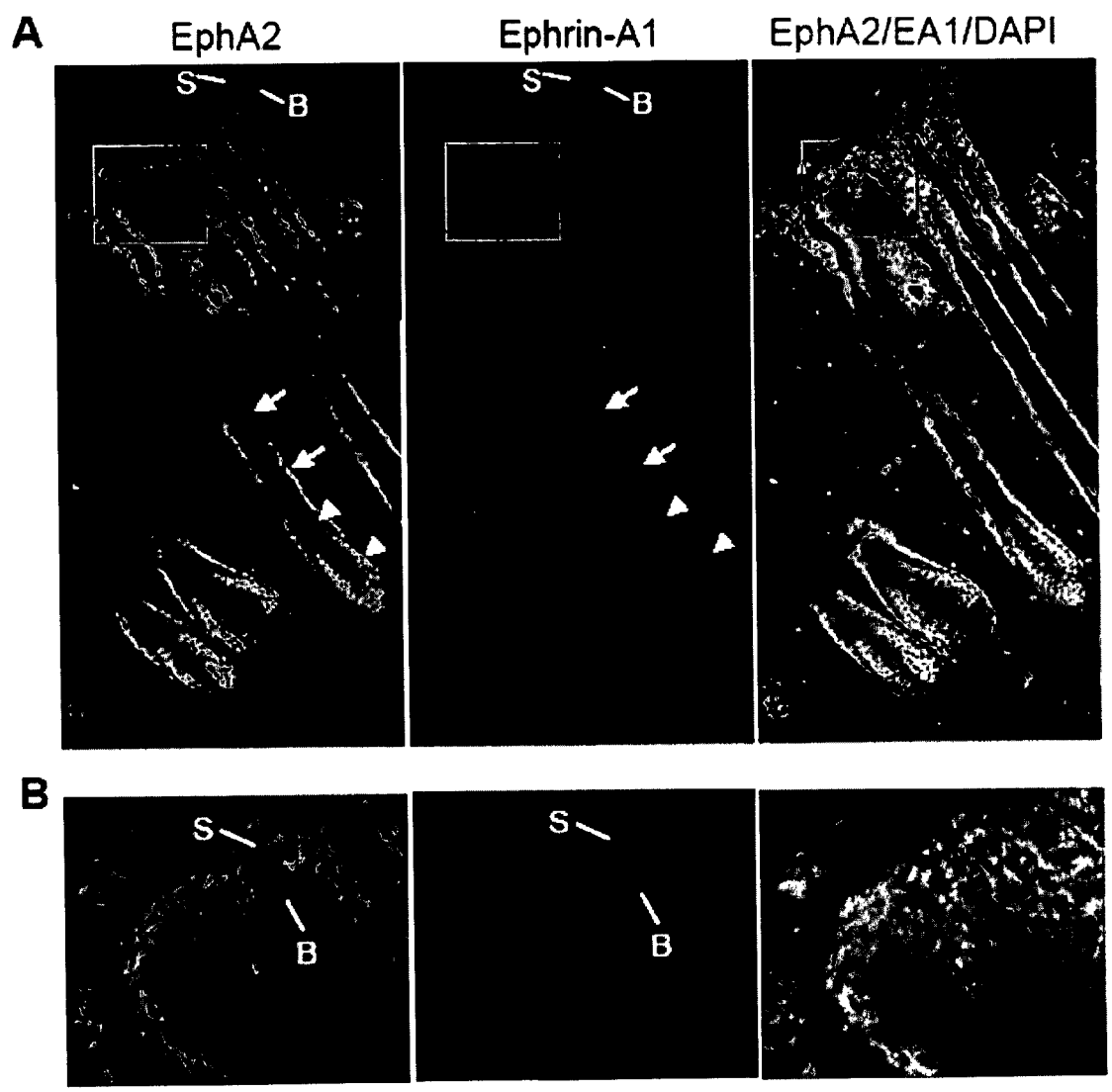
Fig. 42 A,B

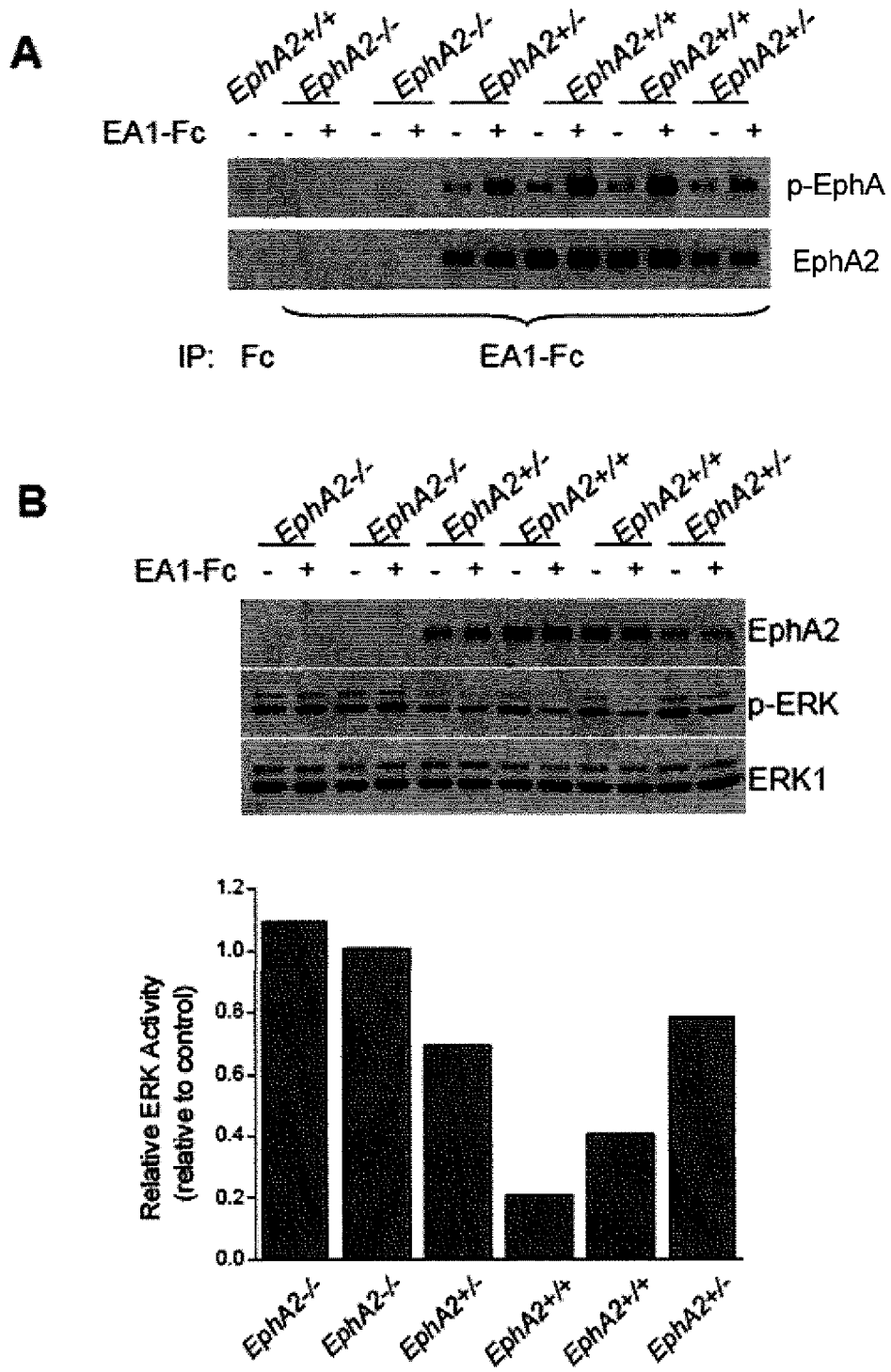
Fig. 43A, B

SEQUENCE LISTING

<160> NUMBER OF SEQ ID NOS: 13

<210> SEQ ID NO 1
<211> LENGTH: 20
<212> TYPE: PRT
<213> ORGANISM: Artificial
<220> FEATURE:
<223> OTHER INFORMATION: Peptide

<400> SEQUENCE: 1

Arg Arg Cys Val Trp Ser Thr Asn Val Tyr Ser Met Glu Pro Ala Leu
1               5                   10                  15

Phe Cys Ala Ala
            20

<210> SEQ ID NO 2
<211> LENGTH: 21
<212> TYPE: PRT
<213> ORGANISM: Artificial
<220> FEATURE:
<223> OTHER INFORMATION: Peptide

```
<400> SEQUENCE: 2

Tyr Ser Cys Cys Leu Asn Leu Tyr Thr Pro Trp Pro Leu Cys Asp Cys
1               5                   10                  15

Val Glu Glu Trp Ala
            20

<210> SEQ ID NO 3
<211> LENGTH: 19
<212> TYPE: PRT
<213> ORGANISM: Artificial
<220> FEATURE:
<223> OTHER INFORMATION: Peptide

<400> SEQUENCE: 3

His Ser Cys Lys Ala Leu Ser Ser Thr His Gly Met Ala Trp Pro Glu
1               5                   10                  15

Ser Ala Leu

<210> SEQ ID NO 4
<211> LENGTH: 976
<212> TYPE: PRT
<213> ORGANISM: Homo sapiens

<400> SEQUENCE: 4

Met Glu Arg Arg Trp Pro Leu Gly Leu Gly Leu Val Leu Leu Leu Cys
1               5                   10                  15

Ala Pro Leu Pro Pro Gly Ala Arg Ala Lys Glu Val Thr Leu Met Asp
            20                  25                  30

Thr Ser Lys Ala Gln Gly Glu Leu Gly Trp Leu Leu Asp Pro Pro Lys
        35                  40                  45

Asp Gly Trp Ser Glu Gln Gln Ile Leu Asn Gly Thr Pro Leu Tyr
    50                  55                  60

Met Tyr Gln Asp Cys Pro Met Gln Gly Arg Arg Asp Thr Asp His Trp
65                  70                  75                  80

Leu Arg Ser Asn Trp Ile Tyr Arg Gly Glu Glu Ala Ser Arg Val His
                85                  90                  95

Val Glu Leu Gln Phe Thr Val Arg Asp Cys Lys Ser Phe Pro Gly Gly
            100                 105                 110

Ala Gly Pro Leu Gly Cys Lys Glu Thr Phe Asn Leu Leu Tyr Met Glu
        115                 120                 125

Ser Asp Gln Asp Val Gly Ile Gln Leu Arg Arg Pro Leu Phe Gln Lys
    130                 135                 140

Val Thr Thr Val Ala Ala Asp Gln Ser Phe Thr Ile Arg Asp Leu Ala
145                 150                 155                 160

Ser Gly Ser Val Lys Leu Asn Val Glu Arg Cys Ser Leu Gly Arg Leu
                165                 170                 175

Thr Arg Arg Gly Leu Tyr Leu Ala Phe His Asn Pro Gly Ala Cys Val
            180                 185                 190

Ala Leu Val Ser Val Arg Val Phe Tyr Gln Arg Cys Pro Glu Thr Leu
        195                 200                 205

Asn Gly Leu Ala Gln Phe Pro Asp Thr Leu Pro Gly Pro Ala Gly Leu
    210                 215                 220

Val Glu Val Ala Gly Thr Cys Leu Pro His Ala Arg Ala Ser Pro Arg
225                 230                 235                 240

Pro Ser Gly Ala Pro Arg Met His Cys Ser Pro Asp Gly Glu Trp Leu
                245                 250                 255
```

```
Val Pro Val Gly Arg Cys His Cys Glu Pro Gly Tyr Glu Glu Gly
            260                 265                 270

Ser Gly Glu Ala Cys Val Ala Cys Pro Ser Gly Ser Tyr Arg Met Asp
        275                 280                 285

Met Asp Thr Pro His Cys Leu Thr Cys Pro Gln Gln Ser Thr Ala Glu
290                 295                 300

Ser Glu Gly Ala Thr Ile Cys Thr Cys Glu Ser Gly His Tyr Arg Ala
305                 310                 315                 320

Pro Gly Glu Gly Pro Gln Val Ala Cys Thr Gly Pro Pro Ser Ala Pro
                325                 330                 335

Arg Asn Leu Ser Phe Ser Ala Ser Gly Thr Gln Leu Ser Leu Arg Trp
            340                 345                 350

Glu Pro Pro Ala Asp Thr Gly Gly Arg Gln Asp Val Arg Tyr Ser Val
        355                 360                 365

Arg Cys Ser Gln Cys Gln Gly Thr Ala Gln Asp Gly Gly Pro Cys Gln
370                 375                 380

Pro Cys Gly Val Gly Val His Phe Ser Pro Gly Ala Arg Gly Leu Thr
385                 390                 395                 400

Thr Pro Ala Val His Val Asn Gly Leu Glu Pro Tyr Ala Asn Tyr Thr
                405                 410                 415

Phe Asn Val Glu Ala Gln Asn Gly Val Ser Gly Leu Gly Ser Ser Gly
            420                 425                 430

His Ala Ser Thr Ser Val Ser Ile Ser Met Gly His Ala Glu Ser Leu
        435                 440                 445

Ser Gly Leu Ser Leu Arg Leu Val Lys Lys Glu Pro Arg Gln Leu Glu
450                 455                 460

Leu Thr Trp Ala Gly Ser Arg Pro Arg Ser Pro Gly Ala Asn Leu Thr
465                 470                 475                 480

Tyr Glu Leu His Val Leu Asn Gln Asp Glu Glu Arg Tyr Gln Met Val
                485                 490                 495

Leu Glu Pro Arg Val Leu Leu Thr Glu Leu Gln Pro Asp Thr Thr Tyr
            500                 505                 510

Ile Val Arg Val Arg Met Leu Thr Pro Leu Gly Pro Gly Pro Phe Ser
        515                 520                 525

Pro Asp His Glu Phe Arg Thr Ser Pro Pro Val Ser Arg Gly Leu Thr
530                 535                 540

Gly Gly Glu Ile Val Ala Val Ile Phe Gly Leu Leu Leu Gly Ala Ala
545                 550                 555                 560

Leu Leu Leu Gly Ile Leu Val Phe Arg Ser Arg Arg Ala Gln Arg Gln
                565                 570                 575

Arg Gln Gln Arg Gln Arg Asp Arg Ala Thr Asp Val Ser Arg Glu Asp
            580                 585                 590

Lys Leu Trp Leu Lys Pro Tyr Val Asp Leu Gln Ala Tyr Glu Asp Pro
        595                 600                 605

Ala Gln Gly Ala Leu Asp Phe Thr Arg Glu Leu Asp Pro Ala Trp Leu
610                 615                 620

Met Val Asp Thr Val Ile Gly Glu Gly Glu Phe Gly Glu Val Tyr Arg
625                 630                 635                 640

Gly Thr Leu Arg Leu Pro Ser Gln Asp Cys Lys Thr Val Ala Ile Lys
                645                 650                 655

Thr Leu Lys Asp Thr Ser Pro Gly Gly Gln Trp Trp Asn Phe Leu Arg
            660                 665                 670

Glu Ala Thr Ile Met Gly Gln Phe Ser His Pro His Ile Leu His Leu
        675                 680                 685
```

```
Glu Gly Val Val Thr Lys Arg Lys Pro Ile Met Ile Ile Thr Glu Phe
            690                 695                 700
Met Glu Asn Gly Ala Leu Asp Ala Phe Leu Arg Glu Arg Glu Asp Gln
705                 710                 715                 720
Leu Val Pro Gly Gln Leu Val Ala Met Leu Gln Gly Ile Ala Ser Gly
                725                 730                 735
Met Asn Tyr Leu Ser Asn His Asn Tyr Val His Arg Asp Leu Ala Ala
            740                 745                 750
Arg Asn Ile Leu Val Asn Gln Asn Leu Cys Cys Lys Val Ser Asp Phe
            755                 760                 765
Gly Leu Thr Arg Leu Leu Asp Asp Phe Asp Gly Thr Tyr Glu Thr Gln
            770                 775                 780
Gly Gly Lys Ile Pro Ile Arg Trp Thr Ala Pro Glu Ala Ile Ala His
785                 790                 795                 800
Arg Ile Phe Thr Thr Ala Ser Asp Val Trp Ser Phe Gly Ile Val Met
                805                 810                 815
Trp Glu Val Leu Ser Phe Gly Asp Lys Pro Tyr Gly Glu Met Ser Asn
                820                 825                 830
Gln Glu Val Met Lys Ser Ile Glu Asp Gly Tyr Arg Leu Pro Pro Pro
            835                 840                 845
Val Asp Cys Pro Ala Pro Leu Tyr Glu Leu Met Lys Asn Cys Trp Ala
850                 855                 860
Tyr Asp Arg Ala Arg Arg Pro His Phe Gln Lys Leu Gln Ala His Leu
865                 870                 875                 880
Glu Gln Leu Leu Ala Asn Pro His Ser Leu Arg Thr Ile Ala Asn Phe
            885                 890                 895
Asp Pro Arg Val Thr Leu Arg Leu Pro Ser Leu Ser Gly Ser Asp Gly
            900                 905                 910
Ile Pro Tyr Arg Thr Val Ser Glu Trp Leu Glu Ser Ile Arg Met Lys
            915                 920                 925
Arg Tyr Ile Leu His Phe His Ser Ala Gly Leu Asp Thr Met Glu Cys
            930                 935                 940
Val Leu Glu Leu Thr Ala Glu Asp Leu Thr Gln Met Gly Ile Thr Leu
945                 950                 955                 960
Pro Gly His Gln Lys Arg Ile Leu Cys Ser Ile Gln Gly Phe Lys Asp
                965                 970                 975

<210> SEQ ID NO 5
<211> LENGTH: 976
<212> TYPE: PRT
<213> ORGANISM: Homo sapiens

<400> SEQUENCE: 5

Met Glu Leu Gln Ala Ala Arg Ala Cys Phe Ala Leu Leu Trp Gly Cys
1               5                   10                  15
Ala Leu Ala Ala Ala Ala Ala Ala Gln Gly Lys Glu Val Val Leu Leu
                20                  25                  30
Asp Phe Ala Ala Ala Gly Gly Glu Leu Gly Trp Leu Thr His Pro Tyr
            35                  40                  45
Gly Lys Gly Trp Asp Leu Met Gln Asn Ile Met Asn Asp Met Pro Ile
        50                  55                  60
Tyr Met Tyr Ser Val Cys Asn Val Met Ser Gly Asp Gln Asp Asn Trp
65                  70                  75                  80
Leu Arg Thr Asn Trp Val Tyr Arg Gly Glu Ala Glu Arg Ile Phe Ile
                85                  90                  95
```

-continued

```
Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
        130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525
```

-continued

Pro Glu Gly Ser Gly Asn Leu Ala Val Ile Gly Gly Val Ala Val Gly
530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
            755                 760                 765

Glu Ala Thr Tyr Thr Thr Ser Gly Gly Lys Ile Pro Ile Arg Trp Thr
770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
                820                 825                 830

Gly Phe Arg Leu Pro Thr Pro Met Asp Cys Pro Ser Ala Ile Tyr Gln
            835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
                900                 905                 910

Leu Glu Ser Ile Lys Met Gln Gln Tyr Thr Glu His Phe Met Ala Ala
            915                 920                 925

Gly Tyr Thr Ala Ile Glu Lys Val Val Gln Met Thr Asn Asp Asp Ile
930                 935                 940

```
Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
            965                 970                 975
```

<210> SEQ ID NO 6
<211> LENGTH: 983
<212> TYPE: PRT
<213> ORGANISM: Homo sapiens

<400> SEQUENCE: 6

```
Met Asp Cys Gln Leu Ser Ile Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
            35                  40                  45

Ser His Gly Trp Glu Glu Ile Ser Gly Val Asp Glu His Tyr Thr Pro
        50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
            115                 120                 125

Asp Asp His Gly Val Lys Phe Arg Glu His Gln Phe Thr Lys Ile Asp
        130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
            195                 200                 205

Leu Ala Met Phe Pro Asp Thr Val Pro Met Asp Ser Gln Ser Leu Val
        210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
            275                 280                 285

Lys Cys Pro Pro His Ser Ser Thr Gln Glu Asp Gly Ser Met Asn Cys
        290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
            340                 345                 350
```

```
Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
    370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
                405                 410                 415

Glu Leu Ser Ser Pro Pro Arg Gln Phe Ala Ala Val Ser Ile Thr Thr
                420                 425                 430

Asn Gln Ala Ala Pro Ser Pro Val Leu Thr Ile Lys Lys Asp Arg Thr
            435                 440                 445

Ser Arg Asn Ser Ile Ser Leu Ser Trp Gln Glu Pro Glu His Pro Asn
    450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
                485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
    515                 520                 525

Ser Pro Asp Ser Phe Ser Ile Ser Gly Glu Ser Ser Gln Val Val Met
530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
                565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Thr
    595                 600                 605

Val His Glu Phe Ala Lys Glu Leu Asp Ala Thr Asn Ile Ser Ile Asp
610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
                645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
    675                 680                 685

Val Thr Lys Ser Lys Pro Val Met Ile Val Thr Glu Tyr Met Glu Asn
690                 695                 700

Gly Ser Leu Asp Ser Phe Leu Arg Lys His Asp Ala Gln Phe Thr Val
705                 710                 715                 720

Ile Gln Leu Val Gly Met Leu Arg Gly Ile Ala Ser Gly Met Lys Tyr
                725                 730                 735

Leu Ser Asp Met Gly Tyr Val His Arg Asp Leu Ala Ala Arg Asn Ile
            740                 745                 750

Leu Ile Asn Ser Asn Leu Val Cys Lys Val Ser Asp Phe Gly Leu Ser
    755                 760                 765

Arg Val Leu Glu Asp Asp Pro Glu Ala Ala Tyr Thr Thr Arg Gly Gly
770                 775                 780
```

```
Lys Ile Pro Ile Arg Trp Thr Ser Pro Glu Ala Ile Ala Tyr Arg Lys
785                 790                 795                 800

Phe Thr Ser Ala Ser Asp Val Trp Ser Tyr Gly Ile Val Leu Trp Glu
                805                 810                 815

Val Met Ser Tyr Gly Glu Arg Pro Tyr Trp Glu Met Ser Asn Gln Asp
            820                 825                 830

Val Ile Lys Ala Val Asp Glu Gly Tyr Arg Leu Pro Pro Pro Met Asp
        835                 840                 845

Cys Pro Ala Ala Leu Tyr Gln Leu Met Leu Asp Cys Trp Gln Lys Asp
    850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Thr Thr
            900                 905                 910

Phe Arg Thr Thr Gly Asp Trp Leu Asn Gly Val Trp Thr Ala His Cys
        915                 920                 925

Lys Glu Ile Phe Thr Gly Val Glu Tyr Ser Ser Cys Asp Thr Ile Ala
    930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

<210> SEQ ID NO 7
<211> LENGTH: 174
<212> TYPE: PRT
<213> ORGANISM: Homo sapiens

<400> SEQUENCE: 7

Glu Val Val Leu Leu Asp Phe Ala Ala Ala Gly Gly Glu Leu Gly Trp
1               5                   10                  15

Leu Thr His Pro Tyr Gly Lys Gly Trp Asp Leu Met Gln Asn Ile Met
                20                  25                  30

Asn Asp Met Pro Ile Tyr Met Tyr Ser Val Cys Asn Val Met Ser Gly
            35                  40                  45

Asp Gln Asp Asn Trp Leu Arg Thr Asn Trp Val Tyr Arg Gly Glu Ala
        50                  55                  60

Glu Arg Ile Phe Ile Glu Leu Lys Phe Thr Val Arg Asp Cys Asn Ser
65                  70                  75                  80

Phe Pro Gly Gly Ala Ser Ser Cys Lys Glu Thr Phe Asn Leu Tyr Tyr
                85                  90                  95

Ala Glu Ser Asp Leu Asp Tyr Gly Thr Asn Phe Gln Lys Arg Leu Phe
            100                 105                 110

Thr Lys Ile Asp Thr Ile Ala Pro Asp Glu Ile Thr Val Ser Ser Asp
        115                 120                 125

Phe Glu Ala Arg His Val Lys Leu Asn Val Glu Arg Ser Val Gly
        130                 135                 140

Pro Leu Thr Arg Lys Gly Phe Tyr Leu Ala Phe Gln Asp Ile Gly Ala
145                 150                 155                 160

Cys Val Ala Leu Leu Ser Val Arg Val Tyr Tyr Lys Lys Cys
                165                 170
```

<210> SEQ ID NO 8
<211> LENGTH: 3367
<212> TYPE: DNA
<213> ORGANISM: Homo sapiens

<400> SEQUENCE: 8

```
gcccccgccc ggcccgcccc gctctcctag tcccttgcaa cctggcgctg ccatccgggc      60
cactgtccca ggtcccggcc cggagctatg gagcggcgct ggcccctggg gctagggctg     120
gtgctgctgc tctgcgcccc gctgccccg ggggcgcgcg ccaaggaagt tactctgatg      180
gacacaagca aggcacaggg agagctgggc tggctgctgg atcccccaaa agatgggtgg     240
agtgaacagc aacagatact gaatgggaca cccctgtaca tgtaccagga ctgcccaatg     300
caaggacgca gagacactga ccactggctt cgctccaatt ggatctaccg cggggaggag     360
gcttcccgcg tccacgtgga gctgcagttc accgtgcggg actgcaagag tttccctggg     420
ggagccgggc tctgggctg caaggagacc ttcaaccttc tgtacatgga gagtgaccag     480
gatgtgggca ttcagctccg acggcccttg ttccagaagg taaccacggt ggctgcagac     540
cagagcttca ccattcgaga ccttgcgtct ggctccgtga agctgaatgt ggagcgctgc     600
tctctgggcc gcctgacccg ccgtggcctc tacctcgctt ccacaacccc gggtgcctgt     660
gtggccctgg tgtctgtccg ggtcttctac cagcgctgtc ctgagaccct gaatggcttg     720
gcccaattcc cagacactct gcctggcccc gctgggttgg tggaagtggc ggggacctgc     780
ttgcccacg cgcgggccag cccaggccc tcaggtgcac cccgcatgca ctgcagccct     840
gatggcgagt ggctggtgcc tgtaggacgg tgccactgtg agcctggcta tgaggaaggt     900
ggcagtggcg aagcatgtgt tgcctgccct agcggctcct accggatgga catggacaca     960
ccccattgtc tcacgtgccc ccagcagagc actgctgagt ctgaggggc caccatctgt    1020
acctgtgaga gcggccatta cagagctccc ggggagggcc cccaggtggc atgcacaggt    1080
cccccctcgg ccccccgaaa cctgagcttc tctgcctcag ggactcagct ctccctgcgt    1140
tgggaacccc cagcagatac gggggacgc caggatgtca gatacagtgt gaggtgttcc    1200
cagtgtcagg gcacagcaca ggacgggggg ccctgccagc cctgtgggt gggcgtgcac    1260
ttctcgccgg gggcccgggg gctcaccaca cctgcagtgc atgtcaatgg ccttgaacct    1320
tatgccaact acaccttaa tgtggaagcc caaatggag tgtcagggct gggcagctct    1380
ggccatgcca gcacctcagt cagcatcagc atggggcatg cagagtcact gtcaggcctg    1440
tctctgagac tggtgaagaa agaaccgagg caactagagc tgacctggc ggggtcccgg    1500
ccccgaagcc ctggggcgaa cctgacctat gagctgcacg tgctgaacca ggatgaagaa    1560
cggtaccaga tggttctaga acccaggtc ttgctgacag agctgcagcc tgacaccaca    1620
tacatcgtca gagtccgaat gctgacccca ctgggtcctg gccctttctc ccctgatcat    1680
gagtttcgga ccagcccacc agtgtccagg ggcctgactg gaggagagat tgtagccgtc    1740
atctttgggc tgctgcttgg tgcagccttg ctgcttggga ttctcgtttt ccggtccagg    1800
agagcccagc ggcagaggca gcagaggcag cgtgaccgcg ccaccgatgt ggatcgagag    1860
gacaagctgt ggctgaagcc ttatgtggac ctccaggcat acgaggaccc tgcacaggga    1920
gccctggact ttaccggga gcttgatcca gcgtggctga tggtggacac tgtcataggA    1980
gaaggagagt ttgggaagt gtatcgaggg acctgagc tccccagcca ggactgcaag    2040
actgtggcca ttaagacctt aaaagacaca tccccaggtg ccagtggtg aacttcctt    2100
cgagaggcaa ctatcatggg ccagtttagc caccgcata ttctgcatct ggaaggcgtc    2160
gtcacaaagc gaaagccgat catgatcatc acagaattta tggagaatgg agccctggat    2220
```

| | | |
|---|---|---|
| gccttcctga gggagcggga ggaccagctg gtccctgggc agctagtggc catgctgcag | 2280 |
| ggcatagcat ctggcatgaa ctacctcagt aatcacaatt atgtccaccg ggacctggct | 2340 |
| gccagaaaca tcttggtgaa tcaaaacctg tgctgcaagg tgtctgactt tggcctgact | 2400 |
| cgcctcctgg atgactttga tggcacatac gaaacccagg gaggaaagat ccctatccgt | 2460 |
| tggacagccc ctgaagccat tgcccatcgg atcttcacca cagccagcga tgtgtggagc | 2520 |
| tttgggattg tgatgtggga ggtgctgagc tttggggaca agccttatgg ggagatgagc | 2580 |
| aatcaggagg ttatgaagag cattgaggat gggtaccggt tgccccctcc tgtggactgc | 2640 |
| cctgcccctc tgtatgagct catgaagaac tgctgggcat atgaccgtgc cgccggcca | 2700 |
| cacttccaga agcttcaggc acatctggag caactgcttg ccaaccccca ctccctgcgg | 2760 |
| accattgcca actttgaccc caggatgact cttcgcctgc ccagcctgag tggctcagat | 2820 |
| gggatcccat atcgaaccgt ctctgagtgg ctcgagtcca tacgcatgaa acgctacatc | 2880 |
| ctgcacttcc actcggctgg gctggacacc atggagtgtg tgctggagct gaccgctgag | 2940 |
| gacctgacgc agatgggaat cacactgccc gggcaccaga agcgcattct ttgcagtatt | 3000 |
| cagggattca aggactgatc cctcctctca ccccatgccc aatcagggtg caaggagcaa | 3060 |
| ggacggggcc aaggtcgctc atggtcactc cctgcgcccc ttcccacaac ctgccagact | 3120 |
| aggctatcgg tgctgcttct gcccactttc aggagaaccc tgctctgcac cccagaaaac | 3180 |
| ctctttgttt taaagggag gtgggggtag aagtaaaagg atgatcatgg gagggagctg | 3240 |
| aggggttaat atatatacat acatacacat atatatattt ttgtaaataa acaggaactg | 3300 |
| attttctgcc tccatcccac ccatgagggc tgcaggcact acaaaagagc tgactactga | 3360 |
| gaaaaaa | 3367 |

<210> SEQ ID NO 9
<211> LENGTH: 2931
<212> TYPE: DNA
<213> ORGANISM: Homo sapiens

<400> SEQUENCE: 9

| | | |
|---|---|---|
| atggagctcc aggcagcccg cgcctgcttc gccctgctgt ggggctgtgc gctggccgcg | 60 |
| gccgcggcgg cgcagggcaa ggaagtggta ctgctggact tgctgcagc tggaggggag | 120 |
| ctcggctggc tcacacaccc gtatggcaaa gggtgggacc tgatgcagaa catcatgaat | 180 |
| gacatgccga tctacatgta ctccgtgtgc aacgtgatgt ctggcgacca ggacaactgg | 240 |
| ctccgcacca actgggtgta ccgaggagag gctgagcgta tcttcattga gctcaagttt | 300 |
| actgtacgtg actgcaacag cttccctggt ggcgccagct cctgcaagga gactttcaac | 360 |
| ctctactatg ccgagtcgga cctggactac ggcaccaact tccagaagcg cctgttcacc | 420 |
| aagattgaca ccattgcgcc cgatgagatc accgtcagca gcgacttcga ggcacgccac | 480 |
| gtgaagctga acgtggagga cgctccgtg gggccgctca cccgcaaagg cttctacctg | 540 |
| gccttccagg atatcggtgc ctgtgtgcg ctgctctccg tccgtgtcta ctacaagaag | 600 |
| tgccccgagc tgctgcaggg cctggcccac ttccctgaga ccatcgccgg ctctgatgca | 660 |
| ccttccctgg ccactgtggc cggcacctgt gtggaccatg ccgtggtgcc accgggggt | 720 |
| gaagagcccc gtatgcactg tgcagtggat ggcgagtggc tggtgcccat gggcagtgc | 780 |
| ctgtgccagg caggctacga gaaggtggag gatgcctgcc aggcctgctc gcctggattt | 840 |
| tttaagtttg aggcatctga gagcccctgc ttggagtgcc ctgagcacac gctgccatcc | 900 |
| cctgagggtg ccacctcctg cgagtgtgag gaaggcttct tccgggcacc tcaggaccca | 960 |

| | |
|---|---|
| gcgtcgatgc cttgcacacg accccctcc gccccacact acctcacagc cgtgggcatg | 1020 |
| ggtgccaagg tggagctgcg ctggacgccc cctcaggaca gcgggggccg cgaggacatt | 1080 |
| gtctacagcg tcacctgcga acagtgctgg cccgagtctg gggaatgcgg gccgtgtgag | 1140 |
| gccagtgtgc gctactcgga gcctcctcac ggactgaccc gcaccagtgt gacagtgagc | 1200 |
| gacctggagc cccacatgaa ctacaccttc accgtggagg cccgcaatgg cgtctcaggc | 1260 |
| ctggtaacca gccgcagctt ccgtactgcc agtgtcagca tcaaccagac agagcccccc | 1320 |
| aaggtgaggc tggagggccg cagcaccacc tcgcttagcg tctcctggag catccccccg | 1380 |
| ccgcagcaga gccgagtgtg gaagtacgag gtcacttacc gcaagaaggg agactccaac | 1440 |
| agctacaatg tgcgccgcac cgagggtttc tccgtgaccc tggacgacct ggccccagac | 1500 |
| accacctacc tggtccaggt gcaggcactg acgcaggagg gccagggggc cggcagcaag | 1560 |
| gtgcacgaat ccagacgct gtccccggag ggatctggca acttggcggt gattggcggc | 1620 |
| gtggctgtcg gtgtggtcct gcttctggtg ctggcaggag ttggcttctt tatccaccgc | 1680 |
| aggaggaaga accagcgtgc ccgccagtcc ccggaggacg tttacttctc caagtcagaa | 1740 |
| caactgaagc ccctgaagac atacgtggac ccccacacat atgaggaccc caaccaggct | 1800 |
| gtgttgaagt tcactaccga gatccatcca tcctgtgtca ctcggcagaa ggtgatcgga | 1860 |
| gcaggagagt ttggggaggt gtacaagggc atgctgaaga catcctcggg gaagaaggag | 1920 |
| gtgccggtgg ccatcaagac gctgaaagcc ggctacacag agaagcagcg agtggacttc | 1980 |
| ctcggcgagg ccggcatcat gggccagttc agccaccaca acatcatccg cctagagggc | 2040 |
| gtcatctcca aatacaagcc catgatgatc atcactgagt acatggagaa tggggccctg | 2100 |
| gacaagttcc ttcgggagaa ggatggcgag ttcagcgtgc tgcagctggt gggcatgctg | 2160 |
| cggggcatcg cagctggcat gaagtacctg gccaacatga actatgtgca ccgtgacctg | 2220 |
| gctgcccgca acatcctcgt caacagcaac ctggtctgca aggtgtctga ctttggcctg | 2280 |
| tcccgcgtgc tggaggacga ccccgaggcc acctacacca ccagtggcgg caagatcccc | 2340 |
| atccgctgga ccgcccccga ggccatttcc taccggaagt tcacctctgc cagcgacgtg | 2400 |
| tggagctttg gcattgtcat gtgggaggtg atgacctatg cgagcggcc ctactgggag | 2460 |
| ttgtccaacc acgaggtgat gaaagccatc aatgatggct ccggctccc cacacccatg | 2520 |
| gactgccccct ccgccatcta ccagctcatg atgcagtgct ggcagcagga gcgtgcccgc | 2580 |
| cgccccaagt cgctgacat cgtcagcatc ctggacaagc tcattcgtgc ccctgactcc | 2640 |
| ctcaagaccc tggctgactt tgaccccgc gtgtctatcc ggctcccag cacgagcggc | 2700 |
| tcggaggggg tgcccttccg cacggtgtcc gagtggctgg agtccatcaa gatgcagcag | 2760 |
| tatacggagc acttcatggc ggccggctac actgccatcg agaaggtggt gcagatgacc | 2820 |
| aacgacgaca tcaagaggat tggggtgcgg ctgcccggcc accagaagcg catcgcctac | 2880 |
| agcctgctgg gactcaagga ccaggtgaac actgtgggga tccccatctg a | 2931 |

<210> SEQ ID NO 10
<211> LENGTH: 5711
<212> TYPE: DNA
<213> ORGANISM: Homo sapiens

<400> SEQUENCE: 10

| | |
|---|---|
| gagtgtcaaa cttgacatca gcctgcgagc ggagcatggt aacttctcca gcaatcagag | 60 |
| cgctccccct cacatcagtg gcatgcttca tggagatatg ctcctctcac tgccctctgc | 120 |
| accagcaaca tggattgtca gctctccatc ctcctccttc tcagctgctc tgttctcgac | 180 |

```
agcttcgggg aactgattcc gcagccttcc aatgaagtca atctactgga ttcaaaaaca    240
attcaagggg agctgggctg gatctcttat ccatcacatg ggtgggaaga gatcagtggt    300
gtggatgaac attacacacc catcaggact taccaggtgt gcaatgtcat ggaccacagt    360
caaaacaatt ggctgagaac aaactgggtc cccaggaact cagctcagaa gatttatgtg    420
gagctcaagt tcactctacg agactgcaat agcattccat tggttttagg aacttgcaag    480
gagacattca acctgtacta catggagtct gatgatgatc atggggtgaa atttcgagag    540
catcagttta caaagattga caccattgca gctgatgaaa gtttcactca aatggatctt    600
ggggaccgta ttctgaagct caacactgag attagagaag taggtcctgt caacaagaag    660 ggatttttatt tggcatttca agatgttggt gcttgtgttg ccttggtgtc tgtgagagta    720
tacttcaaaa agtgcccatt tacagtgaag aatctggcta tgtttccaga cacggtaccc    780
atggactccc agtccctggt ggaggttaga gggtcttgtg tcaacaattc taaggaggaa    840
gatcctccaa ggatgtactg cagtacgaaa ggcgaatggc ttgtacccat ggcaagtgt    900 tcctgcaatg ctggctatga agaaagaggt tttatgtgcc aagcttgtcg accaggtttc    960
tacaaggcat ggatggtaa tatgaagtgt gctaagtgcc cgcctcacag ttctactcag   1020
gaagatggtt caatgaactg caggtgtgag aataattact tccgggcaga caaagaccct   1080
ccatccatgg cttgtacccg acctccatct tcaccaagaa atgttatctc taatataaac   1140
gagacctcag ttatcctgga ctggagttgg cccctggaca caggaggccg gaaagatgtt   1200
accttcaaca tcatatgtaa aaaatgtggg tggaatataa aacagtgtga gccatgcagc   1260
ccaaatgtcc gcttcctccc tcgacagttt ggactcacca acaccacggt gacagtgaca   1320
gaccttctgg cacatactaa ctacacccttt gagattgatg ccgttaatgg ggtgtcagag   1380
ctgagctccc caccaagaca gtttgctgcg gtcagcatca caactaatca ggctgctcca   1440
tcacctgtcc tgacgattaa gaaagatcgg acctccagaa atagcatctc tttgtcctgg   1500
caagaacctg aacatcctaa tgggatcata ttggactacg aggtcaaata ctatgaaaag   1560
caggaacaag aaacaagtta taccattctg agggcaagag gcacaaatgt taccatcagt   1620
agcctcaagc ctgacactat atacgtattc caaatccgag cccgaacagc cgctggatat   1680
gggacgaaca gccgcaagtt tgagtttgaa actagtccag actctttctc catctctggt   1740
gaaagtagcc aagtggtcat gatcgccatt tcagcggcag tagcaattat tctcctcact   1800
gttgtcatct atgttttgat tgggaggttc tgtggctata agtcaaaaca tggggcagat   1860
gaaaaaagac ttcattttgg caatgggcat ttaaaacttc caggtctcag gacttatgtt   1920
gacccacata catatgaaga ccctacccaa actgttcatg agtttgccaa ggaattggat   1980
gccaccaaca tatccattga taagttgtt ggagcaggtg aatttggaga ggtgtgcagt   2040
ggtcgcttaa aacttccttc aaaaaagag atttcagtgg ccattaagac cctgaaagtt   2100
ggctacacag aaaagcagag gagagacttc ctgggagaag caagcattat gggacagttt   2160
gaccacccca atatcattcg actggaagga gttgttacca aaagtaagcc agttatgatt   2220
gtcacagaat acatggagaa tggttccttg gatagtttcc tacgtaaaca cgatgcccag   2280
tttactgtca ttcagctagt ggggatgctt cgagggatag catctggcat gaagtacctg   2340
tcagacatgg gctatgttca ccgagacctc gctgctcgga acatcttgat caacagtaac   2400
ttggtgtgta aggtttctga tttcggactt tcgcgtgtcc tggaggatga cccagaagct   2460
gcttatacaa caagaggagg gaagatccca atcaggtgga catcaccaga agctatagcc   2520
taccgcaagt tcacgtcagc cagcgatgta tggagttatg ggattgttct ctgggaggtg   2580
```

```
atgtcttatg gagagagacc atactgggag atgtccaatc aggatgtaat taaagctgta    2640
gatgagggct atcgactgcc acccccatg gactgcccag ctgccttgta tcagctgatg     2700
ctggactgct ggcagaaaga caggaacaac agacccaagt ttgagcagat tgttagtatt    2760
ctggacaagc ttatccggaa tcccggcagc ctgaagatca tcaccagtgc agccgcaagg    2820
ccatcaaacc ttcttctgga ccaaagcaat gtggatatca ctaccttccg cacaacaggt    2880
gactggctta atggtgtctg gacagcacac tgcaaggaaa tcttcacggg tgtggagtac    2940
agttcttgtg acacaatagc caagatttcc acagatgaca tgaaaaaggt tggtgtcacc    3000
gtggttgggc cacagaagaa gatcatcagt agcattaaag ctctagaaac gcaatcaaag    3060
aatggcccag ttcccgtgta agcacgggga cggaagtgct tctggacgga agtggtggct    3120
gtggaaggcg tagcatcatc ctgcagacag acaataattc tggagatact ggtggaagtt    3180
ccaagtccaa taagacactc aaatatgagt acaaatgcct taaaatggaa ttgaaaaact    3240
ctttattttc ccctatcatt tattggatgg gtgggtgggg tatttttttg taattgcttt    3300
tttaaatatt agttaatgga ttaaatttaa ttcttcagcg taaaatggtg aagaactagc    3360
atatagccat tgatcataaa ctgactatca taaaatcaaa acaagtgaaa taacaaaatg    3420
gacatggtgg ctttgtttag gtagagccac aaaagaaaag acttgtaata ttttatata     3480 cagaggaaat ctgtaacagg tattttgttt cttttaaagc aagcaacaca gaggaattta    3540
tacctcaaac tatctggcca tatttactac cttatcactg cattattctc ttttatctgt    3600
ttaaagcata tagagatgaa gtttgtagtt gttttaagta ctacacattt ttaaattgtt    3660
agcttcctta agtatatcat gtaaagaaat gtcttaattt ttgaaaaaag tacatattta    3720 ttttctttg aattgttttt attgttttct atttatgcct tgatgattta atatggattt      3780
gttacagcca agtgccaaat gctctctcaa attgtcagca atttaactag acacagataa    3840
taatgggttt ctttcagatt ttttgaacca tccacttaca tatattttta aaaaatgaaa    3900
tccttttcct gttcatacac taaccaaatc tctcaaatct gttatcccaa tcattgttgc    3960
ctctccgttt attataaact gtatgctcac aacttagtgt aatataccag cttgtatgca    4020 atggatttc aaccagataa cataccttc ctgctctggt gcttagagac tatcaactcc       4080
ctcctttagt gaaggagccg tgttagagct tccgagaata gctccactgg agagaagtgg    4140
aatcctatat agaatgctgc actaattgac aacacagcct ataggccaat gcatgagtaa    4200
aaaaaaaaac aattactggc tcactggctt tgaaaagtca cttactattg ttgctgaaac    4260
ttgctgagct gtttatagag aatgatgata acagaacttt tcctctgtat cactggtgtt    4320
taggtgaatt aattaaacat tgtgatcatt agtaccaggt attattatct ttaagagtct    4380
tccacttcaa tgcacatggt gcagttttgg tgtgtaactt agaaggattg aacttctttg    4440
aatttactgg acataacatt ttcagaatag ttggtcatct agcaaccgcc tcaaaatgtg    4500
taagcaggag agaaatttct catcacaggg atttagactt actattacat aaaggctaac    4560
tatgagcttg ctcattaatt ttgaaaagat gtacctggtg gatatctagc tagtaatata    4620
ttctgaagca acattttagc tctattgata ctctttctaa tgctgatatg atcttgagta    4680
taagaaatgc atatgtcact agaatggata aaataatgct gcaaacttaa tgttcttatg    4740
caaaatggaa cgctaatgaa acacagctta caatcgcaaa tcaaaactca caagtgctca    4800
tctgttgtag atttagtgta ataagactta gattgtgctc cttcggatat gattgtttct    4860
caaatcttgg caatattcct tagtcaaatc aggctactag aattctgtat tggatatata    4920
agagcatgaa attttttaaaa atacacttgt gattataaaa ttaatcacaa atttcactta    4980
```

```
tacctgctat cagcagctag aaaacatttt tttttaaat caagtatttt gtgtttggaa    5040
tgttagaatg agatctgaat gtggtttcaa tctaatttt tcccagacta ctattttctt    5100
ttttaggtac tattctgagc atactcaaca aaacccatgc atttcataaa ctaatagaag    5160
ttgaggattg ttgaatctat ttcacttatt ttggctgtgg tttccatctg aaagtagagg    5220
ttgtatacac catatactgt tcttcatttt attaatattt ttctccttga cctctcataa    5280
atttacttta cacaattctt accctgtaca tatgtaaaca taagtgtacg attcttaacc    5340
atggagtaga ggtactagaa tgcttacggc catctctttg tacaggaact gcattgactt    5400
tcagtaaaca taaagccaca actcctacat gatgttatgt accatatgat ctgttttgta    5460
tcttaaattt gatttacata tattatttat ttctggtaac tcactcagtt tatgctgtgc    5520
taaatatcaa tcaagccatg tataaatgtg atatgattgg caatatgtgt ttactttaaa    5580
cttgtctttt caaatatatta ctcagtttat gttgtacaat gtagatggcc tcttactaat    5640
gtaaaatgat ttgtagtgga aacatttata tttttataat aaacataatg aaaataaaaa    5700
aaaaaaaaaa a                                                          5711

<210> SEQ ID NO 11
<211> LENGTH: 522
<212> TYPE: DNA
<213> ORGANISM: Homo sapiens

<400> SEQUENCE: 11
gaagtggtac tgctggactt tgctgcagct ggaggggagc tcggctggct cacacacccg     60
tatggcaaag ggtgggacct gatgcagaac atcatgaatg catgccgat ctacatgtac    120 tccgtgtgca acgtgatgtc tggcgaccag gacaactggc tccgcaccaa ctgggtgtac    180
cgaggagagg ctgagcgtat cttcattgag ctcaagttta ctgtacgtga ctgcaacagc    240
ttccctggtg gcgccagctc ctgcaaggag actttcaacc tctactatgc cgagtcggac    300
ctggactacg gcaccaactt ccagaagcgc ctgttcacca gattgacac cattgcgccc    360 gatgagatca ccgtcagcag cgacttcgag gcacgccacg tgaagctgaa cgtggaggag    420
cgctccgtgg ggccgctcac ccgcaaaggc ttctacctgg ccttccagga tatcggtgcc    480
tgtgtggcgc tgctctccgt ccgtgtctac tacaagaagt gc                       522

<210> SEQ ID NO 12
<211> LENGTH: 205
<212> TYPE: PRT
<213> ORGANISM: Homo sapiens

<400> SEQUENCE: 12

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110
```

```
Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
        130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
                165                 170                 175

His Ser Ile Gly His Ser Ala Ala Pro Arg Leu Phe Pro Leu Ala Trp
                180                 185                 190

Thr Val Leu Leu Leu Pro Leu Leu Leu Gln Thr Pro
        195                 200                 205

<210> SEQ ID NO 13
<211> LENGTH: 346
<212> TYPE: PRT
<213> ORGANISM: Homo sapiens

<400> SEQUENCE: 13

Met Ala Arg Pro Gly Gln Arg Trp Leu Gly Lys Trp Leu Val Ala Met
1               5                   10                  15

Val Val Trp Ala Leu Cys Arg Leu Ala Thr Pro Leu Ala Lys Asn Leu
            20                  25                  30

Glu Pro Val Ser Trp Ser Ser Leu Asn Pro Lys Phe Leu Ser Gly Lys
        35                  40                  45

Gly Leu Val Ile Tyr Pro Lys Ile Gly Asp Lys Leu Asp Ile Ile Cys
    50                  55                  60

Pro Arg Ala Glu Ala Gly Arg Pro Tyr Glu Tyr Tyr Lys Leu Tyr Leu
65                  70                  75                  80

Val Arg Pro Glu Gln Ala Ala Cys Ser Thr Val Leu Asp Pro Asn
            85                  90                  95

Val Leu Val Thr Cys Asn Arg Pro Glu Gln Glu Ile Arg Phe Thr Ile
            100                 105                 110

Lys Phe Gln Glu Phe Ser Pro Asn Tyr Met Gly Leu Glu Phe Lys Lys
        115                 120                 125

His His Asp Tyr Tyr Ile Thr Ser Thr Ser Asn Gly Ser Leu Glu Gly
        130                 135                 140

Leu Glu Asn Arg Glu Gly Gly Val Cys Arg Thr Arg Thr Met Lys Ile
145                 150                 155                 160

Ile Met Lys Val Gly Gln Asp Pro Asn Ala Val Thr Pro Glu Gln Leu
                165                 170                 175

Thr Thr Ser Arg Pro Ser Lys Glu Ala Asp Asn Thr Val Lys Met Ala
            180                 185                 190

Thr Gln Ala Pro Gly Ser Arg Gly Ser Leu Gly Asp Ser Asp Gly Lys
        195                 200                 205

His Glu Thr Val Asn Gln Glu Glu Lys Ser Gly Pro Gly Ala Ser Gly
        210                 215                 220

Gly Ser Ser Gly Asp Pro Asp Gly Phe Phe Asn Ser Lys Val Ala Leu
225                 230                 235                 240

Phe Ala Ala Val Gly Ala Gly Cys Val Ile Phe Leu Leu Ile Ile Ile
                245                 250                 255

Phe Leu Thr Val Leu Leu Leu Lys Leu Arg Lys Arg His Arg Lys His
            260                 265                 270

Thr Gln Gln Arg Ala Ala Ala Leu Ser Leu Ser Thr Leu Ala Ser Pro
        275                 280                 285
```

```
Lys Gly Gly Ser Gly Thr Ala Gly Thr Glu Pro Ser Asp Ile Ile Ile
    290             295             300

Pro Leu Arg Thr Thr Glu Asn Asn Tyr Cys Pro His Tyr Glu Lys Val
305             310             315             320

Ser Gly Asp Tyr Gly His Pro Val Tyr Ile Val Gln Glu Met Pro Pro
            325             330             335

Gln Ser Pro Ala Asn Ile Tyr Tyr Lys Val
            340             345
```

PEPTIDE AND SMALL MOLECULE AGONISTS OF EPHA AND THEIR USES

RELATED APPLICATIONS

The present application claims priority from U.S. Provisional Application No. 60/621,041, filed Oct. 23, 2004, which is herein incorporated by reference in its entirety.

BACKGROUND

Cancer is the second leading cause of death in North American, killing 557,000 people in 2002. The overall cancer risk is ½, representing tremendous burden to the all the individuals and fimilaies affected. Despite decades of intense research, a cure for most cancers is still not available. Recently, mechanism-based molecular therapy has emerged as increasingly attractive approach for cancer therapy.

Cancer development is underscored by two types of genetic alterations. One is the loss of function of tumor suppressor genes. The normal function of these genes is to keep cells in non-tumorigenic quiescent state. Another genetic alteration is the activation of oncogenes. While a variety of approaches are being developed to target oncogenes, targeting tumor suppressor genes is more challenging due to their loss of function in tumor development. However, recent studies show that even in malignant cells, tumor suppressor networks frequently remain intact but latent. Harnessing the powerful intrinsic tumor suppressors for cancer therapy has emerged an attractive new approach in contemporary drug discovery.

Since the discovery of the first member from an erythropoietin producing hepatoma cell line nearly two decades ago, the number of Eph receptor protein tyrosine kinases (RPTK) has increased to 16 in vertebrate, making them the largest subfamily of RPTKs. They are divided into EphA and EphB kinases according to sequence homology and ligand binding specificity of the membrane-anchored ligands called ephrins. While EphA kinases bind to GPI-anchored ephrin-As, EphB kinases target transmembrane ephrin-Bs. Earlier studies have established a regulatory role of Eph/ephrin interactions in neural patterning in developing nervous systems, primarily through repulsive guidance of growth cones and neurons. Genetic studies using knockout mice revealed a pivotal role of Eph kinases in the development of cardiovascular system. The past several years have seen explosive growth in investigation on Eph receptors and their ligands, leading to the identification of diverse cellular functions regulated by Eph/ephrin interactions including neural plasticity, brain size determination, blood clotting, epithelial morphogenesis and viral infection.

SUMMARY OF THE INVENTION

The present invention is based at least in part on the discovery that EphA kinase (e.g., EphA1, EphA2, and EphA3) can function as a tumor suppressor and that activation of EphA kinase (e.g., EphA1, EphA2, and EphA3) can inhibit cancer cell growth, migration and/or proliferation in, for example, prostate cancer, breast cancer, colorectal cancer, skin cancer, and lung cancer.

The present invention also provides a method of identifying therapeutic agents for cancer, such as prostate cancer, breast cancer, colorectal cancer, and lung cancer. In the method, an agonist of an EphA receptor protein (e.g., EphA1, EphA2, and EphA3) is identified. The agonist of the EphA receptor protein can be a therapeutic agent for cancer. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In yet another aspect, the invention provides a method of inhibiting cell growth, migration and/or proliferation. In the method, a cell is contacted with an agonist of EphA receptor protein (e.g., EphA1, EphA2, and EphA3). The cell can be a mammalian cell, such as a human cell. In certain cases, the cell can be a cancer cell (e.g., a prostate cancer cell, lung cancer cell, colorectal cancer cell, breast cancer cell, and skin cancer cell). The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In certain aspects, the invention provides a method of treating the onset of cancer in an individual, such as a mammal (e.g., human), comprising administering to the individual a therapeutically effective amount of an agonist of EphA receptor protein (e.g., EphA1, EphA2, and/or EphA3), wherein the agonist inhibits proliferation of cancer cells. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA. In an aspect of the invention, the agonist of the method can be a small molecule.

In certain aspects, the invention provides a method of activating EphA receptor activity in a cell. The method comprises contacting the cell with an agent that binds to the ligand-binding domain of EphA receptor protein. The cell can be a mammalian cell, such as a human cell. In certain cases, the cell can be a cancer cell. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In certain aspects, the invention provides a method of inhibiting the Ras/Raf/MEK/ERK1/2 signaling pathway. The method can comprise administering to the individual a therapeutically effective amount of an agonist of EphA receptor protein (e.g., EphA1, EphA2, and/or EphA3), wherein the agonist inhibits proliferation of cancer cells. The agonist can inhibit activation of the Ras/Raf/MEK/ERK1/2 signaling pathway by growth factor receptors, such as EGFR, PDGFR, and c-MET. The agonist can also bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In other aspects, the invention provides a method of suppressing the PI3/AKT signaling pathway, comprising administering to the individual a therapeutically effective amount of an agonist of EphA receptor protein (e.g., EphA1, EphA2, and/or EphA3), wherein the agonist inhibits survival of cancer cells. The agonist can also bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In other aspects, the invention provides a method of inhibiting epithelial carcinogenesis in an individual, comprising administering to the individual a therapeutically effective amount of an agonist of EphA receptor protein, wherein the agonist inhibits epithelial carcinogenesis. For example, the agonist inhibits epithelial carcinogenesis in the prostate, lung, breast, skin and colorectom. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA. In an aspect of the invention, the agonist of the method can be a small molecule.

In other aspects, the invention provides a method of treating diseases where EphA is overexpressed. These diseases can include, for example, restenosis, inflammation, asthma, chronic obstructive lung diseases and abnormal angiogenesis in eyes. The method can comprise administering to the individual a therapeutically effective amount of an agonist of EphA receptor protein. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In further aspects, the invention provides a method of stimulating at least one of neural synaptogenesis, axon pathfinding, long term potentiation of neural cells. The method can comprise administering to the individual a therapeutically effective amount of an agonist of EphA receptor protein. The agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In other aspects, the EphA agonist can comprise an exogenous or non-native peptide or small molecule have a molecular weight of about 50 daltons to about 2500 daltons. The EphA small molecule agonist in accordance with an aspect of the invention comprises an EphA small molecule agonist having the general formula: A-L-B (II), wherein A and B are independently selected from aryl and heteroaryl; and L is selected from C1-12alkyl and —C1-6alkyl-amino-C1-6alkyl. Exemplary small molecules include, but are not limited to, doxazosin, labetalol, dobutamine, and (di-meo-iso-quinolin-1-ylmethyl)-et-di-meo-pyrido(2,1-a)isoquinolin, hydrobromide S120103. The small molecule agonist can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

In certain aspects, the invention provides an EphA peptide agonist (e.g., EphA1, EphA2, or EphA3 peptide agonist) comprising about 4 to about 20 amino acids. The peptide can be selected from the group consisting of: (a) a peptide having at least 40% sequence identify to any of SEQ ID NOs: 1-3; and (b) a peptide of SEQ ID NOs: 1-3. Or it can be a peptide with discernable structural similarities to the peptides. The EphA peptide can bind to the ligand-binding domain of an EphA receptor protein, bind to the dimerization domain of EphA receptor protein, stimulate tyrosine phosphorylation of an EphA, enhance binding of an EphA ligand to an EphA, and/or enhance dimerization and/or signaling of an EphA.

Optionally, the agonist binds to the ligand-binding domain of an EphA2 receptor protein, binds to the dimerization domain of EphA2 receptor protein, stimulates tyrosine phosphorylation of an EphA2, enhances binding of an EphA2 ligand to an EphA2, and/or enhances dimerization and/or signaling of an EphA2.

In yet another aspect, the invention provides a method of treating or preventing the onset of cancer (e.g., prostate cancer, breast cancer, colorectal cancer, skin cancer, and lung cancer) in an individual comprising administering to the individual a therapeutically effective amount of a small molecule agonist as described above.

In certain aspects, the invention provides a method of treating or preventing the onset of cancer in an individual, comprising administering to the individual a therapeutically effective amount of a peptide agonist as described above.

In certain aspects, the invention provides a transgenic knockout mouse having germline and somatic cells in which at least one allele of the genomic EphA gene (e.g., EphA1, EphA2, or EphA3 gene) is disrupted and at least one allele of a tumor suppressor gene is disrupted. Preferably, the transgenic mouse exhibits increased susceptibility to the formation of prostate tumors as compared to a transgenic mouse having germline and somatic cells in which at least one allele of the tumor suppressor gene alone is disrupted. Exemplary tumor suppressor genes include p53, p63, p73, p16, PTEN, APC, Rb and Nkx 3.1.

In certain aspects, the invention provides a transgenic knockout mouse having germline and somatic cells in which at least one allele of the genomic EphA gene (e.g., EphA1, EphA2, or EphA3 gene) is disrupted and a transgene encoding an oncogene is expressed. Preferably, the transgenic knockout mouse exhibits increased susceptibility to the formation of prostate tumors as compared to a transgenic knockout mouse having expressing the transgene alone (i.e., the TRAMP (transgenic adenocarcinoma mouse prostate) mouse). For example, the oncogene encodes T, Myc, and Ras antigen oncoprotein.

In certain aspects, the invention provides a method of identifying a therapeutic agent for cancer cancer (e.g., prostate cancer, breast cancer, colorectal cancer, skin cancer, and lung cancer), comprising administering a test agent to the transgenic knockout mouse as described above.

In certain aspects, the invention provides a method of identifying a therapeutic agent for cancer cancer (e.g., prostate cancer, breast cancer, colorectal cancer, skin cancer, and lung cancer), comprising administering a test agent to a cell isolated from the transgenic knockout mouse as described above.

In certain aspects, the invention provides a method of assaying for an agonist of EphA kinase (e.g., EphA1, EphA2, or EphA3), comprising: a) contacting an EphA polypeptide with a test agent; and b) determining whether the agent binds to EphA. Optionally, binding of the agent to EphA is determined by a method selected from the group consisting of yeast two-hybrid assay, fluorescence polarization assay, fluorescence resonance energy transfer (FRET) assay, solid phase binding assay, and ELISA.

In certain aspects, the invention provides a method of assaying for an agonist of EphA kinase (e.g., EphA1, EphA2, or EphA3), comprising: a) contacting an EphA polypeptide with a test agent; and b) determining whether the agent stimulates EphA activity. For example, the agent activates EphA tyrosine phosphorylation. Optionally, EphA tyrosine phosphorylation is determined by an immunoassay.

In certain aspects, the invention provides a method of identifying a therapeutic agent for cancer, comprising identifying an agent selected from the group consisting of: 1) an agent which binds to an EphA receptor protein kinase (e.g., EphA1, EphA2, or EphA3); 2) an agent which stimulates phosphorylation of an EphA receptor protein; 3) an agent which enhances dimerization and/or signaling of an EphA receptor protein; and 4) an agent which enhances binding of an EphA ligand to an EphA receptor protein. Optionally, the agent binds to the ligand-binding domain of EphA receptor protein.

In certain aspects, the present invention provides a crystalline molecule comprising an EphA2 ligand binding domain (LBD). In one embodiment, the molecule is an EphA2 protein. In another embodiment, the molecule is an EphA2 LBD. In certain embodiments, the invention provides crystal compositions comprising an EphA2 protein or an EphA2 LBD in the presence or absence of a chemical entity. The invention also provides a method of crystallizing an EphA2 protein or an EphA2 LBD.

The invention further provides a computer comprising a data storage medium which comprises the structure coordinates of a molecule comprising all or part of the EphA2 ligand binding domain (LBD). Such storage medium, when read and utilized by a computer programmed with appropriate software, displays on a computer screen or similar viewing device, a three-dimensional graphical representation of a molecule or molecular complex comprising such ligand binding structure.

The invention provides methods for screening, designing, optimizing, evaluating, and identifying compounds which bind to an EphA2 molecule or its LBD. Such compounds can be potential inhibitors (antagonists) or activators (agonists) of EphA2 proteins.

The invention also provides a method for determining at least a portion of the three-dimensional structure of molecules which contain at least some structurally similar features to an EphA2 protein (e.g., EphA2 LBD). This is achieved by using at least some of the structure coordinates obtained from the EphA2 protein as described herein.

BRIEF DESCRIPTION OF THE DRAWINGS

FIG. 48B illustrates that EphA1 and EphA2 are upregulated in mouse breast tumors induced by HER2/Neu, but not in tumors induced by luteinizinghormone (LH). Upregulation of EphA2 is present in 30% human breast cancer.

FIG. 49B illustrates that proliferation of prostatic epithelial cells expressing EphA1 and activated with Ephrin-A1 is inhibited.

DETAILED DESCRIPTION

Figure 1A:
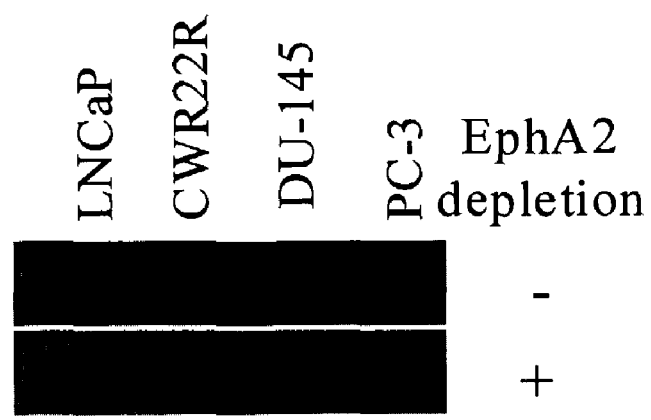
FIG. 1. (A) EphA2 is the primary EphA kinase expressed on human prostate cancer cells. Cell surface proteins were labeled with membrane impermeable biotin (Method). Top panel: Saturating amount of ephrin-A1-Fc (EA1-Fc) was used to precipitate most EphA kinases. Lower panel: EphA2 was first immunodepleted from cell lysates with an EphA2-specific antibody. Saturating amount of ephrin-A1-Fc was then added to the EphA2-depleted cell lysates to precipitate other members of EphA kinases. The precipitates were subject immunoblot with HRP-labeled avidin. (B) Expression of EphA2, but not other EphA kinases and ephrin-As, is elevated in cell lines derived from more malignant prostate cancer. Total cellular proteins were immunoblotted with the indicated antibodies. (C) Immunofluorescence staining of EphA2. Human prostate cancer cells grown on cover slip were stained with anti-EphA2 antibody. Texas-Red labeled secondary was used to visualize the bound primary antibody (D) DU-145 and MatLyLu cells were stimulated with ephrin-A1-Fc for indicated times and lysed. EphA2 immunoprecipitation was carried out to determine the activation status of EphA2 using anti-phosphotyrosine antibody. The same membranes were stripped and re-blotted for total EphA2. To determine the ERK activation status, total cell lysates were analyzed by immunoblot using anti-phospho ERK (p-ERK) antibody. Same membranes were stripped and blotted with total ERK.

The present invention relates to methods and compositions that provide for the treatment, inhibition, and management of diseases and disorders associated with the expression or overexpression of EphA kinases (e.g., EphA1, EphA2, and EphA3) and/or cell hyperproliferative diseases and disorders. The present invention is based at least in part on the discovery that EphA kinases (e.g., EphA1, EphA2, and EphA3) can function as a tumor suppressor and that activation of EphA kinase (e.g., EphA1, EphA2, and EphA3) can inhibit cancer cell growth, migration and/or proliferation in, for example, prostate cancer, breast cancer, colorectal cancer, skin cancer, and lung cancer.

A particular aspect of the invention relates to methods and therapeutic agents or compositions containing compounds that inhibit cancer cell proliferation, invasion, and survival, particularly those cancer cells that overexpress EphA kinase or cancer cells that have a hyperactive Ras/Raf/MEK/ERK1/2 and/or PI3/AKT signaling pathway. The therapeutic agents or compounds can comprise agonists of EphA (e.g., EphA1, EphA2, and EphA3). Exemplary agonists of EphA kinase (e.g., EphA1, EphA2, and EphA3) can include peptide and small molecule EphA kinase agonists.

The present invention further relates to methods and therapeutic agents for the treatment, inhibition, or management of metastases of cancers of epithelial cell origin, especially human cancers of the breast, lung, skin, prostate, bladder, and pancreas, and renal cell carcinomas and melanomas. Other aspects of the present invention relate to methods of inhibiting proliferation of cancer cells by suppressing the Ras/Raf/MEK/ERK1/2 signaling pathway with a therapeutic agent in accordance with the present invention. Still other aspects of the present invention relate to methods of inhibiting cancer cell survival by suppressing PI3/AKT signaling pathway with a therapeutic agent in accordance with the present invention.

Further compositions and methods of the invention include other types of active ingredients in combination with the therapeutic agents of the invention. In other embodiments, the methods of the invention are used to treat, prevent or manage other diseases or disorders associated with cell hyperproliferation, for example but not limited to restenosis, inflammation, asthma, chronic obstructive lung diseases, abnormal angiogenesis (particularly in the eyes), psoriasis, etc. The present invention also relates to methods for the treatment, inhibition, and management of cancer or other hyperproliferative cell disorder or disease that has become partially or completely refractory to current or standard cancer treatment, such as chemotherapy, radiation therapy, hormonal therapy, and biological therapy.

In an additional aspect, the invention provides methods of screening for anti-cancer agents, particularly anti-metastatic cancer agents by administering a test agent to the EphA knockout mouse or to a cell isolated from the knockout mouse. The knockout mouse can have germline and somatic cells in which at least one allele of the genomic EphA gene (e.g., EphA1, EphA2, or EphA3 gene) is disrupted. The mouse can be crossed with other knockout mouse where at least one allele of another tumor suppressor gene is disrupted. An exemplary, knockout mouse exhibits increased susceptibility to the formation of tumors as compared to a knockout mouse having germline and somatic cells in which at least one allele of the tumor suppressor gene alone is disrupted. Exemplary tumor suppressor genes include p53, p63, p73, p16, PTEN, Rb, Apc, and Nkx 3.1. In certain aspects, the knockout mouse can have a germline and somatic cells in which at least one allele of the genomic EphA gene (e.g., EphA1, EphA2, or EphA3 gene) is disrupted and a transgene encoding an oncogene is expressed. The transgenic mouse exhibits increased susceptibility to the formation of tumors as compared to a transgenic mouse having expressing the transgene alone. For example, the oncogene encodes T antigen, Myc, and Ras oncoprotein.

In certain aspects, the invention provides a method of assaying for an agonist of EphA kinase (e.g., EphA 1, EphA2, or EphA3), comprising: a) contacting an EphA polypeptide with a test agent; and b) determining whether the agent binds to EphA. Optionally, binding of the agent to EphA kinase is determined by a method selected from the group consisting of yeast two-hybrid assay, solid phase binding assay, fluorescence polarization assay, fluorescence resonance energy transfer (FRET) assay, and ELISA.

In certain aspects, the invention provides a method of assaying for an agonist of EphA kinase (e.g., EphA1, EphA2, or EphA3), comprising: a) contacting an EphA polypeptide with a test agent; and b) determining whether the agent stimulates EphA activity. For example, the agent activates EphA tyrosine phosphorylation. Optionally, EphA tyrosine phosphorylation is determined by an immunoassay.

In certain aspects, the invention provides a method of identifying a therapeutic agent for cancer, comprising identifying an agent selected from the group consisting of: 1) an agent which binds to an EphA receptor protein kinase (e.g., EphA1, EphA2, or EphA3); 2) an agent which stimulates phosphorylation of an EphA receptor protein; 3) an agent which enhances dimerization of an EphA receptor protein; and 4) an agent which enhances binding of an EphA ligand to an EphA receptor protein. Optionally, the agent binds to the ligand-binding domain of EphA receptor protein.

In certain aspects, the present invention provides a crystalline molecule (crystal structure?) comprising an EphA2 ligand binding domain (LBD). In one embodiment, the molecule is an EphA2 protein. In another embodiment, the molecule is an EphA2 LBD. In certain embodiments, the invention provides crystal compositions comprising an EphA2 protein or an EphA2 LBD in the presence or absence of a chemical entity. The invention also provides a method of crystallizing an EphA2 protein or an EphA2 LBD.

The invention further provides a computer comprising a data storage medium which comprises the structure coordinates of a molecule comprising all or part of the EphA2 ligand binding domain (LBD). Such storage medium, when read and utilized by a computer programmed with appropriate software, displays on a computer screen or similar viewing device, a three-dimensional graphical representation of a molecule or molecular complex comprising such ligand binding structure.

The invention provides methods for screening, designing, optimizing, evaluating, and identifying compounds which bind to an EphA2 molecule or its LBD based on the crystal structure. Such compounds can be potential inhibitors (antagonists) or activators (agonists) of EphA2 proteins.

The invention also provides a method for determining at least a portion of the three-dimensional structure of molecules which contain at least some structurally similar features to an EphA2 protein (e.g., EphA2 LBD). This is achieved by using at least some of the structure coordinates obtained from the EphA2 protein as described herein.

I. EphA Polypeptides and Nucleic Acids

In certain aspects, wildtype or variant EphA polypeptides are used as a target for screening or selecting agonists of EphA. Exemplary EphA polypeptides can comprise EphA1, EphA2, or EphA3. EphA1, EphA2, or EphA3 in accordance with the present invention can have amino sequences substantially similar to native mammalian or wild type EphA1, EphA2, or EphA3. For example, EphA1, EphA2, or EphA3 can have amino sequences substantially similar to, respectively, SEQ ID NO: 4, SEQ ID NO: 5, SEQ ID NO: 6.

The EphA1, EphA2, EphA3 polypeptides of the present invention can also be a variant of native mammalian or wild-type EphA1, EphA2, or EphA3, such as a fragment, analog and derivative of mammalian EphA1, EphA2, or EphA3. Such variants can include, for example, a polypeptide encoded by a naturally occurring allelic variant of a native EphA1, EphA2, or EphA3 gene (i.e., a naturally occurring nucleic acid that encodes a naturally occurring mammalian EphA1, EphA2, or EphA3), a polypeptide encoded by an alternative splice form of a native EphA1, EphA2, or EphA3 gene, a polypeptide encoded by a homolog or ortholog of a native Eph-A1, EphA2, or EphA3 gene, and a polypeptide encoded by a non-naturally occurring variant of a native EphA1, EphA2, or EphA3 gene.

EphA1, EphA2, or EphA3 variants can have a peptide (or amino acid) sequence that differs from native EphA1, EphA2, or EphA3 in one or more amino acids. The peptide sequence of such variants can feature a deletion, addition, or substitution of one or more amino acids of EphA1, EphA2, or EphA3 protein. Amino acid insertions are preferably of about 1 to 4 contiguous amino acids, and deletions are preferably of about 1 to 10 contiguous amino acids. Variant EphA1, EphA2, or EphA3 proteins substantially maintain a native EphA1, EphA2, or EphA3 protein functional activity. Exemplary, EphA1, EphA2, or EphA3 variants can be made by expressing nucleic acid molecules within the invention that feature silent or conservative changes.

In accordance with an aspect of the invention, variant polypeptides have an amino acid sequence that is at least 75% identical to an amino acid sequence as set forth in SEQ ID NO: 4, SEQ ID NO: 5, or SEQ ID NO: 6. In other aspects, the variant polypeptide has an amino acid sequence at least 80%, 85%, 90%, 95%, 97%, 98%, 99% or 100% identical to an amino acid sequence as set forth in SEQ ID NO: 4, SEQ ID NO: 5, or SEQ ID NO: 6.

EphA1, EphA2, or EphA3 fragments corresponding to one or more particular motifs and/or domains or to arbitrary sizes, are within the scope of the present invention. Isolated peptidyl portions of EphA1, EphA2, or EphA3 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a EphA1, EphA2, or EphA3 polypeptide of the present invention may be arbitrarily divided into fragments of desired length with no overlap of the fragments, or preferably divided into overlapping fragments of a desired length. The fragments can be produced recombinantly and tested to identify those peptidyl fragments which can function as agonists of a native EphA1, EphA2, or EphA3.

Variants of EphA1, EphA2, or EphA3 polypeptide can also include recombinant forms of the proteins. Recombinant polypeptides of the present invention, in addition to a EphA1, EphA2, or EphA3, are encoded by a nucleic acid that can have at least 85% sequence identity with the nucleic acid sequence of a gene encoding a mammalian protein. EphA1, EphA2, or EphA3 polypeptides variants can include agonistic forms of the polypeptide that constitutively express the functional activities of a native EphA1, EphA2, or EphA3. Other variants can include those that are resistant to proteolytic cleavage, as for example, due to mutations, which alter protease target sequences. Whether a change in the amino acid sequence of a peptide results in a variant having one or more functional activities of a native EphA1, EphA2, or EphA3 can be readily determined by testing the variant for a native EphA1, EphA2, or EphA3 protein functional activity.

In certain aspects, the application provides various domains or fragments of the EphA2 polypeptide, such as a ligand-binding domain (LBD) of an EphA2 polypeptide. In one embodiment, the application relates to an EphA2 LBD (SEQ ID NO: 7), and variant polypeptides thereof. In certain embodiments, variant polypeptides have an amino acid sequence that is at least 75% identical to an amino acid sequence as set forth in SEQ ID NO: 7. In other embodiments, the variant polypeptide has an amino acid sequence at least 80%, 85%, 90%, 95%, 97%, 98%, 99% or 100% identical to an amino acid sequence as set forth in SEQ ID NO: 7.

In certain aspects, the application provides fusion polypeptides comprising an EphA polypeptide (e.g., EphA1, EphA2, or EphA3) or a domain thereof and a second domain. The second domain may comprise one or more fusion domains. In another aspect, the fusion protein can comprise an EphA polypeptide or a domain thereof and a second domain selected from the group consisting of a dimerizing polypeptide, a purification polypeptide, a stabilizing polypeptide, and a targeting polypeptide. Well known examples of such fusion domains include, for example, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion polypeptide by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. Another fusion domain well known in the art is green fluorescent protein (GFP). This fusion partner serves as a fluorescent "tag" which allows the fusion polypeptide of the invention to be identified by fluorescence microscopy or by flow cytometry. Fusion domains also include "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allow the relevant protease to partially digest the fusion EphA polypeptide (e.g., EphA1, EphA2, or EphA3) and thereby liberate the recombinant polypeptide therefrom. The liberated polypeptide can then be isolated from the fusion partner by subsequent chromatographic separation.

In certain aspects, this application relates to a fusion protein comprising an EphA polypeptide or a domain thereof and an immunoglobulin element. In certain embodiments, the an EphA polypeptide or a domain thereof comprises extracellular portions of the EphA polypeptide.

In certain aspects, the application relates to a fusion protein comprising an EphA2 polypeptide or a domain thereof and an immunoglobulin element, wherein the immunoglobulin element comprises an immunoglobulin heavy chain. In certain embodiments, the immunoglobulin element comprises an Fc domain. In certain instances, the immunoglobulin heavy chain is selected from the group consisting of an IgM, IgD, IgE, and IgA heavy chains. In further aspects, the immunoglobulin heavy chain is selected from the group consisting of an IgG1, IgG2β, IgG2α, and IgG3 heavy chains. The immunoglobulin element may comprise the CH1 and Fc domains in certain embodiments. In certain instances, the immunoglobulin element comprises a CH1 domain of a first immunoglobulin class and a CH1 domain of a second immunoglobulin class, wherein the first and second immunoglobulin classes are not the same.

In additional embodiments, the present application relates to a fusion protein comprising a EphA polypeptide (e.g., EphA1, EphA2, or EphA3) or a domain thereof and an immunoglobulin element, further comprising a dimerizing polypeptide.

In certain embodiments, the application also relates to a composition comprising a fusion protein of the invention and a pharmaceutically acceptable carrier.

In certain embodiments, the dimerizing polypeptide comprises an amphiphilic polypeptide. The amphiphilic polypeptide may comprise up to 50 amino acids, up to 30 amino acids, up to 20 amino acids, or up to 10 amino acids. In certain embodiments, the dimerizing polypeptide comprises a peptide helix bundle. In certain embodiments, the dimerizing polypeptide comprises a leucine zipper. The leucine zipper may be a jun zipper or a fos zipper. In certain embodiments, the dimerizing polypeptide comprises a polypeptide having positively or negatively charged residues wherein said polypeptide binds to another peptide bearing opposite charges.

In further embodiments, the application relates to a fusion protein comprising an amino acid sequence that is at least 90% identical to the amino acid sequence of SEQ ID NO:7. In certain aspects, the application relates to a nucleic acid sequence encoding a polypeptide fusion comprising an EphA polypeptide or a domain thereof and an immunoglobulin element. In certain embodiments, the application relates to a nucleic acid sequence encoding a polypeptide at least 90% identical to the amino acid sequence set forth in SEQ ID NO:7. In additional embodiments, the application relates to a nucleic acid sequence encoding an EphA polypeptide or a domain thereof polypeptide comprising one or more point mutations wherein said point mutations increase the binding affinity of said an EphA polypeptide or a domain thereof.

In other aspects, the invention relates to a nucleic acids encoding EphA polypeptides or variants thereof, such as nucleic acids encoding EphA1, EphA2, EphA3, or EphA2 LBD (e.g., SEQ ID NO: 4, SEQ ID NO: 5, SEQ ID NO: 6, and SEQ ID NO: 7). Nucleic acids that encode EphA1, EphA2, EphA3, or EphA2 can be a native or non-native nucleic acid and be in the form of RNA or in the form of DNA (e.g. cDNA, genomic DNA, and synthetic DNA). The DNA can be double-stranded or single-stranded, and if single-stranded may be the coding (sense) strand or non-coding (anti-sense) strand. For example, nucleic acid molecules that encode the EphA1, EphA2, EphA3, or EphA2 LBD can have sequences substantially similar to, respectively, SEQ ID NO: 8, SEQ ID NO: 9, SEQ ID NO: 10, and SEQ ID NO: 11.

Other nucleic acid molecules that encode EphA1, EphA2, EphA3, or EphA2 LBD within the invention can be variants of a native EphA1, EphA2, EphA3, or EphA2 LBD gene, such as those that encode fragments, analogs and derivatives of a native EphA1, EphA2, EphA3, or EphA2 LBD polypeptides. Such variants may be, for example, a naturally occurring allelic variant of a native EphA1, EphA2, EphA3, or EphA2 LBD gene, a homolog of a native EphA1, EphA2. EphA3, or EphA2 LBD gene, or a non-naturally occurring variant of a native EphA1, EphA2, EphA3, or EphA2 LBD gene. These variants have a nucleotide sequence that differs from a native EphA1, EphA2, EphA3, or EphA2 LBD gene in one or more bases. For example, the nucleotide sequence of such variants can feature a deletion, addition, or substitution of one or more nucleotides of a native EphA1, EphA2, EphA3, or EphA2 LBD gene. Nucleic acid insertions are preferably of about 1 to 10 contiguous nucleotides, and deletions are preferably of about 1 to 10 contiguous nucleotides.

In other aspects, EphA nucleotide sequences also include nucleotide sequences that will hybridize under highly stringent conditions to the nucleotide sequences designated in SEQ ID NO: 8, SEQ ID NO: 9, SEQ ID NO: 10, and SEQ ID NO: 11, or fragments thereof. One of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

In further embodiments, the EphA nucleotide sequences of the invention can be isolated, recombinant, and/or fused with a heterologous nucleotide sequence, or in a DNA library.

In yet other embodiments, the application provides dimers and/or multimeric forms of the EphA polypeptide and domains thereof. Multimeric forms of the EphA2 include: dimers, trimers, tetramers, pentamers and hexamers.

II. Crystallizable Compositions and Crystals of EphA2 Polypeptides

According to one aspect, the invention provides a crystallizable composition or crystal comprising an EphA2 polypeptide, such as an EphA2 ligand binding domain (LBD) in the presence or absence of a chemical entity. The ligand binding domain may be complexed or uncomplexed with a ligand or a compound. The EphA2 protein may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In a preferred embodiment, the protein is overexpressed in an *E. coli* system or a baculovirus system.

The invention also provides a method of making crystals of EphA2 protein (e.g., an EphA2 LBD) in the presence or absence of a chemical entity. Such methods comprise the steps of: a) producing and purifying EphA2 protein: b) combining said EphA2 protein, or a homologue thereof in the presence or absence of a chemical entity with a crystallization solution to produce a crystallizable composition; and c) subjecting said crystallizable composition to conditions which promote crystallization. The crystallization solution may include, but is not limited to, polyethylene glycol (PEG) at between about 10% to 30% v/v, 100-300 mM ammonium sulphate and a buffer that maintains pH at between about 4.0 and 8. In one embodiment, the crystallization solution comprises 25% PEG 3350, 50 mM 2-(N-morpholino) ethanesulfonic acid (MES) at pH 6.0 and 200 mM ammonium sulphate.

By way of example, the crystallizable composition comprises unphosphorylated Aurora-2 protein kinase domain, 25% PEG 3350, 50 mM 2-(Nmorpholino)ethanesulfonic acid (MES) at pH 6.0, and 200 mM ammonium sulphate. In a more preferred embodiment, the crystallizable composition comprises unphosphorylated Aurora-2 protein kinase domain, 25% PEG 3350, 50 mM 2-(Nmorpholino)ethanesulfonic acid (MES) at pH 6 or 200 mM ammonium sulphate and a chemical entity selected from the group consisting of an inhibitor and substrate analogue.

Devices for promoting crystallization can include but are not limited to the hanging-drop, sitting-drop, sandwich-drop, dialysis, microbatch or microtube batch devices (see. e.g., U.S. Pat. Nos. 4,886,646, 5,096,676, 5,130,105, 5,221,410, and 5,400,741 herein incorporated by reference in their entirety). The hanging-drop, sitting-drop and some adaptations of the microbatch methods produce crystals by vapor diffusion. The hanging drop and sitting drop containing the crystallizable composition is equilibrated against a reservoir containing a higher or lower concentration of precipitant. As the drop approaches equilibrium with the reservoir, the saturation of protein in the solution leads to the formation of crystals. Other methods of making crystals of proteins can be found in, for example, U.S. Pat. No. 6,090,609, PCT publication Nos. WO 04/060310, WO 03/092607, and WO 03/022877 (incorporated herein by reference, in their entirety).

It would be appreciated that one can vary the crystallization conditions to identify other crystallization conditions that would produce crystals of EphA2 proteins in the presence or absence of a chemical entity. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brji 30 (4 lauryl ether)), sugars (e.g., glucose, maltose), organic compounds (e.g., dioxane, dimethylformamide), lanthanide ions, or polyionic compounds that aid in crystallizations. High throughput crystallization assays may also be used to assist in finding or optimizing the crystallization condition.

It will also be appreciated that a set of structure coordinates for a molecule or a or a portion thereof, is a relative set of points that define a shape in three dimensions. Thus, it is possible that an entirely different set of coordinates could define a similar or identical shape. Moreover, slight variations in the individual coordinates will have little effect on overall shape. The variations in coordinates may be generated as a result of mathematical manipulations of the EphA2 structure coordinates. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention.

According to another embodiment, this invention provided a machine-readable data storage medium, comprising a data storage material encoded with machine-readable data, Wherein said data defines the above-mentioned EphA2 molecules. In one embodiment, the data defines the above-mentioned EphA2 LBD by comprising the structure coordinates of said amino acid residues according to any one of Table 1.

In order to use the structural coordinates generated for a crystalline substance of this invention, e.g., the structural coordinates shown in Table 1 of the EphA2 LBD (SEQ ID NO: 7), it is often necessary or desirable to display them as, or convert them to, graphical representation, such as a three-dimensional shape, or to otherwise manipulate them. This is typically accomplished by the use of commercially available software such as a program which is capable of generating three-dimensional graphical representations of molecules or portions thereof from a set of structural coordinates.

By way of illustration, a non-exclusive list of computer programs for viewing or otherwise manipulating protein structures include the following: Midas (University of California, San Francisco); MidasPlus (University of California, San Francisco); MOIL (University of Illinois); Yummie (Yale University); Sybyl (Tripos, Inc.); Insight/Discover (Biosym Technologies); MacroModel (Columbia University); Quanta (Molecular Simulations, Inc.); Cerius (Molucular Simulations, Inc.); Alchemy (Tripos, Inc.); LabVision (Tripos, Inc.); Rasmol (Glaxo Research and Development); Ribbon (University of Alabama); NAOMI (Oxford University); Explorer Eyechem (Silicon Graphics, Inc.); Univision (Cray Research); Molscript (Uppsala University); Chem-3D (Cambridge Scientific); Chain (Baylor College of Medicine); 0 (Uppsala University); GRASP (Columbia University); X-Plor (Molecular Simulations, Inc.; Yale University); Spartan (Wavefunction, Inc.); Catalyst (Molecular Simulations, Inc.); Molcadd (Tripos. Inc.); VMD (University of Illinois/Beckman Institute); Sculpt (Interactive Simulations, Inc.): Procheck (Brookhaven National Laboratory): DGEOM (QCPE); RE VIEW (Brunel University); Modeller (Birbeck College, University of London); Xmol (Minnesota Supercomputing Center); Protein Expert (Cambridge Scientific); HyperChem (Hypercube); MD Display (University of Washington); PKB (National Center for Biotechnology Information, NIH); ChemX (Chemical Design, Ltd.); Cameleon (Oxford Molecular, Inc.); Iditis (Oxford Molecular, Inc.).

Therefore, according to another embodiment, this invention provides a machine-readable data storage medium comprising a data storage material encoded with machine readable data. In one embodiment, a machine programmed with instructions for using said data, is capable of generating a three-dimensional structure of the EphA2 molecules that are described herein.

This invention also provides a computer comprising: (a) a machine-readable data storage medium comprising a data storage material encoded with machine-readable data, wherein said data defines an EphA2 molecule; (b) a working memory for storing instructions for processing said machine-readable data; (c) a central processing unit (CPU) coupled to said working memory and to said machine-readable data storage medium for processing said machine readable data and means for generating three-dimensional structural information of said molecule; and (d) output hardware coupled to said central processing unit for outputting three-dimensional structural information of said molecule, or information produced using said three-dimensional structural information of said molecule.

The availability of the three-dimensional structure of EphA2 makes structure-based drug discovery approaches possible. Structure-based approaches include de Novo molecular design, computer-aided optimization of lead molecules, and computer-based selection of candidate drug structures based on structural criteria. New peptidomimetic modules may be developed directly from the structure of a peptide ligand by design or database searches for conformationally-restricted peptide replacements. Alternatively, structure-based lead discovery may be accomplished using the target protein structure stripped of its ligand. Multiple uncomplexed states of EphA2 can be generated by several methods to provide additional target conformations. The experimental coordinates and the resulting uncomplexed models can be subjected to techniques, such as receptor site mapping to identify sites of favorable interaction energies between the structure of the target protein and potential ligands or chemical moieties ("fragments" or "seeds"). Such evaluation may be followed by procedures such as fragment seed linking and growth. Fragment seed linking refers to methods for designing structures that contain "linked" "seeds", i.e. chemical structures comprising two or more of the mapped moieties appropriately spaced to reach the respective sites of favorable interactions. Growth refers to the design of structures which extend, based on receptor site mapping or to fill available space, a given molecule or moiety. Based on the receptor site mapping data, one may also select potential ligands from databases of chemical structures. Potential ligands, or suboptimal ligands, of whatever source, can be refined by using the receptor site maps to filter multiple ligand conformations and orientations according to energetic preferences.

Receptor site mapping encompasses a variety of computational procedures that identify energetically favorable binding sites on macromolecules. The most straightforward procedures involve "painting" a solvent-accessible surface (or an otherwise generated cast) of the macromolecular target according to empirically determined physical properties, such as electrostatic or lipophilic potential, degree of curvature, and hydrogen-bonding character. Such methods for thus characterizing the surface of a macromolecule are incorporated in programs such as Grasp (Columbia University), DelPhi (Biosym Technologies), MOLCAD (Tripos, Inc.), and Hint (Virginia Commonwealth University). Subsequent molecule design involves identification or design of ligands that possess features complimentarity to the identified surface characteristics. More advanced algorithms involve the actual calculation of interaction enthalpies between the target and potential ligands or fragments. In practice, the coordinates of the protein or protein fragment of interest (which may be rotated or otherwise transformed) are stripped of any undesired ligand (or portion thereof) and/or of any undesired solvent molecules. The coordinates are then processed to attach molecular mechanics parameters to the atomic positions to provide a processed target for mapping. The target may be partitioned into discrete binding sites. The target or partitioned sites thereof are flooded with given functional group fragments that are subsequently allowed to relax into desired locations, as in the program MCSS (Molecular Simulations, Inc.), or are encased within a regular lattice of site points on which single fragment probes are positioned sequentially; examples of programs that exploit the site-lattice algorithm include Grin/Grid (Molecular Discovery, Ltd.), Ludi (Biosym Technologies), Leapfrog (Tripos, Inc.), and Legend (University of Tokyo). In both techniques, the enthalpic contribution to binding affinity is estimated with a molecular mechanics force-field, and appropriate positions of selected functional groups are determined systematically.

In the site-lattice approach, a box is defined enclosing a desired portion of the target within a defined lattice. The lattice resolution, i.e., the distance between lattice points, may be defined by the practitioner or may be set by the computer program. Likewise, other parameters of points within the lattice, such as hydrophobicity or other characteristics, may be similarly defined. Probes (i.e. computer models) of one or more selected moieties, functional groups, molecules or molecular fragments are positioned at lattice points and the interaction energy of the probe-target pair is determined for each such lattice point. The data for each selected moiety, functional group, etc. is collected and may be recovered as a data set, visualized on a computer monitor or printed out in various text or graphic formats As an alternative to positioning a moiety at each of a set of lattice points, one may, as previously mentioned, flood the target (defined by the coordinates as described above) with multiple copies of a selected fragment, moiety, molecule, etc. by superimposing the multiple copies into the vicinity of the protein target. The model is then subjected to group minimization (i.e., molecular mechanics minimization) calculations to identify points or areas of favorable interaction. Data may be handled as in the lattice approach.

Receptor site maps provide the seeds for ligand evolution via Database searches and for Grow/link methods for de Novo design of new chemical entities. Programs for ligand growth first access extensible fragment dictionaries in order to place appropriate functional groups at site points. A genetic algorithm or a subgraph isomorphism protocol is then invoked to connect the fragments with small aliphatic chains or rings. Stochastic enhancements may be introduced by modification of internal degrees of freedom as well as translation and rotation of the candidate model within the binding cavity. The resulting sets of molecules are scored and filtered by functions that consider the steric constraints of the binding site, the complimentarity of electrostatic and hydrophobic interactions, and a solvation estimate. Programs of this type that could be applied for the design of new ligands for ZAP-NC (SEQ ID NO: 38) include Ludi (Biosym Technologies), Leapfrog (Tripos, Inc.), Legend (University of Tokyo), Grow (Upjohn), Builder/Delegate (University of California, San Francisco), and Sprout (University of Leeds). Clique detection methods provide an alternative strategy to site mapping and ligand growth. DOCK (University of California, San Francisco) and similar programs fill a given binding site with the smallest set of atom-sized spheres possible; a database search then attempts to orient ligands such that the atoms superimpose onto the centers (or "nuclei") of the site-tilling spheres. The shape complimentarity is augmented by scoring functions that include the steric requirements of the cavity and a potential energy function.

Optimization of ligands (from any source) may be enhanced using the three dimensional structural of EphA2. Use of receptor site maps of EphA2 may be used to identify preferred positions for functional group components of ligands, and can be used to filter or constrain conformational searches of ligand structures which would otherwise typically be controlled by minimal steric considerations of the ligand structures themselves. The availability of an explicit binding site also permits one to determine the mode of ligand binding to the target protein via methods that utilize force-fields directly in simulated annealing, distance geometry, Metropolis Monte Carlo, or stochastic searches for binding modes. Examples of programs that can be applied to rationalize ligand binding to EphA2 include Autodock (Scripps Clinic), DGEOM (QCPE #590), Sculpt (interactive Simulations, Inc.), or any of the molecular dynamics programs described above. Once a tractable set of possible binding orientations is obtained, one can readily identify the appropriate mode of binding through modifications in test ligands designed to alter in a predictable fashion the binding affinity of each model under consideration. For instance, a ligand may be modified to contain a functional group at a position which is inconsistent with one binding model, yet consistent with another model. Binding data can then be used to weed out "disproven" models. Once iterative weeding of unlikely binding modes generates an appropriate model, possibilities for improvement of the lead become readily apparent from the local protein environment.

An alternative protocol for ligand optimization involves 3D database searching in conjunction with knowledge of the binding site. Modeling can reveal multiple candidates for the bioactive conformation of a given ligand. A probe for the correct conformation can include a 3D search to identify several constrained mimics of each possible conformer. Structure-activity relationships of the unconstrained ligand would suggest which functional groups should be retained in the constrained mimics. Finally, the steric and electrostatic requirements of the binding site could constitute a filter for prioritizing the resultant possibilities.

III. EphA Therapeutic Agents

As used herein, the term "Eph-A therapeutic agent" is a generic term which include any compound (agent) which regulates signaling through the EphA pathway. This compound can also suppress or inhibit signaling of the PI3/AKT pathway and/or MAPK/ERK1/2 pathway. Exemplary, EphA therapeutic agents can be used for treating cancer (tumor). In certain embodiments, EphA therapeutic agent can activate function of EphA (e.g., EphA1, EphA2, or EphA3), enhance the interaction of an EphA ligand (e.g., ephrin A1 and ephrin A5) and EphA (e.g., EphA1, EphA2, or EphA3), activate the phosphorylation of EphA (e.g., EphA1, EphA2, or EphA3), enhance dimerization of EphA (e.g., EphA1, EphA2, or EphA3), or activate any of the downstream signaling events upon binding of an EphA ligand (e.g., ephrin A1 and ephrin A5) to EphA (e.g., EphA1, EphA2, or EphA3). For example, the EphA therapeutic agents can be capable of binding to an EphA2 polypeptide (e.g., the ligand-binding domain of an EphA2 polypeptide) and function as EphA2 ligands.

Generally, the EphA therapeutic agents include any substances that act as agonists of EphA. Such EphA therapeutic agents include, but are not limited to, a protein, a peptide, a small organic molecule, a peptidomimetic, an antibody, and a nucleic acid. In an aspect of the invention, these substances can comprise exogenous or non-native peptides or small molecules that have a molecular weight of about 50 daltons to about 2,500 daltons.

In certain specific aspects, the EphA therapeutic agents of the present invention include a peptide, such as those which activate EphA kinase function. These peptides are also referred to herein as EphA agonistic or binding peptides. These agonistic peptides can specifically target the ligand-binding domain of EphA kinase. Optionally, these peptides can activate EphA kinases (EphA1, EphA2 and EphA3) and suppress AKT kinase and/or MAPK/ERK1/2 kinase.

In one aspect, EphA1-, EphA2-, or EphA3-agonistic peptides in accordance with the present invention can have amino sequences or structures substantially similar to native mammalian or wild type ephrins. For example, ephrin-A1 and ephrin-B2 can have amino sequences substantially similar to, respectively, SEQ ID NO: 12 and SEQ ID NO: 13.

The agonistic peptides of EphA1, EphA2, or EphA3 of the present invention can also be a variant of native mammalian or wildtype ephrins, such as a fragment, analog and derivative of mammalian ephrin-As and ephrin-Bs. Such variants can include, for example, a polypeptide encoded by a naturally occurring allelic variant of a native ephrin gene (i.e., a naturally occurring nucleic acid that encodes a naturally occurring mammalian ephrins), a polypeptide encoded by an alternative splice form of a native ephrins gene, a polypeptide encoded by a homolog or ortholog of a native ephrin gene, and a polypeptide encoded by a non-naturally occurring variant of a native ephrin gene.

EphA1-, EphA2-, or EphA3-agonistic peptides can have a peptide (or amino acid) sequence that differs from native ephrins in one or more amino acids. The peptide sequence of such variants can feature a deletion, addition, or substitution of one or more amino acids of ephrin protein. Amino acid insertions are preferably of about 1 to 4 contiguous amino acids, and deletions are preferably of about 1 to 10 contiguous amino acids. Variant EphA1-, EphA2-, or EphA3-binding peptides substantially maintain a native ephrin protein functional activity. Exemplary, EphA1-, EphA2-, or EphA3-binding peptides can be made by expressing nucleic acid molecules within the invention that feature silent or conservative changes.

In accordance with an aspect of the invention, variant EphA1-, EphA2-, or EphA3-agonistic peptides can have an amino acid sequence that is at least 40% identical to an amino acid sequence as set forth in SEQ ID NO: 12 and SEQ ID NO: 13. In other aspects, the variant EphA1-, EphA2-, or EphA3-agonistic peptides has an amino acid sequence at least 40%, 50%, 60%, 70/0/, 80%, 85%, 90%, 95%, 97%, 98%, 99% or 100% identical to an amino acid sequence as set forth in SEQ ID NO: 12 and 13.

Ephrin fragments corresponding to one or more particular motifs and/or domains or to arbitrary sizes, are within the scope of the present invention. Isolated peptidyl portions of ephrin proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a EphA1, EphA2, or EphA3 agonistic peptide of the present invention may be arbitrarily divided into fragments of desired length with no overlap of the fragments, or preferably divided into overlapping fragments of a desired length. The fragments can be produced recombinantly and tested to identify those peptidyl fragments which can function as agonists of a native EphA1, EphA2, or EphA3 receptors.

Variants of ephrin polypeptide can also include recombinant forms of the proteins. Recombinant polypeptides of the present invention, in addition to ephrin-A1, and ephrin-B2, are encoded by a nucleic acid that can have at least 85% sequence identity with the nucleic acid sequence of a gene encoding a mammalian protein. Ephrin polypeptide variants can include agonistic forms of the polypeptide that constitutively express the functional activities of a native ephrins. Other variants can include those that are resistant to proteolytic cleavage, as for example, due to mutations, which alter protease target sequences. Whether a change in the amino acid sequence of a peptide results in a variant having one or more functional activities of a native ephrin can be readily determined by testing the variant for a native ephrin protein functional activity.

In certain aspects, the EphA1-, EphA2-, or EphA3-agonistic peptides can comprise fusion polypeptides including an EphA binding peptide or a domain thereof and a second domain. The second domain may comprise one or more fusion domains. In another aspect, the fusion protein can comprise an EphA binding polypeptide or a domain thereof and a second domain selected from the group consisting of a dimerizing polypeptide, a purification polypeptide, a stabilizing polypeptide, and a targeting polypeptide.

In certain aspects, the EphA1-, EphA2-, or EphA3-agonistic peptides can include a fusion protein comprising an EphA-binding polypeptide or a domain thereof and an immunoglobulin element. In certain embodiments, the an EphA-binding polypeptide or a domain thereof comprises extracellular portions of the ephrin-A polypeptide.

In certain aspects, the EphA1-, EphA2-, or EphA3-agonistic peptides can include a fusion protein comprising an EphA-agonistic peptide or a domain thereof and an immunoglobulin element wherein the immunoglobulin element comprises an immunoglobulin heavy chain. In certain embodiments, the immunoglobulin element comprises an Fc domain. In certain instances, the immunoglobulin heavy chain is selected from the group consisting of an IgM, IgD, IgE, and IgA heavy chains. In further aspects, the immunoglobulin heavy chain is selected from the group consisting of an IgG1, IgG2β, IgG2α, and IgG3 hearty chains. The immunoglobulin element may comprise the CH1 and Fc domains in certain embodiments. In certain instances, the immunoglobulin element comprises a CH1 domain of a first immunoglobulin class and a CH1 domain of a second immunoglobulin class, wherein the first and second immunoglobulin classes are not the same.

In additional embodiments, the present application relates to a fusion protein comprising a polypeptide that binds to EphA kinases (e.g., EphA1, EphA2, or EphA3) or a domain thereof and an immunoglobulin element, further comprising a dimerizing polypeptide.

In certain embodiments, the application also relates to a composition comprising a fusion protein of the invention and a pharmaceutically acceptable carrier.

In certain embodiments, the dimerizing polypeptide comprises an amphiphilic polypeptide. The amphiphilic polypeptide may comprise up to 50 amino acids, up to 30 amino acids, up to 20 amino acids, or up to 10 amino acids. In certain embodiments, the dimerizing polypeptide comprises a peptide helix bundle. In certain embodiments, the dimerizing polypeptide comprises a leucine zipper. The leucine zipper may be a jun zipper or a fos zipper. In certain embodiments, the dimerizing polypeptide comprises a polypeptide having positively or negatively charged residues wherein said polypeptide binds to another peptide bearing opposite charges.

In further embodiments, the application relates to a fusion protein comprising an amino acid sequence that is at least 90% identical to the amino acid sequence of SEQ ID NO: 12 and SEQ ID NO: 13. In certain aspects, the application relates to a nucleic acid sequence encoding a polypeptide fusion comprising an EphA binding peptide or a domain thereof and an immunoglobulin element. In certain embodiments, the application relates to a nucleic acid sequence encoding a polypeptide at least 90% identical to the amino acid sequence set forth in SEQ ID NO: 12 or SEQ ID NO: 2. In additional embodiments, the application relates to a nucleic acid sequence encoding an EphA polypeptide or a domain thereof polypeptide comprising one or more point mutations wherein said point mutations increase the binding affinity of said an EphA polypeptide or a domain thereof.

In another aspect, the EphA agonistic peptides can comprise about 4 to about 20 amino acids and have a molecular weight of about 600 daltons to about 2,500 daltons. The EphA agonistic peptides include, but are not limited to, EP1 (SEQ ID NO: 1), EP2 (SEQ ID NO: 2), and EP3 (SEQ ID NO: 3). In certain embodiments, an EphA agonistic peptide has an amino acid sequence that is at least 80% identical to an amino acid sequence as set forth in SEQ ID NO: 1, 2 or 3. In certain cases, the functional variant has an amino acid sequence at least 40%, 50%, 60%, 70%, 85%, 90%, 95%, 97%, 98%, 99% or 100% identical to an amino acid sequence as set forth in SEQ ID NO: 1, 2 or 3.

In certain embodiments, the present invention contemplates making functional variants by modifying the structure of an EphA agonistic peptide for such purposes as enhancing therapeutic efficacy, or stability (e.g., ex vivo shelf life and resistance to proteolytic degradation in vivo). Modified EphA agonistic peptides can be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an EphA agonistic peptide results in a functional homolog can be readily determined by assessing the ability of the variant EphA agonistic peptide to produce a response in cells in a fashion similar to the wild-type EphA agonistic peptide.

The present invention further contemplates a method of generating mutants, particularly sets of combinatorial mutants of the EphA agonistic peptides, as well as truncation mutants; pools of combinatorial mutants are especially useful for identifying functional variant sequences. The purpose of screening such combinatorial libraries may be to generate, for example, peptide variants which can act as either agonists or antagonist of EphA, or alternatively, which possess novel activities all together. A variety of screening assays are provided below, and such assays may be used to evaluate variants. For example, an EphA2 agonistic peptide variant may be screened for its ability to bind to an EphA2 polypeptide (full-length EphA2 or the LBD of EphA2) or for its ability to enhance binding of an EphA2 ligand to a cell expressing an EphA2 receptor. Optionally, an EphA agonistic peptide variant may be screened for its binding to EphA (full-length EphA or the LBD of EphA) with high affinity and specificity.

In other aspects, the EphA therapeutic agents of the present invention include a small molecule compound, such as those which activate EphA kinase function as well as those that suppress AKT kinase function and MAPK/ERK1/2 function. These small molecule compounds are also referred to herein as EphA agonistic compounds. Optionally, these agonistic compounds specifically target the ligand-binding domain of EphA kinase.

Exemplary, the EphA agonistic compounds include, but are not limited to compounds, such as dobutamine, labetalol, doxazosin, and (di-meo-isoquinolin-1-ylmethyl)-et-di-meo-pyrido(2,1-a)isoquinolin, hydrobromide S120103 shown in FIGS. 28-32.

One aspect of the invention relates to a small molecule compound of Formula (I)

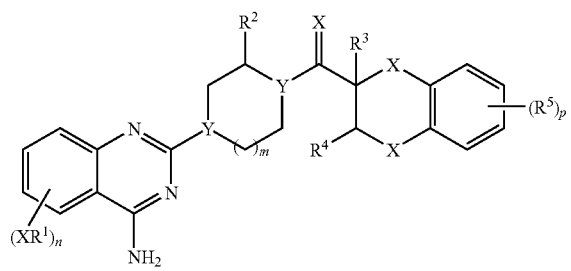

(I)

wherein $R^1$ is selected from H, $C_{1-6}$alkyl, $C_{1-6}$aralkyl, $C_{1-6}$alkanoyl, aryl, heterocyclyl, $C_{1-6}$heterocyclylalkyl, $C_{1-6}$carbocyclylalkyl, and carbocyclyl, or two occurrences of $R^1$ together are $C_{1-6}$alkyl, thereby forming a ring;

$R^2$, $R^3$, and $R^4$ are independently selected from H, $C_{1-6}$alkyl, $C_{1-6}$aralkyl, $C_{1-6}$heterocyclylalkyl, and $C_{1-6}$carbocyclylalkyl, preferably $R^2$, $R^3$, and $R^4$ are independently selected from H and $C_{1-6}$alkyl;

$R^5$ is selected from $C_{1-6}$alkyl, $C_{1-6}$alkoxy, halogen, $C_{1-6}$alkanoyl, $C_{1-6}$alkoxycarbonyl, $C(O)N(R^6)(R^7)$, and $SO_2N(R^6)(R^7)$;

$R^6$ and $R^7$ are independently selected from H and $C_{1-6}$alkyl;

X is selected from $CH_2$, NH, and O;

each Y is independently selected from CH and N;

m is an integer from 1 to 2;

n is an integer from 1 to 3; and p is an integer from 0 to 3.

In certain embodiments, $R^1$ is selected from H and $C_{1-6}$alkyl, X is O, and n is an integer from 1 to 3. In preferred embodiments, n is 2, X is O, and $R^1$ is $C_{1-6}$alkyl. In other embodiments, n is 2, X is O, $R^1$ is methyl, and the substituents are located at the 3- and 4-positions of the aromatic ring.

In certain embodiments, $R^2$, $R^3$, and $R^4$ are independently selected H and $C_{1-6}$ lower alkyl. In still other embodiments, $R^2$, $R^3$, and $R^4$ are all H.

In certain embodiments, m is 1 and each Y is independently selected from CH and N. In preferred embodiments, m is 1 and each occurrence of Y is N.

Another aspect of the invention relates to a compound comprising at least one aryl or heteroaryl ring. In other such embodiments, candidate compounds comprise two aryl or heteroaryl rings connected by a linker that is 5-10 atoms in length. In still other embodiments, candidate compounds have a structure of Formula (II)

A-L-B (II)

wherein

A and B are independently selected from aryl and heteroaryl; and

L is selected from $C_{1-12}$alkyl and —$C_{1-6}$alkyl-amino-$C_{1-6}$alkyl-.

In certain embodiments, candidate compounds have a structure of Formula (III)

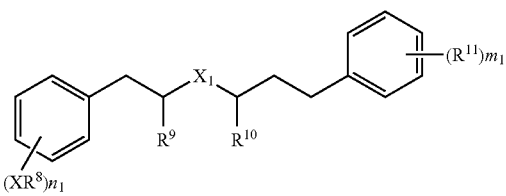

(III)

wherein $R^8$ is selected from H, $C_{1-6}$alkyl, $C_{1-6}$aralkyl, $C_{1-6}$alkanoyl, aryl, heterocyclyl, $C_{1-6}$heterocyclylalkyl, $C_{1-6}$carbocyclylalkyl, and carbocyclyl, or two occurrences of $R^1$ together are $C_{1-6}$alkyl, thereby forming a ring;

$R^9$ and $R^{10}$ are independently selected from H, $C_{1-6}$alkyl, $C_{1-6}$aralkyl, $C_{1-6}$heterocyclylalkyl, and $C_{1-6}$carbocyclylalkyl;

$R^{11}$ is selected from H, OH, $C_{1-6}$alkoxy, and $C_{1-6}$alkanoyl, preferably OH;

$X_1$ is selected from NH and O;

$m_1$ is an integer from 1 to 2; and $n_1$ is an integer from 1 to 3.

In certain embodiments, $R^8$ is selected from H and $C_{1-6}$alkyl, X is NH, and n is an integer from 1 to 3. In other embodiments, n is 2, X is NH, and R$^8$ is H. In still other embodiments, n is 2, X is NH, R$^8$ is H, and the substituents are located at the 3- and 4-positions of the aromatic ring.

In certain embodiments, R$^9$ and R$^{10}$ are independently selected from H and C$_{1-6}$alkyl. In other embodiments, R$^9$ is H and R$^3$ is C$_{1-6}$alkyl. In more preferred embodiments, R$^2$ is H and R$^3$ is methyl.

In certain embodiments, m$_1$ is 1 and R$^{11}$ is selected from H, OH, C$_{1-6}$alkoxy, and C$_{1-6}$alkanoyl. In other embodiments, m$_1$ is 1 and R$^{11}$ is OH. In still other preferred embodiments, m$_1$ is 1, R$^{11}$ is OH, and the R$^{11}$ substituent is located at the 4-position of the aromatic ring.

As used herein, the term "C$_{1-6}$alkanoyl," can be represented by the general formula:

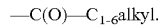
—C(O)—C$_{1-6}$alkyl.

The term "C$_{x-y}$alkyl" refers to substituted or unsubstituted saturated hydrocarbon groups, including straight-chain alkyl and branched-chain alkyl groups that contain from x to y carbons in the chain, including haloalkyl groups, such as trifluoromethyl and 2,2,2-trifluoroethyl, etc. C0 alkyl indicates a hydrogen where the group is in a terminal position, a bond if internal.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "C$_{1-6}$alkoxycarbonyl", as used herein can be represented by the general formula

—C(O)OC$_{1-6}$alkyl.

The term "C$_{1-6}$aralkyl", as used herein, refers to a C$_{1-6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "C$_{1-6}$carbocyclylalkyl", as used herein, refers to a C$_{1-6}$alkyl group substituted with a carbocycle.

The term "carbonyl" is art-recognized and includes such moieties as can be represented by the general formula:

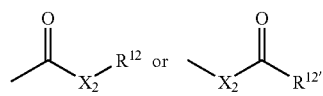

wherein X$_2$ is a bond or represents an oxygen or a sulfur, and R$^{12}$ represents a hydrogen, an alkyl, an alkenyl, —(CH$_2$)$_m$—R$^8$ or a pharmaceutically acceptable salt, R$^{12'}$ represents a hydrogen, an alkyl, an alkenyl or —(CH$_2$)$_m$—R$^8$, where m and R$^8$ are as defined above. Where X$_2$ is an oxygen and R$^{12}$ or R$^{12'}$ is not hydrogen, the formula represents an "ester". Where X$_2$ is an oxygen, and R$^{12}$ is a hydrogen, the formula represents a "carboxylic acid".

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "C$_{1-6}$heterocycloalkyl" refers to a C$_{1-6}$alkyl group substituted with a heterocyclic group.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

In certain aspects, the EphA therapeutic agents of the present invention include a peptidomimetic, for example, peptide-like molecules. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems: San Leandro Calif.), contains about 100,000 compounds that are commercially available and also can be searched to identify potential peptidomimetics of an EphA polypeptide (e.g., an EphA2 LBD).

As described herein, small molecule compounds may encompass numerous chemical classes, though typically they are organic molecules, preferably small organic compounds having a molecular weight of more than about 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group Candidate small molecule compounds can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant, and animal extracts are available or readily produced. Additionally, natural or synthetically produced libraries and compounds can be modified through conventional chemical, physical, and biochemical means. Known pharmacological agents may be subjected to directed or random chemical modifications, such as acylation, alkylation, esterification, and amidification, to produce structural analogs.

In certain aspects, the EphA2 therapeutic agents include antibodies, for example, antibodies that are specifically reactive with an EphA2. Antibodies may be polyclonal or monoclonal: intact or truncated, e.g., F(ab')2, Fab, Fv; xenogeneic, allogeneic, syngeneic, or modified forms thereof, e.g., humanized, chimeric, etc.

For example, by using immunogens derived from an EphA2 polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the peptide. (e.g. a polypeptide or an antigenic fragment which is capable of eliciting an antibody response, or a fusion protein). Techniques for conferring immunogenicity on a protein or peptide include conjugation to carriers or other techniques well known in the art. An immunogenic portion of an EphA2 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, antibodies of the invention are specific for the extracellular portion (e.g., the LBD) of the EphA protein (e.g., EphA1, EphA1, or EphA3). In another embodiment, antibodies of the invention are specific for the intracellular portion or the transmembrane portion of the EphA protein (e.g., EphA1, EphA1, or EphA3). In a further embodiment, antibodies of the invention are specific for the extracellular portion of the EphA2 protein (e.g., EphA1, EphA1, or EphA3).

Following immunization of an animal with an antigenic preparation of an EphA polypeptide (e.g., EphA1, EphA1, or EphA3), antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an EphA2 polypeptide and monoclonal antibodies isolated from a culture comprising such hybridoma cells.

The term antibody as used herein is intended to include fragments thereof which are also specifically reactive with an EphA polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for an EphA polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. In preferred embodiments, the antibodies further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to an EphA polypeptide (e.g., EphA1, EphA1, or EphA3) may comprise administering to a mouse an amount of an immunogenic composition comprising the EphA polypeptide (e.g., EphA1, EphA1, or EphA3) effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the EphA polypeptide. Once obtained, a hybridoma can be propagated in a cell culture, optionally in culture conditions where the hybridoma-derived cells produce the monoclonal antibody that binds specifically to the EphA polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

The present invention also contemplates anti-tumor therapeutic agents obtainable from the screening methods described as below under "Methods of Screening."

IV. Knockout Animals

Another aspect of the invention relates to knockout non-human animals having at least one allele of the genomic EphA gene disrupted (e.g., EphA1 and EphA2 knockout animals). Exemplary, EphA2 knockout mice are described in Iwakura et al., Mechanisms of Development, 102 (2001) 95-1005; and Skames et al., Nature Genetics, vol. 28, July 2001.

In one specific embodiment, the above-mentioned EphA knockout animals further can have at least one allele of another tumor suppressor gene disrupted. For example, the tumor suppressor gene is selected from the group consisting of p53, p63, p73, p16, Mxi1, PTEN, Rb, Apc and Nkx 3.1. Preferably, the double knockout animals exhibits increased susceptibility to the formation of tumors (e.g., prostate, lung, breast, skin and colorectal cancer) as compared to a transgenic mouse having the tumor suppressor gene alone disrupted.

It has been suggested that p53, p63, p73, p16, Mxi1, PTEN, Rb, Apc and Nkx 3.1 play an important role in various human cancers, and decreased expression of one of these tumor suppressor genes may lead to cancer development. See, e.g., US20040132120, WO 04/00010, WO 99/13068, Eagle et al., (1995) Nat Genet 9: 249-55, which are all incorporated herein by reference.

In another specific embodiment, the above-mentioned EphA knockout animals can be bred to other transgenic mouse that express an oncogene. For example, the oncogene encodes T antigen, Myc, Akt, or Ras oncoprotein. Preferably, the knockout animals exhibit increased susceptibility to the formation of tumors (e.g., prostate cancer) as compared to a transgenic mouse having expressing the transgene alone (i.e., the TRAMP (transgenic adenocarcinoma mouse prostate) and MPAKT mouse).

Further, a number of transgenic models of prostate cancer have been reported in the literature (see, e.g. U.S. Pat. Nos. 5,907,078, 5,917,124, 6,323,390, and Zhang et al., Prostate 43: 278-285 (2000), Buttyan et al., Cancer Metatasis Review 12: 11-19 (1993), Shibata et al., Toxicol Pathol 26: 177-183 (1998), and Greenberg et al., Mol Endocrinol 8: 230-239 (1994), which are incorporated herein by reference). Prostate cancer transgenic mice known in the art include the TRAMP model expressing the vital oncogenes large and small T antigen, probasin driving large T antigen, C3 driving c-Myc, probasin driving androgen receptor, probasin driving IGF-1, probasin driving NAT1 and NAT2, ptobasin driving Ras, C3 driving the SV40 large T antigen, C3 driving the SV40 T early region, C3 driving the polyoma virus middle T gene, C3 driving Bcl-2, MMTV LTR driving the SV40 T antigen, MMTV LTR driving int2/fgf3 and wap, CR2 driving the SV40 T antigen, fetal G-y globin driving the SV40 large T antigen, ARR2PB driving the CAT reporter gene, probasin driving Bcl-2, and gp91-phox driving the SV40 early region. Thus, the present invention contemplates use of the above transgenic animal models to cross with the above-mentioned EphA knockout animals.

Another aspect of the invention relates to methods of identifying a therapeutic agent for cancer, comprising administering a test agent to the subject transgenic animals.

In one embodiment, the transgenic non-human animals is a mammal, such as a mouse, rat, rabbit, goat, sheep, dog, cat, cow or non-human primate. Without being bound to theory, it is proposed that such an animal may display a phenomenon associated with reduced or increased chance of cancer development. Accordingly, such a transgenic animal may serve as a useful animal model to study the progression of cancer diseases.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells derived from the above-mentioned transgenic animals. For example, the animal cell (e.g., somatic cell or germ cell) can be obtained from the transgenic animal. Transgenic somatic cells or cell lines can be used, for example, in drug screening assays. Transgenic germ cells, on the other hand, can be used in generating transgenic progeny.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

To illustrate, the transgenic animals and cell lines are particularly useful in screening compounds that have potential as prophylactic or therapeutic treatments of diseases, such as cancer. Screening for a useful drug would involve administering the candidate drug over a range of doses to the transgenic animal, and assaying at various time points for the effect(s) of the drug on the disease or disorder being evaluated.

For example, EphA2 knock out mice can be used to test new EphA2 agonists. A skin carcinogenesis model using EphA2−/− and EphA+/+ mice can serve as a valuable tool to investigate the specificity and potency of future drugs that target EphA2. Because the skin is readily accessible to topical drug application, the compounds can easily and quantitatively tested. For example, if a compound inhibits tumor growth on wild type (EphA2+/+) mice but not knockout (EphA2−/−) mice, it will support the possibility that the compounds has anti-tumor effects by specifically targeting EphA2.

Similarly, the knockout mice can be used to test EphA targeted drugs in other types of cancers induced in other organs, or induced by different mechanisms. For example, by crossing EphA2−/− mice with other tumor-susceptible mice such as TRAMP mice that spontaneously develop prostate cancer, we can see how EphA2 deletion will affect TRAMP tumor development. If EphA2 is found to play a role, new EphA2-targeted drugs can be tested by comparing the effects on EphA+/− and EphA2−/− host animals.

Additionally, the knockout mice can be useful in testing EphA-targeting compounds in other diseases in addition to cancer. Examples include neurodegeneration, blood clotting, inflammation, and cardiovascular diseases.

Alternatively, or additionally, the therapeutic agents or compounds could be administered prior to or simultaneously with exposure to induction of the disease, if applicable.

V. Drug Screening Assays

The present invention provides methods and compositions that enhance expression and/or activity of an EphA receptor. This present application further describes methods and compositions that inhibit cell proliferation and cancer growth. In particular, methods and compositions for inhibiting carcinogenesis are described herein. Exemplary agents have one or more of the following activities: bind to an EphA receptor protein (e.g., a ligand binding domain or a dimerization domain of an EphA1 protein, EphA2 protein, or EphA3 protein), stimulate tyrosine phosphorylation of an EphA, enhance binding of an EphA ligand to an EphA, enhance dimerization of an EphA, enhance expression of an EphA (mRNA or protein), inhibit cancer cell proliferation, inhibit cancer cell adhesion, proliferation, spreading and/or migration, and/or suppress or inhibit signaling of the PI3/AKT pathway and/or MAPK/ERK1/2 pathway. The present invention further contemplates methods of identifying additional agents which possess one or more of these functions. These above-mentioned activities that characterize the agents of the present invention will also be referred to herein as "desired antitumor activity." Without being bound by theory, an agent identified by the subject methods as having one or more of the desired activities may work via any one of a number of mechanisms.

Agent screened (e.g., a single agent, a combination of two or more agents, a library of agents) include nucleic acids, peptides, proteins, antibodies, antisense RNAs, RNAi constructs (including siRNAs), DNA enzymes, ribozymes, morpholino constructs, chemical compounds, and small organic molecules. Agents may be screened individually, in combination, or as a library of agents.

In many drug screening programs that test libraries of nucleic acids, polypeptides, chemical compounds and natural extracts, high throughput assays are desirable to increase the number of agents surveyed in a given period of time. Assays that are performed in cell-free systems, such as may be derived with purified or semi-purified proteins, are often preferred as "primary" screens in that they can be generated to permit rapid development and relatively easy detection of an alteration in a molecular target which is mediated by a test agent. Cell free systems include in vitro systems (preparations of proteins and agents combined in a test tube, Petri dish, etc.), as well as cell free systems such as those prepared from egg extracts or reticulocyte lysates. Moreover, the effects of cellular toxicity and/or bioavailability of the test agents can be generally ignored in such a system, the assay instead being focused primarily on the effect of the agent.

A primary screen can be used to narrow down agents that are more likely to have an effect on cancer progression, in vitro and/or in vivo. Such a cell free system for use in the present invention may include a biochemical assay measuring activity of an EphA protein. To further illustrate, an EphA polypeptide may be contacted with one or more agents (e.g., individual candidate agents, combinations of two or more agents, a library of nucleic acids, polypeptides, small organic molecules, chemical compounds, etc.) and the ability of the agent to enhance the activity of the EphA polypeptide can be measured. The activity of the EphA polypeptide can be assessed by comparing the tyrosine phosphorylation level of the EphA polypeptide. One or more agents which increase the tyrosine phosphorylation level, in comparison to the tyrosine phosphorylation level of the EphA polypeptide in the absence of the one or more agents, is a candidate agent for use in the subject methods. Similarly, an EphA polypeptide may be contacted with one or more agents (e.g., individual candidate agents, combinations of two or more agents, a library of nucleic acids, polypeptides, small organic molecules, chemical compounds, etc.) and the ability of the agent to decrease the tyrosine phosphorylation level of an EphA can be measured.

The efficacy of the agent can be assessed by generating dose response curves from data obtained using various concentrations of the test agent. Moreover, a control assay can also be performed to provide a baseline for comparison. Such candidates can be further tested for efficacy in inhibiting proliferation of cancer cells in vitro, for efficacy in inhibiting adhesion, spreading or migration of cancer cells in vitro, for efficacy in increasing the activity and/or expression of the EphA in other assays, for efficacy in tumor growth or spreading (e.g., prostate cancer) in vitro or in vivo. For example, the efficacy of the agent can be tested in vivo in any of the prostate cancer animal models, as described above.

In addition to cell-free assays, such as described above, the invention further contemplates the generation of cell-based assays for identifying agents having one or more of the desired anti-tumor activities. Cell-based assays may be performed as either a primary screen, or as a secondary screen to confirm the activity of agents identified in a cell free screen, as outlined in detail above. Such cell based assays can employ any cell-type. Exemplary cell types include cancer cell lines, primary tumor xenoplant cultures, and prostate cells. Cells in culture are contacted with one or more agents, and the ability of the one or more agents to inhibit cell proliferation or migration/adhesion is measured. Agents which inhibit cell proliferation or migration/adhesion are candidate agents for use in the subject methods of inhibiting cancer development.

One class of agents that may enhance the activity and/or expression of an EphA are agents which bind directly to an EphA protein, for example, antibodies, small organic molecules, agonistic variants of the wildtype protein, and agonistic fragments of the wildtype protein. Accordingly, the present invention contemplates screening for agents which bind to, either directly or indirectly an EphA protein.

There are numerous approaches to screening for EphA therapeutic agents in tumor therapy. For example, high-throughput screening of compounds or molecules can be carried out to identify agents or drugs which inhibit tumor growth. Test agents to be assessed for their anti-tumor effects can be any chemical (element, molecule, compound, drug), made synthetically, made by recombinant techniques or isolated from a natural source. For example, test agents can be peptides, polypeptides, peptoids, sugars, hormones, or nucleic acid molecules (such as antisense or RNAi nucleic acid molecules). In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

For example, an assay can be carried out to screen for compounds that specifically enhance binding of an EphA ligand to an EphA receptor (e.g., EphA2 ligand to and EphA2 receptor), such as, by enhancing binding of labeled ligand- or receptor-Fc fusion proteins to immortalized cells. As used herein, the term EphA includes a full-length and a portion of an EphA polypeptide such as a ligand-binding domain. Compounds identified through this screening can then be tested in animal models of cancer (e.g., tumor xenografts implanted in nude mice) to assess their anti-tumor activity in vivo. For example, the identified compounds can be tested in prostate cancer models such as the TRAMP (transgenic adenocarcinoma mouse prostate) mouse, the Nkx 3.1 gene knockout mouse, or any other knockout animals as described above, under "Knockout Animals".

In one embodiment of an assay to identify a substance that enhance interaction of two cell surface molecules (e.g., an ephrin A1 and EphA2), samples of cells expressing one type of cell surface molecule (e.g., EphA2, a soluble portion thereof, or a EphA2 fusion protein such as a fusion of the ligand-binding domain and the Fc domain of IgG) are contacted with either labeled ligand (e.g., ephrin A1) plus a test compound (or group of test compounds). The amount of labeled ligand which has bound to the cells is determined. A higher amount of label (where the label can be, for example, a radioactive isotope, a fluorescent or colormetric label) in the sample contacted with the test compound(s) is an indication that the test compound(s) enhance or induce binding. The reciprocal assay using cells expressing an EphA2 ligand (e.g., ephrin A1 or a soluble form thereof) can be used to test for a substance that enhances or induces the binding of an EphA2 receptor or soluble portion thereof.

An assay to identify a substance which enhances interaction between an EphA receptor and an ephrin ligand can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an EphA2\receptor or an ephrin ligand) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all of, or a portion of, a protein (e.g., an EphA receptor or an ephrin ligand) linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein (e.g., an EphA receptor or an ephrin ligand) or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In other embodiments, other assays can be used for screening for compounds that stimulates functions (e.g., phosphorylation or dimerization) of EphA (e.g., EphA1, EphA2, or EphA3). Methods of detecting protein phosphorylation and dimerization can be achieved by techniques such as immunoprecipitations, Western blots, and cross-linking assays. In these cases, antibodies may be used in a variety of detection techniques. Detailed methods have been described in the working examples.

In certain embodiments, the invention relates to methods for selecting or screening for a compound capable of binding to an EphA receptor. The compound may be a naturally occurring biomolecule synthesized in vivo or in vitro. The compound may be optionally derivatized with another compound. One advantage of this modification is that the derivatizing compound may be used to facilitate the EphA compound complex collection, e.g., after separation of compound and an EphA receptor. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

The interaction between the compound and an EphA receptor may be covalent or non-covalent. Optionally, the compound may or may not display affinity for other Eph receptors. For example, binding between EphA2 and a compound can be identified at the protein level using in vitro biochemical methods, including photo-crosslinking, radiolabeled ligand binding, and affinity chromatography (Jakoby W B et al., 1974, Methods in Enzymology 46: 1). Alternatively, small molecules can be immobilized on an agarose matrix and used to screen extracts of a variety of cell types and organisms.

Another useful technique to closely associate binding of a compound with DNA encoding an EphA2 is phage display. In phage display, which has been predominantly used in the monoclonal antibody field, peptide or protein libraries are created on the viral surface and screened for activity (Smith G P, 1985, Science 228:1315). Phages are panned for a target protein which is connected to a solid phase (Parmley S F et al., 1988, Gene 73:305). One of the advantages of phage display is that the cDNA is in the phage and thus no separate cloning step is required.

In a specific embodiment, the invention relate to methods of identifying or selecting a compound capable of binding to an EphA, comprising: (a) providing coordinates defining the three dimensional structure of the EphA ligand-binding domain: (b) characterizing points associated with that three dimensional structure with respect to the favorability of interactions with one or more selected functional groups; (c) providing a database of one or more candidate compounds; and (d) identifying from the database those compounds having VI. Methods of Treatment The present invention provides methods of treating an individual suffering from cancer through administering to the individual a therapeutically effective amount of an EphA therapeutic agent as described above. The present invention provides methods of preventing or reducing the onset of cancer in an individual through administering to the individual an effective amount of an EphA therapeutic agent. These methods are particularly aimed at therapeutic and prophylactic treatments of animals, and more particularly, humans.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

Cancers and related disorders that can be treated, prevented, or managed by methods, EphA therapeutic agents and compositions of the present invention include but are not limited to cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America)

Accordingly, the methods and EphA therapeutic agents of the invention are also useful in the treatment or prevention of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, rectum, breast, prostate, bladder, kidney, pancreas, ovary, or uterus. In other specific embodiments, sarcoma, melanoma, or leukemia is treated or prevented.

In some embodiments, the cancer is malignant and over-expresses EphA. In other embodiments, the disorder to be treated is a pre-cancerous condition associated with cells that overexpress EphA. In a specific embodiments, the pre-cancerous condition is high-grade prostatic intraepithelial neoplasia (PIN), fibroadenoma of the breast, fibrocystic disease, or compound nevi.

In certain embodiments, EphA therapeutic agents of the invention can be delivered to cancer cells by site-specific means. Cell-type-specific delivery can be provided by conjugating a therapeutic agent to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In certain embodiments, one or more EphA therapeutic agents can be administered, together (simultaneously) or at different times (sequentially). In addition, therapy by administration of one or more EphA therapeutic agents is combined with the administration of one or more therapies such as, but not limited to, chemotherapies, radiation therapies, hormonal therapies, and/or biological therapies/immunotherapie-s. Prophylactic/therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including, but not limited to, double-stranded or single-stranded DNA, or double-stranded or single-stranded RNA, as well as triple helix nucleic acid molecules. Prophylavtic/therapeutic agents can be derived from any known organism (including, but not limited to, animals, plants, bacteria, fungi, and protista, or viruses) or from a library of synthetic molecules.

In a specific embodiment, the methods of the invention encompass administration of an EphA the respective agent in combination with the administration of one or more prophylactic/therapeutic agents that are inhibitors of kinases such as, but not limited to, ABL, ACK, AFK, AKT (e.g., AKT-1, AKT-2, and AKT-3), ALK, AMP-PK, ATM, Aurora1, Aurora2, bARKI, bArk2, BLK, BMX, BTK, CAK, CaM kinase, CDC2, CDK, CK, COT, CTD, DNA-PK, EGF-R, ErbB-1, ErbB-2, ErbB-3, ErbB-4, ERK (e.g., ERK1, ERK2, ERK3, ERK4, ERK5, ERK6, ERK7), ERT-PK, FAK, FGR (e.g., FGF1R, FGF2R), FLT (e.g., FLT-1, FLT-2, FLT-3, FLT-4), FRK, FYN, GSK (e.g., GSK1, GSK2, GSK3-alpha, GSK3-beta, GSK4, GSK5), G-protein coupled receptor kinases (GRKs), HCK, HER2, HKII, JAK (e.g., JAK1, JAK2, JAK3, JAK4), JNK (e.g., JNK1, JNK2, JNK3), KDR, KIT, IGF-1 receptor, IKK-1, IKK-2, INSR (insulin receptor), IRAK1 IRAK2, IRK, ITK, LCK, LOK, LYN, MAPK, MAP-KAPK-1, MAPKAPK-2, MEK, MET, MFPK, MHCK, MLCK, MLK3, NEU, NIK, PDGF receptor alpha, PDGF receptor beta, PHK, PI-3 kinase, PKA, PKB, PKC, PKG, PRK1, PYK2, p38 kinases, p135tyk2, p34cdc2, p42cdc2, p42mapk, p44 mpk, RAF, RET, RIP, RIP-2, RK, RON, RS kinase, SRC, SYK, S6K, TAK1, TEC, TIE1, TIE2, TRKA, TXK, TYK2, UL13, VEGFR1, VEGFR2, YES, YRK, ZAP-70, and all subtypes of these kinases (see e.g., Hardie and Hanks (1995) The Protein Kinase Facts Book, I and II, Academic Press, San Diego, Calif.). In other embodiments, an EphA therapeutic agent is administered in combination with the administration of one or more prophylactic/therapeutic agents that are inhibitors of Eph receptor kinases (e.g., EphA2, EphA4). In still another embodiment, an EphA therapeutic agent is administered in combination with the administration of one or more prophylactic/therapeutic agents that are inhibitors of EphA.

In another specific embodiment, the methods of the invention encompass administration of EphA therapeutic agents in combination with the administration of one or more prophylactic/therapeutic agents that are angiogenesis inhibitors such as, but not limited to: Angiostatin (plasminogen fragment); antiangiogenic antithrombin III; Angiozyme; ABT-627; Bay 12-9566; Benefin; Bevacizumab; BMS-275291: cartilage-derived inhibitor (CDI): CAI; CD59 complement fragment; CEP-7055; Col 3; Combretastatin A-4; Endostatin (collagen XVIII fragment); fibronectin fragment. Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide. Thrombospondin-1 (TSP-1); TNP-470; Transforming growth factor-beta (TGF-.beta.); Vasculostatin; Vasostatin (calreticulin fragment); ZD6126; ZD6474; farnesyl transferase inhibitors (FTI); and bisphosphonates.

In another specific embodiment, the methods of the invention encompass administration of EphA therapeutic agents in combination with the administration of one or more prophylactic/therapeutic agents that are anti-cancer agents such as, but not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, onaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3,5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, antidorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-aminotriazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramrantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1 based therapy, mustard anticancer agent mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, R11 retinamide, rogletimide, rohitukine, romurtide, roquinimex, rubiginone B1, ruboxyl, safingol, saintopin, SarCNU, carcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Preferred additional anti-cancer drugs are 5-fluorouracil and leucovorin.

In more particular embodiments, the present invention also comprises the administration of one or more EphA therapeutic agents in combination with the administration of one or more therapies such as, but not limited to anti-cancer agents such as those disclosed.

The invention also encompasses administration of the EphA therapeutic agents in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the Physician's Desk Reference (56th ed., 2002).

In one specific embodiment, patients with breast cancer can be administered an effective amount of EphA therapeutic agent. In another embodiment, the EphA therapeutic agent of the invention can be administered in combination with an effective amount of one or more other agents useful for breast cancer therapy including but not limited to: doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), herceptin, tamoxifen, the combination of tamoxifen and cytotoxic chemotherapy, taxanes (such as docetaxel and paclitaxel). In a further embodiment, EphA therapeutic agents can be administered with taxanes plus standard doxorubicin and cyclophosphamide for adjuvant treatment of node-positive, localized breast cancer.

In another specific embodiment, patients with pre-cancerous fibroadenoma of the breast or fibrocystic disease can be administered EphA therapeutic agents to treat the disorder and decrease the likelihood that it will progress to malignant breast cancer. Additionally, patients refractory to treatment, particularly hormonal therapy, more particularly tamoxifen therapy, can be administered EphA therapeutic agents to treat the cancer and/or render the patient non-refractory or responsive.

In another embodiment, patients with colon cancer can be administered an effective amount of one or more EphA therapeutic agents. In yet another embodiment, EphA therapeutic agents can be administered in combination with an effective amount of one or more other agents useful for colon cancer therapy including but not limited to: the combination of 5-FU and leucovorin, the combination of 5-FU and levamisole, irinotecan (CPT-11) or the combination of irinotecan, 5-FU and leucovorin (IFL).

In other embodiments, patients with prostate cancer can be administered an effective amount of one or more EphA therapeutic agents. In another embodiment, the EphA therapeutic agents can be administered in combination with an effective amount of one or more other agents useful for prostate cancer therapy including but not limited to: external-beam radiation therapy, interstitial implantation of radioisotopes (i.e., I.sup.125, palladium, iridium), leuprolide or other LHRH agonists, non-steroidal antiandrogens (flutamide, nilutamide, bicalutamide), steroidal antiandrogens (cyproterone acetate), the combination of leuprolide and flutamide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxel, paclitaxel, estramustine/docetaxel, estramustine/etoposide, estramustine/vinblastine, and estramustine/paclitaxel.

In a specific embodiment, patients with pre-cancerous high-grade prostatic intraepithelial neoplasia (PIN) are administered an EphA2 therapeutic agents of the invention to treat the disorder and decrease the likelihood that it will progress to malignant prostate cancer.

In specific embodiments, patients with melanoma are administered an effective amount of EphA therapeutic agents of the invention. In another embodiment, the EphA therapeutic agents can be administered in combination with an effective amount of one or more other agents useful for melanoma cancer therapy including but not limited to: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2). In a specific embodiment, an effective amount of one or more EphA therapeutic agents can be administered in combination with isolated hyperthermic limb perfusion (ILP) with melphalan (L-PAM), with or without tumor necrosis factor-alpha (TNF-alpha) to patients with multiple brain metastases, bone metastases, and spinal cord compression to achieve symptom relief and some shrinkage of the tumor with radiation therapy.

In a specific embodiment, patients with pre-cancerous compound nevi are administered EphA therapeutic agents to treat the disorder and decrease the likelihood that it will progress to malignant melanoma.

In specific embodiments, patients with ovarian cancer are administered an effective amount of one or more EphA therapeutic agents of the invention. In another embodiment, the EphA therapeutic agents can be administered in combination with an effective amount of one or more other agents useful for ovarian cancer therapy including but not limited to: intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. It is contemplated that an effective amount of one or more EphA therapeutic agents can be administered in combination with the administration Taxol for patients with platinum-refractory disease. Included is the treatment of patients with refractory ovarian cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

In specific embodiments, patients with small lung cell cancer are administered an effective amount of one or more EphA therapeutic agents. In another embodiment, the antibodies of the invention can be administered in combination with an effective amount of one or more other agents useful for lung cancer therapy including but not limited to: thoracic radiation therapy, cisplatin, vincristine, doxorubicin, and etoposide, alone or in combination, the combination of cyclophosphamide, doxorubicin, vincristine/etoposide, and cisplatin (CAV/EP), local palliation with endobronchial laser therapy, endobronchial stents, and/or brachytherapy.

In other specific embodiments, patients with non-small lung cell cancer are administered an effective amount of one or more EphA therapeutic agents in combination with an effective amount of one or more other agents useful for lung cancer therapy including but not limited to: palliative radiation therapy, the combination of cisplatin, vinblastine and mitomycin, the combination of cisplatin and vinorelbine, paclitaxel, docetaxel or gemcitabine, the combination of carboplatin and paclitaxel, interstitial radiation therapy for endobronchial lesions or stereotactic radiosurgery.

VII. Administration and Pharmaceutical Compositions

EphA therapeutic agents as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the agent that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a therapeutic agent as an active ingredient. A compound may also be administered as a bolus, electuary or paste.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Formulations which are suitable for vaginal administration also include pessaries, tampons, creams, gels, pastes, foams, or spray formulations containing such carriers as are known in the art to be appropriate. Dosage forms for the topical or transdermal administration of a therapeutic agent include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The therapeutic agent can be alternatively administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an therapeutic agent to the body. Such dosage forms can be made by dissolving or dispersing the agent in the proper medium. Absorption enhancers can also be used to increase the flux of the therapeutic agent across the skin. The rate of such flux can be controlled by either providing a rate controlling membrane or dispersing the peptidomimetic in a polymer matrix or gel.

Pharmaceutical compositions of this invention suitable for parenteral administration comprise one or more EphA2 therapeutic agent(s) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of subject therapeutic agent in biodegradable polymers such as polylactide-polyglycolide. Depending on the ratio of drug to polymer, and the nature of the particular polymer employed, the rate of drug release can be controlled Examples of other biodegradable polymers include poly (orthoesters) and poly(anhydrides). Depot injectable formulations are also prepared by entrapping the drug in liposomes or microemulsions which are compatible with body tissue.

When the EphA therapeutic agent(s) of the present invention are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

These EphA therapeutic agent(s) may be administered to humans and other animals for therapy by any suitable route of administration, including orally, nasally, as by, for example, a spray, rectally, intravaginally, parenterally, intracistemally, and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

EXAMPLES

The invention now being generally described, it will be more readily understood by reference to the following examples which are included merely for purposes of illustration of certain aspects and embodiments of the present invention, and are not intended to limit the invention.

Example 1

Stimulation of EphA Kinases on Prostate Adenocarcinoma Cells Antagonizes c-Met-Mediated Chemotaxis and Invasion 1. EphA2, but not its Ephrin-A Ligands, is Highly Expressed in Metastatic Prostate Cancer Cells of Human or Rat Origin.

Figure 1B:
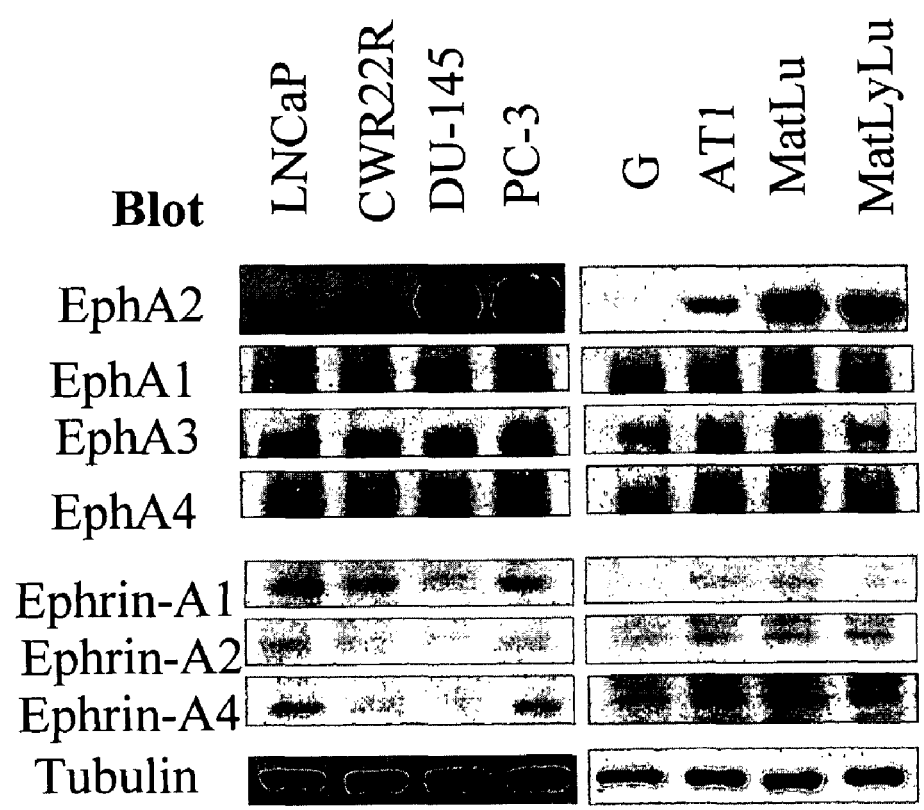
Figure 1C:
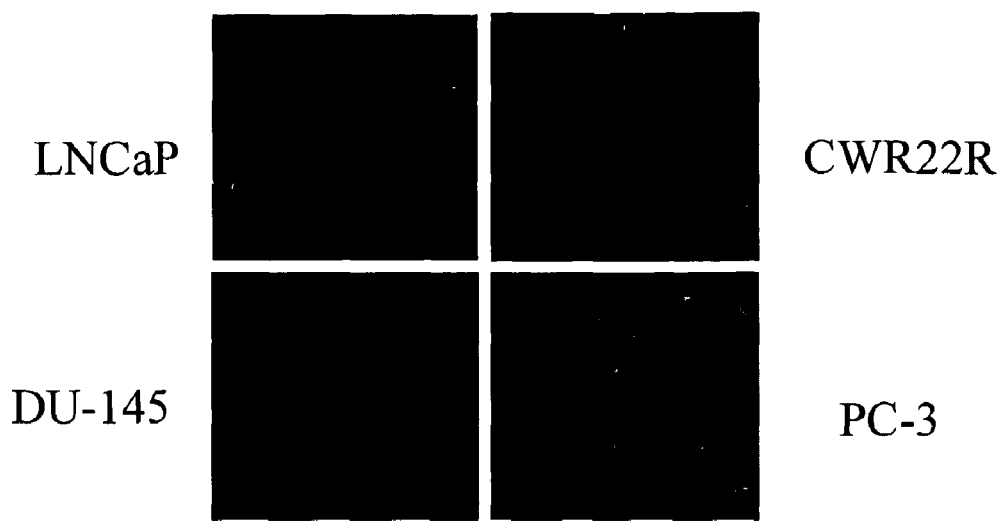

We have previously identified EphA2 as the primary EphA kinase expressed in PC-3 cells. Immunodepletion experiment (Methods) revealed that EphA2 is also the major EphA kinase in other human prostate cancer cell lines (FIG. 1A). Interestingly, cells derived from distal metastasis including PC-3 and DU-145 expressed much higher levels of EphA2 than cells derived from primary tumor (CWR22R) or local metastasis (LNCaP) (FIGS. 1B and C). However, because these cells were derived from different individuals, a correlative relationship between EphA2 expression and tumor progression cannot be established. Thus, we examined the expression of EphA2 in a series of rat prostate cancer cell lines derived from the same original tumor, Dunning rat tumor R-3327. While R-3327-G (G) is a slow growing and androgen responsive subline with low metastatic ability, AT-1 is independent of androgen but remains poorly metastatic. MatLu and MatLyLu arose from AT-1, but are highly metastatic to lung (MatLu and MatLyLu) and lymph node (MatLyLu). We found that EphA2 expression was low in G line, moderately increased in AT-1, and greatly elevated in MatLu and MatLyLu variants (FIG. 1B), suggesting a possible correlation between EphA2 expression and tumor progression. In contrast to EphA2, other EphA kinases, including EphA1, EphA3 and EphA4, showed no consistent changes during tumor progression in human or rat cell lines (FIG. 1B). Like other Eph kinases, EphA2 is promiscuous in ligand recognition and can bind to multiple ephrinA ligands. Immunoblot with a panel of antibodies against several ephrin-As showed that the ligands were expressed in low levels, and did not exhibit significant differences among the cell lines examined (FIG. 1B). In summary, while EphA2 expression is elevated in cell lines derived more metastatic cancers, ephrin-A expression remains low and relatively constant.

Figure 1D:
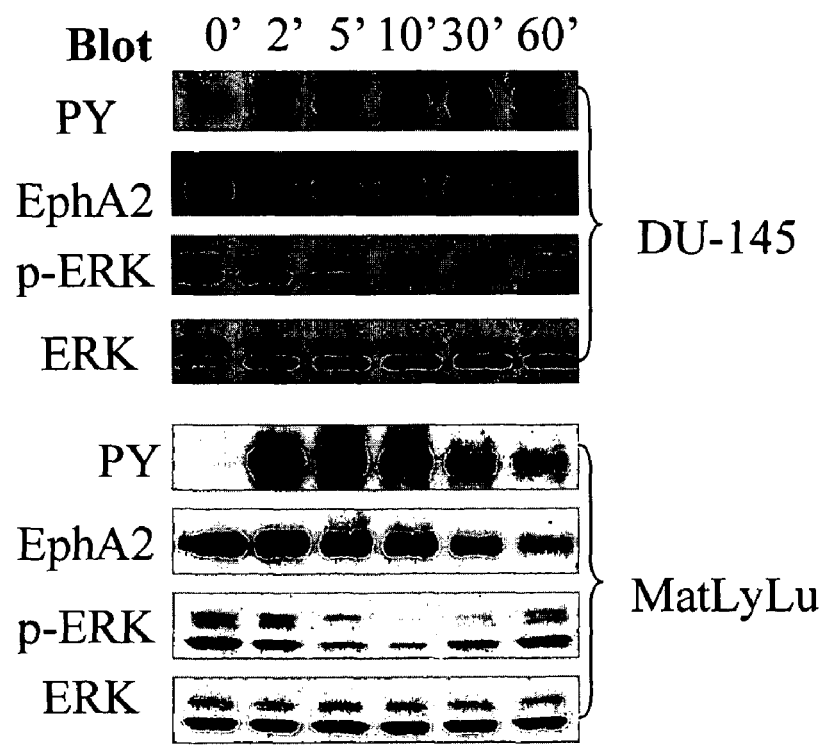

Next, we examined ligand responsiveness and downstream signaling of EphA2 kinase in cells that overexpress it. DU-145 and MatLyLu were stimulated with ephrin-A1 dimerized by fusion to the heavy chain of human IgG1 (ephrin-A1-Fc). Similar to what we reported in PC-3 cells, in both DU-145 and MatLyLu EphA2 activation readily occurred in two minutes after the addition of ephrin-A 1-Fc and persisted for the duration of the experiment (FIG. 1D). ERK1/2 activity was reduced as EphA2 became activated, consistent with our previous report in a number of cell lines, including PC-3 cells. Therefore, EphA2, but not other EphA kinases or its cognitive ligands, was highly expressed in metastatic prostate cancer cells; ligation of unoccupied EphA2 receptor readily transduced signals into cell interior.

Figure 2A:
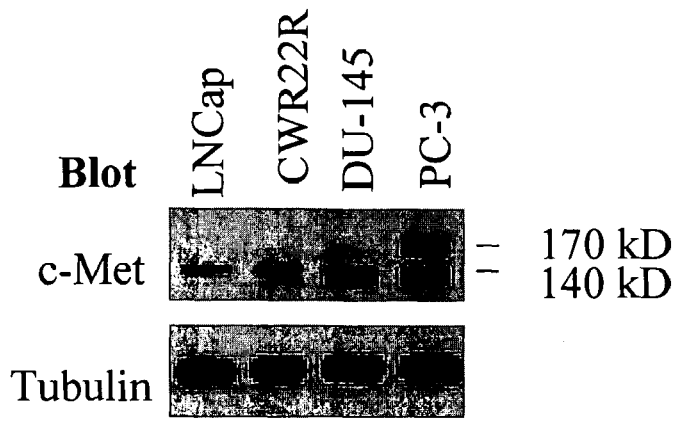
FIG. 2. EphA activation inhibited DU-145 cell migration. (A) Expression of c-Met is elevated in cell lines derived from more malignant prostate cancer. Total cellular proteins were immunoblotted with anti-human c-Met. An anti-tubulin blot was used as a control for protein loading. (B) In a modified Boyden chamber assay, DU-145 cells were placed in the upper chamber and allowed to migrate to the lower chamber containing indicated reagents. After 8 hours, cells were stained with crystal violet and cells remaining in the upper chamber were removed. Top panel: Cells migrated to the undersides of membrane were counted; six high power fields were counted. Results represent means±S.D. Representative fields were shown in the lower panel. (C) Ephrin-A1-Fc inhibits DU-145 cell migration when HGF/SF was uniformly presented in both sides of membranes. The experiment was carried out as described in A. (D) Inhibition of cell scattering by immobilized ephrin-A1 in a SOIL assay (Method). Ephrin-A1-Fc or control Fc was immobilized on 6-well culture dishes. Freshly confluent DU-145 cells on cover slips were transferred to the coated surfaces. Cells were stimulated with HGF/SF to induce migration off the cover slips to immobilized Fc or ephrin-A1-Fc. After 48 hours, cells were fixed and stained with crystal violet. The cells that had migrated to the coated surface were photographed after removing cover slips. (E) DU-145 cells were grown to confluency and a wound was generated by scratching monolayer with a 200 µl pipette tip. The wound healing was recorded prior to and 12 hours after the addition of Fc, ephrin-A1-Fc (1 µg/ml) and/or HGF/SF (20 ng/ml). Representative results from 3 independent experiments are shown.

2. EphA2 Activation Antagonized Stimulatory Effects of HGF/SF on Cell Migration and Wound Healing In prostate cancer, there is a direct correlation between cell motility in vitro and metastasis in vivo. Cell motility in turn is stimulated by the acquisition of paracrine/autocrine loops which frequently develop during prostate cancer progression. HGF/SF is one such cytokine that is suspected to play a critical role in both prostate cancer cell spreading from original tumor site and prostate cancer cell homing to the bones. Interestingly, we found that EphA2 expression paralleled that of c-Met (FIG. 2A); low in LNCaP and CWR22R and high in DU-145 and PC-3, as reported previously. Because HGF/SF-c-Met axis has been implicated in malignant progression of prostate cancer, we next investigated how activation of EphA2 overexpressed on metastatic prostate cancer cells may impact HGF/SF-stimulated cell migration and invasion. DU-145 cells were chosen for these studies because they have been frequently used as a model to assess the role of HGF/SF-c-Met axis in prostate cancer progression.

Figure 2B:
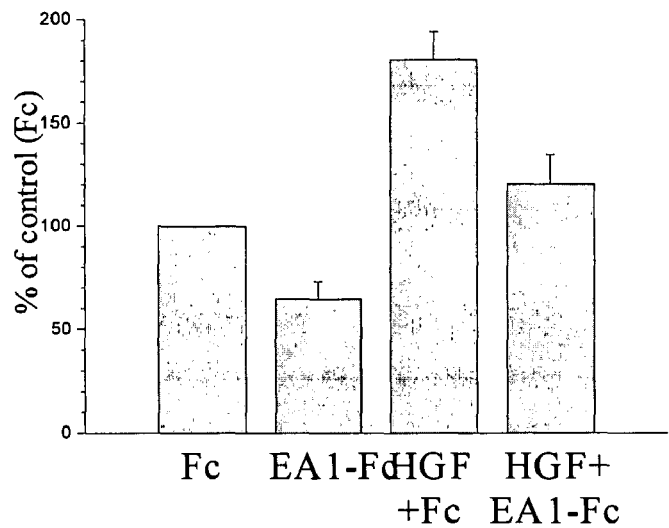
Figure 2B:
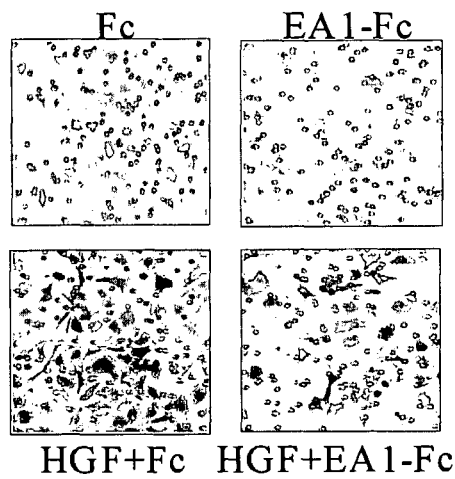

First we performed a chemotactic cell migration assay using modified Boyden chamber system (Methods). DU-145 cells were placed in the upper chamber while Fc, ephrin-A1-Fc, HGF/Fc, or HGF/ephrin-A1-Fc was added into the lower chamber (FIG. 2B). In comparison with Fc control, the presence of ephrin-A1-Fc in the lower chamber reduced the basal level of cell migration (columns 1 vs. 2; $p=4\times10^{-4}$). HGF/SF stimulated cell migration (columns 1 vs. 3; $p=1.5\times10^{-6}$), which was also potently inhibited by ephrin-A1-Fc (columns 3 vs. 4; $p=1.9\times10^{-5}$). Therefore, ephrin-A1 inhibited both basal and HGF/SF-induced cell migration.

Figure 2C:
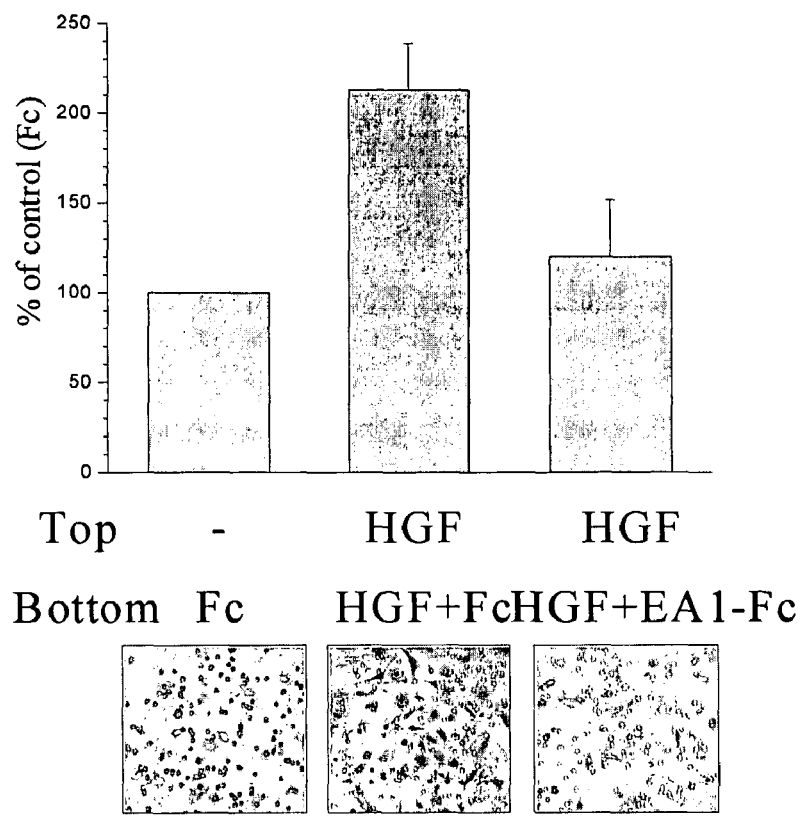

The Boyden chamber assay measures the cellular response to a gradient of HGF/SF and may simulate tumor cell homing to target organs secreting chemotactic factors. On the other hand, tumor cells in original tumor site may be constantly exposed to growth factors produced by tumor cells themselves (autocrine), or surrounding stromal cells, or infiltrating leukocytes (paracrine). We tested if exogenously added ephrin-A1 ligand exhibited inhibitory effect on cell migration in a growth factor-filled environment. To this end, HGF/SF was added to both sides of chambers while Fc or ephrin-A1-Fc was added to the lower chambers only (FIG. 2C). The presence of 1HGF/SF elevated cell motility (columns 1 vs. 2: $p=2.0\times10^{-5}$). When ephrin-A1-Fc was added to the lower chamber, EphA2 activation significantly reduced the number of cells migrated to the underside of membrane (columns 2 vs. 3; $p=5.1\times10^{-4}$).

Figure 2D:
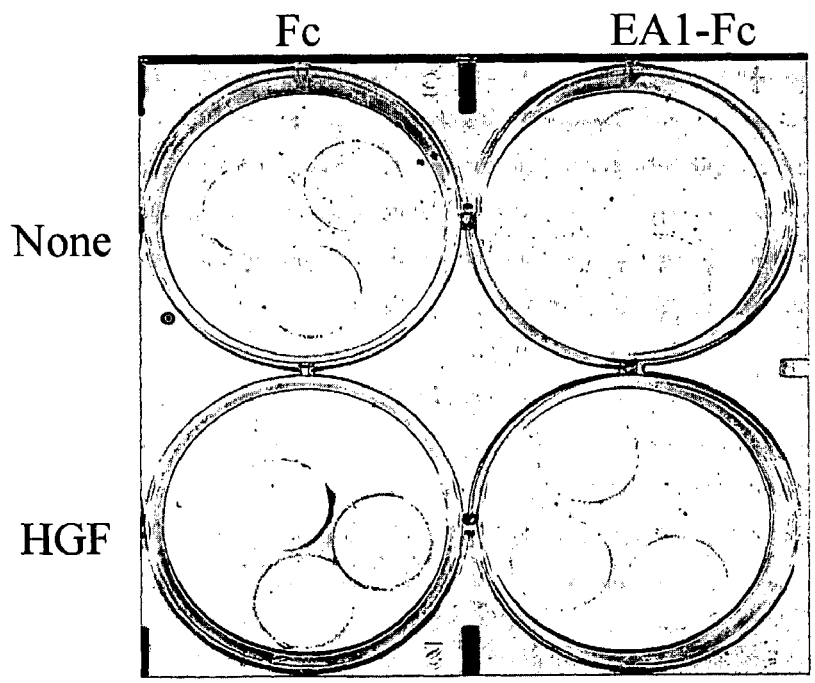

Because both Eph receptors and ephrin ligands are membrane-bound, Eph/ephrin interactions in vivo take place upon cell-cell contact. To simulate this condition, a recently described SOIL assay was carried out to test whether the immobilized ephrin-A1 ligand was able to inhibit chemokinetic cell migration. DU-145 cells grown to near confluence on cover slips were transferred to plates pre-coated with either Fc or ephrin-A1-Fc. HGF/SF or equal volumes of PBS control was added to the culture medium to induce chemokinetic cell migration. FIG. 2D shows that immobilized ephrin-A1-Fc reduced basal levels of cell migration off cover slips. When HGF/SF was applied, cell migration was increased. However, the increase in cell migration induced by HGF/SF was significantly reduced on the ephrin-A1-Fc coated surface.

Figure 2E:
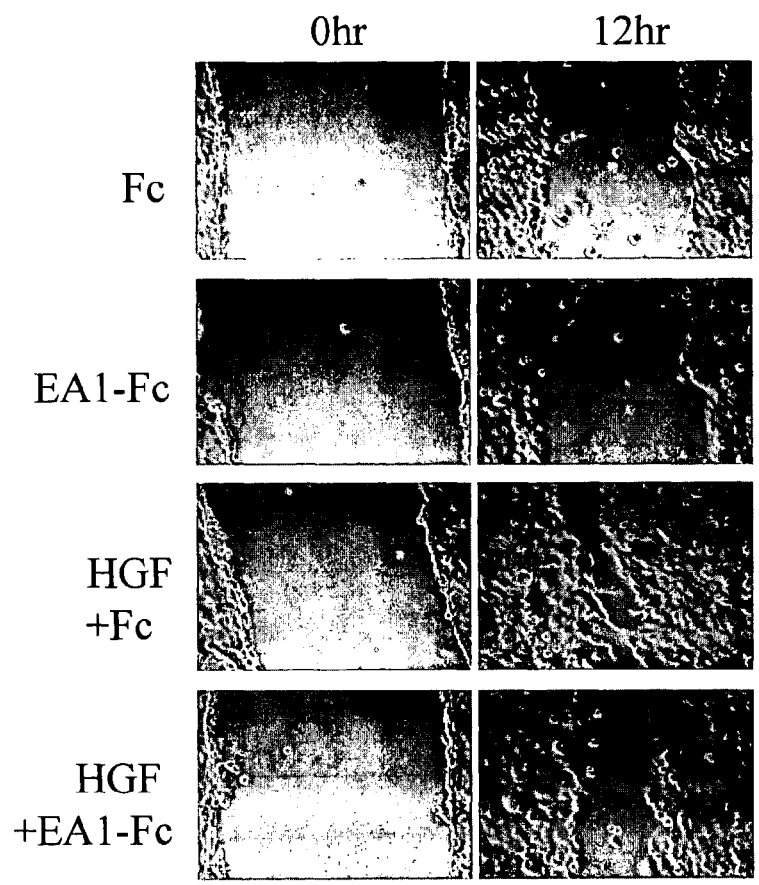

When tumors metastasize, they may disseminate as individual cells or as a group of cells (chain migration). In the latter case, the characteristics of cell-cell adhesion are still present. To test if EphA2 activation inhibited chain migration, a wound-healing assay was carried out (FIG. 2E). A wound was generated on confluent DU-145 cells using a micropipette tip. In comparison with Fc, ephrin-A1-Fc treatment slowed down the speed of wound closing. When ephrin-A1-Fc was used together with HGF/SF, the wound closing was also delayed compared with cells treated HGF/SF and Fc. This again demonstrated in the inhibitory effect of EphA2 activation on cell motility. In sum, EphA2 activation potently antagonizes the stimulatory effects of HGF/SF on four different modes of cell motility.

3. EphA2 Activation Suppressed HGF/SF-Induced Invasion Through MatriGel

Figure 3:
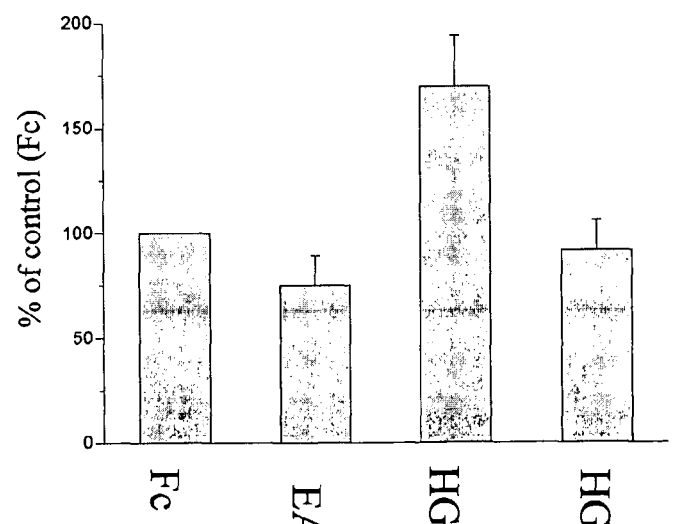
FIG. 3. EphA activation inhibited DU-145 cell invasion. DU-145 cells were placed in the upper chamber of MatriGel-coated Transwell. Fc, ephrin-A1-Fc, HGF/SF/Fc or HGF/SF/ephrin-A1-Fc, were added in the lower chamber. After 24 hours, cells invading through MatriGel and migrated to the undersides of membrane were counted. Representative results (mean±S.D.) from three independent experiments are shown.

In addition to increased cell motility, the ability to invade through extracellular matrix is another characteristic of metastatic tumor cells. Therefore, we next examined the consequence of EphA activation on invasive ability of DU-145 cells induced by HGF/SF. The assay system is similar to Boyden chamber used in the cell migration assay, but the membranes were coated with growth factor-reduced MatriGel. Twenty-four hours after plating, cells invading through MatriGel and migrating to the underside of the membranes were counted (FIG. 3). The presence of ephrin-A1-Fc in the lower chamber marginally reduced the basal cell invasion (columns 1 vs. 2; p=0.06). Addition of HGF/SF to the lower chamber significantly increased chemotactic cell invasion (columns 1 vs. 3; p=0.001). When ephrin-A1-Fc was added together with HGF/SF in the lower chamber, the number of cells invading through MatriGel was significantly reduced (columns 3 vs. 4; p=$2 \times 10^{-4}$). Therefore, activation of EphA receptor has negative effects on malignant prostate cancer cell invasion.

Figure 4A:
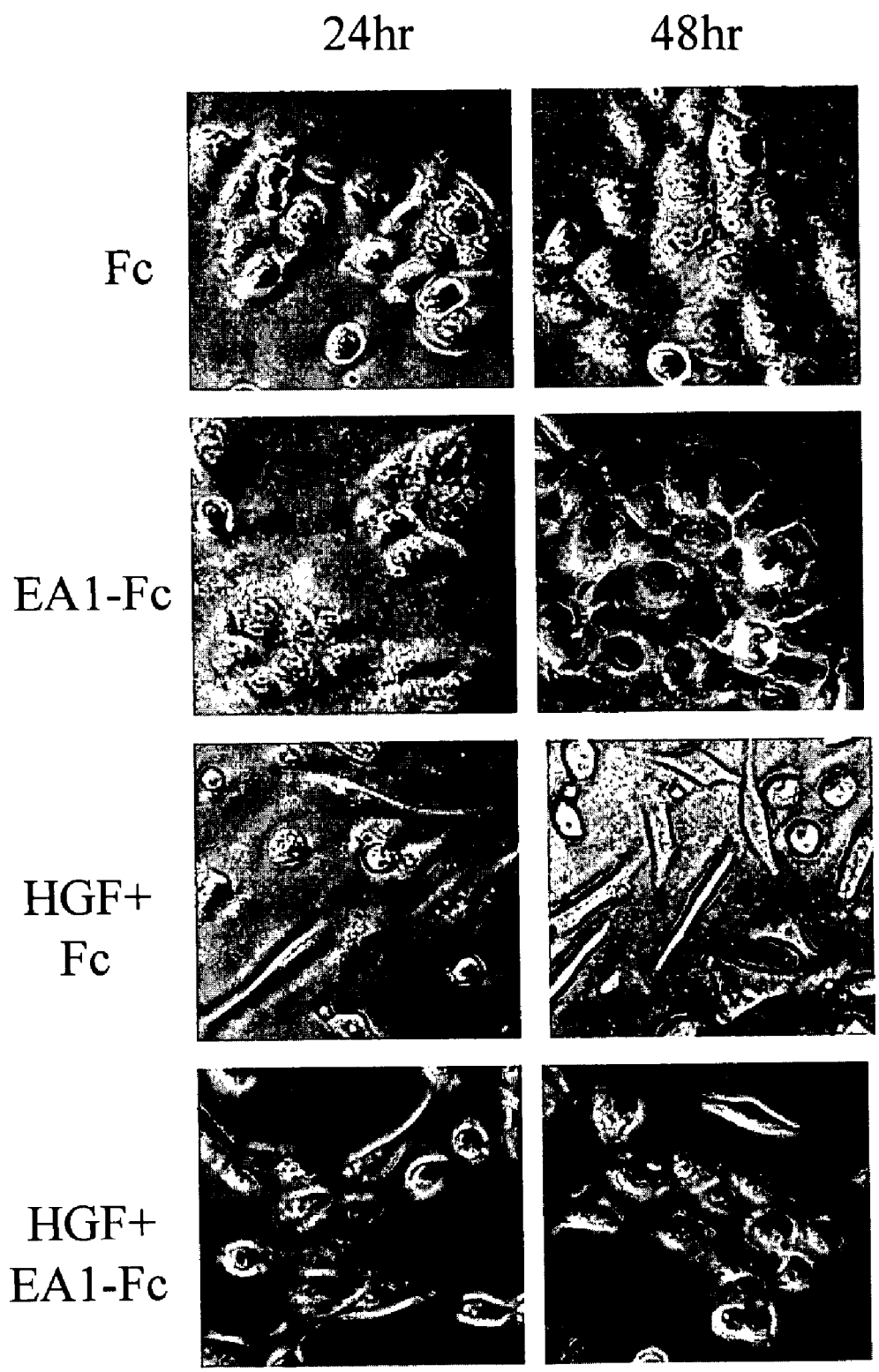
FIG. 4. EphA activation attenuated cell scattering induced by HGF/SF. DU-145 cells were cultured in the presence of indicated reagents. Cell morphology was recorded 24 and 48 hours after the initiation of treatments (A). Numbers of total cells and cells without contact with other cells were counted in 6-8 randomly chosen fields (B). * HGF/SF/Fc vs. HGF/SF/ephrinA1-Fc: $p<10^{-5}$.
Figure 4B:
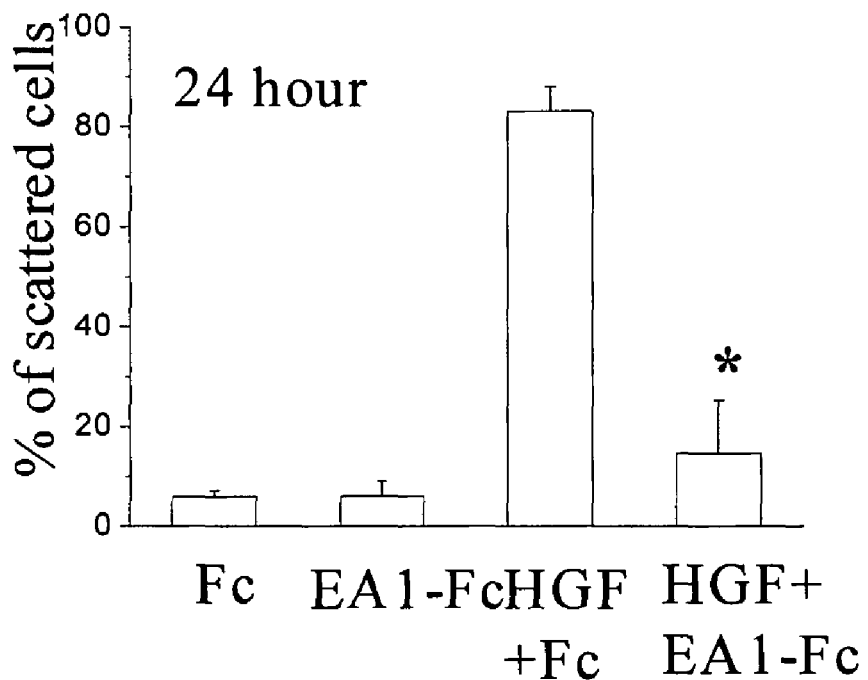
Figure 4B:
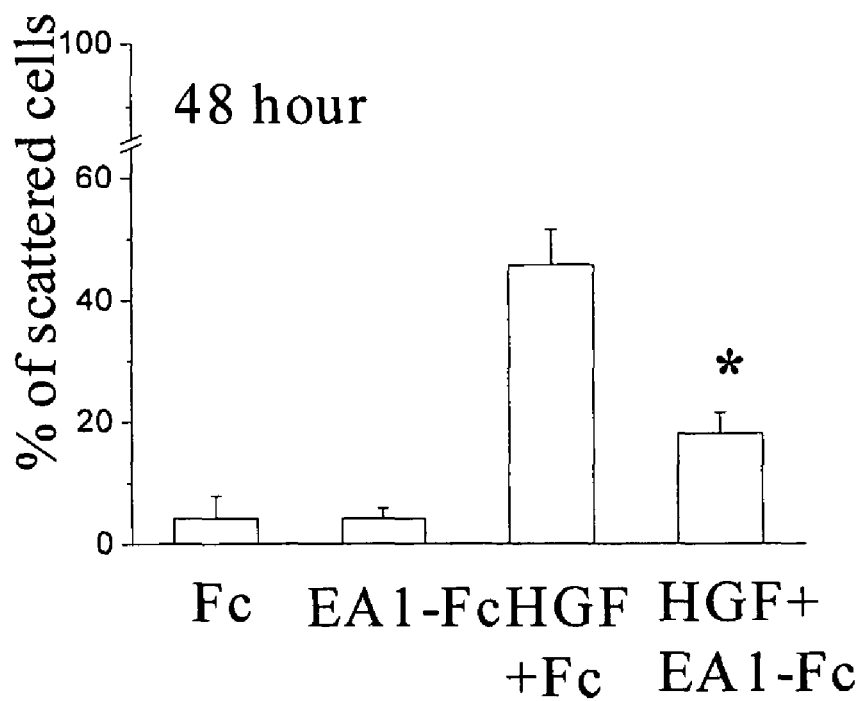

4. EphA2 Activation Inhibited DU-145 Cell Scattering Induced by HGF/SF and Preserved E-Cadherin Mediated Cell-Cell Adhesion Tumor cells scattering/detaching from primary tumors is considered as the first step in tumor metastasis. In addition to promoting cell migration and invasion, HGF/SF is known to disrupt cell-cell adhesion mediated by E-cadherin, induce epithelial-mesenchymal transition (EMT) and cause cell scattering. Therefore, we examined the effects of EphA2 activation on EMT and scattering induced by HGF/SF. DU-145 cells were treated with Fc (control) or ephrin-A1-Fc in the presence or absence of HGF/SF. Cell morphology was recorded 24 and 48 hours after the addition of stimuli (FIGS. 4A and B). In control Fc-treated cells, only about 5% of cells were found as individual cells with no direct contact with neighboring cells, while remaining cells aggregate to form colonies with typical epithelial morphology. Ephrin-A1-Fc treatment consistently induced more compact cobblestone morphology (FIG. 4A). Following 24 hour HGF treatment, most of cells underwent EMT characterized by detachment from each other and transformation into spindle-shaped fibroblastic morphology. However, in the presence of ephrin-A1-Fc cell-cell contact was significantly retained; the fraction of scattered cells was reduced from 95% to 15% accompanied by a more rounded morphology compared with cells treated HGF and Fc. This change of morphology persisted for 48 hours (FIG. 4A right panel and FIG. 4B lower panel). Thus ephrin-A1-Fc significantly suppressed HGF-induced EMT in DU-145 cells.

Figure 5A:
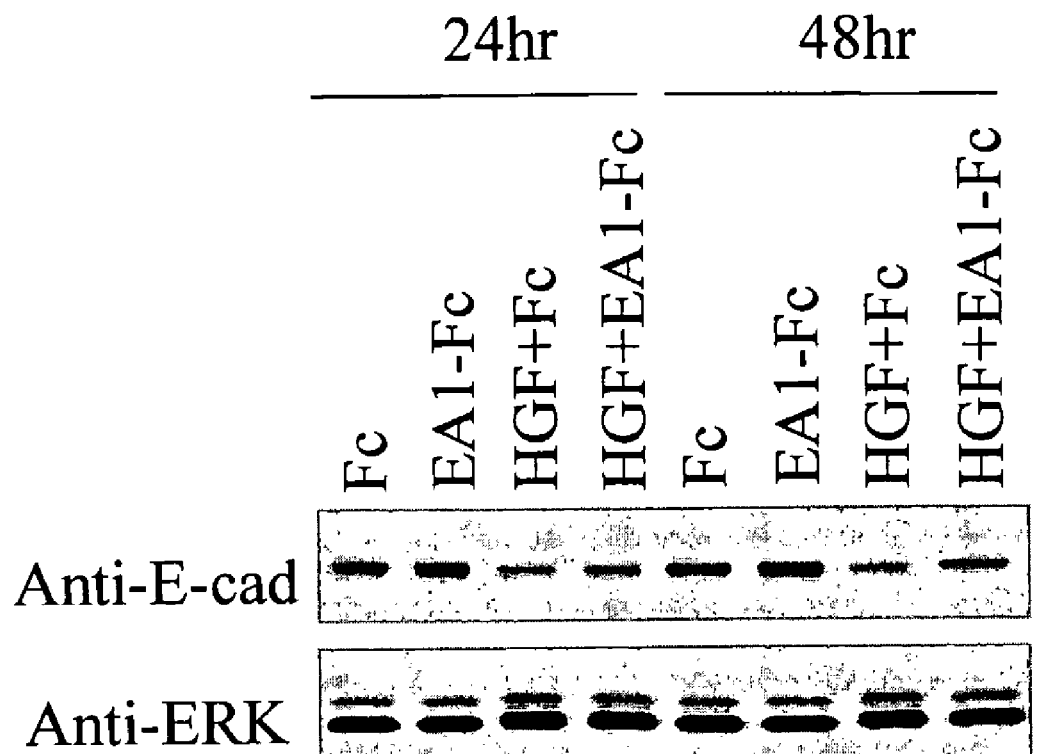
FIG. 5. (A) Ephrin-A1 co-stimulation inhibited the loss of E-cadherin induced by HGF/SF. DU-145 cells were treated as indicated for 24 or 48 hours. Cell lysates were subject to anti-E-cadherin immunoblot. Same membrane was stripped and blotted with anti-ERK1 as loading control. Relative intensity of E-cadherin=intensities of E-cadherin band/intensity of ERK band. (B) Immunofluorescent staining of E-cadherin after 24 hours of the indicated treatment. Note almost exclusive cytoplasmic staining pattern in HGF/SF treated cells, while cotreatment with ephrin-A1 restored significant levels of E-cadherin at cell-cell junction. (C) Ephrin-A1-Fc pre-treatment preserved E-cadherin expression in HGF/SF treated cells. DU-145 cells were pre-treated with Fc or ephrin-A1-Fc for 24 hours. HGF/SF was then added. The cells were cultured for another 24 hours and lysed for anti-E-cadherin immunoblot. Anti-ERK1 was used as loading control. (D) Cells grown on cover slips received same treatment as in C were subject to anti-E-cadherin immunofluorescence analysis. Note the significant preservation of E-cadherin localization at cell-cell adhesion site by ephrin-A1-Fc compared with Fc control. (E) Numbers of total cells and cells without contact with other cells were counted in 6-8 randomly chosen fields. * Fc/HGF/SF vs. ephrin-A1-Fc/HGF/SF: $p=4.6\times10^{-7}$.
Figure 5A:
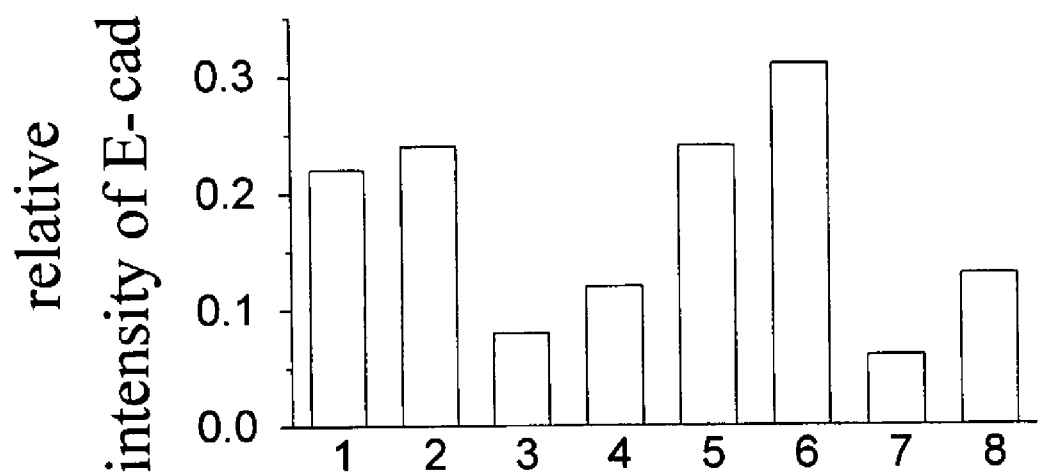
Figure 5B:
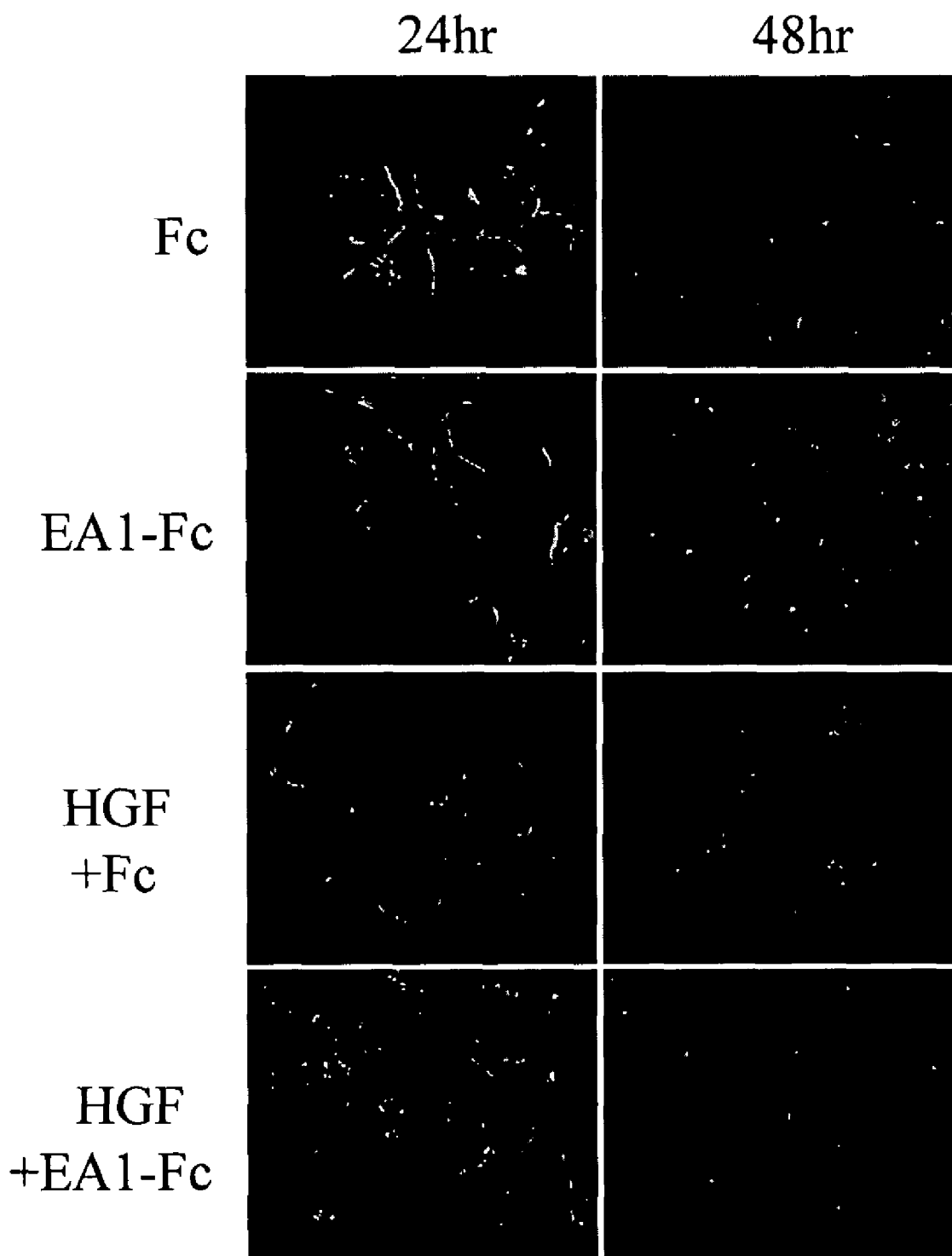

It has been reported that HGF/SF induces E-cadherin degradation in prostate cancer cells, which in turn contributes to its cell scattering effect. We next examined the changes in E-cadherin expression in cells stimulated with HGF/SF, ephrin-A1-Fc or both. Ephrin-A1-Fc treatment moderately increased E-cadherin expression (FIG. 5A, lanes 1 vs. 2 and 5 vs. 6). In agreement with previous reports, HGF/SF treated cells lost most E-cadherin (lanes 3 and 7). When HGF/SF and ephrin-A1-Fc were added together, E-cadherin was significantly preserved when compared with HGF/SF treated cells (lanes 3 vs. 4 and 7 vs. 8). To further verify this result, an immunofluorescence staining was carried out. As shown in FIG. 5B, E-cadherin resided at cell-cell junction in Fc and ephrin-A1-Fc treated cells as expected. In HGF/SF treated cells, E-cadherin staining showed largely cytosolic pattern at 24 hours, which persisted to 48 hours Note that in some HGF/SF-treated cells, E-cadherin disappeared from the cell-cell junctions even in those cells that remained juxtaposed to each other. When ephrin-A1-Fc was added together with HGF/SF, E-cadherin expression at cell-cell junctions was dramatically retained in comparison with HGF/SF/Fc treated cells. This contrasts with immunoblot results (FIG. 5A), where only a moderate increase in E-cadherin level was detected. Therefore, while HGF/SF/ephrin-A1-Fc cotreatment moderately prevents the loss of total cellular E-cadherin, it dramatically preserves the localization of E-cadherin at cell-cell adhesion sites.

Figure 5C:
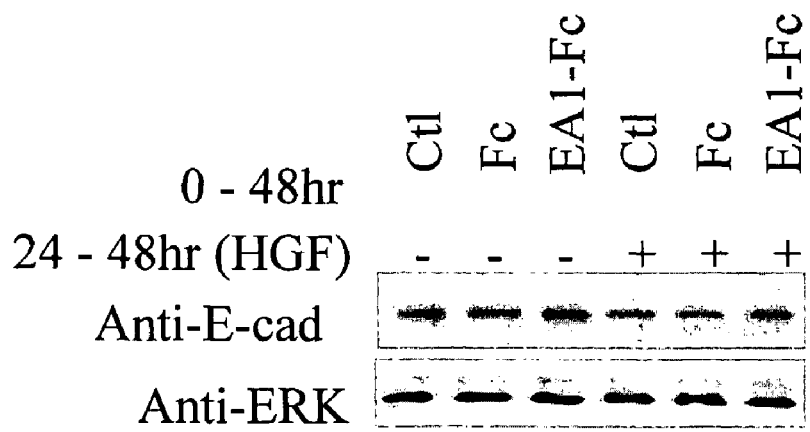
Figure 5C:
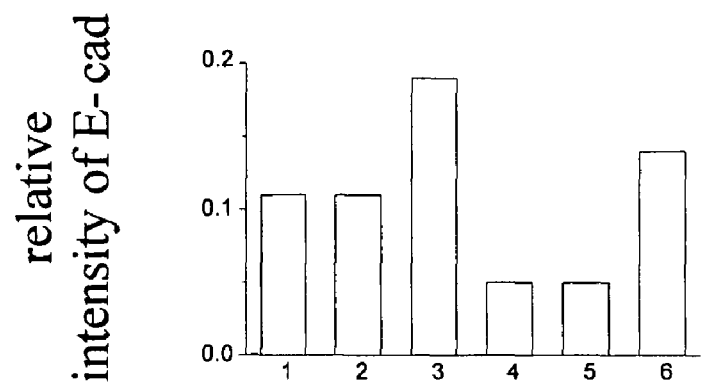
Figure 5D:
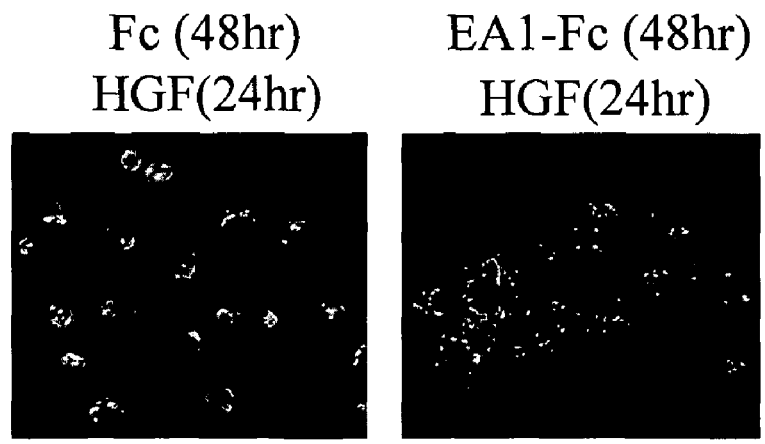
Figure 5E:
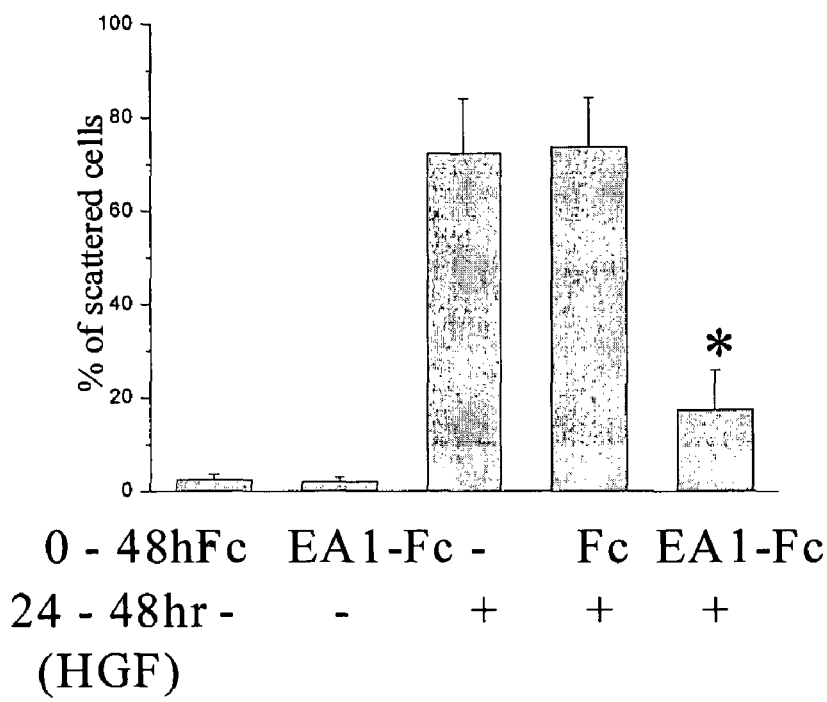

To test if ephrin-A1 can serve as a preventative measure to reduce cell scattering and EMT induced by HGF/SF, we pretreated DU-145 cells with Fc or ephrin-A1-Fc for 24 hours before HGF/SF was added for additional 24 hours. At the end of treatment, immunoblot (FIG. 5C) was carried out to detect E-cadherin expression. Ephrin-A1-Fc treatment increased E-cadherin expression at 48 hours in comparison with Fc treatment (lanes 2 vs. 3), whereas HGF/SF decreased E-cadherin expression (lanes 2 vs. 5). More importantly, pretreatment with ephrin-A1-Fc significantly prevented HGF/SF-induced down-regulation of total cellular E-cadherin (FIG. 5C, lanes 5 vs. 6), to a greater extent than cells exposed to both ephrin-A1 and HGF/SF at the same time (FIG. 5A, lanes 3 and 4, or 7 and 8). Similar to cells co-treated with HGF and ephrin-A1-Fc (FIG. 5B), immunofluorescence staining revealed that significant fraction of E-cadherin was retained at cell-cell junction (FIG. 5D). Our results indicate that EphA2 activation can be used as a preventive measure to reduce metastasis by preserving E-cadherin expression and inhibiting EMT.

5. Materials and Methods

A. Cells and Reagents

CWR22R, PC-3, and LNCaP cells were cultured in RPMI medium (GIBCO) supplemented with 0.29 mg/ml glutamine, 100 µg/ml streptomycin, 100 units/ml penicillin (GIBCO), and 10% fetal bovine serum (HyClone). DU-145 cells and rat prostate cancer cells (G, AT-1, MatLu, and MatLyLu) were maintained in DMEM medium containing same supplements as in RPMI medium. HGF/SF, and goat anti-EphA1, EphA4, ephrin-A1, ephrin-A2, and ephrin-A4 were purchased from R&D Systems. Fc and Ephrin-A1-Fc were prepared as previously described. Rabbit anti-EphA2, rabbit anti-human c-Met, mouse anti-phosphotyrosine (PY99), mouse anti-phospho ERK (p-ERK), rabbit anti-ERK and horse radish peroxidase (HRP)-conjugated goat anti-mouse IgG were purchased from Santa Cruz. Mouse anti-E-cadherin was purchased from Transduction Laboratory Rabbit anti-EphA3 was a gift from Dr. E. Pasquale. HRP-conjugated Protein A, Texas Red-conjugated goat anti-rabbit IgG and FITC-conjugated rabbit anti-mouse IgG were from Jackson ImmunoResearch.

B. Immunofluorescence

Cells were cultured on cover slips in 24-well dishes for 24 hours, fixed in 4% formaldehyde for 20 minutes and permeabilized with 0.5% NP-40 for 10 minutes. Blocking was performed using blocking solution containing 2% BSA and 2% goat serum in PBS. Subsequently, cells were incubated with 1 µg/ml anti-EphA2 or anti-E-cadherin antibody. A Texas Red-conjugated goat anti-rabbit IgG or FITC-conjugated rabbit anti-mouse IgG was used to visualize the primary antibodies. Vector-Shield mounting solution containing DPI (Vector Laboratories) was used to mount the cover slips onto slides.

C. Cell Stimulation, Immunoprecipitation, and Immunoblotting

Cells cultured in 6 well plates at 70-80% confluence were stimulated with 0.5 µg/ml Fc, 1 µg/ml ephrinA1-Fc or 20 ng/ml HGF/SF or their combinations as indicated. After stimulation, cells were lysed in RIPA buffer (20 mM Tris, pH7.4, 125 mM NaCl, 20 mM NaF, 0.1% SDS, 10% glycerol, 0.5% sodium deoxycholate, and 1% TX-100, 0.5 mM $Na_3VO_4$) containing protease inhibitors (1 mM phenylmethylsulphonyl fluoride, and 2 µg/ml each of aprotinin and leupeptin). Cell lysates were clarified by centrifugation at 13,000 rpm for 5 min. Immunoprecipitation was carried out by adding anti-EphA2 antibody to clarified cell lysates and incubated for 1 hour at 4° C. The immunocomplex was captured using γ-bind beads (Pharmacia). Cell lysates or precipitated proteins were separated on 4-20% Tris-glycine gels (Invitrogen) and transferred to Immobilon-P PVDF membranes (Millipore). Membranes were blotted according to manufacturer's suggestion. For quantitative analysis, band densities were measured using KODAK ID imagine analysis software (Eastman Kodak Company).

D. Immunodepletion

Cell surface proteins were labeled with biotin using ImmunoPure NHS-LC-Biotin (Pierce) according to manufacturer's suggestion. Cells were lysed in RIPA buffer and an EphA2-specific antibody was used to remove EphA2 molecules from cell lysates by repeated immunoprecipitation. The specificity of the antibody was verified using EphA2 knockout mice, where EphA2 but not other EphA kinases was absent from homozygous embryonic tissues (not shown). EphrinA1, which recognized all members of EphA kinases, was then used to precipitate the remaining EphA kinases. Avidin immunoblot was carried out to detect the presence of ephrinA1-precipitated EphA kinases in the cell lysates with or without prior EphA2 depletion.

E. Cell Migration and Invasion Assay

Modified Boyden chambers of 8 µm pore size (Costar) were used for migration assay. Both sides of the membranes were coated with 10 µg/ml collagen at 4° C. overnight. Serum free medium containing 20 ng/ml HGF/SF and/or 1 µg/ml ephrin-A1-Fc was added to the lower chamber, while $10^5$ cells in 100 µl RPMI containing 0.5% BSA were placed in the upper chamber. After incubating at 37° C. for 8 hours, cells were fixed in 4% paraformaldehyde and stained with crystal violet. The cells remaining in the upper chamber were removed using cotton swabs. Cells migrated to the underside of the membrane were counted under 200× magnification.

For invasion assay, the upper chamber was coated with 50 µg of growth factor-reduced MatriGel (BD) according to manufacturer's instructions. The same procedure as in migration assay was followed, except that the cells were allowed 24 hours to migrate to the underside of the membranes.

F. Wound Healing Assay

A wound was generated by scratching the monolayer of confluent DU-145 cells using a micropipette tip. The cells were then washed twice with culture medium and imagines of the wounds were taken immediately at marked area using Leica DMIRE2 microscope. Fc or ephrin-A1-Fc in the presence or absence of HGF/SF were then added to the culture medium and cells were cultured for 12 hours. Imagines of the same areas were taken again at the end of incubation.

G. Scattering onto Immobilized Ligand (SOIL) Assay

The SOIL assay was performed essentially as described. Briefly, ephrin-A1-Fc (4 µg/ml) or Fc (2 µg/ml) was coated on 6-well culture dishes overnight at 4° C. and the wells were washed with PBS. DU-145 cells were grown on cover slips in 24-well dishes to near confluence. Cover slips were transferred cell-side-up onto the coated 6-well dishes containing 1.5 ml culture medium with or without HGF/SF. Cover slips were gently pressed down with pipette tips. After 48 hours, cells were fixed with 4% paraformaldehyde for 20 min and stained with crystal violet. Cover slips were removed, and the rings of cells that have scattered and migrated onto the immobilized Fc or ephrin-A1-Fc were photographed.

Example 2

Identification and Characterization of Peptide Agonists of EphA2 Kinase

1. Phage Peptide Display Library Technology

Figure 6:
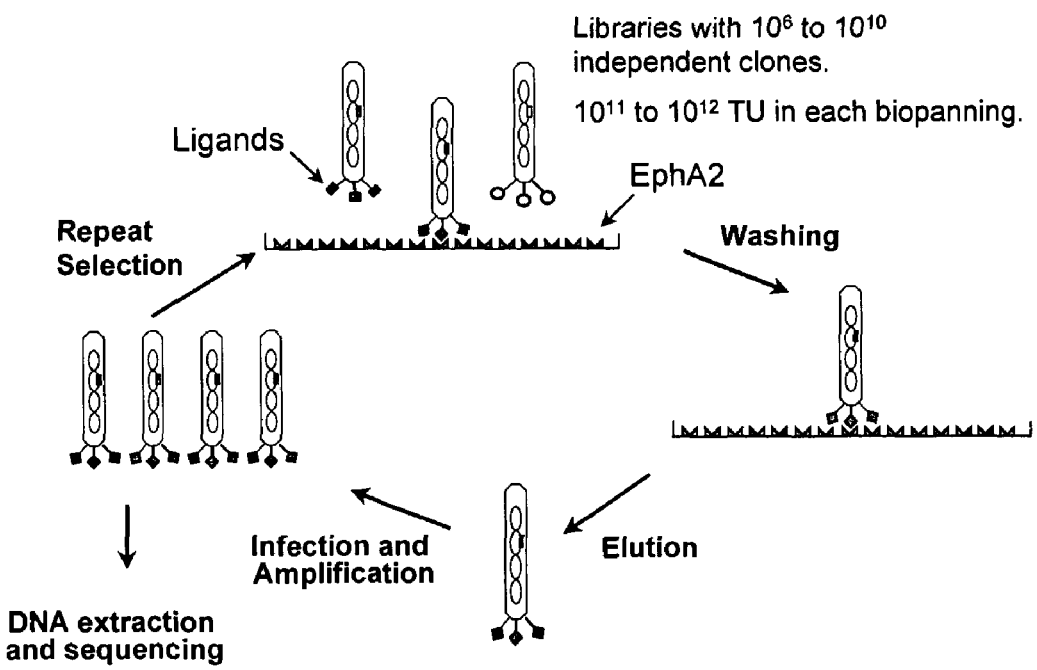
FIG. 6. Schematic illustration of phage display technique that was used to isolate the EphA2-binding peptides.
Figure 7A:
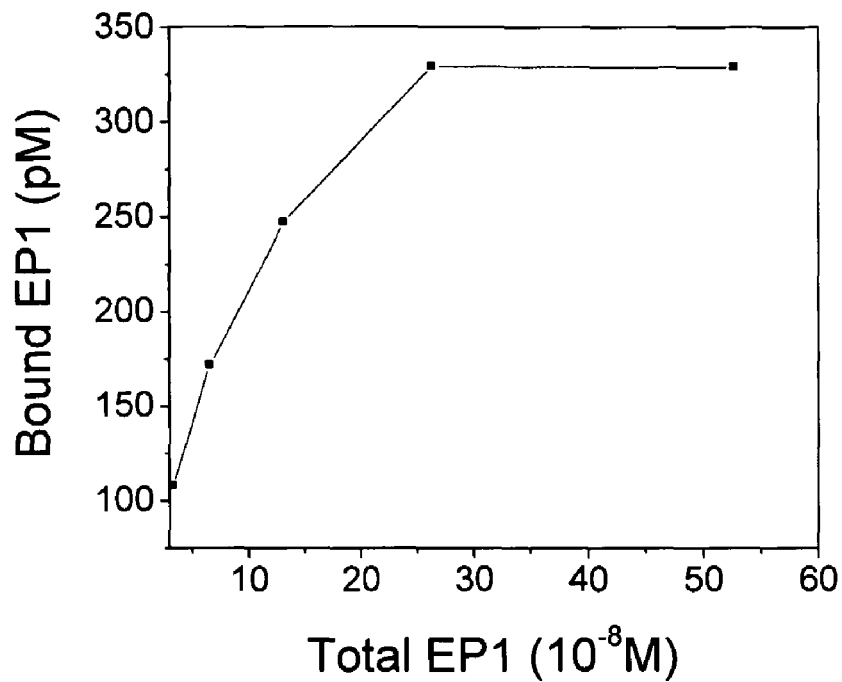
FIG. 7, Kinetics of EP1-Fc Binding to EphA2 Receptor on Cell Surface. 96-well Removawell were coated with 1 mg/mL EphA2-Fc. $^{125}$I-labeled 14-3-3 proteins were allowed to bind to the wells in the presence of serially diluted unlabeled EP1-Fc starting with a 500-fold molar excess. Bound material was counted (left). Data were subject to Scatchard analysis (right). Each data point represents the mean from duplicate wells with variation of less than 10%.
Figure 7B:
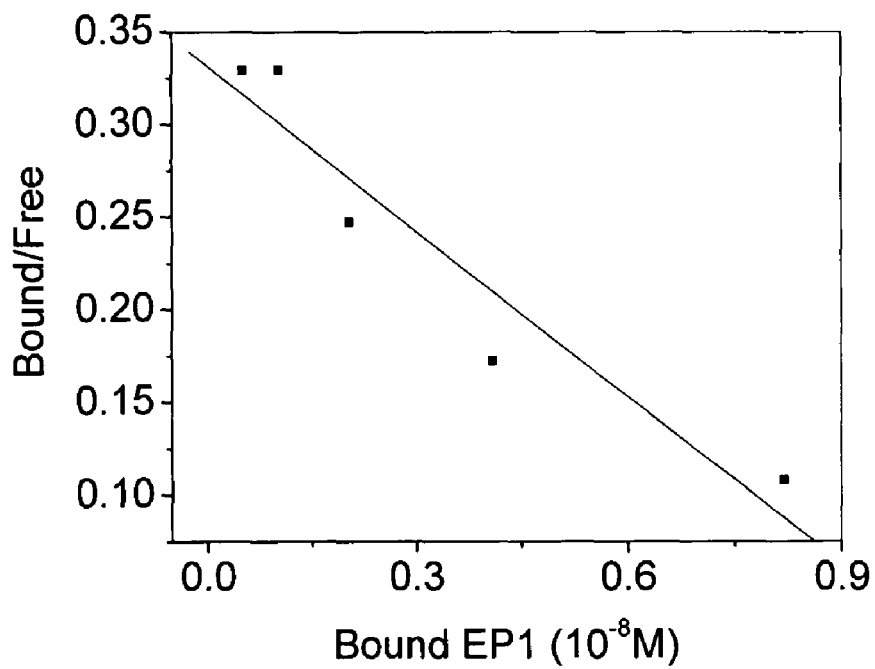
Figure 8A:
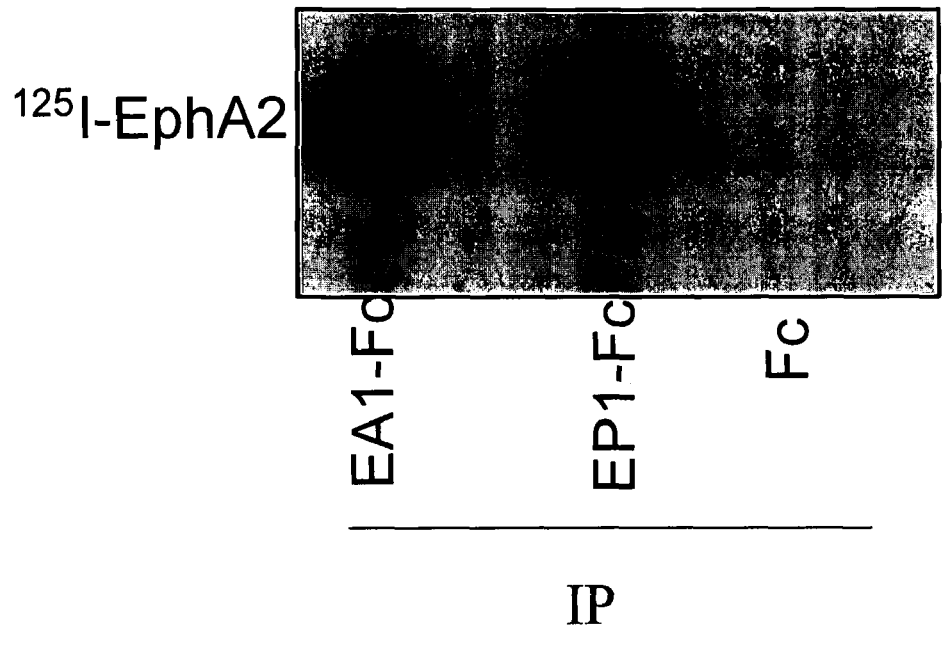
FIG. 8. Specific Binding of EP1-Fc to EphA2 Receptor. A: $^{125}$I labeling of PC3 cells. PC3 cells ($10 \times 10^6$) were labeled with 125I (0.5 mCi). Then, cell lysates were incubated with EP1-Fc fusion peptide, ephrin-A1-Fc (EA1-Fc), or human Fc as indicated. Equal amount of cell lysate was used in each experimental group. EP1-Fc only bound to EphA2. B: Western Blotting Analysis. PC3 cell lysates were incubated with EP1-Fc fusion protein, ephrin-A1 protein, or human Fc. The immune complexes were blotted with anti-EphA2. EP1 specifically precipitated EphA2.
Figure 8B:
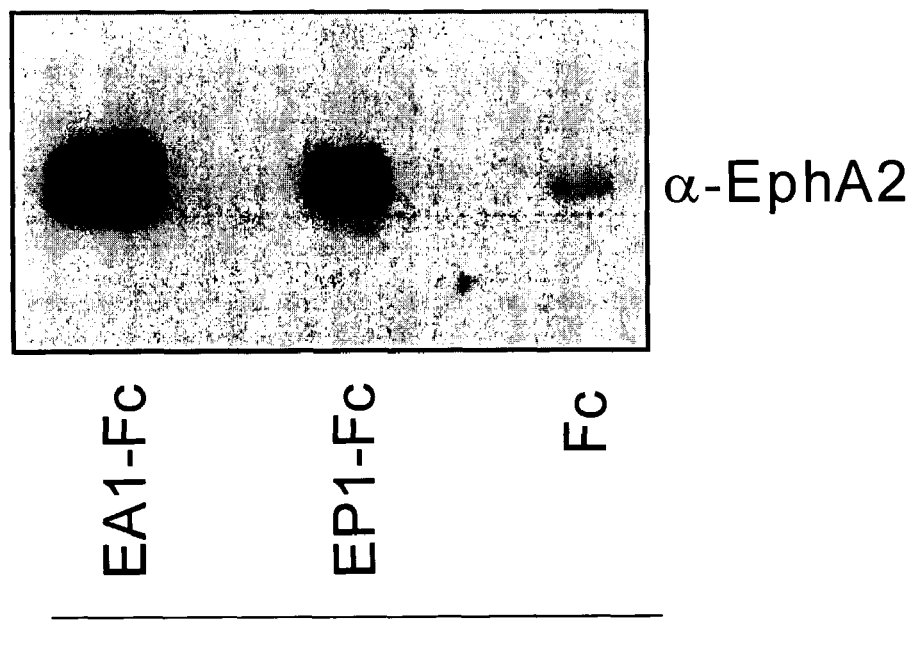
Figure 9:
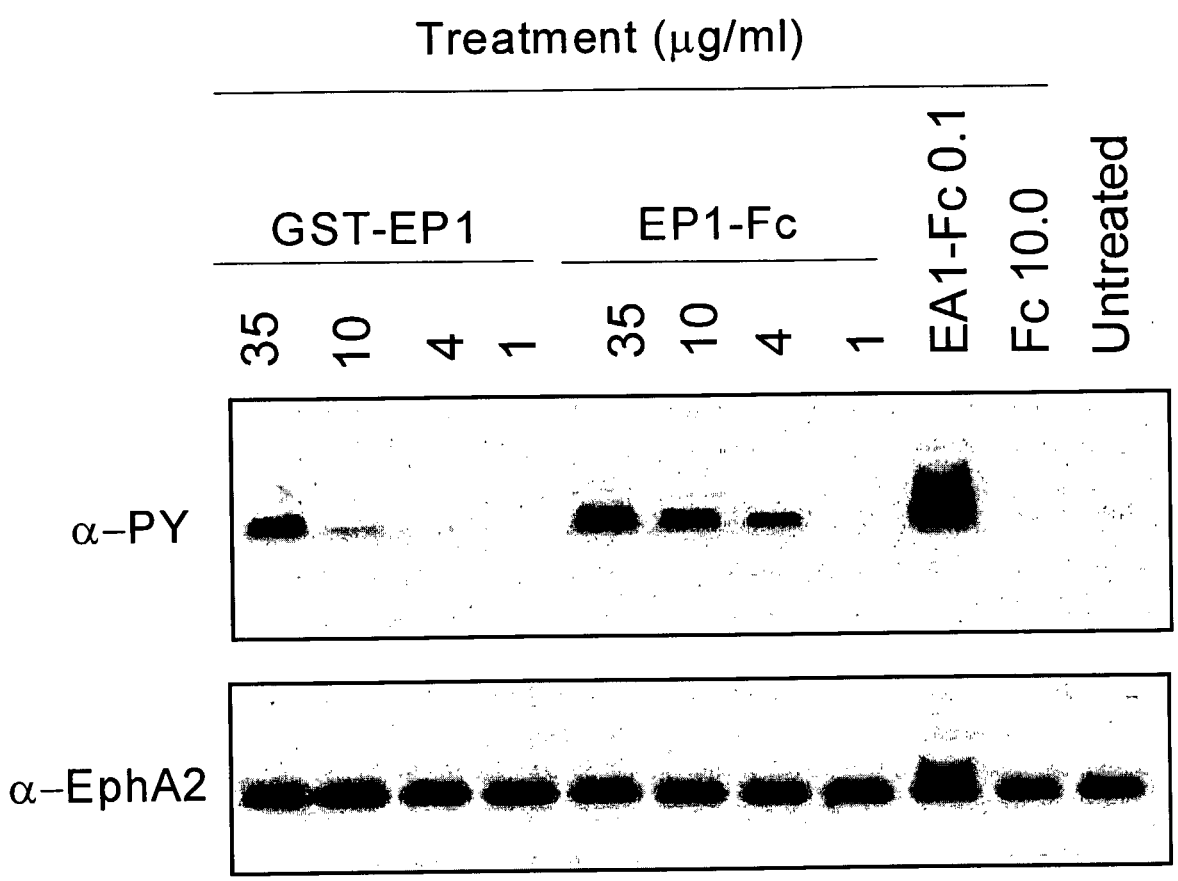
FIG. 9. EP1 is an EphA2 Kinase Agonist. PC3 cells ($1 \times 10^6$ cells/ml) were stimulated with different concentrations of EP1-Fc, GST-EP1, or ephrin-A1-Fc for 10 min. EphA2 was precipitated with anti-EphA2. The immune complex was blotted for PY to detect EphA2 activation (top panel), or for EphA2 to show equal loading (lower panel). Data represents one of three similar experimental results.
Figure 10:
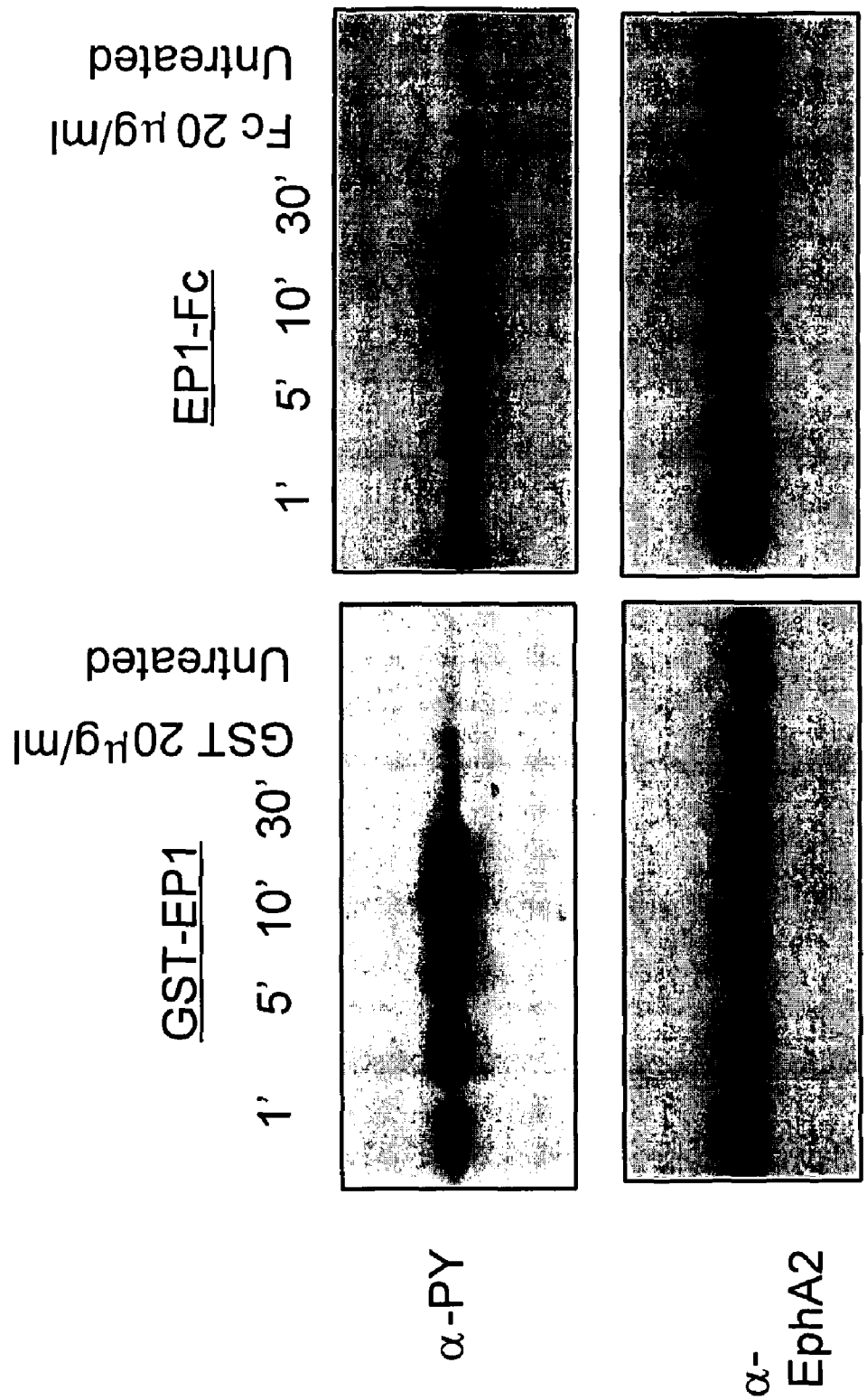
FIG. 10. Time Course Induction of Tyrosine Phosphorylation of EphA2 Receptor by EphrinA1-Fc Fusion Protein. PC3 cells were stimulated with 1 mg/ml ephrinA1-Fc for different periods of time as indicated. After stimulation, cell lysates were made and were incubated with ephrinA1-Fc fusion protein (2 mg EphrinA1/100 mg cell lysate) for 1 hr at 4° C. EphA2 receptor-ligand complex was precipitated with g-bind beads and subjected to Western blotting analysis. Upper panel protein bands were detected by a monoclonal antibody against phosphorylated tyrosine residue and represented the protein tyrosine phosphorylation of EphA2 receptor. Lower panel protein bands were detected by a polyclonal antibody against Eph-A2 receptor and demonstrated a equal amount of protein was loaded on SDS gel. Data represents one of three similar experimental results.
Figure 11:
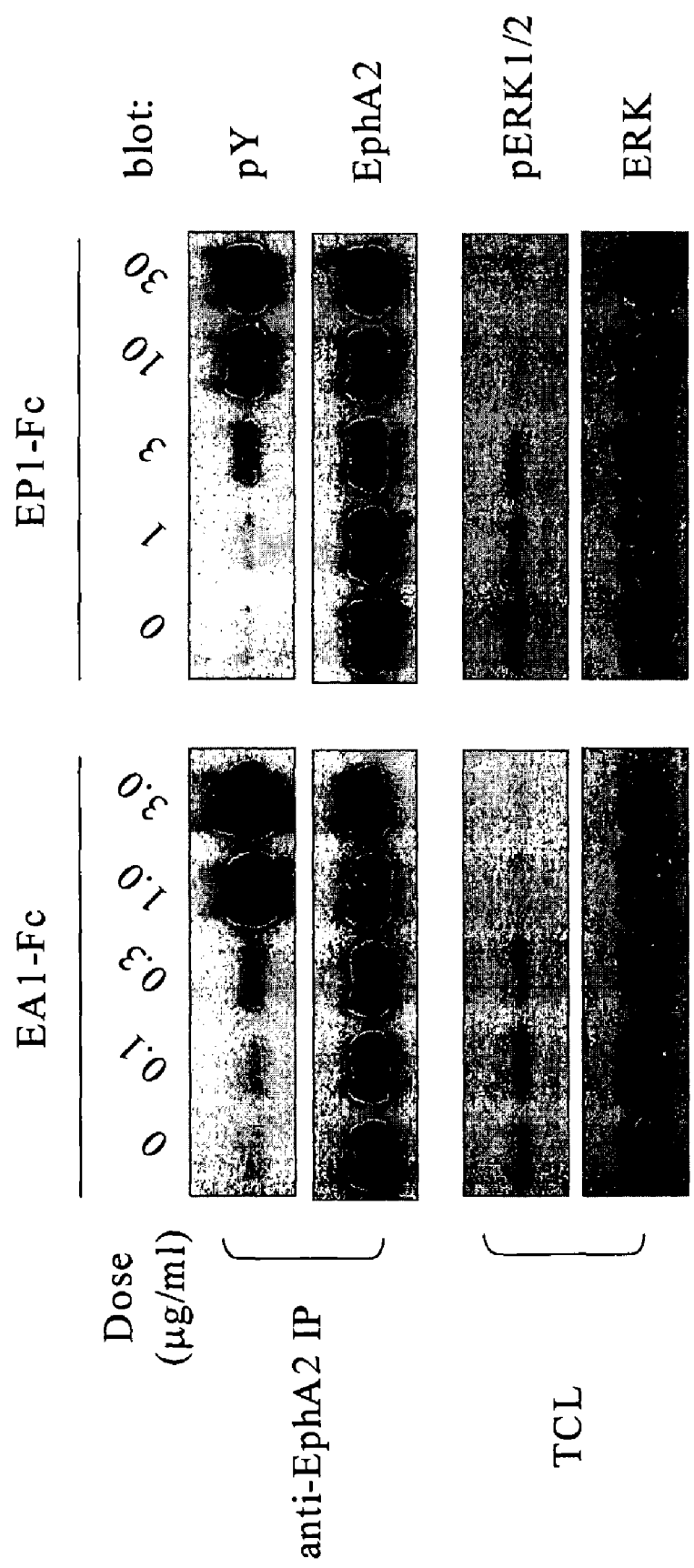
FIG. 11. Activation of EphA2 downstream signaling by EP1-Fc. PC3 cells were stimulated with the indicated concentrations of ephrinA1-Fc or EP1-Fc fusion proteins and lysed in RIPA buffer. EphA2 activation status was examined by immunoprecipitating EphA2 and blotting for phosphotyrosine or EphA2 itself (top panel). Inhibition of ERK1/2, a downstream signaling event of EphA2 characterized in our lab, was examined by blotting total cell lysates with anti-p-ERK1/2.
Figure 12:
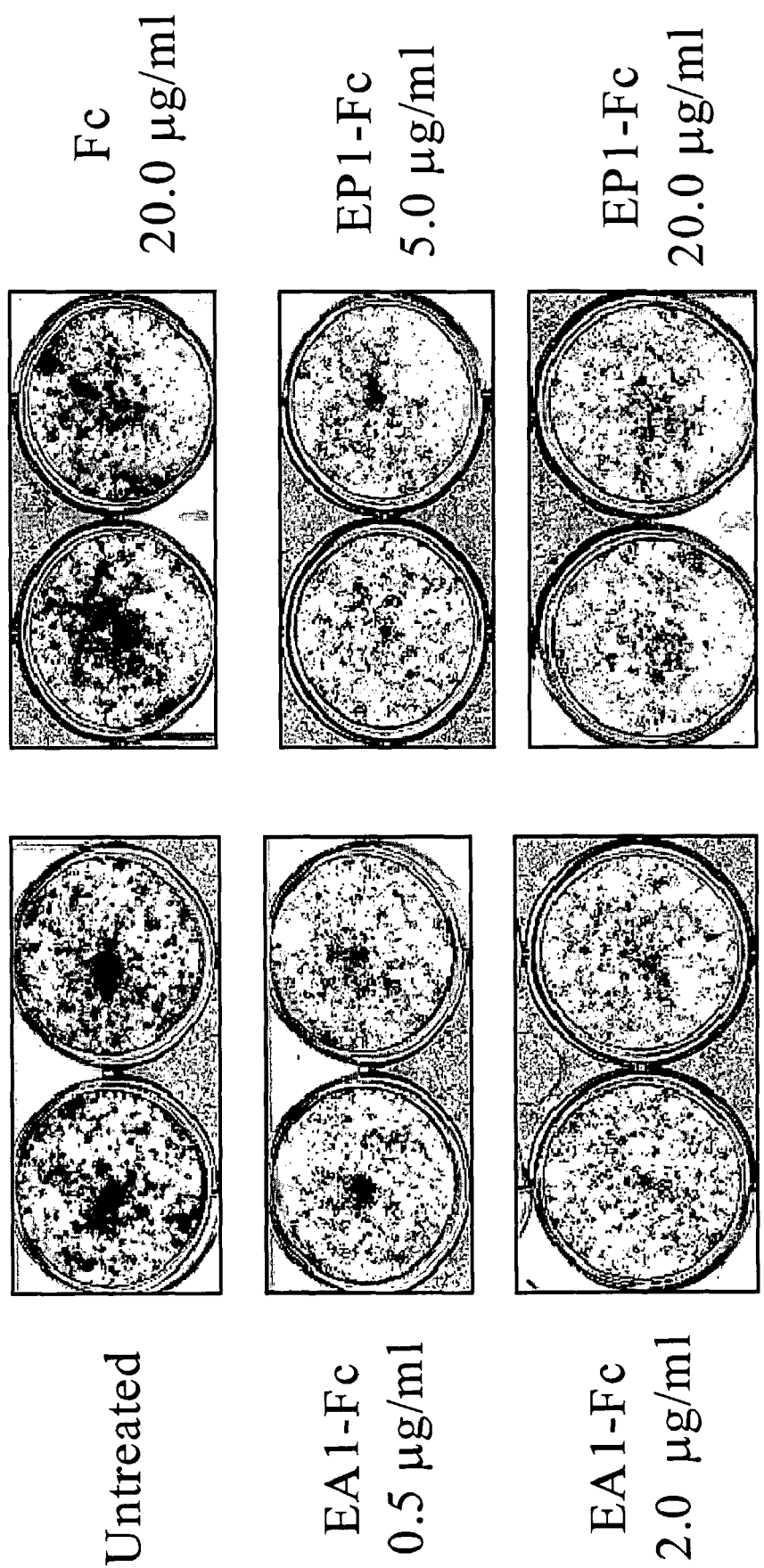
FIG. 12. Inhibition of cell growth by EP1-Fc. About 80 pRNS-1 prostate epithelial cells were seeded into each well on 12-well dishes in the presence of indicated concentrations of ephrin-A1-Fc. Cells were cultured for 10 days. Clonal growth was visualized by crystal violet staining.
Figure 13:
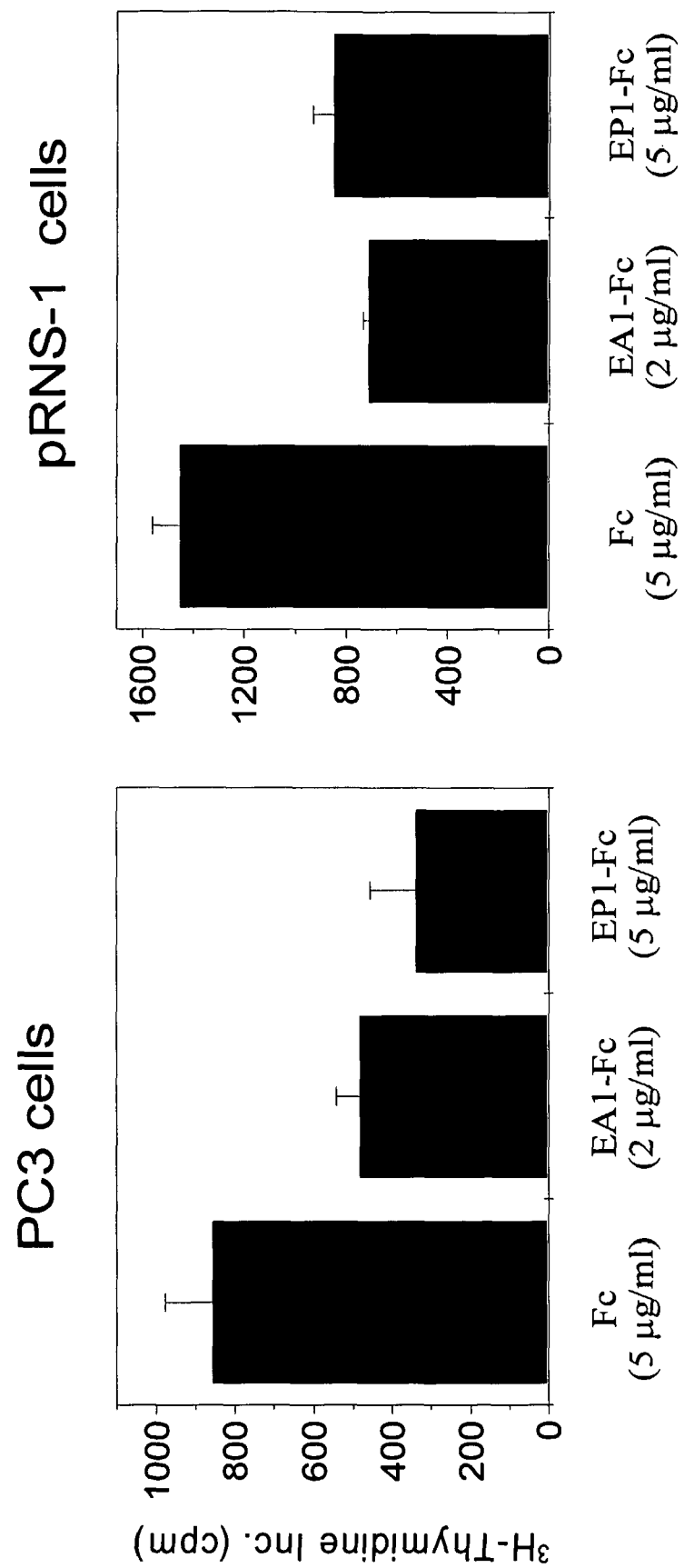
FIG. 13. Inhibition of cell proliferation by EP 1-Fc. Subconfluent PC3 or pRNS-1 cells were stimulated with the indicated reagents overnight. Next day cells were labeled with $^3$H-thymidine for 2 hours. $^3$H-thymidine incorporation into isolated DNA synthesis was determined by scintillation counting.
Figures 14, 15:
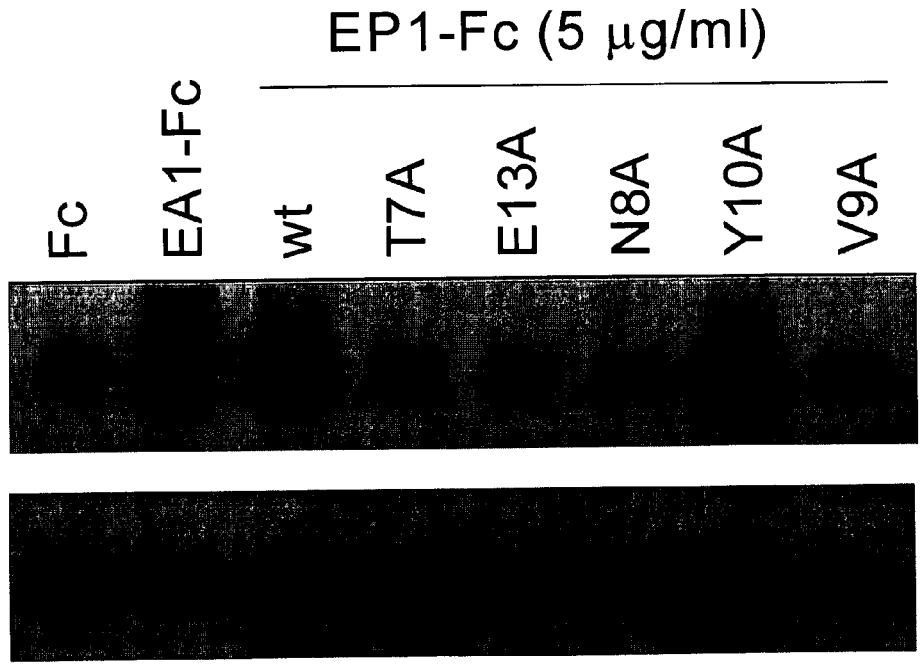
FIG. 14. EP1 and EP2 peptides have sequence similarities to ephrins. Letters underlined in ephrin-A1 and ephrin-B2 indicate major receptor binding residues. Letters underlined in EP1 represent residues that were systemically mutated into alanines to determine the effects on EphA2 binding and activation (see FIG. 15).
FIG. 15. Identification of EP1 residues critical for EphA2 activation. Four out of five EP1 residues that align with receptor-binding regions of ephrins are critical for EphA2 activation. Mutation to alanine was performed at the indicated positions (see letters in FIG. 15 for reference), and the resultant EP 1-Fc mutants were used to stimulate PC3 cells for 10 min at 10 mg/ml for ability to activate EphA2.
Figure 16:
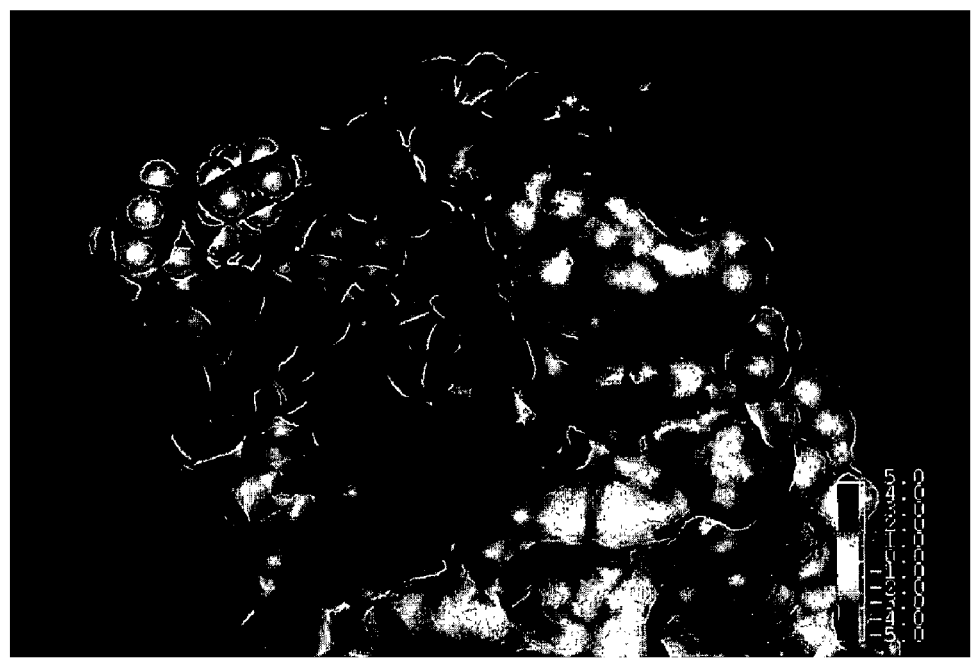
FIG. 16. Predicted binding of EP1 to EphA2 kinase ligand binding domain.
Figure 16:
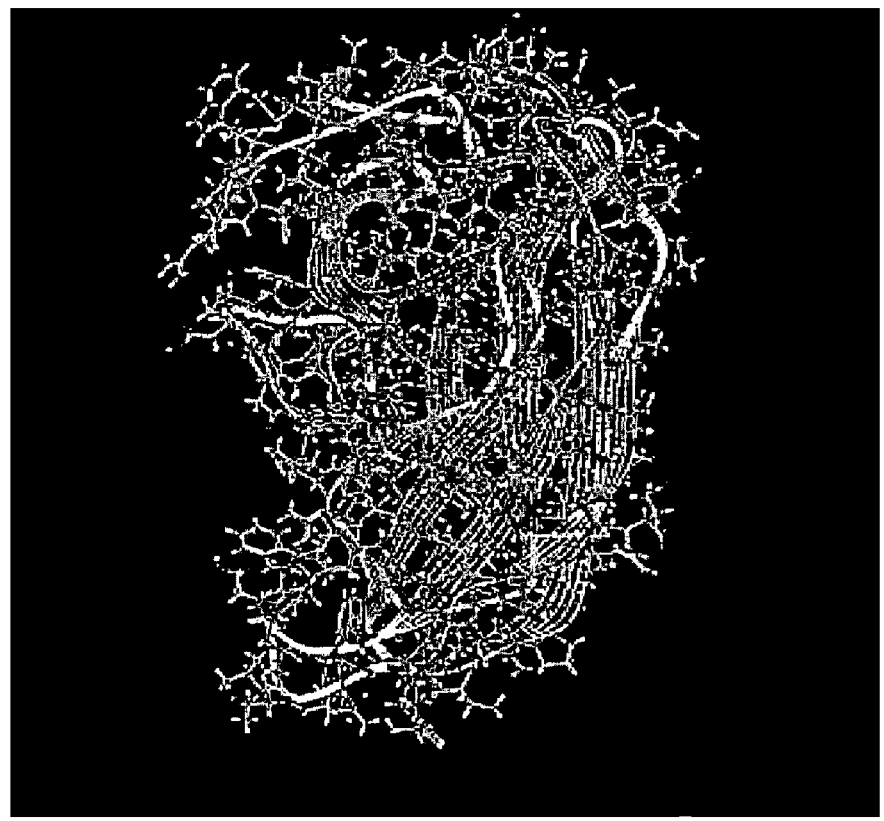
Figure 17:
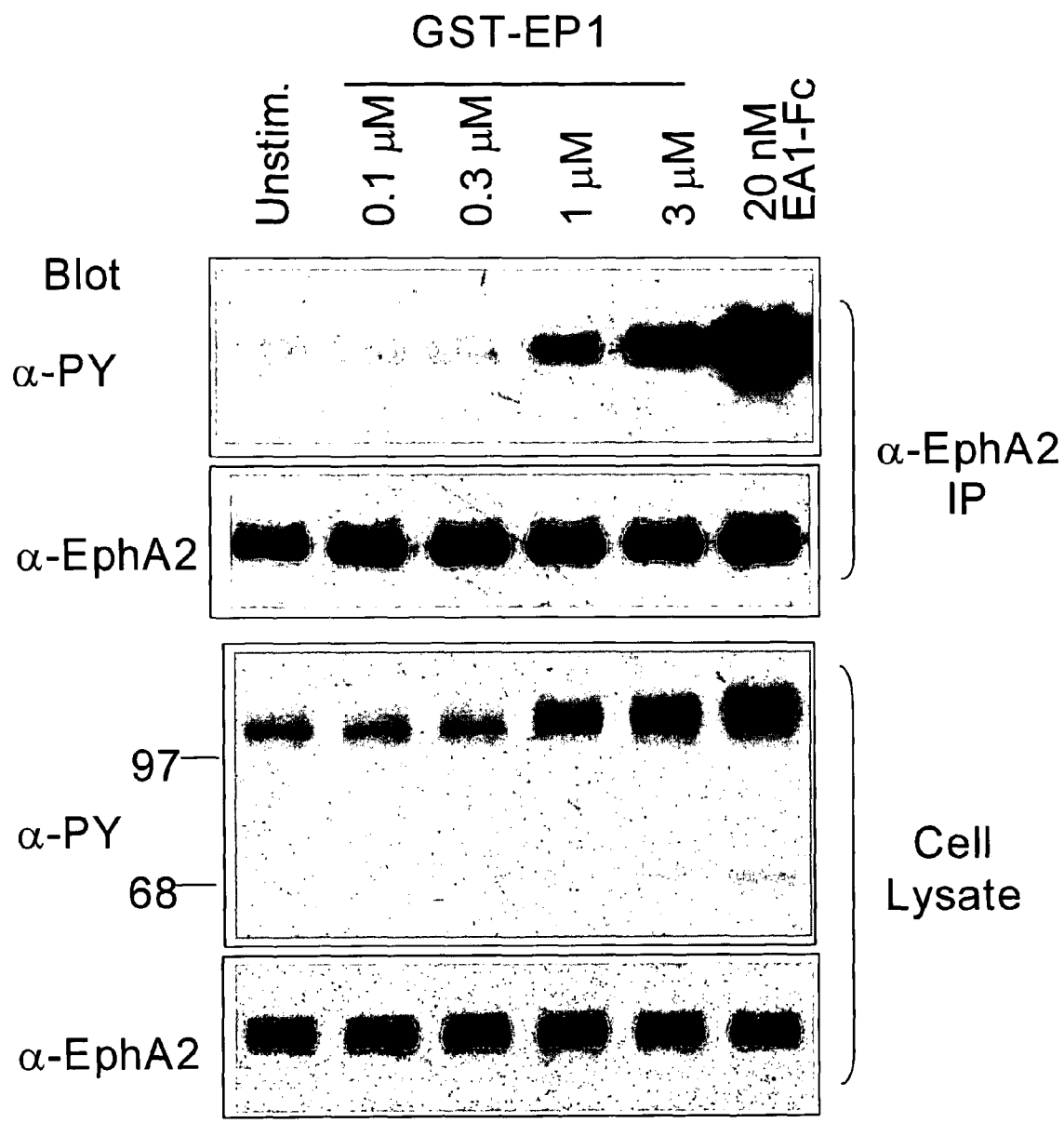
FIG. 17. An agonistic peptide for EphA2 selected from phage display libraries.
Figure 18:
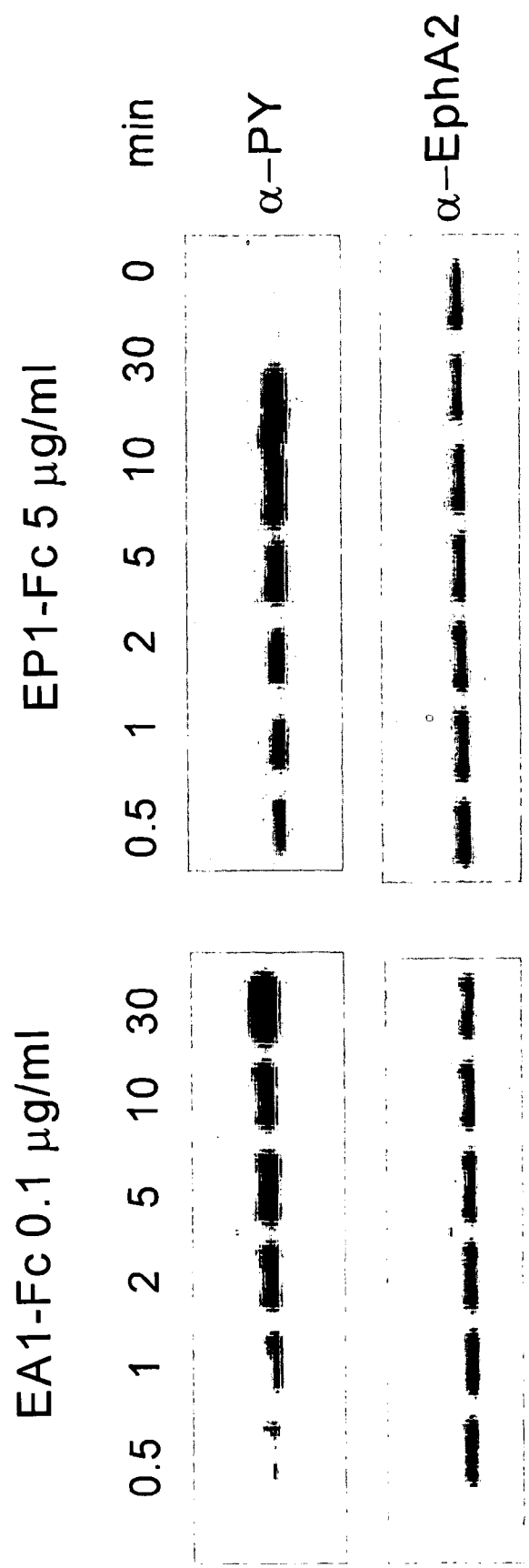
FIG. 18. Time course of EphA2 activation by EP 1-Fc in PC3 cells.
Figure 19:
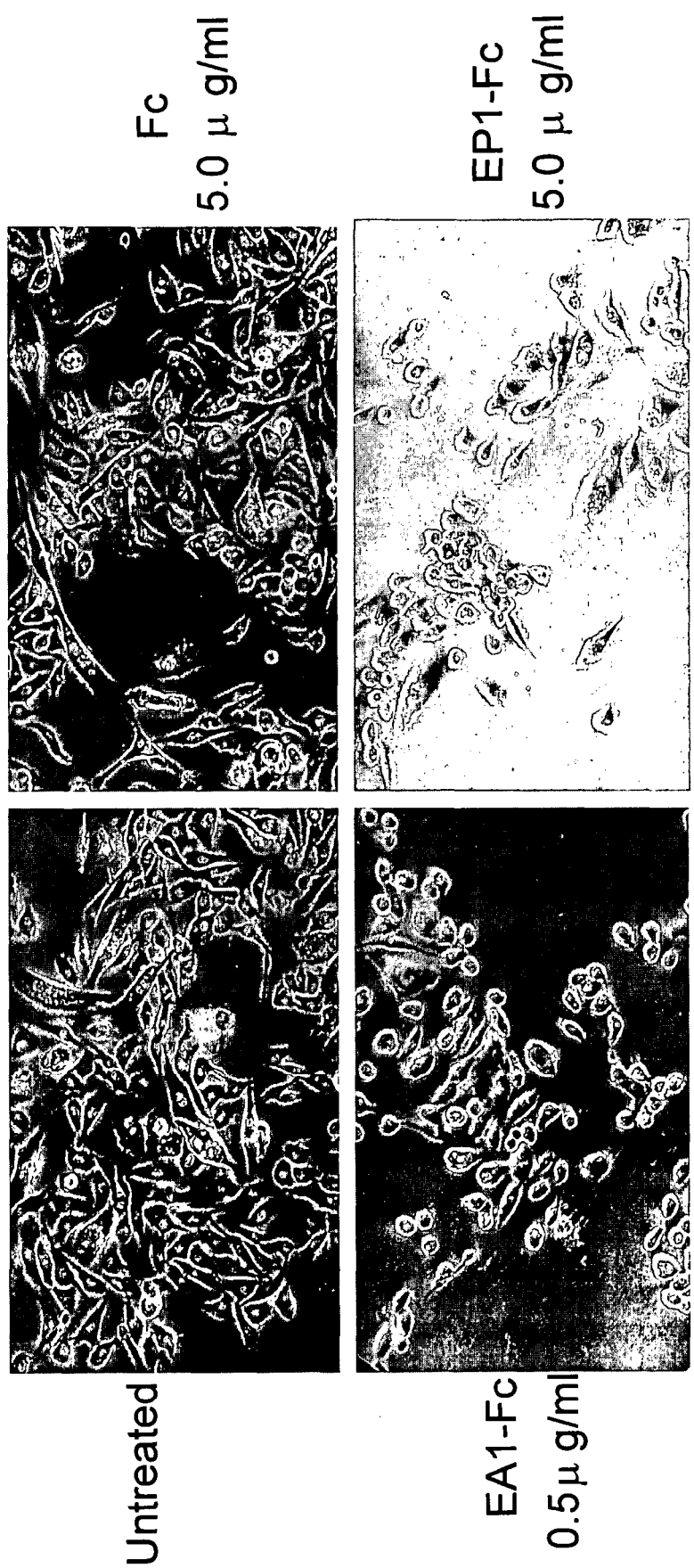
FIG. 19. EP1-Fc induced PC3 cell rounding. PC3 cells cultured on coverslips were stimulated with the indicated concentrations of ephrinA1-Fc, EP1-Fc of Fc for 10 min. Cells were then fixed and photographed.
Figure 20A:
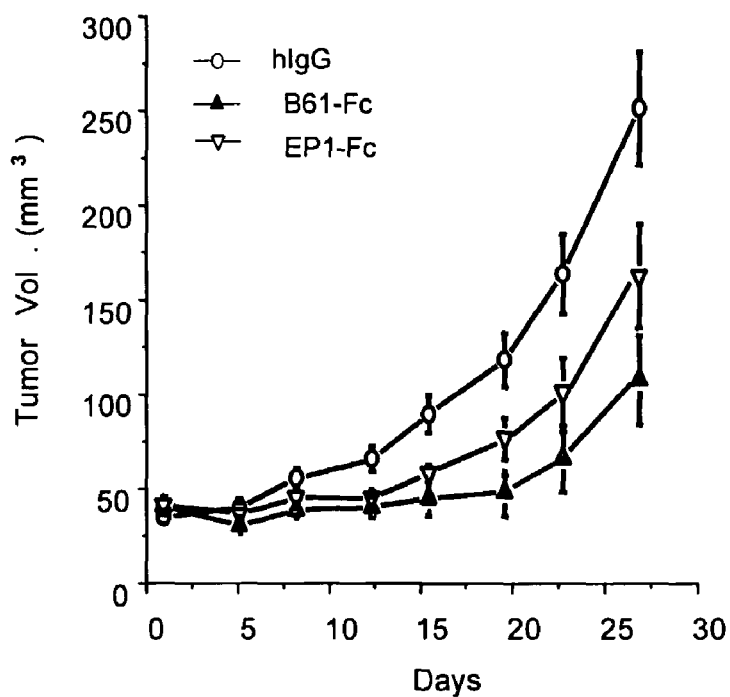
FIG. 20. EP1-Fc has moderate inhibitory effects on PC3 xenograft growth in nude mice. A) Systemic (i.p.) administration of ephrin-A1-Fc (5 mg/g) or EP1-Fc (10 mg/g) inhibited s.c. tumor growth of GFP-PC-3 cells compared with human IgG control (10 mg/g). The lack of effects after three weeks of treatment likely reflects production of anti-ephrin-A-Fc and anti-EP1-Fc antibodies in the recipient animals. B) Both Ephrin-A1-Fc and EP1-Fc, but not human IgG, target to GFP-PC-3 tumors. Frozen sections were stained with biotinylated rabbit anti-human Fc, and HRP-conjugated streptavidin.
Figure 20B:
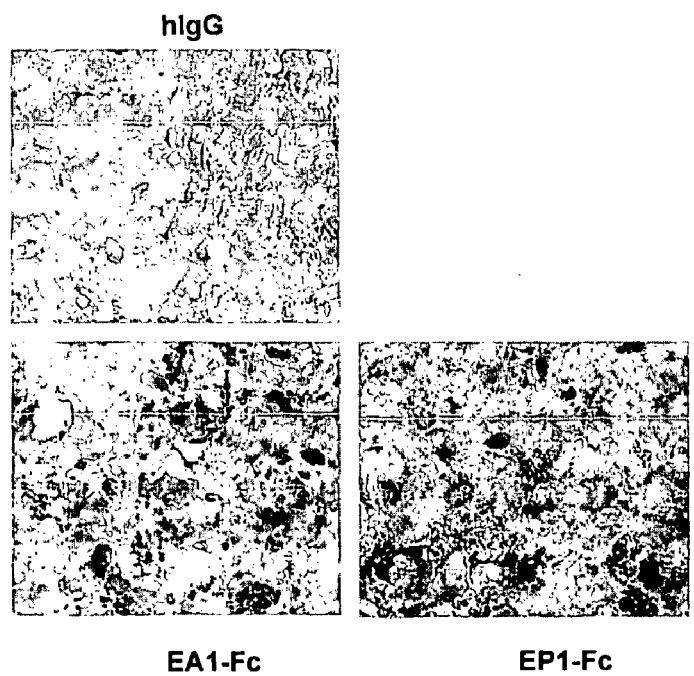

The overall strategy for isolating peptides that bind to target proteins using phage display libraries (Scott and Smith, 1990; Koivunen et al., 1994) is illustrated in FIG. 6. In this powerful technology, random peptide sequences are fused to amino-terminus of pIII coat proteins of M13-derived filamentous bacterial phage by inserting random oligonucleotides into the 5' end of pIII DNA. Libraries containing over 109 peptide motifs can be generated. They are amplified in bacteria and concentrated to 1012-14 phage particles/ml, so that each motif will be represented hundreds of times in a small volume of library for each application. Each phage particle has a copy of single stranded DNA encoding one peptide sequence, and can be readily amplified and sequenced. To isolate peptides that bind to target proteins, phage display libraries are incubated with proteins immobilized on plates. Unbound phage are washed away; bound phage are amplified and used for another round of selection on target proteins. Following such repeated selections, individual clones of phage capable of specific binding to target proteins will be amplified, and insert DNA can be readily sequenced to decipher the displayed peptides.

2. Production of Recombinant Ectodomains of EphA2 and EphB3 Kinases

To produce recombinant EphA2, the entire coding sequences of EphA2 kinase extracellular domain was fused to the heavy chain of human IgG1. The resultant plasmid, pcDNA3-CD5-EphA2-Fc, was transfected into human embryonic kidney cells (293). The attachment of CD5 signal peptide enables secretion of EphA2-Fc chimera into cell culture media, while the disulfide bond formed between the two Fc chains bridges the EphA2-Fc together to form dimers. The recombinant protein was purified from cell culture medium on Protein-A affinity matrix that binds to Fc. EphB3-Fc was produced in the same manner.

3. Affinity Selection

Recombinant EphA2-Fc or EphB3-Fc was coated on 96-well plates at 100 µg/ml overnight at 4° C. Fc fragment alone was used as negative control. Non-specific binding sites were blocked by 1% BSA. In the initial screening, X2CX14CX2 and X2CX18 phage display libraries were used, where C is cysteine and X represents any amino acids. The displayed peptides from X2CX14CX2 library are presumably cyclic due to disulfide bond formed between the two cysteines. Our previous experiences show that biopanning using libraries containing one constant cysteine (such as CX9 or X2CX18 libraries) frequently result in selection of another cysteine, enabling disulfide bond formation within the selected peptides (Wang et al., 1995; Wang et al., 1999). This may reflect better binding affinities of cyclic peptides. For biopanning, about $10^{11}$ transducing units of the phage library were incubated for 4 hr at 25° C. in coated microtiter wells phage biopanning buffer (Tris-buffered saline buffer containing 200 µl of 1% (w/v) BSA). A fixed protein coating concentration (100 µg/ml) was used in the first two biopannings, but in the subsequent biopannings, the recombinant protein was coated at 100- to 10,000-fold lower concentrations to select for high affinity sequences. Phage that remain bound after extensive washing with TBS-0.5% (v/v) Tween 20 were eluted with a low pH buffer (0.1 M glycine buffer, pH 2.2). The eluted phage particles were amplified by infecting F pilus-positive bacteria K91kan. Phage that were secreted into medium were collected from cleared overnight cultures by polyethylene glycol precipitation, and used for subsequent rounds of biopanning.

4. Identification and Characterization of EphA2-Binding Peptides

TABLE 2

EphA2- and EphB3-binding peptides isolated from phage display libraries

| Target Kinase | Name | Peptides Sequence | Library of origin |
|---|---|---|---|
| EphA2 | EP1 | RRCVWSTNVYSMEPALFCAA | X2CX14CX2 |
|  | EP2 | YSCCLNLYTPWPLCDCVEEWA | X2CX18 |
|  | EP3 | HSCKALSSTHGMAWPESAL | Mutant* |
| EphB3 | HP1 | PLCDNARVVRSYTRPRQCSS | X2CX14CX2 |
|  | HP2 | QWWCCDYPNACRLHTTPCDS | Mutant |

*Mutant: We have found over the years that repeated selection for high binders frequently leads to the emergence of mutant phage clones that deviate from the predicted sequences of the libraries used.

We have isolated three EphA2-binding and two-EphB3 binding peptides (see Table 2). One of the peptides, EP1, binds to EphA2 with high affinity and specificity. In fact, EphA2 was the only cell surface protein that was targeted by EP1. Several lines of evidence demonstrate that EP1 is a functional agonist of EphA2 (see FIGS. 7-20 for details).

For example, M13 phage displaying EP1 peptide, or recombinant EP1 fused to Fc or GST can specifically bind to EphA2 with high affinity (Kd=8.2 nM). This affinity is much higher than the recently reported EphA2-binding peptides from others. Those peptides have over 10 fold lower affinities. The affinity is remarkable in light of the fact that EP1 peptide only mimics part of the receptor-ligand interaction interface.

Like the native ligand, ephrin-A1, dimeric EP1-Fc or GST-EP1, but not monomeric EP1 induces dose-dependent EphA2 tyrosine phosphorylation in several different cell lines, including those derived from cancer. Because monomeric form of EP1 peptide binds to EphA2 without activating it, monomeric EP1 peptide or its derivatives can act as antagonists of EphA2 kinase. Therefore, EP: peptide can be either agonist or antagonist, depending on aggregation status.

As shown in FIGS. 7-20, cells treated with EP1-Fc adapt a round morphology. EphA2 activation by EP1 suppressed integrin function and causes reduced cell adhesion. EP1 inhibited mitogen-activated protein kinase or MPK. In keeping with the growth promotion activity of MAPK, EP1 inhibited cancer cell growth. Preliminary studies showed that systemic administration of Ep1-Fc could have suppressive effect on the growth of prostate cancer xenograft in nude mice.

Our results suggest that EP1 peptide is a specific EphA2 agonist. Because of its ability to inhibit cell motility and growth, EP1 represents a novel agent in the management of both physiological and pathological processes where cell growth and motility play a role. Examples include, but not limit to, neural regeneration, dementia, wound healing, inflammation, blood clotting, treatment or prevention of tumor growth and metastasis. In addition, since Eph kinases are highly expressed in brain, and play an important role in the learning in adults and development of nervous system in the embryo, EP1 can also be used in enhancing memory, and correcting developmental defects in nervous system. EP1 and related peptides as well as other therapeutics derived from it can serve as lead molecules for development of new therapeutics for these diseases.

Example 3

Identification and Characterization of Small Molecule Agonists of EphA2 Kinase

1. Materials and Methods

Figure 21:
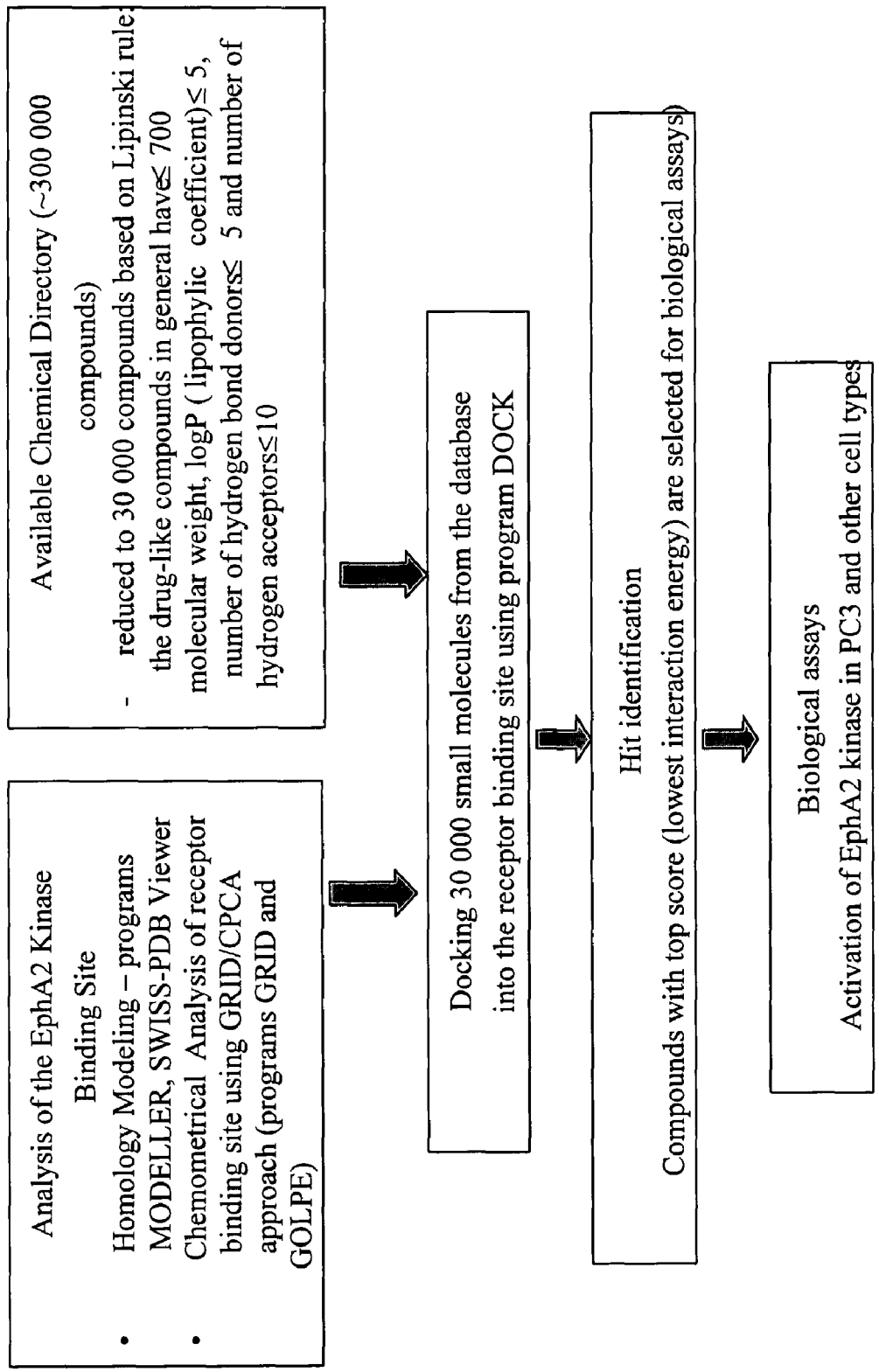
FIG. 21. The overall computer-aided drug design targeting EphA2 kinase.
Figure 22:
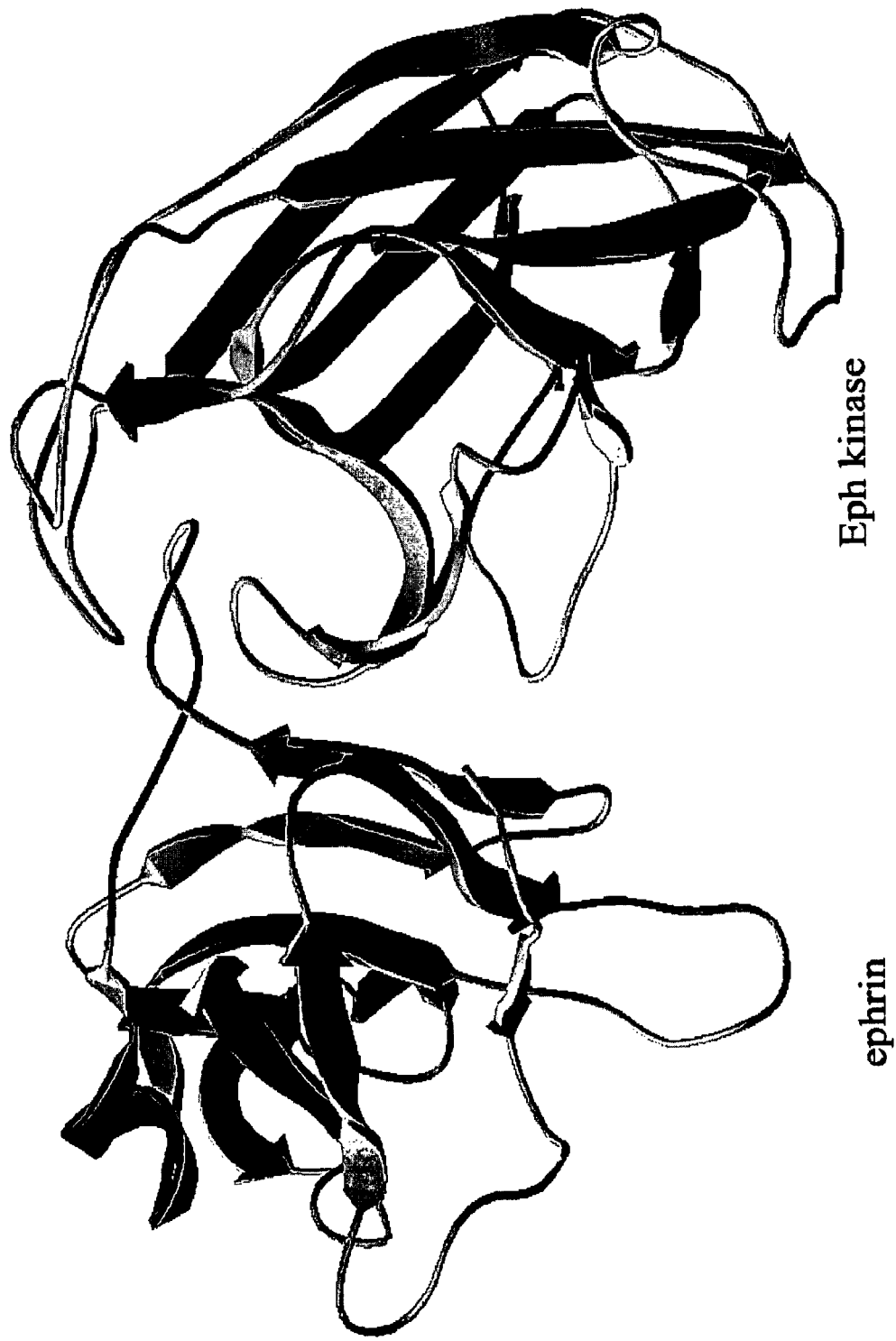
FIG. 22. Structure-based and computer-aided drug design targeting EphA2 kinase.
Figure 23:
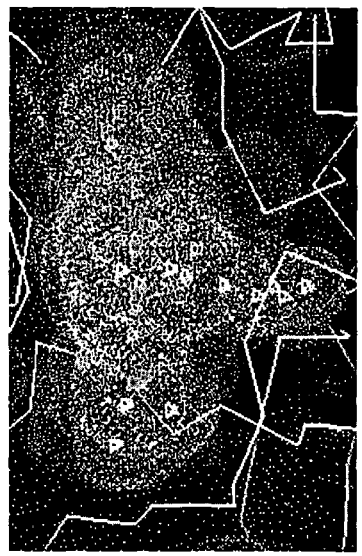
FIG. 23. The steps of DOCK algorithm. The docking calculations were performed on the Linux cluster of the Ohio Supercomputer Center.
Figure 23:
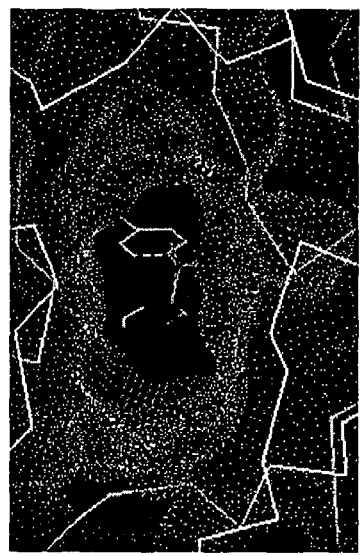
Figure 23:
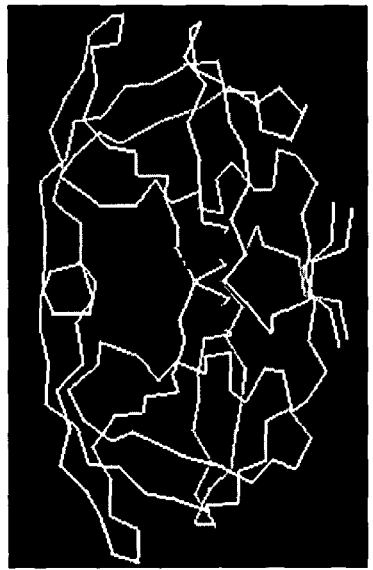
Figure 23:
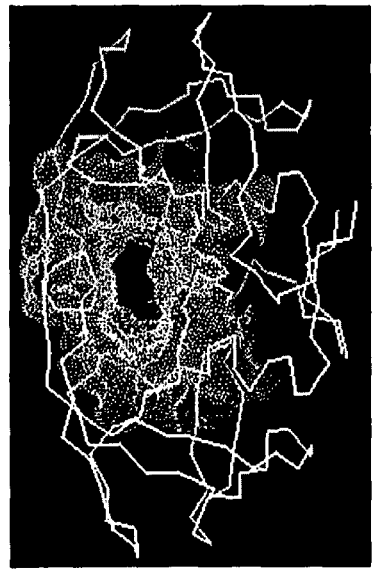
Figure 24:
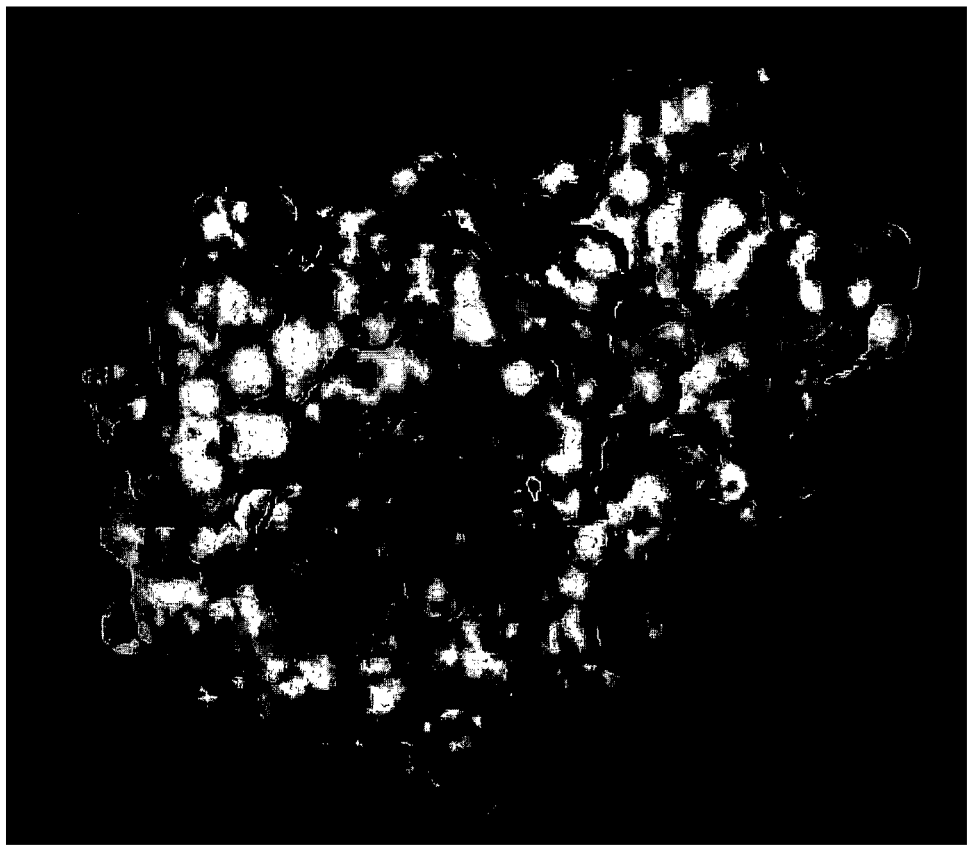
FIG. 24. Step 1 of DOCK: molecular modeling of EphA2 ligand binding domain.
Figure 24:
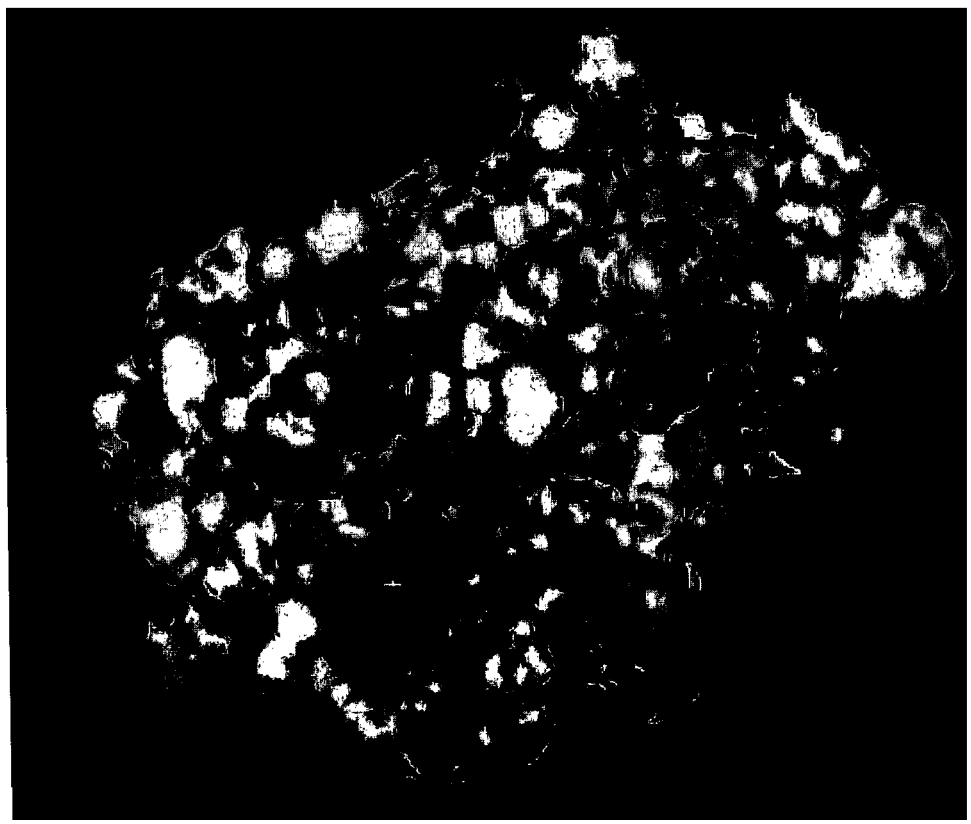
Figure 25:
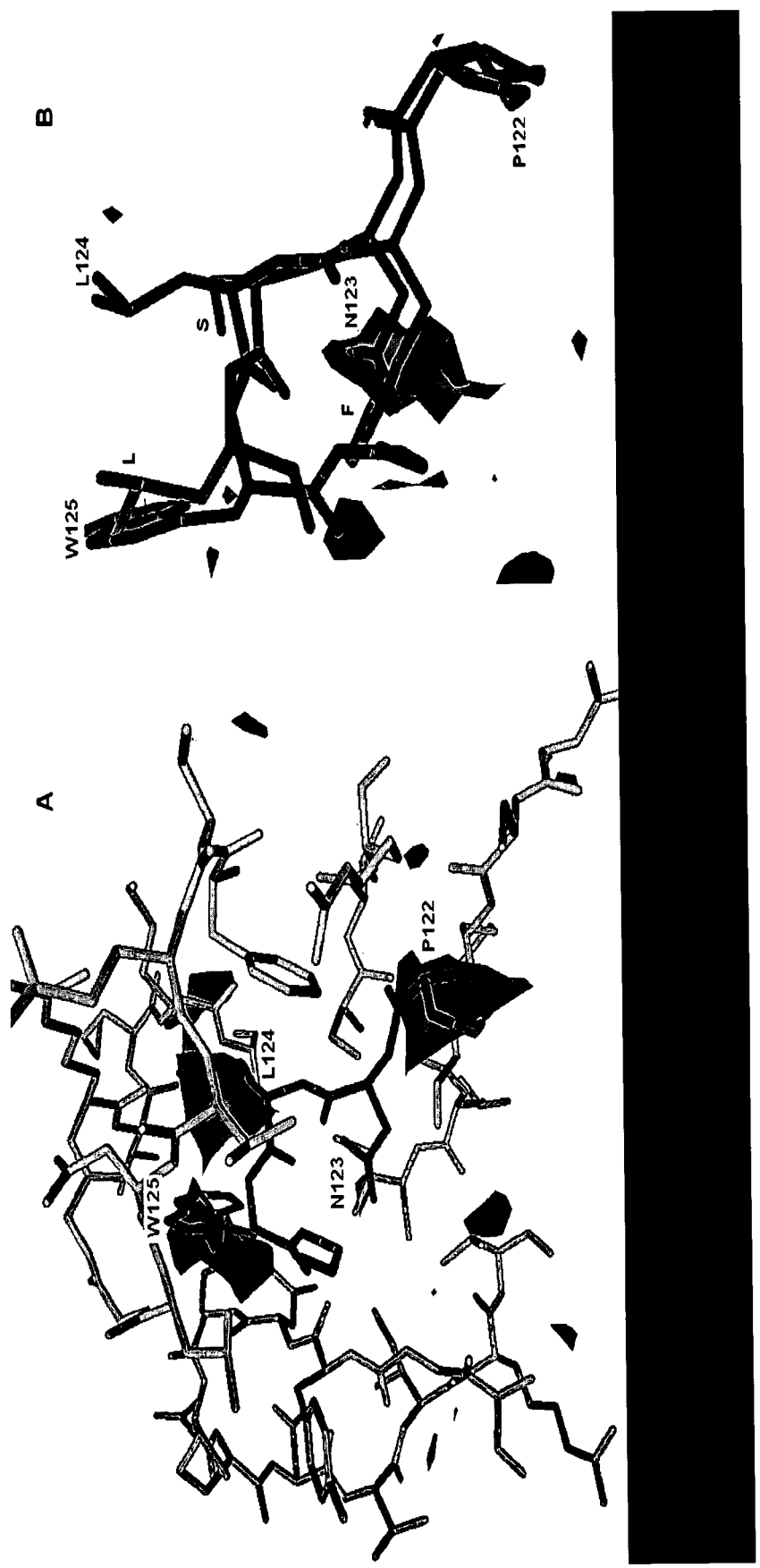
FIG. 25. Step 2 of DOCK: establishing pharmacophore.
Figure 26:
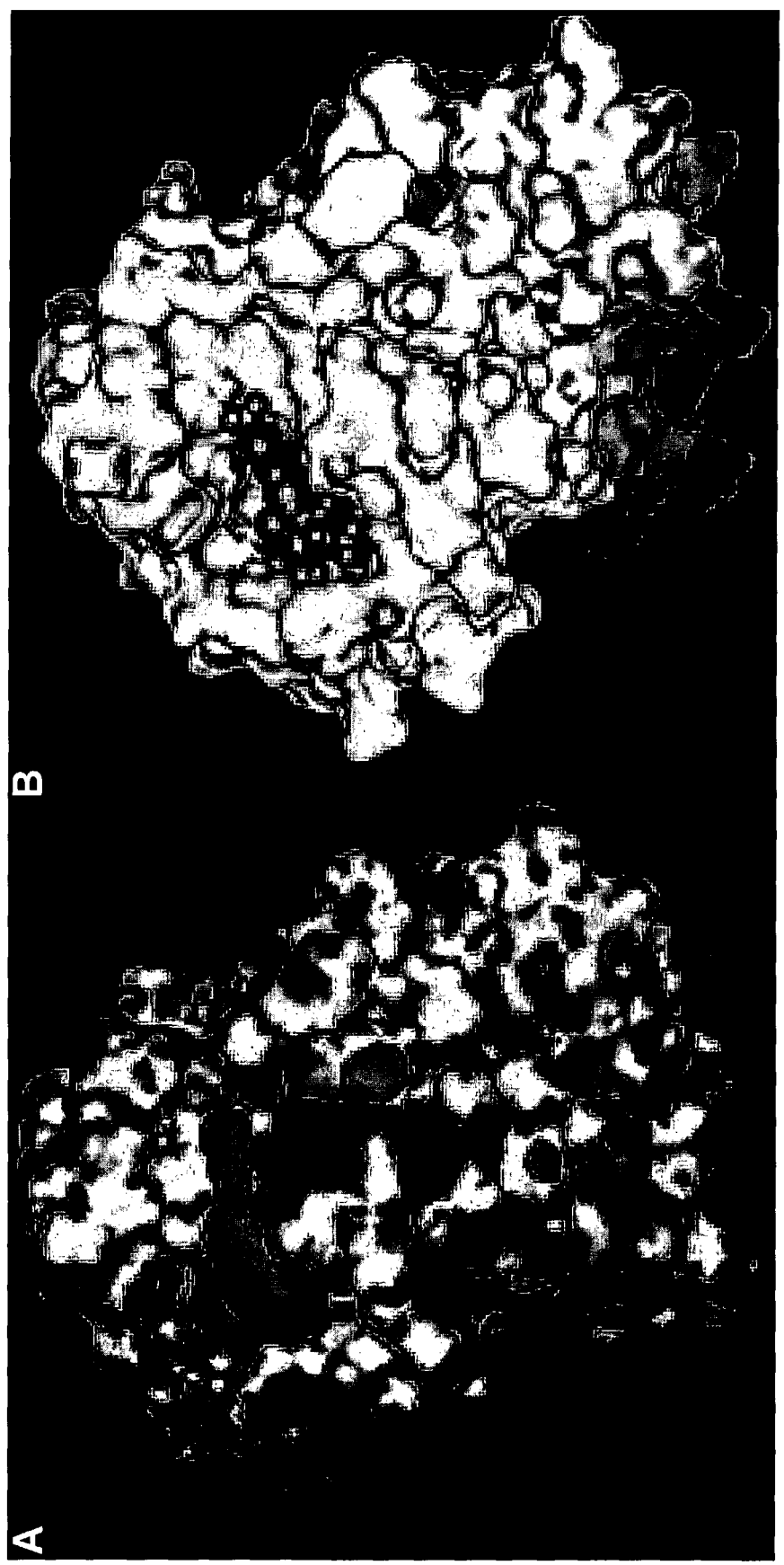
FIG. 26. Step 3 of DOCK: generating spheres fitting into the active site.

The overall scheme of computer-aided drug design targeting EphA2 kinase is illustrated in FIG. 21. See FIGS. 22-26 for details.

DOCK 5.0 was used to screen the Available Chemical Directory (ACD) (Molecular Design Limited Information Systems, San Leandro, Calif.), containing CONCORD generated 3D-coordinates of the ~350,000 commercially available compounds, for potential EphA2 agonists. Prior to screening, ACD was filtered with program FILTER (OpenEye Scientific Software) to remove non-drug like compounds that comply with Lipinski rule of five. According to this rule, the drug-like compounds in general should have $\leq 700$ molecular weight, logP (lipophylic coefficient—an estimate of hydrophobicity based on a calculated logarithm of the octanol-water partitioning)$\leq 5$, number of hydrogen bond donors$\leq 5$, number of hydrogen acceptors$\leq 10$ and no reactive functional groups. This reduced the size of ACD from 350,000 compounds to 30,000 compounds. Of these, the highest scoring 500-1000 compound-bound orientations were output by DOCK and the compounds used for experiments. The Gasteiger-Marsili atomic charges were then assigned to the molecules in the databases using BABEL freeware utility. The rigid conformations for each compound were generated by OMEGA (OpenEye Scientific Software), and docked in turn to EphA2 kinase binding site. EphA2 kinase structure was obtained via homology modeling of EphB2 kinase bound to ephrin-B2 crystal structure using program MODELLER. Program DOCK5.1 implements geometry-based approach for the docking of the small ligands. The computer program SPHGEN was used to create clusters of overlapping spheres within EphA2 kinase solvent accessible surface of the binding site. The sphere positions in the dock sites were selected using interactive graphical display of the surface curvature. The sphere cluster represents a negative image of the docking site. Program DOCK matched atoms of each compound from the database to the centers of the spheres to search for favorable binding orientations. DOCK scored each orientation based on the ligand's complementarity to the protein surface using an AMBER interaction force field that included van der Waals and electrostatic terms. The docking was performed on Beowulf Linux Cluster of the Ohio Supercomputer Center consisting of 128 computing nodes with 1.4 GHz processor and 2 Gb of RAM. Compounds that activated EphA2 kinase in the assays were used in substructure search for additional compounds from the ACD, and these groups of similar compounds were also tested experimentally. All chemicals used in the screening were purchased from Sigma Chemical, Aldrich, the Sigma-Aldrich Library of Rare Chemicals (SALOR), Maybridge (Ryan Scientific, SC), or Acros Organics.

2. Identification and Characterization of Small Molecule Agonists of EphA2 Kinase In these studies, we specifically targeted the ligand-binding domain of EphA2 receptor tyrosine kinase (RTK). We previously found that the predicted major ligand-binding site on EphA2 kinase is unexpectedly small involving only two to three amino acids from the ligand, though the prevailing belief in the field is that large surface areas are involved in RTK-ligand interactions, and as a result, RTK-ligand interaction is very hard, if not impossible, to target with small compounds.

Figure 27:
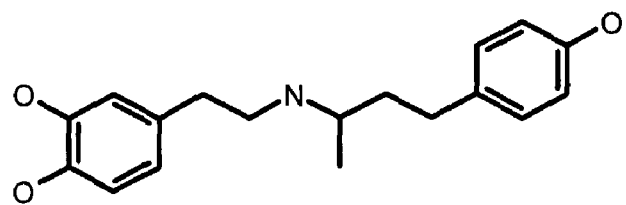
FIG. 27. Structure and function of dobutamine as an EphA2 agonistic compound. PC-3 cells were stimulated with the indicated concentration of dobutamine, EphA2 was immunoprecipitated and tested for activation status by blotting with anti-phosphotyrosine (PY99).
Figure 28A:
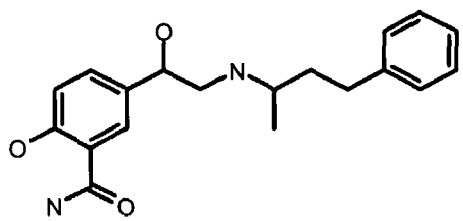
FIG. 28. Structure and function of labetalol as an EphA2 agonistic compound. A) EphA2 activation by labetalol. B) BIAcore binding curves for interaction of labetalol with EphA2 kinase. The increasing concentrations of labetalol (0, 20 mM, 40 mM, 80 mM, 160 mM, 320 mM, 640 nM, 1.25 mM and 2.5 mM) were injected over EphA2 kinase ligand-binding domain immobilized on the sensor chip.
Figure 28A:
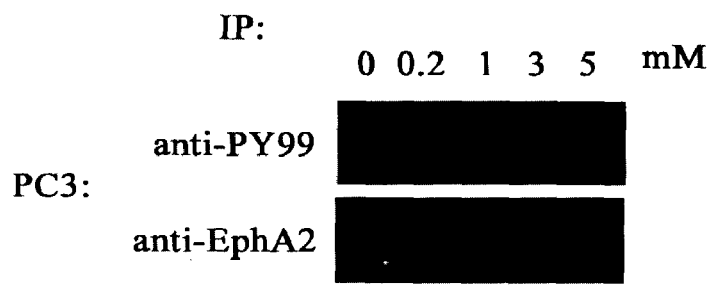
Figure 28B:
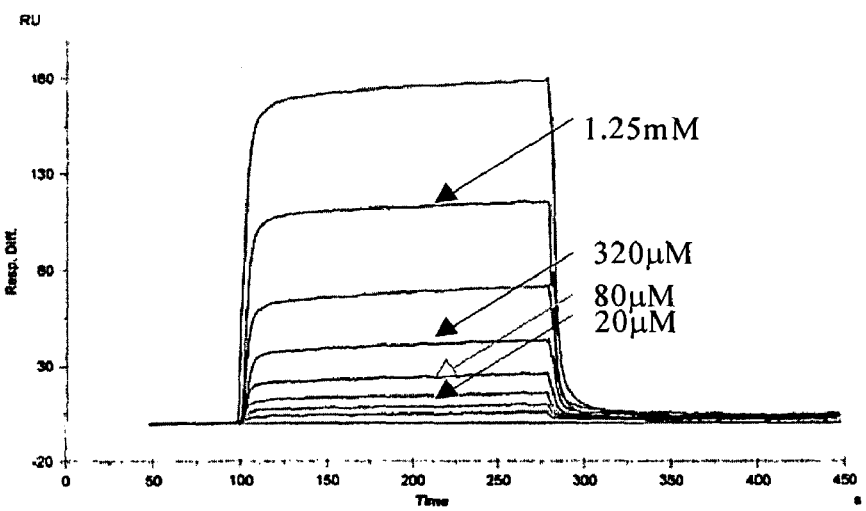
Figure 29:
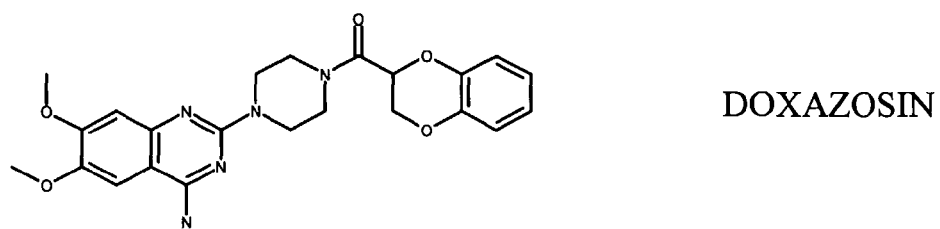
FIG. 29. Structure and function of doxazosin as an EphA2 agonistic compound. A) Doxazosin activates EphA2. Although prominent activation was observed at 200 mM, weaker activation can be seen at 40 mM. B) BIAcore binding curves shows direct binding of Doxazosin to EphA2.
Figure 29:
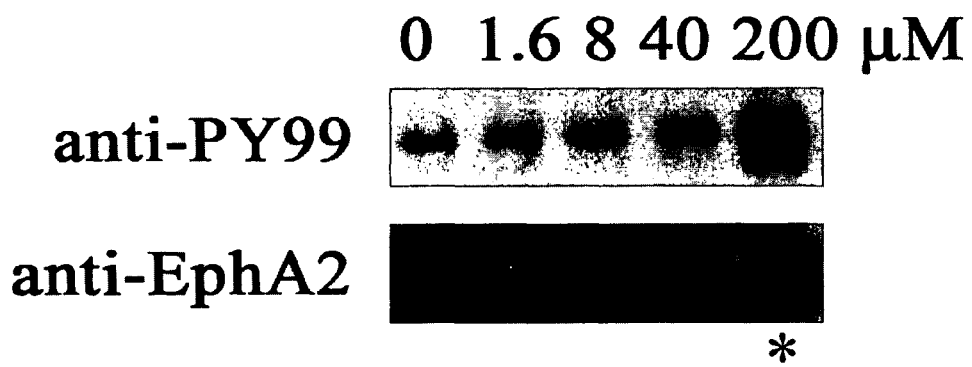
Figure 29:
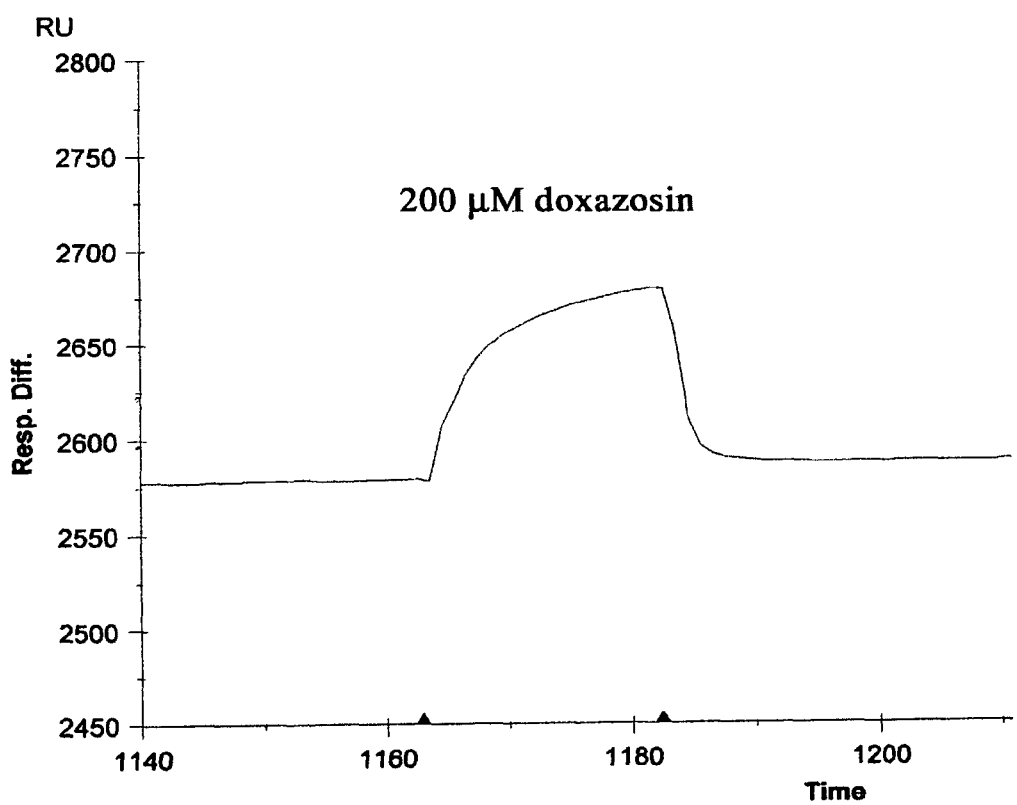
Figure 30:
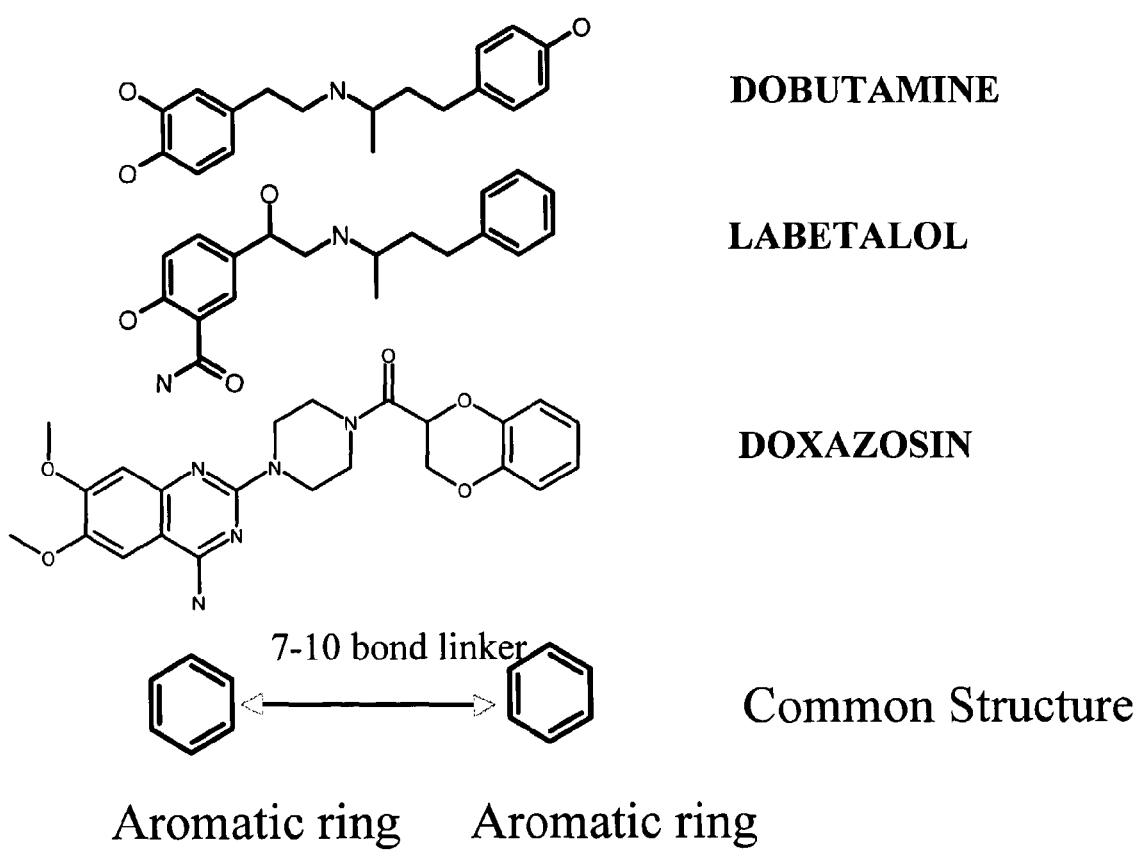
FIG. 30. The EphA2 agonists demonstrate shared structural features.
Figure 31:
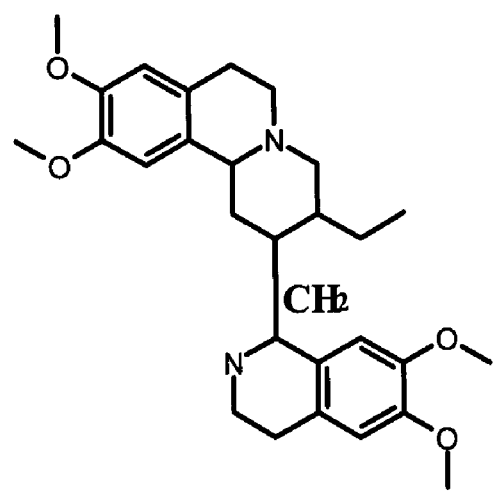
FIG. 31. Structure and function of another EphA2 agonistic compound: (di-meo-isoquinolin-1-ylmethyl)-et-di-meo-pyrido(2,1-a)isoquinolin, hydrobromide S120103. This compound was found by search chemical database with the shared common structure deduced from known binders. The data confirmed the validity of common backbone structures.
Figure 31:
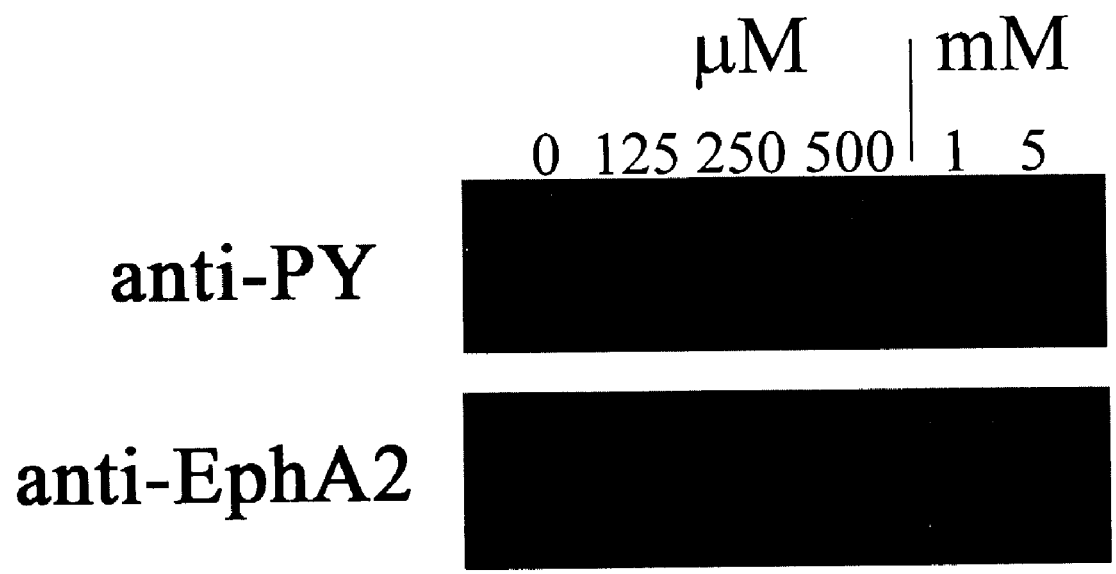
Figure 32:
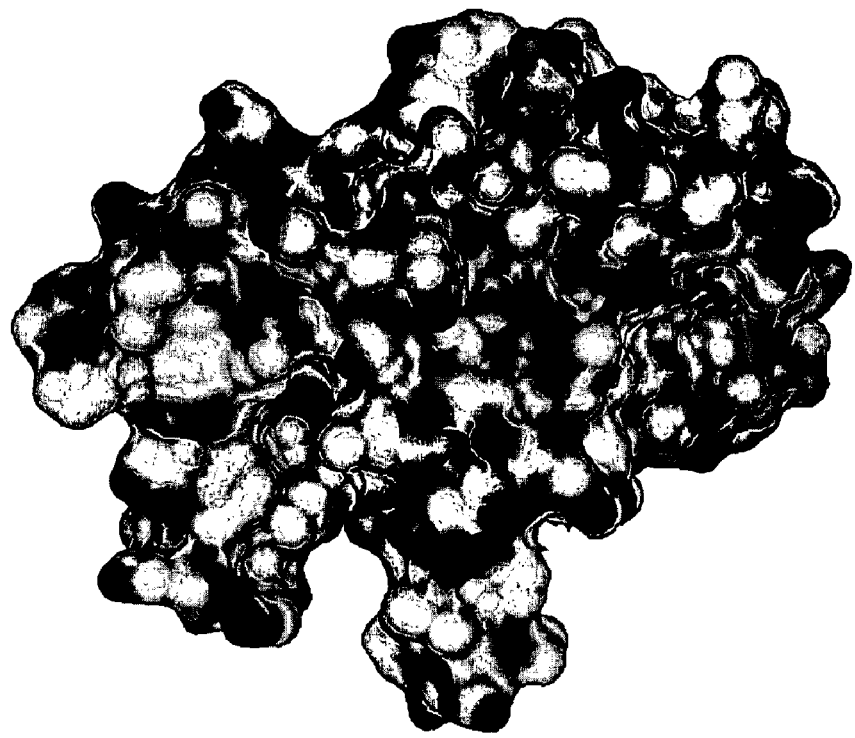
FIG. 32. Crystal structure of EphA2 ligand binding domain. A). Ribbon diagram. B). Molecular surface representation.
Figure 32:
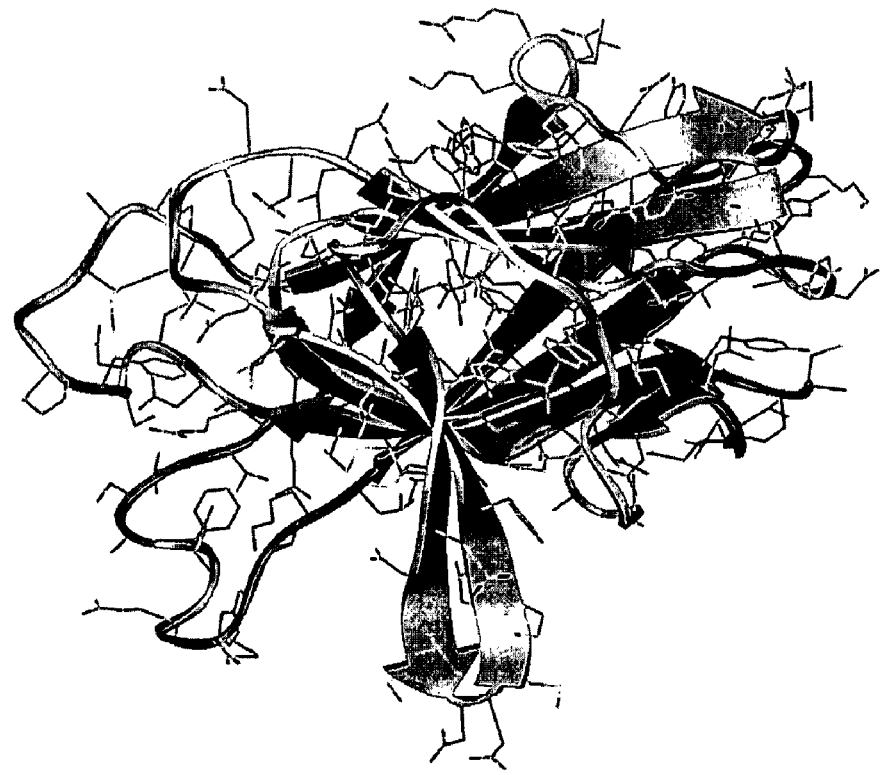

We identified three compounds from these studies: Dobutamine, Doxazosin, and Labetalol. The structures of these compounds and their functions as EphA2 agonists are shown in FIGS. 27-29. Examination of these identified compounds demonstrates shared chemical features (FIG. 30), suggesting that a family of compounds may target Eph kinases. Such features provide a structural framework for derivatization of the compounds.

Thus, we used this minimal structure to search the chemical database for related compounds. Multiple compounds were identified. Among the two compounds that we could order from Sigma, one of them activated EphA2 (see, e.g., FIG. 31). This result confirms our understanding that this structure is suitable for use in finding and testing more compounds, and can lead to the discovery of preferred side chains for higher affinity and better selectivity binding.

All the compounds that we have identified are currently used as clinical drugs. 1) Doxazosin, a long-acting alpha (1)-blocker, is used as a component of combination therapy for patients with stage 1 and stage 2 hypertension and for patients with concomitant hypertension and hyperlipidemia or glucose intolerance. 2) Labetalol, a compound that blocks both alpha- and beta-adrenergic receptors, is the only drug of its class currently available in the United States, and is currently used in managing hypertension that is difficult to control with pure $\beta$- or $\alpha$-blockers. 3) Dobutamine on the other hand is widely used in stress echocardiography, that is considered as a relatively well-tolerated diagnostic modality. The potential future usage of the compounds and their derivatives in treating cancer (e.g., prostate cancer) are unexpected.

Example 4

Crystal Structure of EphA2 Kinase Ligand-Binding Domain: Insight on Cellular Functions and Strategies for Targeted Drug Discovery We have solved the crystal structure of EphA2 ligand-binding domain (LBD) (see FIG. 32). The crystal structure of EphA2 LBD shows overall structural similarities with EphB2 LBD. The coordinates of the crystal structure of EphA2 LBD are listed in Table 1.

Figure 33:
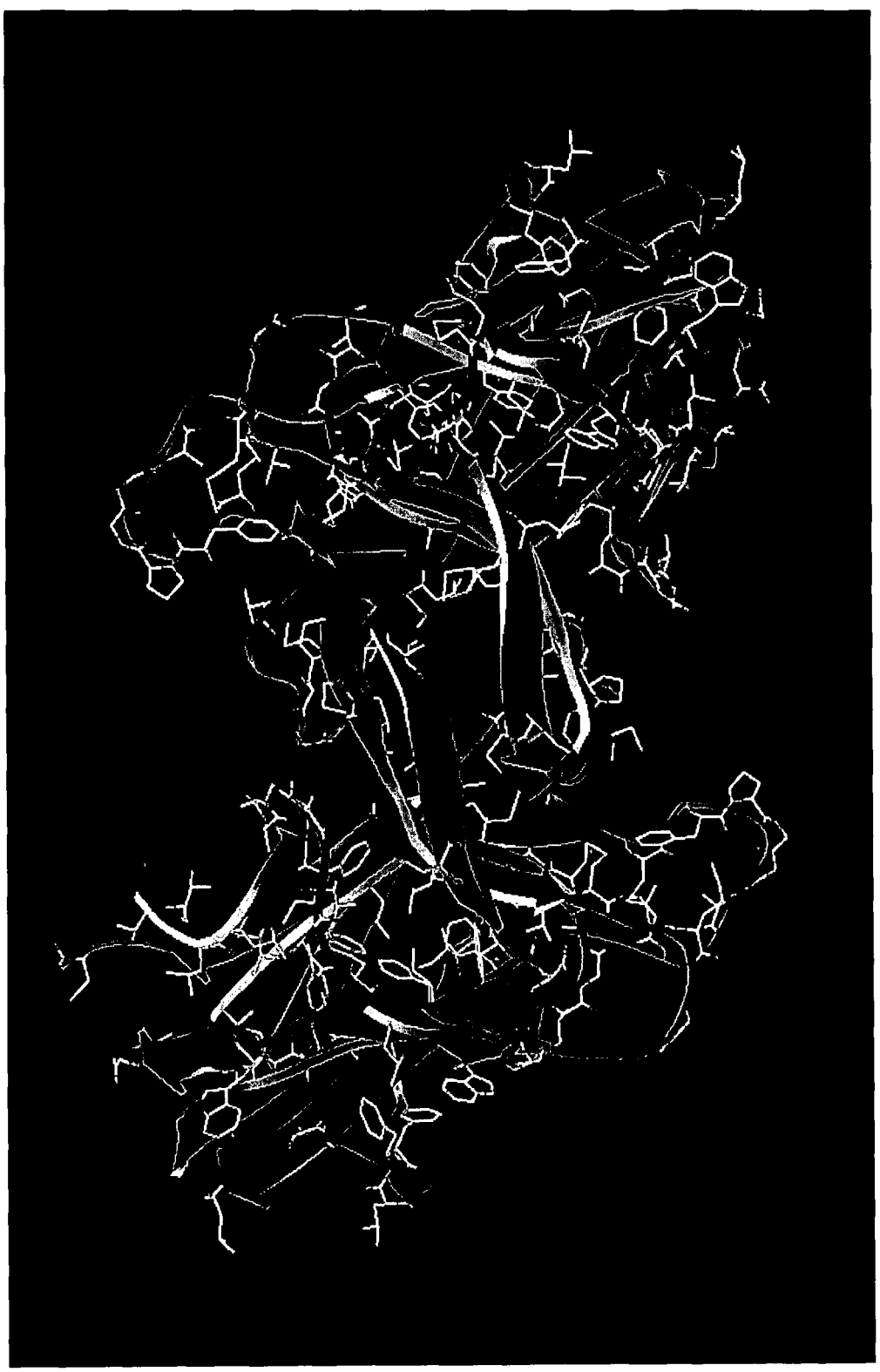
FIG. 33. Dimerization of EphA2 ligand-binding domain through hydrophobic interactions.
Figure 34:
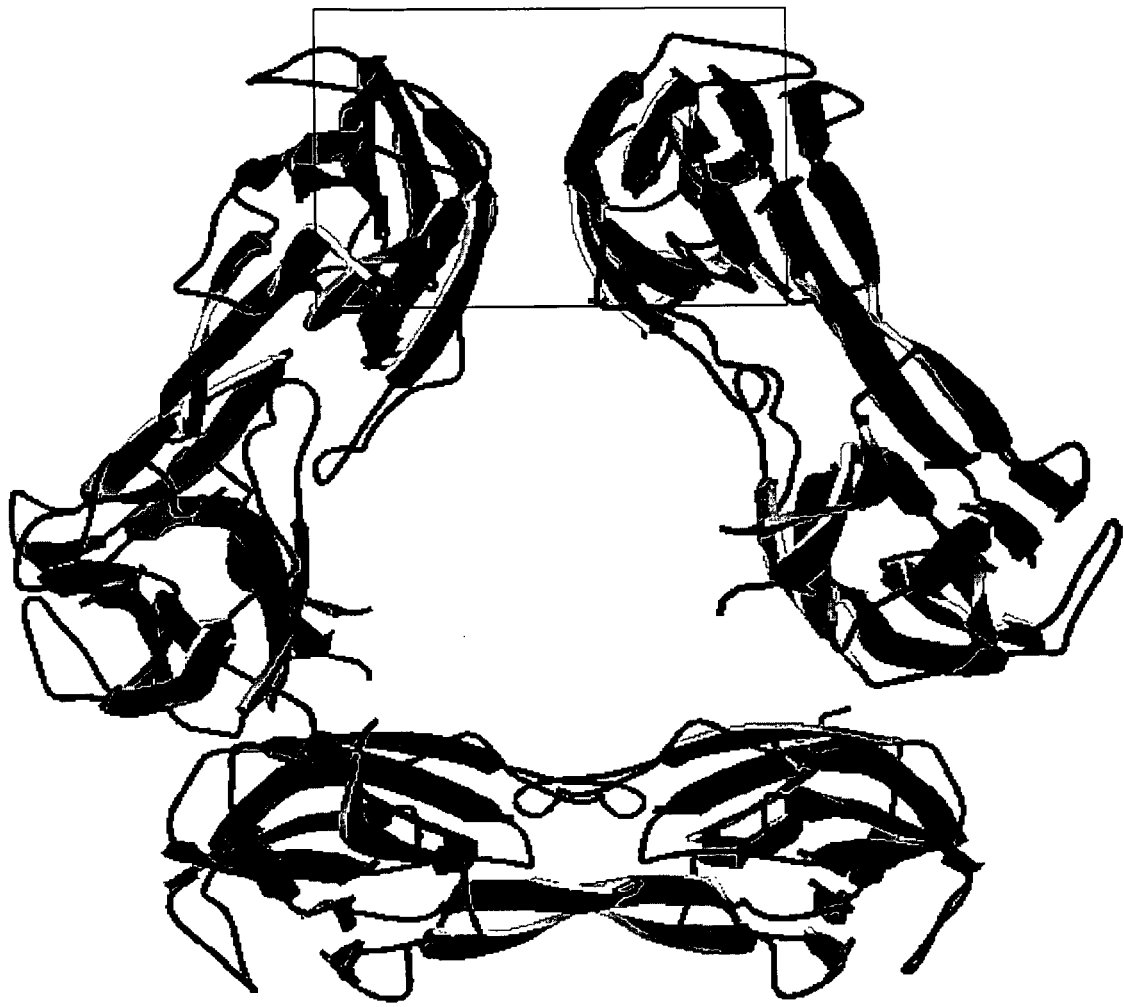
FIG. 34, Arrangement of EphA2-LBD in the crystal indicates a hexamerization interface.
Figure 35:
FIG. 35. Hexamerization interface involves electrostatic interactions.

However, unlike EphB2 LBD which is a monomer, EphA2 LBD form dimers in the crystal through hydrophobic interactions (FIG. 33). The arrangement in the crystal also suggests further assembly of the dimers into hexamers through electrostatic interactions (FIGS. 34-35).

Figure 36:
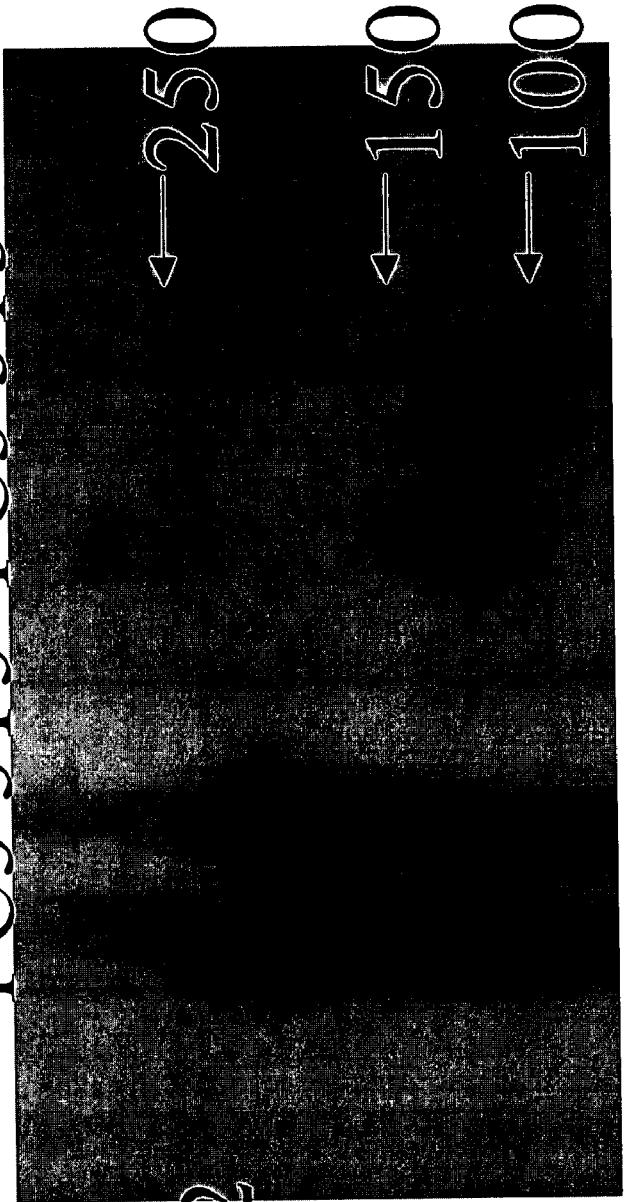
FIG. 36. EphA2 kinase is present on cell surface as a dimer. Cell surface proteins were cross-linked with a membrane impermeable DSP and lysed. EphA2 was immunoprecipitated with anti-EphA2 antibody. The precipitate materials were separated on SDS-PAGE under reducing or non-reducing conditions, and blotted for EphA2.

Consistent with structural data, EphA2, but not EphB2, can be detected in dimeric form on cell surface (FIG. 36). Cell surface proteins were cross-linked with a membrane impermeable DSP and lysed. EphA2 was immunoprecipitated with anti-EphA2 antibody, The precipitate materials were separated on SDS-PAGE under reducing or non-reducing conditions, and blotted for EphA2. Further, the dimeric EphA2 has distinct kinetics of ligand induced activation and requires different aggregation status of ligands for receptor activation.

Figure 37:
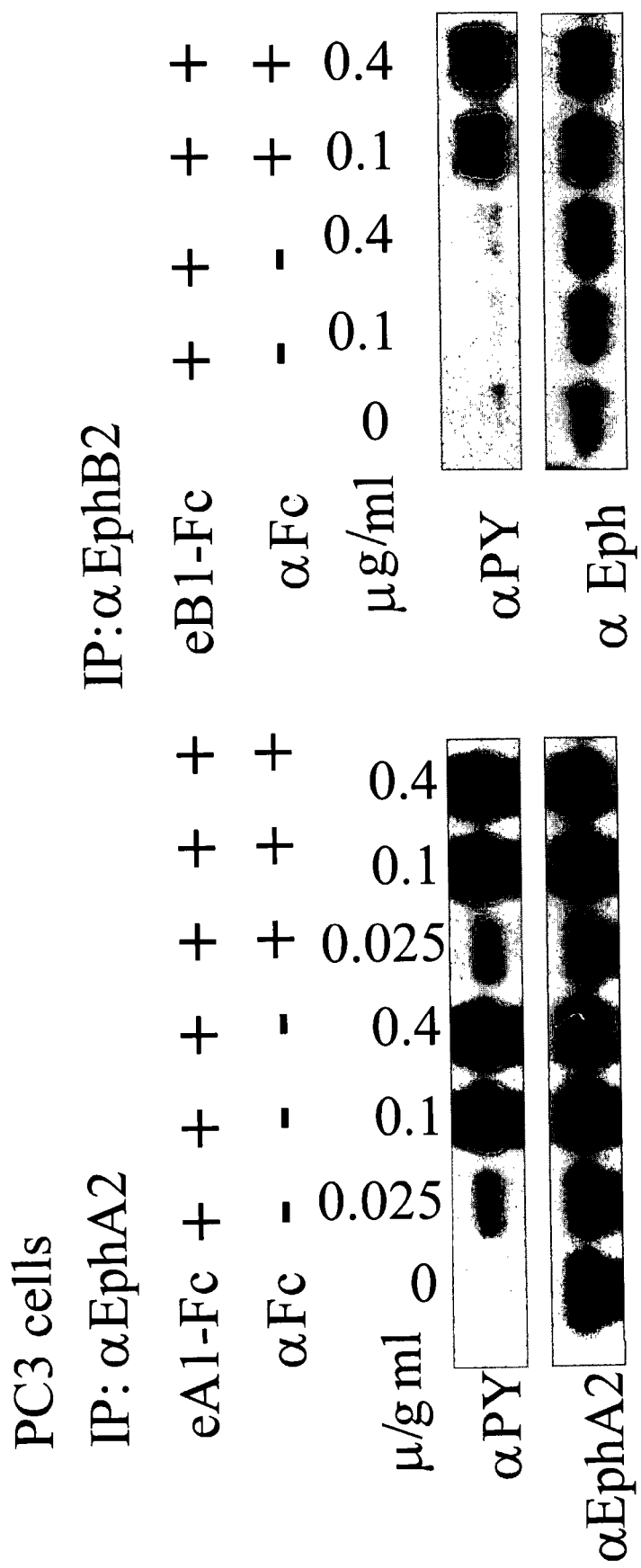
FIG. 37. Activation of EphB2, but not EphA2 on PC-3 cells requires super-clustering of ligands. Ephrin-A1-Fc (EA1-Fc) or ephrin-B1-Fc (EB1-Fc) at indicated final concentrations were either used directly to stimulate PC-3 cells, or pre-clustered with anti-Fc antibody before cell stimulation. EphA2 or EphB2 were immunoprecipitated and blotted for activation status with PY99 antibody.
Figure 38:
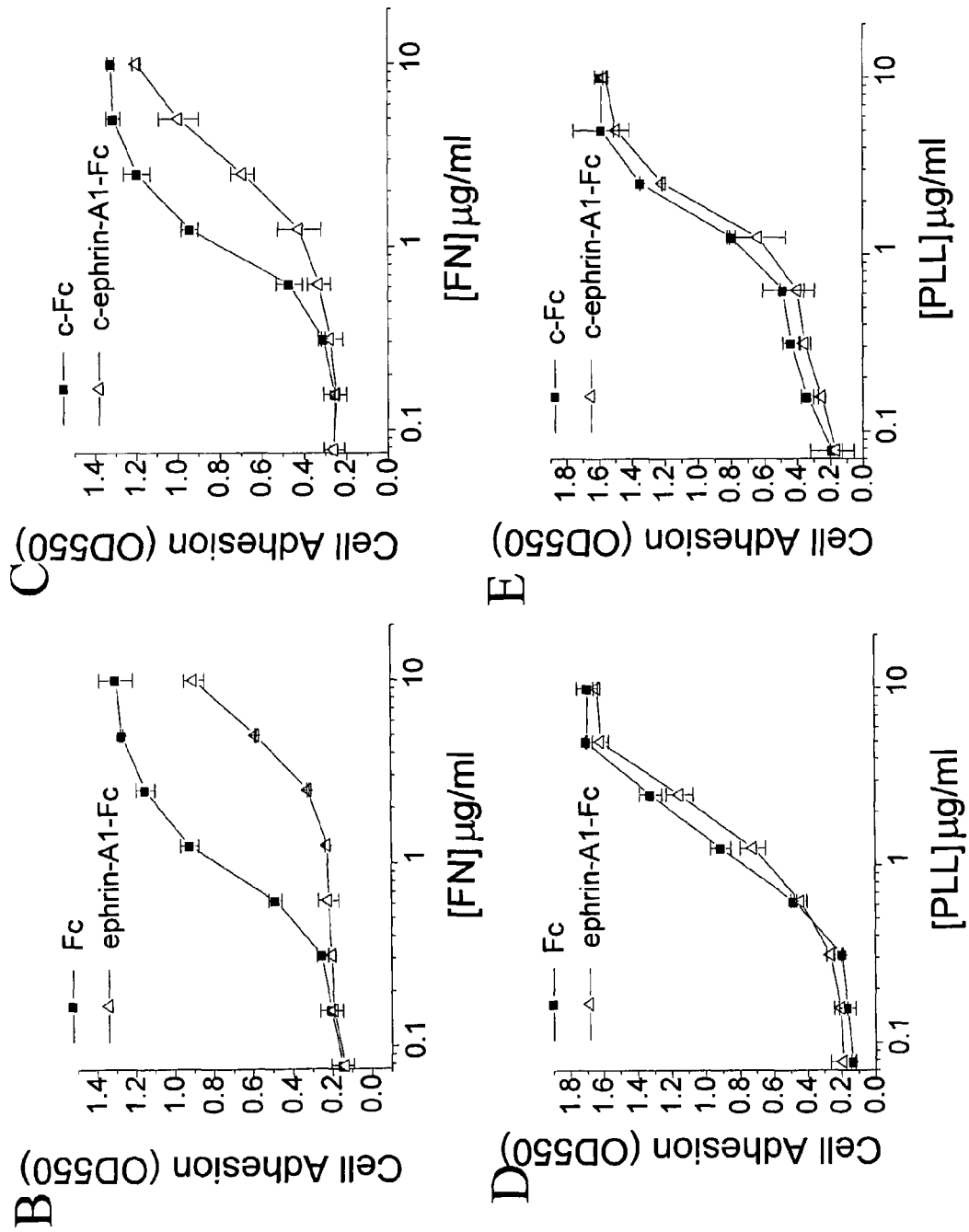
FIG. 38. Clustering of ephrin-A1-Fc did not increase the inhibitory effects of EphA2 activation on integrin-mediated cell adhesion to fibronectin.

FIG. 37 shows that activation of EphB2, but not EphA2 on PC-3 cells requires super-clustering of ligands. Ephrin-A1-Fc (EA1-Fc) or ephrin-B1-Fc (EB1-Fc) at indicated final concentrations were either used directly to stimulate PC-3 cells, or pre-clustered with anti-Fc antibody before cell stimulation. EphA2 or EphB2 were immunoprecipitated and blotted for activation status with PY99 antibody. FIG. 38 shows that clustering of ephrin-A 1-Fc did not increase the inhibitory effects of EphA2 activation on integrin-mediated cell adhesion to fibronectin.

In sum, the structure of EphA2 LBD will facilitate the design and optimization of novel therapeutics targeted at EphA2.

Example 5

Disruption of EphA2 Causes Gene Dosage-Dependent Susceptibility to Carcinogenesis in Mouse Skin We sought to directly test the role of EphA2 in malignant transformation of epithelial cells in vivo using EphA2 knock-out mice. In a classical DMBA/TPA two stage skin carcinogenesis model, homozygous deletion of EphA2 resulted in dramatically elevated susceptibility to skin tumor development and progression. Not only were there increased tumor multiplicity and shortened latency, EphA2-null tumors also showed a significantly accelerated malignant progression toward a more invasive phenotype. Interestingly, similar to what has been reported in many types of human cancer, EphA2 was overexpressed in tumor cells compared adjacent normal tissue. Loss of EphA2 did not appear to affect apoptosis, but was associated with increased tumor cell proliferation. Treatment of primary keratinocytes from wild type mice with ephrin-A1 inhibited ERK1/2 activities and suppressed cell growth; both effects were abolished in EphA2-null keratinocytes. Collectively, these results suggest that EphA2 is a tumor suppressor gene in mammalian skin. Overexpression of EphA2 frequently observed in human cancer may represent a compensatory defensive feedback mechanism to control tumor growth and progression.

Results

Figure 39:
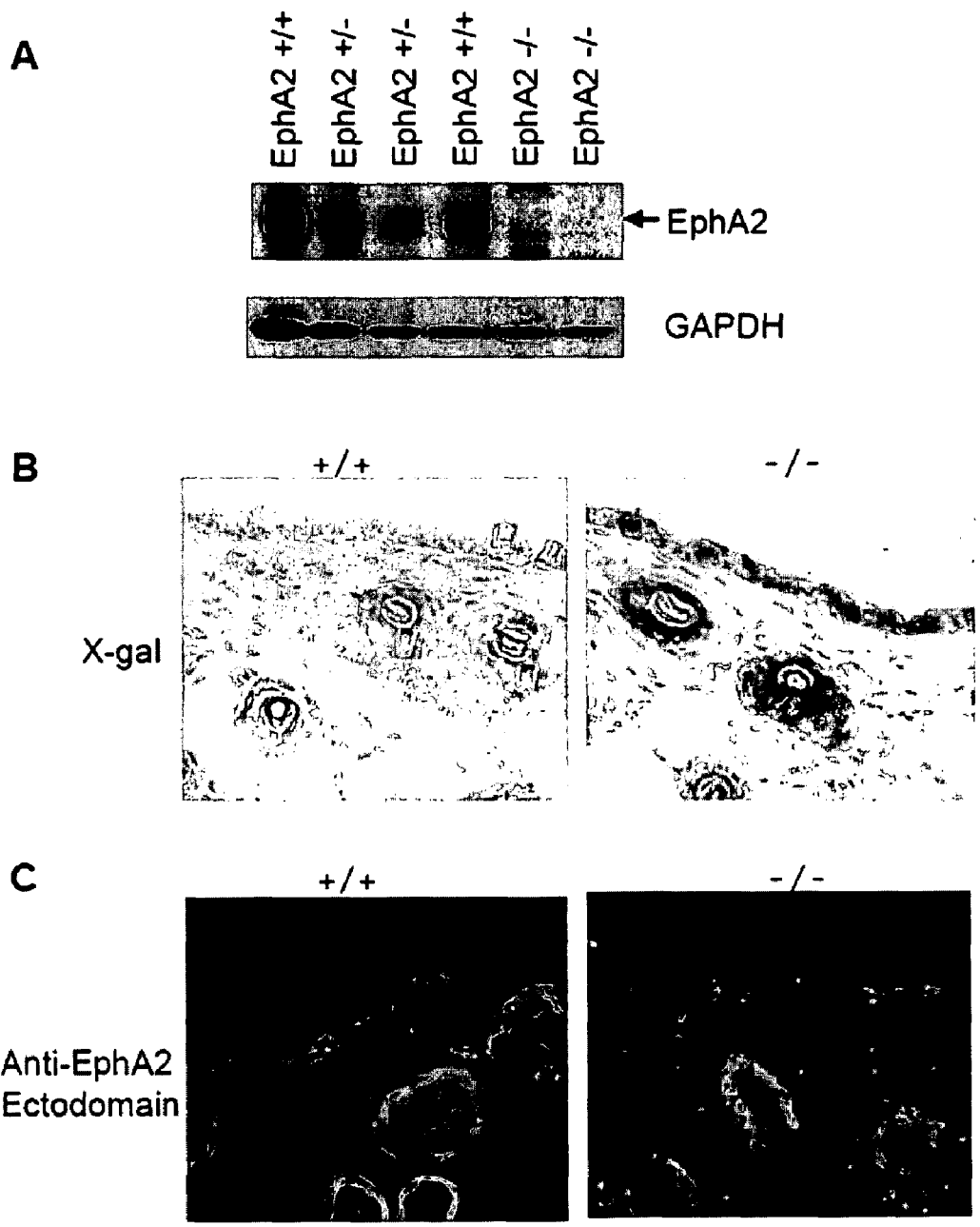
FIG. 39. Characterization of EphA2 expression in mouse skin and role of EphA2 in tumor development. Characterization of EphA2 expression in mouse skin and role of EphA2 in tumor development. A) Expression of EphA2 in skin extracts from wild-type and EphA2 KO mice. Wild-type and EphA2 mutant mice at P8 were sacrificed. Skin tissues were removed from similar regions and snap-frozen in liquid nitrogen. The frozen tissues were grinded, lysed in RIPA buffer, and subjected to immunoblot with rabbit polyclonal anti-EphA2 antibodies. The same membrane was re-probed for GAPDH as loading control. B) Expression of β-gal in EphA2 KO mouse skin. Frozen sections were fixed and stained with X-gal and followed by counterstaining with nuclear Fast-Red. C) Expression of EphA2 in the skin from wild-type and EphA2 KO mice. Skin frozen sections (7 μm) were stained with goat polyclonal antibodies that recognize the ectodomain of EphA2 followed by detection with donkey anti-goat IgG conjugated with FITC. Images were taken on a Leica microscope equipped with SPOT-RT digital camera. Note the cytoplasmic staining pattern of the trapped EphA2-β-geo fusion protein in EphA2-knockout mouse skin D) EphA2 KO mice are more susceptible to DMBA/TPA two-stage chemical carcinogenesis compared to wild-type mice, while heterozygous mice showed an intermediate phenotype. Pictures were taken 13 weeks after DMBA initiation.

Homozygous Deletion or Haploinsufficiency of EphA2 Caused Increased Susceptibility to Skin Carcinogenesis To investigate the role of EphA2 kinase in the development of mammalian skin tumors, we used the previously described EphA2 knockout mice generated by secretory trapping strategy. The secretory trapping vector was inserted at the boundary between exon 4 and intron 5, leading to the truncation of EphA2 from the second fibronectin type III repeat in the ectodomain to the carboxyl terminal end. Similar to other lines of EphA2 knockout mice, the secretory trapping EphA2-null mice are fertile, develop and grow normally. Immunoblot of postnatal day two (P2) skin extract detected EphA2 expression in wild type mice but not in homozygous mutant, while heterozygous mice showed intermediate expression (FIG. 39A). X-gal staining for $\beta$-geo under the control of EphA2 promoter revealed that EphA2 was expressed in interfollicular epidermis, hair follicles and sebaceous glands (FIG. 39B).

Figure 40A:
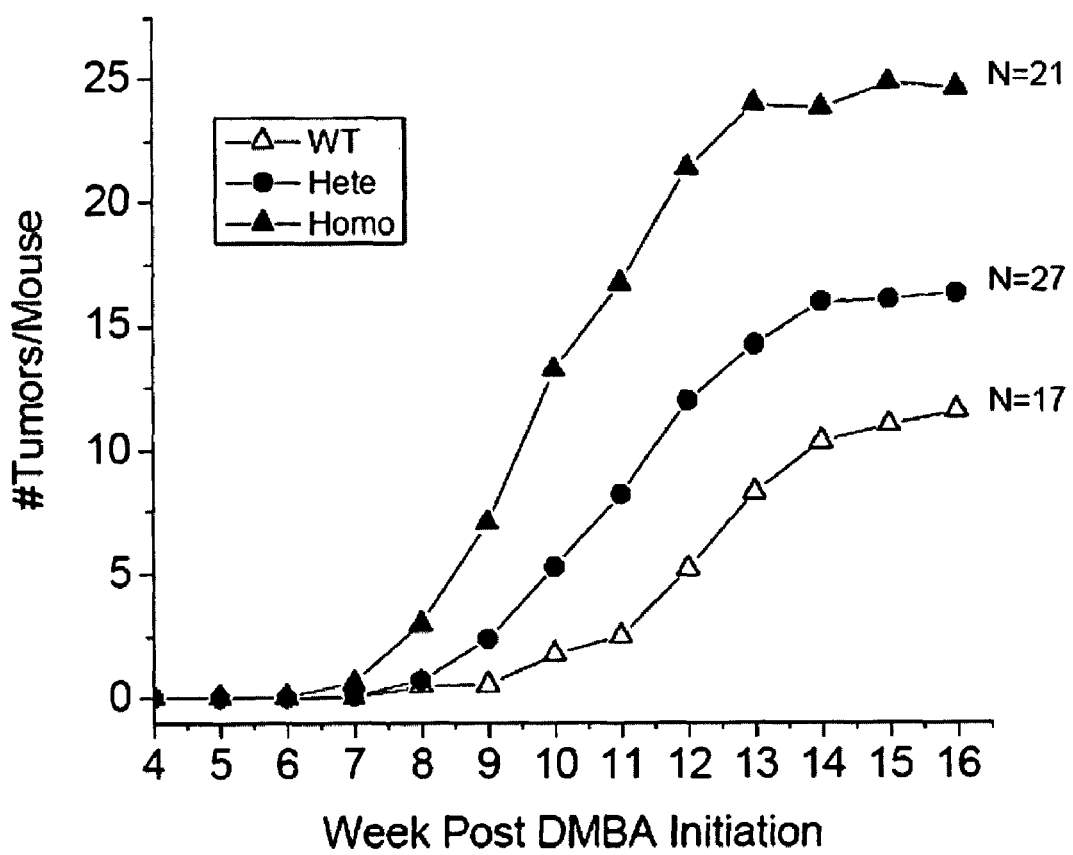
FIG. 40. Skin carcinogenesis of wild-type and EphA2 mutant mice. A) Average number of papillomas per mouse following DMBA/TPA two-stage chemical carcinogenesis. Mice were euthanized at week 16 due to large tumor burden in the knockout group of mice. B) Tumor incidence. C) Growth rate of tumors measured by average number of tumors reaching 4 mm in diameter or larger. D) Immunoblot to show EphA2 expression in tumors from wild type and EphA2 mutant mice.
Figure 40B:
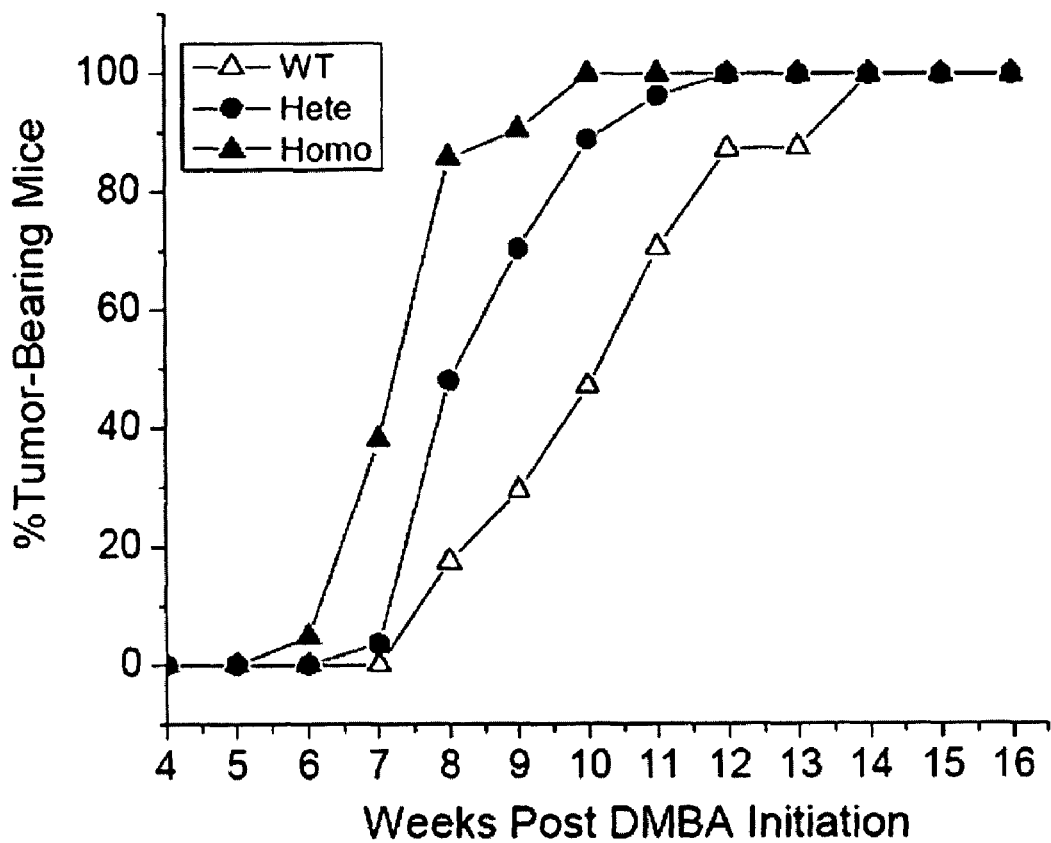

A classical two stage carcinogenesis protocol was carried out to induce skin tumors, which entails tumor initiation by topical application of 7,12-dimethylbenz[a]anthrocene (DMBA) followed by tumor promotion by twice a week applications of 12-O-tetradecanoylphorbol-13-acetate (TPA). It has been well-established that most skin tumors induced using this protocol harbor activating mutation of Ha-Ras. We found that disruption of EphA2 notably increased susceptibility to skin tumorigenesis (FIG. 39D and FIG. 40). In wild type mice, benign tumors (mostly papillomas) started to appear around 8 weeks post DMBA treatment. By 10 weeks, about 50% mice had developed tumors. In contrast, EphA2-null mice developed first tumors at 6 weeks, affecting 50% mice between week 7 and 8, reflecting a 2 to 3 weeks shortening in median tumor latency relative to wild type mice (FIG. 40B). By 10 weeks, the average number of tumors per mouse had reached 13.4, a 7-fold increase over wild type mice (FIG. 40A).

Figure 40C:
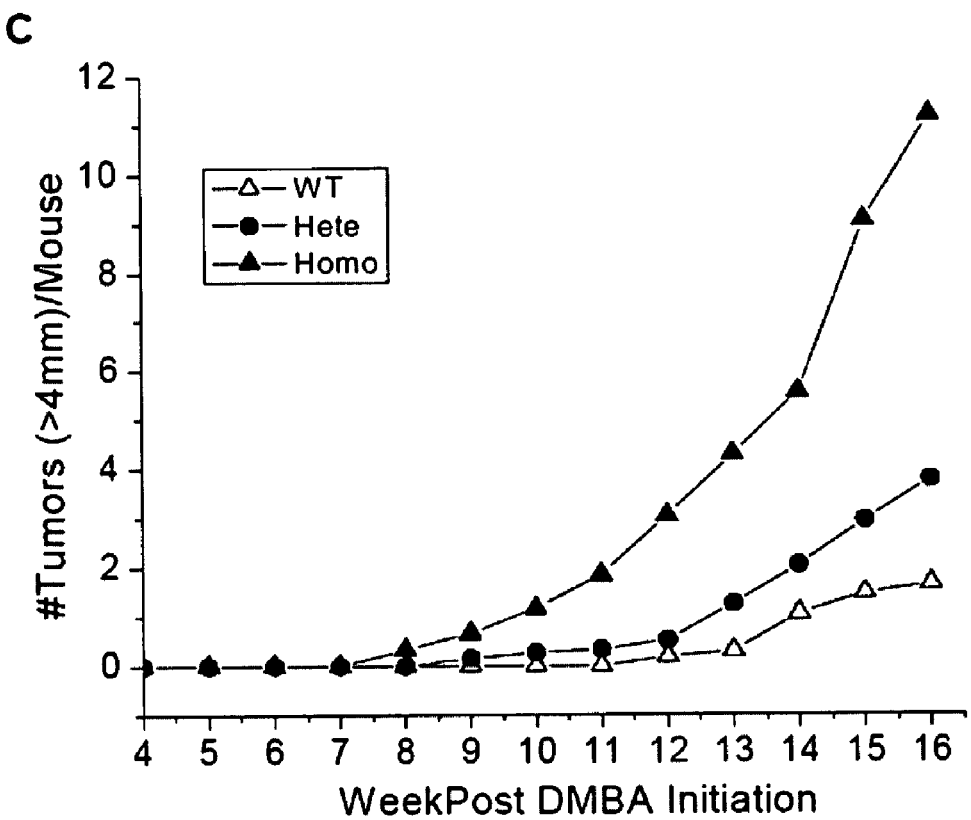

In addition to the increased tumor multiplicity and shortened latency, tumors arising in EphA2 homozygous knockout mice also displayed significantly accelerated growth rate (FIG. 40C). Tumors in knockout mice rapidly grew to 4 mm or larger which contrasted with slow-growing tumors on wild type mice. The large tumor burden in the knockout mice necessitated the termination of the experiment at 16 weeks after DMBA initiation. To monitor tumor progression, a subgroup of mice from each genotype was kept for additional 10 weeks in the absence of further TPA treatment (below).

Figure 40D:
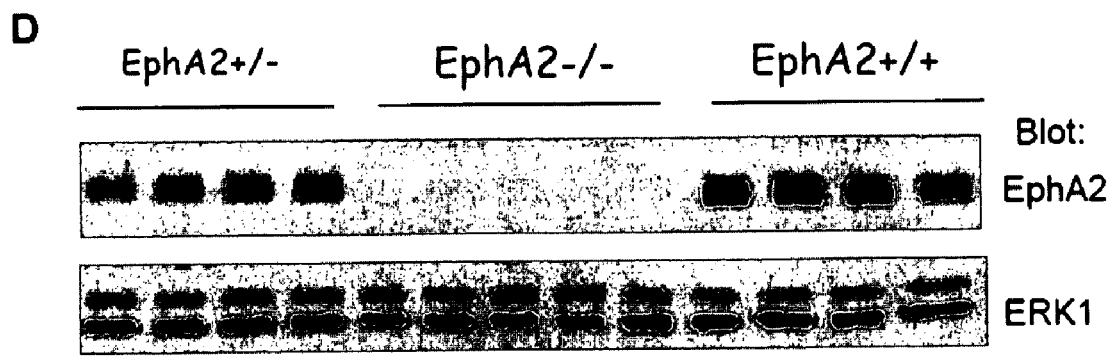

Interestingly, mice heterozygous for EphA2 knockout exhibited intermediate susceptibility to skin carcinogenesis in terms of tumor numbers, incidence as well as growth rate. This did not appear to be due to the loss of heterozygosity, as immunoblot of tumor protein extracts revealed that EphA2 was expressed at the levels consistent with heterozygous deletion (FIG. 40D). Thus the tumor suppressor function of EphA2 is gene dosage-dependent, and EphA2 haploinsufficiency causes increased susceptibility to skin carcinogenesis.

EphA2 was Overexpressed in Chemically-Induced Skin Tumors

Figure 41:
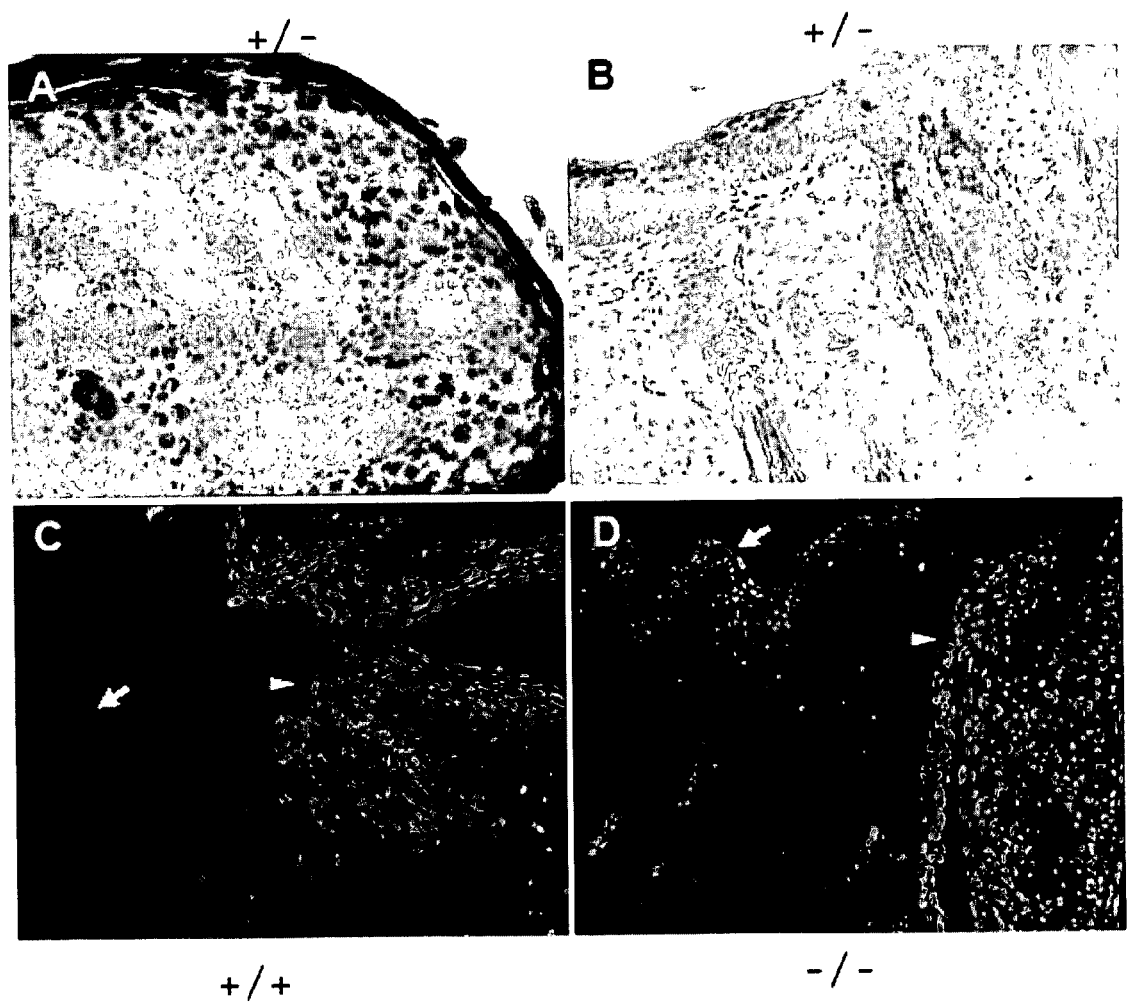
FIG. 41. EphA2 was up-regulated during skin tumorigenesis. Mice were sacrificed 16 weeks after DMBA initiation. Skin tumors were dissected and frozen sections with normal skin attached were cut. They were stained with X-gal (A, B) or a goat polyclonal antibody that recognizes the ectodomain of EphA2 (C, D). A) A tumor from an EphA2$^{+/-}$ mice. B) Normal skin next to tumor shown in A. C) A tumor from an EphA2$^{-/-}$ mouse. Arrow, normal skin; arrow head, papilloma. D) A tumor from an EphA2$^{-/-}$ mouse. Note the substantial upregulation of EphA2 in wild-type tumor with typical membrane-staining pattern; mutant EphA2-β-geo fusion protein was also overexpressed, but was trapped in cytoplasm.

Overexpression of EphA2 has been frequently observed in many different types of human cancers compared with normal tissues, which has led to the suggestion that EphA2 may be an oncoprotein. We next examined expression of EphA2 in chemically induced skin tumors. X-gal staining of papillomas from heterozygous mice showed that EphA2 expression was significantly elevated in tumor cells compared with the surrounding unaffected normal skin (FIG. 41A, B). Similarly, immunofluorescence analysis revealed overexpression of endogenous EphA2 in tumors from wild type with the typical membrane staining pattern (FIG. 41C). Because the antibody was raised against the entire ectodomain of EphA2, it should also recognize the EphA2 (exon 1-4 in the extodomain)-☐-geo fusion protein trapped inside the cells. We found that the fusion protein was also upregulated in tumor parenchyma with the expected intracellular expression pattern (FIG. 41D). These results suggest that EphA2 is upregulated during skin epithelial tumorigenesis.

EphA2 and Ephrin-A1 Showed Complimentary Expression Pattern in Epidermis

Figure 42C:
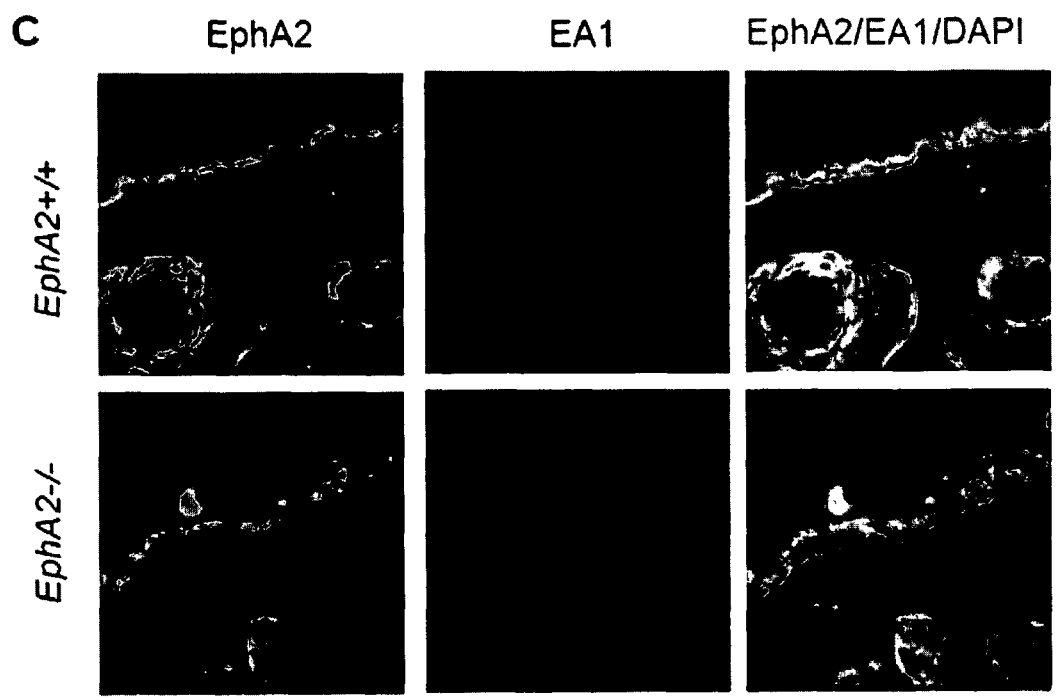
FIG. 42. Compartmentalized expression of EphA2 and ephrin-A1 in mouse skin. A) Frozen sections were obtained from tumor-free areas on DMBA/TPA-treated mice and were co-stained with a goat polyclonal antibody that recognizes EphA2 ectodomain and a rabbit polyclonal anti-ephrin-A1 antibody. Note the thickened epidermal layer due to repeated TPA treatment compared with control untreated skin (panel C below). S, Suprabasal; B, Basal; arrows, outer root shaft; arrow heads, precortex. B) Insets from A showing basal-suprabasal gradient expression of EphA2 and basal expression of ephrin-A1 in epidermis. C) EphA2 and ephrin-A1 expression in untreated normal skin from wild type and knockout mice. D) Representative papillomas from wild type and knockout mice stained for EphA2 and ephrin-A1.

Eph kinases and their membrane-anchored ligands mediate cell-cell contact signaling. To understand how EphA2 may exert its tumor suppressor function in mammalian skin, we sought to determine the expression pattern of ephrin-A1, a cognitive ligand for EphA2. For this purpose we performed double immunofluorescence staining with a goat anti-EphA2 and a rabbit anti-ephrin-A1 antibody. We found that EphA2 and ephrin-A1 were expressed in complementary pattern in mouse skin. In the normal epidermis adjacent to tumors (FIG. 42A, B), EphA2 was expressed in a basal to suprabasal gradient with lower expression in the basal layer and high expression in spinous layer. In contrast, ephrin-A1 expression was primarily restricted to the basal layer of cells (FIG. 42B). Such compartmentalized expression patterns were also noted in hair follicles (FIG. 42A). For example, EphA2 and ephrin-A1 were expressed in complementary gradients in precortex (arrow heads, note the opposing gradients between EphA2 and ephrin-A1) as well as in outer root sheath (arrows). However the exact identities of cell types that express ephrin-A1 or EphA2 remain to be determined. The complementary EphA2/ephrin-A1 expression was also evident in adult mouse skin not exposed to DMBA/TPA (FIG. 42C). The basal-restricted expression of ephrin-A1 suggests that EphA2/ephrin-A1 interactions are largely confined to the basal cells and immediate neighboring suprabasal cells.

Figure 42D:
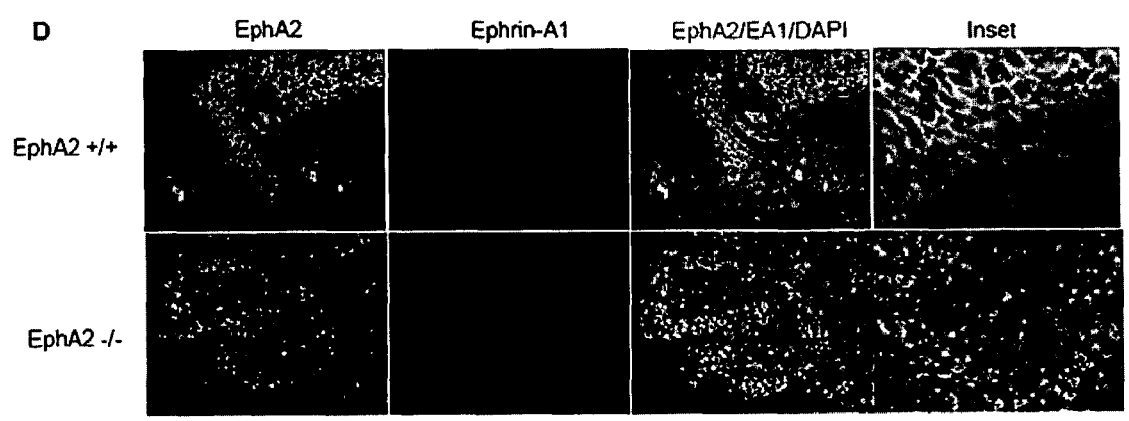

Next we examined EphA2/ephrin-A1 expression in tumor tissues. Similar to normal epidermis, ephrin-A1 was detected at a thin layer of cells abutting the basement membrane. On the other hand, EphA2 was highly expressed in tumor parenchyma with lower expression near the basement membrane. In keeping with secretory trapping of the knockout allele, tumor from wild type mice showed predominantly membrane EphA2 staining in contrast with the mostly cytoplasmic pattern for the homozygous mutant (FIG. 42D). In contrast to EphA2, we did not observe any overexpression of ephrin-A1 in tumors from all three genotypes by immunoblot or immunofluorescence analyses compared with adjacent normal tissues (not shown). In sum, EphA2 and ephrin-A1 were expressed in complementary pattern in normal epidermis. Expression of EphA2 but not ephrin-A1 was upregulated in tumors.

Figure 44:
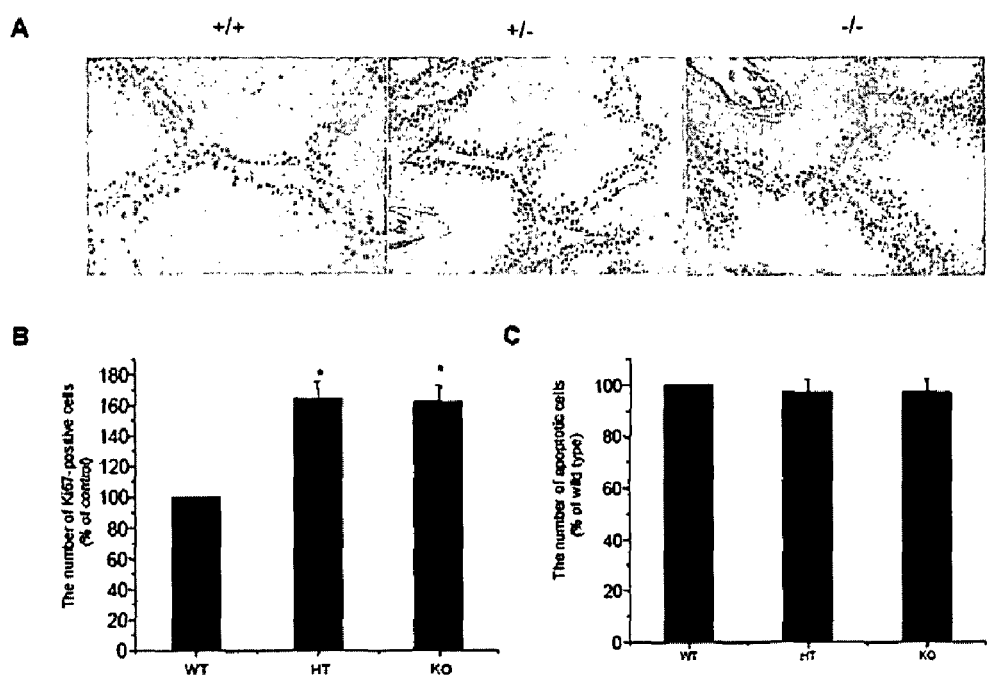
FIG. 44. Deletion of EphA2 leads to accelerated cell proliferation rate in skin tumors. A) Tumors were harvested from mice sacrificed 16 weeks post DMBA initiation, Paraffin-embedded sections were stained with an antibody against Ki67 proliferation marker. B) Quantitative analysis of proliferation index. Randomly selected tumor sections from three different animals of each genotype were stained for Ki67 (EphA2$^{-/+}$, n=9; EphA2$^{-/-}$, n=12; EphA2$^{-/-}$, n=11). Total numbers of Ki67-positive cells were counted on digital images that cover the entire tumor sections. They were divided by total tumor areas measured using MetaMorph 6.2r4 imaging software (Universal Imaging) and normalized to wild type control. The differences between EphA2$^{+/-}$ and EphA2$^{-/-}$ or EphA2$^{-/-}$ were statistically significant (P<0.001, one way ANOVA). C) Quantitative analyses of apoptosis by TUNEL staining. No significant differences were detected among different genotypes.

EphA2 Activation Inhibited ERK1/2 Activities and Reduced Clonal Growth in Wild Type but not EphA2-Null Keratinocytes In Vitro To determine cellular mechanisms underlying the increased susceptibility to skin tumorigenesis, primary keratinocytes were isolated and cultured from epidermis of neonatal (P1) mice. They were stimulated with ephrin-A1 fused to the heavy chain of human IgG1 (ephrin-A1-Fc). EphA kinases including EphA2 were precipitated with excess ephrin-A1-Fc, and blotted with antibody raised against phosphorylated dityrosine peptide that is highly conserved in the juxtamembrane region of all Eph kinases. Phosphorylation of this region has been correlated with Eph receptor activation. We found that EphA2 could be readily activated by ephrin-A1 in wild type and heterozygous keratinocytes (FIG. 44A). Interestingly, p-EphA/B signal were undetectable in EphA2-null keratinocytes despite the fact that ephrin-A1-Fc precipitation should have brought down most EphA kinases, suggesting that EphA2 was the predominant EphA kinase expressed in primary keratinocytes.

Figure 43C:
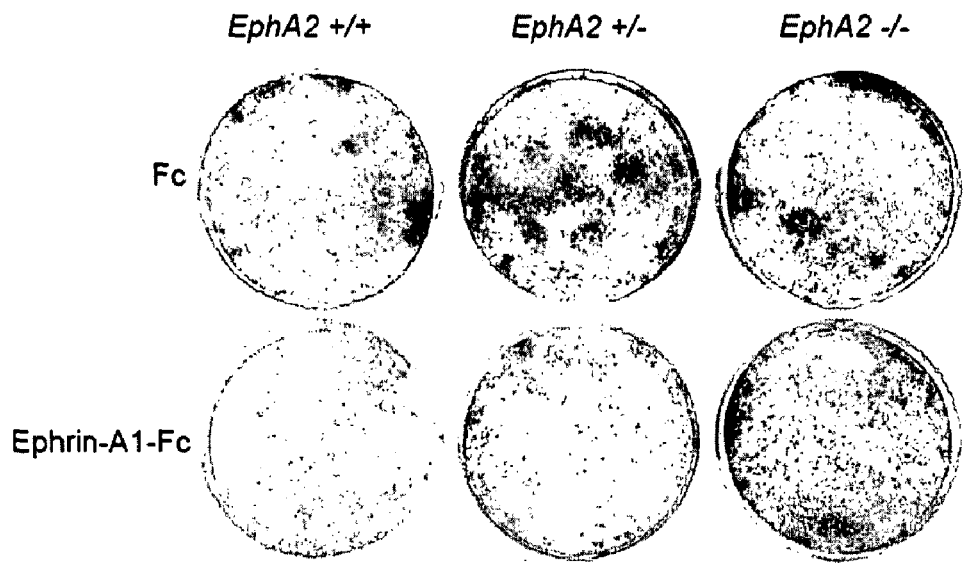
FIG. 43. EphA2 kinase is required for ephrin-A1-induced inhibition of ERK1/2 MAP kinase and growth suppression in primary keratinocytes. A) EphA kinase activation by ephrin-A1 in EphA2$^{+/+}$ and EphA2$^{-/-}$ but not EphA2$^{--}$ keratinocytes. Keratinocytes were isolated from newborn (P1) mice and cultured on matrigel-coated culture plates. They were stimulated with 1.0 μg/ml of ephrin-A 1-Fc for 10 min. The unstimulated cells were used as control. EphA receptors including EphA2 were precipitated from the cell lysates using ephrin-A1-Fc, and were subjected to immunoblot analysis with rabbit polyclonal anti-phospho-EphA/B antibody. Membrane was stripped and blotted again for total EphA2. B) Ephrin-A1 stimulation leads to inactivation of ERK1/2 MAPK in EphA2$^{-+}$ and EphA2$^{-/-}$ but not EphA2$^{-/-}$ keratinocytes. Total cell lysates were analyzed by immunoblot with the indicated antibodies. The band densities from p-ERK blot were normalized to the corresponding total ERK1 blot. The ratios of p-ERK between ephrin-A1-treated and untreated were shown in the lower panel. C). Ephrin-A1 stimulation inhibits clonal growth of EphA2$^{--}$ and EphA2$^{-/-}$ but not EphA2$^{-/-}$ keratinocytes. Primary keratinocytes were plated on 6-well plates coated with matrigel at 5,000 cells/well, and allowed to grow for 12 days in the presence of Fc (0.5 μg/ml) or ephrin-A1-Fc (1.0 μg/ml).

We reported previously EphA2 activation suppressed ERK1/2 activities and reduced cell growth in several different cell types. Similarly, we observed that ERK1/2 activities were significantly attenuated in wild type keratinocytes upon ligand stimulation of EphA2 (FIG. 43B). Homozygous deletion of EphA2 completely abolished the inhibitory effects, while heterozygous keratinocytes showed an intermediate response. In a clonal growth assay, treatment with ephrin-A1-Fc suppressed the growth of wild type and heterozygous keratinocytes (FIG. 43C). In contrast, EphA2 knockout keratinocytes were resistant to ephrin-A1-induced growth inhibition. Thus EphA2 in keratinocytes exerts negative growth regulatory function possibly through inhibition of ERK1/2 MAP kinase.

Deletion of EphA2 Caused Increased Skin Tumor Cell Proliferation.

Increased tumor growth in knockout mice (FIG. 39D and FIG. 40) could result from either increased cell proliferation or decreased apoptosis or both. Staining for Ki67 cell proliferation marker showed EphA2 homozygous deletion led to significantly increased cell proliferation index compared wild type control (FIGS. 44A and B). Cells in heterozygous tumors also exhibited accelerated growth rate indistinguishable from homozygous tumors, which may reflect the increased heterozygous tumor growth rate between 13 to 16 weeks post DMBA treatment (FIG. 40C). Apoptosis did not appear to be a major contributing factor, as TUNEL staining of tumor sections did not detect noticeable differences among different genotypes (FIG. 44C). In both normal epidermis and skin tumors ephrin-A1 expression is localized to basal layer of cells abutting basement membrane (FIG. 42), where there was active cell proliferation. Our data suggest that EphA2 signaling upon contact with ephrin-A1 may exert negative growth in this region; deletion of EphA2 may diminish such inhibitory effects leading to increased cell proliferation.

Accelerated Malignant Tumor Progression in EphA2 Homozygous Knockout Mice

Figure 45A:
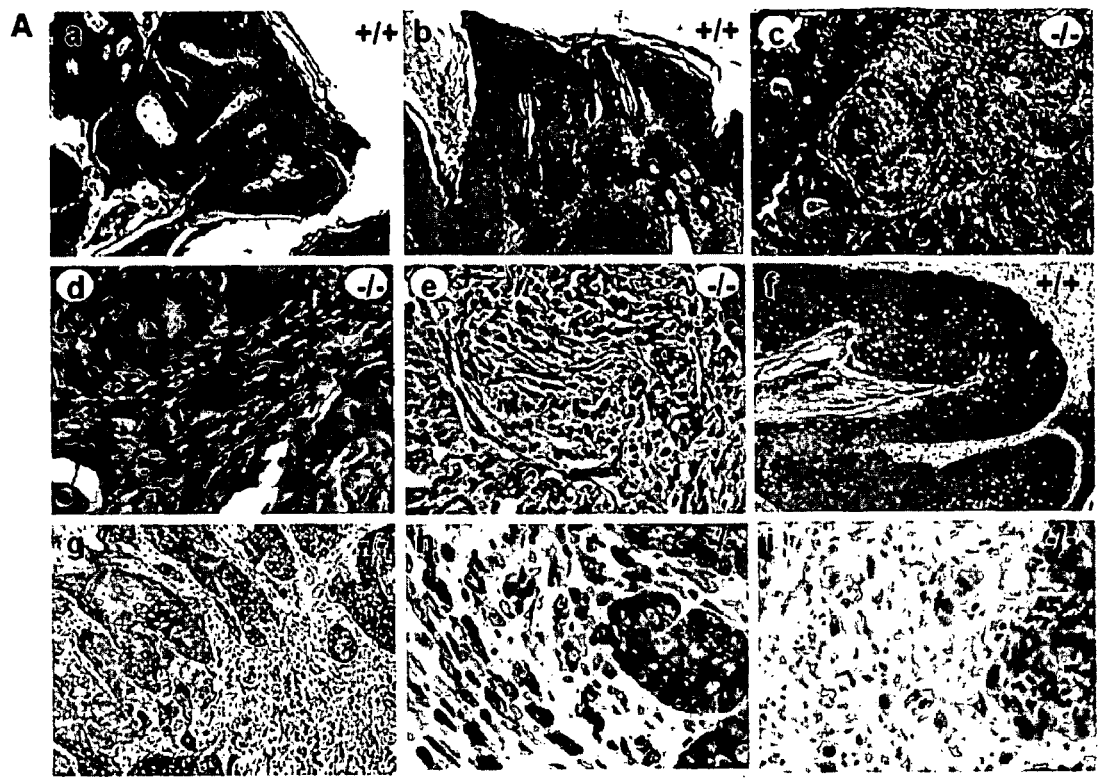
FIG. 45. Malignant progression of DMBA/TPA-induced tumors in wild type and EphA2 mutant mice. A) TPA treatment was stopped at 16 weeks post-DMBA initiation. Tumors were collected 10 weeks later and processed for staining with hematoxylin and eosin (a-e), anti-keratin 14 (f-g) or X-gal (i). a, A benign lesion from a wild type (+/+) mouse. b, An invasive carcinoma from a wild type mouse. c-d, An invasive squamous cell carcinoma from a knockout mice (−/−). e, A knockout spindle cell carcinoma. f, Keratin 14 staining a wild type papilloma. g-h, Keratin 14 staining of an invasive EphA2$^{-/-}$ carcinoma showing spindle cells infiltrating into tumor stroma. i, X-gal staining of a frozen section cut from the same tumor as in (h) showing EphA2-β-geo fusion protein expression. B) Tumors arising in EphA2 knockout exhibited higher incidence of malignant conversion. Histopathological examinations were performed on the indicated numbers of tumors from each genotype. Tumors with clear evidence of invasive growth were quantitated.
Figure 45B:
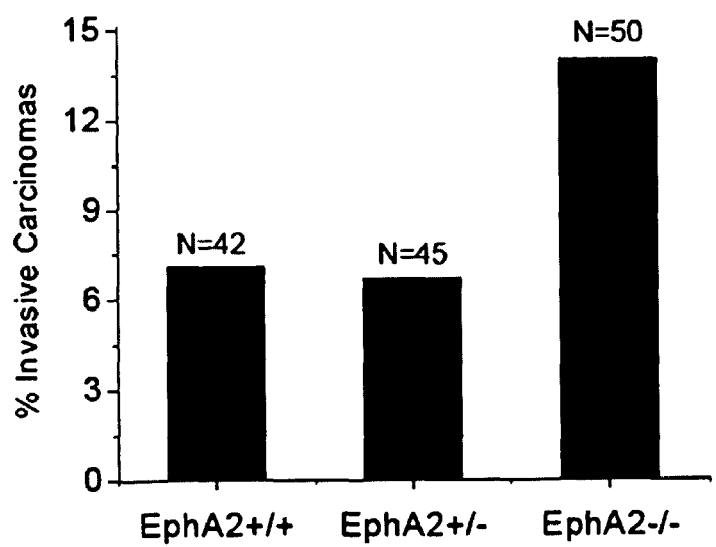

A well-established function of Eph kinases is the regulation of growth cone and cell motility, primarily through repulsive mechanisms (Gale and Yancopoulos, 1997, Flanagan and Vanderhaeghen, 1998). Cell motility is related to tumor progression toward a more invasive and metastatic phenotype. However, because skin tumors rarely metastasize, we focused on invasive progression instead. For this purpose, TPA treatment was stopped at 16 weeks, and subgroups of mice were observed for additional 10 weeks. During this time, most tumors either started to regress or grew slowly, while some tumors showed signs of malignant progression grossly as evidenced by inward growth and bloody appearance in tumor centers. Histopathological analyses revealed that while most tumors comprised of benign papillomas with varying degrees of differentiation (FIG. 45A), a significant fraction of tumors had progressed to squamous cell carcinoma with clear evidence of local invasion by 26 weeks (FIG. 45). Several tumors from EphA2-null mice had developed spindle cell morphology (FIG. 45A). Staining for keratin 14, a keratinocyte marker, confirmed the epithelial origin of invasive spindle cells (FIG. 45A). These invasive cells also express EphA2-β-geo fusion protein revealed by X-gal staining (FIG. 45A). Quantitative analyses show that EphA2-null tumors were twice as likely to develop fully invasive phenotype compared with tumors from wild type mice (FIG. 45B). Interestingly, tumors from heterozygous mice shared similar rate of malignant conversion as wild type tumors. This is in contrast with the intermediate phenotype in tumor number, incidence and growth rate (FIGS. 39D and 40). Thus while haploinsufficiency of EphA2 can predispose cells to tumor development, EphA2 plays a dominant role in suppressing invasive tumor progression.

Discussion

In this report, we provide experimental evidence to demonstrate that EphA2 is expressed in epidermal and follicular keratinocytes and functions as a tumor suppressor gene during mammalian skin carcinogenesis. EphA2 deletion resulted in susceptibility to chemically-induced skin tumorigenesis with significantly increased tumor number, shortened latency, accelerated growth rate, as well as higher rate of malignant conversion. In vitro, ephrin-A1 stimulation of wild type but EphA2-null keratinocytes attenuated ERK1/2 activities and suppressed cell proliferation. EphA2 and ephrin-A1 are expressed in a complementary pattern in epidermis, largely limiting their interactions to the basal layer of epidermal cells where active cell proliferation normally takes place. Consistent with these in vitro and in vivo observations, loss of EphA2 resulted in higher proliferation rate in basal layers of tumor cells, which may be a contributing mechanism of tumor susceptibility.

EphA2 was originally called epithelial cell kinase (Eck) because of its wide distribution in epithelial cells in vitro and in vivo. Since then numerous studies have reported overexpression of EphA2 in a diverse array of human cancer including breast, lung, prostate and gastric cancer. However the role of EphA2 kinase in epithelial tumorigenesis remains unclear. While some in vitro studies support EphA2 as an oncogene, others are more consistent with anti-tumorigenic functions. The EphA2 knockout mice allowed us to directly address the role of EphA2 in tumor etiology and progression in mammalian skin using a well-established two-stage carcinogenesis model. The dramatically increased susceptibility of EphA2 knockout mice supports a tumor suppressor role of EphA2 in mammalian epithelial cells. Interestingly, we found that EphA2 was overexpressed in chemically-induced skin tumors relative to neighboring normal skin, similar to what have been observed in many human cancers. Moreover, treatment of several breast cancer cell lines with U1026, an inhibitor of MEK, reduced EphA2 expression. It has been well-established that most DMBA/TPA-induced mouse skin tumors harbor activating mutation in H-Ras, which may contribute to EphA2 upregulation in these tumors. Since deletion of EphA2 resulted in substantially increased tumor susceptibility, we propose that the upregulated EphA2 suppresses tumor initiation and progression, and may represent a compensatory feedback defensive mechanism against malignant transformation.

Activating point mutations of Ras occur in 15% of all human malignancies, most prominently in pancreatic and colorectal cancers. Moreover, Ras/ERK signaling cascade can be activated by acquisition of paracrine and autocrine loops in different human tumors. Although the relationship between Ras/ERK activation status and EphA2 expression remains to be determined in human cancer, it is possible that abnormal increases in ERK1/2 MAPK activities may be one of the underlying causes for EphA2 overexpression in human cancer. Because activation of MAPK has been linked to malignant, the transcriptional upregulation of EphA2 by the activated MAPK may also explain the reported correlations between EphA2 overexpression and poor prognosis in different types of human cancers. In this context, EphA2 overexpression may be more likely to be a marker of tumor progression rather than an etiological event.

Our results also predict that loss or reduced EphA2 expression may predispose cells to malignant transformation. Supporting this notion, EphA2 is mapped to human chromosome 1p36.13, a region frequently lost in neuroblastoma, melanoma, prostate cancer and other tumors. Cytogenetic and molecular analyses have linked the loss of 1p36 to chordoma, a rare tumor arising from notochordal remnants in axial skeleton Candidate gene screening identified EphA2 as a possible oncosuppressor gene. In keeping with the latter studies, kinked tail has been observed in one line of EphA2 knockout mice associated with abnormal notochord development, although no chordoma has been reported in these mice.

Our data show that haploinsufficiency can predispose mouse skin to chemical carcinogenesis. Further investigation is needed to characterize LOH of EphA2 locus or other mechanisms that may lead to reduced EphA2 expression in human tumors. Indeed, in some existing reports on EphA2 expression in human cancers, down regulation or total lack of EphA2 expression is present in significant fractions of the cases. For example, about 50% human esophageal squamous cell carcinoma are negative for EphA2 expression.

EphA2 homozygous knockout appears to promote invasive progression of mammalian skin tumors. Early studies on Eph kinases have linked Eph kinase activation to repulsive guidance of growth cones and neurons. Recent genetic studies using knockout mice show that negative regulation of cell motility as a predominant outcome upon Eph/ephrin interactions in vivo, not only in the nervous system but also in epithelial tissues. This is mainly achieved through complementary expression of Eph kinases and ephrin ligand. For example, EphB3 is expressed at the bottom of mouse intestinal crypts while its cognitive ligands (ephrin-B1 and -B2) are expressed in the top to bottom gradient along the wall of crypts. Paneth cells expressing EphB3 at the bottom of the crypt becomes mislocalized when EphB3 is deleted suggesting EphB3/ephrin-B interaction inhibit Paneth cell migration in vivo. We found EphA2 and ephrin-A1 expression was compartmentalized in mouse interfollicular epidermis and hair follicles. In epidermis, ephrin-A1 is expressed at the basal layer, while EphA2 is expressed in a basal-suprabasal gradient. Conceivably, invading tumors overexpressing EphA2 may be repulsed or stopped in track upon contact with ephrin-A1-presenting basal layer cells; loss of EphA2 may render invading cells less responsive to the repulsive effects and facilitates tumor invasion.

In sum we have found that EphA2 is a tumor suppressor gene in mammalian skin. Caution may need to be exercised in therapeutic strategies designed to systemically down-regulate EphA2 from cell surfaces.

Materials and Methods

EphA2 Knockout Mice and Multistage Skin Carcinogenesis

EphA2 knockout mice on C57B1/6/129 genetic background were generated through secretory gene trapping. They were backcrossed for 4 generations to FVB/N mice which were then bred with each other to generate cohorts of female Eph-A2$^{-/-}$, EphA2$^{-/-}$ and EphA2$^{-/-}$ mice that were used in subsequent studies. For two-stage chemical carcinogenesis, the backs of 8-week-old mice were shaved and treated with a single application of DMBA (25 μg in 200 μl acetone; Sigma) followed by twice a week applications of TPA (200 μl of 100 μM solution in acetone; Sigma). Mice were visually inspected weekly and tumor number and sizes were quantitated. Sixteen weeks post DMBA initiation, mice were divided into two subgroups; one group were sacrificed while another group were kept for observation of malignant conversion in the absence of further TPA treatment for additional 10 weeks. Mice were sacrificed if moribund, if any individual tumor reached a diameter of 1.5 cm, or at the termination of the experiments. Tumors were processed for biochemical analyses by snap-frozen in liquid nitrogen, embedded in OCT and submerged in liquid nitrogen for frozen section, or fixed in 4% paraformaldehyde for later paraffin embedment and staining with hematoxylin and eosin.

Detection of β-Galactosidase Activity

Skin and tumors were processed for frozen sections (skin 7 μm, and tumor 12 μm). Staining of skin and tumor was performed after fixation in 4% paraformaldehyde for 10 minutes and stained in X-gal solution (1 mg/ml) at 37° C. for 24 hours. Sections were counterstained with nuclear fast red (Vector) for 15 min at room temperature, washed with distilled water, dehydrated by increasing concentrations of ethanol and mounted with Permount (Fisher Scientific).

Tissue Extraction

Tumors were snap-frozen in liquid nitrogen at stored at −80° C. Samples were homogenized in ice-cold lysis buffer containing 20 mM Tris (pH 7.4), 125 mM NaCl, 10%, glycerol, 1% Triton X-100, 0.5% DCA, 0.1% SDS, 20 mM NaF, 1 mM PMSF, 4 μg/ml aprotiniin, 4 μg/ml leupeptina and 1 mM Na$_3$VO$_4$. Then samples were centrifuged at 20,800 g for 10 minutes at 4° C. Protein concentrations in supernatant were measured using the BCA protein assay kit (Bio-Rad, Hercules. Calif.). Equal amounts of protein extracts were resolved by SDS-PAGE and electrotransferred onto polyvinylidene difluoride membranes (Millipore), which were then blotted with the indicated antibodies.

Proliferation and Apoptotic Assays.

Skin tumors were fixed in 4% paraformaldehyde overnight and embedded in paraffin. To detect the proliferative cells in tumors, immunohistochemical studies were performed using a polyclonal NCL-Ki67-p rabbit antibody (Castra). Paraffin embedded sections (5 μm thick) were deparaffinized in xylene, hydrated in series of alcohols, immersed in citrate buffer (10 mM sodium citrate, 0.05% Tween 20, pH 6.0) for 10 minutes at 95° C. After cooling down to RT, sections were blocked with 5% normal goat serum in Tris-buffered saline for 1 h at RT to reduce nonspecific staining and then incubated with primary antibodies (1:1000) overnight at 4° C. Biotinylated secondary antibody (1:500) and avidin-biotin-peroxidase system (Vector) were used. Color immunostaining was revealed using diaminobenzidine with metal enhancer (Vector). The apoptotic tumor cells on paraffin sections were detected using a TUNEL kit without antigen retrieval following the manufacturer's instructions (Roche). Sections were mounted with DAPI-containing mounting medium (Vector).

The number of positive tumor cells was enumerated independently by two researchers. Quotients were converted to density (positive cells/unit arbitrary tumor area). The ANOVA for unpaired samples was used for all statistical analyses. The post-hoc analysis is Bonferroni Test.

Immunofluorescence

Frozen sections of skin or tumors were fixed with 4% Paraformaldehyde. After washing with PBS, the sections were blocked with 50 mM NH$_4$Cl and permeabilized with 0.3% NP-40 for 10 minutes. The sections were then incubated with goat polyclonal antibodies that recognize the ectodomain of mouse Eph-A2 (R&D) and rabbit polyclonal anti-ephrin-A1 (Santa Cruz) at RT for 1 hour followed by detection with donkey anti-goat IgG-FITC and donkey anti-rabbit IgG-Red X (Jackson ImmunoResearch) at RT for 30 min. Images were taken using Leica microscope.

Primary Keratinocyte Isolation, Stimulation, Immunoprecipitation, and Immunoblotting Primary keratinocytes were isolated from neonatal mouse skin as described previously (Caldelari et al., 2000). Briefly, the entire P1 mouse skin was dissected and incubated with 5 U/ml dispase II (Boehringer Mannheim) overnight at 4° C. Epidermal layer was separated from decimal layer using forceps, minced and digested with 0.25% trypsin/0.05 mM EDTA. After neutralizing trypsin by washing with serum-containing medium, cells were filtered through sterile gauze pads, spun down and resuspended in serum-free keratinocytes culture medium (Gibco) containing pituitary extract, 5 ng/ml EGF, 100 U/ml penicillin, 0.1 mg/ml streptomycin, and 0.25 μg/ml amphotericin, and plated on 6-well plates precoated with 50 μg/ml matrigel. Cell stimulation with ephrin-A1-Fc, immunoprecipitation, and immunoblot were carried as described preciously (Miao et al., 2003; Miao et al., 2005).

Example 6

EphA2 Activation Inhibited Akt Activities

Figure 46:
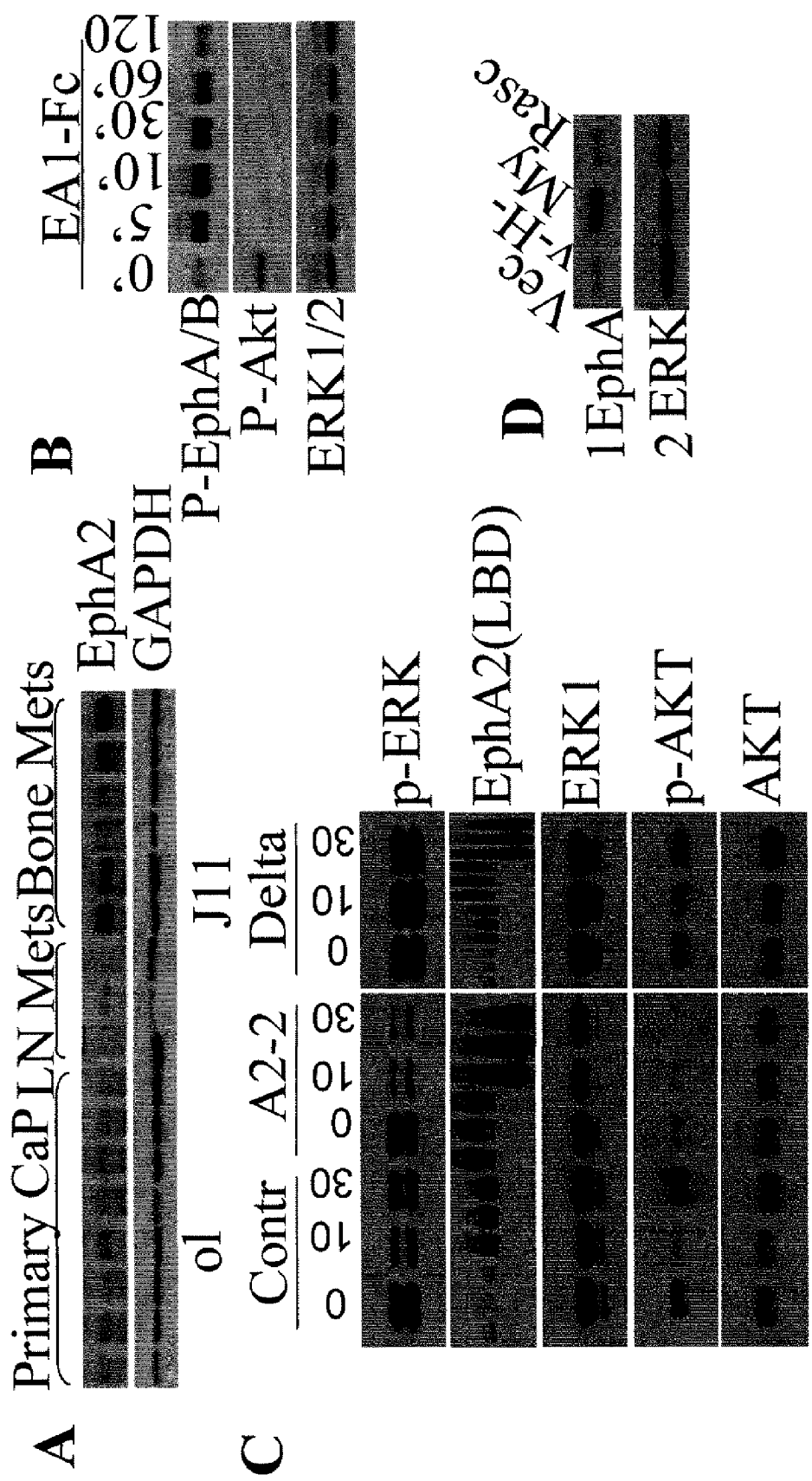
FIG. 46. A) EphA2 is overexpressed in osseous but not lymph node metastases of human prostate cancer specimens obtained from rapid autopsy. B) Inhibition of Akt activities in PC-3 cells upon stimulation of EphA2 with its cognitive ligand ephrin-A1 (EA1-Fe). C) Dominant negative EphA2 abolished the inhibitory effects of ephrin-A1 treatment on Akt and ERK activities. DU145 cells were infected with a retroviral vector expressing wild type (WT) or a dominant negative mutant EphA2 where the entire cytoplasmic tail was replaced with GFP. An antibody against the ectodomain of EphA2 was used to determine the expression of endogenous (vector control). WT- and DN-EphA2. D) Upregulation of EphA2 by Ras but not Myc oncogene in NRP152 normal rat prostate epithelial cells.

We have found that EphA2 activation inhibits Akt kinase activities. We observed that EphA2 is overexpressed in osseous but not lymph node metastases of human prostate cancer specimens obtained from rapid autopsy (FIG. 46A). We further observed inhibition of Akt activities in PC-3 cells upon stimulation of EphA2 with its cognitive ligand ephrin-A1 (EA1-Fc) (FIG. 46B). Additionally, dominant negative EphA2 abolished the inhibitory effects of ephrin-A1 treatment on Akt and ERK activities. DU145 cells were infected with a retroviral vector expressing wild type (WT) or a dominant negative mutant EphA2 where the entire cytoplasmic tail was replaced with GFP. An antibody against the ectodomain of EphA2 was used to determine the expression of endogenous (vector control), WT- and DN-EphA2 (FIG. 46C). We further observed upregulation of EphA2 by Ras but not Myc oncogene in NRP152 normal rat prostate epithelial cells (FIG. 46D).

Example 7

EphA2 Agonists can be Targeted for Treatment of Lung Cancer

We have found that EphA2 is highly overexpressed in mouse lung epithelial cells in vivo, and human lung cancer cells in vitro. Moreover, activation of EphA2 on human lung cancer cells, can inhibit their malignant behaviors including suppression of ERK1/2 MAPK kinase and Akt kinase activities.

Figure 47:
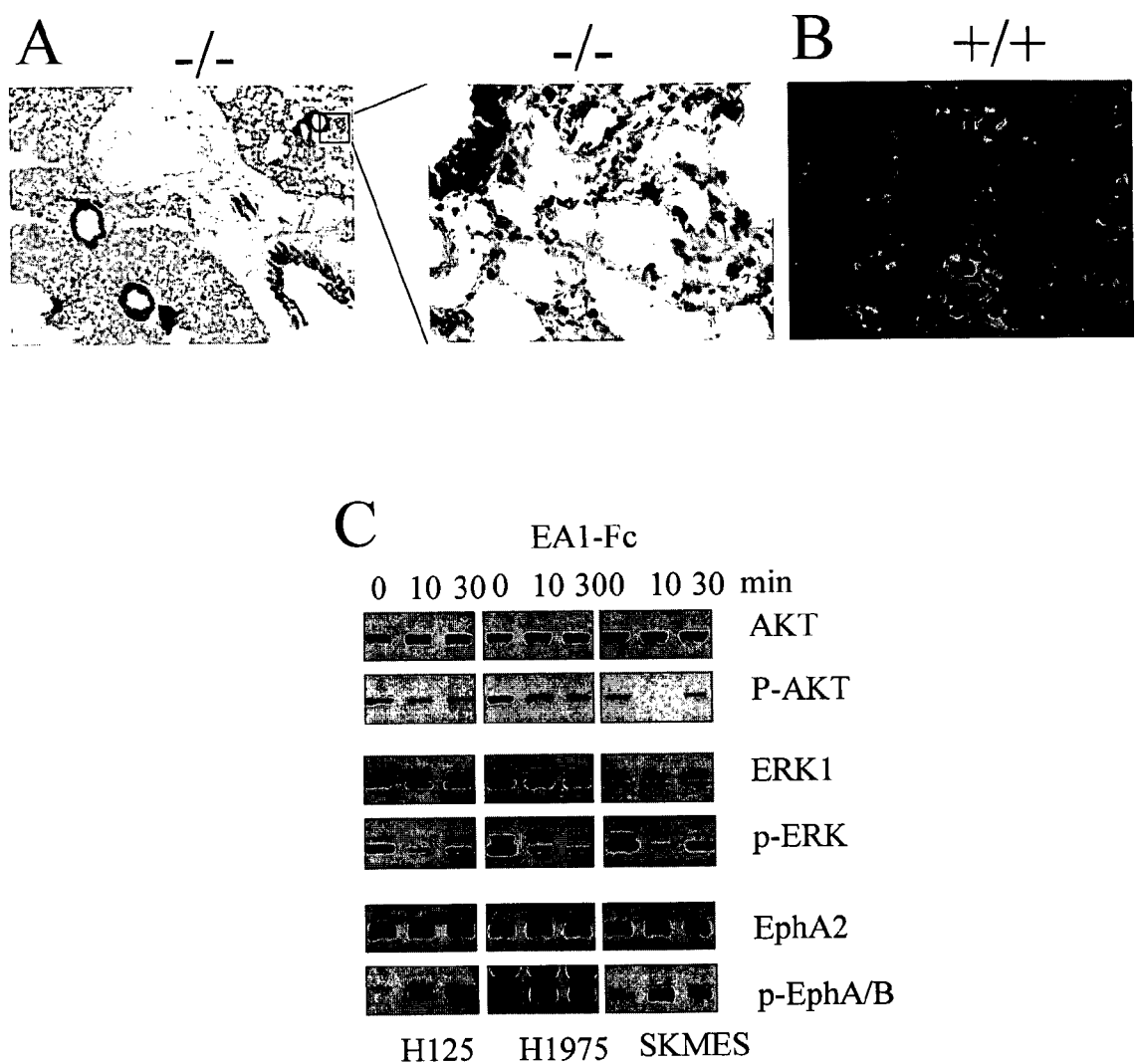
FIG. 47. A) Expression of β-gal in EphA2 KO mouse lung. Frozen sections were fixed and stained with X-gal and followed by counterstaining with nuclear Fast-Red. B) Expression of EphA2 in the lung from wild-type mice. Lung frozen sections were stained with goat polyclonal antibodies that recognize the ectodomain of EphA2 followed by detection with donkey anti-goat IgG conjugated with FITC. C) EphA kinase activation by ephrin-A1 in H125, H1975 and SKMES human non-small cell lung cancer cells. Cells were stimulated with 2 ig/ml of ephrin-A1-Fc for 10 and 30 minutes. Ephrin-A1 stimulation inhibits ERK and AKT phosphorylation. These data suggest that agonists for EphA kinases can also be used to target human lung cancers.

FIG. 47A illustrates the expression of β-gal in EphA2 knockout mouse lung. Frozen sections were fixed and stained with X-gal and followed by counterstaining with nuclear Fast-Red. FIG. 47B illustrates expression of EphA2 in the lung from wild-type mice. Lung frozen sections were stained with goat polyclonal antibodies that recognize the ectodomain of EphA2 followed by detection with donkey anti-goat IgG conjugated with FITC. FIG. 47C illustrates EphA kinase activation by ephrin-A1 in H125, H1975 and SKMES human non-small cell lung cancer cells. Cells were stimulated width 2 ig/ml of ephrin-A1-Fc for 10 and 30 minutes. Ephrin-A1 stimulation inhibits ERK and AKT phosphorylation. These data suggest that agonists for EphA kinases can also be used to target human lung cancers.

Example 8

EphA1 and EphA2 Agonists can be Targeted for Treatment of Breast Cancer

We have found that EphA1 and EphA2 are highly overexpressed in a subset of human breast cancer cells in vitro. Moreover, activation of EphA1 EphA2 on human lung cancer cells, can inhibit their malignant behaviors including suppression of ERK1/2 MAPK kinase and Akt kinase activities.

Figure 48:
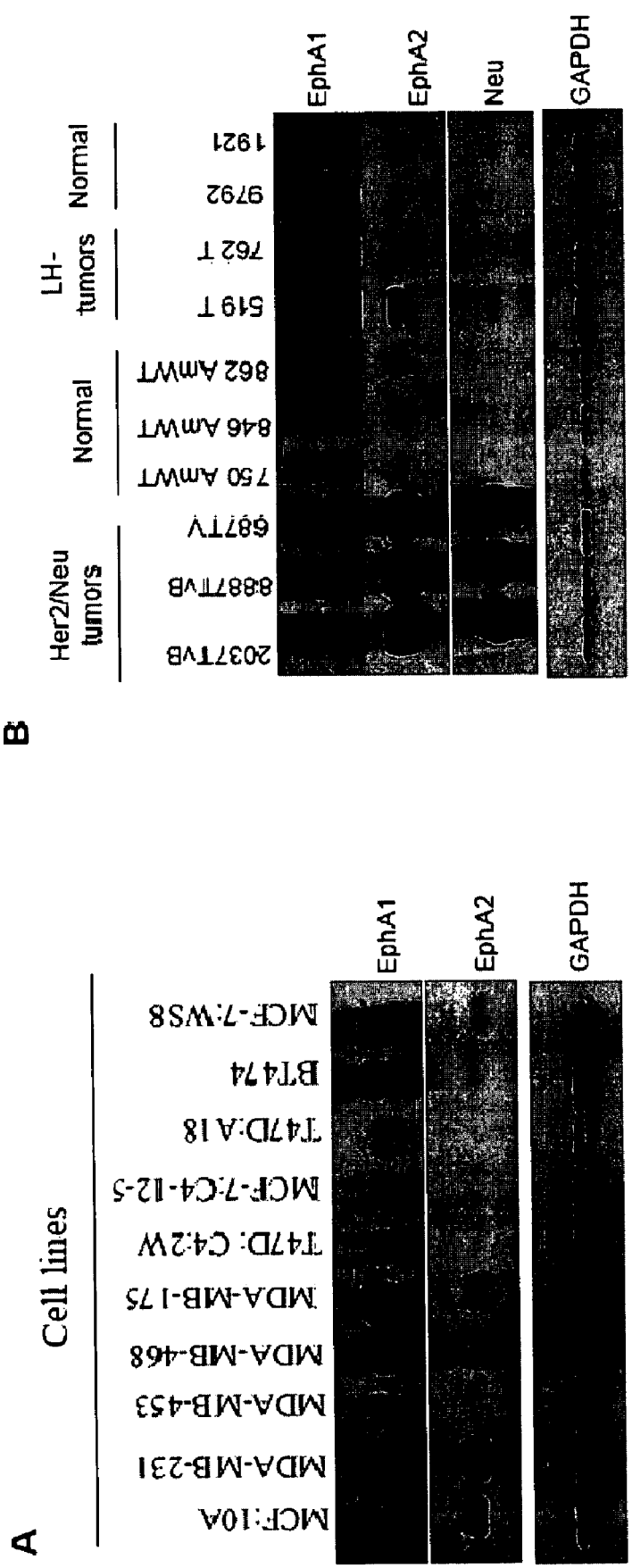
FIG. 48. A illustrates expression of EphA1 and EphA2 in human breast cancer cell lines. Note that EphA1 are more broadly distributed than EphA2.
Figure 49:
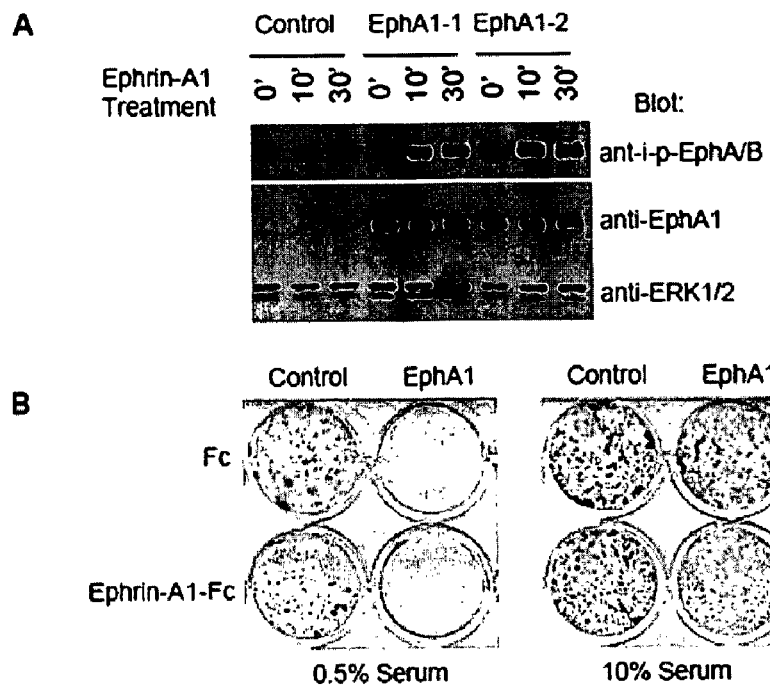
FIG. 49A illustrates expression of EphA1 in DU145 cells infected with vector control (control) and EphA1 expression retrovirus.
FIG. 49B illustrates that about 2,000 cells were plated on 12-well plates in the regular culture medium (10% serum) and low serum medium (0.5%). Cell were cultured for 7 days (10% serum) or 18 days (0.5%).

FIG. 49A illustrates expression of EphA1 and EphA2 in human breast cancer cell lines. Note that EphA1 are more broadly distributed than EphA2. FIG. 48B illustrates that EphA1 and EphA2 are upregulated in mouse breast tumors induced by HER2/Neu, but not in tumors induced by luteinizinghormone (LH). Upregulation of EphA2 is present in 30% human breast cancer. These data suggest that EphA1 and EphA2 agonists can be used together with HER2/Neu inhibitor such as Herceptin for breast cancer treatment.

Example 9

Expression of EphA1 in Prostatic Epithelial Cells Suppressed Cell Proliferation

We have found that EphA1 is expressed in prostatic epithelial cells. Moreover, activation of EphA1 on prostatic epithelial cells can inhibit their malignant behaviors.

DU145 human prostatic epithelial cells were infected with retrovirus expressing EphA1. FIG. 49A illustrates expression of EphA1 in DU145 cells infected with vector control (control) and EphA1 expression retrovirus. FIG. 49B illustrates that about 2,000 cells were plated on 12-well plates in the regular culture medium (10% serum) and low serum medium (0.5%). Cell were cultured for 7 days (10% serum) or 18 days (0.5%). FIG. 49B illustrates that proliferation of prostatic epithelial cells expressing EphA1 and activated with Ephrin-A1 is inhibited.

Example 10

Figure 50:
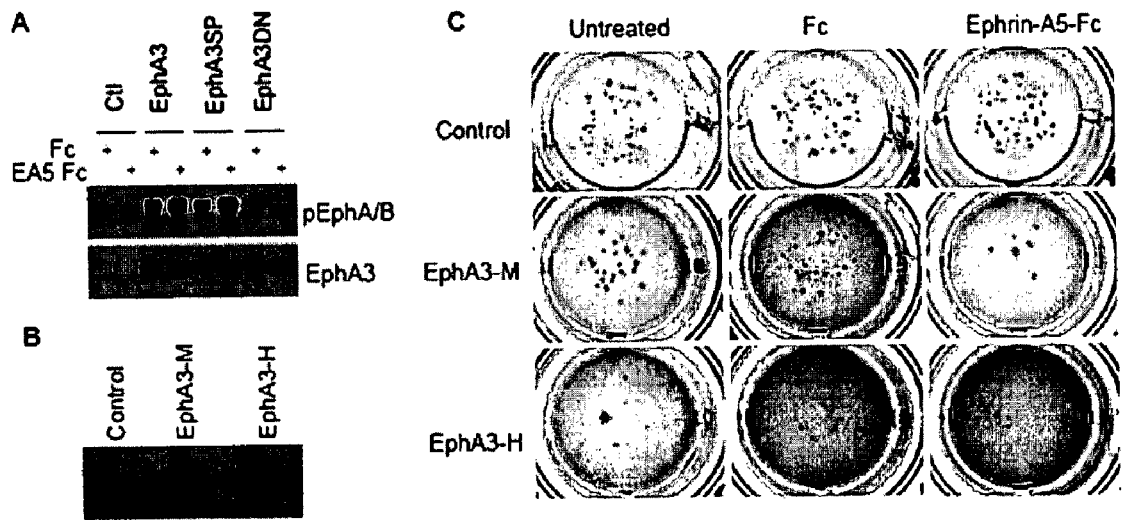
FIG. 50A illustrates that the mutation (EphA3DN) in VACO 451 cells caused loss of EphA3 kinase activities (Note that there is no pEphA/B signal).
FIG. 50B illustrates that VACO-451 cells were infected with retroviral vectors that express wild type (WT) EphA3. Clones that express high (EphA3-H) and medium (EphA3-M) levels of EphA3 as well as vector control cells were subject to growth in soft agar assay shown in FIG. 50C.

Expression of Wild Type EphA3 in VACO 451 Human Colorectal Cancer Cells Inhibited Cell Growth in Soft Afar FIG. 50 shows that either EphA3 overexpression or activation by its agonists (ephrin-A5) can suppress human colorectal cancer growth. Please note EphA3 receptor prefers ephrin-A5 as its ligand. Both EphA1 receptor only uses ephrin-A1 as ligand. EphA2 uses both ephrin-A1 and ephrin-A5 as ligands. Kinch's patent only claims ephrin-A1 on EphA2.

VACO-451 human colorectal cancer cells harbor Aspartate to Asparagine mutation at position 806 (D806N) in EphA3 that was first reported two year ago (Science 300:949). However the role of this mutation is not known. FIG. 50A illustrates that the mutation (EphA3DN) in VACO 451 cells caused loss of EphA3 kinase activities (Note that there is no pEphA/B signal). FIG. 50B illustrates that VACO-451 cells were infected with retroviral vectors that express wild type (WT) EphA3. Clones that express high (EphA3-H) and medium (EphA3-M) levels of EphA3 as well as vector control cells were subject to growth in soft agar assay shown in FIG. 50C. Ephrin-A5-Fc, the preferred ligand for EphA3 were used to stimulate EphA3.Fc was used as controls. Note that high level of expression of WT-EphA3 inhibited basal proliferation of VACO-451 cells (EphA3-H, untreated). Cells expressing medium levels of EphA3 can growth-inhibited by ephrin-A5-Fc treatment (EphA3-M, Ephrin-A5-Fc). Therefore, overexpression or agonist activation of WT-EphA3 can overcome the effects of mutant EphA3 and mediate suppression of human colorectal cancer cell growth. These data strongly suggest that EphA3 is a tumor suppressor gene in human colorectal cancer. Because colorectal tumors frequently express wild type EphA3 agonists such as its native ephrin-A5 ligand, peptides or small molecules for EphA3 can have therapeutic efficacy against this disease.

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

TABLE 1

```
REMARK   coordinates from minimization and B-factor refinement
REMARK   refinement resolution: 20-2.5 A
REMARK   starting r = 0.3042 free_r = 0.3245
REMARK   final r = 0.2761 free_r = 0.3129
REMARK   rmsd bonds = 0.041983 rmsd angles = 3.03383
REMARK   B rmsd for bonded mainchain atoms = 1.066 target = 1.5
REMARK   B rmsd for bonded sidechain atoms = 1.696 target = 2.0
REMARK   B rmsd for angle mainchain atoms = 1.623 target = 2.0
REMARK   B rmsd for angle sidechain atoms = 2.369 target = 2.5
REMARK   target = mlf final wa = 45
REMARK   final rweight = 0.9016 (with wa = 45)
REMARK   md-method = torsion annealing schedule = slowcool
REMARK   starting temperature = 6000 total md steps = 60 * 6 .786
REMARK   cycles = 1 coordinate steps = 20 B-factor steps = 10)
REMARK   sg = P1 a = 41.271 b = 91.187 c = 91.132 alpha = 117.144 beta = 97.270
         gamma = 10⁰
REMARK   topology file 1: CNS_TOPPAR:protein.top
REMARK   topology file 2: CNS_TOPPAR:dna-rna.top
REMARK   topology file 3: CNS_TOPPAR:water.top
REMARK   topology file 4: CNS_TOPPAR:ion.top
REMARK   parameter file 1: CNS_TOPPAR:protein_rep.param
REMARK   parameter file 2: CNS_TOPPAR:dna-rna_rep.param
REMARK   parameter file 3: CNS_TOPPAR:water_rep.param
REMARK   parameter file 4: CNS_TOPPAR:ion.param
REMARK   molecular structure file: generate_A2E_m1.mtf
REMARK   input coordinates: generate_A2E_m1.pdb
REMARK   anomalous f' f" library: CNS_XRAYLIB:anom_cu.lib
REMARK   reflection file = A2E1_P1.rfree.xhkl
REMARK   ncs = restrain ncs file = ncs_restrain.def
REMARK   B-correction resolution: 6.0-2.5
REMARK   initial B-factor correction applied to fobs:
REMARK   B11 = 3.647 B22 = −4.919 B33 = 1.272
REMARK   B12 = −3.796 B13 = −4.111 B23 = −4.116
REMARK   B-factor correction applied to coordinate array B: −6.062
REMARK   bulk solvent: density level = 0.391263 e/A^3, B-factor = 26.9639 A^2
REMARK   reflections with |Fobs|/sigma_F < 0.0 rejected
REMARK   reflections with |Fobs| > 10000 * rms(Fobs) rejected
REMARK   theoretical total number of refl. in resol. range:    38923 (100.0%)
REMARK   number of unobserved reflections (no entry or |F| = 0): 3427 (8.8%)
REMARK   number of reflections rejected:         0 (0.0%)
REMARK   total number of reflections used:         35496 (91.2%)
REMARK   number of reflections in working set:       33700 (86.6%)
REMARK   number of reflections in test set:        1796 (4.6%)
CRYST1   41.271 91.187 91.132 117.14 97.27 100.79 P 1
REMARK   FILENAME = "refine_A2E_m1.pdb"
REMARK   DATE: 10-Jun-2004 17:00:27 created by user: raj
REMARK   VERSION: 1.1
ATOM    1   CB   GLU  C  1   −15.004   4.724  13.078  1.00  17.75  C
ATOM    2   CG   GLU  C  1   −14.257   3.538  13.626  1.00  18.82  C
ATOM    3   CD   GLU  C  1   −12.754   3.914  14.007  1.00  21.05  C
ATOM    4   OE1  GLU  C  1   −12.447   4.771  14.930  1.00  19.92  C
ATOM    5   OE2  GLU  C  1   −11.900   3.321  13.327  1.00  20.67  C
ATOM    6   C    GLU  C  1   −17.072   3.828  11.802  1.00  16.40  C
ATOM    7   O    GLU  C  1   −17.439   2.690  11.967  1.00  15.52  C
ATOM    8   N    GLU  C  1   −17.074   4.262  14.301  1.00  18.29  C
ATOM    9   CA   GLU  C  1   −16.556   4.692  13.003  1.00  16.80  C
ATOM    10  N    VAL  C  2   −17.090   4.405  10.609  1.00  15.76  C
ATOM    11  CA   VAL  C  2   −17.528   3.693   9.441  1.00  15.70  C
ATOM    12  CB   VAL  C  2   −18.411   4.621   8.634  1.00  16.83  C
ATOM    13  CG1  VAL  C  2   −18.683   4.079   7.316  1.00  16.18  C
ATOM    14  CG2  VAL  C  2   −19.650   4.887   9.413  1.00  15.55  C
ATOM    15  C    VAL  C  2   −16.237   3.303   8.704  1.00  16.27  C
ATOM    16  O    VAL  C  2   −15.370   4.117   8.547  1.00  15.66  C
ATOM    17  N    VAL  C  3   −16.122   2.055   8.293  1.00  16.15  C
ATOM    18  CA   VAL  C  3   −14.958   1.529   7.694  1.00  14.85  C
ATOM    19  CB   VAL  C  3   −14.541   0.179   8.340  1.00  15.10  C
ATOM    20  CG1  VAL  C  3   −13.210  −0.257   7.763  1.00  14.66  C
ATOM    21  CG2  VAL  C  3   −14.378   0.292   9.857  1.00  14.16  C
ATOM    22  C    VAL  C  3   −15.110   1.253   6.301  1.00  17.23  C
ATOM    23  O    VAL  C  3   −15.962   0.423   5.917  1.00  18.22  C
ATOM    24  N    LEU  C  4   −14.254   1.871   5.498  1.00  17.37  C
ATOM    25  CA   LEU  C  4   −14.228   1.647   4.005  1.00  17.09  C
ATOM    26  CB   LEU  C  4   −14.170   2.991   3.292  1.00  16.69  C
ATOM    27  CG   LEU  C  4   −14.961   4.115   3.949  1.00  17.30  C
ATOM    28  CD1  LEU  C  4   −14.708   5.451   3.203  1.00  17.74  C
ATOM    29  CD2  LEU  C  4   −16.522   3.787   3.929  1.00  16.42  C
ATOM    30  C    LEU  C  4   −12.942   0.942   3.667  1.00  16.85  C
```

TABLE 1-continued

| | | | | | | | | | | |
|---|---|---|---|---|---|---|---|---|---|---|
| ATOM | 31 | O | LEU | C | 4 | −11.981 | 1.557 | 3.451 | 1.00 | 19.17 | C |
| ATOM | 32 | N | LEU | C | 5 | −12.848 | −0.306 | 3.497 | 1.00 | 15.95 | C |
| ATOM | 33 | CA | LEU | C | 5 | −11.504 | −0.831 | 3.312 | 1.00 | 14.42 | C |
| ATOM | 34 | CB | LEU | C | 5 | −10.593 | 0.084 | 2.487 | 1.00 | 13.73 | C |
| ATOM | 35 | CG | LEU | C | 5 | −9.240 | −0.637 | 2.321 | 1.00 | 14.68 | C |
| ATOM | 36 | CD1 | LEU | C | 5 | −9.471 | −2.088 | 2.129 | 1.00 | 16.89 | C |
| ATOM | 37 | CD2 | LEU | C | 5 | −8.536 | −0.165 | 1.088 | 1.00 | 14.75 | C |
| ATOM | 38 | C | LEU | C | 5 | −10.785 | −1.223 | 4.638 | 1.00 | 14.88 | C |
| ATOM | 39 | O | LEU | C | 5 | −10.450 | −0.383 | 5.511 | 1.00 | 15.75 | C |
| ATOM | 40 | N | ASP | C | 6 | −10.505 | −2.511 | 4.743 | 1.00 | 14.34 | C |
| ATOM | 41 | CA | ASP | C | 6 | −9.847 | −3.120 | 5.846 | 1.00 | 13.16 | C |
| ATOM | 42 | CB | ASP | C | 6 | −10.857 | −3.464 | 6.861 | 1.00 | 14.82 | C |
| ATOM | 43 | CG | ASP | C | 6 | −10.255 | −3.927 | 8.078 | 1.00 | 15.96 | C |
| ATOM | 44 | OD1 | ASP | C | 6 | −10.949 | −4.555 | 8.907 | 1.00 | 17.35 | C |
| ATOM | 45 | OD2 | ASP | C | 6 | −9.057 | −3.659 | 8.215 | 1.00 | 18.85 | C |
| ATOM | 46 | C | ASP | C | 6 | −9.149 | −4.394 | 5.412 | 1.00 | 14.48 | C |
| ATOM | 47 | O | ASP | C | 6 | −9.701 | −5.537 | 5.423 | 1.00 | 13.67 | C |
| ATOM | 48 | N | PHE | C | 7 | −7.918 | −4.200 | 5.020 | 1.00 | 14.40 | C |
| ATOM | 49 | CA | PHE | C | 7 | −7.061 | −5.258 | 4.587 | 1.00 | 14.40 | C |
| ATOM | 50 | CB | PHE | C | 7 | −5.647 | −4.712 | 4.395 | 1.00 | 16.49 | C |
| ATOM | 51 | CG | PHE | C | 7 | −4.669 | −5.762 | 3.989 | 1.00 | 17.58 | C |
| ATOM | 52 | CD1 | PHE | C | 7 | −4.660 | −6.242 | 2.672 | 1.00 | 18.30 | C |
| ATOM | 53 | CD2 | PHE | C | 7 | −3.790 | −6.322 | 4.937 | 1.00 | 16.90 | C |
| ATOM | 54 | CE1 | PHE | C | 7 | −3.755 | −7.320 | 2.311 | 1.00 | 19.82 | C |
| ATOM | 55 | CE2 | PHE | C | 7 | −2.895 | −7.355 | 4.591 | 1.00 | 16.72 | C |
| ATOM | 56 | CZ | PHE | C | 7 | −2.864 | −7.867 | 3.293 | 1.00 | 18.15 | C |
| ATOM | 57 | C | PHE | C | 7 | −7.010 | −6.520 | 5.464 | 1.00 | 15.38 | C |
| ATOM | 58 | O | PHE | C | 7 | −7.197 | −7.590 | 4.939 | 1.00 | 14.26 | C |
| ATOM | 59 | N | ALA | C | 8 | −6.710 | −6.395 | 6.772 | 1.00 | 15.28 | C |
| ATOM | 60 | CA | ALA | C | 8 | −6.653 | −7.605 | 7.612 | 1.00 | 15.33 | C |
| ATOM | 61 | CB | ALA | C | 8 | −6.164 | −7.255 | 8.976 | 1.00 | 14.79 | C |
| ATOM | 62 | C | ALA | C | 8 | −7.965 | −8.476 | 7.711 | 1.00 | 16.23 | C |
| ATOM | 63 | O | ALA | C | 8 | −7.902 | −9.588 | 8.236 | 1.00 | 16.77 | C |
| ATOM | 64 | N | ALA | C | 9 | −9.132 | −8.011 | 7.223 | 1.00 | 15.41 | C |
| ATOM | 65 | CA | ALA | C | 9 | −10.345 | −8.793 | 7.318 | 1.00 | 15.60 | C |
| ATOM | 66 | CB | ALA | C | 9 | −11.474 | −7.940 | 7.596 | 1.00 | 8.58 | C |
| ATOM | 67 | C | ALA | C | 9 | −10.642 | −9.596 | 6.037 | 1.00 | 17.90 | C |
| ATOM | 68 | O | ALA | C | 9 | −11.451 | −10.514 | 6.066 | 1.00 | 20.08 | C |
| ATOM | 69 | N | ALA | C | 10 | −10.026 | −9.264 | 4.894 | 1.00 | 19.38 | C |
| ATOM | 70 | CA | ALA | C | 10 | −10.354 | −9.904 | 3.567 | 1.00 | 19.92 | C |
| ATOM | 71 | CB | ALA | C | 10 | −10.108 | −8.914 | 2.437 | 1.00 | 18.74 | C |
| ATOM | 72 | C | ALA | C | 10 | −9.653 | −11.226 | 3.288 | 1.00 | 20.97 | C |
| ATOM | 73 | O | ALA | C | 10 | −8.472 | −11.273 | 2.793 | 1.00 | 20.38 | C |
| ATOM | 74 | N | GLY | C | 11 | −10.416 | −12.278 | 3.696 | 1.00 | 22.55 | C |
| ATOM | 75 | CA | GLY | C | 11 | −10.074 | −13.755 | 3.669 | 1.00 | 23.79 | C |
| ATOM | 76 | C | GLY | C | 11 | −9.661 | −14.443 | 2.317 | 1.00 | 23.88 | C |
| ATOM | 77 | O | GLY | C | 11 | −10.210 | −15.434 | 1.778 | 1.00 | 23.75 | C |
| ATOM | 78 | N | GLY | C | 12 | −8.572 | −13.847 | 1.823 | 1.00 | 23.88 | C |
| ATOM | 79 | CA | GLY | C | 12 | −7.889 | −14.175 | 0.581 | 1.00 | 23.28 | C |
| ATOM | 80 | C | GLY | C | 12 | −7.055 | −12.921 | 0.206 | 1.00 | 22.26 | C |
| ATOM | 81 | O | GLY | C | 12 | −6.915 | −12.601 | −1.016 | 1.00 | 21.82 | C |
| ATOM | 82 | N | GLU | C | 13 | −6.552 | −12.211 | 1.220 | 1.00 | 21.36 | C |
| ATOM | 83 | CA | GLU | C | 13 | −5.712 | −11.060 | 0.981 | 1.00 | 21.86 | C |
| ATOM | 84 | CB | GLU | C | 13 | −4.552 | −11.514 | 0.072 | 1.00 | 23.26 | C |
| ATOM | 85 | CG | GLU | C | 13 | −4.451 | −13.134 | −0.427 | 1.00 | 25.86 | C |
| ATOM | 86 | CD | GLU | C | 13 | −2.946 | −13.608 | −0.960 | 1.00 | 27.90 | C |
| ATOM | 87 | OE1 | GLU | C | 13 | −1.897 | −12.904 | −0.354 | 1.00 | 29.27 | C |
| ATOM | 88 | OE2 | GLU | C | 13 | −2.788 | −14.655 | −1.925 | 1.00 | 22.76 | C |
| ATOM | 89 | C | GLU | C | 13 | −6.374 | −9.709 | 0.378 | 1.00 | 22.11 | C |
| ATOM | 90 | O | GLU | C | 13 | −6.506 | −8.669 | 1.111 | 1.00 | 21.05 | C |
| ATOM | 91 | N | LEU | C | 14 | −6.730 | −9.765 | −0.930 | 1.00 | 21.29 | C |
| ATOM | 92 | CA | LEU | C | 14 | −7.419 | −8.725 | −1.566 | 1.00 | 22.15 | C |
| ATOM | 93 | CB | LEU | C | 14 | −7.119 | −7.407 | −0.816 | 1.00 | 21.79 | C |
| ATOM | 94 | CG | LEU | C | 14 | −8.419 | −6.952 | −0.086 | 1.00 | 22.91 | C |
| ATOM | 95 | CD1 | LEU | C | 14 | −7.996 | −6.434 | 1.317 | 1.00 | 19.58 | C |
| ATOM | 96 | CD2 | LEU | C | 14 | −9.350 | −5.790 | −0.951 | 1.00 | 21.91 | C |
| ATOM | 97 | C | LEU | C | 14 | −7.183 | −8.491 | −3.081 | 1.00 | 23.19 | C |
| ATOM | 98 | O | LEU | C | 14 | −6.079 | −8.868 | −3.720 | 1.00 | 23.58 | C |
| ATOM | 99 | N | GLY | C | 15 | −8.157 | −7.723 | −3.622 | 1.00 | 22.34 | C |
| ATOM | 100 | CA | GLY | C | 15 | −8.075 | −7.305 | −5.012 | 1.00 | 21.66 | C |
| ATOM | 101 | C | GLY | C | 15 | −7.140 | −6.091 | −5.126 | 1.00 | 20.91 | C |
| ATOM | 102 | O | GLY | C | 15 | −7.722 | −4.974 | −5.262 | 1.00 | 21.83 | C |
| ATOM | 103 | N | TRP | C | 16 | −5.774 | −6.251 | −5.067 | 1.00 | 19.98 | C |
| ATOM | 104 | CA | TRP | C | 16 | −4.838 | −5.052 | −5.159 | 1.00 | 19.24 | C |
| ATOM | 105 | CB | TRP | C | 16 | −3.974 | −4.830 | −3.829 | 1.00 | 18.05 | C |
| ATOM | 106 | CG | TRP | C | 16 | −4.839 | −4.377 | −2.597 | 1.00 | 17.76 | C |
| ATOM | 107 | CD2 | TRP | C | 16 | −4.487 | −3.566 | −1.452 | 1.00 | 17.05 | C |
| ATOM | 108 | CE2 | TRP | C | 16 | −5.617 | −3.602 | −0.595 | 1.00 | 17.12 | C |
| ATOM | 109 | CE3 | TRP | C | 16 | −3.394 | −2.845 | −1.085 | 1.00 | 16.14 | C |
| ATOM | 110 | CD1 | TRP | C | 16 | −6.069 | −4.805 | −2.361 | 1.00 | 18.77 | C |

TABLE 1-continued

| | | | | | | | | | | |
|---|---|---|---|---|---|---|---|---|---|---|
| ATOM | 111 | NE1 | TRP | C | 16 | −6.546 | −4.369 | −1.191 | 1.00 | 18.83 | C |
| ATOM | 112 | CZ2 | TRP | C | 16 | −5.637 | −2.957 | 0.633 | 1.00 | 15.62 | C |
| ATOM | 113 | CZ3 | TRP | C | 16 | −3.455 | −2.192 | 0.155 | 1.00 | 16.51 | C |
| ATOM | 114 | CH2 | TRP | C | 16 | −4.565 | −2.258 | 0.976 | 1.00 | 15.46 | C |
| ATOM | 115 | C | TRP | C | 16 | −3.919 | −5.094 | −6.340 | 1.00 | 16.61 | C |
| ATOM | 116 | O | TRP | C | 16 | −3.550 | −6.108 | −6.732 | 1.00 | 17.35 | C |
| ATOM | 117 | N | LEU | C | 17 | −3.557 | −3.944 | −6.830 | 1.00 | 15.80 | C |
| ATOM | 118 | CA | LEU | C | 17 | −2.646 | −3.690 | −7.928 | 1.00 | 15.71 | C |
| ATOM | 119 | CB | LEU | C | 17 | −3.107 | −2.437 | −8.695 | 1.00 | 14.73 | C |
| ATOM | 120 | CG | LEU | C | 17 | −2.314 | −2.286 | −9.962 | 1.00 | 16.81 | C |
| ATOM | 121 | CD1 | LEU | C | 17 | −2.216 | −3.708 | −10.549 | 1.00 | 19.36 | C |
| ATOM | 122 | CD2 | LEU | C | 17 | −2.891 | −1.396 | −10.997 | 1.00 | 17.17 | C |
| ATOM | 123 | C | LEU | C | 17 | −1.144 | −3.500 | −7.447 | 1.00 | 14.20 | C |
| ATOM | 124 | O | LEU | C | 17 | −0.831 | −2.796 | −6.485 | 1.00 | 14.02 | C |
| ATOM | 125 | N | THR | C | 18 | −0.248 | −4.124 | −8.185 | 1.00 | 14.48 | C |
| ATOM | 126 | CA | THR | C | 18 | 1.161 | −4.110 | −7.834 | 1.00 | 16.26 | C |
| ATOM | 127 | CB | THR | C | 18 | 1.536 | −5.471 | −7.327 | 1.00 | 15.53 | C |
| ATOM | 128 | OG1 | THR | C | 18 | 1.520 | −5.436 | −5.903 | 1.00 | 13.54 | C |
| ATOM | 129 | CG2 | THR | C | 18 | 2.802 | −5.879 | −7.832 | 1.00 | 17.28 | C |
| ATOM | 130 | C | THR | C | 18 | 1.912 | −3.711 | −9.016 | 1.00 | 15.70 | C |
| ATOM | 131 | O | THR | C | 18 | 1.863 | −4.409 | −9.953 | 1.00 | 14.52 | C |
| ATOM | 132 | N | HIS | C | 19 | 2.597 | −2.575 | −8.971 | 1.00 | 17.08 | C |
| ATOM | 133 | CA | HIS | C | 19 | 3.222 | −2.102 | −10.143 | 1.00 | 18.52 | C |
| ATOM | 134 | CB | HIS | C | 19 | 3.354 | −0.643 | −10.159 | 1.00 | 19.18 | C |
| ATOM | 135 | CG | HIS | C | 19 | 3.559 | −0.056 | −11.547 | 1.00 | 20.82 | C |
| ATOM | 136 | CD2 | HIS | C | 19 | 4.234 | 1.063 | −11.963 | 1.00 | 20.60 | C |
| ATOM | 137 | ND1 | HIS | C | 19 | 3.237 | −0.752 | −12.694 | 1.00 | 20.78 | C |
| ATOM | 138 | CE1 | HIS | C | 19 | 3.718 | −0.105 | −13.747 | 1.00 | 21.27 | C |
| ATOM | 139 | NE2 | HIS | C | 19 | 4.335 | 0.995 | −13.335 | 1.00 | 22.21 | C |
| ATOM | 140 | C | HIS | C | 19 | 4.513 | −2.888 | −10.472 | 1.00 | 21.18 | C |
| ATOM | 141 | O | HIS | C | 19 | 4.679 | −4.038 | −9.970 | 1.00 | 21.99 | C |
| ATOM | 142 | N | PRO | C | 20 | 5.561 | −2.267 | −10.972 | 1.00 | 20.76 | C |
| ATOM | 143 | CD | PRO | C | 20 | 6.051 | −1.414 | −9.844 | 1.00 | 19.53 | C |
| ATOM | 144 | CA | PRO | C | 20 | 6.552 | −3.327 | −11.309 | 1.00 | 19.69 | C |
| ATOM | 145 | CB | PRO | C | 20 | 7.556 | −3.246 | −10.174 | 1.00 | 21.06 | C |
| ATOM | 146 | CG | PRO | C | 20 | 7.623 | −1.692 | −9.891 | 1.00 | 20.36 | C |
| ATOM | 147 | C | PRO | C | 20 | 5.803 | −4.767 | −11.576 | 1.00 | 20.95 | C |
| ATOM | 148 | O | PRO | C | 20 | 5.440 | −5.196 | −12.756 | 1.00 | 22.36 | C |
| ATOM | 149 | N | TYR | C | 21 | 5.466 | −5.478 | −10.519 | 1.00 | 19.20 | C |
| ATOM | 150 | CA | TYR | C | 21 | 4.794 | −6.805 | −10.535 | 1.00 | 16.82 | C |
| ATOM | 151 | CB | TYR | C | 21 | 3.674 | −6.944 | −11.528 | 1.00 | 17.06 | C |
| ATOM | 152 | CG | TYR | C | 21 | 3.072 | −8.321 | −11.379 | 1.00 | 18.30 | C |
| ATOM | 153 | CD1 | TYR | C | 21 | 2.327 | −8.642 | −10.217 | 1.00 | 17.87 | C |
| ATOM | 154 | CE1 | TYR | C | 21 | 2.016 | −9.968 | −9.857 | 1.00 | 16.08 | C |
| ATOM | 155 | CD2 | TYR | C | 21 | 3.484 | −9.422 | −12.211 | 1.00 | 19.33 | C |
| ATOM | 156 | CE2 | TYR | C | 21 | 3.197 | −10.764 | −11.803 | 1.00 | 16.95 | C |
| ATOM | 157 | CZ | TYR | C | 21 | 2.470 | −10.996 | −10.626 | 1.00 | 16.92 | C |
| ATOM | 158 | OH | TYR | C | 21 | 2.211 | −12.271 | −10.119 | 1.00 | 17.61 | C |
| ATOM | 159 | C | TYR | C | 21 | 5.837 | −7.871 | −10.844 | 1.00 | 15.77 | C |
| ATOM | 160 | O | TYR | C | 21 | 6.248 | −7.947 | −11.960 | 1.00 | 15.52 | C |
| ATOM | 161 | N | GLY | C | 22 | 6.184 | −8.688 | −9.860 | 1.00 | 14.91 | C |
| ATOM | 162 | CA | GLY | C | 22 | 7.204 | −9.676 | −10.023 | 1.00 | 15.48 | C |
| ATOM | 163 | C | GLY | C | 22 | 8.279 | −9.684 | −8.926 | 1.00 | 15.80 | C |
| ATOM | 164 | O | GLY | C | 22 | 8.519 | −10.714 | −8.292 | 1.00 | 16.63 | C |
| ATOM | 165 | N | LYS | C | 23 | 8.832 | −8.505 | −8.673 | 1.00 | 15.76 | C |
| ATOM | 166 | CA | LYS | C | 23 | 9.93 1 | −8.225 | −7.798 | 1.00 | 15.49 | C |
| ATOM | 167 | CB | LYS | C | 23 | 11.128 | −7.757 | −8.643 | 1.00 | 15.81 | C |
| ATOM | 168 | CG | LYS | C | 23 | 11.847 | −8.749 | −9.451 | 1.00 | 17.47 | C |
| ATOM | 169 | CD | LYS | C | 23 | 11.530 | −8.488 | −11.028 | 1.00 | 21.34 | C |
| ATOM | 170 | CE | LYS | C | 23 | 11.892 | −9.694 | −11.940 | 1.00 | 20.67 | C |
| ATOM | 171 | NZ | LYS | C | 23 | 13.372 | −9.866 | −12.235 | 1.00 | 23.93 | C |
| ATOM | 172 | C | LYS | C | 23 | 9.632 | −7.144 | −6.744 | 1.00 | 14.48 | C |
| ATOM | 173 | O | LYS | C | 23 | 10.412 | −7.000 | −5.832 | 1.00 | 14.66 | C |
| ATOM | 174 | N | GLY | C | 24 | 8.575 | −6.363 | −6.928 | 1.00 | 13.83 | C |
| ATOM | 175 | CA | GLY | C | 24 | 8.160 | −5.378 | −5.942 | 1.00 | 12.38 | C |
| ATOM | 176 | C | GLY | C | 24 | 7.396 | −5.995 | −4.739 | 1.00 | 12.13 | C |
| ATOM | 177 | O | GLY | C | 24 | 7.775 | −7.006 | −4.128 | 1.00 | 8.63 | C |
| ATOM | 178 | N | TRP | C | 25 | 6.299 | −5.307 | −4.430 | 1.00 | 13.10 | C |
| ATOM | 179 | CA | TRP | C | 25 | 5.349 | −5.704 | −3.396 | 1.00 | 13.94 | C |
| ATOM | 180 | CB | TRP | C | 25 | 4.292 | −4.620 | −3.317 | 1.00 | 15.51 | C |
| ATOM | 181 | CG | TRP | C | 25 | 4.648 | −3.271 | −2.788 | 1.00 | 15.71 | C |
| ATOM | 182 | CD2 | TRP | C | 25 | 4.765 | −2.912 | −1.385 | 1.00 | 15.60 | C |
| ATOM | 183 | CE2 | TRP | C | 25 | 4.966 | −1.528 | −1.318 | 1.00 | 15.15 | C |
| ATOM | 184 | CE3 | TRP | C | 25 | 4.697 | −3.639 | −0.197 | 1.00 | 14.68 | C |
| ATOM | 185 | CD1 | TRP | C | 25 | 4.799 | −2.112 | −3.480 | 1.00 | 15.32 | C |
| ATOM | 186 | NE1 | TRP | C | 25 | 4.986 | −1.055 | −2.595 | 1.00 | 15.46 | C |
| ATOM | 187 | CZ2 | TRP | C | 25 | 5.106 | −0.888 | −0.158 | 1.00 | 15.58 | C |
| ATOM | 188 | CZ3 | TRP | C | 25 | 4.839 | −2.974 | 0.958 | 1.00 | 15.80 | C |
| ATOM | 189 | CH2 | TRP | C | 25 | 5.030 | −1.622 | 0.985 | 1.00 | 14.18 | C |
| ATOM | 190 | C | TRP | C | 25 | 4.667 | −7.133 | −3.766 | 1.00 | 14.77 | C |

TABLE 1-continued

| | | | | | | | | | | |
|---|---|---|---|---|---|---|---|---|---|---|
| ATOM | 191 | O | TRP | C | 25 | 4.160 | −7.407 | −4.894 | 1.00 | 12.76 | C |
| ATOM | 192 | N | ASP | C | 26 | 4.723 | −8.048 | −2.798 | 1.00 | 15.85 | C |
| ATOM | 193 | CA | ASP | C | 26 | 4.147 | −9.363 | −2.916 | 1.00 | 16.48 | C |
| ATOM | 194 | CB | ASP | C | 26 | 5.184 | −10.536 | −2.917 | 1.00 | 19.04 | C |
| ATOM | 195 | CG | ASP | C | 26 | 6.058 | −10.686 | −4.199 | 1.00 | 23.71 | C |
| ATOM | 196 | OD1 | ASP | C | 26 | 6.109 | −9.866 | −5.305 | 1.00 | 24.73 | C |
| ATOM | 197 | OD2 | ASP | C | 26 | 6.797 | −11.759 | −4.110 | 1.00 | 26.80 | C |
| ATOM | 198 | C | ASP | C | 26 | 3.222 | −9.661 | −1.707 | 1.00 | 16.33 | C |
| ATOM | 199 | O | ASP | C | 26 | 3.560 | −9.438 | −0.555 | 1.00 | 15.68 | C |
| ATOM | 200 | N | LEU | C | 27 | 2.062 | −10.208 | −2.012 | 1.00 | 16.44 | C |
| ATOM | 201 | CA | LEU | C | 27 | 1.114 | −10.649 | −1.028 | 1.00 | 16.23 | C |
| ATOM | 202 | CB | LEU | C | 27 | −0.190 | −10.854 | −1.703 | 1.00 | 16.58 | C |
| ATOM | 203 | CG | LEU | C | 27 | −1.307 | −10.911 | −0.729 | 1.00 | 16.90 | C |
| ATOM | 204 | CD1 | LEU | C | 27 | −1.354 | −9.795 | 0.274 | 1.00 | 17.08 | C |
| ATOM | 205 | CD2 | LEU | C | 27 | −2.461 | −10.910 | −1.619 | 1.00 | 16.77 | C |
| ATOM | 206 | C | LEU | C | 27 | 1.680 | −11.942 | −0.532 | 1.00 | 15.66 | C |
| ATOM | 207 | O | LEU | C | 27 | 2.128 | −12.754 | −1.314 | 1.00 | 15.50 | C |
| ATOM | 208 | N | MET | C | 28 | 1.701 | −12.132 | 0.778 | 1.00 | 15.44 | C |
| ATOM | 209 | CA | MET | C | 28 | 2.231 | −13.346 | 1.360 | 1.00 | 13.78 | C |
| ATOM | 210 | CB | MET | C | 28 | 3.659 | −13.158 | 1.946 | 1.00 | 17.79 | C |
| ATOM | 211 | CG | MET | C | 28 | 4.536 | −12.246 | 1.142 | 1.00 | 21.18 | C |
| ATOM | 212 | SD | MET | C | 28 | 6.291 | −12.114 | 1.400 | 1.00 | 26.24 | C |
| ATOM | 213 | CE | MET | C | 28 | 6.825 | −13.986 | 2.081 | 1.00 | 25.34 | C |
| ATOM | 214 | C | MET | C | 28 | 1.296 | −13.634 | 2.472 | 1.00 | 14.21 | C |
| ATOM | 215 | O | MET | C | 28 | 0.660 | −12.708 | 3.089 | 1.00 | 11.21 | C |
| ATOM | 216 | N | GLN | C | 29 | 1.293 | −14.947 | 2.791 | 1.00 | 15.27 | C |
| ATOM | 217 | CA | GLN | C | 29 | 0.444 | −15.481 | 3.801 | 1.00 | 16.73 | C |
| ATOM | 218 | CB | GLN | C | 29 | −0.528 | −16.484 | 3.213 | 1.00 | 17.54 | C |
| ATOM | 219 | CG | GLN | C | 29 | −1.726 | −16.589 | 4.051 | 1.00 | 20.17 | C |
| ATOM | 220 | CD | GLN | C | 29 | −2.438 | −17.927 | 3.960 | 1.00 | 21.49 | C |
| ATOM | 221 | OE1 | GLN | C | 29 | −3.619 | −17.942 | 3.647 | 1.00 | 23.22 | C |
| ATOM | 222 | NE2 | GLN | C | 29 | −1.743 | −19.041 | 4.297 | 1.00 | 21.22 | C |
| ATOM | 223 | C | GLN | C | 29 | 1.073 | −16.101 | 5.006 | 1.00 | 19.00 | C |
| ATOM | 224 | O | GLN | C | 29 | 1.692 | −17.117 | 4.905 | 1.00 | 21.71 | C |
| ATOM | 225 | N | ASN | C | 30 | 0.950 | −15.560 | 6.213 | 1.00 | 18.32 | C |
| ATOM | 226 | CA | ASN | C | 30 | 1.531 | −16.333 | 7.291 | 1.00 | 14.58 | C |
| ATOM | 227 | CB | ASN | C | 30 | 2.282 | −15.440 | 8.252 | 1.00 | 14.70 | C |
| ATOM | 228 | CG | ASN | C | 30 | 3.616 | −15.053 | 7.762 | 1.00 | 13.44 | C |
| ATOM | 229 | OD1 | ASN | C | 30 | 4.054 | −14.021 | 8.005 | 1.00 | 13.88 | C |
| ATOM | 230 | ND2 | ASN | C | 30 | 4.263 | −15.913 | 7.092 | 1.00 | 14.82 | C |
| ATOM | 231 | C | ASN | C | 30 | 0.388 | −16.975 | 8.024 | 1.00 | 15.16 | C |
| ATOM | 232 | O | ASN | C | 30 | −0.820 | −16.683 | 7.869 | 1.00 | 13.52 | C |
| ATOM | 233 | N | ILE | C | 31 | 0.741 | −17.880 | 8.876 | 1.00 | 14.87 | C |
| ATOM | 234 | CA | ILE | C | 31 | −0.281 | −18.455 | 9.605 | 1.00 | 15.34 | C |
| ATOM | 235 | CB | ILE | C | 31 | −0.701 | −19.681 | 8.903 | 1.00 | 17.37 | C |
| ATOM | 236 | CG2 | ILE | C | 31 | 0.482 | −20.607 | 8.844 | 1.00 | 21.11 | C |
| ATOM | 237 | CG1 | ILE | C | 31 | −1.895 | −20.337 | 9.612 | 1.00 | 17.91 | C |
| ATOM | 238 | CD1 | ILE | C | 31 | −2.177 | −21.603 | 8.969 | 1.00 | 16.50 | C |
| ATOM | 239 | C | ILE | C | 31 | 0.039 | −18.649 | 11.048 | 1.00 | 14.95 | C |
| ATOM | 240 | O | ILE | C | 31 | 1.109 | −19.041 | 11.459 | 1.00 | 14.93 | C |
| ATOM | 241 | N | MET | C | 32 | −0.933 | −18.329 | 11.871 | 1.00 | 15.04 | C |
| ATOM | 242 | CA | MET | C | 32 | −0.785 | −18.430 | 13.374 | 1.00 | 14.55 | C |
| ATOM | 243 | CB | MET | C | 32 | −0.646 | −17.071 | 14.045 | 1.00 | 15.86 | C |
| ATOM | 244 | CG | MET | C | 32 | 0.721 | −16.489 | 14.179 | 1.00 | 17.67 | C |
| ATOM | 245 | SD | MET | C | 32 | 1.919 | −17.682 | 14.969 | 1.00 | 20.19 | C |
| ATOM | 246 | CE | MET | C | 32 | 0.684 | −18.349 | 16.331 | 1.00 | 18.20 | C |
| ATOM | 247 | C | MET | C | 32 | −2.014 | −18.991 | 13.960 | 1.00 | 14.04 | C |
| ATOM | 248 | O | MET | C | 32 | −3.046 | −18.352 | 13.907 | 1.00 | 12.26 | C |
| ATOM | 249 | N | ASN | C | 33 | −1.844 | −20.117 | 14.623 | 1.00 | 14.69 | C |
| ATOM | 250 | CA | ASN | C | 33 | −2.924 | −20.884 | 15.208 | 1.00 | 15.93 | C |
| ATOM | 251 | CB | ASN | C | 33 | −3.487 | −20.236 | 16.473 | 1.00 | 17.27 | C |
| ATOM | 252 | CG | ASN | C | 33 | −2.456 | −19.929 | 17.473 | 1.00 | 18.35 | C |
| ATOM | 253 | OD1 | ASN | C | 33 | −1.800 | −20.819 | 18.107 | 1.00 | 19.28 | C |
| ATOM | 254 | ND2 | ASN | C | 33 | −2.243 | −18.642 | 17.621 | 1.00 | 18.73 | C |
| ATOM | 255 | C | ASN | C | 33 | −4.052 | −21.034 | 14.183 | 1.00 | 16.26 | C |
| ATOM | 256 | O | ASN | C | 33 | −5.197 | −20.714 | 14.458 | 1.00 | 16.56 | C |
| ATOM | 257 | N | ASP | C | 34 | −3.683 | −21.518 | 13.010 | 1.00 | 16.32 | C |
| ATOM | 258 | CA | ASP | C | 34 | −4.558 | −21.752 | 11.958 | 1.00 | 15.92 | C |
| ATOM | 259 | CB | ASP | C | 34 | −5.588 | −22.822 | 12.330 | 1.00 | 16.38 | C |
| ATOM | 260 | CG | ASP | C | 34 | −5.016 | −24.191 | 12.395 | 1.00 | 18.08 | C |
| ATOM | 261 | OD1 | ASP | C | 34 | −3.808 | −24.400 | 12.539 | 1.00 | 19.11 | C |
| ATOM | 262 | OD2 | ASP | C | 34 | −5.828 | −25.108 | 12.322 | 1.00 | 22.27 | C |
| ATOM | 263 | C | ASP | C | 34 | −5.199 | −20.511 | 11.478 | 1.00 | 16.91 | C |
| ATOM | 264 | O | ASP | C | 34 | −6.165 | −20.558 | 10.720 | 1.00 | 18.46 | C |
| ATOM | 265 | N | MET | C | 35 | −4.772 | −19.358 | 11.906 | 1.00 | 17.43 | C |
| ATOM | 266 | CA | MET | C | 35 | −5.403 | −18.173 | 11.285 | 1.00 | 17.50 | C |
| ATOM | 267 | CB | MET | C | 35 | −5.652 | −17.116 | 12.349 | 1.00 | 18.01 | C |
| ATOM | 268 | CG | MET | C | 35 | −6.768 | −17.487 | 13.254 | 1.00 | 18.47 | C |
| ATOM | 269 | SD | MET | C | 35 | −8.470 | −17.564 | 12.502 | 1.00 | 21.76 | C |
| ATOM | 270 | CE | MET | C | 35 | −8.399 | −19.587 | 12.396 | 1.00 | 20.90 | C |

TABLE 1-continued

| | | | | | | | | | | |
|---|---|---|---|---|---|---|---|---|---|---|
| ATOM | 271 | C | MET | C | 35 | −4.510 | −17.612 | 10.121 | 1.00 | 16.67 | C |
| ATOM | 272 | O | MET | C | 35 | −3.314 | −17.504 | 10.265 | 1.00 | 17.59 | C |
| ATOM | 273 | N | PRO | C | 36 | −5.059 | −17.428 | 8.922 | 1.00 | 17.02 | C |
| ATOM | 274 | CD | PRO | C | 36 | −6.270 | −18.030 | 8.307 | 1.00 | 16.90 | C |
| ATOM | 275 | CA | PRO | C | 36 | −4.186 | −16.879 | 7.879 | 1.00 | 16.22 | C |
| ATOM | 276 | CB | PRO | C | 36 | −4.980 | −17.086 | 6.549 | 1.00 | 15.98 | C |
| ATOM | 277 | CG | PRO | C | 36 | −6.418 | −17.193 | 6.988 | 1.00 | 16.13 | C |
| ATOM | 278 | C | PRO | C | 36 | −4.020 | −15.385 | 8.152 | 1.00 | 16.23 | C |
| ATOM | 279 | O | PRO | C | 36 | −4.984 | −14.690 | 8.340 | 1.00 | 15.04 | C |
| ATOM | 280 | N | ILE | C | 37 | −2.776 | −14.916 | 8.115 | 1.00 | 16.96 | C |
| ATOM | 281 | CA | ILE | C | 37 | −2.394 | −13.522 | 8.352 | 1.00 | 16.12 | C |
| ATOM | 282 | CB | ILE | C | 37 | −1.285 | −13.510 | 9.477 | 1.00 | 17.38 | C |
| ATOM | 283 | CG2 | ILE | C | 37 | −1.025 | −12.155 | 9.920 | 1.00 | 17.18 | C |
| ATOM | 284 | CG1 | ILE | C | 37 | −1.741 | −14.364 | 10.732 | 1.00 | 17.97 | C |
| ATOM | 285 | CD1 | ILE | C | 37 | −3.072 | −14.095 | 11.112 | 1.00 | 15.01 | C |
| ATOM | 286 | C | ILE | C | 37 | −1.805 | −13.003 | 7.018 | 1.00 | 17.59 | C |
| ATOM | 287 | O | ILE | C | 37 | −0.650 | −13.322 | 6.625 | 1.00 | 17.01 | C |
| ATOM | 288 | N | TYR | C | 38 | −2.566 | −12.270 | 6.242 | 1.00 | 17.42 | C |
| ATOM | 289 | CA | TYR | C | 38 | −1.982 | −11.777 | 5.040 | 1.00 | 17.51 | C |
| ATOM | 290 | CB | TYR | C | 38 | −3.058 | −11.470 | 4.047 | 1.00 | 17.90 | C |
| ATOM | 291 | CG | TYR | C | 38 | −3.703 | −12.732 | 3.537 | 1.00 | 17.43 | C |
| ATOM | 292 | CD1 | TYR | C | 38 | −4.640 | −13.412 | 4.296 | 1.00 | 17.04 | C |
| ATOM | 293 | CE1 | TYR | C | 38 | −5.101 | −14.601 | 3.832 | 1.00 | 15.48 | C |
| ATOM | 294 | CD2 | TYR | C | 38 | −3.280 | −13.315 | 2.311 | 1.00 | 16.75 | C |
| ATOM | 295 | CE2 | TYR | C | 38 | −3.734 | −14.468 | 1.893 | 1.00 | 13.66 | C |
| ATOM | 296 | CZ | TYR | C | 38 | −4.629 | −15.103 | 2.634 | 1.00 | 14.25 | C |
| ATOM | 297 | OH | TYR | C | 38 | −5.073 | −16.260 | 2.262 | 1.00 | 11.37 | C |
| ATOM | 298 | C | TYR | C | 38 | −1.159 | −10.513 | 5.174 | 1.00 | 18.42 | C |
| ATOM | 299 | O | TYR | C | 38 | −1.462 | −9.692 | 6.049 | 1.00 | 18.62 | C |
| ATOM | 300 | N | MET | C | 39 | −0.158 | −10.319 | 4.297 | 1.00 | 16.82 | C |
| ATOM | 301 | CA | MET | C | 39 | 0.585 | −9.093 | 4.340 | 1.00 | 15.74 | C |
| ATOM | 302 | CB | MET | C | 39 | 1.756 | −9.186 | 5.312 | 1.00 | 14.27 | C |
| ATOM | 303 | CG | MET | C | 39 | 3.034 | −9.705 | 4.787 | 1.00 | 14.04 | C |
| ATOM | 304 | SD | MET | C | 39 | 3.712 | −10.557 | 6.122 | 1.00 | 16.96 | C |
| ATOM | 305 | CE | MET | C | 39 | 5.352 | −11.469 | 5.422 | 1.00 | 18.70 | C |
| ATOM | 306 | C | MET | C | 39 | 1.081 | −8.690 | 2.979 | 1.00 | 16.55 | C |
| ATOM | 307 | O | MET | C | 39 | 1.146 | −9.530 | 2.125 | 1.00 | 16.81 | C |
| ATOM | 308 | N | TYR | C | 40 | 1.385 | −7.406 | 2.742 | 1.00 | 15.57 | C |
| ATOM | 309 | CA | TYR | C | 40 | 2.041 | −7.029 | 1.501 | 1.00 | 15.44 | C |
| ATOM | 310 | CB | TYR | C | 40 | 1.297 | −5.830 | 0.900 | 1.00 | 16.44 | C |
| ATOM | 311 | CG | TYR | C | 40 | 0.354 | −6.227 | −0.199 | 1.00 | 17.62 | C |
| ATOM | 312 | CD1 | TYR | C | 40 | −1.026 | −6.230 | −0.003 | 1.00 | 16.88 | C |
| ATOM | 313 | CE1 | TYR | C | 40 | −1.882 | −6.700 | −0.954 | 1.00 | 17.13 | C |
| ATOM | 314 | CD2 | TYR | C | 40 | 0.855 | −6.709 | −1.430 | 1.00 | 18.88 | C |
| ATOM | 315 | CE2 | TYR | C | 40 | −0.031 | −7.191 | −2.426 | 1.00 | 18.98 | C |
| ATOM | 316 | CZ | TYR | C | 40 | −1.391 | −7.189 | −2.159 | 1.00 | 18.47 | C |
| ATOM | 317 | OH | TYR | C | 40 | −2.170 | −7.766 | −3.074 | 1.00 | 19.23 | C |
| ATOM | 318 | C | TYR | C | 40 | 3.538 | −6.664 | 1.852 | 1.00 | 14.48 | C |
| ATOM | 319 | O | TYR | C | 40 | 3.810 | −5.892 | 2.726 | 1.00 | 14.77 | C |
| ATOM | 320 | N | SER | C | 41 | 4.516 | −7.286 | 1.261 | 1.00 | 14.82 | C |
| ATOM | 321 | CA | SER | C | 41 | 5.897 | −6.869 | 1.588 | 1.00 | 16.01 | C |
| ATOM | 322 | CB | SER | C | 41 | 6.528 | −7.731 | 2.638 | 1.00 | 15.65 | C |
| ATOM | 323 | OG | SER | C | 41 | 6.051 | −8.986 | 2.515 | 1.00 | 16.99 | C |
| ATOM | 324 | C | SER | C | 41 | 6.889 | −6.724 | 0.429 | 1.00 | 14.68 | C |
| ATOM | 325 | O | SER | C | 41 | 6.610 | −7.158 | −0.666 | 1.00 | 15.09 | C |
| ATOM | 326 | N | VAL | C | 42 | 8.020 | −6.087 | 0.704 | 1.00 | 15.16 | C |
| ATOM | 327 | CA | VAL | C | 42 | 9.050 | −5.903 | −0.300 | 1.00 | 15.80 | C |
| ATOM | 328 | CB | VAL | C | 42 | 9.231 | −4.507 | −0.958 | 1.00 | 15.47 | C |
| ATOM | 329 | CG1 | VAL | C | 42 | 9.416 | −4.680 | −2.420 | 1.00 | 13.89 | C |
| ATOM | 330 | CG2 | VAL | C | 42 | 8.216 | −3.501 | −0.493 | 1.00 | 14.31 | C |
| ATOM | 331 | C | VAL | C | 42 | 10.235 | −5.830 | 0.478 | 1.00 | 15.19 | C |
| ATOM | 332 | O | VAL | C | 42 | 10.162 | −5.303 | 1.552 | 1.00 | 15.32 | C |
| ATOM | 333 | N | CYS | C | 43 | 11.336 | −6.249 | −0.130 | 1.00 | 15.63 | C |
| ATOM | 334 | CA | CYS | C | 43 | 12.641 | −6.162 | 0.479 | 1.00 | 17.26 | C |
| ATOM | 335 | C | CYS | C | 43 | 13.772 | −6.010 | −0.627 | 1.00 | 16.60 | C |
| ATOM | 336 | O | CYS | C | 43 | 14.716 | −6.729 | −0.709 | 1.00 | 17.93 | C |
| ATOM | 337 | CB | CYS | C | 43 | 12.847 | −7.395 | 1.425 | 1.00 | 15.56 | C |
| ATOM | 338 | SG | CYS | C | 43 | 14.172 | −7.176 | 2.674 | 1.00 | 14.73 | C |
| ATOM | 339 | N | ASN | C | 44 | 13.692 | −5.060 | −1.490 | 1.00 | 16.41 | C |
| ATOM | 340 | CA | ASN | C | 44 | 14.773 | −4.953 | −2.454 | 1.00 | 15.99 | C |
| ATOM | 341 | CB | ASN | C | 44 | 14.231 | −4.585 | −3.855 | 1.00 | 15.86 | C |
| ATOM | 342 | CG | ASN | C | 44 | 13.285 | −5.595 | −4.346 | 1.00 | 15.89 | C |
| ATOM | 343 | OD1 | ASN | C | 44 | 12.363 | −5.255 | −5.084 | 1.00 | 18.30 | C |
| ATOM | 344 | ND2 | ASN | C | 44 | 13.477 | −6.857 | −3.947 | 1.00 | 13.28 | C |
| ATOM | 345 | C | ASN | C | 44 | 15.729 | −3.909 | −2.008 | 1.00 | 14.64 | C |
| ATOM | 346 | O | ASN | C | 44 | 15.881 | −2.903 | −2.664 | 1.00 | 13.26 | C |
| ATOM | 347 | N | VAL | C | 45 | 16.389 | −4.218 | −0.898 | 1.00 | 14.55 | C |
| ATOM | 348 | CA | VAL | C | 45 | 17.314 | −3.314 | −0.205 | 1.00 | 15.57 | C |
| ATOM | 349 | CB | VAL | C | 45 | 17.383 | −3.552 | 1.358 | 1.00 | 15.52 | C |
| ATOM | 350 | CG1 | VAL | C | 45 | 16.058 | −3.285 | 1.982 | 1.00 | 15.10 | C |

TABLE 1-continued

| | | | | | | | | | | |
|---|---|---|---|---|---|---|---|---|---|---|
| ATOM | 351 | CG2 | VAL | C | 45 | 17.936 | −4.986 | 1.712 | 1.00 | 13.86 | C |
| ATOM | 352 | C | VAL | C | 45 | 18.684 | −3.439 | −0.726 | 1.00 | 15.57 | C |
| ATOM | 353 | O | VAL | C | 45 | 19.619 | −2.683 | −0.349 | 1.00 | 15.67 | C |
| ATOM | 354 | N | MET | C | 46 | 18.832 | −4.373 | −1.612 | 1.00 | 16.14 | C |
| ATOM | 355 | CA | MET | C | 46 | 20.145 | −4.545 | −2.131 | 1.00 | 17.08 | C |
| ATOM | 356 | CB | MET | C | 46 | 20.405 | −6.040 | −2.040 | 1.00 | 19.61 | C |
| ATOM | 357 | CG | MET | C | 46 | 21.723 | −6.486 | −1.469 | 1.00 | 23.59 | C |
| ATOM | 358 | SD | MET | C | 46 | 22.190 | −6.004 | 0.240 | 1.00 | 26.46 | C |
| ATOM | 359 | CE | MET | C | 46 | 21.505 | −7.450 | 1.233 | 1.00 | 24.33 | C |
| ATOM | 360 | C | MET | C | 46 | 20.274 | −3.973 | −3.592 | 1.00 | 16.44 | C |
| ATOM | 361 | O | MET | C | 46 | 21.226 | −4.237 | −4.265 | 1.00 | 15.50 | C |
| ATOM | 362 | N | SER | C | 47 | 19.332 | −3.208 | −4.077 | 1.00 | 16.14 | C |
| ATOM | 363 | CA | SER | C | 47 | 19.446 | −2.718 | −5.427 | 1.00 | 17.24 | C |
| ATOM | 364 | CB | SER | C | 47 | 18.596 | −3.580 | −6.390 | 1.00 | 18.07 | C |
| ATOM | 365 | OG | SER | C | 47 | 18.238 | −4.856 | −5.729 | 1.00 | 24.24 | C |
| ATOM | 366 | C | SER | C | 47 | 18.893 | −1.324 | −5.372 | 1.00 | 17.18 | C |
| ATOM | 367 | O | SER | C | 47 | 17.985 | −1.043 | −4.602 | 1.00 | 17.58 | C |
| ATOM | 368 | N | GLY | C | 48 | 19.370 | −0.411 | −6.210 | 1.00 | 17.77 | C |
| ATOM | 369 | CA | GLY | C | 48 | 18.920 | 0.959 | −6.056 | 1.00 | 18.52 | C |
| ATOM | 370 | C | GLY | C | 48 | 17.716 | 1.340 | −6.865 | 1.00 | 19.80 | C |
| ATOM | 371 | O | GLY | C | 48 | 17.057 | 0.459 | −7.555 | 1.00 | 19.82 | C |
| ATOM | 372 | N | ASP | C | 49 | 17.349 | 2.614 | −6.739 | 1.00 | 20.17 | C |
| ATOM | 373 | CA | ASP | C | 49 | 16.300 | 3.056 | −7.601 | 1.00 | 19.90 | C |
| ATOM | 374 | CB | ASP | C | 49 | 16.766 | 2.841 | −9.017 | 1.00 | 21.41 | C |
| ATOM | 375 | CG | ASP | C | 49 | 18.121 | 3.539 | −9.341 | 1.00 | 23.59 | C |
| ATOM | 376 | OD1 | ASP | C | 49 | 19.021 | 2.845 | −9.946 | 1.00 | 23.24 | C |
| ATOM | 377 | OD2 | ASP | C | 49 | 18.264 | 4.772 | −9.019 | 1.00 | 23.68 | C |
| ATOM | 378 | C | ASP | C | 49 | 15.025 | 2.220 | −7.454 | 1.00 | 20.73 | C |
| ATOM | 379 | O | ASP | C | 49 | 14.442 | 1.820 | −8.493 | 1.00 | 21.44 | C |
| ATOM | 380 | N | GLN | C | 50 | 14.599 | 1.843 | −6.244 | 1.00 | 19.56 | C |
| ATOM | 381 | CA | GLN | C | 50 | 13.324 | 1.117 | −6.237 | 1.00 | 16.81 | C |
| ATOM | 382 | CB | GLN | C | 50 | 13.150 | 0.309 | −4.951 | 1.00 | 17.39 | C |
| ATOM | 383 | CG | GLN | C | 50 | 14.168 | −0.710 | −4.702 | 1.00 | 16.10 | C |
| ATOM | 384 | CD | GLN | C | 50 | 14.195 | −1.686 | −5.816 | 1.00 | 16.66 | C |
| ATOM | 385 | OE1 | GLN | C | 50 | 13.257 | −2.387 | −6.034 | 1.00 | 14.47 | C |
| ATOM | 386 | NE2 | GLN | C | 50 | 15.302 | −1.705 | −6.579 | 1.00 | 19.03 | C |
| ATOM | 387 | C | GLN | C | 50 | 12.204 | 2.168 | −6.365 | 1.00 | 16.44 | C |
| ATOM | 388 | O | GLN | C | 50 | 12.304 | 3.328 | −5.896 | 1.00 | 15.48 | C |
| ATOM | 389 | N | ASP | C | 51 | 11.144 | 1.755 | −7.043 | 1.00 | 14.63 | C |
| ATOM | 390 | CA | ASP | C | 51 | 9.965 | 2.597 | −7.183 | 1.00 | 13.54 | C |
| ATOM | 391 | CB | ASP | C | 51 | 10.067 | 3.519 | −8.405 | 1.00 | 12.26 | C |
| ATOM | 392 | CG | ASP | C | 51 | 8.926 | 4.540 | −8.462 | 1.00 | 13.54 | C |
| ATOM | 393 | OD1 | ASP | C | 51 | 8.742 | 5.212 | −9.546 | 1.00 | 15.68 | C |
| ATOM | 394 | OD2 | ASP | C | 51 | 8.206 | 4.699 | −7.482 | 1.00 | 6.49 | C |
| ATOM | 395 | C | ASP | C | 51 | 8.791 | 1.618 | −7.306 | 1.00 | 12.72 | C |
| ATOM | 396 | O | ASP | C | 51 | 8.164 | 1.463 | −8.318 | 1.00 | 10.92 | C |
| ATOM | 397 | N | ASN | C | 52 | 8.555 | 0.906 | −6.266 | 1.00 | 13.08 | C |
| ATOM | 398 | CA | ASN | C | 52 | 7.467 | −0.069 | −6.259 | 1.00 | 14.86 | C |
| ATOM | 399 | CB | ASN | C | 52 | 7.918 | −1.310 | −5.516 | 1.00 | 16.00 | C |
| ATOM | 400 | CG | ASN | C | 52 | 9.214 | −1.764 | −5.968 | 1.00 | 15.83 | C |
| ATOM | 401 | OD1 | ASN | C | 52 | 9.315 | −2.289 | −7.045 | 1.00 | 17.59 | C |
| ATOM | 402 | ND2 | ASN | C | 52 | 10.230 | −1.531 | −5.185 | 1.00 | 15.66 | C |
| ATOM | 403 | C | ASN | C | 52 | 6.144 | 0.443 | −5.644 | 1.00 | 14.59 | C |
| ATOM | 404 | O | ASN | C | 52 | 6.109 | 1.050 | −4.553 | 1.00 | 13.67 | C |
| ATOM | 405 | N | TRP | C | 53 | 5.072 | 0.185 | −6.381 | 1.00 | 14.67 | C |
| ATOM | 406 | CA | TRP | C | 53 | 3.770 | 0.663 | −6.031 | 1.00 | 14.81 | C |
| ATOM | 407 | CB | TRP | C | 53 | 3.267 | 1.605 | −7.110 | 1.00 | 15.06 | C |
| ATOM | 408 | CG | TRP | C | 53 | 4.022 | 2.883 | −7.095 | 1.00 | 14.87 | C |
| ATOM | 409 | CD2 | TRP | C | 53 | 3.603 | 4.155 | −6.565 | 1.00 | 14.90 | C |
| ATOM | 410 | CE2 | TRP | C | 53 | 4.603 | 5.070 | −6.845 | 1.00 | 15.37 | C |
| ATOM | 411 | CE3 | TRP | C | 53 | 2.479 | 4.605 | −5.902 | 1.00 | 15.09 | C |
| ATOM | 412 | CD1 | TRP | C | 53 | 5.191 | 3.074 | −7.621 | 1.00 | 14.18 | C |
| ATOM | 413 | NE1 | TRP | C | 53 | 5.581 | 4.377 | −7.500 | 1.00 | 15.13 | C |
| ATOM | 414 | CZ2 | TRP | C | 53 | 4.517 | 6.412 | −6.486 | 1.00 | 14.96 | C |
| ATOM | 415 | CZ3 | TRP | C | 53 | 2.401 | 5.952 | −5.554 | 1.00 | 14.48 | C |
| ATOM | 416 | CH2 | TRP | C | 53 | 3.403 | 6.819 | −5.844 | 1.00 | 14.84 | C |
| ATOM | 417 | C | TRP | C | 53 | 2.733 | −0.345 | −5.746 | 1.00 | 14.12 | C |
| ATOM | 418 | O | TRP | C | 53 | 2.596 | −1.322 | −6.437 | 1.00 | 12.93 | C |
| ATOM | 419 | N | LEU | C | 54 | 2.007 | −0.064 | −4.657 | 1.00 | 14.58 | C |
| ATOM | 420 | CA | LEU | C | 54 | 0.872 | −0.916 | −4.177 | 1.00 | 14.59 | C |
| ATOM | 421 | CB | LEU | C | 54 | 1.127 | −1.493 | −2.785 | 1.00 | 15.39 | C |
| ATOM | 422 | CG | LEU | C | 54 | −0.081 | −2.242 | −2.262 | 1.00 | 15.10 | C |
| ATOM | 423 | CD1 | LEU | C | 54 | −0.309 | −3.415 | −3.129 | 1.00 | 12.99 | C |
| ATOM | 424 | CD2 | LEU | C | 54 | 0.151 | −2.671 | −0.822 | 1.00 | 13.24 | C |
| ATOM | 425 | C | LEU | C | 54 | −0.354 | −0.032 | −4.138 | 1.00 | 13.10 | C |
| ATOM | 426 | O | LEU | C | 54 | −0.381 | 0.940 | −3.481 | 1.00 | 10.78 | C |
| ATOM | 427 | N | ARG | C | 55 | −1.374 | −0.390 | −4.914 | 1.00 | 13.50 | C |
| ATOM | 428 | CA | ARG | C | 55 | −2.561 | 0.427 | −4.939 | 1.00 | 13.73 | C |
| ATOM | 429 | CB | ARG | C | 55 | −2.831 | 1.053 | −6.301 | 1.00 | 14.24 | C |
| ATOM | 430 | CG | ARG | C | 55 | −4.088 | 1.876 | −6.283 | 1.00 | 15.23 | C |

TABLE 1-continued

| | | | | | | | | | | |
|---|---|---|---|---|---|---|---|---|---|---|
| ATOM | 431 | CD | ARG | C | 55 | −4.432 | 2.595 | −7.462 | 1.00 | 14.95 | C |
| ATOM | 432 | NE | ARG | C | 55 | −5.417 | 2.000 | −8.419 | 1.00 | 17.98 | C |
| ATOM | 433 | CZ | ARG | C | 55 | −5.486 | 0.714 | −8.754 | 1.00 | 18.51 | C |
| ATOM | 434 | NH1 | ARG | C | 55 | −4.646 | −0.173 | −8.164 | 1.00 | 21.52 | C |
| ATOM | 435 | NH2 | ARG | C | 55 | −6.278 | 0.308 | −9.738 | 1.00 | 17.10 | C |
| ATOM | 436 | C | ARG | C | 55 | −3.721 | −0.391 | −4.498 | 1.00 | 13.75 | C |
| ATOM | 437 | O | ARG | C | 55 | −3.844 | −1.526 | −4.839 | 1.00 | 14.16 | C |
| ATOM | 438 | N | THR | C | 56 | −4.538 | 0.196 | −3.646 | 1.00 | 12.99 | C |
| ATOM | 439 | CA | THR | C | 56 | −5.664 | −0.466 | −3.167 | 1.00 | 12.35 | C |
| ATOM | 440 | CB | THR | C | 56 | −6.325 | 0.308 | −2.077 | 1.00 | 13.02 | C |
| ATOM | 441 | OG1 | THR | C | 56 | −6.880 | 1.499 | −2.639 | 1.00 | 10.81 | C |
| ATOM | 442 | CG2 | THR | C | 56 | −5.376 | 0.614 | −0.981 | 1.00 | 13.51 | C |
| ATOM | 443 | C | THR | C | 56 | −6.700 | −0.443 | −4.352 | 1.00 | 13.32 | C |
| ATOM | 444 | O | THR | C | 56 | −6.524 | 0.196 | −5.431 | 1.00 | 9.12 | C |
| ATOM | 445 | N | ASN | C | 57 | −7.836 | −1.123 | −4.096 | 1.00 | 14.07 | C |
| ATOM | 446 | CA | ASN | C | 57 | −8.901 | −0.987 | −5.065 | 1.00 | 16.18 | C |
| ATOM | 447 | CB | ASN | C | 57 | −9.829 | −2.129 | −5.020 | 1.00 | 19.82 | C |
| ATOM | 448 | CG | ASN | C | 57 | −9.642 | −3.056 | −6.267 | 1.00 | 23.43 | C |
| ATOM | 449 | OD1 | ASN | C | 57 | −8.589 | −3.777 | −6.397 | 1.00 | 23.30 | C |
| ATOM | 450 | ND2 | ASN | C | 57 | −10.652 | −3.013 | −7.218 | 1.00 | 23.69 | C |
| ATOM | 451 | C | ASN | C | 57 | −9.722 | 0.264 | −4.911 | 1.00 | 16.38 | C |
| ATOM | 452 | O | ASN | C | 57 | −9.671 | 1.016 | −3.904 | 1.00 | 16.53 | C |
| ATOM | 453 | N | TRP | C | 58 | −10.468 | 0.525 | −5.941 | 1.00 | 15.57 | C |
| ATOM | 454 | CA | TRP | C | 58 | −11.404 | 1.665 | −6.002 | 1.00 | 15.61 | C |
| ATOM | 455 | CB | TRP | C | 58 | −12.307 | 1.442 | −7.223 | 1.00 | 16.24 | C |
| ATOM | 456 | CG | TRP | C | 58 | −13.423 | 2.350 | −7.437 | 1.00 | 18.26 | C |
| ATOM | 457 | CD2 | TRP | C | 58 | −13.344 | 3.709 | −7.578 | 1.00 | 18.32 | C |
| ATOM | 458 | CE2 | TRP | C | 58 | −14.634 | 4.178 | −7.989 | 1.00 | 19.74 | C |
| ATOM | 459 | CE3 | TRP | C | 58 | −12.343 | 4.575 | −7.412 | 1.00 | 18.59 | C |
| ATOM | 460 | CD1 | TRP | C | 58 | −14.753 | 2.018 | −7.730 | 1.00 | 21.57 | C |
| ATOM | 461 | NE1 | TRP | C | 58 | −15.468 | 3.122 | −8.069 | 1.00 | 21.88 | C |
| ATOM | 462 | CZ2 | TRP | C | 58 | −14.896 | 5.491 | −8.251 | 1.00 | 19.42 | C |
| ATOM | 463 | CZ3 | TRP | C | 58 | −12.588 | 5.879 | −7.678 | 1.00 | 19.66 | C |
| ATOM | 464 | CH2 | TRP | C | 58 | −13.852 | 6.334 | −8.095 | 1.00 | 21.01 | C |
| ATOM | 465 | C | TRP | C | 58 | −12.242 | 1.670 | −4.694 | 1.00 | 15.46 | C |
| ATOM | 466 | O | TRP | C | 58 | −12.898 | 0.688 | −4.349 | 1.00 | 15.54 | C |
| ATOM | 467 | N | VAL | C | 59 | −12.257 | 2.776 | −3.993 | 1.00 | 15.25 | C |
| ATOM | 468 | CA | VAL | C | 59 | −12.992 | 2.860 | −2.740 | 1.00 | 15.38 | C |
| ATOM | 469 | CB | VAL | C | 59 | −12.025 | 3.110 | −1.498 | 1.00 | 15.71 | C |
| ATOM | 470 | CG1 | VAL | C | 59 | −12.826 | 3.253 | −0.214 | 1.00 | 14.97 | C |
| ATOM | 471 | CG2 | VAL | C | 59 | −11.023 | 1.981 | −1.363 | 1.00 | 14.53 | C |
| ATOM | 472 | C | VAL | C | 59 | −13.941 | 4.009 | −2.838 | 1.00 | 14.14 | C |
| ATOM | 473 | O | VAL | C | 59 | −13.521 | 5.128 | −3.071 | 1.00 | 15.05 | C |
| ATOM | 474 | N | TYR | C | 60 | −15.221 | 3.709 | −2.689 | 1.00 | 12.50 | C |
| ATOM | 475 | CA | TYR | C | 60 | −16.288 | 4.697 | −2.752 | 1.00 | 12.76 | C |
| ATOM | 476 | CB | TYR | C | 60 | −17.682 | 4.023 | −2.667 | 1.00 | 12.55 | C |
| ATOM | 477 | CG | TYR | C | 60 | −18.168 | 3.379 | −3.889 | 1.00 | 14.86 | C |
| ATOM | 478 | CD1 | TYR | C | 60 | −18.129 | 1.970 | −4.013 | 1.00 | 16.43 | C |
| ATOM | 479 | CE1 | TYR | C | 60 | −18.453 | 1.332 | −5.208 | 1.00 | 16.67 | C |
| ATOM | 480 | CD2 | TYR | C | 60 | −18.557 | 4.126 | −5.032 | 1.00 | 16.15 | C |
| ATOM | 481 | CE2 | TYR | C | 60 | −18.870 | 3.448 | −6.246 | 1.00 | 16.37 | C |
| ATOM | 482 | CZ | TYR | C | 60 | −18.805 | 2.073 | −6.270 | 1.00 | 16.74 | C |
| ATOM | 483 | OH | TYR | C | 60 | −19.081 | 1.399 | −7.394 | 1.00 | 19.79 | C |
| ATOM | 484 | C | TYR | C | 60 | −16.148 | 5.645 | −1.547 | 1.00 | 12.01 | C |
| ATOM | 485 | O | TYR | C | 60 | −15.858 | 5.238 | −0.405 | 1.00 | 10.57 | C |
| ATOM | 486 | N | ARG | C | 61 | −16.389 | 6.889 | −1.793 | 1.00 | 13.41 | C |
| ATOM | 487 | CA | ARG | C | 61 | −16.303 | 7.873 | −0.756 | 1.00 | 16.13 | C |
| ATOM | 488 | CB | ARG | C | 61 | −16.035 | 9.289 | −1.344 | 1.00 | 16.34 | C |
| ATOM | 489 | CG | ARG | C | 61 | −16.213 | 10.472 | −0.326 | 1.00 | 15.50 | C |
| ATOM | 490 | CD | ARG | C | 61 | −15.825 | 11.817 | −0.899 | 1.00 | 14.99 | C |
| ATOM | 491 | NE | ARG | C | 61 | −16.858 | 12.376 | −1.756 | 1.00 | 14.84 | C |
| ATOM | 492 | CZ | ARG | C | 61 | −17.972 | 12.953 | −1.348 | 1.00 | 14.09 | C |
| ATOM | 493 | NH1 | ARG | C | 61 | −18.235 | 13.093 | −0.068 | 1.00 | 14.64 | C |
| ATOM | 494 | NH2 | ARG | C | 61 | −18.882 | 13.340 | −2.230 | 1.00 | 17.65 | C |
| ATOM | 495 | C | ARG | C | 61 | −17.566 | 7.928 | 0.054 | 1.00 | 17.40 | C |
| ATOM | 496 | O | ARG | C | 61 | −17.563 | 8.099 | 1.269 | 1.00 | 18.04 | C |
| ATOM | 497 | N | GLY | C | 62 | −18.689 | 7.764 | −0.628 | 1.00 | 18.83 | C |
| ATOM | 498 | CA | GLY | C | 62 | −19.999 | 7.899 | 0.052 | 1.00 | 19.72 | C |
| ATOM | 499 | C | GLY | C | 62 | −20.215 | 9.296 | 0.663 | 1.00 | 20.09 | C |
| ATOM | 500 | O | GLY | C | 62 | −20.187 | 10.334 | 0.028 | 1.00 | 20.22 | C |
| ATOM | 501 | N | GLU | C | 63 | −20.451 | 9.334 | 1.956 | 1.00 | 20.61 | C |
| ATOM | 502 | CA | GLU | C | 63 | −20.643 | 10.608 | 2.642 | 1.00 | 20.87 | C |
| ATOM | 503 | CB | GLU | C | 63 | −21.786 | 10.393 | 3.630 | 1.00 | 21.19 | C |
| ATOM | 504 | CG | GLU | C | 63 | −22.081 | 11.555 | 4.452 | 1.00 | 22.23 | C |
| ATOM | 505 | CD | GLU | C | 63 | −22.822 | 12.702 | 3.645 | 1.00 | 25.26 | C |
| ATOM | 506 | OE1 | GLU | C | 63 | −22.979 | 13.940 | 4.218 | 1.00 | 25.31 | C |
| ATOM | 507 | OE2 | GLU | C | 63 | −23.257 | 12.359 | 2.431 | 1.00 | 25.18 | C |
| ATOM | 508 | C | GLU | C | 63 | −19.326 | 11.140 | 3.356 | 1.00 | 20.95 | C |
| ATOM | 509 | O | GLU | C | 63 | −19.345 | 12.210 | 3.906 | 1.00 | 21.09 | C |
| ATOM | 510 | N | ALA | C | 64 | −18.196 | 10.419 | 3.307 | 1.00 | 19.93 | C |

TABLE 1-continued

| | | | | | | | | | | |
|---|---|---|---|---|---|---|---|---|---|---|
| ATOM | 511 | CA | ALA | C | 64 | −16.973 | 10.896 | 3.907 | 1.00 | 19.42 | C |
| ATOM | 512 | CB | ALA | C | 64 | −15.910 | 9.827 | 3.700 | 1.00 | 16.08 | C |
| ATOM | 513 | C | ALA | C | 64 | −16.434 | 12.279 | 3.369 | 1.00 | 20.27 | C |
| ATOM | 514 | O | ALA | C | 64 | −16.559 | 12.584 | 2.153 | 1.00 | 21.09 | C |
| ATOM | 515 | N | GLU | C | 65 | −15.890 | 13.133 | 4.266 | 1.00 | 19.73 | C |
| ATOM | 516 | CA | GLU | C | 65 | −15.164 | 14.401 | 3.832 | 1.00 | 19.14 | C |
| ATOM | 517 | CB | GLU | C | 65 | −15.596 | 15.667 | 4.553 | 1.00 | 19.64 | C |
| ATOM | 518 | CG | GLU | C | 65 | −17.104 | 15.883 | 4.640 | 1.00 | 23.17 | C |
| ATOM | 519 | CD | GLU | C | 65 | −17.707 | 16.641 | 3.433 | 1.00 | 24.28 | C |
| ATOM | 520 | OE1 | GLU | C | 65 | −17.312 | 17.860 | 3.348 | 1.00 | 22.82 | C |
| ATOM | 521 | OE2 | GLU | C | 65 | −18.550 | 16.004 | 2.579 | 1.00 | 25.96 | C |
| ATOM | 522 | C | GLU | C | 65 | −13.643 | 14.162 | 4.217 | 1.00 | 17.69 | C |
| ATOM | 523 | O | GLU | C | 65 | −12.725 | 14.429 | 3.475 | 1.00 | 17.49 | C |
| ATOM | 524 | N | ARG | C | 66 | −13.411 | 13.658 | 5.410 | 1.00 | 17.03 | C |
| ATOM | 525 | CA | ARG | C | 66 | −12.061 | 13.352 | 5.893 | 1.00 | 17.12 | C |
| ATOM | 526 | CB | ARG | C | 66 | −11.764 | 14.133 | 7.218 | 1.00 | 16.91 | C |
| ATOM | 527 | CG | ARG | C | 66 | −10.306 | 14.046 | 7.605 | 1.00 | 18.27 | C |
| ATOM | 528 | CD | ARG | C | 66 | −9.683 | 15.458 | 7.790 | 1.00 | 20.62 | C |
| ATOM | 529 | NE | ARG | C | 66 | −8.180 | 15.454 | 7.909 | 1.00 | 21.59 | C |
| ATOM | 530 | CZ | ARG | C | 66 | −7.304 | 16.080 | 7.082 | 1.00 | 21.79 | C |
| ATOM | 531 | NH1 | ARG | C | 66 | −7.670 | 16.817 | 6.030 | 1.00 | 18.07 | C |
| ATOM | 532 | NH2 | ARG | C | 66 | −6.010 | 15.959 | 7.354 | 1.00 | 23.80 | C |
| ATOM | 533 | C | ARG | C | 66 | −12.048 | 11.833 | 6.151 | 1.00 | 15.75 | C |
| ATOM | 534 | O | ARG | C | 66 | −13.047 | 11.278 | 6.541 | 1.00 | 15.91 | C |
| ATOM | 535 | N | ASN | C | 67 | −10.961 | 11.138 | 5.918 | 1.00 | 17.05 | C |
| ATOM | 536 | CA | ASN | C | 67 | −10.997 | 9.696 | 6.222 | 1.00 | 16.61 | C |
| ATOM | 537 | CB | ASN | C | 67 | −10.965 | 8.812 | 4.970 | 1.00 | 17.01 | C |
| ATOM | 538 | CG | ASN | C | 67 | −10.022 | 9.370 | 3.954 | 1.00 | 20.16 | C |
| ATOM | 539 | OD1 | ASN | C | 67 | −10.002 | 10.651 | 3.847 | 1.00 | 23.04 | C |
| ATOM | 540 | ND2 | ASN | C | 67 | −9.281 | 8.533 | 3.158 | 1.00 | 15.55 | C |
| ATOM | 541 | C | ASN | C | 67 | −9.750 | 9.544 | 6.958 | 1.00 | 16.39 | C |
| ATOM | 542 | O | ASN | C | 67 | −8.885 | 10.271 | 6.791 | 1.00 | 16.08 | C |
| ATOM | 543 | N | ASN | C | 68 | −9.668 | 8.591 | 7.819 | 1.00 | 16.80 | C |
| ATOM | 544 | CA | ASN | C | 68 | −8.494 | 8.368 | 8.564 | 1.00 | 17.27 | C |
| ATOM | 545 | CB | ASN | C | 68 | −9.009 | 8.233 | 9.959 | 1.00 | 17.76 | C |
| ATOM | 546 | CG | ASN | C | 68 | −9.423 | 9.586 | 10.567 | 1.00 | 18.95 | C |
| ATOM | 547 | OD1 | ASN | C | 68 | −8.538 | 10.273 | 11.035 | 1.00 | 16.81 | C |
| ATOM | 548 | ND2 | ASN | C | 68 | −10.765 | 9.985 | 10.527 | 1.00 | 18.00 | C |
| ATOM | 549 | C | ASN | C | 68 | −7.922 | 7.041 | 8.067 | 1.00 | 18.61 | C |
| ATOM | 550 | O | ASN | C | 68 | −8.704 | 6.106 | 7.574 | 1.00 | 19.02 | C |
| ATOM | 551 | N | PHE | C | 69 | −6.620 | 6.883 | 8.099 | 1.00 | 17.64 | C |
| ATOM | 552 | CA | PHE | C | 69 | −6.165 | 5.541 | 7.749 | 1.00 | 17.28 | C |
| ATOM | 553 | CB | PHE | C | 69 | −5.688 | 5.298 | 6.321 | 1.00 | 17.92 | C |
| ATOM | 554 | CG | PHE | C | 69 | −5.419 | 6.452 | 5.626 | 1.00 | 19.58 | C |
| ATOM | 555 | CD1 | PHE | C | 69 | −4.551 | 7.381 | 6.168 | 1.00 | 21.45 | C |
| ATOM | 556 | CD2 | PHE | C | 69 | −6.019 | 6.652 | 4.415 | 1.00 | 19.61 | C |
| ATOM | 557 | CE1 | PHE | C | 69 | −4.254 | 8.573 | 5.512 | 1.00 | 24.20 | C |
| ATOM | 558 | CE2 | PHE | C | 69 | −5.774 | 7.790 | 3.673 | 1.00 | 21.19 | C |
| ATOM | 559 | CZ | PHE | C | 69 | −4.874 | 8.815 | 4.209 | 1.00 | 24.38 | C |
| ATOM | 560 | C | PHE | C | 69 | −5.081 | 5.088 | 8.623 | 1.00 | 18.10 | C |
| ATOM | 561 | O | PHE | C | 69 | −4.054 | 5.805 | 8.827 | 1.00 | 18.03 | C |
| ATOM | 562 | N | GLU | C | 70 | −5.340 | 3.895 | 9.143 | 1.00 | 16.63 | C |
| ATOM | 563 | CA | GLU | C | 70 | −4.470 | 3.266 | 10.031 | 1.00 | 15.02 | C |
| ATOM | 564 | CB | GLU | C | 70 | −5.324 | 2.700 | 11.168 | 1.00 | 17.52 | C |
| ATOM | 565 | CG | GLU | C | 70 | −4.617 | 2.442 | 12.509 | 1.00 | 18.57 | C |
| ATOM | 566 | CD | GLU | C | 70 | −5.382 | 1.493 | 13.346 | 1.00 | 19.86 | C |
| ATOM | 567 | OE1 | GLU | C | 70 | −5.453 | 1.687 | 14.626 | 1.00 | 21.08 | C |
| ATOM | 568 | OE2 | GLU | C | 70 | −5.899 | 0.509 | 12.706 | 1.00 | 19.56 | C |
| ATOM | 569 | C | GLU | C | 70 | −3.677 | 2.159 | 9.292 | 1.00 | 14.57 | C |
| ATOM | 570 | O | GLU | C | 70 | −4.285 | 1.242 | 8.678 | 1.00 | 10.89 | C |
| ATOM | 571 | N | LEU | C | 71 | −2.327 | 2.330 | 9.409 | 1.00 | 14.10 | C |
| ATOM | 572 | CA | LEU | C | 71 | −1.222 | 1.478 | 8.894 | 1.00 | 14.43 | C |
| ATOM | 573 | CB | LEU | C | 71 | −0.209 | 2.317 | 8.044 | 1.00 | 14.85 | C |
| ATOM | 574 | CG | LEU | C | 71 | −0.854 | 2.930 | 6.831 | 1.00 | 15.51 | C |
| ATOM | 575 | CD1 | LEU | C | 71 | 0.030 | 3.890 | 6.192 | 1.00 | 15.35 | C |
| ATOM | 576 | CD2 | LEU | C | 71 | −1.217 | 1.812 | 5.786 | 1.00 | 16.96 | C |
| ATOM | 577 | C | LEU | C | 71 | −0.416 | 0.749 | 10.032 | 1.00 | 15.05 | C |
| ATOM | 578 | O | LEU | C | 71 | 0.033 | 1.357 | 10.966 | 1.00 | 14.64 | C |
| ATOM | 579 | N | ASN | C | 72 | −0.281 | −0.568 | 9.911 | 1.00 | 15.72 | C |
| ATOM | 580 | CA | ASN | C | 72 | 0.437 | −1.440 | 10.812 | 1.00 | 16.49 | C |
| ATOM | 581 | CB | ASN | C | 72 | −0.504 | −2.530 | 11.469 | 1.00 | 17.41 | C |
| ATOM | 582 | CG | ASN | C | 72 | −1.252 | −2.016 | 12.655 | 1.00 | 19.02 | C |
| ATOM | 583 | OD1 | ASN | C | 72 | −2.275 | −2.582 | 13.142 | 1.00 | 17.92 | C |
| ATOM | 584 | ND2 | ASN | C | 72 | −0.757 | −0.872 | 13.150 | 1.00 | 23.18 | C |
| ATOM | 585 | C | ASN | C | 72 | 1.476 | −2.108 | 9.854 | 1.00 | 16.50 | C |
| ATOM | 586 | O | ASN | C | 72 | 1.129 | −2.747 | 8.861 | 1.00 | 16.04 | C |
| ATOM | 587 | N | PHE | C | 73 | 2.767 | −1.970 | 10.208 | 1.00 | 17.42 | C |
| ATOM | 588 | CA | PHE | C | 73 | 3.860 | −2.495 | 9.376 | 1.00 | 17.24 | C |
| ATOM | 589 | CB | PHE | C | 73 | 4.191 | −1.486 | 8.275 | 1.00 | 17.53 | C |
| ATOM | 590 | CG | PHE | C | 73 | 4.538 | −0.071 | 8.835 | 1.00 | 17.80 | C |

TABLE 1-continued

| | | | | | | | | | | |
|---|---|---|---|---|---|---|---|---|---|---|
| ATOM | 591 | CD1 | PHE | C | 73 | 5.837 | 0.321 | 9.039 | 1.00 | 17.98 | C |
| ATOM | 592 | CD2 | PHE | C | 73 | 3.566 | 0.835 | 9.224 | 1.00 | 16.76 | C |
| ATOM | 593 | CE1 | PHE | C | 73 | 6.150 | 1.586 | 9.622 | 1.00 | 17.28 | C |
| ATOM | 594 | CE2 | PHE | C | 73 | 3.938 | 2.042 | 9.783 | 1.00 | 17.58 | C |
| ATOM | 595 | CZ | PHE | C | 73 | 5.236 | 2.391 | 9.968 | 1.00 | 15.99 | C |
| ATOM | 596 | C | PHE | C | 73 | 5.079 | −2.690 | 10.222 | 1.00 | 16.69 | C |
| ATOM | 597 | O | PHE | C | 73 | 5.099 | −2.240 | 11.356 | 1.00 | 16.65 | C |
| ATOM | 598 | N | THR | C | 74 | 6.070 | −3.389 | 9.648 | 1.00 | 16.30 | C |
| ATOM | 599 | CA | THR | C | 74 | 7.323 | −3.602 | 10.344 | 1.00 | 15.99 | C |
| ATOM | 600 | CB | THR | C | 74 | 7.637 | −5.030 | 10.708 | 1.00 | 16.29 | C |
| ATOM | 601 | OG1 | THR | C | 74 | 8.102 | −5.725 | 9.559 | 1.00 | 16.84 | C |
| ATOM | 602 | CG2 | THR | C | 74 | 6.462 | −5.687 | 11.238 | 1.00 | 16.04 | C |
| ATOM | 603 | C | THR | C | 74 | 8.296 | −3.207 | 9.354 | 1.00 | 16.08 | C |
| ATOM | 604 | O | THR | C | 74 | 7.978 | −3.263 | 8.164 | 1.00 | 15.79 | C |
| ATOM | 605 | N | VAL | C | 75 | 9.486 | −2.846 | 9.859 | 1.00 | 15.67 | C |
| ATOM | 606 | CA | VAL | C | 75 | 10.588 | −2.430 | 9.041 | 1.00 | 15.14 | C |
| ATOM | 607 | CB | VAL | C | 75 | 10.631 | −0.968 | 9.038 | 1.00 | 14.70 | C |
| ATOM | 608 | CG1 | VAL | C | 75 | 11.718 | −0.486 | 8.153 | 1.00 | 14.81 | C |
| ATOM | 609 | CG2 | VAL | C | 75 | 9.328 | −0.459 | 8.619 | 1.00 | 11.48 | C |
| ATOM | 610 | C | VAL | C | 75 | 11.910 | −3.082 | 9.458 | 1.00 | 16.55 | C |
| ATOM | 611 | O | VAL | C | 75 | 12.390 | −2.865 | 10.562 | 1.00 | 17.70 | C |
| ATOM | 612 | N | ARG | C | 76 | 12.478 | −3.900 | 8.572 | 1.00 | 16.81 | C |
| ATOM | 613 | CA | ARG | C | 76 | 13.674 | −4.587 | 8.899 | 1.00 | 17.67 | C |
| ATOM | 614 | CB | ARG | C | 76 | 14.010 | −5.644 | 7.878 | 1.00 | 15.23 | C |
| ATOM | 615 | CG | ARG | C | 76 | 15.251 | −6.412 | 8.301 | 1.00 | 13.87 | C |
| ATOM | 616 | CD | ARG | C | 76 | 15.321 | −7.760 | 7.806 | 1.00 | 11.63 | C |
| ATOM | 617 | NE | ARG | C | 76 | 16.684 | −8.167 | 7.765 | 1.00 | 13.29 | C |
| ATOM | 618 | CZ | ARG | C | 76 | 17.177 | −9.168 | 7.054 | 1.00 | 14.89 | C |
| ATOM | 619 | NH1 | ARG | C | 76 | 16.407 | −9.953 | 6.262 | 1.00 | 16.10 | C |
| ATOM | 620 | NH2 | ARG | C | 76 | 18.447 | −9.352 | 7.078 | 1.00 | 12.90 | C |
| ATOM | 621 | C | ARG | C | 76 | 14.741 | −3.563 | 8.944 | 1.00 | 18.32 | C |
| ATOM | 622 | O | ARG | C | 76 | 14.731 | −2.718 | 8.072 | 1.00 | 20.70 | C |
| ATOM | 623 | N | ASP | C | 77 | 15.584 | −3.590 | 9.975 | 1.00 | 17.83 | C |
| ATOM | 624 | CA | ASP | C | 77 | 16.687 | −2.651 | 10.177 | 1.00 | 17.11 | C |
| ATOM | 625 | CB | ASP | C | 77 | 17.387 | −3.056 | 11.471 | 1.00 | 16.72 | C |
| ATOM | 626 | CG | ASP | C | 77 | 18.739 | −2.405 | 11.641 | 1.00 | 16.50 | C |
| ATOM | 627 | OD1 | ASP | C | 77 | 19.051 | −1.441 | 10.921 | 1.00 | 15.73 | C |
| ATOM | 628 | OD2 | ASP | C | 77 | 19.517 | −2.876 | 12.498 | 1.00 | 18.00 | C |
| ATOM | 629 | C | ASP | C | 77 | 17.654 | −2.688 | 9.020 | 1.00 | 16.72 | C |
| ATOM | 630 | O | ASP | C | 77 | 18.189 | −3.743 | 8.681 | 1.00 | 15.85 | C |
| ATOM | 631 | N | CYS | C | 78 | 17.895 | −1.566 | 8.376 | 1.00 | 16.47 | C |
| ATOM | 632 | CA | CYS | C | 78 | 18.850 | −1.606 | 7.297 | 1.00 | 15.68 | C |
| ATOM | 633 | C | CYS | C | 78 | 20.228 | −2.120 | 7.616 | 1.00 | 15.97 | C |
| ATOM | 634 | O | CYS | C | 78 | 20.903 | −2.609 | 6.688 | 1.00 | 17.02 | C |
| ATOM | 635 | CB | CYS | C | 78 | 18.954 | −0.269 | 6.649 | 1.00 | 15.33 | C |
| ATOM | 636 | SG | CYS | C | 78 | 17.666 | 0.104 | 5.300 | 1.00 | 16.43 | C |
| ATOM | 637 | N | ASN | C | 79 | 20.655 | −2.064 | 8.880 | 1.00 | 15.32 | C |
| ATOM | 638 | CA | ASN | C | 79 | 21.992 | −2.583 | 9.271 | 1.00 | 14.36 | C |
| ATOM | 639 | CB | ASN | C | 79 | 22.566 | −1.877 | 10.504 | 1.00 | 14.39 | C |
| ATOM | 640 | CG | ASN | C | 79 | 22.841 | −0.470 | 10.251 | 1.00 | 14.59 | C |
| ATOM | 641 | OD1 | ASN | C | 79 | 22.765 | 0.327 | 11.117 | 1.00 | 14.40 | C |
| ATOM | 642 | ND2 | ASN | C | 79 | 23.162 | −0.151 | 9.035 | 1.00 | 17.51 | C |
| ATOM | 643 | C | ASN | C | 79 | 22.072 | −4.065 | 9.523 | 1.00 | 13.32 | C |
| ATOM | 644 | O | ASN | C | 79 | 23.139 | −4.570 | 9.862 | 1.00 | 13.38 | C |
| ATOM | 645 | N | SER | C | 80 | 20.953 | −4.746 | 9.367 | 1.00 | 13.54 | C |
| ATOM | 646 | CA | SER | C | 80 | 20.858 | −6.200 | 9.522 | 1.00 | 13.57 | C |
| ATOM | 647 | CB | SER | C | 80 | 19.492 | −6.642 | 9.998 | 1.00 | 14.15 | C |
| ATOM | 648 | OG | SER | C | 80 | 18.456 | −6.293 | 9.068 | 1.00 | 17.60 | C |
| ATOM | 649 | C | SER | C | 80 | 21.145 | −6.916 | 8.229 | 1.00 | 13.26 | C |
| ATOM | 650 | O | SER | C | 80 | 20.878 | −8.057 | 8.149 | 1.00 | 12.58 | C |
| ATOM | 651 | N | PHE | C | 81 | 21.623 | −6.255 | 7.207 | 1.00 | 14.32 | C |
| ATOM | 652 | CA | PHE | C | 81 | 21.992 | −6.997 | 6.031 | 1.00 | 15.91 | C |
| ATOM | 653 | CB | PHE | C | 81 | 21.382 | −6.284 | 4.788 | 1.00 | 16.99 | C |
| ATOM | 654 | CG | PHE | C | 81 | 19.855 | −6.248 | 4.760 | 1.00 | 17.54 | C |
| ATOM | 655 | CD1 | PHE | C | 81 | 19.136 | −5.135 | 5.252 | 1.00 | 17.59 | C |
| ATOM | 656 | CD2 | PHE | C | 81 | 19.163 | −7.330 | 4.321 | 1.00 | 16.61 | C |
| ATOM | 657 | CE1 | PHE | C | 81 | 17.740 | −5.163 | 5.273 | 1.00 | 18.11 | C |
| ATOM | 658 | CE2 | PHE | C | 81 | 17.751 | −7.356 | 4.348 | 1.00 | 16.61 | C |
| ATOM | 659 | CZ | PHE | C | 81 | 17.032 | −6.288 | 4.814 | 1.00 | 15.81 | C |
| ATOM | 660 | C | PHE | C | 81 | 23.522 | −6.900 | 6.020 | 1.00 | 15.87 | C |
| ATOM | 661 | O | PHE | C | 81 | 24.029 | −5.885 | 5.664 | 1.00 | 16.90 | C |
| ATOM | 662 | N | PRO | C | 82 | 24.261 | −7.946 | 6.369 | 1.00 | 16.15 | C |
| ATOM | 663 | CD | PRO | C | 82 | 23.706 | −9.294 | 6.221 | 1.00 | 16.60 | C |
| ATOM | 664 | CA | PRO | C | 82 | 25.757 | −8.016 | 6.437 | 1.00 | 16.00 | C |
| ATOM | 665 | CB | PRO | C | 82 | 26.070 | −9.513 | 6.476 | 1.00 | 15.93 | C |
| ATOM | 666 | CG | PRO | C | 82 | 24.801 | −10.158 | 6.915 | 1.00 | 15.66 | C |
| ATOM | 667 | C | PRO | C | 82 | 26.565 | −7.315 | 5.358 | 1.00 | 15.67 | C |
| ATOM | 668 | O | PRO | C | 82 | 26.282 | −7.451 | 4.175 | 1.00 | 15.19 | C |
| ATOM | 669 | N | GLY | C | 83 | 27.600 | −6.569 | 5.762 | 1.00 | 15.91 | C |
| ATOM | 670 | CA | GLY | C | 83 | 28.419 | −5.840 | 4.808 | 1.00 | 16.39 | C |

TABLE 1-continued

| | | | | | | | | | | |
|---|---|---|---|---|---|---|---|---|---|---|
| ATOM | 671 | C | GLY | C | 83 | 27.499 | −4.683 | 4.619 | 1.00 | 16.93 | C |
| ATOM | 672 | O | GLY | C | 83 | 26.349 | −4.746 | 5.007 | 1.00 | 17.54 | C |
| ATOM | 673 | N | GLY | C | 84 | 27.838 | −3.590 | 4.009 | 1.00 | 17.51 | C |
| ATOM | 674 | CA | GLY | C | 84 | 26.750 | −2.546 | 4.081 | 1.00 | 17.82 | C |
| ATOM | 675 | C | GLY | C | 84 | 25.539 | −2.647 | 3.197 | 1.00 | 17.97 | C |
| ATOM | 676 | O | GLY | C | 84 | 25.512 | −3.587 | 2.394 | 1.00 | 18.51 | C |
| ATOM | 677 | N | ALA | C | 85 | 24.495 | −1.798 | 3.321 | 1.00 | 17.97 | C |
| ATOM | 678 | CA | ALA | C | 85 | 23.365 | −1.883 | 2.304 | 1.00 | 17.60 | C |
| ATOM | 679 | CB | ALA | C | 85 | 22.093 | −2.662 | 2.830 | 1.00 | 18.25 | C |
| ATOM | 680 | C | ALA | C | 85 | 23.024 | −0.503 | 1.916 | 1.00 | 16.46 | C |
| ATOM | 681 | O | ALA | C | 85 | 21.941 | −0.129 | 2.099 | 1.00 | 16.70 | C |
| ATOM | 682 | N | SER | C | 86 | 23.986 | 0.235 | 1.388 | 1.00 | 15.18 | C |
| ATOM | 683 | CA | SER | C | 86 | 23.820 | 1.616 | 0.977 | 1.00 | 13.85 | C |
| ATOM | 684 | CB | SER | C | 86 | 24.953 | 2.013 | 0.043 | 1.00 | 14.60 | C |
| ATOM | 685 | OG | SER | C | 86 | 24.943 | 1.373 | −1.209 | 1.00 | 16.68 | C |
| ATOM | 686 | C | SER | C | 86 | 22.544 | 2.083 | 0.454 | 1.00 | 11.83 | C |
| ATOM | 687 | O | SER | C | 86 | 22.170 | 3.104 | 0.821 | 1.00 | 10.67 | C |
| ATOM | 688 | N | SER | C | 87 | 21.856 | 1.342 | −0.416 | 1.00 | 11.52 | C |
| ATOM | 689 | CA | SER | C | 87 | 20.506 | 1.837 | −0.939 | 1.00 | 12.31 | C |
| ATOM | 690 | CB | SER | C | 87 | 20.287 | 1.403 | −2.407 | 1.00 | 12.25 | C |
| ATOM | 691 | OG | SER | C | 87 | 20.027 | 0.025 | −2.444 | 1.00 | 9.42 | C |
| ATOM | 692 | C | SER | C | 87 | 19.245 | 1.433 | −0.086 | 1.00 | 10.33 | C |
| ATOM | 693 | O | SER | C | 87 | 18.131 | 1.854 | −0.342 | 1.00 | 9.89 | C |
| ATOM | 694 | N | CYS | C | 88 | 19.470 | 0.661 | 0.938 | 1.00 | 9.34 | C |
| ATOM | 695 | CA | CYS | C | 88 | 18.422 | 0.293 | 1.794 | 1.00 | 11.87 | C |
| ATOM | 696 | C | CYS | C | 88 | 17.806 | 1.521 | 2.488 | 1.00 | 11.37 | C |
| ATOM | 697 | O | CYS | C | 88 | 18.447 | 2.435 | 2.759 | 1.00 | 10.75 | C |
| ATOM | 698 | CB | CYS | C | 88 | 18.948 | −0.718 | 2.807 | 1.00 | 10.90 | C |
| ATOM | 699 | SG | CYS | C | 88 | 17.825 | −1.457 | 4.014 | 1.00 | 12.35 | C |
| ATOM | 700 | N | LYS | C | 89 | 16.535 | 1.508 | 2.757 | 1.00 | 12.48 | C |
| ATOM | 701 | CA | LYS | C | 89 | 15.884 | 2.668 | 3.303 | 1.00 | 15.53 | C |
| ATOM | 702 | CB | LYS | C | 89 | 14.892 | 3.302 | 2.251 | 1.00 | 15.24 | C |
| ATOM | 703 | CG | LYS | C | 89 | 15.582 | 3.906 | 0.991 | 1.00 | 16.83 | C |
| ATOM | 704 | CD | LYS | C | 89 | 16.380 | 5.159 | 1.363 | 1.00 | 16.74 | C |
| ATOM | 705 | CE | LYS | C | 89 | 17.025 | 5.752 | 0.096 | 1.00 | 19.87 | C |
| ATOM | 706 | NZ | LYS | C | 89 | 17.564 | 7.165 | 0.144 | 1.00 | 23.75 | C |
| ATOM | 707 | C | LYS | C | 89 | 15.072 | 2.273 | 4.503 | 1.00 | 16.48 | C |
| ATOM | 708 | O | LYS | C | 89 | 14.856 | 1.065 | 4.661 | 1.00 | 17.34 | C |
| ATOM | 709 | N | GLU | C | 90 | 14.628 | 3.229 | 5.366 | 1.00 | 16.18 | C |
| ATOM | 710 | CA | GLU | C | 90 | 13.717 | 2.795 | 6.445 | 1.00 | 17.21 | C |
| ATOM | 711 | CB | GLU | C | 90 | 14.417 | 2.642 | 7.793 | 1.00 | 15.58 | C |
| ATOM | 712 | CG | GLU | C | 90 | 15.566 | 1.626 | 7.714 | 1.00 | 16.97 | C |
| ATOM | 713 | CD | GLU | C | 90 | 16.467 | 1.605 | 8.878 | 1.00 | 17.68 | C |
| ATOM | 714 | OE1 | GLU | C | 90 | 16.867 | 2.716 | 9.343 | 1.00 | 19.21 | C |
| ATOM | 715 | OE2 | GLU | C | 90 | 16.753 | 0.460 | 9.305 | 1.00 | 16.91 | C |
| ATOM | 716 | C | GLU | C | 90 | 12.429 | 3.575 | 6.543 | 1.00 | 17.15 | C |
| ATOM | 717 | O | GLU | C | 90 | 11.935 | 3.874 | 7.628 | 1.00 | 18.73 | C |
| ATOM | 718 | N | THR | C | 91 | 11.880 | 3.920 | 5.389 | 1.00 | 16.29 | C |
| ATOM | 719 | CA | THR | C | 91 | 10.604 | 4.591 | 5.386 | 1.00 | 14.86 | C |
| ATOM | 720 | CB | THR | C | 91 | 10.731 | 6.096 | 5.377 | 1.00 | 13.50 | C |
| ATOM | 721 | OG1 | THR | C | 91 | 11.535 | 6.442 | 4.278 | 1.00 | 12.68 | C |
| ATOM | 722 | CG2 | THR | C | 91 | 11.417 | 6.649 | 6.720 | 1.00 | 12.90 | C |
| ATOM | 723 | C | THR | C | 91 | 9.959 | 4.125 | 4.075 | 1.00 | 15.38 | C |
| ATOM | 724 | O | THR | C | 91 | 10.607 | 3.461 | 3.254 | 1.00 | 14.39 | C |
| ATOM | 725 | N | PHE | C | 92 | 8.663 | 4.463 | 3.930 | 1.00 | 16.22 | C |
| ATOM | 726 | CA | PHE | C | 92 | 7.884 | 4.306 | 2.690 | 1.00 | 16.61 | C |
| ATOM | 727 | CB | PHE | C | 92 | 7.141 | 2.997 | 2.620 | 1.00 | 17.58 | C |
| ATOM | 728 | CG | PHE | C | 92 | 6.152 | 2.805 | 3.684 | 1.00 | 17.54 | C |
| ATOM | 729 | CD1 | PHE | C | 92 | 4.831 | 2.974 | 3.433 | 1.00 | 16.76 | C |
| ATOM | 730 | CD2 | PHE | C | 92 | 6.530 | 2.290 | 4.898 | 1.00 | 16.83 | C |
| ATOM | 731 | CE1 | PHE | C | 92 | 3.908 | 2.584 | 4.386 | 1.00 | 18.27 | C |
| ATOM | 732 | CE2 | PHE | C | 92 | 5.621 | 1.911 | 5.828 | 1.00 | 16.18 | C |
| ATOM | 733 | CZ | PHE | C | 92 | 4.322 | 2.044 | 5.587 | 1.00 | 15.78 | C |
| ATOM | 734 | C | PHE | C | 92 | 6.920 | 5.407 | 2.539 | 1.00 | 17.38 | C |
| ATOM | 735 | O | PHE | C | 92 | 6.611 | 6.018 | 3.513 | 1.00 | 17.53 | C |
| ATOM | 736 | N | ASN | C | 93 | 6.379 | 5.618 | 1.345 | 1.00 | 16.65 | C |
| ATOM | 737 | CA | ASN | C | 93 | 5.453 | 6.697 | 1.087 | 1.00 | 15.55 | C |
| ATOM | 738 | CB | ASN | C | 93 | 5.905 | 7.407 | −0.084 | 1.00 | 15.47 | C |
| ATOM | 739 | CG | ASN | C | 93 | 7.140 | 8.053 | 0.180 | 1.00 | 15.77 | C |
| ATOM | 740 | OD1 | ASN | C | 93 | 7.264 | 8.675 | 1.220 | 1.00 | 16.38 | C |
| ATOM | 741 | ND2 | ASN | C | 93 | 8.079 | 7.941 | −0.716 | 1.00 | 12.39 | C |
| ATOM | 742 | C | ASN | C | 93 | 4.005 | 6.423 | 0.918 | 1.00 | 15.95 | C |
| ATOM | 743 | O | ASN | C | 93 | 3.643 | 5.387 | 0.455 | 1.00 | 15.02 | C |
| ATOM | 744 | N | LEU | C | 94 | 3.167 | 7.356 | 1.356 | 1.00 | 15.08 | C |
| ATOM | 745 | CA | LEU | C | 94 | 1.795 | 7.138 | 1.246 | 1.00 | 15.41 | C |
| ATOM | 746 | CB | LEU | C | 94 | 1.130 | 7.217 | 2.622 | 1.00 | 14.54 | C |
| ATOM | 747 | CG | LEU | C | 94 | −0.407 | 7.139 | 2.781 | 1.00 | 13.57 | C |
| ATOM | 748 | CD1 | LEU | C | 94 | −0.896 | 5.742 | 2.229 | 1.00 | 12.30 | C |
| ATOM | 749 | CD2 | LEU | C | 94 | −0.738 | 7.387 | 4.237 | 1.00 | 11.51 | C |
| ATOM | 750 | C | LEU | C | 94 | 1.101 | 8.099 | 0.276 | 1.00 | 16.76 | C |

TABLE 1-continued

| | | | | | | | | | | |
|---|---|---|---|---|---|---|---|---|---|---|
| ATOM | 751 | O | LEU | C | 94 | 1.243 | 9.318 | 0.447 | 1.00 | 17.39 | C |
| ATOM | 752 | N | TYR | C | 95 | 0.309 | 7.596 | −0.706 | 1.00 | 16.13 | C |
| ATOM | 753 | CA | TYR | C | 95 | −0.403 | 8.472 | −1.645 | 1.00 | 14.79 | C |
| ATOM | 754 | CB | TYR | C | 95 | 0.202 | 8.401 | −3.007 | 1.00 | 15.35 | C |
| ATOM | 755 | CG | TYR | C | 95 | 1.595 | 8.955 | −3.207 | 1.00 | 16.40 | C |
| ATOM | 756 | CD1 | TYR | C | 95 | 2.737 | 8.392 | −2.598 | 1.00 | 14.72 | C |
| ATOM | 757 | CE1 | TYR | C | 95 | 3.984 | 8.880 | −2.864 | 1.00 | 15.06 | C |
| ATOM | 758 | CD2 | TYR | C | 95 | 1.779 | 10.015 | −4.096 | 1.00 | 17.38 | C |
| ATOM | 759 | CE2 | TYR | C | 95 | 3.040 | 10.478 | −4.377 | 1.00 | 17.62 | C |
| ATOM | 760 | CZ | TYR | C | 95 | 4.119 | 9.923 | −3.761 | 1.00 | 16.43 | C |
| ATOM | 761 | OH | TYR | C | 95 | 5.237 | 10.596 | −4.075 | 1.00 | 17.48 | C |
| ATOM | 762 | C | TYR | C | 95 | −1.828 | 8.080 | −1.826 | 1.00 | 14.51 | C |
| ATOM | 763 | O | TYR | C | 95 | −2.292 | 6.995 | −1.436 | 1.00 | 13.37 | C |
| ATOM | 764 | N | TYR | C | 96 | −2.548 | 8.952 | −2.496 | 1.00 | 14.66 | C |
| ATOM | 765 | CA | TYR | C | 96 | −3.976 | 8.672 | −2.809 | 1.00 | 14.95 | C |
| ATOM | 766 | CB | TYR | C | 96 | −4.914 | 9.099 | −1.663 | 1.00 | 14.56 | C |
| ATOM | 767 | CG | TYR | C | 96 | −5.192 | 10.566 | −1.638 | 1.00 | 14.19 | C |
| ATOM | 768 | CD1 | TYR | C | 96 | −6.346 | 11.081 | −2.172 | 1.00 | 14.77 | C |
| ATOM | 769 | CE1 | TYR | C | 96 | −6.609 | 12.447 | −2.162 | 1.00 | 15.77 | C |
| ATOM | 770 | CD2 | TYR | C | 96 | −4.293 | 11.420 | −1.102 | 1.00 | 14.17 | C |
| ATOM | 771 | CE2 | TYR | C | 96 | −4.529 | 12.798 | −1.072 | 1.00 | 15.90 | C |
| ATOM | 772 | CZ | TYR | C | 96 | −5.677 | 13.313 | −1.589 | 1.00 | 15.84 | C |
| ATOM | 773 | OH | TYR | C | 96 | −5.829 | 14.661 | −1.515 | 1.00 | 15.15 | C |
| ATOM | 774 | C | TYR | C | 96 | −4.327 | 9.444 | −4.048 | 1.00 | 14.09 | C |
| ATOM | 775 | O | TYR | C | 96 | −3.531 | 10.213 | −4.529 | 1.00 | 13.38 | C |
| ATOM | 776 | N | ALA | C | 97 | −5.528 | 9.218 | −4.564 | 1.00 | 14.37 | C |
| ATOM | 777 | CA | ALA | C | 97 | −6.007 | 9.991 | −5.760 | 1.00 | 15.65 | C |
| ATOM | 778 | CB | ALA | C | 97 | −5.420 | 9.446 | −7.170 | 1.00 | 13.99 | C |
| ATOM | 779 | C | ALA | C | 97 | −7.462 | 9.811 | −5.658 | 1.00 | 14.46 | C |
| ATOM | 780 | O | ALA | C | 97 | −7.922 | 8.853 | −5.023 | 1.00 | 14.24 | C |
| ATOM | 781 | N | GLU | C | 98 | −8.156 | 10.799 | −6.163 | 1.00 | 14.58 | C |
| ATOM | 782 | CA | GLU | C | 98 | −9.643 | 10.833 | −6.175 | 1.00 | 16.26 | C |
| ATOM | 783 | CB | GLU | C | 98 | −10.158 | 12.151 | −5.655 | 1.00 | 14.43 | C |
| ATOM | 784 | CG | GLU | C | 98 | −10.205 | 12.254 | −4.171 | 1.00 | 14.61 | C |
| ATOM | 785 | CD | GLU | C | 98 | −10.760 | 13.660 | −3.701 | 1.00 | 15.33 | C |
| ATOM | 786 | OE1 | GLU | C | 98 | −10.001 | 14.686 | −3.589 | 1.00 | 16.29 | C |
| ATOM | 787 | OE2 | GLU | C | 98 | −11.972 | 13.747 | −3.465 | 1.00 | 13.77 | C |
| ATOM | 788 | C | GLU | C | 98 | −10.162 | 10.751 | −7.609 | 1.00 | 15.27 | C |
| ATOM | 789 | O | GLU | C | 98 | −9.568 | 11.304 | −8.524 | 1.00 | 16.65 | C |
| ATOM | 790 | N | SER | C | 99 | −11.210 | 10.021 | −7.854 | 1.00 | 14.95 | C |
| ATOM | 791 | CA | SER | C | 99 | −11.792 | 10.038 | −9.217 | 1.00 | 15.27 | C |
| ATOM | 792 | CB | SER | C | 99 | −11.070 | 9.251 | −10.343 | 1.00 | 12.89 | C |
| ATOM | 793 | OG | SER | C | 99 | −10.998 | 7.950 | −10.079 | 1.00 | 11.54 | C |
| ATOM | 794 | C | SER | C | 99 | −13.248 | 9.702 | −9.256 | 1.00 | 15.17 | C |
| ATOM | 795 | O | SER | C | 99 | −13.785 | 9.114 | −8.380 | 1.00 | 15.16 | C |
| ATOM | 796 | N | ASP | C | 100 | −13.916 | 10.193 | −10.290 | 1.00 | 16.26 | C |
| ATOM | 797 | CA | ASP | C | 100 | −15.279 | 9.862 | −10.348 | 1.00 | 17.25 | C |
| ATOM | 798 | CB | ASP | C | 100 | −16.049 | 10.981 | −11.001 | 1.00 | 17.20 | C |
| ATOM | 799 | CG | ASP | C | 100 | −16.102 | 12.299 | −10.116 | 1.00 | 18.84 | C |
| ATOM | 800 | OD1 | ASP | C | 100 | −16.354 | 12.201 | −8.873 | 1.00 | 15.96 | C |
| ATOM | 801 | OD2 | ASP | C | 100 | −15.880 | 13.436 | −10.736 | 1.00 | 18.65 | C |
| ATOM | 802 | C | ASP | C | 100 | −15.517 | 8.541 | −11.023 | 1.00 | 16.98 | C |
| ATOM | 803 | O | ASP | C | 100 | −16.594 | 8.067 | −10.928 | 1.00 | 17.07 | C |
| ATOM | 804 | N | LEU | C | 101 | −14.502 | 7.981 | −11.662 | 1.00 | 16.55 | C |
| ATOM | 805 | CA | LEU | C | 101 | −14.579 | 6.782 | −12.384 | 1.00 | 17.40 | C |
| ATOM | 806 | CB | LEU | C | 101 | −14.164 | 6.934 | −13.872 | 1.00 | 17.11 | C |
| ATOM | 807 | CG | LEU | C | 101 | −14.332 | 8.115 | −14.768 | 1.00 | 18.53 | C |
| ATOM | 808 | CD1 | LEU | C | 101 | −13.833 | 9.320 | −14.105 | 1.00 | 17.20 | C |
| ATOM | 809 | CD2 | LEU | C | 101 | −13.515 | 7.888 | −16.055 | 1.00 | 17.86 | C |
| ATOM | 810 | C | LEU | C | 101 | −13.548 | 5.813 | −11.772 | 1.00 | 17.42 | C |
| ATOM | 811 | O | LEU | C | 101 | −12.594 | 6.199 | −11.165 | 1.00 | 16.28 | C |
| ATOM | 812 | N | ASP | C | 102 | −13.785 | 4.539 | −12.022 | 1.00 | 17.92 | C |
| ATOM | 813 | CA | ASP | C | 102 | −12.969 | 3.443 | −11.584 | 1.00 | 20.65 | C |
| ATOM | 814 | CB | ASP | C | 102 | −13.814 | 2.165 | −11.557 | 1.00 | 18.60 | C |
| ATOM | 815 | CG | ASP | C | 102 | −13.106 | 1.028 | −10.918 | 1.00 | 18.96 | C |
| ATOM | 816 | OD1 | ASP | C | 102 | −11.808 | 0.985 | −10.963 | 1.00 | 20.16 | C |
| ATOM | 817 | OD2 | ASP | C | 102 | −13.806 | 0.129 | −10.332 | 1.00 | 16.85 | C |
| ATOM | 818 | C | ASP | C | 102 | −11.846 | 3.270 | −12.661 | 1.00 | 21.62 | C |
| ATOM | 819 | O | ASP | C | 102 | −12.116 | 2.808 | −13.800 | 1.00 | 23.44 | C |
| ATOM | 820 | N | TYR | C | 103 | −10.586 | 3.518 | −12.294 | 1.00 | 21.22 | C |
| ATOM | 821 | CA | TYR | C | 103 | −9.476 | 3.377 | −13.288 | 1.00 | 20.10 | C |
| ATOM | 822 | CB | TYR | C | 103 | −8.109 | 3.910 | −12.681 | 1.00 | 20.71 | C |
| ATOM | 823 | CG | TYR | C | 103 | −8.002 | 5.399 | −12.673 | 1.00 | 21.26 | C |
| ATOM | 824 | CD1 | TYR | C | 103 | −8.209 | 6.137 | −13.820 | 1.00 | 22.06 | C |
| ATOM | 825 | CE1 | TYR | C | 103 | −8.104 | 7.532 | −13.810 | 1.00 | 23.09 | C |
| ATOM | 826 | CD2 | TYR | C | 103 | −7.695 | 6.054 | −11.514 | 1.00 | 21.47 | C |
| ATOM | 827 | CE2 | TYR | C | 103 | −7.580 | 7.464 | −11.458 | 1.00 | 22.82 | C |
| ATOM | 828 | CZ | TYR | C | 103 | −7.773 | 8.218 | −12.584 | 1.00 | 23.49 | C |
| ATOM | 829 | OH | TYR | C | 103 | −7.629 | 9.620 | −12.491 | 1.00 | 23.07 | C |
| ATOM | 830 | C | TYR | C | 103 | −9.200 | 1.978 | −13.748 | 1.00 | 18.60 | C |

TABLE 1-continued

| | | | | | | | | | | |
|---|---|---|---|---|---|---|---|---|---|---|
| ATOM | 831 | O | TYR | C | 103 | −8.315 | 1.768 | −14.617 | 1.00 | 16.86 C |
| ATOM | 832 | N | GLY | C | 104 | −9.909 | 1.016 | −13.152 | 1.00 | 17.81 C |
| ATOM | 833 | CA | GLY | C | 104 | −9.606 | −0.366 | −13.501 | 1.00 | 18.05 C |
| ATOM | 834 | C | GLY | C | 104 | −8.088 | −0.603 | −13.234 | 1.00 | 18.59 C |
| ATOM | 835 | O | GLY | C | 104 | −7.583 | −0.280 | −12.170 | 1.00 | 18.80 C |
| ATOM | 836 | N | THR | C | 105 | −7.352 | −1.083 | −14.218 | 1.00 | 18.58 C |
| ATOM | 837 | CA | THR | C | 105 | −5.963 | −1.423 | −14.061 | 1.00 | 17.73 C |
| ATOM | 838 | CB | THR | C | 105 | −5.781 | −2.686 | −14.867 | 1.00 | 19.00 C |
| ATOM | 839 | OG1 | THR | C | 105 | −6.033 | −3.777 | −14.001 | 1.00 | 19.76 C |
| ATOM | 840 | CG2 | THR | C | 105 | −4.489 | −2.848 | −15.430 | 1.00 | 19.62 C |
| ATOM | 841 | C | THR | C | 105 | −4.940 | −0.279 | −14.386 | 1.00 | 18.86 C |
| ATOM | 842 | O | THR | C | 105 | −3.725 | −0.382 | −14.108 | 1.00 | 17.71 C |
| ATOM | 843 | N | ASN | C | 106 | −5.450 | 0.825 | −14.934 | 1.00 | 18.05 C |
| ATOM | 844 | CA | ASN | C | 106 | −4.671 | 2.012 | −15.206 | 1.00 | 17.77 C |
| ATOM | 845 | CB | ASN | C | 106 | −5.514 | 3.140 | −15.781 | 1.00 | 20.51 C |
| ATOM | 846 | CG | ASN | C | 106 | −5.817 | 2.948 | −17.216 | 1.00 | 22.54 C |
| ATOM | 847 | OD1 | ASN | C | 106 | −6.661 | 3.690 | −17.843 | 1.00 | 23.63 C |
| ATOM | 848 | ND2 | ASN | C | 106 | −5.146 | 1.938 | −17.791 | 1.00 | 23.46 C |
| ATOM | 849 | C | ASN | C | 106 | −4.090 | 2.649 | −14.013 | 1.00 | 17.25 C |
| ATOM | 850 | O | ASN | C | 106 | −4.651 | 3.511 | −13.468 | 1.00 | 14.62 C |
| ATOM | 851 | N | PHE | C | 107 | −2.906 | 2.288 | −13.659 | 1.00 | 18.46 C |
| ATOM | 852 | CA | PHE | C | 107 | −2.346 | 2.998 | −12.509 | 1.00 | 19.89 C |
| ATOM | 853 | CB | PHE | C | 107 | −1.622 | 2.055 | −11.575 | 1.00 | 19.98 C |
| ATOM | 854 | CG | PHE | C | 107 | −0.824 | 2.782 | −10.557 | 1.00 | 19.62 C |
| ATOM | 855 | CD1 | PHE | C | 107 | −1.475 | 3.471 | −9.536 | 1.00 | 19.36 C |
| ATOM | 856 | CD2 | PHE | C | 107 | 0.534 | 2.782 | −10.608 | 1.00 | 19.04 C |
| ATOM | 857 | CE1 | PHE | C | 107 | −0.818 | 4.136 | −8.601 | 1.00 | 19.11 C |
| ATOM | 858 | CE2 | PHE | C | 107 | 1.265 | 3.448 | −9.656 | 1.00 | 20.27 C |
| ATOM | 859 | CZ | PHE | C | 107 | 0.566 | 4.130 | −8.643 | 1.00 | 21.42 C |
| ATOM | 860 | C | PHE | C | 107 | −1.348 | 4.084 | −12.989 | 1.00 | 20.78 C |
| ATOM | 861 | O | PHE | C | 107 | −0.392 | 3.825 | −13.772 | 1.00 | 22.06 C |
| ATOM | 862 | N | GLN | C | 108 | −1.529 | 5.298 | −12.519 | 1.00 | 21.35 C |
| ATOM | 863 | CA | GLN | C | 108 | −0.649 | 6.398 | −13.022 | 1.00 | 21.28 C |
| ATOM | 864 | CB | GLN | C | 108 | −1.498 | 7.442 | −13.724 | 1.00 | 23.32 C |
| ATOM | 865 | CG | GLN | C | 108 | −2.486 | 6.903 | −14.807 | 1.00 | 25.78 C |
| ATOM | 866 | CD | GLN | C | 108 | −1.785 | 6.786 | −16.145 | 1.00 | 25.85 C |
| ATOM | 867 | OE1 | GLN | C | 108 | −2.447 | 6.308 | −17.091 | 1.00 | 29.58 C |
| ATOM | 868 | NE2 | GLN | C | 108 | −0.484 | 7.219 | −16.254 | 1.00 | 21.35 C |
| ATOM | 869 | C | GLN | C | 108 | −0.031 | 7.128 | −11.872 | 1.00 | 19.53 C |
| ATOM | 870 | O | GLN | C | 108 | −0.701 | 8.041 | −11.329 | 1.00 | 19.54 C |
| ATOM | 871 | N | LYS | C | 109 | 1.191 | 6.790 | −11.493 | 1.00 | 17.60 C |
| ATOM | 872 | CA | LYS | C | 109 | 1.754 | 7.445 | −10.256 | 1.00 | 17.03 C |
| ATOM | 873 | CB | LYS | C | 109 | 3.206 | 7.047 | −10.021 | 1.00 | 16.95 C |
| ATOM | 874 | CG | LYS | C | 109 | 4.126 | 8.186 | −10.323 | 1.00 | 17.11 C |
| ATOM | 875 | CD | LYS | C | 109 | 5.549 | 7.735 | −10.579 | 1.00 | 18.36 C |
| ATOM | 876 | CE | LYS | C | 109 | 6.183 | 7.039 | −9.391 | 1.00 | 18.42 C |
| ATOM | 877 | NZ | LYS | C | 109 | 7.700 | 7.235 | −9.639 | 1.00 | 19.07 C |
| ATOM | 878 | C | LYS | C | 109 | 1.652 | 9.004 | −10.297 | 1.00 | 16.60 C |
| ATOM | 879 | O | LYS | C | 109 | 1.364 | 9.638 | −9.328 | 1.00 | 16.33 C |
| ATOM | 880 | N | ARG | C | 110 | 1.815 | 9.587 | −11.457 | 1.00 | 16.33 C |
| ATOM | 881 | CA | ARG | C | 110 | 1.753 | 10.955 | −11.531 | 1.00 | 15.92 C |
| ATOM | 882 | CB | ARG | C | 110 | 2.175 | 11.355 | −12.894 | 1.00 | 17.89 C |
| ATOM | 883 | CG | ARG | C | 110 | 3.663 | 11.535 | −12.862 | 1.00 | 20.69 C |
| ATOM | 884 | CD | ARG | C | 110 | 4.493 | 10.195 | −12.977 | 1.00 | 21.88 C |
| ATOM | 885 | NE | ARG | C | 110 | 5.921 | 10.471 | −12.658 | 1.00 | 22.87 C |
| ATOM | 886 | CZ | ARG | C | 110 | 6.421 | 10.787 | −11.425 | 1.00 | 23.51 C |
| ATOM | 887 | NH1 | ARG | C | 110 | 5.583 | 10.904 | −10.319 | 1.00 | 22.39 C |
| ATOM | 888 | NH2 | ARG | C | 110 | 7.764 | 10.880 | −11.300 | 1.00 | 20.43 C |
| ATOM | 889 | C | ARG | C | 110 | 0.463 | 11.557 | −11.156 | 1.00 | 16.16 C |
| ATOM | 890 | O | ARG | C | 110 | 0.442 | 12.768 | −10.913 | 1.00 | 14.92 C |
| ATOM | 891 | N | LEU | C | 111 | −0.583 | 10.706 | −11.057 | 1.00 | 16.99 C |
| ATOM | 892 | CA | LEU | C | 111 | −1.977 | 11.126 | −10.747 | 1.00 | 18.63 C |
| ATOM | 893 | CB | LEU | C | 111 | −3.002 | 10.210 | −11.444 | 1.00 | 17.82 C |
| ATOM | 894 | CG | LEU | C | 111 | −2.912 | 10.475 | −12.965 | 1.00 | 18.40 C |
| ATOM | 895 | CD1 | LEU | C | 111 | −4.070 | 9.592 | −13.642 | 1.00 | 19.34 C |
| ATOM | 896 | CD2 | LEU | C | 111 | −2.955 | 11.920 | −13.409 | 1.00 | 12.31 C |
| ATOM | 897 | C | LEU | C | 111 | −2.195 | 11.189 | −9.279 | 1.00 | 17.61 C |
| ATOM | 898 | O | LEU | C | 111 | −3.019 | 11.916 | −8.816 | 1.00 | 20.04 C |
| ATOM | 899 | N | PHE | C | 112 | −1.396 | 10.449 | −8.561 | 1.00 | 17.22 C |
| ATOM | 900 | CA | PHE | C | 112 | −1.425 | 10.432 | −7.097 | 1.00 | 16.36 C |
| ATOM | 901 | CB | PHE | C | 112 | −0.866 | 9.103 | −6.616 | 1.00 | 15.03 C |
| ATOM | 902 | CG | PHE | C | 112 | −1.825 | 8.007 | −6.798 | 1.00 | 15.70 C |
| ATOM | 903 | CD1 | PHE | C | 112 | −2.258 | 7.635 | −8.087 | 1.00 | 17.36 C |
| ATOM | 904 | CD2 | PHE | C | 112 | −2.350 | 7.332 | −5.667 | 1.00 | 16.44 C |
| ATOM | 905 | CE1 | PHE | C | 112 | −3.238 | 6.575 | −8.265 | 1.00 | 16.99 C |
| ATOM | 906 | CE2 | PHE | C | 112 | −3.300 | 6.296 | −5.760 | 1.00 | 16.53 C |
| ATOM | 907 | CZ | PHE | C | 112 | −3.771 | 5.901 | −7.081 | 1.00 | 17.72 C |
| ATOM | 908 | C | PHE | C | 112 | −0.700 | 11.584 | −6.387 | 1.00 | 14.41 C |
| ATOM | 909 | O | PHE | C | 112 | 0.262 | 12.140 | −6.855 | 1.00 | 14.04 C |
| ATOM | 910 | N | THR | C | 113 | −1.189 | 11.929 | −5.225 | 1.00 | 14.82 C |

TABLE 1-continued

| | | | | | | | | | | |
|---|---|---|---|---|---|---|---|---|---|---|
| ATOM | 911 | CA | THR | C | 113 | −0.640 | 12.974 | −4.398 | 1.00 | 16.04 | C |
| ATOM | 912 | CB | THR | C | 113 | −1.725 | 13.885 | −3.932 | 1.00 | 15.19 | C |
| ATOM | 913 | OG1 | THR | C | 113 | −2.138 | 14.659 | −5.045 | 1.00 | 15.56 | C |
| ATOM | 914 | CG2 | THR | C | 113 | −1.266 | 14.802 | −2.853 | 1.00 | 13.51 | C |
| ATOM | 915 | C | THR | C | 113 | −0.048 | 12.317 | −3.209 | 1.00 | 16.12 | C |
| ATOM | 916 | O | THR | C | 113 | −0.621 | 11.386 | −2.657 | 1.00 | 17.22 | C |
| ATOM | 917 | N | LYS | C | 114 | 1.115 | 12.785 | −2.820 | 1.00 | 15.60 | C |
| ATOM | 918 | CA | LYS | C | 114 | 1.720 | 12.212 | −1.619 | 1.00 | 16.33 | C |
| ATOM | 919 | CB | LYS | C | 114 | 3.220 | 12.571 | −1.473 | 1.00 | 16.05 | C |
| ATOM | 920 | CG | LYS | C | 114 | 3.926 | 11.969 | −0.260 | 1.00 | 15.39 | C |
| ATOM | 921 | CD | LYS | C | 114 | 5.473 | 12.137 | −0.269 | 1.00 | 17.26 | C |
| ATOM | 922 | CE | LYS | C | 114 | 6.073 | 11.587 | 1.093 | 1.00 | 18.39 | C |
| ATOM | 923 | NZ | LYS | C | 114 | 7.534 | 11.693 | 1.303 | 1.00 | 17.84 | C |
| ATOM | 924 | C | LYS | C | 114 | 0.939 | 12.700 | −0.368 | 1.00 | 15.30 | C |
| ATOM | 925 | O | LYS | C | 114 | 0.565 | 13.882 | −0.276 | 1.00 | 13.95 | C |
| ATOM | 926 | N | ILE | C | 115 | 0.672 | 11.766 | 0.556 | 1.00 | 14.93 | C |
| ATOM | 927 | CA | ILE | C | 115 | 0.070 | 12.181 | 1.813 | 1.00 | 16.71 | C |
| ATOM | 928 | CB | ILE | C | 115 | −0.872 | 11.184 | 2.381 | 1.00 | 16.08 | C |
| ATOM | 929 | CG2 | ILE | C | 115 | −1.161 | 11.504 | 3.777 | 1.00 | 14.42 | C |
| ATOM | 930 | CG1 | ILE | C | 115 | −2.147 | 11.197 | 1.485 | 1.00 | 17.47 | C |
| ATOM | 931 | CD1 | ILE | C | 115 | −3.112 | 10.001 | 1.568 | 1.00 | 14.68 | C |
| ATOM | 932 | C | ILE | C | 115 | 1.198 | 12.469 | 2.815 | 1.00 | 16.70 | C |
| ATOM | 933 | O | ILE | C | 115 | 1.193 | 13.590 | 3.402 | 1.00 | 17.46 | C |
| ATOM | 934 | N | ASP | C | 116 | 2.160 | 11.534 | 2.962 | 1.00 | 15.34 | C |
| ATOM | 935 | CA | ASP | C | 116 | 3.214 | 11.688 | 3.922 | 1.00 | 15.16 | C |
| ATOM | 936 | CB | ASP | C | 116 | 2.565 | 11.631 | 5.337 | 1.00 | 16.72 | C |
| ATOM | 937 | CG | ASP | C | 116 | 3.507 | 11.967 | 6.518 | 1.00 | 18.35 | C |
| ATOM | 938 | OD1 | ASP | C | 116 | 3.039 | 11.685 | 7.657 | 1.00 | 20.63 | C |
| ATOM | 939 | OD2 | ASP | C | 116 | 4.629 | 12.546 | 6.399 | 1.00 | 19.13 | C |
| ATOM | 940 | C | ASP | C | 116 | 4.165 | 10.546 | 3.824 | 1.00 | 14.13 | C |
| ATOM | 941 | O | ASP | C | 116 | 3.829 | 9.530 | 3.269 | 1.00 | 12.38 | C |
| ATOM | 942 | N | THR | C | 117 | 5.352 | 10.736 | 4.423 | 1.00 | 13.35 | C |
| ATOM | 943 | CA | THR | C | 117 | 6.382 | 9.720 | 4.576 | 1.00 | 14.15 | C |
| ATOM | 944 | CB | THR | C | 117 | 7.749 | 10.346 | 4.842 | 1.00 | 14.06 | C |
| ATOM | 945 | OG1 | THR | C | 117 | 8.146 | 11.164 | 3.742 | 1.00 | 15.03 | C |
| ATOM | 946 | CG2 | THR | C | 117 | 8.766 | 9.295 | 5.153 | 1.00 | 10.20 | C |
| ATOM | 947 | C | THR | C | 117 | 5.984 | 8.862 | 5.851 | 1.00 | 14.73 | C |
| ATOM | 948 | O | THR | C | 117 | 5.722 | 9.431 | 6.877 | 1.00 | 14.43 | C |
| ATOM | 949 | N | ILE | C | 118 | 5.897 | 7.528 | 5.744 | 1.00 | 14.43 | C |
| ATOM | 950 | CA | ILE | C | 118 | 5.584 | 6.689 | 6.856 | 1.00 | 14.79 | C |
| ATOM | 951 | CB | ILE | C | 118 | 4.711 | 5.525 | 6.393 | 1.00 | 13.52 | C |
| ATOM | 952 | CG2 | ILE | C | 118 | 4.368 | 4.585 | 7.553 | 1.00 | 10.20 | C |
| ATOM | 953 | CG1 | ILE | C | 118 | 3.485 | 6.138 | 5.677 | 1.00 | 13.33 | C |
| ATOM | 954 | CD1 | ILE | C | 118 | 2.715 | 7.304 | 6.326 | 1.00 | 10.59 | C |
| ATOM | 955 | C | ILE | C | 118 | 6.905 | 6.192 | 7.507 | 1.00 | 16.12 | C |
| ATOM | 956 | O | ILE | C | 118 | 7.762 | 5.635 | 6.851 | 1.00 | 16.34 | C |
| ATOM | 957 | N | ALA | C | 119 | 7.087 | 6.400 | 8.798 | 1.00 | 15.22 | C |
| ATOM | 958 | CA | ALA | C | 119 | 8.319 | 5.994 | 9.384 | 1.00 | 15.08 | C |
| ATOM | 959 | CB | ALA | C | 119 | 9.107 | 7.202 | 9.723 | 1.00 | 14.05 | C |
| ATOM | 960 | C | ALA | C | 119 | 8.078 | 5.127 | 10.607 | 1.00 | 15.05 | C |
| ATOM | 961 | O | ALA | C | 119 | 7.129 | 5.318 | 11.314 | 1.00 | 14.96 | C |
| ATOM | 962 | N | PRO | C | 120 | 8.904 | 4.098 | 10.827 | 1.00 | 13.67 | C |
| ATOM | 963 | CD | PRO | C | 120 | 9.971 | 3.513 | 9.999 | 1.00 | 13.16 | C |
| ATOM | 964 | CA | PRO | C | 120 | 8.667 | 3.279 | 12.001 | 1.00 | 13.68 | C |
| ATOM | 965 | CB | PRO | C | 120 | 9.373 | 1.965 | 11.653 | 1.00 | 13.97 | C |
| ATOM | 966 | CG | PRO | C | 120 | 10.542 | 2.445 | 10.918 | 1.00 | 12.91 | C |
| ATOM | 967 | C | PRO | C | 120 | 9.261 | 3.881 | 13.313 | 1.00 | 14.60 | C |
| ATOM | 968 | O | PRO | C | 120 | 10.363 | 4.385 | 13.363 | 1.00 | 13.32 | C |
| ATOM | 969 | N | ASP | C | 121 | 8.485 | 3.769 | 14.377 | 1.00 | 16.21 | C |
| ATOM | 970 | CA | ASP | C | 121 | 8.896 | 4.206 | 15.656 | 1.00 | 17.91 | C |
| ATOM | 971 | CB | ASP | C | 121 | 7.738 | 4.225 | 16.561 | 1.00 | 20.47 | C |
| ATOM | 972 | CG | ASP | C | 121 | 6.647 | 4.925 | 15.961 | 1.00 | 23.77 | C |
| ATOM | 973 | OD1 | ASP | C | 121 | 6.090 | 4.302 | 14.857 | 1.00 | 27.96 | C |
| ATOM | 974 | OD2 | ASP | C | 121 | 6.331 | 6.078 | 16.524 | 1.00 | 22.54 | C |
| ATOM | 975 | C | ASP | C | 121 | 9.867 | 3.212 | 16.163 | 1.00 | 17.96 | C |
| ATOM | 976 | O | ASP | C | 121 | 10.600 | 3.535 | 17.059 | 1.00 | 18.85 | C |
| ATOM | 977 | N | GLU | C | 122 | 9.864 | 2.037 | 15.562 | 1.00 | 17.75 | C |
| ATOM | 978 | CA | GLU | C | 122 | 10.676 | 0.951 | 15.999 | 1.00 | 17.87 | C |
| ATOM | 979 | CB | GLU | C | 122 | 9.970 | 0.156 | 17.070 | 1.00 | 18.40 | C |
| ATOM | 980 | CG | GLU | C | 122 | 9.711 | 0.846 | 18.383 | 1.00 | 21.02 | C |
| ATOM | 981 | CD | GLU | C | 122 | 9.368 | −0.224 | 19.512 | 1.00 | 24.88 | C |
| ATOM | 982 | OE1 | GLU | C | 122 | 8.172 | −0.711 | 19.571 | 1.00 | 23.80 | C |
| ATOM | 983 | OE2 | GLU | C | 122 | 10.336 | −0.622 | 20.334 | 1.00 | 27.42 | C |
| ATOM | 984 | C | GLU | C | 122 | 11.075 | −0.022 | 14.900 | 1.00 | 17.91 | C |
| ATOM | 985 | O | GLU | C | 122 | 10.316 | −0.863 | 14.417 | 1.00 | 17.57 | C |
| ATOM | 986 | N | ILE | C | 123 | 12.335 | 0.064 | 14.571 | 1.00 | 17.91 | C |
| ATOM | 987 | CA | ILE | C | 123 | 12.863 | −0.683 | 13.527 | 1.00 | 18.35 | C |
| ATOM | 988 | CB | ILE | C | 123 | 14.144 | 0.005 | 13.151 | 1.00 | 20.03 | C |
| ATOM | 989 | CG2 | ILE | C | 123 | 15.060 | 0.171 | 14.414 | 1.00 | 20.64 | C |
| ATOM | 990 | CG1 | ILE | C | 123 | 14.926 | −0.887 | 12.194 | 1.00 | 21.95 | C |

TABLE 1-continued

| | | | | | | | | | | |
|---|---|---|---|---|---|---|---|---|---|---|
| ATOM | 991 | CD1 | ILE | C | 123 | 16.340 | −0.245 | 11.974 | 1.00 | 24.39 | C |
| ATOM | 992 | C | ILE | C | 123 | 13.060 | −2.058 | 14.054 | 1.00 | 18.60 | C |
| ATOM | 993 | O | ILE | C | 123 | 13.309 | −2.157 | 15.203 | 1.00 | 18.92 | C |
| ATOM | 994 | N | THR | C | 124 | 12.955 | −3.137 | 13.277 | 1.00 | 17.58 | C |
| ATOM | 995 | CA | THR | C | 124 | 13.211 | −4.456 | 13.911 | 1.00 | 16.37 | C |
| ATOM | 996 | CB | THR | C | 124 | 12.405 | −5.571 | 13.220 | 1.00 | 15.20 | C |
| ATOM | 997 | OG1 | THR | C | 124 | 11.032 | −5.459 | 13.545 | 1.00 | 16.03 | C |
| ATOM | 998 | CG2 | THR | C | 124 | 12.806 | −6.901 | 13.661 | 1.00 | 12.84 | C |
| ATOM | 999 | C | THR | C | 124 | 14.675 | −4.809 | 13.759 | 1.00 | 15.64 | C |
| ATOM | 1000 | O | THR | C | 124 | 15.173 | −4.844 | 12.638 | 1.00 | 17.40 | C |
| ATOM | 1001 | N | VAL | C | 125 | 15.397 | −5.103 | 14.804 | 1.00 | 14.78 | C |
| ATOM | 1002 | CA | VAL | C | 125 | 16.851 | −5.376 | 14.544 | 1.00 | 14.89 | C |
| ATOM | 1003 | CB | VAL | C | 125 | 17.901 | −4.802 | 15.665 | 1.00 | 12.90 | C |
| ATOM | 1004 | CG1 | VAL | C | 125 | 17.999 | −3.280 | 15.513 | 1.00 | 12.50 | C |
| ATOM | 1005 | CG2 | VAL | C | 125 | 17.526 | −5.280 | 17.071 | 1.00 | 7.31 | C |
| ATOM | 1006 | C | VAL | C | 125 | 17.140 | −6.828 | 14.433 | 1.00 | 12.40 | C |
| ATOM | 1007 | O | VAL | C | 125 | 16.341 | −7.608 | 14.814 | 1.00 | 11.55 | C |
| ATOM | 1008 | N | SER | C | 126 | 18.310 | −7.125 | 13.922 | 1.00 | 12.82 | C |
| ATOM | 1009 | CA | SER | C | 126 | 18.729 | −8.470 | 13.729 | 1.00 | 15.48 | C |
| ATOM | 1010 | CB | SER | C | 126 | 20.166 | −8.530 | 13.330 | 1.00 | 15.12 | C |
| ATOM | 1011 | OG | SER | C | 126 | 20.670 | −9.724 | 13.803 | 1.00 | 16.64 | C |
| ATOM | 1012 | C | SER | C | 126 | 18.513 | −9.418 | 14.888 | 1.00 | 15.96 | C |
| ATOM | 1013 | O | SER | C | 126 | 18.022 | −10.554 | 14.699 | 1.00 | 16.98 | C |
| ATOM | 1014 | N | SER | C | 127 | 18.804 | −9.021 | 16.089 | 1.00 | 16.15 | C |
| ATOM | 1015 | CA | SER | C | 127 | 18.607 | −9.977 | 17.114 | 1.00 | 16.97 | C |
| ATOM | 1016 | CB | SER | C | 127 | 19.433 | −9.596 | 18.302 | 1.00 | 18.26 | C |
| ATOM | 1017 | OG | SER | C | 127 | 18.923 | −8.342 | 18.847 | 1.00 | 18.77 | C |
| ATOM | 1018 | C | SER | C | 127 | 17.186 | −10.086 | 17.549 | 1.00 | 16.94 | C |
| ATOM | 1019 | O | SER | C | 127 | 16.907 | −10.972 | 18.348 | 1.00 | 16.88 | C |
| ATOM | 1020 | N | ASP | C | 128 | 16.326 | −9.150 | 17.089 | 1.00 | 17.11 | C |
| ATOM | 1021 | CA | ASP | C | 128 | 14.866 | −9.095 | 17.322 | 1.00 | 16.94 | C |
| ATOM | 1022 | CB | ASP | C | 128 | 14.252 | −7.854 | 16.657 | 1.00 | 19.22 | C |
| ATOM | 1023 | CG | ASP | C | 128 | 14.345 | −6.675 | 17.498 | 1.00 | 20.29 | C |
| ATOM | 1024 | OD1 | ASP | C | 128 | 14.171 | −5.536 | 16.992 | 1.00 | 18.82 | C |
| ATOM | 1025 | OD2 | ASP | C | 128 | 14.613 | −6.956 | 18.691 | 1.00 | 22.88 | C |
| ATOM | 1026 | C | ASP | C | 128 | 14.153 | −10.289 | 16.795 | 1.00 | 15.76 | C |
| ATOM | 1027 | O | ASP | C | 128 | 13.204 | −10.757 | 17.424 | 1.00 | 14.59 | C |
| ATOM | 1028 | N | PHE | C | 129 | 14.576 | −10.756 | 15.634 | 1.00 | 16.85 | C |
| ATOM | 1029 | CA | PHE | C | 129 | 13.981 | −12.047 | 15.098 | 1.00 | 19.44 | C |
| ATOM | 1030 | CB | PHE | C | 129 | 14.496 | −12.320 | 13.657 | 1.00 | 17.91 | C |
| ATOM | 1031 | CG | PHE | C | 129 | 14.135 | −11.171 | 12.704 | 1.00 | 17.50 | C |
| ATOM | 1032 | CD1 | PHE | C | 129 | 15.042 | −10.156 | 12.423 | 1.00 | 16.43 | C |
| ATOM | 1033 | CD2 | PHE | C | 129 | 12.825 | −11.092 | 12.164 | 1.00 | 17.70 | C |
| ATOM | 1034 | CE1 | PHE | C | 129 | 14.644 | −9.106 | 11.622 | 1.00 | 16.15 | C |
| ATOM | 1035 | CE2 | PHE | C | 129 | 12.427 | −10.034 | 11.353 | 1.00 | 17.36 | C |
| ATOM | 1036 | CZ | PHE | C | 129 | 13.318 | −9.055 | 11.081 | 1.00 | 16.61 | C |
| ATOM | 1037 | C | PHE | C | 129 | 14.608 | −12.883 | 16.094 | 1.00 | 18.93 | C |
| ATOM | 1038 | O | PHE | C | 129 | 15.124 | −12.347 | 17.055 | 1.00 | 22.39 | C |
| ATOM | 1039 | N | GLU | C | 130 | 14.576 | −14.168 | 16.031 | 1.00 | 19.21 | C |
| ATOM | 1040 | CA | GLU | C | 130 | 15.421 | −14.921 | 17.095 | 1.00 | 19.34 | C |
| ATOM | 1041 | CB | GLU | C | 130 | 16.878 | −14.462 | 17.117 | 1.00 | 17.61 | C |
| ATOM | 1042 | CG | GLU | C | 130 | 17.850 | −15.455 | 16.393 | 1.00 | 20.72 | C |
| ATOM | 1043 | CD | GLU | C | 130 | 19.365 | −15.257 | 16.801 | 1.00 | 22.99 | C |
| ATOM | 1044 | OE1 | GLU | C | 130 | 20.086 | −16.272 | 16.743 | 1.00 | 27.11 | C |
| ATOM | 1045 | OE2 | GLU | C | 130 | 19.872 | −14.148 | 17.203 | 1.00 | 23.98 | C |
| ATOM | 1046 | C | GLU | C | 130 | 14.833 | −14.733 | 18.468 | 1.00 | 17.85 | C |
| ATOM | 1047 | O | GLU | C | 130 | 14.485 | −15.667 | 19.111 | 1.00 | 17.80 | C |
| ATOM | 1048 | N | ALA | C | 131 | 14.796 | −13.513 | 18.914 | 1.00 | 18.18 | C |
| ATOM | 1049 | CA | ALA | C | 131 | 14.100 | −13.221 | 20.100 | 1.00 | 20.17 | C |
| ATOM | 1050 | CB | ALA | C | 131 | 14.516 | −11.897 | 20.555 | 1.00 | 18.74 | C |
| ATOM | 1051 | C | ALA | C | 131 | 12.714 | −13.133 | 19.383 | 1.00 | 21.44 | C |
| ATOM | 1052 | O | ALA | C | 131 | 12.678 | −13.020 | 18.111 | 1.00 | 23.59 | C |
| ATOM | 1053 | N | ARG | C | 132 | 11.565 | −13.167 | 20.037 | 1.00 | 20.71 | C |
| ATOM | 1054 | CA | ARG | C | 132 | 10.445 | −13.093 | 19.110 | 1.00 | 20.05 | C |
| ATOM | 1055 | CB | ARG | C | 132 | 9.402 | −14.170 | 19.390 | 1.00 | 20.95 | C |
| ATOM | 1056 | CG | ARG | C | 132 | 9.466 | −15.391 | 18.338 | 1.00 | 22.36 | C |
| ATOM | 1057 | CD | ARG | C | 132 | 10.856 | −16.007 | 17.969 | 1.00 | 19.04 | C |
| ATOM | 1058 | NE | ARG | C | 132 | 10.696 | −17.249 | 17.181 | 1.00 | 17.98 | C |
| ATOM | 1059 | CZ | ARG | C | 132 | 11.404 | −17.553 | 16.094 | 1.00 | 16.18 | C |
| ATOM | 1060 | NH1 | ARG | C | 132 | 12.284 | −16.709 | 15.670 | 1.00 | 17.02 | C |
| ATOM | 1061 | NH2 | ARG | C | 132 | 11.289 | −18.685 | 15.444 | 1.00 | 15.79 | C |
| ATOM | 1062 | C | ARG | C | 132 | 9.871 | −11.741 | 19.233 | 1.00 | 20.40 | C |
| ATOM | 1063 | O | ARG | C | 132 | 8.662 | −11.561 | 19.379 | 1.00 | 19.61 | C |
| ATOM | 1064 | N | HIS | C | 133 | 10.727 | −10.760 | 19.089 | 1.00 | 19.25 | C |
| ATOM | 1065 | CA | HIS | C | 133 | 10.248 | −9.438 | 19.340 | 1.00 | 18.99 | C |
| ATOM | 1066 | CB | HIS | C | 133 | 11.194 | −8.721 | 20.346 | 1.00 | 20.52 | C |
| ATOM | 1067 | CG | HIS | C | 133 | 11.339 | −9.406 | 21.674 | 1.00 | 22.22 | C |
| ATOM | 1068 | CD2 | HIS | C | 133 | 10.805 | −10.568 | 22.162 | 1.00 | 22.76 | C |
| ATOM | 1069 | ND1 | HIS | C | 133 | 12.011 | −8.804 | 22.722 | 1.00 | 23.05 | C |
| ATOM | 1070 | CE1 | HIS | C | 133 | 11.869 | −9.558 | 23.811 | 1.00 | 23.50 | C |

TABLE 1-continued

| | | | | | | | | | | |
|---|---|---|---|---|---|---|---|---|---|---|
| ATOM | 1071 | NE2 | HIS | C | 133 | 11.142 | −10.634 | 23.500 | 1.00 | 23.71 | C |
| ATOM | 1072 | C | HIS | C | 133 | 10.190 | −8.639 | 18.117 | 1.00 | 19.04 | C |
| ATOM | 1073 | O | HIS | C | 133 | 10.863 | −7.604 | 18.029 | 1.00 | 18.89 | C |
| ATOM | 1074 | N | VAL | C | 134 | 9.405 | −9.059 | 17.139 | 1.00 | 18.94 | C |
| ATOM | 1075 | CA | VAL | C | 134 | 9.383 | −8.243 | 15.938 | 1.00 | 19.11 | C |
| ATOM | 1076 | CB | VAL | C | 134 | 8.788 | −8.993 | 14.801 | 1.00 | 19.31 | C |
| ATOM | 1077 | CG1 | VAL | C | 134 | 8.843 | −8.135 | 13.548 | 1.00 | 18.74 | C |
| ATOM | 1078 | CG2 | VAL | C | 134 | 9.645 | −10.165 | 14.580 | 1.00 | 20.64 | C |
| ATOM | 1079 | C | VAL | C | 134 | 8.617 | −6.982 | 16.219 | 1.00 | 18.47 | C |
| ATOM | 1080 | O | VAL | C | 134 | 7.635 | −7.045 | 16.885 | 1.00 | 18.73 | C |
| ATOM | 1081 | N | LYS | C | 135 | 9.027 | −5.844 | 15.712 | 1.00 | 18.50 | C |
| ATOM | 1082 | CA | LYS | C | 135 | 8.337 | −4.599 | 16.068 | 1.00 | 18.59 | C |
| ATOM | 1083 | CB | LYS | C | 135 | 9.391 | −3.507 | 16.323 | 1.00 | 18.68 | C |
| ATOM | 1084 | CG | LYS | C | 135 | 10.630 | −4.004 | 17.112 | 1.00 | 18.29 | C |
| ATOM | 1085 | CD | LYS | C | 135 | 10.223 | −4.466 | 18.519 | 1.00 | 18.52 | C |
| ATOM | 1086 | CE | LYS | C | 135 | 11.394 | −4.339 | 19.441 | 1.00 | 19.17 | C |
| ATOM | 1087 | NZ | LYS | C | 135 | 11.049 | −5.140 | 20.613 | 1.00 | 21.80 | C |
| ATOM | 1088 | C | LYS | C | 135 | 7.320 | −4.076 | 15.075 | 1.00 | 18.01 | C |
| ATOM | 1089 | O | LYS | C | 135 | 7.628 | −3.674 | 13.918 | 1.00 | 17.93 | C |
| ATOM | 1090 | N | LEU | C | 136 | 6.111 | −4.086 | 15.575 | 1.00 | 16.80 | C |
| ATOM | 1091 | CA | LEU | C | 136 | 4.893 | −3.714 | 14.896 | 1.00 | 16.57 | C |
| ATOM | 1092 | CB | LEU | C | 136 | 3.835 | −4.725 | 15.373 | 1.00 | 15.74 | C |
| ATOM | 1093 | CG | LEU | C | 136 | 2.580 | −4.743 | 14.585 | 1.00 | 16.98 | C |
| ATOM | 1094 | CD1 | LEU | C | 136 | 1.866 | −3.552 | 15.056 | 1.00 | 20.09 | C |
| ATOM | 1095 | CD2 | LEU | C | 136 | 2.757 | −4.722 | 13.063 | 1.00 | 15.42 | C |
| ATOM | 1096 | C | LEU | C | 136 | 4.564 | −2.205 | 15.184 | 1.00 | 16.88 | C |
| ATOM | 1097 | O | LEU | C | 136 | 4.283 | −1.785 | 16.293 | 1.00 | 16.37 | C |
| ATOM | 1098 | N | ASN | C | 137 | 4.659 | −1.405 | 14.162 | 1.00 | 16.58 | C |
| ATOM | 1099 | CA | ASN | C | 137 | 4.368 | −0.023 | 14.256 | 1.00 | 16.46 | C |
| ATOM | 1100 | CB | ASN | C | 137 | 5.291 | 0.701 | 13.355 | 1.00 | 17.29 | C |
| ATOM | 1101 | CG | ASN | C | 137 | 6.699 | 0.633 | 13.813 | 1.00 | 18.26 | C |
| ATOM | 1102 | OD1 | ASN | C | 137 | 7.166 | 1.395 | 14.710 | 1.00 | 14.12 | C |
| ATOM | 1103 | ND2 | ASN | C | 137 | 7.439 | −0.268 | 13.143 | 1.00 | 18.71 | C |
| ATOM | 1104 | C | ASN | C | 137 | 2.935 | 0.338 | 13.791 | 1.00 | 17.10 | C |
| ATOM | 1105 | O | ASN | C | 137 | 2.379 | −0.300 | 12.838 | 1.00 | 16.99 | C |
| ATOM | 1106 | N | VAL | C | 138 | 2.331 | 1.368 | 14.417 | 1.00 | 15.92 | C |
| ATOM | 1107 | CA | VAL | C | 138 | 0.990 | 1.780 | 13.998 | 1.00 | 14.40 | C |
| ATOM | 1108 | CB | VAL | C | 138 | −0.019 | 1.695 | 15.096 | 1.00 | 14.26 | C |
| ATOM | 1109 | CG1 | VAL | C | 138 | −1.307 | 2.137 | 14.586 | 1.00 | 12.91 | C |
| ATOM | 1110 | CG2 | VAL | C | 138 | −0.079 | 0.298 | 15.652 | 1.00 | 14.68 | C |
| ATOM | 1111 | C | VAL | C | 138 | 1.096 | 3.186 | 13.550 | 1.00 | 15.51 | C |
| ATOM | 1112 | O | VAL | C | 138 | 1.618 | 3.990 | 14.285 | 1.00 | 15.05 | C |
| ATOM | 1113 | N | GLU | C | 139 | 0.665 | 3.480 | 12.329 | 1.00 | 15.47 | C |
| ATOM | 1114 | CA | GLU | C | 139 | 0.758 | 4.842 | 11.868 | 1.00 | 17.22 | C |
| ATOM | 1115 | CB | GLU | C | 139 | 1.892 | 5.031 | 10.866 | 1.00 | 16.43 | C |
| ATOM | 1116 | CG | GLU | C | 139 | 3.328 | 5.152 | 11.459 | 1.00 | 14.63 | C |
| ATOM | 1117 | CD | GLU | C | 139 | 3.525 | 6.271 | 12.462 | 1.00 | 11.48 | C |
| ATOM | 1118 | OE1 | GLU | C | 139 | 2.812 | 7.222 | 12.366 | 1.00 | 10.36 | C |
| ATOM | 1119 | OE2 | GLU | C | 139 | 4.404 | 6.176 | 13.285 | 1.00 | 10.49 | C |
| ATOM | 1120 | C | GLU | C | 139 | −0.532 | 5.294 | 11.222 | 1.00 | 18.19 | C |
| ATOM | 1121 | O | GLU | C | 139 | −1.016 | 4.633 | 10.284 | 1.00 | 19.36 | C |
| ATOM | 1122 | N | GLU | C | 140 | −1.116 | 6.385 | 11.694 | 1.00 | 16.67 | C |
| ATOM | 1123 | CA | GLU | C | 140 | −2.371 | 6.832 | 11.124 | 1.00 | 15.97 | C |
| ATOM | 1124 | CB | GLU | C | 140 | −3.475 | 6.890 | 12.162 | 1.00 | 18.08 | C |
| ATOM | 1125 | CG | GLU | C | 140 | −4.802 | 7.308 | 11.564 | 1.00 | 20.03 | C |
| ATOM | 1126 | CD | GLU | C | 140 | −6.042 | 6.829 | 12.412 | 1.00 | 22.88 | C |
| ATOM | 1127 | OE1 | GLU | C | 140 | −6.496 | 7.661 | 13.297 | 1.00 | 23.16 | C |
| ATOM | 1128 | OE2 | GLU | C | 140 | −6.544 | 5.636 | 12.199 | 1.00 | 21.79 | C |
| ATOM | 1129 | C | GLU | C | 140 | −2.265 | 8.153 | 10.507 | 1.00 | 14.69 | C |
| ATOM | 1130 | O | GLU | C | 140 | −1.588 | 9.011 | 11.022 | 1.00 | 14.14 | C |
| ATOM | 1131 | N | ARG | C | 141 | −2.898 | 8.346 | 9.371 | 1.00 | 12.49 | C |
| ATOM | 1132 | CA | ARG | C | 141 | −2.788 | 9.666 | 8.798 | 1.00 | 12.49 | C |
| ATOM | 1133 | CB | ARG | C | 141 | −1.830 | 9.778 | 7.625 | 1.00 | 12.74 | C |
| ATOM | 1134 | CG | ARG | C | 141 | −0.396 | 9.431 | 7.802 | 1.00 | 13.13 | C |
| ATOM | 1135 | CD | ARG | C | 141 | 0.582 | 10.531 | 8.077 | 1.00 | 10.46 | C |
| ATOM | 1136 | NE | ARG | C | 141 | 1.150 | 10.038 | 9.254 | 1.00 | 11.34 | C |
| ATOM | 1137 | CZ | ARG | C | 141 | 2.300 | 9.443 | 9.419 | 1.00 | 10.91 | C |
| ATOM | 1138 | NH1 | ARG | C | 141 | 3.143 | 9.272 | 8.510 | 1.00 | 13.01 | C |
| ATOM | 1139 | NH2 | ARG | C | 141 | 2.474 | 8.757 | 10.497 | 1.00 | 11.47 | C |
| ATOM | 1140 | C | ARG | C | 141 | −4.129 | 9.957 | 8.338 | 1.00 | 11.65 | C |
| ATOM | 1141 | O | ARG | C | 141 | −4.958 | 9.159 | 8.529 | 1.00 | 9.33 | C |
| ATOM | 1142 | N | SER | C | 142 | −4.315 | 11.083 | 7.683 | 1.00 | 13.04 | C |
| ATOM | 1143 | CA | SER | C | 142 | −5.632 | 11.479 | 7.265 | 1.00 | 15.38 | C |
| ATOM | 1144 | CB | SER | C | 142 | −6.442 | 11.975 | 8.456 | 1.00 | 17.13 | C |
| ATOM | 1145 | OG | SER | C | 142 | −6.341 | 13.383 | 8.533 | 1.00 | 23.20 | C |
| ATOM | 1146 | C | SER | C | 142 | −5.618 | 12.507 | 6.177 | 1.00 | 15.69 | C |
| ATOM | 1147 | O | SER | C | 142 | −4.673 | 13.275 | 5.988 | 1.00 | 15.02 | C |
| ATOM | 1148 | N | VAL | C | 143 | −6.688 | 12.495 | 5.400 | 1.00 | 16.53 | C |
| ATOM | 1149 | CA | VAL | C | 143 | −6.673 | 13.388 | 4.286 | 1.00 | 16.86 | C |
| ATOM | 1150 | CB | VAL | C | 143 | −5.827 | 12.708 | 3.084 | 1.00 | 19.58 | C |

TABLE 1-continued

| | | | | | | | | | | |
|---|---|---|---|---|---|---|---|---|---|---|
| ATOM | 1151 | CG1 | VAL | C | 143 | −6.419 | 11.387 | 2.573 | 1.00 | 20.57 | C |
| ATOM | 1152 | CG2 | VAL | C | 143 | −5.766 | 13.671 | 1.939 | 1.00 | 22.25 | C |
| ATOM | 1153 | C | VAL | C | 143 | −8.058 | 13.846 | 3.911 | 1.00 | 15.79 | C |
| ATOM | 1154 | O | VAL | C | 143 | −9.055 | 13.274 | 4.341 | 1.00 | 15.61 | C |
| ATOM | 1155 | N | GLY | C | 144 | −8.117 | 14.952 | 3.189 | 1.00 | 14.79 | C |
| ATOM | 1156 | CA | GLY | C | 144 | −9.395 | 15.482 | 2.830 | 1.00 | 13.21 | C |
| ATOM | 1157 | C | GLY | C | 144 | −9.428 | 16.973 | 2.789 | 1.00 | 13.26 | C |
| ATOM | 1158 | O | GLY | C | 144 | −8.384 | 17.552 | 2.995 | 1.00 | 11.03 | C |
| ATOM | 1159 | N | PRO | C | 145 | −10.609 | 17.604 | 2.496 | 1.00 | 15.31 | C |
| ATOM | 1160 | CD | PRO | C | 145 | −10.937 | 19.046 | 2.512 | 1.00 | 13.87 | C |
| ATOM | 1161 | CA | PRO | C | 145 | −11.818 | 16.816 | 2.223 | 1.00 | 15.80 | C |
| ATOM | 1162 | CB | PRO | C | 145 | −12.915 | 17.833 | 2.328 | 1.00 | 15.43 | C |
| ATOM | 1163 | CG | PRO | C | 145 | −12.274 | 19.082 | 1.952 | 1.00 | 13.64 | C |
| ATOM | 1164 | C | PRO | C | 145 | −11.867 | 16.130 | 0.873 | 1.00 | 18.60 | C |
| ATOM | 1165 | O | PRO | C | 145 | −11.427 | 16.680 | −0.187 | 1.00 | 21.50 | C |
| ATOM | 1166 | N | LEU | C | 146 | −12.381 | 14.908 | 0.893 | 1.00 | 19.39 | C |
| ATOM | 1167 | CA | LEU | C | 146 | −12.606 | 14.111 | −0.351 | 1.00 | 18.25 | C |
| ATOM | 1168 | CB | LEU | C | 146 | −12.741 | 12.651 | 0.040 | 1.00 | 16.86 | C |
| ATOM | 1169 | CG | LEU | C | 146 | −11.410 | 11.862 | −0.009 | 1.00 | 16.11 | C |
| ATOM | 1170 | CD1 | LEU | C | 146 | −10.321 | 12.665 | 0.401 | 1.00 | 16.87 | C |
| ATOM | 1171 | CD2 | LEU | C | 146 | −11.499 | 10.597 | 0.774 | 1.00 | 13.50 | C |
| ATOM | 1172 | C | LEU | C | 146 | −13.882 | 14.682 | −0.942 | 1.00 | 17.64 | C |
| ATOM | 1173 | O | LEU | C | 146 | −14.709 | 15.223 | −0.201 | 1.00 | 18.04 | C |
| ATOM | 1174 | N | THR | C | 147 | −14.009 | 14.633 | −2.250 | 1.00 | 17.08 | C |
| ATOM | 1175 | CA | THR | C | 147 | −15.231 | 15.109 | −2.921 | 1.00 | 16.67 | C |
| ATOM | 1176 | CB | THR | C | 147 | −15.070 | 16.528 | −3.516 | 1.00 | 15.26 | C |
| ATOM | 1177 | OG1 | THR | C | 147 | −14.069 | 16.495 | −4.568 | 1.00 | 15.39 | C |
| ATOM | 1178 | CG2 | THR | C | 147 | −14.761 | 17.514 | −2.467 | 1.00 | 12.84 | C |
| ATOM | 1179 | C | THR | C | 147 | −15.738 | 14.229 | −4.112 | 1.00 | 16.65 | C |
| ATOM | 1180 | O | THR | C | 147 | −16.826 | 14.425 | −4.492 | 1.00 | 17.31 | C |
| ATOM | 1181 | N | ARG | C | 148 | −14.932 | 13.316 | −4.683 | 1.00 | 16.30 | C |
| ATOM | 1182 | CA | ARG | C | 148 | −15.300 | 12.522 | −5.834 | 1.00 | 15.65 | C |
| ATOM | 1183 | CB | ARG | C | 148 | −14.081 | 12.114 | −6.654 | 1.00 | 16.33 | C |
| ATOM | 1184 | CG | ARG | C | 148 | −13.103 | 13.229 | −6.804 | 1.00 | 16.53 | C |
| ATOM | 1185 | CD | ARG | C | 148 | −13.467 | 14.244 | −7.845 | 1.00 | 16.51 | C |
| ATOM | 1186 | NE | ARG | C | 148 | −14.265 | 15.300 | −7.266 | 1.00 | 18.28 | C |
| ATOM | 1187 | CZ | ARG | C | 148 | −15.378 | 15.770 | −7.830 | 1.00 | 19.65 | C |
| ATOM | 1188 | NH1 | ARG | C | 148 | −15.815 | 15.261 | −8.959 | 1.00 | 18.97 | C |
| ATOM | 1189 | NH2 | ARG | C | 148 | −16.053 | 16.762 | −7.280 | 1.00 | 18.92 | C |
| ATOM | 1190 | C | ARG | C | 148 | −16.070 | 11.289 | −5.440 | 1.00 | 14.87 | C |
| ATOM | 1191 | O | ARG | C | 148 | −16.195 | 10.981 | −4.276 | 1.00 | 13.89 | C |
| ATOM | 1192 | N | LYS | C | 149 | −16.529 | 10.551 | −6.425 | 1.00 | 14.82 | C |
| ATOM | 1193 | CA | LYS | C | 149 | −17.332 | 9.391 | −6.161 | 1.00 | 15.19 | C |
| ATOM | 1194 | CB | LYS | C | 149 | −17.806 | 8.838 | −7.486 | 1.00 | 16.32 | C |
| ATOM | 1195 | CG | LYS | C | 149 | −19.073 | 7.962 | −7.516 | 1.00 | 17.87 | C |
| ATOM | 1196 | CD | LYS | C | 149 | −19.334 | 7.378 | −8.986 | 1.00 | 20.75 | C |
| ATOM | 1197 | CE | LYS | C | 149 | −20.288 | 6.173 | −8.961 | 1.00 | 22.45 | C |
| ATOM | 1198 | NZ | LYS | C | 149 | −19.765 | 4.816 | −9.600 | 1.00 | 24.66 | C |
| ATOM | 1199 | C | LYS | C | 149 | −16.466 | 8.422 | −5.437 | 1.00 | 14.88 | C |
| ATOM | 1200 | O | LYS | C | 149 | −16.930 | 7.686 | −4.620 | 1.00 | 15.41 | C |
| ATOM | 1201 | N | GLY | C | 150 | −15.181 | 8.433 | −5.759 | 1.00 | 14.10 | C |
| ATOM | 1202 | CA | GLY | C | 150 | −14.273 | 7.544 | −5.095 | 1.00 | 12.16 | C |
| ATOM | 1203 | C | GLY | C | 150 | −12.789 | 7.935 | −4.982 | 1.00 | 10.99 | C |
| ATOM | 1204 | O | GLY | C | 150 | −12.402 | 9.020 | −5.349 | 1.00 | 9.42 | C |
| ATOM | 1205 | N | PHE | C | 151 | −12.015 | 6.996 | −4.452 | 1.00 | 10.22 | C |
| ATOM | 1206 | CA | PHE | C | 151 | −10.655 | 7.183 | −4.256 | 1.00 | 11.34 | C |
| ATOM | 1207 | CB | PHE | C | 151 | −10.497 | 8.108 | −3.042 | 1.00 | 12.39 | C |
| ATOM | 1208 | CG | PHE | C | 151 | −10.757 | 7.434 | −1.742 | 1.00 | 13.49 | C |
| ATOM | 1209 | CD1 | PHE | C | 151 | −9.726 | 6.677 | −1.085 | 1.00 | 14.82 | C |
| ATOM | 1210 | CD2 | PHE | C | 151 | −12.004 | 7.409 | −1.200 | 1.00 | 12.88 | C |
| ATOM | 1211 | CE1 | PHE | C | 151 | −10.024 | 5.945 | 0.049 | 1.00 | 13.30 | C |
| ATOM | 1212 | CE2 | PHE | C | 151 | −12.240 | 6.690 | −0.097 | 1.00 | 11.97 | C |
| ATOM | 1213 | CZ | PHE | C | 151 | −11.270 | 5.962 | 0.524 | 1.00 | 12.66 | C |
| ATOM | 1214 | C | PHE | C | 151 | −9.788 | 5.903 | −4.104 | 1.00 | 10.68 | C |
| ATOM | 1215 | O | PHE | C | 151 | −10.229 | 4.792 | −3.808 | 1.00 | 8.97 | C |
| ATOM | 1216 | N | TYR | C | 152 | −8.504 | 6.135 | −4.277 | 1.00 | 12.40 | C |
| ATOM | 1217 | CA | TYR | C | 152 | −7.502 | 5.081 | −4.170 | 1.00 | 15.55 | C |
| ATOM | 1218 | CB | TYR | C | 152 | −6.769 | 4.789 | −5.515 | 1.00 | 16.45 | C |
| ATOM | 1219 | CG | TYR | C | 152 | −7.561 | 4.258 | −6.648 | 1.00 | 16.56 | C |
| ATOM | 1220 | CD1 | TYR | C | 152 | −8.128 | 5.100 | −7.554 | 1.00 | 16.73 | C |
| ATOM | 1221 | CE1 | TYR | C | 152 | −8.953 | 4.650 | −8.608 | 1.00 | 17.90 | C |
| ATOM | 1222 | CD2 | TYR | C | 152 | −7.782 | 2.917 | −6.772 | 1.00 | 17.59 | C |
| ATOM | 1223 | CE2 | TYR | C | 152 | −8.587 | 2.422 | −7.800 | 1.00 | 17.82 | C |
| ATOM | 1224 | CZ | TYR | C | 152 | −9.185 | 3.321 | −8.752 | 1.00 | 18.54 | C |
| ATOM | 1225 | OH | TYR | C | 152 | −9.925 | 2.916 | −9.917 | 1.00 | 18.81 | C |
| ATOM | 1226 | C | TYR | C | 152 | −6.446 | 5.535 | −3.156 | 1.00 | 14.75 | C |
| ATOM | 1227 | O | TYR | C | 152 | −6.138 | 6.720 | −2.949 | 1.00 | 13.40 | C |
| ATOM | 1228 | N | LEU | C | 153 | −5.901 | 4.506 | −2.570 | 1.00 | 15.80 | C |
| ATOM | 1229 | CA | LEU | C | 153 | −4.775 | 4.630 | −1.711 | 1.00 | 17.48 | C |
| ATOM | 1230 | CB | LEU | C | 153 | −5.082 | 4.004 | −0.379 | 1.00 | 16.77 | C |

TABLE 1-continued

| | | | | | | | | | | |
|---|---|---|---|---|---|---|---|---|---|---|
| ATOM | 1231 | CG | LEU | C | 153 | −5.108 | 5.033 | 0.767 | 1.00 | 16.27 | C |
| ATOM | 1232 | CD1 | LEU | C | 153 | −5.999 | 6.219 | 0.533 | 1.00 | 13.82 | C |
| ATOM | 1233 | CD2 | LEU | C | 153 | −5.514 | 4.235 | 1.942 | 1.00 | 15.52 | C |
| ATOM | 1234 | C | LEU | C | 153 | −3.619 | 3.839 | −2.415 | 1.00 | 17.30 | C |
| ATOM | 1235 | O | LEU | C | 153 | −3.865 | 2.841 | −3.127 | 1.00 | 18.68 | C |
| ATOM | 1236 | N | ALA | C | 154 | −2.376 | 4.319 | −2.247 | 1.00 | 16.79 | C |
| ATOM | 1237 | CA | ALA | C | 154 | −1.224 | 3.671 | −2.828 | 1.00 | 15.00 | C |
| ATOM | 1238 | CB | ALA | C | 154 | −0.975 | 4.254 | −4.284 | 1.00 | 13.77 | C |
| ATOM | 1239 | C | ALA | C | 154 | 0.020 | 3.821 | −1.901 | 1.00 | 13.98 | C |
| ATOM | 1240 | O | ALA | C | 154 | 0.172 | 4.734 | −1.146 | 1.00 | 12.97 | C |
| ATOM | 1241 | N | PHE | C | 155 | 0.896 | 2.870 | −2.042 | 1.00 | 15.24 | C |
| ATOM | 1242 | CA | PHE | C | 155 | 2.096 | 2.767 | −1.330 | 1.00 | 16.11 | C |
| ATOM | 1243 | CB | PHE | C | 155 | 1.993 | 1.624 | −0.308 | 1.00 | 16.37 | C |
| ATOM | 1244 | CG | PHE | C | 155 | 0.732 | 1.641 | 0.473 | 1.00 | 15.83 | C |
| ATOM | 1245 | CD1 | PHE | C | 155 | −0.372 | 1.068 | −0.020 | 1.00 | 16.52 | C |
| ATOM | 1246 | CD2 | PHE | C | 155 | 0.700 | 2.187 | 1.762 | 1.00 | 14.95 | C |
| ATOM | 1247 | CE1 | PHE | C | 155 | −1.498 | 1.008 | 0.768 | 1.00 | 17.05 | C |
| ATOM | 1248 | CE2 | PHE | C | 155 | −0.405 | 2.162 | 2.585 | 1.00 | 14.86 | C |
| ATOM | 1249 | CZ | PHE | C | 155 | −1.487 | 1.587 | 2.126 | 1.00 | 17.75 | C |
| ATOM | 1250 | C | PHE | C | 155 | 3.332 | 2.595 | −2.190 | 1.00 | 14.69 | C |
| ATOM | 1251 | O | PHE | C | 155 | 3.474 | 1.658 | −3.008 | 1.00 | 15.30 | C |
| ATOM | 1252 | N | GLN | C | 156 | 4.237 | 3.540 | −1.979 | 1.00 | 14.37 | C |
| ATOM | 1253 | CA | GLN | C | 156 | 5.478 | 3.558 | −2.698 | 1.00 | 13.82 | C |
| ATOM | 1254 | CB | GLN | C | 156 | 5.686 | 4.928 | −3.276 | 1.00 | 14.37 | C |
| ATOM | 1255 | CG | GLN | C | 156 | 6.803 | 4.896 | −4.183 | 1.00 | 16.30 | C |
| ATOM | 1256 | CD | GLN | C | 156 | 7.477 | 6.270 | −4.211 | 1.00 | 19.36 | C |
| ATOM | 1257 | OE1 | GLN | C | 156 | 7.073 | 7.159 | −3.449 | 1.00 | 22.97 | C |
| ATOM | 1258 | NE2 | GLN | C | 156 | 8.469 | 6.480 | −5.085 | 1.00 | 18.07 | C |
| ATOM | 1259 | C | GLN | C | 156 | 6.662 | 3.066 | −1.849 | 1.00 | 12.04 | C |
| ATOM | 1260 | O | GLN | C | 156 | 6.924 | 3.583 | −0.813 | 1.00 | 9.77 | C |
| ATOM | 1261 | N | ASP | C | 157 | 7.284 | 1.960 | −2.285 | 1.00 | 12.99 | C |
| ATOM | 1262 | CA | ASP | C | 157 | 8.439 | 1.437 | −1.628 | 1.00 | 13.12 | C |
| ATOM | 1263 | CB | ASP | C | 157 | 8.463 | 0.004 | −1.606 | 1.00 | 13.69 | C |
| ATOM | 1264 | CG | ASP | C | 157 | 9.772 | −0.507 | −1.371 | 1.00 | 14.74 | C |
| ATOM | 1265 | OD1 | ASP | C | 157 | 10.255 | −1.142 | −2.309 | 1.00 | 19.26 | C |
| ATOM | 1266 | OD2 | ASP | C | 157 | 10.373 | −0.346 | −0.321 | 1.00 | 12.98 | C |
| ATOM | 1267 | C | ASP | C | 157 | 9.593 | 1.996 | −2.398 | 1.00 | 15.54 | C |
| ATOM | 1268 | O | ASP | C | 157 | 9.641 | 2.043 | −3.617 | 1.00 | 15.20 | C |
| ATOM | 1269 | N | ILE | C | 158 | 10.523 | 2.510 | −1.619 | 1.00 | 17.08 | C |
| ATOM | 1270 | CA | ILE | C | 158 | 11.632 | 3.195 | −2.112 | 1.00 | 16.04 | C |
| ATOM | 1271 | CB | ILE | C | 158 | 11.574 | 4.599 | −1.477 | 1.00 | 18.55 | C |
| ATOM | 1272 | CG2 | ILE | C | 158 | 12.598 | 4.831 | −0.309 | 1.00 | 18.76 | C |
| ATOM | 1273 | CG1 | ILE | C | 158 | 11.654 | 5.595 | −2.595 | 1.00 | 19.12 | C |
| ATOM | 1274 | CD1 | ILE | C | 158 | 10.376 | 5.838 | −3.161 | 1.00 | 19.37 | C |
| ATOM | 1275 | C | ILE | C | 158 | 12.868 | 2.424 | −1.873 | 1.00 | 16.72 | C |
| ATOM | 1276 | O | ILE | C | 158 | 13.964 | 2.894 | −2.158 | 1.00 | 16.75 | C |
| ATOM | 1277 | N | GLY | C | 159 | 12.734 | 1.163 | −1.500 | 1.00 | 15.75 | C |
| ATOM | 1278 | CA | GLY | C | 159 | 13.979 | 0.451 | −1.213 | 1.00 | 14.22 | C |
| ATOM | 1279 | C | GLY | C | 159 | 14.170 | −0.005 | 0.257 | 1.00 | 13.55 | C |
| ATOM | 1280 | O | GLY | C | 159 | 15.274 | −0.298 | 0.691 | 1.00 | 13.37 | C |
| ATOM | 1281 | N | ALA | C | 160 | 13.076 | −0.063 | 0.995 | 1.00 | 12.98 | C |
| ATOM | 1282 | CA | ALA | C | 160 | 13.070 | −0.478 | 2.372 | 1.00 | 14.02 | C |
| ATOM | 1283 | CB | ALA | C | 160 | 12.130 | 0.324 | 3.137 | 1.00 | 11.02 | C |
| ATOM | 1284 | C | ALA | C | 160 | 12.610 | −1.902 | 2.386 | 1.00 | 15.55 | C |
| ATOM | 1285 | O | ALA | C | 160 | 12.159 | −2.414 | 1.376 | 1.00 | 17.74 | C |
| ATOM | 1286 | N | CYS | C | 161 | 12.764 | −2.572 | 3.519 | 1.00 | 15.31 | C |
| ATOM | 1287 | CA | CYS | C | 161 | 12.301 | −3.928 | 3.713 | 1.00 | 13.33 | C |
| ATOM | 1288 | C | CYS | C | 161 | 11.128 | −3.757 | 4.711 | 1.00 | 14.35 | C |
| ATOM | 1289 | O | CYS | C | 161 | 11.271 | −3.767 | 5.942 | 1.00 | 12.41 | C |
| ATOM | 1290 | CB | CYS | C | 161 | 13.370 | −4.707 | 4.360 | 1.00 | 13.85 | C |
| ATOM | 1291 | SG | CYS | C | 161 | 13.204 | −6.501 | 4.441 | 1.00 | 15.17 | C |
| ATOM | 1292 | N | VAL | C | 162 | 9.953 | −3.588 | 4.126 | 1.00 | 14.84 | C |
| ATOM | 1293 | CA | VAL | C | 162 | 8.730 | −3.386 | 4.852 | 1.00 | 15.10 | C |
| ATOM | 1294 | CB | VAL | C | 162 | 7.900 | −2.192 | 4.301 | 1.00 | 16.83 | C |
| ATOM | 1295 | CG1 | VAL | C | 162 | 6.952 | −1.666 | 5.347 | 1.00 | 17.71 | C |
| ATOM | 1296 | CG2 | VAL | C | 162 | 8.767 | −1.142 | 3.768 | 1.00 | 16.83 | C |
| ATOM | 1297 | C | VAL | C | 162 | 7.752 | −4.542 | 4.743 | 1.00 | 15.20 | C |
| ATOM | 1298 | O | VAL | C | 162 | 7.612 | −5.183 | 3.701 | 1.00 | 14.43 | C |
| ATOM | 1299 | N | ALA | C | 163 | 6.998 | −4.715 | 5.823 | 1.00 | 15.44 | C |
| ATOM | 1300 | CA | ALA | C | 163 | 5.911 | −5.708 | 5.815 | 1.00 | 16.00 | C |
| ATOM | 1301 | CB | ALA | C | 163 | 6.240 | −6.865 | 6.768 | 1.00 | 15.45 | C |
| ATOM | 1302 | C | ALA | C | 163 | 4.602 | −4.989 | 6.189 | 1.00 | 15.74 | C |
| ATOM | 1303 | O | ALA | C | 163 | 4.355 | −4.657 | 7.347 | 1.00 | 17.21 | C |
| ATOM | 1304 | N | LEU | C | 164 | 3.771 | −4.702 | 5.224 | 1.00 | 14.86 | C |
| ATOM | 1305 | CA | LEU | C | 164 | 2.589 | −4.029 | 5.601 | 1.00 | 14.15 | C |
| ATOM | 1306 | CB | LEU | C | 164 | 2.167 | −3.143 | 4.446 | 1.00 | 14.73 | C |
| ATOM | 1307 | CG | LEU | C | 164 | 1.013 | −2.152 | 4.751 | 1.00 | 16.19 | C |
| ATOM | 1308 | CD1 | LEU | C | 164 | 1.303 | −1.263 | 5.898 | 1.00 | 15.73 | C |
| ATOM | 1309 | CD2 | LEU | C | 164 | 0.687 | −1.305 | 3.493 | 1.00 | 16.58 | C |
| ATOM | 1310 | C | LEU | C | 164 | 1.530 | −5.024 | 6.017 | 1.00 | 14.06 | C |

TABLE 1-continued

| ATOM | 1311 | O | LEU | C | 164 | 0.945 | −5.713 | 5.233 | 1.00 | 13.78 | C |
|---|---|---|---|---|---|---|---|---|---|---|---|
| ATOM | 1312 | N | LEU | C | 165 | 1.249 | −5.141 | 7.287 | 1.00 | 14.72 | C |
| ATOM | 1313 | CA | LEU | C | 165 | 0.241 | −6.098 | 7.685 | 1.00 | 14.71 | C |
| ATOM | 1314 | CB | LEU | C | 165 | 0.676 | −6.678 | 8.983 | 1.00 | 17.36 | C |
| ATOM | 1315 | CG | LEU | C | 165 | 2.191 | −6.783 | 9.134 | 1.00 | 19.08 | C |
| ATOM | 1316 | CD1 | LEU | C | 165 | 2.505 | −7.270 | 10.574 | 1.00 | 20.83 | C |
| ATOM | 1317 | CD2 | LEU | C | 165 | 2.650 | −7.759 | 8.125 | 1.00 | 18.59 | C |
| ATOM | 1318 | C | LEU | C | 165 | −1.185 | −5.598 | 7.868 | 1.00 | 13.83 | C |
| ATOM | 1319 | O | LEU | C | 165 | −2.099 | −6.348 | 8.204 | 1.00 | 13.10 | C |
| ATOM | 1320 | N | SER | C | 166 | −1.413 | −4.324 | 7.714 | 1.00 | 13.38 | C |
| ATOM | 1321 | CA | SER | C | 166 | −2.770 | −3.861 | 7.984 | 1.00 | 14.28 | C |
| ATOM | 1322 | CB | SER | C | 166 | −3.070 | −3.821 | 9.530 | 1.00 | 14.83 | C |
| ATOM | 1323 | OG | SER | C | 166 | −4.363 | −3.423 | 9.794 | 1.00 | 15.81 | C |
| ATOM | 1324 | C | SER | C | 166 | −3.000 | −2.514 | 7.391 | 1.00 | 12.48 | C |
| ATOM | 1325 | O | SER | C | 166 | −2.093 | −1.658 | 7.421 | 1.00 | 11.92 | C |
| ATOM | 1326 | N | VAL | C | 167 | −4.177 | −2.350 | 6.802 | 1.00 | 11.32 | C |
| ATOM | 1327 | CA | VAL | C | 167 | −4.498 | −1.088 | 6.223 | 1.00 | 11.82 | C |
| ATOM | 1328 | CB | VAL | C | 167 | −4.408 | −1.133 | 4.735 | 1.00 | 12.98 | C |
| ATOM | 1329 | CG1 | VAL | C | 167 | −4.779 | 0.255 | 4.082 | 1.00 | 14.70 | C |
| ATOM | 1330 | CG2 | VAL | C | 167 | −3.137 | −1.590 | 4.360 | 1.00 | 13.51 | C |
| ATOM | 1331 | C | VAL | C | 167 | −5.916 | −0.831 | 6.557 | 1.00 | 12.08 | C |
| ATOM | 1332 | O | VAL | C | 167 | −6.744 | −1.523 | 5.981 | 1.00 | 8.67 | C |
| ATOM | 1333 | N | ARG | C | 168 | −6.212 | 0.099 | 7.520 | 1.00 | 13.23 | C |
| ATOM | 1334 | CA | ARG | C | 168 | −7.628 | 0.397 | 7.800 | 1.00 | 15.58 | C |
| ATOM | 1335 | CB | ARG | C | 168 | −8.096 | 0.278 | 9.225 | 1.00 | 17.24 | C |
| ATOM | 1336 | CG | ARG | C | 168 | −8.951 | −0.940 | 9.407 | 1.00 | 18.34 | C |
| ATOM | 1337 | CD | ARG | C | 168 | −9.865 | −0.944 | 10.642 | 1.00 | 19.27 | C |
| ATOM | 1338 | NE | ARG | C | 168 | −9.636 | 0.244 | 11.473 | 1.00 | 20.09 | C |
| ATOM | 1339 | CZ | ARG | C | 168 | −10.609 | 0.799 | 12.205 | 1.00 | 20.67 | C |
| ATOM | 1340 | NH1 | ARG | C | 168 | −11.875 | 0.266 | 12.193 | 1.00 | 17.38 | C |
| ATOM | 1341 | NH2 | ARG | C | 168 | −10.287 | 1.842 | 12.963 | 1.00 | 20.84 | C |
| ATOM | 1342 | C | ARG | C | 168 | −7.879 | 1.754 | 7.351 | 1.00 | 16.98 | C |
| ATOM | 1343 | O | ARG | C | 168 | −6.957 | 2.579 | 7.503 | 1.00 | 17.76 | C |
| ATOM | 1344 | N | VAL | C | 169 | −9.088 | 1.951 | 6.730 | 1.00 | 16.72 | C |
| ATOM | 1345 | CA | VAL | C | 169 | −9.591 | 3.252 | 6.205 | 1.00 | 15.30 | C |
| ATOM | 1346 | CB | VAL | C | 169 | −9.706 | 3.326 | 4.683 | 1.00 | 14.52 | C |
| ATOM | 1347 | CG1 | VAL | C | 169 | −10.179 | 4.738 | 4.252 | 1.00 | 13.37 | C |
| ATOM | 1348 | CG2 | VAL | C | 169 | −8.448 | 3.022 | 4.085 | 1.00 | 14.06 | C |
| ATOM | 1349 | C | VAL | C | 169 | −10.995 | 3.479 | 6.728 | 1.00 | 15.01 | C |
| ATOM | 1350 | O | VAL | C | 169 | −11.877 | 2.693 | 6.470 | 1.00 | 13.61 | C |
| ATOM | 1351 | N | TYR | C | 170 | −11.194 | 4.603 | 7.425 | 1.00 | 15.47 | C |
| ATOM | 1352 | CA | TYR | C | 170 | −12.479 | 4.879 | 8.024 | 1.00 | 15.46 | C |
| ATOM | 1353 | CB | TYR | C | 170 | −12.586 | 4.167 | 9.375 | 1.00 | 16.79 | C |
| ATOM | 1354 | CG | TYR | C | 170 | −11.674 | 4.763 | 10.386 | 1.00 | 18.16 | C |
| ATOM | 1355 | CD1 | TYR | C | 170 | −12.113 | 5.844 | 11.175 | 1.00 | 18.90 | C |
| ATOM | 1356 | CE1 | TYR | C | 170 | −11.268 | 6.473 | 12.116 | 1.00 | 18.78 | C |
| ATOM | 1357 | CD2 | TYR | C | 170 | −10.353 | 4.298 | 10.536 | 1.00 | 18.22 | C |
| ATOM | 1358 | CE2 | TYR | C | 170 | −9.474 | 4.917 | 11.448 | 1.00 | 17.98 | C |
| ATOM | 1359 | CZ | TYR | C | 170 | −9.944 | 6.008 | 12.254 | 1.00 | 18.15 | C |
| ATOM | 1360 | OH | TYR | C | 170 | −9.151 | 6.594 | 13.188 | 1.00 | 14.60 | C |
| ATOM | 1361 | C | TYR | C | 170 | −12.720 | 6.328 | 8.209 | 1.00 | 14.88 | C |
| ATOM | 1362 | O | TYR | C | 170 | −11.794 | 7.107 | 8.180 | 1.00 | 14.31 | C |
| ATOM | 1363 | N | TYR | C | 171 | −13.992 | 6.671 | 8.346 | 1.00 | 14.84 | C |
| ATOM | 1364 | CA | TYR | C | 171 | −14.302 | 8.010 | 8.612 | 1.00 | 15.86 | C |
| ATOM | 1365 | CB | TYR | C | 171 | −14.795 | 8.701 | 7.341 | 1.00 | 16.35 | C |
| ATOM | 1366 | CG | TYR | C | 171 | −16.154 | 8.362 | 6.931 | 1.00 | 17.45 | C |
| ATOM | 1367 | CD1 | TYR | C | 171 | −17.192 | 9.144 | 7.252 | 1.00 | 17.20 | C |
| ATOM | 1368 | CE1 | TYR | C | 171 | −18.475 | 8.797 | 6.918 | 1.00 | 19.15 | C |
| ATOM | 1369 | CD2 | TYR | C | 171 | −16.387 | 7.219 | 6.260 | 1.00 | 18.50 | C |
| ATOM | 1370 | CE2 | TYR | C | 171 | −17.643 | 6.852 | 5.920 | 1.00 | 20.16 | C |
| ATOM | 1371 | CZ | TYR | C | 171 | −18.721 | 7.637 | 6.244 | 1.00 | 20.05 | C |
| ATOM | 1372 | OH | TYR | C | 171 | −20.038 | 7.319 | 5.875 | 1.00 | 20.35 | C |
| ATOM | 1373 | C | TYR | C | 171 | −15.274 | 8.142 | 9.845 | 1.00 | 16.95 | C |
| ATOM | 1374 | O | TYR | C | 171 | −15.907 | 7.151 | 10.271 | 1.00 | 16.33 | C |
| ATOM | 1375 | N | LYS | C | 172 | −15.321 | 9.332 | 10.446 | 1.00 | 17.75 | C |
| ATOM | 1376 | CA | LYS | C | 172 | −16.183 | 9.489 | 11.571 | 1.00 | 18.48 | C |
| ATOM | 1377 | CB | LYS | C | 172 | −15.823 | 10.704 | 12.373 | 1.00 | 18.50 | C |
| ATOM | 1378 | CG | LYS | C | 172 | −14.937 | 10.407 | 13.521 | 1.00 | 18.95 | C |
| ATOM | 1379 | CD | LYS | C | 172 | −13.741 | 9.624 | 13.129 | 1.00 | 20.66 | C |
| ATOM | 1380 | CE | LYS | C | 172 | −12.885 | 9.228 | 14.397 | 1.00 | 23.41 | C |
| ATOM | 1381 | NZ | LYS | C | 172 | −11.660 | 10.288 | 14.683 | 1.00 | 27.40 | C |
| ATOM | 1382 | C | LYS | C | 172 | −17.669 | 9.502 | 11.266 | 1.00 | 20.58 | C |
| ATOM | 1383 | O | LYS | C | 172 | −18.188 | 10.327 | 10.490 | 1.00 | 20.57 | C |
| ATOM | 1384 | N | LYS | C | 173 | −18.343 | 8.562 | 11.975 | 1.00 | 22.28 | C |
| ATOM | 1385 | CA | LYS | C | 173 | −19.779 | 8.239 | 11.944 | 1.00 | 21.82 | C |
| ATOM | 1386 | CB | LYS | C | 173 | −20.190 | 7.802 | 13.285 | 1.00 | 23.19 | C |
| ATOM | 1387 | CG | LYS | C | 173 | −19.122 | 6.895 | 13.888 | 1.00 | 22.78 | C |
| ATOM | 1388 | CD | LYS | C | 173 | −18.318 | 7.810 | 14.944 | 1.00 | 24.22 | C |
| ATOM | 1389 | CE | LYS | C | 173 | −16.888 | 7.193 | 15.257 | 1.00 | 23.12 | C |
| ATOM | 1390 | NZ | LYS | C | 173 | −16.244 | 7.299 | 13.885 | 1.00 | 23.30 | C |

TABLE 1-continued

| | | | | | | | | | | |
|---|---|---|---|---|---|---|---|---|---|---|
| ATOM | 1391 | C | LYS | C | 173 | −20.622 | 9.374 | 11.531 | 1.00 | 22.79 | C |
| ATOM | 1392 | O | LYS | C | 173 | −20.873 | 9.534 | 10.316 | 1.00 | 22.95 | C |
| ATOM | 1393 | N | CYS | C | 174 | −21.092 | 10.134 | 12.506 | 1.00 | 22.56 | C |
| ATOM | 1394 | CA | CYS | C | 174 | −21.914 | 11.370 | 12.247 | 1.00 | 22.70 | C |
| ATOM | 1395 | CB | CYS | C | 174 | −21.552 | 12.124 | 10.948 | 1.00 | 20.84 | C |
| ATOM | 1396 | SG | CYS | C | 174 | −23.020 | 13.047 | 9.898 | 1.00 | 21.57 | C |
| ATOM | 1397 | C | CYS | C | 174 | −23.390 | 11.086 | 12.239 | 1.00 | 23.42 | C |
| ATOM | 1398 | O | CYS | C | 174 | −23.982 | 10.802 | 13.397 | 1.00 | 25.84 | C |
| ATOM | 1399 | OXT | CYS | C | 174 | −23.889 | 11.074 | 11.082 | 1.00 | 23.67 | C |
| ATOM | 1400 | CB | GLU | A | 1 | −30.144 | 22.219 | 47.292 | 1.00 | 20.61 | A |
| ATOM | 1401 | CG | GLU | A | 1 | −29.420 | 22.176 | 45.924 | 1.00 | 18.39 | A |
| ATOM | 1402 | CD | GLU | A | 1 | −27.869 | 21.751 | 46.036 | 1.00 | 19.19 | A |
| ATOM | 1403 | OE1 | GLU | A | 1 | −27.491 | 20.565 | 46.356 | 1.00 | 16.42 | A |
| ATOM | 1404 | OE2 | GLU | A | 1 | −27.012 | 22.625 | 45.773 | 1.00 | 17.29 | A |
| ATOM | 1405 | C | GLU | A | 1 | −32.206 | 23.708 | 47.128 | 1.00 | 20.09 | A |
| ATOM | 1406 | O | GLU | A | 1 | −32.651 | 24.092 | 46.009 | 1.00 | 19.59 | A |
| ATOM | 1407 | N | GLU | A | 1 | −32.193 | 21.395 | 46.144 | 1.00 | 21.48 | A |
| ATOM | 1408 | CA | GLU | A | 1 | −31.708 | 22.273 | 47.272 | 1.00 | 20.31 | A |
| ATOM | 1409 | N | VAL | A | 2 | −32.131 | 24.493 | 48.221 | 1.00 | 19.76 | A |
| ATOM | 1410 | CA | VAL | A | 2 | −32.599 | 25.889 | 48.166 | 1.00 | 18.22 | A |
| ATOM | 1411 | CB | VAL | A | 2 | −33.555 | 26.198 | 49.402 | 1.00 | 20.00 | A |
| ATOM | 1412 | CG1 | VAL | A | 2 | −33.860 | 27.734 | 49.566 | 1.00 | 19.89 | A |
| ATOM | 1413 | CG2 | VAL | A | 2 | −34.874 | 25.500 | 49.229 | 1.00 | 19.78 | A |
| ATOM | 1414 | C | VAL | A | 2 | −31.372 | 26.753 | 48.169 | 1.00 | 16.63 | A |
| ATOM | 1415 | O | VAL | A | 2 | −30.481 | 26.600 | 48.973 | 1.00 | 15.44 | A |
| ATOM | 1416 | N | VAL | A | 3 | −31.336 | 27.680 | 47.254 | 1.00 | 16.56 | A |
| ATOM | 1417 | CA | VAL | A | 3 | −30.182 | 28.551 | 47.119 | 1.00 | 16.56 | A |
| ATOM | 1418 | CB | VAL | A | 3 | −29.752 | 28.620 | 45.607 | 1.00 | 15.55 | A |
| ATOM | 1419 | CG1 | VAL | A | 3 | −28.557 | 29.469 | 45.397 | 1.00 | 13.95 | A |
| ATOM | 1420 | CG2 | VAL | A | 3 | −29.534 | 27.184 | 45.105 | 1.00 | 13.72 | A |
| ATOM | 1421 | C | VAL | A | 3 | −30.328 | 29.914 | 47.627 | 1.00 | 15.87 | A |
| ATOM | 1422 | O | VAL | A | 3 | −31.111 | 30.679 | 47.164 | 1.00 | 16.59 | A |
| ATOM | 1423 | N | LEU | A | 4 | −29.469 | 30.255 | 48.559 | 1.00 | 17.69 | A |
| ATOM | 1424 | CA | LEU | A | 4 | −29.444 | 31.625 | 49.161 | 1.00 | 18.80 | A |
| ATOM | 1425 | CB | LEU | A | 4 | −29.254 | 31.412 | 50.675 | 1.00 | 17.97 | A |
| ATOM | 1426 | CG | LEU | A | 4 | −30.023 | 30.285 | 51.345 | 1.00 | 17.71 | A |
| ATOM | 1427 | CD1 | LEU | A | 4 | −29.841 | 30.209 | 52.865 | 1.00 | 15.89 | A |
| ATOM | 1428 | CD2 | LEU | A | 4 | −31.496 | 30.638 | 51.029 | 1.00 | 18.91 | A |
| ATOM | 1429 | C | LEU | A | 4 | −28.154 | 32.144 | 48.532 | 1.00 | 18.69 | A |
| ATOM | 1430 | O | LEU | A | 4 | −27.149 | 31.528 | 48.663 | 1.00 | 21.16 | A |
| ATOM | 1431 | N | LEU | A | 5 | −28.042 | 33.218 | 47.858 | 1.00 | 18.50 | A |
| ATOM | 1432 | CA | LEU | A | 5 | −26.641 | 33.388 | 47.352 | 1.00 | 17.67 | A |
| ATOM | 1433 | CB | LEU | A | 5 | −25.640 | 33.680 | 48.491 | 1.00 | 16.77 | A |
| ATOM | 1434 | CG | LEU | A | 5 | −24.339 | 34.238 | 47.916 | 1.00 | 16.76 | A |
| ATOM | 1435 | CD1 | LEU | A | 5 | −24.725 | 35.287 | 46.951 | 1.00 | 17.28 | A |
| ATOM | 1436 | CD2 | LEU | A | 5 | −23.563 | 34.925 | 48.972 | 1.00 | 17.78 | A |
| ATOM | 1437 | C | LEU | A | 5 | −25.946 | 32.395 | 46.403 | 1.00 | 16.46 | A |
| ATOM | 1438 | O | LEU | A | 5 | −25.640 | 31.213 | 46.694 | 1.00 | 16.11 | A |
| ATOM | 1439 | N | ASP | A | 6 | −25.637 | 32.974 | 45.259 | 1.00 | 17.45 | A |
| ATOM | 1440 | CA | ASP | A | 6 | −24.994 | 32.322 | 44.135 | 1.00 | 17.21 | A |
| ATOM | 1441 | CB | ASP | A | 6 | −26.048 | 31.652 | 43.297 | 1.00 | 17.99 | A |
| ATOM | 1442 | CG | ASP | A | 6 | −25.436 | 30.781 | 42.271 | 1.00 | 18.73 | A |
| ATOM | 1443 | OD1 | ASP | A | 6 | −26.150 | 30.375 | 41.329 | 1.00 | 19.01 | A |
| ATOM | 1444 | OD2 | ASP | A | 6 | −24.220 | 30.478 | 42.415 | 1.00 | 19.10 | A |
| ATOM | 1445 | C | ASP | A | 6 | −24.271 | 33.349 | 43.269 | 1.00 | 16.89 | A |
| ATOM | 1446 | O | ASP | A | 6 | −24.848 | 33.954 | 42.318 | 1.00 | 17.73 | A |
| ATOM | 1447 | N | PHE | A | 7 | −22.998 | 33.521 | 43.582 | 1.00 | 15.87 | A |
| ATOM | 1448 | CA | PHE | A | 7 | −22.177 | 34.483 | 42.899 | 1.00 | 14.20 | A |
| ATOM | 1449 | CB | PHE | A | 7 | −20.747 | 34.339 | 43.461 | 1.00 | 14.14 | A |
| ATOM | 1450 | CG | PHE | A | 7 | −19.773 | 35.207 | 42.762 | 1.00 | 14.00 | A |
| ATOM | 1451 | CD1 | PHE | A | 7 | −19.815 | 36.546 | 42.946 | 1.00 | 12.77 | A |
| ATOM | 1452 | CD2 | PHE | A | 7 | −18.867 | 34.650 | 41.843 | 1.00 | 13.64 | A |
| ATOM | 1453 | CE1 | PHE | A | 7 | −18.979 | 37.324 | 42.246 | 1.00 | 16.65 | A |
| ATOM | 1454 | CE2 | PHE | A | 7 | −18.020 | 35.449 | 41.119 | 1.00 | 15.75 | A |
| ATOM | 1455 | CZ | PHE | A | 7 | −18.058 | 36.792 | 41.307 | 1.00 | 16.19 | A |
| ATOM | 1456 | C | PHE | A | 7 | −22.175 | 34.424 | 41.352 | 1.00 | 12.61 | A |
| ATOM | 1457 | O | PHE | A | 7 | −22.361 | 35.381 | 40.674 | 1.00 | 10.68 | A |
| ATOM | 1458 | N | ALA | A | 8 | −21.845 | 33.261 | 40.841 | 1.00 | 13.83 | A |
| ATOM | 1459 | CA | ALA | A | 8 | −21.813 | 33.043 | 39.385 | 1.00 | 16.56 | A |
| ATOM | 1460 | CB | ALA | A | 8 | −21.367 | 31.569 | 39.049 | 1.00 | 14.94 | A |
| ATOM | 1461 | C | ALA | A | 8 | −23.102 | 33.403 | 38.581 | 1.00 | 17.05 | A |
| ATOM | 1462 | O | ALA | A | 8 | −23.007 | 33.517 | 37.414 | 1.00 | 18.55 | A |
| ATOM | 1463 | N | ALA | A | 9 | −24.280 | 33.623 | 39.186 | 1.00 | 18.47 | A |
| ATOM | 1464 | CA | ALA | A | 9 | −25.461 | 34.041 | 38.397 | 1.00 | 19.00 | A |
| ATOM | 1465 | CB | ALA | A | 9 | −26.632 | 33.335 | 38.873 | 1.00 | 17.92 | A |
| ATOM | 1466 | C | ALA | A | 9 | −25.770 | 35.522 | 38.426 | 1.00 | 19.68 | A |
| ATOM | 1467 | O | ALA | A | 9 | −26.648 | 36.004 | 37.628 | 1.00 | 20.64 | A |
| ATOM | 1468 | N | ALA | A | 10 | −25.150 | 36.283 | 39.348 | 1.00 | 19.73 | A |
| ATOM | 1469 | CA | ALA | A | 10 | −25.415 | 37.756 | 39.476 | 1.00 | 20.11 | A |
| ATOM | 1470 | CB | ALA | A | 10 | −25.066 | 38.145 | 40.845 | 1.00 | 17.25 | A |

TABLE 1-continued

| | | | | | | | | | |
|---|---|---|---|---|---|---|---|---|---|
| ATOM | 1471 | C | ALA | A | 10 | −24.755 | 38.691 | 38.395 | 1.00 21.21 A |
| ATOM | 1472 | O | ALA | A | 10 | −23.530 | 39.184 | 38.455 | 1.00 21.50 A |
| ATOM | 1473 | N | GLY | A | 11 | −25.572 | 38.868 | 37.348 | 1.00 23.06 A |
| ATOM | 1474 | CA | GLY | A | 11 | −25.287 | 39.668 | 36.087 | 1.00 24.47 A |
| ATOM | 1475 | C | GLY | A | 11 | −24.812 | 41.144 | 36.120 | 1.00 24.88 A |
| ATOM | 1476 | O | GLY | A | 11 | −25.264 | 42.074 | 35.393 | 1.00 24.62 A |
| ATOM | 1477 | N | GLY | A | 12 | −23.799 | 41.296 | 36.979 | 1.00 25.59 A |
| ATOM | 1478 | CA | GLY | A | 12 | −23.119 | 42.559 | 37.330 | 1.00 25.75 A |
| ATOM | 1479 | C | GLY | A | 12 | −22.229 | 42.203 | 38.540 | 1.00 24.97 A |
| ATOM | 1480 | O | GLY | A | 12 | −22.008 | 43.073 | 39.415 | 1.00 25.38 A |
| ATOM | 1481 | N | GLU | A | 13 | −21.742 | 40.939 | 38.610 | 1.00 25.09 A |
| ATOM | 1482 | CA | GLU | A | 13 | −20.785 | 40.492 | 39.719 | 1.00 25.73 A |
| ATOM | 1483 | CB | GLU | A | 13 | −19.589 | 41.534 | 39.826 | 1.00 25.00 A |
| ATOM | 1484 | CG | GLU | A | 13 | −19.560 | 42.881 | 38.834 | 1.00 25.50 A |
| ATOM | 1485 | CD | GLU | A | 13 | −18.014 | 43.635 | 38.552 | 1.00 26.00 A |
| ATOM | 1486 | OE1 | GLU | A | 13 | −16.929 | 42.909 | 38.672 | 1.00 25.65 A |
| ATOM | 1487 | OE2 | GLU | A | 13 | −17.946 | 44.908 | 38.178 | 1.00 22.20 A |
| ATOM | 1488 | C | GLU | A | 13 | −21.596 | 40.403 | 41.145 | 1.00 25.32 A |
| ATOM | 1489 | O | GLU | A | 13 | −22.099 | 39.304 | 41.567 | 1.00 26.20 A |
| ATOM | 1490 | N | LEU | A | 14 | −21.815 | 41.575 | 41.773 | 1.00 25.22 A |
| ATOM | 1491 | CA | LEU | A | 14 | −22.562 | 41.641 | 43.023 | 1.00 24.81 A |
| ATOM | 1492 | CB | LEU | A | 14 | −22.315 | 40.353 | 43.781 | 1.00 24.37 A |
| ATOM | 1493 | CG | LEU | A | 14 | −23.588 | 39.413 | 43.704 | 1.00 24.64 A |
| ATOM | 1494 | CD1 | LEU | A | 14 | −23.058 | 37.951 | 43.554 | 1.00 21.79 A |
| ATOM | 1495 | CD2 | LEU | A | 14 | −24.607 | 39.555 | 45.108 | 1.00 22.80 A |
| ATOM | 1496 | C | LEU | A | 14 | −22.278 | 42.821 | 43.976 | 1.00 23.76 A |
| ATOM | 1497 | O | LEU | A | 14 | −21.183 | 43.607 | 43.888 | 1.00 24.51 A |
| ATOM | 1498 | N | GLY | A | 15 | −23.202 | 42.903 | 44.930 | 1.00 21.61 A |
| ATOM | 1499 | CA | GLY | A | 15 | −23.082 | 43.933 | 45.937 | 1.00 20.41 A |
| ATOM | 1500 | C | GLY | A | 15 | −22.153 | 43.371 | 47.043 | 1.00 20.40 A |
| ATOM | 1501 | O | GLY | A | 15 | −22.760 | 42.961 | 48.035 | 1.00 21.06 A |
| ATOM | 1502 | N | TRP | A | 16 | −20.779 | 43.315 | 46.923 | 1.00 19.56 A |
| ATOM | 1503 | CA | TRP | A | 16 | −19.930 | 42.783 | 48.039 | 1.00 18.45 A |
| ATOM | 1504 | CB | TRP | A | 16 | −19.130 | 41.488 | 47.648 | 1.00 17.83 A |
| ATOM | 1505 | CG | TRP | A | 16 | −19.978 | 40.253 | 47.290 | 1.00 16.30 A |
| ATOM | 1506 | CD2 | TRP | A | 16 | −19.631 | 38.866 | 47.365 | 1.00 15.31 A |
| ATOM | 1507 | CE2 | TRP | A | 16 | −20.715 | 38.147 | 46.873 | 1.00 14.76 A |
| ATOM | 1508 | CE3 | TRP | A | 16 | −18.522 | 38.162 | 47.787 | 1.00 15.63 A |
| ATOM | 1509 | CD1 | TRP | A | 16 | −21.230 | 40.283 | 46.746 | 1.00 16.24 A |
| ATOM | 1510 | NE1 | TRP | A | 16 | −21.667 | 39.050 | 46.500 | 1.00 14.81 A |
| ATOM | 1511 | CZ2 | TRP | A | 16 | −20.729 | 36.747 | 46.792 | 1.00 14.10 A |
| ATOM | 1512 | CZ3 | TRP | A | 16 | −18.531 | 36.761 | 47.703 | 1.00 16.22 A |
| ATOM | 1513 | CH2 | TRP | A | 16 | −19.645 | 36.067 | 47.204 | 1.00 15.07 A |
| ATOM | 1514 | C | TRP | A | 16 | −18.907 | 43.835 | 48.553 | 1.00 17.68 A |
| ATOM | 1515 | O | TRP | A | 16 | −18.430 | 44.712 | 47.844 | 1.00 17.87 A |
| ATOM | 1516 | N | LEU | A | 17 | −18.552 | 43.663 | 49.791 | 1.00 16.41 A |
| ATOM | 1517 | CA | LEU | A | 17 | −17.614 | 44.533 | 50.513 | 1.00 14.62 A |
| ATOM | 1518 | CB | LEU | A | 17 | −18.088 | 44.664 | 51.981 | 1.00 16.20 A |
| ATOM | 1519 | CG | LEU | A | 17 | −17.258 | 45.615 | 52.729 | 1.00 17.18 A |
| ATOM | 1520 | CD1 | LEU | A | 17 | −17.153 | 46.831 | 51.840 | 1.00 19.80 A |
| ATOM | 1521 | CD2 | LEU | A | 17 | −17.858 | 46.013 | 54.027 | 1.00 18.98 A |
| ATOM | 1522 | C | LEU | A | 17 | −16.169 | 43.956 | 50.431 | 1.00 13.85 A |
| ATOM | 1523 | O | LEU | A | 17 | −15.885 | 42.704 | 50.539 | 1.00 11.11 A |
| ATOM | 1524 | N | THR | A | 18 | −15.275 | 44.924 | 50.271 | 1.00 14.24 A |
| ATOM | 1525 | CA | THR | A | 18 | −13.866 | 44.675 | 50.074 | 1.00 15.95 A |
| ATOM | 1526 | CB | THR | A | 18 | −13.526 | 45.037 | 48.650 | 1.00 16.79 A |
| ATOM | 1527 | OG1 | THR | A | 18 | −13.611 | 43.849 | 47.892 | 1.00 19.07 A |
| ATOM | 1528 | CG2 | THR | A | 18 | −12.264 | 45.588 | 48.512 | 1.00 17.50 A |
| ATOM | 1529 | C | THR | A | 18 | −13.071 | 45.458 | 51.044 | 1.00 17.17 A |
| ATOM | 1530 | O | THR | A | 18 | −12.979 | 46.664 | 50.920 | 1.00 15.32 A |
| ATOM | 1531 | N | HIS | A | 19 | −12.474 | 44.757 | 52.004 | 1.00 19.08 A |
| ATOM | 1532 | CA | HIS | A | 19 | −11.805 | 45.523 | 52.994 | 1.00 19.72 A |
| ATOM | 1533 | CB | HIS | A | 19 | −11.563 | 44.847 | 54.296 | 1.00 21.56 A |
| ATOM | 1534 | CG | HIS | A | 19 | −11.382 | 45.815 | 55.457 | 1.00 22.29 A |
| ATOM | 1535 | CD2 | HIS | A | 19 | −10.804 | 45.623 | 56.693 | 1.00 22.19 A |
| ATOM | 1536 | ND1 | HIS | A | 19 | −11.707 | 47.164 | 55.377 | 1.00 21.42 A |
| ATOM | 1537 | CE1 | HIS | A | 19 | −11.325 | 47.754 | 56.502 | 1.00 21.73 A |
| ATOM | 1538 | NE2 | HIS | A | 19 | −10.776 | 46.848 | 57.321 | 1.00 22.58 A |
| ATOM | 1539 | C | HIS | A | 19 | −10.609 | 46.227 | 52.451 | 1.00 21.35 A |
| ATOM | 1540 | O | HIS | A | 19 | −10.626 | 46.446 | 51.228 | 1.00 22.86 A |
| ATOM | 1541 | N | PRO | A | 20 | −9.478 | 46.362 | 53.204 | 1.00 21.93 A |
| ATOM | 1542 | CD | PRO | A | 20 | −8.929 | 45.000 | 53.370 | 1.00 18.35 A |
| ATOM | 1543 | CA | PRO | A | 20 | −8.451 | 47.209 | 52.594 | 1.00 17.85 A |
| ATOM | 1544 | CB | PRO | A | 20 | −7.416 | 46.245 | 52.216 | 1.00 18.59 A |
| ATOM | 1545 | CG | PRO | A | 20 | −7.437 | 45.347 | 53.310 | 1.00 17.43 A |
| ATOM | 1546 | C | PRO | A | 20 | −9.157 | 48.120 | 51.495 | 1.00 19.39 A |
| ATOM | 1547 | O | PRO | A | 20 | −9.565 | 49.283 | 51.775 | 1.00 21.39 A |
| ATOM | 1548 | N | TYR | A | 21 | −9.393 | 47.642 | 50.289 | 1.00 19.03 A |
| ATOM | 1549 | CA | TYR | A | 21 | −10.068 | 48.381 | 49.176 | 1.00 16.97 A |
| ATOM | 1550 | CB | TYR | A | 21 | −11.165 | 49.409 | 49.519 | 1.00 16.41 A |

TABLE 1-continued

| | | | | | | | | | | |
|---|---|---|---|---|---|---|---|---|---|---|
| ATOM | 1551 | CG  | TYR | A | 21 | −11.722 | 49.888 | 48.213 | 1.00 | 16.93 A |
| ATOM | 1552 | CD1 | TYR | A | 21 | −12.522 | 48.987 | 47.357 | 1.00 | 16.85 A |
| ATOM | 1553 | CE1 | TYR | A | 21 | −12.909 | 49.349 | 46.040 | 1.00 | 14.93 A |
| ATOM | 1554 | CD2 | TYR | A | 21 | −11.346 | 51.131 | 47.675 | 1.00 | 16.75 A |
| ATOM | 1555 | CE2 | TYR | A | 21 | −11.708 | 51.461 | 46.362 | 1.00 | 16.00 A |
| ATOM | 1556 | CZ  | TYR | A | 21 | −12.497 | 50.571 | 45.559 | 1.00 | 15.78 A |
| ATOM | 1557 | OH  | TYR | A | 21 | −12.830 | 50.913 | 44.277 | 1.00 | 14.59 A |
| ATOM | 1558 | C   | TYR | A | 21 | −9.055  | 49.148 | 48.408 | 1.00 | 17.07 A |
| ATOM | 1559 | O   | TYR | A | 21 | −8.600  | 50.185 | 48.833 | 1.00 | 17.64 A |
| ATOM | 1560 | N   | GLY | A | 22 | −8.690  | 48.649 | 47.239 | 1.00 | 17.38 A |
| ATOM | 1561 | CA  | GLY | A | 22 | −7.721  | 49.344 | 46.441 | 1.00 | 17.28 A |
| ATOM | 1562 | C   | GLY | A | 22 | −6.691  | 48.419 | 45.891 | 1.00 | 17.91 A |
| ATOM | 1563 | O   | GLY | A | 22 | −6.416  | 48.489 | 44.691 | 1.00 | 18.44 A |
| ATOM | 1564 | N   | LYS | A | 23 | −6.188  | 47.541 | 46.763 | 1.00 | 18.11 A |
| ATOM | 1565 | CA  | LYS | A | 23 | −5.157  | 46.626 | 46.504 | 1.00 | 16.98 A |
| ATOM | 1566 | CB  | LYS | A | 23 | −3.917  | 47.067 | 47.264 | 1.00 | 17.85 A |
| ATOM | 1567 | CG  | LYS | A | 23 | −3.263  | 48.363 | 46.848 | 1.00 | 19.43 A |
| ATOM | 1568 | CD  | LYS | A | 23 | −3.598  | 49.529 | 47.804 | 1.00 | 21.52 A |
| ATOM | 1569 | CE  | LYS | A | 23 | −3.140  | 50.942 | 47.303 | 1.00 | 22.17 A |
| ATOM | 1570 | NZ  | LYS | A | 23 | −1.619  | 51.220 | 47.303 | 1.00 | 24.09 A |
| ATOM | 1571 | C   | LYS | A | 23 | −5.475  | 45.237 | 46.912 | 1.00 | 17.24 A |
| ATOM | 1572 | O   | LYS | A | 23 | −4.685  | 44.329 | 46.642 | 1.00 | 17.00 A |
| ATOM | 1573 | N   | GLY | A | 24 | −6.558  | 45.018 | 47.663 | 1.00 | 17.20 A |
| ATOM | 1574 | CA  | GLY | A | 24 | −6.872  | 43.601 | 48.035 | 1.00 | 15.98 A |
| ATOM | 1575 | C   | GLY | A | 24 | −7.693  | 42.939 | 46.863 | 1.00 | 15.70 A |
| ATOM | 1576 | O   | GLY | A | 24 | −7.356  | 43.007 | 45.674 | 1.00 | 13.53 A |
| ATOM | 1577 | N   | TRP | A | 25 | −8.783  | 42.319 | 47.289 | 1.00 | 15.85 A |
| ATOM | 1578 | CA  | TRP | A | 25 | −9.720  | 41.663 | 46.493 | 1.00 | 16.43 A |
| ATOM | 1579 | CB  | TRP | A | 25 | −10.776 | 41.080 | 47.418 | 1.00 | 15.35 A |
| ATOM | 1580 | CG  | TRP | A | 25 | −10.373 | 39.929 | 48.289 | 1.00 | 13.73 A |
| ATOM | 1581 | CD2 | TRP | A | 25 | −10.297 | 38.541 | 47.903 | 1.00 | 14.01 A |
| ATOM | 1582 | CE2 | TRP | A | 25 | −10.114 | 37.799 | 49.085 | 1.00 | 13.88 A |
| ATOM | 1583 | CE3 | TRP | A | 25 | −10.379 | 37.877 | 46.691 | 1.00 | 14.00 A |
| ATOM | 1584 | CD1 | TRP | A | 25 | −10.211 | 39.955 | 49.584 | 1.00 | 12.03 A |
| ATOM | 1585 | NE1 | TRP | A | 25 | −10.052 | 38.719 | 50.080 | 1.00 | 11.95 A |
| ATOM | 1586 | CZ2 | TRP | A | 25 | −10.030 | 36.379 | 49.113 | 1.00 | 15.46 A |
| ATOM | 1587 | CZ3 | TRP | A | 25 | −10.292 | 36.517 | 46.676 | 1.00 | 16.23 A |
| ATOM | 1588 | CH2 | TRP | A | 25 | −10.123 | 35.748 | 47.877 | 1.00 | 15.71 A |
| ATOM | 1589 | C   | TRP | A | 25 | −10.370 | 42.613 | 45.446 | 1.00 | 16.61 A |
| ATOM | 1590 | O   | TRP | A | 25 | −10.837 | 43.641 | 45.808 | 1.00 | 16.49 A |
| ATOM | 1591 | N   | ASP | A | 26 | −10.287 | 42.293 | 44.137 | 1.00 | 17.06 A |
| ATOM | 1592 | CA  | ASP | A | 26 | −10.963 | 43.081 | 43.075 | 1.00 | 17.84 A |
| ATOM | 1593 | CB  | ASP | A | 26 | −10.090 | 43.807 | 41.968 | 1.00 | 21.07 A |
| ATOM | 1594 | CG  | ASP | A | 26 | −9.046  | 44.799 | 42.484 | 1.00 | 26.72 A |
| ATOM | 1595 | OD1 | ASP | A | 26 | −9.001  | 45.248 | 43.817 | 1.00 | 29.43 A |
| ATOM | 1596 | OD2 | ASP | A | 26 | −8.228  | 45.212 | 41.472 | 1.00 | 28.76 A |
| ATOM | 1597 | C   | ASP | A | 26 | −11.911 | 42.086 | 42.259 | 1.00 | 15.88 A |
| ATOM | 1598 | O   | ASP | A | 26 | −11.624 | 40.876 | 41.982 | 1.00 | 13.97 A |
| ATOM | 1599 | N   | LEU | A | 27 | −13.028 | 42.692 | 41.866 | 1.00 | 15.66 A |
| ATOM | 1600 | CA  | LEU | A | 27 | −14.071 | 42.091 | 41.046 | 1.00 | 15.83 A |
| ATOM | 1601 | CB  | LEU | A | 27 | −15.302 | 42.866 | 41.255 | 1.00 | 16.02 A |
| ATOM | 1602 | CG  | LEU | A | 27 | −16.475 | 42.089 | 40.716 | 1.00 | 17.41 A |
| ATOM | 1603 | CD1 | LEU | A | 27 | −16.681 | 40.580 | 41.010 | 1.00 | 16.07 A |
| ATOM | 1604 | CD2 | LEU | A | 27 | −17.498 | 43.010 | 41.266 | 1.00 | 17.28 A |
| ATOM | 1605 | C   | LEU | A | 27 | −13.519 | 42.248 | 39.648 | 1.00 | 15.27 A |
| ATOM | 1606 | O   | LEU | A | 27 | −13.029 | 43.278 | 39.298 | 1.00 | 15.19 A |
| ATOM | 1607 | N   | MET | A | 28 | −13.508 | 41.173 | 38.904 | 1.00 | 16.05 A |
| ATOM | 1608 | CA  | MET | A | 28 | −12.929 | 41.211 | 37.584 | 1.00 | 17.04 A |
| ATOM | 1609 | CB  | MET | A | 28 | −11.574 | 40.513 | 37.532 | 1.00 | 18.58 A |
| ATOM | 1610 | CG  | MET | A | 28 | −10.629 | 40.936 | 38.604 | 1.00 | 21.13 A |
| ATOM | 1611 | SD  | MET | A | 28 | −8.865  | 40.466 | 38.338 | 1.00 | 24.21 A |
| ATOM | 1612 | CE  | MET | A | 28 | −8.470  | 41.463 | 36.671 | 1.00 | 18.54 A |
| ATOM | 1613 | C   | MET | A | 28 | −13.889 | 40.476 | 36.710 | 1.00 | 16.61 A |
| ATOM | 1614 | O   | MET | A | 28 | −14.555 | 39.478 | 37.139 | 1.00 | 16.17 A |
| ATOM | 1615 | N   | GLN | A | 29 | −14.005 | 41.021 | 35.502 | 1.00 | 17.51 A |
| ATOM | 1616 | CA  | GLN | A | 29 | −14.852 | 40.427 | 34.484 | 1.00 | 18.12 A |
| ATOM | 1617 | CB  | GLN | A | 29 | −15.790 | 41.437 | 33.962 | 1.00 | 17.95 A |
| ATOM | 1618 | CG  | GLN | A | 29 | −16.883 | 40.666 | 33.235 | 1.00 | 20.50 A |
| ATOM | 1619 | CD  | GLN | A | 29 | −17.684 | 41.533 | 32.242 | 1.00 | 21.15 A |
| ATOM | 1620 | OE1 | GLN | A | 29 | −18.832 | 41.870 | 32.517 | 1.00 | 21.69 A |
| ATOM | 1621 | NE2 | GLN | A | 29 | −17.069 | 41.904 | 31.087 | 1.00 | 20.45 A |
| ATOM | 1622 | C   | GLN | A | 29 | −14.196 | 39.759 | 33.272 | 1.00 | 18.32 A |
| ATOM | 1623 | O   | GLN | A | 29 | −13.741 | 40.443 | 32.397 | 1.00 | 19.74 A |
| ATOM | 1624 | N   | ASN | A | 30 | −14.146 | 38.431 | 33.201 | 1.00 | 17.77 A |
| ATOM | 1625 | CA  | ASN | A | 30 | −13.623 | 37.797 | 32.005 | 1.00 | 15.07 A |
| ATOM | 1626 | CB  | ASN | A | 30 | −12.947 | 36.529 | 32.369 | 1.00 | 12.46 A |
| ATOM | 1627 | CG  | ASN | A | 30 | −11.639 | 36.736 | 32.903 | 1.00 | 9.35 A |
| ATOM | 1628 | OD1 | ASN | A | 30 | −11.214 | 35.902 | 33.593 | 1.00 | 10.48 A |
| ATOM | 1629 | ND2 | ASN | A | 30 | −10.978 | 37.793 | 32.588 | 1.00 | 5.89 A |
| ATOM | 1630 | C   | ASN | A | 30 | −14.783 | 37.487 | 31.060 | 1.00 | 15.49 A |

TABLE 1-continued

| ATOM | 1631 | O | ASN | A | 30 | −16.006 | 37.487 | 31.399 | 1.00 | 15.16 | A |
|---|---|---|---|---|---|---|---|---|---|---|---|
| ATOM | 1632 | N | ILE | A | 31 | −14.419 | 37.163 | 29.854 | 1.00 | 16.09 | A |
| ATOM | 1633 | CA | ILE | A | 31 | −15.465 | 36.835 | 28.946 | 1.00 | 16.13 | A |
| ATOM | 1634 | CB | ILE | A | 31 | −15.857 | 38.058 | 28.227 | 1.00 | 16.78 | A |
| ATOM | 1635 | CG2 | ILE | A | 31 | −14.699 | 38.552 | 27.514 | 1.00 | 19.70 | A |
| ATOM | 1636 | CG1 | ILE | A | 31 | −16.945 | 37.757 | 27.285 | 1.00 | 16.56 | A |
| ATOM | 1637 | CD1 | ILE | A | 31 | −17.497 | 38.969 | 26.625 | 1.00 | 17.54 | A |
| ATOM | 1638 | C | ILE | A | 31 | −15.140 | 35.703 | 28.050 | 1.00 | 14.66 | A |
| ATOM | 1639 | O | ILE | A | 31 | −14.112 | 35.550 | 27.493 | 1.00 | 14.57 | A |
| ATOM | 1640 | N | MET | A | 32 | −16.096 | 34.853 | 27.960 | 1.00 | 15.06 | A |
| ATOM | 1641 | CA | MET | A | 32 | −16.026 | 33.641 | 27.173 | 1.00 | 15.91 | A |
| ATOM | 1642 | CB | MET | A | 32 | −16.014 | 32.389 | 28.107 | 1.00 | 17.12 | A |
| ATOM | 1643 | CG | MET | A | 32 | −14.608 | 31.880 | 28.320 | 1.00 | 22.20 | A |
| ATOM | 1644 | SD | MET | A | 32 | −13.604 | 31.795 | 26.555 | 1.00 | 25.10 | A |
| ATOM | 1645 | CE | MET | A | 32 | −14.699 | 30.970 | 25.767 | 1.00 | 19.44 | A |
| ATOM | 1646 | C | MET | A | 32 | −17.218 | 33.520 | 26.327 | 1.00 | 13.81 | A |
| ATOM | 1647 | O | MET | A | 32 | −18.282 | 33.427 | 26.872 | 1.00 | 13.32 | A |
| ATOM | 1648 | N | ASN | A | 33 | −17.033 | 33.424 | 25.019 | 1.00 | 14.24 | A |
| ATOM | 1649 | CA | ASN | A | 33 | −18.193 | 33.255 | 24.074 | 1.00 | 15.59 | A |
| ATOM | 1650 | CB | ASN | A | 33 | −18.776 | 31.866 | 24.145 | 1.00 | 14.39 | A |
| ATOM | 1651 | CG | ASN | A | 33 | −17.777 | 30.830 | 23.791 | 1.00 | 15.26 | A |
| ATOM | 1652 | OD1 | ASN | A | 33 | −17.188 | 30.799 | 22.648 | 1.00 | 15.93 | A |
| ATOM | 1653 | ND2 | ASN | A | 33 | −17.543 | 29.959 | 24.742 | 1.00 | 13.46 | A |
| ATOM | 1654 | C | ASN | A | 33 | −19.291 | 34.261 | 24.323 | 1.00 | 14.63 | A |
| ATOM | 1655 | O | ASN | A | 33 | −20.483 | 33.922 | 24.375 | 1.00 | 14.99 | A |
| ATOM | 1656 | N | ASP | A | 34 | −18.846 | 35.500 | 24.473 | 1.00 | 14.29 | A |
| ATOM | 1657 | CA | ASP | A | 34 | −19.742 | 36.544 | 24.841 | 1.00 | 14.93 | A |
| ATOM | 1658 | CB | ASP | A | 34 | −20.758 | 36.667 | 23.709 | 1.00 | 13.79 | A |
| ATOM | 1659 | CG | ASP | A | 34 | −20.246 | 37.466 | 22.589 | 1.00 | 13.87 | A |
| ATOM | 1660 | OD1 | ASP | A | 34 | −19.035 | 37.382 | 22.303 | 1.00 | 14.27 | A |
| ATOM | 1661 | OD2 | ASP | A | 34 | −21.079 | 38.165 | 22.002 | 1.00 | 15.44 | A |
| ATOM | 1662 | C | ASP | A | 34 | −20.409 | 36.389 | 26.250 | 1.00 | 14.80 | A |
| ATOM | 1663 | O | ASP | A | 34 | −21.340 | 37.112 | 26.585 | 1.00 | 15.37 | A |
| ATOM | 1664 | N | MET | A | 35 | −20.008 | 35.437 | 27.060 | 1.00 | 15.26 | A |
| ATOM | 1665 | CA | MET | A | 35 | −20.638 | 35.359 | 28.394 | 1.00 | 15.61 | A |
| ATOM | 1666 | CB | MET | A | 35 | −20.894 | 33.916 | 28.864 | 1.00 | 17.23 | A |
| ATOM | 1667 | CG | MET | A | 35 | −21.928 | 33.152 | 28.026 | 1.00 | 18.09 | A |
| ATOM | 1668 | SD | MET | A | 35 | −23.650 | 33.777 | 28.179 | 1.00 | 21.57 | A |
| ATOM | 1669 | CE | MET | A | 35 | −23.615 | 35.064 | 26.686 | 1.00 | 17.94 | A |
| ATOM | 1670 | C | MET | A | 35 | −19.689 | 36.057 | 29.421 | 1.00 | 15.02 | A |
| ATOM | 1671 | O | MET | A | 35 | −18.525 | 35.808 | 29.416 | 1.00 | 14.05 | A |
| ATOM | 1672 | N | PRO | A | 36 | −20.174 | 37.078 | 30.159 | 1.00 | 15.31 | A |
| ATOM | 1673 | CD | PRO | A | 36 | −21.473 | 37.772 | 30.084 | 1.00 | 15.65 | A |
| ATOM | 1674 | CA | PRO | A | 36 | −19.303 | 37.690 | 31.168 | 1.00 | 14.10 | A |
| ATOM | 1675 | CB | PRO | A | 36 | −20.092 | 38.930 | 31.608 | 1.00 | 14.62 | A |
| ATOM | 1676 | CG | PRO | A | 36 | −21.477 | 38.545 | 31.367 | 1.00 | 16.28 | A |
| ATOM | 1677 | C | PRO | A | 36 | −19.137 | 36.635 | 32.331 | 1.00 | 13.66 | A |
| ATOM | 1678 | O | PRO | A | 36 | −20.069 | 36.042 | 32.787 | 1.00 | 13.00 | A |
| ATOM | 1679 | N | ILE | A | 37 | −17.903 | 36.383 | 32.734 | 1.00 | 15.08 | A |
| ATOM | 1680 | CA | ILE | A | 37 | −17.554 | 35.429 | 33.825 | 1.00 | 14.63 | A |
| ATOM | 1681 | CB | ILE | A | 37 | −16.448 | 34.505 | 33.320 | 1.00 | 14.48 | A |
| ATOM | 1682 | CG2 | ILE | A | 37 | −16.130 | 33.423 | 34.286 | 1.00 | 12.08 | A |
| ATOM | 1683 | CG1 | ILE | A | 37 | −16.903 | 33.865 | 31.967 | 1.00 | 14.43 | A |
| ATOM | 1684 | CD1 | ILE | A | 37 | −18.267 | 33.310 | 31.998 | 1.00 | 13.79 | A |
| ATOM | 1685 | C | ILE | A | 37 | −17.013 | 36.299 | 34.925 | 1.00 | 16.18 | A |
| ATOM | 1686 | O | ILE | A | 37 | −15.926 | 36.868 | 34.803 | 1.00 | 16.90 | A |
| ATOM | 1687 | N | TYR | A | 38 | −17.719 | 36.486 | 36.020 | 1.00 | 17.36 | A |
| ATOM | 1688 | CA | TYR | A | 38 | −17.136 | 37.378 | 37.053 | 1.00 | 16.88 | A |
| ATOM | 1689 | CB | TYR | A | 38 | −18.207 | 38.141 | 37.793 | 1.00 | 16.17 | A |
| ATOM | 1690 | CG | TYR | A | 38 | −18.755 | 39.244 | 36.962 | 1.00 | 15.71 | A |
| ATOM | 1691 | CD1 | TYR | A | 38 | −19.825 | 39.040 | 36.162 | 1.00 | 15.39 | A |
| ATOM | 1692 | CE1 | TYR | A | 38 | −20.344 | 40.048 | 35.404 | 1.00 | 15.51 | A |
| ATOM | 1693 | CD2 | TYR | A | 38 | −18.168 | 40.515 | 36.987 | 1.00 | 15.78 | A |
| ATOM | 1694 | CE2 | TYR | A | 38 | −18.653 | 41.547 | 36.261 | 1.00 | 15.96 | A |
| ATOM | 1695 | CZ | TYR | A | 38 | −19.784 | 41.338 | 35.447 | 1.00 | 16.85 | A |
| ATOM | 1696 | OH | TYR | A | 38 | −20.311 | 42.442 | 34.756 | 1.00 | 14.56 | A |
| ATOM | 1697 | C | TYR | A | 38 | −16.359 | 36.580 | 38.057 | 1.00 | 17.33 | A |
| ATOM | 1698 | O | TYR | A | 38 | −16.652 | 35.385 | 38.239 | 1.00 | 17.90 | A |
| ATOM | 1699 | N | MET | A | 39 | −15.328 | 37.195 | 38.647 | 1.00 | 16.65 | A |
| ATOM | 1700 | CA | MET | A | 39 | −14.554 | 36.520 | 39.695 | 1.00 | 15.61 | A |
| ATOM | 1701 | CB | MET | A | 39 | −13.444 | 35.654 | 39.106 | 1.00 | 15.80 | A |
| ATOM | 1702 | CG | MET | A | 39 | −12.125 | 36.399 | 38.902 | 1.00 | 17.77 | A |
| ATOM | 1703 | SD | MET | A | 39 | −11.333 | 35.681 | 37.416 | 1.00 | 18.25 | A |
| ATOM | 1704 | CE | MET | A | 39 | −9.922 | 36.945 | 37.071 | 1.00 | 19.47 | A |
| ATOM | 1705 | C | MET | A | 39 | −13.930 | 37.578 | 40.677 | 1.00 | 14.10 | A |
| ATOM | 1706 | O | MET | A | 39 | −13.762 | 38.720 | 40.330 | 1.00 | 12.66 | A |
| ATOM | 1707 | N | TYR | A | 40 | −13.695 | 37.164 | 41.903 | 1.00 | 13.25 | A |
| ATOM | 1708 | CA | TYR | A | 40 | −13.048 | 38.004 | 42.885 | 1.00 | 14.58 | A |
| ATOM | 1709 | CB | TYR | A | 40 | −13.850 | 37.931 | 44.183 | 1.00 | 15.11 | A |
| ATOM | 1710 | CG | TYR | A | 40 | −14.791 | 39.088 | 44.370 | 1.00 | 16.47 | A |

TABLE 1-continued

| | | | | | | | | | | |
|---|---|---|---|---|---|---|---|---|---|---|
| ATOM | 1711 | CD1 | TYR | A | 40 | −16.107 | 38.943 | 44.230 | 1.00 | 16.78 | A |
| ATOM | 1712 | CE1 | TYR | A | 40 | −16.985 | 40.028 | 44.308 | 1.00 | 16.22 | A |
| ATOM | 1713 | CD2 | TYR | A | 40 | −14.335 | 40.371 | 44.633 | 1.00 | 18.19 | A |
| ATOM | 1714 | CE2 | TYR | A | 40 | −15.213 | 41.444 | 44.740 | 1.00 | 17.31 | A |
| ATOM | 1715 | CZ | TYR | A | 40 | −16.547 | 41.239 | 44.556 | 1.00 | 16.46 | A |
| ATOM | 1716 | OH | TYR | A | 40 | −17.443 | 42.240 | 44.593 | 1.00 | 17.01 | A |
| ATOM | 1717 | C | TYR | A | 40 | −11.521 | 37.546 | 43.091 | 1.00 | 13.43 | A |
| ATOM | 1718 | O | TYR | A | 40 | −11.202 | 36.380 | 43.510 | 1.00 | 13.34 | A |
| ATOM | 1719 | N | SER | A | 41 | −10.566 | 38.388 | 42.740 | 1.00 | 12.81 | A |
| ATOM | 1720 | CA | SER | A | 41 | −9.165 | 37.920 | 42.931 | 1.00 | 14.33 | A |
| ATOM | 1721 | CB | SER | A | 41 | −8.522 | 37.466 | 41.601 | 1.00 | 14.23 | A |
| ATOM | 1722 | OG | SER | A | 41 | −8.781 | 38.351 | 40.593 | 1.00 | 13.54 | A |
| ATOM | 1723 | C | SER | A | 41 | −8.181 | 38.874 | 43.668 | 1.00 | 14.20 | A |
| ATOM | 1724 | O | SER | A | 41 | −8.498 | 40.070 | 43.870 | 1.00 | 13.80 | A |
| ATOM | 1725 | N | VAL | A | 42 | −7.026 | 38.330 | 44.063 | 1.00 | 14.03 | A |
| ATOM | 1726 | CA | VAL | A | 42 | −5.999 | 39.088 | 44.766 | 1.00 | 13.16 | A |
| ATOM | 1727 | CB | VAL | A | 42 | −5.810 | 38.894 | 46.320 | 1.00 | 14.01 | A |
| ATOM | 1728 | CG1 | VAL | A | 42 | −5.471 | 40.231 | 46.977 | 1.00 | 12.12 | A |
| ATOM | 1729 | CG2 | VAL | A | 42 | −6.907 | 38.054 | 46.969 | 1.00 | 10.35 | A |
| ATOM | 1730 | C | VAL | A | 42 | −4.858 | 38.309 | 44.506 | 1.00 | 14.94 | A |
| ATOM | 1731 | O | VAL | A | 42 | −4.897 | 37.109 | 44.575 | 1.00 | 14.80 | A |
| ATOM | 1732 | N | CYS | A | 43 | −3.766 | 38.999 | 44.414 | 1.00 | 16.23 | A |
| ATOM | 1733 | CA | CYS | A | 43 | −2.470 | 38.369 | 44.163 | 1.00 | 16.19 | A |
| ATOM | 1734 | C | CYS | A | 43 | −1.376 | 39.298 | 44.775 | 1.00 | 16.34 | A |
| ATOM | 1735 | O | CYS | A | 43 | −0.508 | 39.783 | 44.100 | 1.00 | 17.73 | A |
| ATOM | 1736 | CB | CYS | A | 43 | −2.304 | 38.170 | 42.625 | 1.00 | 15.20 | A |
| ATOM | 1737 | SG | CYS | A | 43 | −1.074 | 36.921 | 42.058 | 1.00 | 14.30 | A |
| ATOM | 1738 | N | ASN | A | 44 | −1.432 | 39.585 | 46.053 | 1.00 | 16.39 | A |
| ATOM | 1739 | CA | ASN | A | 44 | −0.340 | 40.409 | 46.677 | 1.00 | 15.98 | A |
| ATOM | 1740 | CB | ASN | A | 44 | −0.923 | 41.328 | 47.714 | 1.00 | 14.91 | A |
| ATOM | 1741 | CG | ASN | A | 44 | −1.731 | 42.344 | 47.126 | 1.00 | 14.66 | A |
| ATOM | 1742 | OD1 | ASN | A | 44 | −2.623 | 42.872 | 47.755 | 1.00 | 12.27 | A |
| ATOM | 1743 | ND2 | ASN | A | 44 | −1.408 | 42.694 | 45.863 | 1.00 | 16.87 | A |
| ATOM | 1744 | C | ASN | A | 44 | 0.643 | 39.429 | 47.361 | 1.00 | 14.72 | A |
| ATOM | 1745 | O | ASN | A | 44 | 0.780 | 39.410 | 48.596 | 1.00 | 14.08 | A |
| ATOM | 1746 | N | VAL | A | 45 | 1.244 | 38.581 | 46.531 | 1.00 | 14.47 | A |
| ATOM | 1747 | CA | VAL | A | 45 | 2.163 | 37.528 | 46.960 | 1.00 | 16.62 | A |
| ATOM | 1748 | CB | VAL | A | 45 | 2.358 | 36.337 | 45.873 | 1.00 | 16.01 | A |
| ATOM | 1749 | CG1 | VAL | A | 45 | 1.098 | 35.682 | 45.677 | 1.00 | 19.11 | A |
| ATOM | 1750 | CG2 | VAL | A | 45 | 2.894 | 36.838 | 44.474 | 1.00 | 13.44 | A |
| ATOM | 1751 | C | VAL | A | 45 | 3.551 | 37.996 | 47.258 | 1.00 | 15.11 | A |
| ATOM | 1752 | O | VAL | A | 45 | 4.309 | 37.271 | 47.917 | 1.00 | 15.44 | A |
| ATOM | 1753 | N | MET | A | 46 | 3.839 | 39.176 | 46.773 | 1.00 | 15.58 | A |
| ATOM | 1754 | CA | MET | A | 46 | 5.148 | 39.827 | 46.864 | 1.00 | 17.80 | A |
| ATOM | 1755 | CB | MET | A | 46 | 5.353 | 40.558 | 45.523 | 1.00 | 17.71 | A |
| ATOM | 1756 | CG | MET | A | 46 | 6.582 | 40.245 | 44.799 | 1.00 | 18.80 | A |
| ATOM | 1757 | SD | MET | A | 46 | 7.128 | 38.569 | 44.461 | 1.00 | 20.77 | A |
| ATOM | 1758 | CE | MET | A | 46 | 6.495 | 38.470 | 42.581 | 1.00 | 19.70 | A |
| ATOM | 1759 | C | MET | A | 46 | 5.241 | 40.848 | 48.064 | 1.00 | 17.95 | A |
| ATOM | 1760 | O | MET | A | 46 | 6.213 | 41.588 | 48.188 | 1.00 | 17.74 | A |
| ATOM | 1761 | N | SER | A | 47 | 4.232 | 40.910 | 48.925 | 1.00 | 18.15 | A |
| ATOM | 1762 | CA | SER | A | 47 | 4.355 | 41.829 | 50.065 | 1.00 | 18.92 | A |
| ATOM | 1763 | CB | SER | A | 47 | 3.519 | 43.018 | 49.819 | 1.00 | 17.61 | A |
| ATOM | 1764 | OG | SER | A | 47 | 3.317 | 43.020 | 48.362 | 1.00 | 21.61 | A |
| ATOM | 1765 | C | SER | A | 47 | 3.840 | 40.989 | 51.212 | 1.00 | 19.31 | A |
| ATOM | 1766 | O | SER | A | 47 | 2.977 | 40.071 | 50.970 | 1.00 | 20.83 | A |
| ATOM | 1767 | N | GLY | A | 48 | 4.367 | 41.192 | 52.425 | 1.00 | 18.04 | A |
| ATOM | 1768 | CA | GLY | A | 48 | 3.916 | 40.397 | 53.543 | 1.00 | 16.84 | A |
| ATOM | 1769 | C | GLY | A | 48 | 2.708 | 40.926 | 54.324 | 1.00 | 16.90 | A |
| ATOM | 1770 | O | GLY | A | 48 | 2.107 | 41.981 | 54.005 | 1.00 | 16.51 | A |
| ATOM | 1771 | N | ASP | A | 49 | 2.301 | 40.155 | 55.320 | 1.00 | 16.64 | A |
| ATOM | 1772 | CA | ASP | A | 49 | 1.248 | 40.677 | 56.137 | 1.00 | 17.21 | A |
| ATOM | 1773 | CB | ASP | A | 49 | 1.724 | 42.035 | 56.746 | 1.00 | 18.61 | A |
| ATOM | 1774 | CG | ASP | A | 49 | 3.197 | 41.983 | 57.403 | 1.00 | 20.95 | A |
| ATOM | 1775 | OD1 | ASP | A | 49 | 4.020 | 42.820 | 56.969 | 1.00 | 18.22 | A |
| ATOM | 1776 | OD2 | ASP | A | 49 | 3.486 | 41.115 | 58.326 | 1.00 | 20.34 | A |
| ATOM | 1777 | C | ASP | A | 49 | −0.037 | 40.942 | 55.395 | 1.00 | 16.54 | A |
| ATOM | 1778 | O | ASP | A | 49 | −0.665 | 41.916 | 55.629 | 1.00 | 16.58 | A |
| ATOM | 1779 | N | GLN | A | 50 | −0.472 | 40.112 | 54.477 | 1.00 | 16.90 | A |
| ATOM | 1780 | CA | GLN | A | 50 | −1.706 | 40.492 | 53.814 | 1.00 | 16.35 | A |
| ATOM | 1781 | CB | GLN | A | 50 | −1.830 | 39.819 | 52.486 | 1.00 | 17.36 | A |
| ATOM | 1782 | CG | GLN | A | 50 | −0.809 | 40.260 | 51.433 | 1.00 | 15.30 | A |
| ATOM | 1783 | CD | GLN | A | 50 | −0.855 | 41.683 | 51.124 | 1.00 | 14.08 | A |
| ATOM | 1784 | OE1 | GLN | A | 50 | −1.806 | 42.190 | 50.601 | 1.00 | 10.11 | A |
| ATOM | 1785 | NE2 | GLN | A | 50 | 0.205 | 42.365 | 51.478 | 1.00 | 15.68 | A |
| ATOM | 1786 | C | GLN | A | 50 | −2.810 | 40.052 | 54.680 | 1.00 | 15.01 | A |
| ATOM | 1787 | O | GLN | A | 50 | −2.688 | 38.994 | 55.291 | 1.00 | 13.81 | A |
| ATOM | 1788 | N | ASP | A | 51 | −3.851 | 40.893 | 54.753 | 1.00 | 14.67 | A |
| ATOM | 1789 | CA | ASP | A | 51 | −5.062 | 40.582 | 55.508 | 1.00 | 14.53 | A |
| ATOM | 1790 | CB | ASP | A | 51 | −4.920 | 41.146 | 56.957 | 1.00 | 15.70 | A |

TABLE 1-continued

| | | | | | | | | | | |
|---|---|---|---|---|---|---|---|---|---|---|
| ATOM | 1791 | CG | ASP | A | 51 | −6.074 | 40.697 | 57.895 | 1.00 | 17.32 | A |
| ATOM | 1792 | OD1 | ASP | A | 51 | −6.348 | 41.439 | 58.855 | 1.00 | 17.12 | A |
| ATOM | 1793 | OD2 | ASP | A | 51 | −6.719 | 39.628 | 57.630 | 1.00 | 15.67 | A |
| ATOM | 1794 | C | ASP | A | 51 | −6.205 | 41.241 | 54.743 | 1.00 | 12.91 | A |
| ATOM | 1795 | O | ASP | A | 51 | −6.825 | 42.199 | 55.158 | 1.00 | 10.60 | A |
| ATOM | 1796 | N | ASN | A | 52 | −6.473 | 40.726 | 53.590 | 1.00 | 13.33 | A |
| ATOM | 1797 | CA | ASN | A | 52 | −7.579 | 41.301 | 52.776 | 1.00 | 13.33 | A |
| ATOM | 1798 | CB | ASN | A | 52 | −7.145 | 41.345 | 51.350 | 1.00 | 13.76 | A |
| ATOM | 1799 | CG | ASN | A | 52 | −5.788 | 41.894 | 51.220 | 1.00 | 13.29 | A |
| ATOM | 1800 | OD1 | ASN | A | 52 | −5.626 | 43.066 | 51.416 | 1.00 | 11.04 | A |
| ATOM | 1801 | ND2 | ASN | A | 52 | −4.795 | 41.030 | 50.960 | 1.00 | 10.02 | A |
| ATOM | 1802 | C | ASN | A | 52 | −8.872 | 40.505 | 52.926 | 1.00 | 12.57 | A |
| ATOM | 1803 | O | ASN | A | 52 | −8.830 | 39.325 | 52.989 | 1.00 | 11.99 | A |
| ATOM | 1804 | N | TRP | A | 53 | −9.993 | 41.211 | 53.021 | 1.00 | 12.58 | A |
| ATOM | 1805 | CA | TRP | A | 53 | −11.264 | 40.663 | 53.276 | 1.00 | 12.59 | A |
| ATOM | 1806 | CB | TRP | A | 53 | −11.724 | 41.102 | 54.640 | 1.00 | 12.71 | A |
| ATOM | 1807 | CG | TRP | A | 53 | −10.998 | 40.454 | 55.727 | 1.00 | 13.17 | A |
| ATOM | 1808 | CD2 | TRP | A | 53 | −11.422 | 39.380 | 56.544 | 1.00 | 13.99 | A |
| ATOM | 1809 | CE2 | TRP | A | 53 | −10.419 | 39.203 | 57.524 | 1.00 | 14.37 | A |
| ATOM | 1810 | CE3 | TRP | A | 53 | −12.526 | 38.557 | 56.561 | 1.00 | 14.91 | A |
| ATOM | 1811 | CD1 | TRP | A | 53 | −9.815 | 40.833 | 56.199 | 1.00 | 12.85 | A |
| ATOM | 1812 | NE1 | TRP | A | 53 | −9.438 | 40.108 | 57.254 | 1.00 | 13.28 | A |
| ATOM | 1813 | CZ2 | TRP | A | 53 | −10.514 | 38.220 | 58.533 | 1.00 | 14.42 | A |
| ATOM | 1814 | CZ3 | TRP | A | 53 | −12.598 | 37.606 | 57.534 | 1.00 | 15.27 | A |
| ATOM | 1815 | CH2 | TRP | A | 53 | −11.602 | 37.439 | 58.516 | 1.00 | 15.14 | A |
| ATOM | 1816 | C | TRP | A | 53 | −12.315 | 40.986 | 52.286 | 1.00 | 13.00 | A |
| ATOM | 1817 | O | TRP | A | 53 | −12.464 | 42.103 | 51.820 | 1.00 | 12.18 | A |
| ATOM | 1818 | N | LEU | A | 54 | −13.102 | 39.965 | 52.035 | 1.00 | 13.32 | A |
| ATOM | 1819 | CA | LEU | A | 54 | −14.171 | 40.016 | 51.098 | 1.00 | 13.42 | A |
| ATOM | 1820 | CB | LEU | A | 54 | −13.930 | 39.043 | 49.882 | 1.00 | 13.96 | A |
| ATOM | 1821 | CG | LEU | A | 54 | −15.117 | 38.905 | 48.870 | 1.00 | 13.44 | A |
| ATOM | 1822 | CD1 | LEU | A | 54 | −15.399 | 40.219 | 48.098 | 1.00 | 9.17 | A |
| ATOM | 1823 | CD2 | LEU | A | 54 | −14.860 | 37.786 | 47.872 | 1.00 | 13.81 | A |
| ATOM | 1824 | C | LEU | A | 54 | −15.363 | 39.529 | 51.873 | 1.00 | 14.07 | A |
| ATOM | 1825 | O | LEU | A | 54 | −15.400 | 38.376 | 52.408 | 1.00 | 13.77 | A |
| ATOM | 1826 | N | ARG | A | 55 | −16.370 | 40.389 | 51.905 | 1.00 | 12.79 | A |
| ATOM | 1827 | CA | ARG | A | 55 | −17.565 | 40.038 | 52.552 | 1.00 | 12.60 | A |
| ATOM | 1828 | CB | ARG | A | 55 | −17.892 | 41.012 | 53.702 | 1.00 | 13.35 | A |
| ATOM | 1829 | CG | ARG | A | 55 | −19.114 | 40.510 | 54.434 | 1.00 | 15.65 | A |
| ATOM | 1830 | CD | ARG | A | 55 | −19.448 | 41.114 | 55.684 | 1.00 | 16.71 | A |
| ATOM | 1831 | NE | ARG | A | 55 | −20.442 | 42.245 | 55.672 | 1.00 | 17.61 | A |
| ATOM | 1832 | CZ | ARG | A | 55 | −20.532 | 43.173 | 54.720 | 1.00 | 16.94 | A |
| ATOM | 1833 | NH1 | ARG | A | 55 | −19.732 | 43.093 | 53.678 | 1.00 | 20.71 | A |
| ATOM | 1834 | NH2 | ARG | A | 55 | −21.252 | 44.252 | 54.859 | 1.00 | 13.85 | A |
| ATOM | 1835 | C | ARG | A | 55 | −18.727 | 39.991 | 51.599 | 1.00 | 12.37 | A |
| ATOM | 1836 | O | ARG | A | 55 | −18.904 | 40.856 | 50.765 | 1.00 | 11.74 | A |
| ATOM | 1837 | N | THR | A | 56 | −19.566 | 39.001 | 51.795 | 1.00 | 12.35 | A |
| ATOM | 1838 | CA | THR | A | 56 | −20.722 | 38.858 | 50.974 | 1.00 | 13.39 | A |
| ATOM | 1839 | CB | THR | A | 56 | −21.391 | 37.522 | 51.123 | 1.00 | 13.61 | A |
| ATOM | 1840 | OG1 | THR | A | 56 | −21.942 | 37.436 | 52.436 | 1.00 | 11.92 | A |
| ATOM | 1841 | CG2 | THR | A | 56 | −20.465 | 36.436 | 50.847 | 1.00 | 11.93 | A |
| ATOM | 1842 | C | THR | A | 56 | −21.695 | 39.824 | 51.579 | 1.00 | 14.05 | A |
| ATOM | 1843 | O | THR | A | 56 | −21.446 | 40.457 | 52.634 | 1.00 | 13.41 | A |
| ATOM | 1844 | N | ASN | A | 57 | −22.853 | 39.910 | 50.906 | 1.00 | 15.23 | A |
| ATOM | 1845 | CA | ASN | A | 57 | −23.887 | 40.768 | 51.416 | 1.00 | 16.42 | A |
| ATOM | 1846 | CB | ASN | A | 57 | −24.714 | 41.330 | 50.324 | 1.00 | 19.08 | A |
| ATOM | 1847 | CG | ASN | A | 57 | −24.625 | 42.843 | 50.266 | 1.00 | 22.41 | A |
| ATOM | 1848 | OD1 | ASN | A | 57 | −23.609 | 43.375 | 49.810 | 1.00 | 21.78 | A |
| ATOM | 1849 | ND2 | ASN | A | 57 | −25.690 | 43.585 | 50.788 | 1.00 | 24.12 | A |
| ATOM | 1850 | C | ASN | A | 57 | −24.712 | 40.016 | 52.363 | 1.00 | 15.24 | A |
| ATOM | 1851 | O | ASN | A | 57 | −24.608 | 38.813 | 52.440 | 1.00 | 15.05 | A |
| ATOM | 1852 | N | TRP | A | 58 | −25.472 | 40.775 | 53.131 | 1.00 | 15.35 | A |
| ATOM | 1853 | CA | TRP | A | 58 | −26.412 | 40.268 | 54.157 | 1.00 | 16.65 | A |
| ATOM | 1854 | CB | TRP | A | 58 | −27.316 | 41.436 | 54.605 | 1.00 | 17.35 | A |
| ATOM | 1855 | CG | TRP | A | 58 | −28.455 | 41.168 | 55.513 | 1.00 | 20.52 | A |
| ATOM | 1856 | CD2 | TRP | A | 58 | −28.365 | 40.564 | 56.777 | 1.00 | 21.19 | A |
| ATOM | 1857 | CE2 | TRP | A | 58 | −29.626 | 40.717 | 57.428 | 1.00 | 22.55 | A |
| ATOM | 1858 | CE3 | TRP | A | 58 | −27.343 | 39.910 | 57.432 | 1.00 | 20.49 | A |
| ATOM | 1859 | CD1 | TRP | A | 58 | −29.748 | 41.647 | 55.405 | 1.00 | 23.58 | A |
| ATOM | 1860 | NE1 | TRP | A | 58 | −30.476 | 41.366 | 56.582 | 1.00 | 24.89 | A |
| ATOM | 1861 | CZ2 | TRP | A | 58 | −29.846 | 40.243 | 58.723 | 1.00 | 22.52 | A |
| ATOM | 1862 | CZ3 | TRP | A | 58 | −27.569 | 39.432 | 58.719 | 1.00 | 21.09 | A |
| ATOM | 1863 | CH2 | TRP | A | 58 | −28.815 | 39.607 | 59.353 | 1.00 | 22.11 | A |
| ATOM | 1864 | C | TRP | A | 58 | −27.266 | 39.134 | 53.551 | 1.00 | 15.75 | A |
| ATOM | 1865 | O | TRP | A | 58 | −27.919 | 39.330 | 52.584 | 1.00 | 15.79 | A |
| ATOM | 1866 | N | VAL | A | 59 | −27.263 | 37.973 | 54.153 | 1.00 | 16.08 | A |
| ATOM | 1867 | CA | VAL | A | 59 | −28.047 | 36.917 | 53.641 | 1.00 | 16.01 | A |
| ATOM | 1868 | CB | VAL | A | 59 | −27.130 | 35.760 | 53.208 | 1.00 | 17.38 | A |
| ATOM | 1869 | CG1 | VAL | A | 59 | −27.979 | 34.549 | 52.660 | 1.00 | 17.74 | A |
| ATOM | 1870 | CG2 | VAL | A | 59 | −26.071 | 36.278 | 52.228 | 1.00 | 14.35 | A |

TABLE 1-continued

| | | | | | | | | | | |
|---|---|---|---|---|---|---|---|---|---|---|
| ATOM | 1871 | C | VAL | A | 59 | −29.034 | 36.412 | 54.693 | 1.00 | 16.20 | A |
| ATOM | 1872 | O | VAL | A | 59 | −28.583 | 35.952 | 55.791 | 1.00 | 17.04 | A |
| ATOM | 1873 | N | TYR | A | 60 | −30.360 | 36.456 | 54.354 | 1.00 | 13.74 | A |
| ATOM | 1874 | CA | TYR | A | 60 | −31.427 | 35.933 | 55.193 | 1.00 | 11.31 | A |
| ATOM | 1875 | CB | TYR | A | 60 | −32.778 | 36.150 | 54.573 | 1.00 | 12.23 | A |
| ATOM | 1876 | CG | TYR | A | 60 | −33.201 | 37.576 | 54.599 | 1.00 | 14.43 | A |
| ATOM | 1877 | CD1 | TYR | A | 60 | −33.333 | 38.302 | 53.427 | 1.00 | 14.20 | A |
| ATOM | 1878 | CE1 | TYR | A | 60 | −33.702 | 39.665 | 53.491 | 1.00 | 15.83 | A |
| ATOM | 1879 | CD2 | TYR | A | 60 | −33.435 | 38.267 | 55.848 | 1.00 | 15.03 | A |
| ATOM | 1880 | CE2 | TYR | A | 60 | −33.799 | 39.653 | 55.876 | 1.00 | 14.90 | A |
| ATOM | 1881 | CZ | TYR | A | 60 | −33.939 | 40.335 | 54.738 | 1.00 | 14.54 | A |
| ATOM | 1882 | OH | TYR | A | 60 | −34.369 | 41.678 | 54.756 | 1.00 | 14.78 | A |
| ATOM | 1883 | C | TYR | A | 60 | −31.265 | 34.448 | 55.413 | 1.00 | 11.30 | A |
| ATOM | 1884 | O | TYR | A | 60 | −30.940 | 33.749 | 54.517 | 1.00 | 8.53 | A |
| ATOM | 1885 | N | ARG | A | 61 | −31.507 | 33.990 | 56.621 | 1.00 | 11.48 | A |
| ATOM | 1886 | CA | ARG | A | 61 | −31.355 | 32.641 | 56.961 | 1.00 | 13.28 | A |
| ATOM | 1887 | CB | ARG | A | 61 | −31.174 | 32.500 | 58.440 | 1.00 | 14.14 | A |
| ATOM | 1888 | CG | ARG | A | 61 | −31.306 | 31.023 | 58.935 | 1.00 | 16.63 | A |
| ATOM | 1889 | CD | ARG | A | 61 | −30.924 | 30.790 | 60.460 | 1.00 | 18.13 | A |
| ATOM | 1890 | NE | ARG | A | 61 | −31.953 | 31.360 | 61.361 | 1.00 | 17.67 | A |
| ATOM | 1891 | CZ | ARG | A | 61 | −33.131 | 30.791 | 61.627 | 1.00 | 15.86 | A |
| ATOM | 1892 | NH1 | ARG | A | 61 | −33.415 | 29.602 | 61.088 | 1.00 | 15.52 | A |
| ATOM | 1893 | NH2 | ARG | A | 61 | −34.031 | 31.470 | 62.317 | 1.00 | 14.08 | A |
| ATOM | 1894 | C | ARG | A | 61 | −32.606 | 31.904 | 56.583 | 1.00 | 16.13 | A |
| ATOM | 1895 | O | ARG | A | 61 | −32.528 | 30.770 | 56.118 | 1.00 | 16.81 | A |
| ATOM | 1896 | N | GLY | A | 62 | −33.759 | 32.579 | 56.717 | 1.00 | 17.25 | A |
| ATOM | 1897 | CA | GLY | A | 62 | −35.087 | 31.993 | 56.526 | 1.00 | 18.15 | A |
| ATOM | 1898 | C | GLY | A | 62 | −35.272 | 30.769 | 57.438 | 1.00 | 19.05 | A |
| ATOM | 1899 | O | GLY | A | 62 | −35.106 | 30.832 | 58.619 | 1.00 | 19.19 | A |
| ATOM | 1900 | N | GLU | A | 63 | −35.557 | 29.617 | 56.861 | 1.00 | 19.16 | A |
| ATOM | 1901 | CA | GLU | A | 63 | −35.739 | 28.421 | 57.619 | 1.00 | 19.78 | A |
| ATOM | 1902 | CB | GLU | A | 63 | −36.917 | 27.663 | 56.954 | 1.00 | 19.93 | A |
| ATOM | 1903 | CG | GLU | A | 63 | −37.178 | 26.276 | 57.537 | 1.00 | 21.72 | A |
| ATOM | 1904 | CD | GLU | A | 63 | −37.919 | 26.346 | 58.911 | 1.00 | 25.80 | A |
| ATOM | 1905 | OE1 | GLU | A | 63 | −38.009 | 25.273 | 59.724 | 1.00 | 26.27 | A |
| ATOM | 1906 | OE2 | GLU | A | 63 | −38.406 | 27.531 | 59.188 | 1.00 | 27.57 | A |
| ATOM | 1907 | C | GLU | A | 63 | −34.448 | 27.534 | 57.719 | 1.00 | 19.89 | A |
| ATOM | 1908 | O | GLU | A | 63 | −34.496 | 26.467 | 58.286 | 1.00 | 21.37 | A |
| ATOM | 1909 | N | ALA | A | 64 | −33.292 | 27.937 | 57.196 | 1.00 | 19.68 | A |
| ATOM | 1910 | CA | ALA | A | 64 | −32.076 | 27.094 | 57.281 | 1.00 | 18.50 | A |
| ATOM | 1911 | CB | ALA | A | 64 | −31.053 | 27.699 | 56.386 | 1.00 | 18.35 | A |
| ATOM | 1912 | C | ALA | A | 64 | −31.446 | 26.879 | 58.658 | 1.00 | 17.72 | A |
| ATOM | 1913 | O | ALA | A | 64 | −31.413 | 27.790 | 59.422 | 1.00 | 17.67 | A |
| ATOM | 1914 | N | GLU | A | 65 | −31.001 | 25.671 | 58.987 | 1.00 | 17.83 | A |
| ATOM | 1915 | CA | GLU | A | 65 | −30.284 | 25.394 | 60.262 | 1.00 | 17.38 | A |
| ATOM | 1916 | CB | GLU | A | 65 | −30.760 | 24.136 | 60.961 | 1.00 | 18.13 | A |
| ATOM | 1917 | CG | GLU | A | 65 | −32.285 | 23.982 | 61.075 | 1.00 | 23.15 | A |
| ATOM | 1918 | CD | GLU | A | 65 | −32.922 | 24.513 | 62.373 | 1.00 | 24.29 | A |
| ATOM | 1919 | OE1 | GLU | A | 65 | −32.455 | 23.863 | 63.379 | 1.00 | 25.84 | A |
| ATOM | 1920 | OE2 | GLU | A | 65 | −33.805 | 25.493 | 62.345 | 1.00 | 23.65 | A |
| ATOM | 1921 | C | GLU | A | 65 | −28.797 | 25.158 | 59.876 | 1.00 | 16.53 | A |
| ATOM | 1922 | O | GLU | A | 65 | −27.901 | 25.623 | 60.511 | 1.00 | 16.58 | A |
| ATOM | 1923 | N | ARG | A | 66 | −28.551 | 24.329 | 58.869 | 1.00 | 16.58 | A |
| ATOM | 1924 | CA | ARG | A | 66 | −27.187 | 24.072 | 58.290 | 1.00 | 17.43 | A |
| ATOM | 1925 | CB | ARG | A | 66 | −26.807 | 22.598 | 58.288 | 1.00 | 17.81 | A |
| ATOM | 1926 | CG | ARG | A | 66 | −25.342 | 22.405 | 58.047 | 1.00 | 18.30 | A |
| ATOM | 1927 | CD | ARG | A | 66 | −24.815 | 21.331 | 59.039 | 1.00 | 20.74 | A |
| ATOM | 1928 | NE | ARG | A | 66 | −23.350 | 21.159 | 59.040 | 1.00 | 22.55 | A |
| ATOM | 1929 | CZ | ARG | A | 66 | −22.547 | 21.542 | 60.049 | 1.00 | 23.63 | A |
| ATOM | 1930 | NH1 | ARG | A | 66 | −23.043 | 22.123 | 61.173 | 1.00 | 24.37 | A |
| ATOM | 1931 | NH2 | ARG | A | 66 | −21.244 | 21.333 | 59.940 | 1.00 | 24.53 | A |
| ATOM | 1932 | C | ARG | A | 66 | −27.203 | 24.544 | 56.787 | 1.00 | 17.07 | A |
| ATOM | 1933 | O | ARG | A | 66 | −28.201 | 24.307 | 56.078 | 1.00 | 17.08 | A |
| ATOM | 1934 | N | ASN | A | 67 | −26.187 | 25.253 | 56.340 | 1.00 | 17.17 | A |
| ATOM | 1935 | CA | ASN | A | 67 | −26.167 | 25.698 | 54.981 | 1.00 | 18.28 | A |
| ATOM | 1936 | CB | ASN | A | 67 | −26.093 | 27.216 | 54.818 | 1.00 | 18.83 | A |
| ATOM | 1937 | CG | ASN | A | 67 | −25.183 | 27.796 | 55.806 | 1.00 | 21.35 | A |
| ATOM | 1938 | OD1 | ASN | A | 67 | −25.104 | 27.249 | 56.949 | 1.00 | 25.96 | A |
| ATOM | 1939 | ND2 | ASN | A | 67 | −24.519 | 28.897 | 55.499 | 1.00 | 19.58 | A |
| ATOM | 1940 | C | ASN | A | 67 | −24.916 | 25.107 | 54.524 | 1.00 | 18.09 | A |
| ATOM | 1941 | O | ASN | A | 67 | −24.002 | 24.869 | 55.308 | 1.00 | 18.74 | A |
| ATOM | 1942 | N | ASN | A | 68 | −24.889 | 24.801 | 53.237 | 1.00 | 17.86 | A |
| ATOM | 1943 | CA | ASN | A | 68 | −23.691 | 24.262 | 52.616 | 1.00 | 18.28 | A |
| ATOM | 1944 | CB | ASN | A | 68 | −24.179 | 23.077 | 51.817 | 1.00 | 19.82 | A |
| ATOM | 1945 | CG | ASN | A | 68 | −24.515 | 22.017 | 52.687 | 1.00 | 22.30 | A |
| ATOM | 1946 | OD1 | ASN | A | 68 | −23.561 | 21.328 | 53.208 | 1.00 | 23.10 | A |
| ATOM | 1947 | ND2 | ASN | A | 68 | −25.861 | 21.844 | 52.994 | 1.00 | 23.44 | A |
| ATOM | 1948 | C | ASN | A | 68 | −23.092 | 25.400 | 51.728 | 1.00 | 16.96 | A |
| ATOM | 1949 | O | ASN | A | 68 | −23.860 | 26.277 | 51.200 | 1.00 | 16.56 | A |
| ATOM | 1950 | N | PHE | A | 69 | −21.766 | 25.451 | 51.593 | 1.00 | 16.86 | A |

TABLE 1-continued

| | | | | | | | | | | |
|---|---|---|---|---|---|---|---|---|---|---|
| ATOM | 1951 | CA | PHE | A | 69 | −21.235 | 26.425 | 50.592 | 1.00 | 17.91 | A |
| ATOM | 1952 | CB | PHE | A | 69 | −20.743 | 27.691 | 51.112 | 1.00 | 17.80 | A |
| ATOM | 1953 | CG | PHE | A | 69 | −20.526 | 27.630 | 52.477 | 1.00 | 19.28 | A |
| ATOM | 1954 | CD1 | PHE | A | 69 | −19.633 | 26.693 | 52.977 | 1.00 | 21.07 | A |
| ATOM | 1955 | CD2 | PHE | A | 69 | −21.127 | 28.572 | 53.320 | 1.00 | 18.31 | A |
| ATOM | 1956 | CE1 | PHE | A | 69 | −19.335 | 26.745 | 54.384 | 1.00 | 24.18 | A |
| ATOM | 1957 | CE2 | PHE | A | 69 | −20.861 | 28.653 | 54.682 | 1.00 | 19.30 | A |
| ATOM | 1958 | CZ | PHE | A | 69 | −19.975 | 27.766 | 55.255 | 1.00 | 20.98 | A |
| ATOM | 1959 | C | PHE | A | 69 | −20.152 | 25.883 | 49.800 | 1.00 | 17.93 | A |
| ATOM | 1960 | O | PHE | A | 69 | −19.184 | 25.230 | 50.300 | 1.00 | 18.87 | A |
| ATOM | 1961 | N | GLU | A | 70 | −20.402 | 26.084 | 48.518 | 1.00 | 17.62 | A |
| ATOM | 1962 | CA | GLU | A | 70 | −19.563 | 25.578 | 47.497 | 1.00 | 16.65 | A |
| ATOM | 1963 | CB | GLU | A | 70 | −20.476 | 24.911 | 46.452 | 1.00 | 17.59 | A |
| ATOM | 1964 | CG | GLU | A | 70 | −19.766 | 23.887 | 45.635 | 1.00 | 18.37 | A |
| ATOM | 1965 | CD | GLU | A | 70 | −20.473 | 23.617 | 44.312 | 1.00 | 18.22 | A |
| ATOM | 1966 | OE1 | GLU | A | 70 | −20.606 | 22.406 | 43.938 | 1.00 | 18.80 | A |
| ATOM | 1967 | OE2 | GLU | A | 70 | −20.861 | 24.637 | 43.689 | 1.00 | 17.15 | A |
| ATOM | 1968 | C | GLU | A | 70 | −18.765 | 26.734 | 46.979 | 1.00 | 14.76 | A |
| ATOM | 1969 | O | GLU | A | 70 | −19.298 | 27.804 | 46.583 | 1.00 | 13.26 | A |
| ATOM | 1970 | N | LEU | A | 71 | −17.461 | 26.480 | 47.021 | 1.00 | 14.00 | A |
| ATOM | 1971 | CA | LEU | A | 71 | −16.424 | 27.400 | 46.513 | 1.00 | 14.48 | A |
| ATOM | 1972 | CB | LEU | A | 71 | −15.410 | 27.708 | 47.638 | 1.00 | 15.21 | A |
| ATOM | 1973 | CG | LEU | A | 71 | −16.089 | 28.303 | 48.784 | 1.00 | 15.78 | A |
| ATOM | 1974 | CD1 | LEU | A | 71 | −15.260 | 28.207 | 49.919 | 1.00 | 17.13 | A |
| ATOM | 1975 | CD2 | LEU | A | 71 | −16.514 | 29.700 | 48.423 | 1.00 | 16.10 | A |
| ATOM | 1976 | C | LEU | A | 71 | −15.628 | 26.782 | 45.360 | 1.00 | 12.93 | A |
| ATOM | 1977 | O | LEU | A | 71 | −15.178 | 25.663 | 45.525 | 1.00 | 12.07 | A |
| ATOM | 1978 | N | ASN | A | 72 | −15.435 | 27.555 | 44.297 | 1.00 | 12.98 | A |
| ATOM | 1979 | CA | ASN | A | 72 | −14.714 | 27.243 | 43.075 | 1.00 | 14.94 | A |
| ATOM | 1980 | CB | ASN | A | 72 | −15.681 | 27.159 | 41.788 | 1.00 | 17.39 | A |
| ATOM | 1981 | CG | ASN | A | 72 | −16.447 | 25.804 | 41.709 | 1.00 | 21.16 | A |
| ATOM | 1982 | OD1 | ASN | A | 72 | −17.411 | 25.553 | 40.931 | 1.00 | 21.52 | A |
| ATOM | 1983 | ND2 | ASN | A | 72 | −15.948 | 24.861 | 42.529 | 1.00 | 25.39 | A |
| ATOM | 1984 | C | ASN | A | 72 | −13.699 | 28.362 | 42.884 | 1.00 | 13.68 | A |
| ATOM | 1985 | O | ASN | A | 72 | −14.047 | 29.525 | 42.778 | 1.00 | 13.31 | A |
| ATOM | 1986 | N | PHE | A | 73 | −12.417 | 27.993 | 42.800 | 1.00 | 14.73 | A |
| ATOM | 1987 | CA | PHE | A | 73 | −11.311 | 28.959 | 42.717 | 1.00 | 15.21 | A |
| ATOM | 1988 | CB | PHE | A | 73 | −10.975 | 29.403 | 44.151 | 1.00 | 14.12 | A |
| ATOM | 1989 | CG | PHE | A | 73 | −10.622 | 28.191 | 45.061 | 1.00 | 13.08 | A |
| ATOM | 1990 | CD1 | PHE | A | 73 | −9.314 | 27.783 | 45.226 | 1.00 | 10.42 | A |
| ATOM | 1991 | CD2 | PHE | A | 73 | −11.611 | 27.463 | 45.682 | 1.00 | 12.01 | A |
| ATOM | 1992 | CE1 | PHE | A | 73 | −8.983 | 26.657 | 46.033 | 1.00 | 12.55 | A |
| ATOM | 1993 | CE2 | PHE | A | 73 | −11.262 | 26.353 | 46.465 | 1.00 | 15.26 | A |
| ATOM | 1994 | CZ | PHE | A | 73 | −9.918 | 25.953 | 46.652 | 1.00 | 11.88 | A |
| ATOM | 1995 | C | PHE | A | 73 | −10.079 | 28.276 | 42.157 | 1.00 | 14.55 | A |
| ATOM | 1996 | O | PHE | A | 73 | −10.007 | 27.077 | 42.023 | 1.00 | 15.70 | A |
| ATOM | 1997 | N | THR | A | 74 | −9.072 | 29.088 | 41.952 | 1.00 | 15.15 | A |
| ATOM | 1998 | CA | THR | A | 74 | −7.798 | 28.661 | 41.436 | 1.00 | 16.00 | A |
| ATOM | 1999 | CB | THR | A | 74 | −7.531 | 29.062 | 40.002 | 1.00 | 15.00 | A |
| ATOM | 2000 | OG1 | THR | A | 74 | −7.152 | 30.433 | 39.908 | 1.00 | 16.70 | A |
| ATOM | 2001 | CG2 | THR | A | 74 | −8.677 | 28.961 | 39.307 | 1.00 | 15.46 | A |
| ATOM | 2002 | C | THR | A | 74 | −6.787 | 29.331 | 42.249 | 1.00 | 14.55 | A |
| ATOM | 2003 | O | THR | A | 74 | −7.052 | 30.365 | 42.830 | 1.00 | 14.86 | A |
| ATOM | 2004 | N | VAL | A | 75 | −5.629 | 28.726 | 42.272 | 1.00 | 14.53 | A |
| ATOM | 2005 | CA | VAL | A | 75 | −4.531 | 29.201 | 43.070 | 1.00 | 14.75 | A |
| ATOM | 2006 | CB | VAL | A | 75 | −4.524 | 28.379 | 44.355 | 1.00 | 14.30 | A |
| ATOM | 2007 | CG1 | VAL | A | 75 | −3.366 | 28.682 | 45.211 | 1.00 | 14.75 | A |
| ATOM | 2008 | CG2 | VAL | A | 75 | −5.783 | 28.611 | 45.052 | 1.00 | 10.73 | A |
| ATOM | 2009 | C | VAL | A | 75 | −3.225 | 29.127 | 42.281 | 1.00 | 14.09 | A |
| ATOM | 2010 | O | VAL | A | 75 | −2.837 | 28.073 | 41.847 | 1.00 | 13.03 | A |
| ATOM | 2011 | N | ARG | A | 76 | −2.621 | 30.299 | 42.020 | 1.00 | 14.12 | A |
| ATOM | 2012 | CA | ARG | A | 76 | −1.370 | 30.335 | 41.284 | 1.00 | 14.41 | A |
| ATOM | 2013 | CB | ARG | A | 76 | −1.062 | 31.712 | 40.814 | 1.00 | 13.21 | A |
| ATOM | 2014 | CG | ARG | A | 76 | 0.125 | 31.760 | 40.042 | 1.00 | 10.77 | A |
| ATOM | 2015 | CD | ARG | A | 76 | 0.073 | 32.882 | 39.018 | 1.00 | 9.49 | A |
| ATOM | 2016 | NE | ARG | A | 76 | 1.431 | 33.136 | 38.674 | 1.00 | 10.33 | A |
| ATOM | 2017 | CZ | ARG | A | 76 | 1.934 | 34.262 | 38.198 | 1.00 | 12.71 | A |
| ATOM | 2018 | NH1 | ARG | A | 76 | 1.147 | 35.286 | 37.949 | 1.00 | 11.89 | A |
| ATOM | 2019 | NH2 | ARG | A | 76 | 3.282 | 34.425 | 38.136 | 1.00 | 12.56 | A |
| ATOM | 2020 | C | ARG | A | 76 | −0.285 | 29.777 | 42.231 | 1.00 | 16.34 | A |
| ATOM | 2021 | O | ARG | A | 76 | −0.220 | 30.041 | 43.464 | 1.00 | 17.36 | A |
| ATOM | 2022 | N | ASP | A | 77 | 0.448 | 28.844 | 41.677 | 1.00 | 17.02 | A |
| ATOM | 2023 | CA | ASP | A | 77 | 1.543 | 28.184 | 42.337 | 1.00 | 17.11 | A |
| ATOM | 2024 | CB | ASP | A | 77 | 2.197 | 27.213 | 41.330 | 1.00 | 18.78 | A |
| ATOM | 2025 | CG | ASP | A | 77 | 3.650 | 26.713 | 41.783 | 1.00 | 20.06 | A |
| ATOM | 2026 | OD1 | ASP | A | 77 | 4.021 | 26.820 | 42.955 | 1.00 | 19.73 | A |
| ATOM | 2027 | OD2 | ASP | A | 77 | 4.385 | 26.189 | 40.954 | 1.00 | 20.07 | A |
| ATOM | 2028 | C | ASP | A | 77 | 2.541 | 29.233 | 42.802 | 1.00 | 16.81 | A |
| ATOM | 2029 | O | ASP | A | 77 | 2.923 | 30.156 | 42.018 | 1.00 | 16.50 | A |
| ATOM | 2030 | N | CYS | A | 78 | 2.914 | 29.153 | 44.078 | 1.00 | 16.36 | A |

TABLE 1-continued

| | | | | | | | | | | |
|---|---|---|---|---|---|---|---|---|---|---|
| ATOM | 2031 | CA | CYS | A | 78 | 3.871 | 30.143 | 44.662 | 1.00 | 16.72 | A |
| ATOM | 2032 | C | CYS | A | 78 | 5.236 | 30.207 | 44.007 | 1.00 | 15.14 | A |
| ATOM | 2033 | O | CYS | A | 78 | 5.811 | 31.270 | 43.850 | 1.00 | 14.09 | A |
| ATOM | 2034 | CB | CYS | A | 78 | 4.027 | 29.991 | 46.187 | 1.00 | 17.53 | A |
| ATOM | 2035 | SG | CYS | A | 78 | 2.644 | 30.934 | 47.082 | 1.00 | 19.32 | A |
| ATOM | 2036 | N | ASN | A | 79 | 5.707 | 29.051 | 43.551 | 1.00 | 14.59 | A |
| ATOM | 2037 | CA | ASN | A | 79 | 6.938 | 29.011 | 42.826 | 1.00 | 13.80 | A |
| ATOM | 2038 | CB | ASN | A | 79 | 7.395 | 27.615 | 42.834 | 1.00 | 14.81 | A |
| ATOM | 2039 | CG | ASN | A | 79 | 7.709 | 27.132 | 44.175 | 1.00 | 15.52 | A |
| ATOM | 2040 | OD1 | ASN | A | 79 | 7.873 | 25.956 | 44.415 | 1.00 | 14.64 | A |
| ATOM | 2041 | ND2 | ASN | A | 79 | 7.833 | 28.061 | 45.100 | 1.00 | 21.08 | A |
| ATOM | 2042 | C | ASN | A | 79 | 6.893 | 29.589 | 41.352 | 1.00 | 13.29 | A |
| ATOM | 2043 | O | ASN | A | 79 | 7.881 | 29.519 | 40.666 | 1.00 | 12.02 | A |
| ATOM | 2044 | N | SER | A | 80 | 5.771 | 30.168 | 40.922 | 1.00 | 12.90 | A |
| ATOM | 2045 | CA | SER | A | 80 | 5.672 | 30.682 | 39.587 | 1.00 | 14.97 | A |
| ATOM | 2046 | CB | SER | A | 80 | 4.310 | 30.444 | 38.931 | 1.00 | 15.80 | A |
| ATOM | 2047 | OG | SER | A | 80 | 3.335 | 31.267 | 39.612 | 1.00 | 24.05 | A |
| ATOM | 2048 | C | SER | A | 80 | 5.961 | 32.138 | 39.622 | 1.00 | 14.22 | A |
| ATOM | 2049 | O | SER | A | 80 | 5.705 | 32.842 | 38.711 | 1.00 | 13.44 | A |
| ATOM | 2050 | N | PHE | A | 81 | 6.425 | 32.641 | 40.723 | 1.00 | 14.95 | A |
| ATOM | 2051 | CA | PHE | A | 81 | 6.838 | 34.018 | 40.661 | 1.00 | 16.50 | A |
| ATOM | 2052 | CB | PHE | A | 81 | 6.228 | 34.685 | 41.855 | 1.00 | 17.07 | A |
| ATOM | 2053 | CG | PHE | A | 81 | 4.705 | 34.708 | 41.834 | 1.00 | 16.77 | A |
| ATOM | 2054 | CD1 | PHE | A | 81 | 3.942 | 33.742 | 42.498 | 1.00 | 15.78 | A |
| ATOM | 2055 | CD2 | PHE | A | 81 | 4.008 | 35.702 | 41.117 | 1.00 | 15.43 | A |
| ATOM | 2056 | CE1 | PHE | A | 81 | 2.544 | 33.764 | 42.440 | 1.00 | 13.87 | A |
| ATOM | 2057 | CE2 | PHE | A | 81 | 2.619 | 35.686 | 41.097 | 1.00 | 13.42 | A |
| ATOM | 2058 | CZ | PHE | A | 81 | 1.887 | 34.707 | 41.762 | 1.00 | 11.30 | A |
| ATOM | 2059 | C | PHE | A | 81 | 8.425 | 33.937 | 40.665 | 1.00 | 17.18 | A |
| ATOM | 2060 | O | PHE | A | 81 | 9.011 | 33.579 | 41.632 | 1.00 | 18.01 | A |
| ATOM | 2061 | N | PRO | A | 82 | 9.106 | 34.283 | 39.580 | 1.00 | 17.28 | A |
| ATOM | 2062 | CD | PRO | A | 82 | 8.540 | 35.231 | 38.632 | 1.00 | 17.29 | A |
| ATOM | 2063 | CA | PRO | A | 82 | 10.601 | 34.233 | 39.436 | 1.00 | 18.20 | A |
| ATOM | 2064 | CB | PRO | A | 82 | 10.888 | 35.012 | 38.154 | 1.00 | 17.89 | A |
| ATOM | 2065 | CG | PRO | A | 82 | 9.613 | 35.169 | 37.510 | 1.00 | 17.42 | A |
| ATOM | 2066 | C | PRO | A | 82 | 11.399 | 34.834 | 40.584 | 1.00 | 18.30 | A |
| ATOM | 2067 | O | PRO | A | 82 | 11.098 | 35.962 | 40.991 | 1.00 | 17.90 | A |
| ATOM | 2068 | N | GLY | A | 83 | 12.447 | 34.103 | 41.011 | 1.00 | 19.38 | A |
| ATOM | 2069 | CA | GLY | A | 83 | 13.305 | 34.445 | 42.159 | 1.00 | 20.29 | A |
| ATOM | 2070 | C | GLY | A | 83 | 12.408 | 33.965 | 43.261 | 1.00 | 20.44 | A |
| ATOM | 2071 | O | GLY | A | 83 | 11.251 | 33.524 | 42.944 | 1.00 | 21.15 | A |
| ATOM | 2072 | N | GLY | A | 84 | 12.785 | 33.977 | 44.549 | 1.00 | 20.09 | A |
| ATOM | 2073 | CA | GLY | A | 84 | 11.711 | 33.434 | 45.472 | 1.00 | 19.03 | A |
| ATOM | 2074 | C | GLY | A | 84 | 10.452 | 34.298 | 45.792 | 1.00 | 18.38 | A |
| ATOM | 2075 | O | GLY | A | 84 | 10.394 | 35.471 | 45.386 | 1.00 | 16.33 | A |
| ATOM | 2076 | N | ALA | A | 85 | 9.400 | 33.760 | 46.447 | 1.00 | 19.08 | A |
| ATOM | 2077 | CA | ALA | A | 85 | 8.262 | 34.697 | 46.823 | 1.00 | 20.80 | A |
| ATOM | 2078 | CB | ALA | A | 85 | 6.942 | 34.524 | 45.898 | 1.00 | 19.17 | A |
| ATOM | 2079 | C | ALA | A | 85 | 7.932 | 34.332 | 48.220 | 1.00 | 20.07 | A |
| ATOM | 2080 | O | ALA | A | 85 | 6.869 | 33.824 | 48.490 | 1.00 | 22.94 | A |
| ATOM | 2081 | N | SER | A | 86 | 8.854 | 34.538 | 49.103 | 1.00 | 18.77 | A |
| ATOM | 2082 | CA | SER | A | 86 | 8.737 | 34.167 | 50.529 | 1.00 | 16.77 | A |
| ATOM | 2083 | CB | SER | A | 86 | 9.883 | 34.851 | 51.283 | 1.00 | 14.82 | A |
| ATOM | 2084 | OG | SER | A | 86 | 9.869 | 36.252 | 51.035 | 1.00 | 10.04 | A |
| ATOM | 2085 | C | SER | A | 86 | 7.414 | 34.362 | 51.253 | 1.00 | 14.87 | A |
| ATOM | 2086 | O | SER | A | 86 | 7.045 | 33.465 | 51.954 | 1.00 | 14.56 | A |
| ATOM | 2087 | N | SER | A | 87 | 6.676 | 35.449 | 51.067 | 1.00 | 12.96 | A |
| ATOM | 2088 | CA | SER | A | 87 | 5.388 | 35.598 | 51.774 | 1.00 | 12.45 | A |
| ATOM | 2089 | CB | SER | A | 87 | 5.128 | 37.031 | 52.118 | 1.00 | 9.17 | A |
| ATOM | 2090 | OG | SER | A | 87 | 4.876 | 37.737 | 50.961 | 1.00 | 7.17 | A |
| ATOM | 2091 | C | SER | A | 87 | 4.136 | 35.046 | 51.040 | 1.00 | 13.90 | A |
| ATOM | 2092 | O | SER | A | 87 | 3.020 | 35.088 | 51.565 | 1.00 | 14.54 | A |
| ATOM | 2093 | N | CYS | A | 88 | 4.331 | 34.511 | 49.832 | 1.00 | 14.94 | A |
| ATOM | 2094 | CA | CYS | A | 88 | 3.258 | 33.989 | 49.047 | 1.00 | 15.17 | A |
| ATOM | 2095 | C | CYS | A | 88 | 2.773 | 32.796 | 49.736 | 1.00 | 14.84 | A |
| ATOM | 2096 | O | CYS | A | 88 | 3.511 | 32.087 | 50.299 | 1.00 | 13.64 | A |
| ATOM | 2097 | CB | CYS | A | 88 | 3.733 | 33.654 | 47.657 | 1.00 | 17.44 | A |
| ATOM | 2098 | SG | CYS | A | 88 | 2.587 | 32.896 | 46.469 | 1.00 | 17.56 | A |
| ATOM | 2099 | N | LYS | A | 89 | 1.458 | 32.671 | 49.744 | 1.00 | 16.19 | A |
| ATOM | 2100 | CA | LYS | A | 89 | 0.734 | 31.552 | 50.369 | 1.00 | 16.99 | A |
| ATOM | 2101 | CB | LYS | A | 89 | −0.232 | 32.151 | 51.413 | 1.00 | 18.17 | A |
| ATOM | 2102 | CG | LYS | A | 89 | 0.525 | 32.873 | 52.478 | 1.00 | 20.10 | A |
| ATOM | 2103 | CD | LYS | A | 89 | 1.413 | 31.897 | 53.399 | 1.00 | 19.59 | A |
| ATOM | 2104 | CE | LYS | A | 89 | 1.967 | 32.736 | 54.645 | 1.00 | 21.69 | A |
| ATOM | 2105 | NZ | LYS | A | 89 | 2.642 | 31.850 | 55.706 | 1.00 | 24.41 | A |
| ATOM | 2106 | C | LYS | A | 89 | −0.092 | 30.795 | 49.369 | 1.00 | 15.95 | A |
| ATOM | 2107 | O | LYS | A | 89 | −0.358 | 31.297 | 48.351 | 1.00 | 15.66 | A |
| ATOM | 2108 | N | GLU | A | 90 | −0.574 | 29.623 | 49.713 | 1.00 | 18.02 | A |
| ATOM | 2109 | CA | GLU | A | 90 | −1.418 | 28.853 | 48.782 | 1.00 | 18.81 | A |
| ATOM | 2110 | CB | GLU | A | 90 | −0.683 | 27.705 | 48.112 | 1.00 | 17.83 | A |

TABLE 1-continued

| | | | | | | | | | | |
|---|---|---|---|---|---|---|---|---|---|---|
| ATOM | 2111 | CG | GLU | A | 90 | 0.571 | 28.238 | 47.339 | 1.00 | 18.11 | A |
| ATOM | 2112 | CD | GLU | A | 90 | 1.358 | 27.195 | 46.672 | 1.00 | 17.99 | A |
| ATOM | 2113 | OE1 | GLU | A | 90 | 1.537 | 26.122 | 47.269 | 1.00 | 17.80 | A |
| ATOM | 2114 | OE2 | GLU | A | 90 | 1.778 | 27.466 | 45.540 | 1.00 | 19.48 | A |
| ATOM | 2115 | C | GLU | A | 90 | −2.640 | 28.343 | 49.430 | 1.00 | 19.05 | A |
| ATOM | 2116 | O | GLU | A | 90 | −3.068 | 27.227 | 49.160 | 1.00 | 21.56 | A |
| ATOM | 2117 | N | THR | A | 91 | −3.216 | 29.165 | 50.307 | 1.00 | 18.83 | A |
| ATOM | 2118 | CA | THR | A | 91 | −4.505 | 28.775 | 50.906 | 1.00 | 17.39 | A |
| ATOM | 2119 | CB | THR | A | 91 | −4.365 | 27.932 | 52.214 | 1.00 | 16.31 | A |
| ATOM | 2120 | OG1 | THR | A | 91 | −3.676 | 28.712 | 53.163 | 1.00 | 16.46 | A |
| ATOM | 2121 | CG2 | THR | A | 91 | −3.650 | 26.654 | 51.997 | 1.00 | 11.93 | A |
| ATOM | 2122 | C | THR | A | 91 | −5.142 | 30.143 | 51.235 | 1.00 | 15.93 | A |
| ATOM | 2123 | O | THR | A | 91 | −4.452 | 31.225 | 51.074 | 1.00 | 14.38 | A |
| ATOM | 2124 | N | PHE | A | 92 | −6.430 | 30.044 | 51.621 | 1.00 | 14.99 | A |
| ATOM | 2125 | CA | PHE | A | 92 | −7.213 | 31.203 | 52.064 | 1.00 | 15.58 | A |
| ATOM | 2126 | CB | PHE | A | 92 | −7.876 | 31.983 | 50.900 | 1.00 | 15.72 | A |
| ATOM | 2127 | CG | PHE | A | 92 | −8.920 | 31.221 | 50.168 | 1.00 | 16.39 | A |
| ATOM | 2128 | CD1 | PHE | A | 92 | −10.264 | 31.409 | 50.449 | 1.00 | 15.99 | A |
| ATOM | 2129 | CD2 | PHE | A | 92 | −8.540 | 30.377 | 49.124 | 1.00 | 16.52 | A |
| ATOM | 2130 | CE1 | PHE | A | 92 | −11.263 | 30.773 | 49.690 | 1.00 | 18.53 | A |
| ATOM | 2131 | CE2 | PHE | A | 92 | −9.476 | 29.707 | 48.322 | 1.00 | 17.39 | A |
| ATOM | 2132 | CZ | PHE | A | 92 | −10.886 | 29.882 | 48.578 | 1.00 | 18.44 | A |
| ATOM | 2133 | C | PHE | A | 92 | −8.242 | 30.805 | 53.055 | 1.00 | 14.35 | A |
| ATOM | 2134 | O | PHE | A | 92 | −8.581 | 29.657 | 53.092 | 1.00 | 14.78 | A |
| ATOM | 2135 | N | ASN | A | 93 | −8.766 | 31.755 | 53.813 | 1.00 | 13.07 | A |
| ATOM | 2136 | CA | ASN | A | 93 | −9.714 | 31.493 | 54.878 | 1.00 | 11.84 | A |
| ATOM | 2137 | CB | ASN | A | 93 | −9.257 | 32.211 | 56.077 | 1.00 | 12.12 | A |
| ATOM | 2138 | CG | ASN | A | 93 | −8.055 | 31.647 | 56.603 | 1.00 | 12.16 | A |
| ATOM | 2139 | OD1 | ASN | A | 93 | −7.889 | 30.458 | 56.699 | 1.00 | 11.78 | A |
| ATOM | 2140 | ND2 | ASN | A | 93 | −7.169 | 32.508 | 56.946 | 1.00 | 13.65 | A |
| ATOM | 2141 | C | ASN | A | 93 | −11.107 | 31.792 | 54.732 | 1.00 | 10.74 | A |
| ATOM | 2142 | O | ASN | A | 93 | −11.444 | 32.821 | 54.158 | 1.00 | 10.01 | A |
| ATOM | 2143 | N | LEU | A | 94 | −11.939 | 30.915 | 55.262 | 1.00 | 10.68 | A |
| ATOM | 2144 | CA | LEU | A | 94 | −13.362 | 31.142 | 55.202 | 1.00 | 11.85 | A |
| ATOM | 2145 | CB | LEU | A | 94 | −14.033 | 29.936 | 54.596 | 1.00 | 11.21 | A |
| ATOM | 2146 | CG | LEU | A | 94 | −15.566 | 29.808 | 54.593 | 1.00 | 12.23 | A |
| ATOM | 2147 | CD1 | LEU | A | 94 | −16.166 | 30.993 | 53.718 | 1.00 | 13.28 | A |
| ATOM | 2148 | CD2 | LEU | A | 94 | −15.934 | 28.439 | 54.106 | 1.00 | 11.46 | A |
| ATOM | 2149 | C | LEU | A | 94 | −13.975 | 31.416 | 56.578 | 1.00 | 12.45 | A |
| ATOM | 2150 | O | LEU | A | 94 | −13.774 | 30.654 | 57.510 | 1.00 | 12.43 | A |
| ATOM | 2151 | N | TYR | A | 95 | −14.800 | 32.453 | 56.665 | 1.00 | 14.58 | A |
| ATOM | 2152 | CA | TYR | A | 95 | −15.509 | 32.934 | 57.901 | 1.00 | 16.11 | A |
| ATOM | 2153 | CB | TYR | A | 95 | −14.860 | 34.250 | 58.457 | 1.00 | 17.37 | A |
| ATOM | 2154 | CG | TYR | A | 95 | −13.433 | 34.175 | 58.995 | 1.00 | 17.38 | A |
| ATOM | 2155 | CD1 | TYR | A | 95 | −12.323 | 33.880 | 58.157 | 1.00 | 16.12 | A |
| ATOM | 2156 | CE1 | TYR | A | 95 | −11.035 | 33.773 | 58.685 | 1.00 | 16.68 | A |
| ATOM | 2157 | CD2 | TYR | A | 95 | −13.217 | 34.367 | 60.358 | 1.00 | 17.38 | A |
| ATOM | 2158 | CE2 | TYR | A | 95 | −11.975 | 34.265 | 60.902 | 1.00 | 17.10 | A |
| ATOM | 2159 | CZ | TYR | A | 95 | −10.881 | 33.972 | 60.086 | 1.00 | 16.95 | A |
| ATOM | 2160 | OH | TYR | A | 95 | −9.726 | 33.813 | 60.723 | 1.00 | 17.24 | A |
| ATOM | 2161 | C | TYR | A | 95 | −16.945 | 33.360 | 57.649 | 1.00 | 15.17 | A |
| ATOM | 2162 | O | TYR | A | 95 | −17.387 | 33.689 | 56.528 | 1.00 | 14.25 | A |
| ATOM | 2163 | N | TYR | A | 96 | −17.651 | 33.481 | 58.764 | 1.00 | 15.31 | A |
| ATOM | 2164 | CA | TYR | A | 96 | −19.049 | 33.954 | 58.691 | 1.00 | 14.79 | A |
| ATOM | 2165 | CB | TYR | A | 96 | −20.051 | 32.801 | 58.489 | 1.00 | 14.57 | A |
| ATOM | 2166 | CG | TYR | A | 96 | −20.276 | 31.976 | 59.696 | 1.00 | 13.64 | A |
| ATOM | 2167 | CD1 | TYR | A | 96 | −21.503 | 31.994 | 60.301 | 1.00 | 14.40 | A |
| ATOM | 2168 | CE1 | TYR | A | 96 | −21.750 | 31.254 | 61.431 | 1.00 | 15.60 | A |
| ATOM | 2169 | CD2 | TYR | A | 96 | −19.274 | 31.206 | 60.232 | 1.00 | 13.00 | A |
| ATOM | 2170 | CE2 | TYR | A | 96 | −19.482 | 30.446 | 61.362 | 1.00 | 13.72 | A |
| ATOM | 2171 | CZ | TYR | A | 96 | −20.713 | 30.444 | 61.979 | 1.00 | 14.85 | A |
| ATOM | 2172 | OH | TYR | A | 96 | −20.885 | 29.572 | 63.041 | 1.00 | 13.43 | A |
| ATOM | 2173 | C | TYR | A | 96 | −19.321 | 34.638 | 60.007 | 1.00 | 13.97 | A |
| ATOM | 2174 | O | TYR | A | 96 | −18.519 | 34.591 | 60.855 | 1.00 | 12.95 | A |
| ATOM | 2175 | N | ALA | A | 97 | −20.441 | 35.324 | 60.093 | 1.00 | 14.90 | A |
| ATOM | 2176 | CA | ALA | A | 97 | −20.986 | 35.935 | 61.308 | 1.00 | 16.05 | A |
| ATOM | 2177 | CB | ALA | A | 97 | −20.441 | 37.367 | 61.529 | 1.00 | 16.09 | A |
| ATOM | 2178 | C | ALA | A | 97 | −22.516 | 35.933 | 61.106 | 1.00 | 16.05 | A |
| ATOM | 2179 | O | ALA | A | 97 | −23.006 | 36.047 | 60.005 | 1.00 | 16.49 | A |
| ATOM | 2180 | N | GLU | A | 98 | −23.257 | 35.713 | 62.177 | 1.00 | 16.04 | A |
| ATOM | 2181 | CA | GLU | A | 98 | −24.710 | 35.685 | 62.149 | 1.00 | 16.83 | A |
| ATOM | 2182 | CB | GLU | A | 98 | −25.173 | 34.568 | 63.003 | 1.00 | 16.04 | A |
| ATOM | 2183 | CG | GLU | A | 98 | −25.241 | 33.303 | 62.337 | 1.00 | 15.83 | A |
| ATOM | 2184 | CD | GLU | A | 98 | −25.813 | 32.170 | 63.298 | 1.00 | 17.91 | A |
| ATOM | 2185 | OE1 | GLU | A | 98 | −25.029 | 31.501 | 64.068 | 1.00 | 19.30 | A |
| ATOM | 2186 | OE2 | GLU | A | 98 | −27.057 | 31.949 | 63.289 | 1.00 | 16.71 | A |
| ATOM | 2187 | C | GLU | A | 98 | −25.202 | 36.987 | 62.786 | 1.00 | 16.82 | A |
| ATOM | 2188 | O | GLU | A | 98 | −24.498 | 37.476 | 63.700 | 1.00 | 18.03 | A |
| ATOM | 2189 | N | SER | A | 99 | −26.305 | 37.574 | 62.320 | 1.00 | 14.68 | A |
| ATOM | 2190 | CA | SER | A | 99 | −26.799 | 38.703 | 63.003 | 1.00 | 14.15 | A |

TABLE 1-continued

| ATOM | 2191 | CB  | SER | A | 99  | −26.002 | 40.050 | 62.908 | 1.00 | 13.68 | A |
| ATOM | 2192 | OG  | SER | A | 99  | −26.041 | 40.773 | 61.729 | 1.00 | 13.53 | A |
| ATOM | 2193 | C   | SER | A | 99  | −28.229 | 38.919 | 62.707 | 1.00 | 14.72 | A |
| ATOM | 2194 | O   | SER | A | 99  | −28.675 | 38.491 | 61.714 | 1.00 | 13.40 | A |
| ATOM | 2195 | N   | ASP | A | 100 | −28.966 | 39.559 | 63.636 | 1.00 | 14.50 | A |
| ATOM | 2196 | CA  | ASP | A | 100 | −30.330 | 39.791 | 63.401 | 1.00 | 15.71 | A |
| ATOM | 2197 | CB  | ASP | A | 100 | −31.152 | 39.835 | 64.702 | 1.00 | 16.92 | A |
| ATOM | 2198 | CG  | ASP | A | 100 | −31.199 | 38.523 | 65.407 | 1.00 | 19.17 | A |
| ATOM | 2199 | OD1 | ASP | A | 100 | −31.517 | 37.513 | 64.703 | 1.00 | 19.49 | A |
| ATOM | 2200 | OD2 | ASP | A | 100 | −30.913 | 38.454 | 66.703 | 1.00 | 19.99 | A |
| ATOM | 2201 | C   | ASP | A | 100 | −30.541 | 41.046 | 62.605 | 1.00 | 16.56 | A |
| ATOM | 2202 | O   | ASP | A | 100 | −31.627 | 41.209 | 62.081 | 1.00 | 17.24 | A |
| ATOM | 2203 | N   | LEU | A | 101 | −29.527 | 41.886 | 62.490 | 1.00 | 16.21 | A |
| ATOM | 2204 | CA  | LEU | A | 101 | −29.594 | 43.192 | 61.824 | 1.00 | 15.59 | A |
| ATOM | 2205 | CB  | LEU | A | 101 | −29.110 | 44.365 | 62.731 | 1.00 | 17.35 | A |
| ATOM | 2206 | CG  | LEU | A | 101 | −29.383 | 44.587 | 64.202 | 1.00 | 20.31 | A |
| ATOM | 2207 | CD1 | LEU | A | 101 | −28.909 | 43.361 | 64.925 | 1.00 | 20.38 | A |
| ATOM | 2208 | CD2 | LEU | A | 101 | −28.596 | 45.820 | 64.815 | 1.00 | 21.78 | A |
| ATOM | 2209 | C   | LEU | A | 101 | −28.541 | 43.160 | 60.727 | 1.00 | 15.15 | A |
| ATOM | 2210 | O   | LEU | A | 101 | −27.517 | 42.494 | 60.897 | 1.00 | 13.01 | A |
| ATOM | 2211 | N   | ASP | A | 102 | −28.799 | 43.984 | 59.693 | 1.00 | 15.38 | A |
| ATOM | 2212 | CA  | ASP | A | 102 | −27.984 | 44.195 | 58.530 | 1.00 | 16.74 | A |
| ATOM | 2213 | CB  | ASP | A | 102 | −28.825 | 44.867 | 57.532 | 1.00 | 17.87 | A |
| ATOM | 2214 | CG  | ASP | A | 102 | −28.172 | 44.991 | 56.198 | 1.00 | 20.24 | A |
| ATOM | 2215 | OD1 | ASP | A | 102 | −26.981 | 45.278 | 56.061 | 1.00 | 20.82 | A |
| ATOM | 2216 | OD2 | ASP | A | 102 | −28.893 | 44.772 | 55.214 | 1.00 | 22.85 | A |
| ATOM | 2217 | C   | ASP | A | 102 | −26.866 | 45.151 | 58.833 | 1.00 | 17.55 | A |
| ATOM | 2218 | O   | ASP | A | 102 | −27.129 | 46.361 | 58.955 | 1.00 | 18.18 | A |
| ATOM | 2219 | N   | TYR | A | 103 | −25.612 | 44.674 | 58.892 | 1.00 | 17.54 | A |
| ATOM | 2220 | CA  | TYR | A | 103 | −24.469 | 45.564 | 59.255 | 1.00 | 17.18 | A |
| ATOM | 2221 | CB  | TYR | A | 103 | −23.133 | 44.807 | 59.425 | 1.00 | 18.78 | A |
| ATOM | 2222 | CG  | TYR | A | 103 | −22.965 | 44.114 | 60.690 | 1.00 | 21.08 | A |
| ATOM | 2223 | CD1 | TYR | A | 103 | −23.215 | 44.710 | 61.948 | 1.00 | 22.54 | A |
| ATOM | 2224 | CE1 | TYR | A | 103 | −23.067 | 43.921 | 63.196 | 1.00 | 22.15 | A |
| ATOM | 2225 | CD2 | TYR | A | 103 | −22.584 | 42.823 | 60.681 | 1.00 | 22.23 | A |
| ATOM | 2226 | CE2 | TYR | A | 103 | −22.445 | 42.069 | 61.899 | 1.00 | 22.86 | A |
| ATOM | 2227 | CZ  | TYR | A | 103 | −22.688 | 42.594 | 63.100 | 1.00 | 23.05 | A |
| ATOM | 2228 | OH  | TYR | A | 103 | −22.587 | 41.581 | 64.091 | 1.00 | 23.96 | A |
| ATOM | 2229 | C   | TYR | A | 103 | −24.163 | 46.715 | 58.302 | 1.00 | 16.77 | A |
| ATOM | 2230 | O   | TYR | A | 103 | −23.333 | 47.635 | 58.606 | 1.00 | 15.36 | A |
| ATOM | 2231 | N   | GLY | A | 104 | −24.805 | 46.687 | 57.165 | 1.00 | 16.27 | A |
| ATOM | 2232 | CA  | GLY | A | 104 | −24.529 | 47.699 | 56.198 | 1.00 | 16.52 | A |
| ATOM | 2233 | C   | GLY | A | 104 | −23.022 | 47.628 | 55.844 | 1.00 | 17.80 | A |
| ATOM | 2234 | O   | GLY | A | 104 | −22.396 | 46.560 | 55.526 | 1.00 | 18.17 | A |
| ATOM | 2235 | N   | THR | A | 105 | −22.360 | 48.781 | 55.867 | 1.00 | 18.37 | A |
| ATOM | 2236 | CA  | THR | A | 105 | −20.946 | 48.817 | 55.539 | 1.00 | 18.03 | A |
| ATOM | 2237 | CB  | THR | A | 105 | −20.694 | 50.173 | 54.925 | 1.00 | 19.27 | A |
| ATOM | 2238 | OG1 | THR | A | 105 | −20.974 | 50.101 | 53.542 | 1.00 | 20.04 | A |
| ATOM | 2239 | CG2 | THR | A | 105 | −19.335 | 50.536 | 54.991 | 1.00 | 20.09 | A |
| ATOM | 2240 | C   | THR | A | 105 | −19.939 | 48.448 | 56.693 | 1.00 | 17.66 | A |
| ATOM | 2241 | O   | THR | A | 105 | −18.730 | 48.251 | 56.517 | 1.00 | 16.55 | A |
| ATOM | 2242 | N   | ASN | A | 106 | −20.479 | 48.249 | 57.872 | 1.00 | 18.01 | A |
| ATOM | 2243 | CA  | ASN | A | 106 | −19.667 | 47.899 | 59.036 | 1.00 | 18.91 | A |
| ATOM | 2244 | CB  | ASN | A | 106 | −20.483 | 47.870 | 60.327 | 1.00 | 20.77 | A |
| ATOM | 2245 | CG  | ASN | A | 106 | −20.837 | 49.209 | 60.828 | 1.00 | 22.33 | A |
| ATOM | 2246 | OD1 | ASN | A | 106 | −21.671 | 49.336 | 61.794 | 1.00 | 24.28 | A |
| ATOM | 2247 | ND2 | ASN | A | 106 | −20.228 | 50.243 | 60.224 | 1.00 | 24.12 | A |
| ATOM | 2248 | C   | ASN | A | 106 | −19.019 | 46.577 | 59.027 | 1.00 | 17.88 | A |
| ATOM | 2249 | O   | ASN | A | 106 | −19.488 | 45.635 | 59.616 | 1.00 | 17.47 | A |
| ATOM | 2250 | N   | PHE | A | 107 | −17.896 | 46.479 | 58.436 | 1.00 | 17.57 | A |
| ATOM | 2251 | CA  | PHE | A | 107 | −17.321 | 45.192 | 58.609 | 1.00 | 18.13 | A |
| ATOM | 2252 | CB  | PHE | A | 107 | −16.576 | 44.850 | 57.350 | 1.00 | 17.71 | A |
| ATOM | 2253 | CG  | PHE | A | 107 | −15.874 | 43.556 | 57.451 | 1.00 | 17.42 | A |
| ATOM | 2254 | CD1 | PHE | A | 107 | −16.591 | 42.369 | 57.509 | 1.00 | 17.57 | A |
| ATOM | 2255 | CD2 | PHE | A | 107 | −14.503 | 43.519 | 57.556 | 1.00 | 15.83 | A |
| ATOM | 2256 | CE1 | PHE | A | 107 | −15.900 | 41.212 | 57.679 | 1.00 | 18.23 | A |
| ATOM | 2257 | CE2 | PHE | A | 107 | −13.788 | 42.355 | 57.726 | 1.00 | 15.10 | A |
| ATOM | 2258 | CZ  | PHE | A | 107 | −14.428 | 41.220 | 57.789 | 1.00 | 17.88 | A |
| ATOM | 2259 | C   | PHE | A | 107 | −16.379 | 45.074 | 59.874 | 1.00 | 19.33 | A |
| ATOM | 2260 | O   | PHE | A | 107 | −15.532 | 45.942 | 60.155 | 1.00 | 18.82 | A |
| ATOM | 2261 | N   | GLN | A | 108 | −16.487 | 44.019 | 60.620 | 1.00 | 19.60 | A |
| ATOM | 2262 | CA  | GLN | A | 108 | −15.640 | 43.896 | 61.798 | 1.00 | 20.41 | A |
| ATOM | 2263 | CB  | GLN | A | 108 | −16.473 | 43.904 | 63.082 | 1.00 | 22.43 | A |
| ATOM | 2264 | CG  | GLN | A | 108 | −17.496 | 45.134 | 63.280 | 1.00 | 25.28 | A |
| ATOM | 2265 | CD  | GLN | A | 108 | −16.718 | 46.364 | 63.879 | 1.00 | 25.17 | A |
| ATOM | 2266 | OE1 | GLN | A | 108 | −17.315 | 47.423 | 64.137 | 1.00 | 27.70 | A |
| ATOM | 2267 | NE2 | GLN | A | 108 | −15.390 | 46.206 | 64.069 | 1.00 | 23.26 | A |
| ATOM | 2268 | C   | GLN | A | 108 | −15.028 | 42.520 | 61.793 | 1.00 | 21.53 | A |
| ATOM | 2269 | O   | GLN | A | 108 | −15.685 | 41.530 | 62.285 | 1.00 | 22.45 | A |
| ATOM | 2270 | N   | LYS | A | 109 | −13.820 | 42.366 | 61.284 | 1.00 | 19.79 | A |

TABLE 1-continued

| | | | | | | | | | | |
|---|---|---|---|---|---|---|---|---|---|---|
| ATOM | 2271 | CA | LYS | A | 109 | −13.287 | 41.012 | 61.256 | 1.00 | 18.63 | A |
| ATOM | 2272 | CB | LYS | A | 109 | −11.809 | 41.058 | 60.830 | 1.00 | 18.31 | A |
| ATOM | 2273 | CG | LYS | A | 109 | −10.908 | 40.525 | 61.919 | 1.00 | 18.87 | A |
| ATOM | 2274 | CD | LYS | A | 109 | −9.470 | 40.939 | 61.728 | 1.00 | 21.42 | A |
| ATOM | 2275 | CE | LYS | A | 109 | −8.809 | 40.206 | 60.651 | 1.00 | 21.73 | A |
| ATOM | 2276 | NZ | LYS | A | 109 | −7.380 | 40.488 | 61.013 | 1.00 | 22.81 | A |
| ATOM | 2277 | C | LYS | A | 109 | −13.423 | 40.262 | 62.608 | 1.00 | 18.13 | A |
| ATOM | 2278 | O | LYS | A | 109 | −13.624 | 39.060 | 62.694 | 1.00 | 18.78 | A |
| ATOM | 2279 | N | ARG | A | 110 | −13.329 | 40.977 | 63.682 | 1.00 | 17.45 | A |
| ATOM | 2280 | CA | ARG | A | 110 | −13.368 | 40.287 | 64.955 | 1.00 | 17.69 | A |
| ATOM | 2281 | CB | ARG | A | 110 | −12.862 | 41.250 | 66.045 | 1.00 | 17.73 | A |
| ATOM | 2282 | CG | ARG | A | 110 | −11.322 | 41.059 | 66.094 | 1.00 | 18.44 | A |
| ATOM | 2283 | CD | ARG | A | 110 | −10.555 | 41.810 | 64.919 | 1.00 | 20.47 | A |
| ATOM | 2284 | NE | ARG | A | 110 | −9.106 | 41.417 | 64.948 | 1.00 | 22.91 | A |
| ATOM | 2285 | CZ | ARG | A | 110 | −8.628 | 40.151 | 64.662 | 1.00 | 24.85 | A |
| ATOM | 2286 | NH1 | ARG | A | 110 | −9.486 | 39.118 | 64.318 | 1.00 | 25.48 | A |
| ATOM | 2287 | NH2 | ARG | A | 110 | −7.324 | 39.871 | 64.717 | 1.00 | 22.96 | A |
| ATOM | 2288 | C | ARG | A | 110 | −14.622 | 39.661 | 65.314 | 1.00 | 16.37 | A |
| ATOM | 2289 | O | ARG | A | 110 | −14.601 | 38.845 | 66.205 | 1.00 | 16.01 | A |
| ATOM | 2290 | N | LEU | A | 111 | −15.663 | 40.011 | 64.555 | 1.00 | 16.52 | A |
| ATOM | 2291 | CA | LEU | A | 111 | −16.978 | 39.529 | 64.754 | 1.00 | 17.54 | A |
| ATOM | 2292 | CB | LEU | A | 111 | −17.959 | 40.574 | 64.341 | 1.00 | 17.09 | A |
| ATOM | 2293 | CG | LEU | A | 111 | −17.843 | 41.842 | 65.276 | 1.00 | 17.28 | A |
| ATOM | 2294 | CD1 | LEU | A | 111 | −19.065 | 42.772 | 64.863 | 1.00 | 17.11 | A |
| ATOM | 2295 | CD2 | LEU | A | 111 | −17.880 | 41.439 | 66.775 | 1.00 | 15.51 | A |
| ATOM | 2296 | C | LEU | A | 111 | −17.203 | 38.303 | 64.032 | 1.00 | 16.72 | A |
| ATOM | 2297 | O | LEU | A | 111 | −18.138 | 37.612 | 64.295 | 1.00 | 17.85 | A |
| ATOM | 2298 | N | PHE | A | 112 | −16.322 | 37.995 | 63.125 | 1.00 | 16.34 | A |
| ATOM | 2299 | CA | PHE | A | 112 | −16.450 | 36.737 | 62.307 | 1.00 | 16.65 | A |
| ATOM | 2300 | CB | PHE | A | 112 | −15.868 | 36.980 | 60.883 | 1.00 | 15.82 | A |
| ATOM | 2301 | CG | PHE | A | 112 | −16.806 | 37.678 | 59.985 | 1.00 | 16.56 | A |
| ATOM | 2302 | CD1 | PHE | A | 112 | −17.158 | 38.994 | 60.218 | 1.00 | 17.89 | A |
| ATOM | 2303 | CD2 | PHE | A | 112 | −17.365 | 37.004 | 58.878 | 1.00 | 17.94 | A |
| ATOM | 2304 | CE1 | PHE | A | 112 | −18.050 | 39.659 | 59.383 | 1.00 | 17.24 | A |
| ATOM | 2305 | CE2 | PHE | A | 112 | −18.237 | 37.610 | 58.032 | 1.00 | 17.18 | A |
| ATOM | 2306 | CZ | PHE | A | 112 | −18.590 | 38.952 | 58.282 | 1.00 | 19.79 | A |
| ATOM | 2307 | C | PHE | A | 112 | −15.774 | 35.500 | 62.932 | 1.00 | 15.53 | A |
| ATOM | 2308 | O | PHE | A | 112 | −14.821 | 35.597 | 63.700 | 1.00 | 15.65 | A |
| ATOM | 2309 | N | THR | A | 113 | −16.325 | 34.351 | 62.638 | 1.00 | 15.63 | A |
| ATOM | 2310 | CA | THR | A | 113 | −15.764 | 33.079 | 63.055 | 1.00 | 16.35 | A |
| ATOM | 2311 | CB | THR | A | 113 | −16.855 | 32.285 | 63.666 | 1.00 | 16.84 | A |
| ATOM | 2312 | OG1 | THR | A | 113 | −17.322 | 33.061 | 64.785 | 1.00 | 18.03 | A |
| ATOM | 2313 | CG2 | THR | A | 113 | −16.409 | 30.809 | 63.999 | 1.00 | 14.82 | A |
| ATOM | 2314 | C | THR | A | 113 | −15.198 | 32.327 | 61.822 | 1.00 | 15.72 | A |
| ATOM | 2315 | O | THR | A | 113 | −15.704 | 32.373 | 60.706 | 1.00 | 14.96 | A |
| ATOM | 2316 | N | LYS | A | 114 | −14.104 | 31.676 | 62.044 | 1.00 | 15.64 | A |
| ATOM | 2317 | CA | LYS | A | 114 | −13.443 | 31.008 | 61.014 | 1.00 | 15.90 | A |
| ATOM | 2318 | CB | LYS | A | 114 | −11.912 | 30.819 | 61.310 | 1.00 | 16.29 | A |
| ATOM | 2319 | CG | LYS | A | 114 | −11.099 | 29.965 | 60.180 | 1.00 | 16.29 | A |
| ATOM | 2320 | CD | LYS | A | 114 | −9.570 | 30.011 | 60.191 | 1.00 | 15.56 | A |
| ATOM | 2321 | CE | LYS | A | 114 | −8.940 | 28.971 | 59.236 | 1.00 | 17.03 | A |
| ATOM | 2322 | NZ | LYS | A | 114 | −7.415 | 28.710 | 59.138 | 1.00 | 13.54 | A |
| ATOM | 2323 | C | LYS | A | 114 | −14.157 | 29.679 | 60.876 | 1.00 | 16.82 | A |
| ATOM | 2324 | O | LYS | A | 114 | −14.449 | 29.032 | 61.875 | 1.00 | 16.00 | A |
| ATOM | 2325 | N | ILE | A | 115 | −14.470 | 29.301 | 59.616 | 1.00 | 16.38 | A |
| ATOM | 2326 | CA | ILE | A | 115 | −15.053 | 28.039 | 59.382 | 1.00 | 15.89 | A |
| ATOM | 2327 | CB | ILE | A | 115 | −15.992 | 28.100 | 58.230 | 1.00 | 15.93 | A |
| ATOM | 2328 | CG2 | ILE | A | 115 | −16.314 | 26.715 | 57.782 | 1.00 | 13.30 | A |
| ATOM | 2329 | CG1 | ILE | A | 115 | −17.195 | 28.951 | 58.668 | 1.00 | 16.64 | A |
| ATOM | 2330 | CD1 | ILE | A | 115 | −18.272 | 29.496 | 57.610 | 1.00 | 10.99 | A |
| ATOM | 2331 | C | ILE | A | 115 | −13.897 | 27.041 | 59.092 | 1.00 | 16.73 | A |
| ATOM | 2332 | O | ILE | A | 115 | −13.840 | 25.960 | 59.635 | 1.00 | 15.74 | A |
| ATOM | 2333 | N | ASP | A | 116 | −12.961 | 27.442 | 58.242 | 1.00 | 17.50 | A |
| ATOM | 2334 | CA | ASP | A | 116 | −11.915 | 26.546 | 57.868 | 1.00 | 17.61 | A |
| ATOM | 2335 | CB | ASP | A | 116 | −12.548 | 25.412 | 57.023 | 1.00 | 18.39 | A |
| ATOM | 2336 | CG | ASP | A | 116 | −11.629 | 24.148 | 56.836 | 1.00 | 17.79 | A |
| ATOM | 2337 | OD1 | ASP | A | 116 | −12.094 | 23.193 | 56.151 | 1.00 | 17.14 | A |
| ATOM | 2338 | OD2 | ASP | A | 116 | −10.537 | 24.091 | 57.402 | 1.00 | 18.20 | A |
| ATOM | 2339 | C | ASP | A | 116 | −10.957 | 27.343 | 56.973 | 1.00 | 17.39 | A |
| ATOM | 2340 | O | ASP | A | 116 | −11.214 | 28.461 | 56.561 | 1.00 | 16.71 | A |
| ATOM | 2341 | N | THR | A | 117 | −9.831 | 26.684 | 56.722 | 1.00 | 18.12 | A |
| ATOM | 2342 | CA | THR | A | 117 | −8.768 | 27.065 | 55.771 | 1.00 | 18.26 | A |
| ATOM | 2343 | CB | THR | A | 117 | −7.455 | 26.400 | 56.193 | 1.00 | 18.79 | A |
| ATOM | 2344 | OG1 | THR | A | 117 | −7.110 | 26.908 | 57.494 | 1.00 | 21.00 | A |
| ATOM | 2345 | CG2 | THR | A | 117 | −6.377 | 26.619 | 55.096 | 1.00 | 15.58 | A |
| ATOM | 2346 | C | THR | A | 117 | −9.215 | 26.347 | 54.433 | 1.00 | 16.73 | A |
| ATOM | 2347 | O | THR | A | 117 | −9.551 | 25.151 | 54.450 | 1.00 | 16.01 | A |
| ATOM | 2348 | N | ILE | A | 118 | −9.213 | 27.077 | 53.347 | 1.00 | 15.95 | A |
| ATOM | 2349 | CA | ILE | A | 118 | −9.545 | 26.536 | 52.040 | 1.00 | 15.82 | A |
| ATOM | 2350 | CB | ILE | A | 118 | −10.449 | 27.571 | 51.270 | 1.00 | 14.60 | A |

TABLE 1-continued

| | | | | | | | | | | |
|---|---|---|---|---|---|---|---|---|---|---|
| ATOM | 2351 | CG2 | ILE | A | 118 | −10.742 | 27.117 | 49.805 | 1.00 | 13.61 | A |
| ATOM | 2352 | CG1 | ILE | A | 118 | −11.725 | 27.826 | 52.133 | 1.00 | 13.78 | A |
| ATOM | 2353 | CD1 | ILE | A | 118 | −12.492 | 26.658 | 52.696 | 1.00 | 7.19 | A |
| ATOM | 2354 | C | ILE | A | 118 | −8.220 | 26.300 | 51.271 | 1.00 | 15.52 | A |
| ATOM | 2355 | O | ILE | A | 118 | −7.455 | 27.219 | 51.007 | 1.00 | 14.88 | A |
| ATOM | 2356 | N | ALA | A | 119 | −7.948 | 25.052 | 50.942 | 1.00 | 15.84 | A |
| ATOM | 2357 | CA | ALA | A | 119 | −6.751 | 24.637 | 50.253 | 1.00 | 16.43 | A |
| ATOM | 2358 | CB | ALA | A | 119 | −6.074 | 23.626 | 51.071 | 1.00 | 14.00 | A |
| ATOM | 2359 | C | ALA | A | 119 | −7.050 | 24.003 | 48.918 | 1.00 | 16.98 | A |
| ATOM | 2360 | O | ALA | A | 119 | −7.880 | 23.140 | 48.901 | 1.00 | 18.64 | A |
| ATOM | 2361 | N | PRO | A | 120 | −6.328 | 24.350 | 47.820 | 1.00 | 17.80 | A |
| ATOM | 2362 | CD | PRO | A | 120 | −5.112 | 25.193 | 47.718 | 1.00 | 16.98 | A |
| ATOM | 2363 | CA | PRO | A | 120 | −6.586 | 23.729 | 46.504 | 1.00 | 17.40 | A |
| ATOM | 2364 | CB | PRO | A | 120 | −5.861 | 24.631 | 45.502 | 1.00 | 17.55 | A |
| ATOM | 2365 | CG | PRO | A | 120 | −4.633 | 24.817 | 46.167 | 1.00 | 17.39 | A |
| ATOM | 2366 | C | PRO | A | 120 | −5.985 | 22.369 | 46.399 | 1.00 | 17.81 | A |
| ATOM | 2367 | O | PRO | A | 120 | −4.844 | 22.132 | 46.795 | 1.00 | 18.69 | A |
| ATOM | 2368 | N | ASP | A | 121 | −6.762 | 21.451 | 45.824 | 1.00 | 18.67 | A |
| ATOM | 2369 | CA | ASP | A | 121 | −6.275 | 20.076 | 45.509 | 1.00 | 18.28 | A |
| ATOM | 2370 | CB | ASP | A | 121 | −7.402 | 19.252 | 45.051 | 1.00 | 21.03 | A |
| ATOM | 2371 | CG | ASP | A | 121 | −8.617 | 19.451 | 45.922 | 1.00 | 24.83 | A |
| ATOM | 2372 | OD1 | ASP | A | 121 | −9.329 | 20.691 | 45.822 | 1.00 | 28.44 | A |
| ATOM | 2373 | OD2 | ASP | A | 121 | −8.844 | 18.394 | 46.670 | 1.00 | 20.99 | A |
| ATOM | 2374 | C | ASP | A | 121 | −5.311 | 20.228 | 44.338 | 1.00 | 17.03 | A |
| ATOM | 2375 | O | ASP | A | 121 | −4.451 | 19.395 | 44.165 | 1.00 | 16.57 | A |
| ATOM | 2376 | N | GLU | A | 122 | −5.447 | 21.319 | 43.599 | 1.00 | 15.97 | A |
| ATOM | 2377 | CA | GLU | A | 122 | −4.618 | 21.542 | 42.494 | 1.00 | 17.00 | A |
| ATOM | 2378 | CB | GLU | A | 122 | −5.276 | 20.994 | 41.213 | 1.00 | 16.86 | A |
| ATOM | 2379 | CG | GLU | A | 122 | −5.559 | 19.473 | 41.144 | 1.00 | 20.41 | A |
| ATOM | 2380 | CD | GLU | A | 122 | −5.887 | 18.941 | 39.688 | 1.00 | 23.62 | A |
| ATOM | 2381 | OE1 | GLU | A | 122 | −7.048 | 19.093 | 39.185 | 1.00 | 24.17 | A |
| ATOM | 2382 | OE2 | GLU | A | 122 | −4.946 | 18.385 | 39.027 | 1.00 | 26.00 | A |
| ATOM | 2383 | C | GLU | A | 122 | −4.167 | 22.995 | 42.284 | 1.00 | 16.38 | A |
| ATOM | 2384 | O | GLU | A | 122 | −4.887 | 23.946 | 41.860 | 1.00 | 16.97 | A |
| ATOM | 2385 | N | ILE | A | 123 | −2.900 | 23.149 | 42.463 | 1.00 | 15.91 | A |
| ATOM | 2386 | CA | ILE | A | 123 | −2.316 | 24.443 | 42.305 | 1.00 | 17.38 | A |
| ATOM | 2387 | CB | ILE | A | 123 | −0.971 | 24.367 | 43.115 | 1.00 | 17.70 | A |
| ATOM | 2388 | CG2 | ILE | A | 123 | −0.093 | 23.163 | 42.540 | 1.00 | 17.69 | A |
| ATOM | 2389 | CG1 | ILE | A | 123 | −0.204 | 25.587 | 42.953 | 1.00 | 19.25 | A |
| ATOM | 2390 | CD1 | ILE | A | 123 | 1.230 | 25.355 | 43.544 | 1.00 | 22.89 | A |
| ATOM | 2391 | C | ILE | A | 123 | −2.128 | 24.626 | 40.799 | 1.00 | 15.56 | A |
| ATOM | 2392 | O | ILE | A | 123 | −1.918 | 23.689 | 40.163 | 1.00 | 15.45 | A |
| ATOM | 2393 | N | THR | A | 124 | −2.165 | 25.814 | 40.244 | 1.00 | 15.05 | A |
| ATOM | 2394 | CA | THR | A | 124 | −1.959 | 25.968 | 38.794 | 1.00 | 15.55 | A |
| ATOM | 2395 | CB | THR | A | 124 | −2.804 | 27.068 | 38.247 | 1.00 | 13.97 | A |
| ATOM | 2396 | OG1 | THR | A | 124 | −4.115 | 26.619 | 38.208 | 1.00 | 13.46 | A |
| ATOM | 2397 | CG2 | THR | A | 124 | −2.447 | 27.405 | 36.932 | 1.00 | 15.40 | A |
| ATOM | 2398 | C | THR | A | 124 | −0.538 | 26.337 | 38.519 | 1.00 | 16.06 | A |
| ATOM | 2399 | O | THR | A | 124 | −0.164 | 27.475 | 38.851 | 1.00 | 18.24 | A |
| ATOM | 2400 | N | VAL | A | 125 | 0.289 | 25.479 | 37.951 | 1.00 | 15.30 | A |
| ATOM | 2401 | CA | VAL | A | 125 | 1.685 | 25.902 | 37.739 | 1.00 | 14.15 | A |
| ATOM | 2402 | CB | VAL | A | 125 | 2.688 | 24.716 | 37.643 | 1.00 | 14.84 | A |
| ATOM | 2403 | CG1 | VAL | A | 125 | 2.705 | 23.977 | 38.955 | 1.00 | 14.73 | A |
| ATOM | 2404 | CG2 | VAL | A | 125 | 2.295 | 23.725 | 36.483 | 1.00 | 15.11 | A |
| ATOM | 2405 | C | VAL | A | 125 | 1.943 | 26.795 | 36.561 | 1.00 | 13.94 | A |
| ATOM | 2406 | O | VAL | A | 125 | 1.109 | 27.042 | 35.750 | 1.00 | 12.19 | A |
| ATOM | 2407 | N | SER | A | 126 | 3.142 | 27.321 | 36.544 | 1.00 | 14.58 | A |
| ATOM | 2408 | CA | SER | A | 126 | 3.562 | 28.174 | 35.503 | 1.00 | 16.85 | A |
| ATOM | 2409 | CB | SER | A | 126 | 5.043 | 28.365 | 35.607 | 1.00 | 19.38 | A |
| ATOM | 2410 | OG | SER | A | 126 | 5.598 | 28.622 | 34.297 | 1.00 | 25.35 | A |
| ATOM | 2411 | C | SER | A | 126 | 3.230 | 27.677 | 34.076 | 1.00 | 16.00 | A |
| ATOM | 2412 | O | SER | A | 126 | 2.605 | 28.417 | 33.258 | 1.00 | 16.05 | A |
| ATOM | 2413 | N | SER | A | 127 | 3.647 | 26.463 | 33.777 | 1.00 | 15.26 | A |
| ATOM | 2414 | CA | SER | A | 127 | 3.371 | 26.007 | 32.446 | 1.00 | 15.44 | A |
| ATOM | 2415 | CB | SER | A | 127 | 4.203 | 24.792 | 32.130 | 1.00 | 14.37 | A |
| ATOM | 2416 | OG | SER | A | 127 | 3.762 | 23.767 | 32.959 | 1.00 | 15.90 | A |
| ATOM | 2417 | C | SER | A | 127 | 1.896 | 25.754 | 32.173 | 1.00 | 14.54 | A |
| ATOM | 2418 | O | SER | A | 127 | 1.561 | 25.669 | 31.056 | 1.00 | 15.91 | A |
| ATOM | 2419 | N | ASP | A | 128 | 1.045 | 25.670 | 33.211 | 1.00 | 14.80 | A |
| ATOM | 2420 | CA | ASP | A | 128 | −0.438 | 25.478 | 33.134 | 1.00 | 15.58 | A |
| ATOM | 2421 | CB | ASP | A | 128 | −1.097 | 25.349 | 34.543 | 1.00 | 17.66 | A |
| ATOM | 2422 | CG | ASP | A | 128 | −0.975 | 23.978 | 35.125 | 1.00 | 21.33 | A |
| ATOM | 2423 | OD1 | ASP | A | 128 | −1.170 | 23.805 | 36.394 | 1.00 | 22.26 | A |
| ATOM | 2424 | OD2 | ASP | A | 128 | −0.693 | 22.975 | 34.354 | 1.00 | 25.25 | A |
| ATOM | 2425 | C | ASP | A | 128 | −1.153 | 26.617 | 32.331 | 1.00 | 13.45 | A |
| ATOM | 2426 | O | ASP | A | 128 | −2.083 | 26.406 | 31.566 | 1.00 | 12.49 | A |
| ATOM | 2427 | N | PHE | A | 129 | −0.752 | 27.818 | 32.520 | 1.00 | 13.93 | A |
| ATOM | 2428 | CA | PHE | A | 129 | −1.312 | 28.837 | 31.679 | 1.00 | 17.22 | A |
| ATOM | 2429 | CB | PHE | A | 129 | −0.793 | 30.191 | 32.184 | 1.00 | 17.05 | A |
| ATOM | 2430 | CG | PHE | A | 129 | −1.139 | 30.441 | 33.600 | 1.00 | 17.73 | A |

TABLE 1-continued

| | | | | | | | | | | |
|---|---|---|---|---|---|---|---|---|---|---|
| ATOM | 2431 | CD1 | PHE | A | 129 | −0.262 | 30.097 | 34.628 | 1.00 | 17.88 | A |
| ATOM | 2432 | CD2 | PHE | A | 129 | −2.400 | 30.922 | 33.934 | 1.00 | 18.02 | A |
| ATOM | 2433 | CE1 | PHE | A | 129 | −0.646 | 30.222 | 35.962 | 1.00 | 16.12 | A |
| ATOM | 2434 | CE2 | PHE | A | 129 | −2.790 | 31.053 | 35.268 | 1.00 | 16.75 | A |
| ATOM | 2435 | CZ | PHE | A | 129 | −1.886 | 30.689 | 36.286 | 1.00 | 16.66 | A |
| ATOM | 2436 | C | PHE | A | 129 | −0.649 | 28.463 | 30.449 | 1.00 | 16.93 | A |
| ATOM | 2437 | O | PHE | A | 129 | −0.090 | 27.443 | 30.480 | 1.00 | 19.64 | A |
| ATOM | 2438 | N | GLU | A | 130 | −0.589 | 29.214 | 29.382 | 1.00 | 16.76 | A |
| ATOM | 2439 | CA | GLU | A | 130 | 0.227 | 28.725 | 28.118 | 1.00 | 16.09 | A |
| ATOM | 2440 | CB | GLU | A | 130 | 1.679 | 28.449 | 28.424 | 1.00 | 15.22 | A |
| ATOM | 2441 | CG | GLU | A | 130 | 2.645 | 29.502 | 27.986 | 1.00 | 16.93 | A |
| ATOM | 2442 | CD | GLU | A | 130 | 4.074 | 28.955 | 27.913 | 1.00 | 20.23 | A |
| ATOM | 2443 | OE1 | GLU | A | 130 | 4.901 | 29.664 | 27.260 | 1.00 | 23.39 | A |
| ATOM | 2444 | OE2 | GLU | A | 130 | 4.418 | 27.834 | 28.492 | 1.00 | 21.59 | A |
| ATOM | 2445 | C | GLU | A | 130 | −0.378 | 27.435 | 27.626 | 1.00 | 16.79 | A |
| ATOM | 2446 | O | GLU | A | 130 | −0.778 | 27.445 | 26.535 | 1.00 | 17.11 | A |
| ATOM | 2447 | N | ALA | A | 131 | −0.340 | 26.341 | 28.419 | 1.00 | 17.32 | A |
| ATOM | 2448 | CA | ALA | A | 131 | −1.079 | 25.165 | 28.170 | 1.00 | 18.32 | A |
| ATOM | 2449 | CB | ALA | A | 131 | −0.715 | 24.257 | 29.167 | 1.00 | 18.08 | A |
| ATOM | 2450 | C | ALA | A | 131 | −2.477 | 25.730 | 28.478 | 1.00 | 19.42 | A |
| ATOM | 2451 | O | ALA | A | 131 | −2.592 | 26.880 | 28.989 | 1.00 | 22.36 | A |
| ATOM | 2452 | N | ARG | A | 132 | −3.599 | 25.095 | 28.244 | 1.00 | 18.69 | A |
| ATOM | 2453 | CA | ARG | A | 132 | −4.726 | 25.950 | 28.725 | 1.00 | 16.77 | A |
| ATOM | 2454 | CB | ARG | A | 132 | −5.636 | 26.248 | 27.562 | 1.00 | 18.47 | A |
| ATOM | 2455 | CG | ARG | A | 132 | −5.750 | 27.745 | 27.137 | 1.00 | 20.86 | A |
| ATOM | 2456 | CD | ARG | A | 132 | −4.500 | 28.474 | 26.757 | 1.00 | 19.10 | A |
| ATOM | 2457 | NE | ARG | A | 132 | −4.750 | 29.790 | 26.148 | 1.00 | 16.56 | A |
| ATOM | 2458 | CZ | ARG | A | 132 | −3.988 | 30.886 | 26.383 | 1.00 | 16.52 | A |
| ATOM | 2459 | NH1 | ARG | A | 132 | −2.990 | 30.828 | 27.232 | 1.00 | 16.01 | A |
| ATOM | 2460 | NH2 | ARG | A | 132 | −4.095 | 32.020 | 25.669 | 1.00 | 13.84 | A |
| ATOM | 2461 | C | ARG | A | 132 | −5.327 | 25.029 | 29.756 | 1.00 | 15.97 | A |
| ATOM | 2462 | O | ARG | A | 132 | −6.441 | 24.569 | 29.688 | 1.00 | 14.52 | A |
| ATOM | 2463 | N | HIS | A | 133 | −4.517 | 24.746 | 30.726 | 1.00 | 16.18 | A |
| ATOM | 2464 | CA | HIS | A | 133 | −4.893 | 23.823 | 31.725 | 1.00 | 17.38 | A |
| ATOM | 2465 | CB | HIS | A | 133 | −3.889 | 22.645 | 31.801 | 1.00 | 19.77 | A |
| ATOM | 2466 | CG | HIS | A | 133 | −3.820 | 21.795 | 30.569 | 1.00 | 22.45 | A |
| ATOM | 2467 | CD2 | HIS | A | 133 | −4.362 | 21.935 | 29.313 | 1.00 | 23.99 | A |
| ATOM | 2468 | ND1 | HIS | A | 133 | −3.130 | 20.588 | 30.556 | 1.00 | 24.20 | A |
| ATOM | 2469 | CE1 | HIS | A | 133 | −3.253 | 20.023 | 29.349 | 1.00 | 23.96 | A |
| ATOM | 2470 | NE2 | HIS | A | 133 | −3.995 | 20.816 | 28.578 | 1.00 | 23.21 | A |
| ATOM | 2471 | C | HIS | A | 133 | −4.963 | 24.478 | 33.092 | 1.00 | 17.44 | A |
| ATOM | 2472 | O | HIS | A | 133 | −4.365 | 23.961 | 34.088 | 1.00 | 16.09 | A |
| ATOM | 2473 | N | VAL | A | 134 | −5.690 | 25.599 | 33.180 | 1.00 | 18.14 | A |
| ATOM | 2474 | CA | VAL | A | 134 | −5.757 | 26.229 | 34.528 | 1.00 | 19.36 | A |
| ATOM | 2475 | CB | VAL | A | 134 | −6.376 | 27.591 | 34.454 | 1.00 | 18.62 | A |
| ATOM | 2476 | CG1 | VAL | A | 134 | −6.472 | 28.157 | 35.826 | 1.00 | 18.67 | A |
| ATOM | 2477 | CG2 | VAL | A | 134 | −5.473 | 28.462 | 33.654 | 1.00 | 16.73 | A |
| ATOM | 2478 | C | VAL | A | 134 | −6.536 | 25.279 | 35.490 | 1.00 | 19.78 | A |
| ATOM | 2479 | O | VAL | A | 134 | −7.496 | 24.600 | 35.075 | 1.00 | 21.16 | A |
| ATOM | 2480 | N | LYS | A | 135 | −6.095 | 25.152 | 36.730 | 1.00 | 18.73 | A |
| ATOM | 2481 | CA | LYS | A | 135 | −6.819 | 24.228 | 37.616 | 1.00 | 17.83 | A |
| ATOM | 2482 | CB | LYS | A | 135 | −5.807 | 23.424 | 38.448 | 1.00 | 17.21 | A |
| ATOM | 2483 | CG | LYS | A | 135 | −4.605 | 22.951 | 37.727 | 1.00 | 15.58 | A |
| ATOM | 2484 | CD | LYS | A | 135 | −5.036 | 22.087 | 36.574 | 1.00 | 18.48 | A |
| ATOM | 2485 | CE | LYS | A | 135 | −3.866 | 21.168 | 36.147 | 1.00 | 20.04 | A |
| ATOM | 2486 | NZ | LYS | A | 135 | −4.299 | 20.273 | 34.987 | 1.00 | 20.60 | A |
| ATOM | 2487 | C | LYS | A | 135 | −7.886 | 24.883 | 38.550 | 1.00 | 16.46 | A |
| ATOM | 2488 | O | LYS | A | 135 | −7.627 | 25.714 | 39.417 | 1.00 | 15.08 | A |
| ATOM | 2489 | N | LEU | A | 136 | −9.111 | 24.439 | 38.292 | 1.00 | 16.27 | A |
| ATOM | 2490 | CA | LEU | A | 136 | −10.317 | 24.834 | 38.985 | 1.00 | 16.45 | A |
| ATOM | 2491 | CB | LEU | A | 136 | −11.383 | 24.858 | 37.946 | 1.00 | 16.50 | A |
| ATOM | 2492 | CG | LEU | A | 136 | −12.595 | 25.597 | 38.350 | 1.00 | 16.78 | A |
| ATOM | 2493 | CD1 | LEU | A | 136 | −13.241 | 24.627 | 39.277 | 1.00 | 18.17 | A |
| ATOM | 2494 | CD2 | LEU | A | 136 | −12.315 | 26.942 | 38.982 | 1.00 | 14.56 | A |
| ATOM | 2495 | C | LEU | A | 136 | −10.600 | 23.835 | 40.139 | 1.00 | 16.32 | A |
| ATOM | 2496 | O | LEU | A | 136 | −10.750 | 22.644 | 39.951 | 1.00 | 16.33 | A |
| ATOM | 2497 | N | ASN | A | 137 | −10.596 | 24.353 | 41.363 | 1.00 | 16.39 | A |
| ATOM | 2498 | CA | ASN | A | 137 | −10.850 | 23.524 | 42.566 | 1.00 | 16.74 | A |
| ATOM | 2499 | CB | ASN | A | 137 | −9.871 | 23.892 | 43.685 | 1.00 | 15.25 | A |
| ATOM | 2500 | CG | ASN | A | 137 | −8.452 | 23.530 | 43.300 | 1.00 | 15.41 | A |
| ATOM | 2501 | OD1 | ASN | A | 137 | −8.028 | 22.366 | 43.427 | 1.00 | 10.58 | A |
| ATOM | 2502 | ND2 | ASN | A | 137 | −7.711 | 24.535 | 42.810 | 1.00 | 14.69 | A |
| ATOM | 2503 | C | ASN | A | 137 | −12.244 | 23.662 | 43.082 | 1.00 | 15.08 | A |
| ATOM | 2504 | O | ASN | A | 137 | −12.844 | 24.683 | 42.934 | 1.00 | 15.46 | A |
| ATOM | 2505 | N | VAL | A | 138 | −12.800 | 22.630 | 43.670 | 1.00 | 15.12 | A |
| ATOM | 2506 | CA | VAL | A | 138 | −14.144 | 22.834 | 44.209 | 1.00 | 15.70 | A |
| ATOM | 2507 | CB | VAL | A | 138 | −15.233 | 21.997 | 43.540 | 1.00 | 14.13 | A |
| ATOM | 2508 | CG1 | VAL | A | 138 | −16.480 | 22.304 | 44.141 | 1.00 | 13.82 | A |
| ATOM | 2509 | CG2 | VAL | A | 138 | −15.315 | 22.291 | 42.116 | 1.00 | 12.43 | A |
| ATOM | 2510 | C | VAL | A | 138 | −14.035 | 22.453 | 45.633 | 1.00 | 13.50 | A |

TABLE 1-continued

| | | | | | | | | | | |
|---|---|---|---|---|---|---|---|---|---|---|
| ATOM | 2511 | O | VAL | A | 138 | −13.567 | 21.403 | 45.950 | 1.00 | 13.10 | A |
| ATOM | 2512 | N | GLU | A | 139 | −14.425 | 23.363 | 46.511 | 1.00 | 14.73 | A |
| ATOM | 2513 | CA | GLU | A | 139 | −14.335 | 23.033 | 47.932 | 1.00 | 16.50 | A |
| ATOM | 2514 | CB | GLU | A | 139 | −13.186 | 23.796 | 48.575 | 1.00 | 14.98 | A |
| ATOM | 2515 | CG | GLU | A | 139 | −11.803 | 23.266 | 48.364 | 1.00 | 12.51 | A |
| ATOM | 2516 | CD | GLU | A | 139 | −11.619 | 21.920 | 48.901 | 1.00 | 13.08 | A |
| ATOM | 2517 | OE1 | GLU | A | 139 | −12.391 | 21.506 | 49.769 | 1.00 | 14.13 | A |
| ATOM | 2518 | OE2 | GLU | A | 139 | −10.670 | 21.195 | 48.490 | 1.00 | 14.62 | A |
| ATOM | 2519 | C | GLU | A | 139 | −15.657 | 23.366 | 48.552 | 1.00 | 17.15 | A |
| ATOM | 2520 | O | GLU | A | 139 | −16.223 | 24.406 | 48.245 | 1.00 | 18.65 | A |
| ATOM | 2521 | N | GLU | A | 140 | −16.171 | 22.495 | 49.398 | 1.00 | 18.43 | A |
| ATOM | 2522 | CA | GLU | A | 140 | −17.467 | 22.780 | 50.014 | 1.00 | 19.20 | A |
| ATOM | 2523 | CB | GLU | A | 140 | −18.593 | 21.819 | 49.576 | 1.00 | 21.05 | A |
| ATOM | 2524 | CG | GLU | A | 140 | −19.955 | 22.098 | 50.298 | 1.00 | 21.51 | A |
| ATOM | 2525 | CD | GLU | A | 140 | −21.206 | 21.645 | 49.532 | 1.00 | 22.50 | A |
| ATOM | 2526 | OE1 | GLU | A | 140 | −21.587 | 20.401 | 49.716 | 1.00 | 20.99 | A |
| ATOM | 2527 | OE2 | GLU | A | 140 | −21.738 | 22.561 | 48.760 | 1.00 | 21.17 | A |
| ATOM | 2528 | C | GLU | A | 140 | −17.318 | 22.578 | 51.455 | 1.00 | 18.30 | A |
| ATOM | 2529 | O | GLU | A | 140 | −16.613 | 21.694 | 51.824 | 1.00 | 17.70 | A |
| ATOM | 2530 | N | ARG | A | 141 | −18.003 | 23.406 | 52.265 | 1.00 | 17.54 | A |
| ATOM | 2531 | CA | ARG | A | 141 | −17.920 | 23.317 | 53.722 | 1.00 | 16.16 | A |
| ATOM | 2532 | CB | ARG | A | 141 | −16.975 | 24.387 | 54.362 | 1.00 | 16.13 | A |
| ATOM | 2533 | CG | ARG | A | 141 | −15.468 | 24.396 | 53.924 | 1.00 | 14.95 | A |
| ATOM | 2534 | CD | ARG | A | 141 | −14.572 | 23.598 | 54.787 | 1.00 | 14.90 | A |
| ATOM | 2535 | NE | ARG | A | 141 | −13.905 | 22.646 | 53.936 | 1.00 | 19.63 | A |
| ATOM | 2536 | CZ | ARG | A | 141 | −12.788 | 22.875 | 53.246 | 1.00 | 21.12 | A |
| ATOM | 2537 | NH1 | ARG | A | 141 | −12.142 | 24.007 | 53.321 | 1.00 | 24.71 | A |
| ATOM | 2538 | NH2 | ARG | A | 141 | −12.445 | 22.078 | 52.269 | 1.00 | 23.25 | A |
| ATOM | 2539 | C | ARG | A | 141 | −19.297 | 23.623 | 54.165 | 1.00 | 16.33 | A |
| ATOM | 2540 | O | ARG | A | 141 | −20.133 | 24.040 | 53.389 | 1.00 | 15.48 | A |
| ATOM | 2541 | N | SER | A | 142 | −19.512 | 23.475 | 55.449 | 1.00 | 16.69 | A |
| ATOM | 2542 | CA | SER | A | 142 | −20.811 | 23.737 | 55.958 | 1.00 | 17.43 | A |
| ATOM | 2543 | CB | SER | A | 142 | −21.663 | 22.497 | 55.758 | 1.00 | 17.22 | A |
| ATOM | 2544 | OG | SER | A | 142 | −21.450 | 21.569 | 56.777 | 1.00 | 20.06 | A |
| ATOM | 2545 | C | SER | A | 142 | −20.824 | 24.223 | 57.404 | 1.00 | 17.75 | A |
| ATOM | 2546 | O | SER | A | 142 | −19.934 | 23.958 | 58.201 | 1.00 | 18.77 | A |
| ATOM | 2547 | N | VAL | A | 143 | −21.838 | 24.954 | 57.759 | 1.00 | 17.53 | A |
| ATOM | 2548 | CA | VAL | A | 143 | −21.859 | 25.452 | 59.080 | 1.00 | 17.98 | A |
| ATOM | 2549 | CB | VAL | A | 143 | −21.033 | 26.804 | 59.185 | 1.00 | 18.53 | A |
| ATOM | 2550 | CG1 | VAL | A | 143 | −21.717 | 27.949 | 58.377 | 1.00 | 18.87 | A |
| ATOM | 2551 | CG2 | VAL | A | 143 | −20.898 | 27.170 | 60.620 | 1.00 | 18.81 | A |
| ATOM | 2552 | C | VAL | A | 143 | −23.277 | 25.544 | 59.679 | 1.00 | 17.11 | A |
| ATOM | 2553 | O | VAL | A | 143 | −24.269 | 25.588 | 58.970 | 1.00 | 15.63 | A |
| ATOM | 2554 | N | GLY | A | 144 | −23.356 | 25.461 | 61.012 | 1.00 | 16.75 | A |
| ATOM | 2555 | CA | GLY | A | 144 | −24.663 | 25.493 | 61.642 | 1.00 | 17.48 | A |
| ATOM | 2556 | C | GLY | A | 144 | −24.702 | 24.825 | 63.010 | 1.00 | 17.29 | A |
| ATOM | 2557 | O | GLY | A | 144 | −23.745 | 24.257 | 63.448 | 1.00 | 18.36 | A |
| ATOM | 2558 | N | PRO | A | 145 | −25.831 | 24.877 | 63.699 | 1.00 | 16.61 | A |
| ATOM | 2559 | CD | PRO | A | 145 | −26.125 | 24.003 | 64.832 | 1.00 | 15.62 | A |
| ATOM | 2560 | CA | PRO | A | 145 | −27.075 | 25.554 | 63.212 | 1.00 | 17.28 | A |
| ATOM | 2561 | CB | PRO | A | 145 | −28.182 | 24.952 | 64.050 | 1.00 | 15.36 | A |
| ATOM | 2562 | CG | PRO | A | 145 | −27.514 | 24.511 | 65.251 | 1.00 | 14.52 | A |
| ATOM | 2563 | C | PRO | A | 145 | −27.129 | 27.051 | 63.260 | 1.00 | 17.91 | A |
| ATOM | 2564 | O | PRO | A | 145 | −26.682 | 27.663 | 64.197 | 1.00 | 19.36 | A |
| ATOM | 2565 | N | LEU | A | 146 | −27.664 | 27.661 | 62.230 | 1.00 | 18.61 | A |
| ATOM | 2566 | CA | LEU | A | 146 | −27.728 | 29.101 | 62.174 | 1.00 | 18.08 | A |
| ATOM | 2567 | CB | LEU | A | 146 | −27.793 | 29.511 | 60.733 | 1.00 | 17.61 | A |
| ATOM | 2568 | CG | LEU | A | 146 | −26.448 | 29.981 | 60.097 | 1.00 | 17.71 | A |
| ATOM | 2569 | CD1 | LEU | A | 146 | −25.325 | 29.104 | 60.545 | 1.00 | 15.07 | A |
| ATOM | 2570 | CD2 | LEU | A | 146 | −26.614 | 30.067 | 58.576 | 1.00 | 14.26 | A |
| ATOM | 2571 | C | LEU | A | 146 | −29.034 | 29.353 | 62.872 | 1.00 | 19.06 | A |
| ATOM | 2572 | O | LEU | A | 146 | −29.975 | 28.513 | 62.791 | 1.00 | 19.16 | A |
| ATOM | 2573 | N | THR | A | 147 | −29.136 | 30.515 | 63.526 | 1.00 | 18.42 | A |
| ATOM | 2574 | CA | THR | A | 147 | −30.362 | 30.863 | 64.269 | 1.00 | 17.55 | A |
| ATOM | 2575 | CB | THR | A | 147 | −30.202 | 30.609 | 65.815 | 1.00 | 17.02 | A |
| ATOM | 2576 | OG1 | THR | A | 147 | −29.216 | 31.528 | 66.365 | 1.00 | 16.67 | A |
| ATOM | 2577 | CG2 | THR | A | 147 | −29.862 | 29.225 | 66.061 | 1.00 | 14.10 | A |
| ATOM | 2578 | C | THR | A | 147 | −30.839 | 32.298 | 64.123 | 1.00 | 16.88 | A |
| ATOM | 2579 | O | THR | A | 147 | −32.005 | 32.545 | 64.449 | 1.00 | 17.08 | A |
| ATOM | 2580 | N | ARG | A | 148 | −29.967 | 33.200 | 63.659 | 1.00 | 16.22 | A |
| ATOM | 2581 | CA | ARG | A | 148 | −30.316 | 34.639 | 63.503 | 1.00 | 15.89 | A |
| ATOM | 2582 | CB | ARG | A | 148 | −29.062 | 35.541 | 63.497 | 1.00 | 16.69 | A |
| ATOM | 2583 | CG | ARG | A | 148 | −28.038 | 35.232 | 64.583 | 1.00 | 17.98 | A |
| ATOM | 2584 | CD | ARG | A | 148 | −28.543 | 35.611 | 65.942 | 1.00 | 17.51 | A |
| ATOM | 2585 | NE | ARG | A | 148 | −29.354 | 34.517 | 66.526 | 1.00 | 19.64 | A |
| ATOM | 2586 | CZ | ARG | A | 148 | −30.469 | 34.723 | 67.227 | 1.00 | 20.42 | A |
| ATOM | 2587 | NH1 | ARG | A | 148 | −30.917 | 35.982 | 67.398 | 1.00 | 21.38 | A |
| ATOM | 2588 | NH2 | ARG | A | 148 | −31.089 | 33.711 | 67.817 | 1.00 | 18.15 | A |
| ATOM | 2589 | C | ARG | A | 148 | −31.129 | 34.947 | 62.287 | 1.00 | 14.37 | A |
| ATOM | 2590 | O | ARG | A | 148 | −31.299 | 34.104 | 61.468 | 1.00 | 13.36 | A |

TABLE 1-continued

| | | | | | | | | | | |
|---|---|---|---|---|---|---|---|---|---|---|
| ATOM | 2591 | N | LYS | A | 149 | −31.579 | 36.168 | 62.154 | 1.00 | 13.83 | A |
| ATOM | 2592 | CA | LYS | A | 149 | −32.416 | 36.489 | 61.083 | 1.00 | 14.61 | A |
| ATOM | 2593 | CB | LYS | A | 149 | −32.897 | 37.930 | 61.237 | 1.00 | 15.01 | A |
| ATOM | 2594 | CG | LYS | A | 149 | −34.057 | 38.412 | 60.378 | 1.00 | 15.29 | A |
| ATOM | 2595 | CD | LYS | A | 149 | −34.424 | 39.801 | 60.648 | 1.00 | 17.79 | A |
| ATOM | 2596 | CE | LYS | A | 149 | −35.340 | 40.284 | 59.560 | 1.00 | 19.23 | A |
| ATOM | 2597 | NZ | LYS | A | 149 | −34.937 | 41.563 | 58.825 | 1.00 | 21.75 | A |
| ATOM | 2598 | C | LYS | A | 149 | −31.590 | 36.310 | 59.859 | 1.00 | 15.86 | A |
| ATOM | 2599 | O | LYS | A | 149 | −32.102 | 35.907 | 58.851 | 1.00 | 15.91 | A |
| ATOM | 2600 | N | GLY | A | 150 | −30.280 | 36.558 | 59.982 | 1.00 | 16.26 | A |
| ATOM | 2601 | CA | GLY | A | 150 | −29.339 | 36.463 | 58.862 | 1.00 | 15.32 | A |
| ATOM | 2602 | C | GLY | A | 150 | −27.814 | 36.239 | 59.124 | 1.00 | 14.43 | A |
| ATOM | 2603 | O | GLY | A | 150 | −27.379 | 35.958 | 60.227 | 1.00 | 13.14 | A |
| ATOM | 2604 | N | PHE | A | 151 | −27.041 | 36.352 | 58.039 | 1.00 | 13.31 | A |
| ATOM | 2605 | CA | PHE | A | 151 | −25.682 | 36.028 | 58.018 | 1.00 | 12.33 | A |
| ATOM | 2606 | CB | PHE | A | 151 | −25.526 | 34.554 | 58.108 | 1.00 | 13.58 | A |
| ATOM | 2607 | CG | PHE | A | 151 | −25.881 | 33.854 | 56.916 | 1.00 | 14.77 | A |
| ATOM | 2608 | CD1 | PHE | A | 151 | −24.930 | 33.577 | 55.924 | 1.00 | 14.61 | A |
| ATOM | 2609 | CD2 | PHE | A | 151 | −27.120 | 33.350 | 56.724 | 1.00 | 16.07 | A |
| ATOM | 2610 | CE1 | PHE | A | 151 | −25.221 | 32.818 | 54.822 | 1.00 | 12.57 | A |
| ATOM | 2611 | CE2 | PHE | A | 151 | −27.356 | 32.567 | 55.536 | 1.00 | 14.88 | A |
| ATOM | 2612 | CZ | PHE | A | 151 | −26.381 | 32.330 | 54.638 | 1.00 | 13.09 | A |
| ATOM | 2613 | C | PHE | A | 151 | −24.843 | 36.538 | 56.852 | 1.00 | 12.81 | A |
| ATOM | 2614 | O | PHE | A | 151 | −25.378 | 36.968 | 55.805 | 1.00 | 11.71 | A |
| ATOM | 2615 | N | TYR | A | 152 | −23.510 | 36.522 | 57.094 | 1.00 | 11.83 | A |
| ATOM | 2616 | CA | TYR | A | 152 | −22.502 | 36.957 | 56.211 | 1.00 | 11.41 | A |
| ATOM | 2617 | CB | TYR | A | 152 | −21.777 | 38.187 | 56.695 | 1.00 | 12.88 | A |
| ATOM | 2618 | CG | TYR | A | 152 | −22.576 | 39.456 | 56.766 | 1.00 | 13.73 | A |
| ATOM | 2619 | CD1 | TYR | A | 152 | −23.156 | 39.827 | 57.909 | 1.00 | 12.41 | A |
| ATOM | 2620 | CE1 | TYR | A | 152 | −23.885 | 40.918 | 57.962 | 1.00 | 14.83 | A |
| ATOM | 2621 | CD2 | TYR | A | 152 | −22.747 | 40.231 | 55.692 | 1.00 | 13.12 | A |
| ATOM | 2622 | CE2 | TYR | A | 152 | −23.474 | 41.332 | 55.762 | 1.00 | 14.32 | A |
| ATOM | 2623 | CZ | TYR | A | 152 | −24.075 | 41.709 | 56.881 | 1.00 | 14.37 | A |
| ATOM | 2624 | OH | TYR | A | 152 | −24.912 | 42.884 | 56.879 | 1.00 | 14.66 | A |
| ATOM | 2625 | C | TYR | A | 152 | −21.472 | 35.918 | 56.115 | 1.00 | 12.73 | A |
| ATOM | 2626 | O | TYR | A | 152 | −21.174 | 35.174 | 57.015 | 1.00 | 12.39 | A |
| ATOM | 2627 | N | LEU | A | 153 | −20.900 | 35.885 | 54.949 | 1.00 | 12.34 | A |
| ATOM | 2628 | CA | LEU | A | 153 | −19.824 | 35.042 | 54.690 | 1.00 | 12.32 | A |
| ATOM | 2629 | CB | LEU | A | 153 | −20.205 | 34.227 | 53.512 | 1.00 | 13.52 | A |
| ATOM | 2630 | CG | LEU | A | 153 | −20.286 | 32.792 | 53.658 | 1.00 | 15.11 | A |
| ATOM | 2631 | CD1 | LEU | A | 153 | −21.089 | 32.379 | 54.833 | 1.00 | 16.91 | A |
| ATOM | 2632 | CD2 | LEU | A | 153 | −20.802 | 32.266 | 52.368 | 1.00 | 15.24 | A |
| ATOM | 2633 | C | LEU | A | 153 | −18.668 | 36.011 | 54.366 | 1.00 | 12.63 | A |
| ATOM | 2634 | O | LEU | A | 153 | −18.897 | 37.135 | 53.812 | 1.00 | 12.38 | A |
| ATOM | 2635 | N | ALA | A | 154 | −17.433 | 35.610 | 54.681 | 1.00 | 12.02 | A |
| ATOM | 2636 | CA | ALA | A | 154 | −16.304 | 36.449 | 54.324 | 1.00 | 12.50 | A |
| ATOM | 2637 | CB | ALA | A | 154 | −16.011 | 37.539 | 55.447 | 1.00 | 12.18 | A |
| ATOM | 2638 | C | ALA | A | 154 | −15.051 | 35.624 | 54.016 | 1.00 | 13.66 | A |
| ATOM | 2639 | O | ALA | A | 154 | −14.813 | 34.528 | 54.494 | 1.00 | 12.69 | A |
| ATOM | 2640 | N | PHE | A | 155 | −14.241 | 36.199 | 53.184 | 1.00 | 13.96 | A |
| ATOM | 2641 | CA | PHE | A | 155 | −13.036 | 35.558 | 52.824 | 1.00 | 14.10 | A |
| ATOM | 2642 | CB | PHE | A | 155 | −13.071 | 35.266 | 51.335 | 1.00 | 16.08 | A |
| ATOM | 2643 | CG | PHE | A | 155 | −14.345 | 34.561 | 50.850 | 1.00 | 16.01 | A |
| ATOM | 2644 | CD1 | PHE | A | 155 | −15.470 | 35.248 | 50.639 | 1.00 | 16.10 | A |
| ATOM | 2645 | CD2 | PHE | A | 155 | −14.376 | 33.241 | 50.665 | 1.00 | 15.30 | A |
| ATOM | 2646 | CE1 | PHE | A | 155 | −16.487 | 34.639 | 50.302 | 1.00 | 16.20 | A |
| ATOM | 2647 | CE2 | PHE | A | 155 | −15.461 | 32.617 | 50.300 | 1.00 | 16.47 | A |
| ATOM | 2648 | CZ | PHE | A | 155 | −16.478 | 33.288 | 50.123 | 1.00 | 16.92 | A |
| ATOM | 2649 | C | PHE | A | 155 | −11.697 | 36.397 | 53.166 | 1.00 | 14.58 | A |
| ATOM | 2650 | O | PHE | A | 155 | −11.445 | 37.591 | 52.803 | 1.00 | 13.24 | A |
| ATOM | 2651 | N | GLN | A | 156 | −10.807 | 35.700 | 53.823 | 1.00 | 13.93 | A |
| ATOM | 2652 | CA | GLN | A | 156 | −9.625 | 36.323 | 54.112 | 1.00 | 13.71 | A |
| ATOM | 2653 | CB | GLN | A | 156 | −9.379 | 36.203 | 55.602 | 1.00 | 13.83 | A |
| ATOM | 2654 | CG | GLN | A | 156 | −8.257 | 36.950 | 56.057 | 1.00 | 13.02 | A |
| ATOM | 2655 | CD | GLN | A | 156 | −7.571 | 36.311 | 57.281 | 1.00 | 14.74 | A |
| ATOM | 2656 | OE1 | GLN | A | 156 | −7.728 | 35.132 | 57.614 | 1.00 | 15.14 | A |
| ATOM | 2657 | NE2 | GLN | A | 156 | −6.783 | 37.120 | 57.961 | 1.00 | 14.94 | A |
| ATOM | 2658 | C | GLN | A | 156 | −8.477 | 35.764 | 53.289 | 1.00 | 13.37 | A |
| ATOM | 2659 | O | GLN | A | 156 | −8.144 | 34.588 | 53.340 | 1.00 | 12.61 | A |
| ATOM | 2660 | N | ASP | A | 157 | −7.925 | 36.641 | 52.486 | 1.00 | 13.45 | A |
| ATOM | 2661 | CA | ASP | A | 157 | −6.735 | 36.333 | 51.769 | 1.00 | 13.90 | A |
| ATOM | 2662 | CB | ASP | A | 157 | −6.657 | 37.129 | 50.447 | 1.00 | 12.65 | A |
| ATOM | 2663 | CG | ASP | A | 157 | −5.218 | 37.263 | 49.918 | 1.00 | 10.99 | A |
| ATOM | 2664 | OD1 | ASP | A | 157 | −4.764 | 38.356 | 49.670 | 1.00 | 10.97 | A |
| ATOM | 2665 | OD2 | ASP | A | 157 | −4.556 | 36.263 | 49.760 | 1.00 | 9.35 | A |
| ATOM | 2666 | C | ASP | A | 157 | −5.518 | 36.691 | 52.692 | 1.00 | 14.12 | A |
| ATOM | 2667 | O | ASP | A | 157 | −5.392 | 37.778 | 53.263 | 1.00 | 12.79 | A |
| ATOM | 2668 | N | ILE | A | 158 | −4.579 | 35.759 | 52.672 | 1.00 | 14.90 | A |
| ATOM | 2669 | CA | ILE | A | 158 | −3.407 | 35.849 | 53.505 | 1.00 | 15.25 | A |
| ATOM | 2670 | CB | ILE | A | 158 | −3.426 | 34.544 | 54.397 | 1.00 | 17.06 | A |

TABLE 1-continued

| | | | | | | | | | | |
|---|---|---|---|---|---|---|---|---|---|---|
| ATOM | 2671 | CG2 | ILE | A | 158 | −2.443 | 33.544 | 54.027 | 1.00 | 17.78 | A |
| ATOM | 2672 | CG1 | ILE | A | 158 | −3.447 | 34.949 | 55.787 | 1.00 | 17.51 | A |
| ATOM | 2673 | CD1 | ILE | A | 158 | −4.757 | 35.545 | 56.100 | 1.00 | 19.43 | A |
| ATOM | 2674 | C | ILE | A | 158 | −2.138 | 36.059 | 52.749 | 1.00 | 15.38 | A |
| ATOM | 2675 | O | ILE | A | 158 | −1.064 | 35.821 | 53.283 | 1.00 | 13.62 | A |
| ATOM | 2676 | N | GLY | A | 159 | −2.254 | 36.599 | 51.542 | 1.00 | 15.77 | A |
| ATOM | 2677 | CA | GLY | A | 159 | −1.097 | 36.712 | 50.680 | 1.00 | 17.22 | A |
| ATOM | 2678 | C | GLY | A | 159 | −0.931 | 35.557 | 49.594 | 1.00 | 18.21 | A |
| ATOM | 2679 | O | GLY | A | 159 | 0.196 | 35.154 | 49.117 | 1.00 | 19.55 | A |
| ATOM | 2680 | N | ALA | A | 160 | −2.063 | 34.965 | 49.212 | 1.00 | 17.80 | A |
| ATOM | 2681 | CA | ALA | A | 160 | −2.121 | 33.947 | 48.142 | 1.00 | 16.39 | A |
| ATOM | 2682 | CB | ALA | A | 160 | −3.070 | 32.938 | 48.487 | 1.00 | 13.65 | A |
| ATOM | 2683 | C | ALA | A | 160 | −2.564 | 34.706 | 46.851 | 1.00 | 16.03 | A |
| ATOM | 2684 | O | ALA | A | 160 | −2.943 | 35.866 | 46.905 | 1.00 | 16.85 | A |
| ATOM | 2685 | N | CYS | A | 161 | −2.415 | 34.033 | 45.709 | 1.00 | 16.56 | A |
| ATOM | 2686 | CA | CYS | A | 161 | −2.797 | 34.457 | 44.381 | 1.00 | 15.69 | A |
| ATOM | 2687 | C | CYS | A | 161 | −3.995 | 33.557 | 44.102 | 1.00 | 16.70 | A |
| ATOM | 2688 | O | CYS | A | 161 | −3.909 | 32.436 | 43.476 | 1.00 | 19.03 | A |
| ATOM | 2689 | CB | CYS | A | 161 | −1.731 | 34.174 | 43.315 | 1.00 | 12.72 | A |
| ATOM | 2690 | SG | CYS | A | 161 | −1.995 | 35.055 | 41.728 | 1.00 | 12.05 | A |
| ATOM | 2691 | N | VAL | A | 162 | −5.146 | 34.032 | 44.558 | 1.00 | 17.69 | A |
| ATOM | 2692 | CA | VAL | A | 162 | −6.410 | 33.301 | 44.360 | 1.00 | 18.16 | A |
| ATOM | 2693 | CB | VAL | A | 162 | −7.206 | 33.192 | 45.632 | 1.00 | 18.04 | A |
| ATOM | 2694 | CG1 | VAL | A | 162 | −8.109 | 31.968 | 45.524 | 1.00 | 19.49 | A |
| ATOM | 2695 | CG2 | VAL | A | 162 | −6.374 | 33.165 | 46.788 | 1.00 | 16.56 | A |
| ATOM | 2696 | C | VAL | A | 162 | −7.398 | 33.957 | 43.382 | 1.00 | 16.54 | A |
| ATOM | 2697 | O | VAL | A | 162 | −7.427 | 35.164 | 43.252 | 1.00 | 15.67 | A |
| ATOM | 2698 | N | ALA | A | 163 | −8.162 | 33.146 | 42.705 | 1.00 | 16.38 | A |
| ATOM | 2699 | CA | ALA | A | 163 | −9.198 | 33.665 | 41.862 | 1.00 | 17.65 | A |
| ATOM | 2700 | CB | ALA | A | 163 | −8.904 | 33.381 | 40.454 | 1.00 | 17.99 | A |
| ATOM | 2701 | C | ALA | A | 163 | −10.499 | 32.981 | 42.304 | 1.00 | 17.25 | A |
| ATOM | 2702 | O | ALA | A | 163 | −10.755 | 31.756 | 42.021 | 1.00 | 17.62 | A |
| ATOM | 2703 | N | LEU | A | 164 | −11.313 | 33.710 | 43.077 | 1.00 | 15.86 | A |
| ATOM | 2704 | CA | LEU | A | 164 | −12.560 | 33.053 | 43.531 | 1.00 | 16.46 | A |
| ATOM | 2705 | CB | LEU | A | 164 | −12.935 | 33.638 | 44.856 | 1.00 | 15.91 | A |
| ATOM | 2706 | CG | LEU | A | 164 | −14.132 | 32.863 | 45.309 | 1.00 | 16.76 | A |
| ATOM | 2707 | CD1 | LEU | A | 164 | −13.934 | 31.386 | 45.420 | 1.00 | 16.22 | A |
| ATOM | 2708 | CD2 | LEU | A | 164 | −14.483 | 33.431 | 46.679 | 1.00 | 17.86 | A |
| ATOM | 2709 | C | LEU | A | 164 | −13.672 | 33.198 | 42.456 | 1.00 | 16.32 | A |
| ATOM | 2710 | O | LEU | A | 164 | −14.228 | 34.303 | 42.214 | 1.00 | 15.35 | A |
| ATOM | 2711 | N | LEU | A | 165 | −13.965 | 32.086 | 41.786 | 1.00 | 15.90 | A |
| ATOM | 2712 | CA | LEU | A | 165 | −14.893 | 32.173 | 40.683 | 1.00 | 15.98 | A |
| ATOM | 2713 | CB | LEU | A | 165 | −14.371 | 31.338 | 39.523 | 1.00 | 18.46 | A |
| ATOM | 2714 | CG | LEU | A | 165 | −12.904 | 31.401 | 39.149 | 1.00 | 19.16 | A |
| ATOM | 2715 | CD1 | LEU | A | 165 | −12.786 | 30.532 | 37.975 | 1.00 | 18.88 | A |
| ATOM | 2716 | CD2 | LEU | A | 165 | −12.455 | 32.781 | 38.875 | 1.00 | 19.34 | A |
| ATOM | 2717 | C | LEU | A | 165 | −16.314 | 31.792 | 40.942 | 1.00 | 15.01 | A |
| ATOM | 2718 | O | LEU | A | 165 | −17.169 | 32.033 | 40.143 | 1.00 | 12.87 | A |
| ATOM | 2719 | N | SER | A | 166 | −16.588 | 31.206 | 42.093 | 1.00 | 15.03 | A |
| ATOM | 2720 | CA | SER | A | 166 | −17.973 | 30.832 | 42.330 | 1.00 | 15.35 | A |
| ATOM | 2721 | CB | SER | A | 166 | −18.337 | 29.517 | 41.645 | 1.00 | 16.26 | A |
| ATOM | 2722 | OG | SER | A | 166 | −19.616 | 29.064 | 42.030 | 1.00 | 15.63 | A |
| ATOM | 2723 | C | SER | A | 166 | −18.183 | 30.642 | 43.763 | 1.00 | 15.44 | A |
| ATOM | 2724 | O | SER | A | 166 | −17.285 | 30.080 | 44.426 | 1.00 | 15.59 | A |
| ATOM | 2725 | N | VAL | A | 167 | −19.376 | 31.038 | 44.222 | 1.00 | 14.76 | A |
| ATOM | 2726 | CA | VAL | A | 167 | −19.661 | 30.929 | 45.617 | 1.00 | 14.49 | A |
| ATOM | 2727 | CB | VAL | A | 167 | −19.475 | 32.274 | 46.342 | 1.00 | 14.49 | A |
| ATOM | 2728 | CG1 | VAL | A | 167 | −19.871 | 32.137 | 47.811 | 1.00 | 16.55 | A |
| ATOM | 2729 | CG2 | VAL | A | 167 | −18.106 | 32.722 | 46.248 | 1.00 | 13.26 | A |
| ATOM | 2730 | C | VAL | A | 167 | −21.094 | 30.635 | 45.679 | 1.00 | 15.69 | A |
| ATOM | 2731 | O | VAL | A | 167 | −21.910 | 31.490 | 45.391 | 1.00 | 15.32 | A |
| ATOM | 2732 | N | ARG | A | 168 | −21.435 | 29.443 | 46.080 | 1.00 | 16.34 | A |
| ATOM | 2733 | CA | ARG | A | 168 | −22.815 | 29.103 | 46.159 | 1.00 | 17.42 | A |
| ATOM | 2734 | CB | ARG | A | 168 | −23.190 | 27.884 | 45.257 | 1.00 | 19.57 | A |
| ATOM | 2735 | CG | ARG | A | 168 | −24.058 | 28.268 | 44.101 | 1.00 | 20.89 | A |
| ATOM | 2736 | CD | ARG | A | 168 | −25.063 | 27.120 | 43.548 | 1.00 | 22.42 | A |
| ATOM | 2737 | NE | ARG | A | 168 | −24.827 | 25.805 | 44.163 | 1.00 | 22.02 | A |
| ATOM | 2738 | CZ | ARG | A | 168 | −25.783 | 24.866 | 44.333 | 1.00 | 22.04 | A |
| ATOM | 2739 | NH1 | ARG | A | 168 | −27.044 | 25.067 | 43.943 | 1.00 | 18.96 | A |
| ATOM | 2740 | NH2 | ARG | A | 168 | −25.430 | 23.702 | 44.851 | 1.00 | 20.64 | A |
| ATOM | 2741 | C | ARG | A | 168 | −23.019 | 28.677 | 47.601 | 1.00 | 18.43 | A |
| ATOM | 2742 | O | ARG | A | 168 | −22.142 | 27.961 | 48.194 | 1.00 | 17.76 | A |
| ATOM | 2743 | N | VAL | A | 169 | −24.201 | 29.103 | 48.121 | 1.00 | 17.97 | A |
| ATOM | 2744 | CA | VAL | A | 169 | −24.649 | 28.809 | 49.473 | 1.00 | 17.47 | A |
| ATOM | 2745 | CB | VAL | A | 169 | −24.753 | 30.115 | 50.303 | 1.00 | 18.56 | A |
| ATOM | 2746 | CG1 | VAL | A | 169 | −25.135 | 29.776 | 51.832 | 1.00 | 17.98 | A |
| ATOM | 2747 | CG2 | VAL | A | 169 | −23.485 | 30.866 | 50.198 | 1.00 | 18.50 | A |
| ATOM | 2748 | C | VAL | A | 169 | −26.021 | 28.233 | 49.421 | 1.00 | 17.60 | A |
| ATOM | 2749 | O | VAL | A | 169 | −26.930 | 28.852 | 48.855 | 1.00 | 17.71 | A |
| ATOM | 2750 | N | TYR | A | 170 | −26.245 | 27.092 | 50.050 | 1.00 | 16.67 | A |

TABLE 1-continued

| | | | | | | | | | | |
|---|---|---|---|---|---|---|---|---|---|---|
| ATOM | 2751 | CA | TYR | A | 170 | −27.574 | 26.517 | 49.910 | 1.00 | 15.97 | A |
| ATOM | 2752 | CB | TYR | A | 170 | −27.659 | 25.729 | 48.589 | 1.00 | 15.88 | A |
| ATOM | 2753 | CG | TYR | A | 170 | −26.793 | 24.476 | 48.632 | 1.00 | 15.42 | A |
| ATOM | 2754 | CD1 | TYR | A | 170 | −27.283 | 23.263 | 49.097 | 1.00 | 16.32 | A |
| ATOM | 2755 | CE1 | TYR | A | 170 | −26.473 | 22.165 | 49.189 | 1.00 | 15.91 | A |
| ATOM | 2756 | CD2 | TYR | A | 170 | −25.464 | 24.536 | 48.265 | 1.00 | 15.99 | A |
| ATOM | 2757 | CE2 | TYR | A | 170 | −24.646 | 23.465 | 48.330 | 1.00 | 13.92 | A |
| ATOM | 2758 | CZ | TYR | A | 170 | −25.141 | 22.300 | 48.772 | 1.00 | 15.55 | A |
| ATOM | 2759 | OH | TYR | A | 170 | −24.377 | 21.157 | 48.786 | 1.00 | 15.77 | A |
| ATOM | 2760 | C | TYR | A | 170 | −27.814 | 25.600 | 50.996 | 1.00 | 14.37 | A |
| ATOM | 2761 | O | TYR | A | 170 | −26.855 | 25.170 | 51.584 | 1.00 | 13.51 | A |
| ATOM | 2762 | N | TYR | A | 171 | −29.093 | 25.270 | 51.230 | 1.00 | 14.25 | A |
| ATOM | 2763 | CA | TYR | A | 171 | −29.415 | 24.314 | 52.282 | 1.00 | 17.08 | A |
| ATOM | 2764 | CB | TYR | A | 171 | −29.960 | 25.061 | 53.513 | 1.00 | 16.40 | A |
| ATOM | 2765 | CG | TYR | A | 171 | −31.336 | 25.620 | 53.395 | 1.00 | 17.35 | A |
| ATOM | 2766 | CD1 | TYR | A | 171 | −32.400 | 24.964 | 53.943 | 1.00 | 17.57 | A |
| ATOM | 2767 | CE1 | TYR | A | 171 | −33.714 | 25.492 | 53.874 | 1.00 | 19.28 | A |
| ATOM | 2768 | CD2 | TYR | A | 171 | −31.546 | 26.821 | 52.751 | 1.00 | 18.36 | A |
| ATOM | 2769 | CE2 | TYR | A | 171 | −32.814 | 27.372 | 52.661 | 1.00 | 20.15 | A |
| ATOM | 2770 | CZ | TYR | A | 171 | −33.923 | 26.694 | 53.243 | 1.00 | 19.74 | A |
| ATOM | 2771 | OH | TYR | A | 171 | −35.161 | 27.253 | 53.227 | 1.00 | 19.54 | A |
| ATOM | 2772 | C | TYR | A | 171 | −30.379 | 23.248 | 51.797 | 1.00 | 17.02 | A |
| ATOM | 2773 | O | TYR | A | 171 | −31.028 | 23.427 | 50.735 | 1.00 | 17.21 | A |
| ATOM | 2774 | N | LYS | A | 172 | −30.503 | 22.202 | 52.574 | 1.00 | 17.77 | A |
| ATOM | 2775 | CA | LYS | A | 172 | −31.377 | 21.122 | 52.162 | 1.00 | 20.62 | A |
| ATOM | 2776 | CB | LYS | A | 172 | −31.026 | 19.829 | 52.787 | 1.00 | 18.75 | A |
| ATOM | 2777 | CG | LYS | A | 172 | −30.212 | 19.065 | 51.840 | 1.00 | 20.24 | A |
| ATOM | 2778 | CD | LYS | A | 172 | −28.875 | 19.676 | 51.625 | 1.00 | 19.52 | A |
| ATOM | 2779 | CE | LYS | A | 172 | −28.109 | 18.749 | 50.724 | 1.00 | 21.99 | A |
| ATOM | 2780 | NZ | LYS | A | 172 | −26.875 | 18.114 | 51.301 | 1.00 | 22.59 | A |
| ATOM | 2781 | C | LYS | A | 172 | −32.843 | 21.247 | 52.307 | 1.00 | 22.07 | A |
| ATOM | 2782 | O | LYS | A | 172 | −33.402 | 21.254 | 53.447 | 1.00 | 23.49 | A |
| ATOM | 2783 | N | LYS | A | 173 | −33.462 | 21.187 | 51.134 | 1.00 | 22.88 | A |
| ATOM | 2784 | CA | LYS | A | 173 | −34.906 | 21.408 | 50.891 | 1.00 | 23.62 | A |
| ATOM | 2785 | CB | LYS | A | 173 | −35.420 | 20.479 | 49.769 | 1.00 | 23.63 | A |
| ATOM | 2786 | CG | LYS | A | 173 | −34.377 | 20.336 | 48.611 | 1.00 | 23.88 | A |
| ATOM | 2787 | CD | LYS | A | 173 | −33.517 | 19.081 | 48.962 | 1.00 | 24.16 | A |
| ATOM | 2788 | CE | LYS | A | 173 | −32.101 | 19.153 | 48.374 | 1.00 | 24.59 | A |
| ATOM | 2789 | NZ | LYS | A | 173 | −31.326 | 20.209 | 49.130 | 1.00 | 23.73 | A |
| ATOM | 2790 | C | LYS | A | 173 | −35.722 | 21.191 | 52.081 | 1.00 | 23.37 | A |
| ATOM | 2791 | O | LYS | A | 173 | −36.163 | 22.164 | 52.782 | 1.00 | 22.35 | A |
| ATOM | 2792 | N | CYS | A | 174 | −35.822 | 19.868 | 52.308 | 1.00 | 23.68 | A |
| ATOM | 2793 | CA | CYS | A | 174 | −36.653 | 19.339 | 53.420 | 1.00 | 25.47 | A |
| ATOM | 2794 | CB | CYS | A | 174 | −36.310 | 20.061 | 54.820 | 1.00 | 28.65 | A |
| ATOM | 2795 | SG | CYS | A | 174 | −37.928 | 20.841 | 55.663 | 1.00 | 38.26 | A |
| ATOM | 2796 | C | CYS | A | 174 | −38.188 | 19.492 | 53.081 | 1.00 | 23.26 | A |
| ATOM | 2797 | O | CYS | A | 174 | −38.793 | 18.418 | 53.021 | 1.00 | 21.44 | A |
| ATOM | 2798 | OXT | CYS | A | 174 | −38.738 | 20.665 | 52.935 | 1.00 | 22.35 | A |
| ATOM | 2799 | CB | GLU | D | 1 | 23.133 | −17.287 | 30.637 | 1.00 | 18.26 | D |
| ATOM | 2800 | CG | GLU | D | 1 | 22.443 | −16.571 | 29.605 | 1.00 | 19.88 | D |
| ATOM | 2801 | CD | GLU | D | 1 | 20.960 | −16.165 | 30.052 | 1.00 | 22.33 | D |
| ATOM | 2802 | OE1 | GLU | D | 1 | 20.840 | −15.311 | 30.988 | 1.00 | 22.04 | D |
| ATOM | 2803 | OE2 | GLU | D | 1 | 19.926 | −16.683 | 29.498 | 1.00 | 22.42 | D |
| ATOM | 2804 | C | GLU | D | 1 | 25.184 | −18.446 | 29.450 | 1.00 | 16.10 | D |
| ATOM | 2805 | O | GLU | D | 1 | 25.611 | −18.051 | 28.387 | 1.00 | 14.62 | D |
| ATOM | 2806 | N | GLU | D | 1 | 25.238 | −16.052 | 30.537 | 1.00 | 18.38 | D |
| ATOM | 2807 | CA | GLU | D | 1 | 24.686 | −17.410 | 30.546 | 1.00 | 17.26 | D |
| ATOM | 2808 | N | VAL | D | 2 | 25.185 | −19.745 | 29.779 | 1.00 | 16.37 | D |
| ATOM | 2809 | CA | VAL | D | 2 | 25.660 | −20.782 | 28.836 | 1.00 | 19.16 | D |
| ATOM | 2810 | CB | VAL | D | 2 | 26.600 | −21.854 | 29.528 | 1.00 | 18.63 | D |
| ATOM | 2811 | CG1 | VAL | D | 2 | 26.955 | −22.952 | 28.556 | 1.00 | 18.71 | D |
| ATOM | 2812 | CG2 | VAL | D | 2 | 27.841 | −21.167 | 30.040 | 1.00 | 16.94 | D |
| ATOM | 2813 | C | VAL | D | 2 | 24.472 | −21.449 | 28.137 | 1.00 | 17.16 | D |
| ATOM | 2814 | O | VAL | D | 2 | 23.555 | −21.985 | 28.745 | 1.00 | 17.83 | D |
| ATOM | 2815 | N | VAL | D | 3 | 24.476 | −21.370 | 26.830 | 1.00 | 16.85 | D |
| ATOM | 2816 | CA | VAL | D | 3 | 23.296 | −21.845 | 26.149 | 1.00 | 18.25 | D |
| ATOM | 2817 | CB | VAL | D | 3 | 22.838 | −20.797 | 25.025 | 1.00 | 16.66 | D |
| ATOM | 2818 | CG1 | VAL | D | 3 | 21.493 | −21.162 | 24.414 | 1.00 | 16.08 | D |
| ATOM | 2819 | CG2 | VAL | D | 3 | 22.691 | −19.506 | 25.598 | 1.00 | 15.53 | D |
| ATOM | 2820 | C | VAL | D | 3 | 23.381 | −23.195 | 25.496 | 1.00 | 17.54 | D |
| ATOM | 2821 | O | VAL | D | 3 | 24.037 | −23.312 | 24.475 | 1.00 | 16.88 | D |
| ATOM | 2822 | N | LEU | D | 4 | 22.688 | −24.172 | 26.059 | 1.00 | 17.89 | D |
| ATOM | 2823 | CA | LEU | D | 4 | 22.573 | −25.518 | 25.455 | 1.00 | 19.77 | D |
| ATOM | 2824 | CB | LEU | D | 4 | 22.442 | −26.529 | 26.591 | 1.00 | 17.98 | D |
| ATOM | 2825 | CG | LEU | D | 4 | 23.225 | −26.130 | 27.835 | 1.00 | 17.46 | D |
| ATOM | 2826 | CD1 | LEU | D | 4 | 23.113 | −27.153 | 28.967 | 1.00 | 14.15 | D |
| ATOM | 2827 | CD2 | LEU | D | 4 | 24.727 | −26.064 | 27.318 | 1.00 | 18.38 | D |
| ATOM | 2828 | C | LEU | D | 4 | 21.245 | −25.597 | 24.635 | 1.00 | 21.14 | D |
| ATOM | 2829 | O | LEU | D | 4 | 20.160 | −25.821 | 25.193 | 1.00 | 24.43 | D |
| ATOM | 2830 | N | LEU | D | 5 | 21.186 | −25.543 | 23.344 | 1.00 | 20.80 | D |

TABLE 1-continued

| | | | | | | | | | | |
|---|---|---|---|---|---|---|---|---|---|---|
| ATOM | 2831 | CA | LEU | D | 5 | 19.799 | −25.575 | 22.762 | 1.00 | 18.34 | D |
| ATOM | 2832 | CB | LEU | D | 5 | 18.890 | −26.609 | 23.398 | 1.00 | 17.64 | D |
| ATOM | 2833 | CG | LEU | D | 5 | 17.600 | −26.612 | 22.627 | 1.00 | 16.76 | D |
| ATOM | 2834 | CD1 | LEU | D | 5 | 17.963 | −26.672 | 21.241 | 1.00 | 17.33 | D |
| ATOM | 2835 | CD2 | LEU | D | 5 | 16.804 | −27.816 | 22.972 | 1.00 | 15.84 | D |
| ATOM | 2836 | C | LEU | D | 5 | 19.042 | −24.240 | 22.767 | 1.00 | 17.42 | D |
| ATOM | 2837 | O | LEU | D | 5 | 18.670 | −23.668 | 23.799 | 1.00 | 17.75 | D |
| ATOM | 2838 | N | ASP | D | 6 | 18.799 | −23.828 | 21.519 | 1.00 | 16.76 | D |
| ATOM | 2839 | CA | ASP | D | 6 | 18.157 | −22.591 | 21.152 | 1.00 | 16.04 | D |
| ATOM | 2840 | CB | ASP | D | 6 | 19.177 | −21.459 | 21.171 | 1.00 | 16.52 | D |
| ATOM | 2841 | CG | ASP | D | 6 | 18.504 | −20.118 | 21.147 | 1.00 | 17.49 | D |
| ATOM | 2842 | OD1 | ASP | D | 6 | 19.212 | −19.065 | 20.882 | 1.00 | 19.98 | D |
| ATOM | 2843 | OD2 | ASP | D | 6 | 17.267 | −20.104 | 21.385 | 1.00 | 16.83 | D |
| ATOM | 2844 | C | ASP | D | 6 | 17.469 | −22.664 | 19.767 | 1.00 | 14.86 | D |
| ATOM | 2845 | O | ASP | D | 6 | 17.998 | −22.319 | 18.694 | 1.00 | 12.99 | D |
| ATOM | 2846 | N | PHE | D | 7 | 16.238 | −23.068 | 19.870 | 1.00 | 15.80 | D |
| ATOM | 2847 | CA | PHE | D | 7 | 15.355 | −23.291 | 18.760 | 1.00 | 16.74 | D |
| ATOM | 2848 | CB | PHE | D | 7 | 13.941 | −23.531 | 19.271 | 1.00 | 16.84 | D |
| ATOM | 2849 | CG | PHE | D | 7 | 12.942 | −23.677 | 18.172 | 1.00 | 16.20 | D |
| ATOM | 2850 | CD1 | PHE | D | 7 | 12.855 | −24.868 | 17.476 | 1.00 | 15.83 | D |
| ATOM | 2851 | CD2 | PHE | D | 7 | 12.118 | −22.592 | 17.797 | 1.00 | 14.38 | D |
| ATOM | 2852 | CE1 | PHE | D | 7 | 11.958 | −24.963 | 16.432 | 1.00 | 16.41 | D |
| ATOM | 2853 | CE2 | PHE | D | 7 | 11.209 | −22.679 | 16.744 | 1.00 | 13.94 | D |
| ATOM | 2854 | CZ | PHE | D | 7 | 11.109 | −23.827 | 16.061 | 1.00 | 14.35 | D |
| ATOM | 2855 | C | PHE | D | 7 | 15.327 | −22.180 | 17.745 | 1.00 | 17.65 | D |
| ATOM | 2856 | O | PHE | D | 7 | 15.493 | −22.459 | 16.600 | 1.00 | 17.38 | D |
| ATOM | 2857 | N | ALA | D | 8 | 15.055 | −20.956 | 18.192 | 1.00 | 18.28 | D |
| ATOM | 2858 | CA | ALA | D | 8 | 14.986 | −19.825 | 17.324 | 1.00 | 19.21 | D |
| ATOM | 2859 | CB | ALA | D | 8 | 14.433 | −18.497 | 18.097 | 1.00 | 19.34 | D |
| ATOM | 2860 | C | ALA | D | 8 | 16.303 | −19.488 | 16.619 | 1.00 | 19.50 | D |
| ATOM | 2861 | O | ALA | D | 8 | 16.334 | −18.546 | 15.855 | 1.00 | 20.94 | D |
| ATOM | 2862 | N | ALA | D | 9 | 17.411 | −20.184 | 16.841 | 1.00 | 19.75 | D |
| ATOM | 2863 | CA | ALA | D | 9 | 18.618 | −19.795 | 16.150 | 1.00 | 19.50 | D |
| ATOM | 2864 | CB | ALA | D | 9 | 19.717 | −19.700 | 17.137 | 1.00 | 15.15 | D |
| ATOM | 2865 | C | ALA | D | 9 | 18.915 | −20.778 | 15.040 | 1.00 | 19.76 | D |
| ATOM | 2866 | O | ALA | D | 9 | 19.682 | −20.474 | 14.089 | 1.00 | 22.02 | D |
| ATOM | 2867 | N | ALA | D | 10 | 18.296 | −21.952 | 15.089 | 1.00 | 20.29 | D |
| ATOM | 2868 | CA | ALA | D | 10 | 18.629 | −23.092 | 14.085 | 1.00 | 20.80 | D |
| ATOM | 2869 | CB | ALA | D | 10 | 18.375 | −24.470 | 14.796 | 1.00 | 17.31 | D |
| ATOM | 2870 | C | ALA | D | 10 | 17.925 | −23.004 | 12.647 | 1.00 | 21.69 | D |
| ATOM | 2871 | O | ALA | D | 10 | 16.721 | −23.525 | 12.352 | 1.00 | 21.42 | D |
| ATOM | 2872 | N | GLY | D | 11 | 18.661 | −22.275 | 11.806 | 1.00 | 22.77 | D |
| ATOM | 2873 | CA | GLY | D | 11 | 18.307 | −21.909 | 10.406 | 1.00 | 25.02 | D |
| ATOM | 2874 | C | GLY | D | 11 | 17.979 | −23.070 | 9.436 | 1.00 | 26.27 | D |
| ATOM | 2875 | O | GLY | D | 11 | 18.668 | −23.388 | 8.385 | 1.00 | 26.22 | D |
| ATOM | 2876 | N | GLY | D | 12 | 16.891 | −23.743 | 9.891 | 1.00 | 26.12 | D |
| ATOM | 2877 | CA | GLY | D | 12 | 16.326 | −24.985 | 9.285 | 1.00 | 25.36 | D |
| ATOM | 2878 | C | GLY | D | 12 | 15.558 | −25.673 | 10.462 | 1.00 | 24.70 | D |
| ATOM | 2879 | O | GLY | D | 12 | 15.608 | −26.929 | 10.617 | 1.00 | 23.78 | D |
| ATOM | 2880 | N | GLU | D | 13 | 14.946 | −24.821 | 11.345 | 1.00 | 23.90 | D |
| ATOM | 2881 | CA | GLU | D | 13 | 14.056 | −25.309 | 12.439 | 1.00 | 22.69 | D |
| ATOM | 2882 | CB | GLU | D | 13 | 12.902 | −26.124 | 11.776 | 1.00 | 24.76 | D |
| ATOM | 2883 | CG | GLU | D | 13 | 12.838 | −26.281 | 10.219 | 1.00 | 25.93 | D |
| ATOM | 2884 | CD | GLU | D | 13 | 11.367 | −26.658 | 9.554 | 1.00 | 26.31 | D |
| ATOM | 2885 | OE1 | GLU | D | 13 | 10.399 | −26.138 | 10.237 | 1.00 | 26.05 | D |
| ATOM | 2886 | OE2 | GLU | D | 13 | 11.270 | −27.359 | 8.391 | 1.00 | 22.11 | D |
| ATOM | 2887 | C | GLU | D | 13 | 14.787 | −26.239 | 13.539 | 1.00 | 23.02 | D |
| ATOM | 2888 | O | GLU | D | 13 | 15.117 | −25.784 | 14.666 | 1.00 | 20.63 | D |
| ATOM | 2889 | N | LEU | D | 14 | 15.056 | −27.503 | 13.110 | 1.00 | 22.70 | D |
| ATOM | 2890 | CA | LEU | D | 14 | 15.817 | −28.380 | 13.896 | 1.00 | 22.97 | D |
| ATOM | 2891 | CB | LEU | D | 14 | 15.569 | −28.037 | 15.344 | 1.00 | 23.47 | D |
| ATOM | 2892 | CG | LEU | D | 14 | 16.874 | −27.502 | 15.990 | 1.00 | 23.92 | D |
| ATOM | 2893 | CD1 | LEU | D | 14 | 16.440 | −26.161 | 16.869 | 1.00 | 23.60 | D |
| ATOM | 2894 | CD2 | LEU | D | 14 | 17.689 | −28.653 | 16.806 | 1.00 | 17.35 | D |
| ATOM | 2895 | C | LEU | D | 14 | 15.561 | −29.878 | 13.709 | 1.00 | 23.92 | D |
| ATOM | 2896 | O | LEU | D | 14 | 14.460 | −30.327 | 13.128 | 1.00 | 25.25 | D |
| ATOM | 2897 | N | GLY | D | 15 | 16.497 | −30.637 | 14.338 | 1.00 | 22.70 | D |
| ATOM | 2898 | CA | GLY | D | 15 | 16.379 | −32.077 | 14.402 | 1.00 | 19.66 | D |
| ATOM | 2899 | C | GLY | D | 15 | 15.522 | −32.510 | 15.643 | 1.00 | 19.22 | D |
| ATOM | 2900 | O | GLY | D | 15 | 16.127 | −32.959 | 16.667 | 1.00 | 18.12 | D |
| ATOM | 2901 | N | TRP | D | 16 | 14.156 | −32.404 | 15.598 | 1.00 | 19.56 | D |
| ATOM | 2902 | CA | TRP | D | 16 | 13.287 | −32.805 | 16.791 | 1.00 | 20.14 | D |
| ATOM | 2903 | CB | TRP | D | 16 | 12.362 | −31.660 | 17.402 | 1.00 | 19.90 | D |
| ATOM | 2904 | CG | TRP | D | 16 | 13.115 | −30.500 | 17.892 | 1.00 | 19.90 | D |
| ATOM | 2905 | CD2 | TRP | D | 16 | 12.767 | −29.561 | 18.937 | 1.00 | 19.40 | D |
| ATOM | 2906 | CE2 | TRP | D | 16 | 13.840 | −28.667 | 19.057 | 1.00 | 19.94 | D |
| ATOM | 2907 | CE3 | TRP | D | 16 | 11.710 | −29.404 | 19.752 | 1.00 | 17.02 | D |
| ATOM | 2908 | CD1 | TRP | D | 16 | 14.343 | −30.116 | 17.436 | 1.00 | 21.03 | D |
| ATOM | 2909 | NE1 | TRP | D | 16 | 14.784 | −29.018 | 18.135 | 1.00 | 22.34 | D |
| ATOM | 2910 | CZ2 | TRP | D | 16 | 13.842 | −27.617 | 20.011 | 1.00 | 19.77 | D |

TABLE 1-continued

| | | | | | | | | | | |
|---|---|---|---|---|---|---|---|---|---|---|
| ATOM | 2911 | CZ3 | TRP | D | 16 | 11.736 | −28.335 | 20.709 | 1.00 | 17.86 | D |
| ATOM | 2912 | CH2 | TRP | D | 16 | 12.774 | −27.482 | 20.822 | 1.00 | 17.65 | D |
| ATOM | 2913 | C | TRP | D | 16 | 12.383 | −33.924 | 16.352 | 1.00 | 20.53 | D |
| ATOM | 2914 | O | TRP | D | 16 | 12.136 | −34.037 | 15.173 | 1.00 | 22.33 | D |
| ATOM | 2915 | N | LEU | D | 17 | 11.885 | −34.672 | 17.327 | 1.00 | 19.02 | D |
| ATOM | 2916 | CA | LEU | D | 17 | 11.024 | −35.806 | 17.144 | 1.00 | 16.88 | D |
| ATOM | 2917 | CB | LEU | D | 17 | 11.525 | −36.960 | 18.027 | 1.00 | 17.70 | D |
| ATOM | 2918 | CG | LEU | D | 17 | 10.641 | −38.166 | 17.961 | 1.00 | 18.58 | D |
| ATOM | 2919 | CD1 | LEU | D | 17 | 10.424 | −38.386 | 16.363 | 1.00 | 20.41 | D |
| ATOM | 2920 | CD2 | LEU | D | 17 | 11.290 | −39.343 | 18.676 | 1.00 | 19.12 | D |
| ATOM | 2921 | C | LEU | D | 17 | 9.580 | −35.434 | 17.507 | 1.00 | 15.78 | D |
| ATOM | 2922 | O | LEU | D | 17 | 9.302 | −34.696 | 18.477 | 1.00 | 13.95 | D |
| ATOM | 2923 | N | THR | D | 18 | 8.680 | −36.029 | 16.746 | 1.00 | 14.57 | D |
| ATOM | 2924 | CA | THR | D | 18 | 7.267 | −35.707 | 16.829 | 1.00 | 14.95 | D |
| ATOM | 2925 | CB | THR | D | 18 | 6.839 | −34.956 | 15.609 | 1.00 | 13.77 | D |
| ATOM | 2926 | OG1 | THR | D | 18 | 6.822 | −33.608 | 15.955 | 1.00 | 13.59 | D |
| ATOM | 2927 | CG2 | THR | D | 18 | 5.595 | −35.378 | 15.076 | 1.00 | 13.63 | D |
| ATOM | 2928 | C | THR | D | 18 | 6.592 | −36.998 | 16.902 | 1.00 | 18.64 | D |
| ATOM | 2929 | O | THR | D | 18 | 6.605 | −37.745 | 15.888 | 1.00 | 18.69 | D |
| ATOM | 2930 | N | HIS | D | 19 | 5.945 | −37.260 | 18.043 | 1.00 | 19.91 | D |
| ATOM | 2931 | CA | HIS | D | 19 | 5.336 | −38.526 | 18.184 | 1.00 | 22.13 | D |
| ATOM | 2932 | CB | HIS | D | 19 | 5.056 | −38.890 | 19.620 | 1.00 | 22.27 | D |
| ATOM | 2933 | CG | HIS | D | 19 | 4.712 | −40.342 | 19.805 | 1.00 | 22.49 | D |
| ATOM | 2934 | CD2 | HIS | D | 19 | 4.108 | −41.012 | 20.822 | 1.00 | 21.23 | D |
| ATOM | 2935 | ND1 | HIS | D | 19 | 5.057 | −41.303 | 18.870 | 1.00 | 23.27 | D |
| ATOM | 2936 | CE1 | HIS | D | 19 | 4.691 | −42.494 | 19.311 | 1.00 | 21.94 | D |
| ATOM | 2937 | NE2 | HIS | D | 19 | 4.125 | −42.347 | 20.495 | 1.00 | 21.24 | D |
| ATOM | 2938 | C | HIS | D | 19 | 4.126 | −38.724 | 17.288 | 1.00 | 25.10 | D |
| ATOM | 2939 | O | HIS | D | 19 | 4.246 | −38.321 | 16.073 | 1.00 | 26.98 | D |
| ATOM | 2940 | N | PRO | D | 20 | 2.923 | −39.223 | 17.801 | 1.00 | 24.54 | D |
| ATOM | 2941 | CD | PRO | D | 20 | 2.337 | −38.414 | 18.904 | 1.00 | 23.36 | D |
| ATOM | 2942 | CA | PRO | D | 20 | 1.943 | −39.360 | 16.673 | 1.00 | 22.95 | D |
| ATOM | 2943 | CB | PRO | D | 20 | 0.908 | −38.311 | 16.988 | 1.00 | 23.40 | D |
| ATOM | 2944 | CG | PRO | D | 20 | 0.757 | −38.621 | 18.588 | 1.00 | 23.20 | D |
| ATOM | 2945 | C | PRO | D | 20 | 2.669 | −39.178 | 15.291 | 1.00 | 23.63 | D |
| ATOM | 2946 | O | PRO | D | 20 | 3.179 | −40.170 | 14.725 | 1.00 | 24.25 | D |
| ATOM | 2947 | N | TYR | D | 21 | 2.837 | −37.936 | 14.792 | 1.00 | 22.75 | D |
| ATOM | 2948 | CA | TYR | D | 21 | 3.567 | −37.676 | 13.486 | 1.00 | 22.40 | D |
| ATOM | 2949 | CB | TYR | D | 21 | 4.702 | −38.650 | 13.092 | 1.00 | 21.58 | D |
| ATOM | 2950 | CG | TYR | D | 21 | 5.308 | −38.068 | 11.811 | 1.00 | 22.38 | D |
| ATOM | 2951 | CD1 | TYR | D | 21 | 5.951 | −36.809 | 11.851 | 1.00 | 22.41 | D |
| ATOM | 2952 | CE1 | TYR | D | 21 | 6.306 | −36.090 | 10.613 | 1.00 | 23.51 | D |
| ATOM | 2953 | CD2 | TYR | D | 21 | 5.024 | −38.655 | 10.522 | 1.00 | 23.15 | D |
| ATOM | 2954 | CE2 | TYR | D | 21 | 5.360 | −37.975 | 9.271 | 1.00 | 23.29 | D |
| ATOM | 2955 | CZ | TYR | D | 21 | 5.987 | −36.701 | 9.354 | 1.00 | 23.84 | D |
| ATOM | 2956 | OH | TYR | D | 21 | 6.207 | −35.964 | 8.260 | 1.00 | 25.73 | D |
| ATOM | 2957 | C | TYR | D | 21 | 2.588 | −37.757 | 12.349 | 1.00 | 21.78 | D |
| ATOM | 2958 | O | TYR | D | 21 | 2.263 | −38.865 | 11.900 | 1.00 | 22.23 | D |
| ATOM | 2959 | N | GLY | D | 22 | 2.150 | −36.605 | 11.903 | 1.00 | 22.04 | D |
| ATOM | 2960 | CA | GLY | D | 22 | 1.171 | −36.620 | 10.882 | 1.00 | 23.00 | D |
| ATOM | 2961 | C | GLY | D | 22 | 0.169 | −35.551 | 11.242 | 1.00 | 23.84 | D |
| ATOM | 2962 | O | GLY | D | 22 | 0.012 | −34.530 | 10.475 | 1.00 | 24.54 | D |
| ATOM | 2963 | N | LYS | D | 23 | −0.448 | −35.735 | 12.429 | 1.00 | 23.43 | D |
| ATOM | 2964 | CA | LYS | D | 23 | −1.508 | −34.778 | 12.857 | 1.00 | 23.57 | D |
| ATOM | 2965 | CB | LYS | D | 23 | −2.860 | −35.530 | 13.037 | 1.00 | 22.92 | D |
| ATOM | 2966 | CG | LYS | D | 23 | −3.463 | −36.240 | 11.737 | 1.00 | 22.29 | D |
| ATOM | 2967 | CD | LYS | D | 23 | −2.928 | −37.785 | 11.512 | 1.00 | 21.61 | D |
| ATOM | 2968 | CE | LYS | D | 23 | −3.277 | −38.354 | 10.084 | 1.00 | 21.28 | D |
| ATOM | 2969 | NZ | LYS | D | 23 | −4.818 | −38.278 | 9.622 | 1.00 | 20.96 | D |
| ATOM | 2970 | C | LYS | D | 23 | −1.158 | −33.990 | 14.144 | 1.00 | 22.88 | D |
| ATOM | 2971 | O | LYS | D | 23 | −1.876 | −33.023 | 14.539 | 1.00 | 23.25 | D |
| ATOM | 2972 | N | GLY | D | 24 | −0.036 | −34.368 | 14.774 | 1.00 | 21.47 | D |
| ATOM | 2973 | CA | GLY | D | 24 | 0.314 | −33.642 | 15.964 | 1.00 | 18.97 | D |
| ATOM | 2974 | C | GLY | D | 24 | 1.055 | −32.353 | 15.610 | 1.00 | 17.81 | D |
| ATOM | 2975 | O | GLY | D | 24 | 0.657 | −31.609 | 14.751 | 1.00 | 15.25 | D |
| ATOM | 2976 | N | TRP | D | 25 | 2.155 | −32.160 | 16.324 | 1.00 | 18.12 | D |
| ATOM | 2977 | CA | TRP | D | 25 | 3.026 | −31.027 | 16.240 | 1.00 | 18.49 | D |
| ATOM | 2978 | CB | TRP | D | 25 | 4.076 | −31.184 | 17.355 | 1.00 | 18.84 | D |
| ATOM | 2979 | CG | TRP | D | 25 | 3.671 | −31.032 | 18.815 | 1.00 | 17.23 | D |
| ATOM | 2980 | CD2 | TRP | D | 25 | 3.561 | −29.789 | 19.500 | 1.00 | 16.26 | D |
| ATOM | 2981 | CE2 | TRP | D | 25 | 3.342 | −30.094 | 20.871 | 1.00 | 15.33 | D |
| ATOM | 2982 | CE3 | TRP | D | 25 | 3.620 | −28.453 | 19.087 | 1.00 | 14.96 | D |
| ATOM | 2983 | CD1 | TRP | D | 25 | 3.509 | −32.038 | 19.781 | 1.00 | 16.74 | D |
| ATOM | 2984 | NE1 | TRP | D | 25 | 3.326 | −31.455 | 21.016 | 1.00 | 15.48 | D |
| ATOM | 2985 | CZ2 | TRP | D | 25 | 3.190 | −29.105 | 21.793 | 1.00 | 14.61 | D |
| ATOM | 2986 | CZ3 | TRP | D | 25 | 3.471 | −27.484 | 20.016 | 1.00 | 15.02 | D |
| ATOM | 2987 | CH2 | TRP | D | 25 | 3.258 | −27.812 | 21.361 | 1.00 | 13.66 | D |
| ATOM | 2988 | C | TRP | D | 25 | 3.718 | −30.935 | 14.847 | 1.00 | 19.46 | D |
| ATOM | 2989 | O | TRP | D | 25 | 4.318 | −31.960 | 14.358 | 1.00 | 18.97 | D |
| ATOM | 2990 | N | ASP | D | 26 | 3.630 | −29.749 | 14.188 | 1.00 | 18.86 | D |

TABLE 1-continued

| | | | | | | | | | | |
|---|---|---|---|---|---|---|---|---|---|---|
| ATOM | 2991 | CA | ASP | D | 26 | 4.270 | −29.557 | 12.867 | 1.00 | 18.98 | D |
| ATOM | 2992 | CB | ASP | D | 26 | 3.295 | −29.332 | 11.600 | 1.00 | 20.80 | D |
| ATOM | 2993 | CG | ASP | D | 26 | 2.246 | −30.515 | 11.315 | 1.00 | 23.26 | D |
| ATOM | 2994 | OD1 | ASP | D | 26 | 2.364 | −31.729 | 11.789 | 1.00 | 23.75 | D |
| ATOM | 2995 | OD2 | ASP | D | 26 | 1.259 | −30.212 | 10.525 | 1.00 | 24.99 | D |
| ATOM | 2996 | C | ASP | D | 26 | 5.177 | −28.313 | 12.877 | 1.00 | 18.61 | D |
| ATOM | 2997 | O | ASP | D | 26 | 4.819 | −27.237 | 13.406 | 1.00 | 17.77 | D |
| ATOM | 2998 | N | LEU | D | 27 | 6.332 | −28.491 | 12.248 | 1.00 | 16.76 | D |
| ATOM | 2999 | CA | LEU | D | 27 | 7.291 | −27.469 | 12.091 | 1.00 | 15.84 | D |
| ATOM | 3000 | CB | LEU | D | 27 | 8.585 | −28.130 | 11.796 | 1.00 | 15.13 | D |
| ATOM | 3001 | CG | LEU | D | 27 | 9.797 | −27.199 | 11.978 | 1.00 | 16.33 | D |
| ATOM | 3002 | CD1 | LEU | D | 27 | 9.818 | −26.291 | 13.274 | 1.00 | 13.17 | D |
| ATOM | 3003 | CD2 | LEU | D | 27 | 10.959 | −28.147 | 11.769 | 1.00 | 13.31 | D |
| ATOM | 3004 | C | LEU | D | 27 | 6.812 | −26.576 | 10.944 | 1.00 | 16.06 | D |
| ATOM | 3005 | O | LEU | D | 27 | 6.507 | −27.021 | 9.914 | 1.00 | 15.81 | D |
| ATOM | 3006 | N | MET | D | 28 | 6.678 | −25.286 | 11.174 | 1.00 | 16.42 | D |
| ATOM | 3007 | CA | MET | D | 28 | 6.161 | −24.418 | 10.170 | 1.00 | 15.75 | D |
| ATOM | 3008 | CB | MET | D | 28 | 4.752 | −23.895 | 10.549 | 1.00 | 19.93 | D |
| ATOM | 3009 | CG | MET | D | 28 | 3.791 | −24.913 | 11.165 | 1.00 | 23.75 | D |
| ATOM | 3010 | SD | MET | D | 28 | 1.897 | −24.566 | 11.233 | 1.00 | 28.97 | D |
| ATOM | 3011 | CE | MET | D | 28 | 1.614 | −23.732 | 9.400 | 1.00 | 25.86 | D |
| ATOM | 3012 | C | MET | D | 28 | 7.113 | −23.263 | 10.174 | 1.00 | 15.06 | D |
| ATOM | 3013 | O | MET | D | 28 | 7.696 | −22.914 | 11.178 | 1.00 | 13.55 | D |
| ATOM | 3014 | N | GLN | D | 29 | 7.242 | −22.684 | 9.006 | 1.00 | 15.98 | D |
| ATOM | 3015 | CA | GLN | D | 29 | 8.084 | −21.579 | 8.797 | 1.00 | 17.30 | D |
| ATOM | 3016 | CB | GLN | D | 29 | 9.052 | −21.867 | 7.667 | 1.00 | 17.68 | D |
| ATOM | 3017 | CG | GLN | D | 29 | 10.139 | −20.782 | 7.671 | 1.00 | 19.83 | D |
| ATOM | 3018 | CD | GLN | D | 29 | 10.861 | −20.601 | 6.364 | 1.00 | 20.83 | D |
| ATOM | 3019 | OE1 | GLN | D | 29 | 11.980 | −21.074 | 6.107 | 1.00 | 21.25 | D |
| ATOM | 3020 | NE2 | GLN | D | 29 | 10.223 | −19.864 | 5.534 | 1.00 | 21.94 | D |
| ATOM | 3021 | C | GLN | D | 29 | 7.413 | −20.282 | 8.448 | 1.00 | 17.75 | D |
| ATOM | 3022 | O | GLN | D | 29 | 6.899 | −20.181 | 7.387 | 1.00 | 19.59 | D |
| ATOM | 3023 | N | ASN | D | 30 | 7.399 | −19.251 | 9.290 | 1.00 | 18.30 | D |
| ATOM | 3024 | CA | ASN | D | 30 | 6.829 | −17.988 | 8.824 | 1.00 | 17.01 | D |
| ATOM | 3025 | CB | ASN | D | 30 | 6.061 | −17.306 | 9.935 | 1.00 | 15.89 | D |
| ATOM | 3026 | CG | ASN | D | 30 | 4.628 | −17.813 | 10.078 | 1.00 | 14.36 | D |
| ATOM | 3027 | OD1 | ASN | D | 30 | 4.107 | −17.728 | 11.081 | 1.00 | 14.81 | D |
| ATOM | 3028 | ND2 | ASN | D | 30 | 4.038 | −18.303 | 9.077 | 1.00 | 13.62 | D |
| ATOM | 3029 | C | ASN | D | 30 | 7.938 | −17.088 | 8.323 | 1.00 | 16.09 | D |
| ATOM | 3030 | O | ASN | D | 30 | 9.123 | −17.344 | 8.420 | 1.00 | 16.57 | D |
| ATOM | 3031 | N | ILE | D | 31 | 7.566 | −16.014 | 7.730 | 1.00 | 16.06 | D |
| ATOM | 3032 | CA | ILE | D | 31 | 8.634 | −15.175 | 7.290 | 1.00 | 16.21 | D |
| ATOM | 3033 | CB | ILE | D | 31 | 9.034 | −15.590 | 5.892 | 1.00 | 16.02 | D |
| ATOM | 3034 | CG2 | ILE | D | 31 | 7.780 | −15.568 | 4.976 | 1.00 | 15.37 | D |
| ATOM | 3035 | CG1 | ILE | D | 31 | 10.090 | −14.649 | 5.424 | 1.00 | 16.11 | D |
| ATOM | 3036 | CD1 | ILE | D | 31 | 10.638 | −15.207 | 4.167 | 1.00 | 18.88 | D |
| ATOM | 3037 | C | ILE | D | 31 | 8.229 | −13.757 | 7.370 | 1.00 | 13.70 | D |
| ATOM | 3038 | O | ILE | D | 31 | 7.129 | −13.388 | 7.080 | 1.00 | 12.60 | D |
| ATOM | 3039 | N | MET | D | 32 | 9.163 | −12.981 | 7.795 | 1.00 | 14.26 | D |
| ATOM | 3040 | CA | MET | D | 32 | 8.968 | −11.585 | 8.045 | 1.00 | 15.46 | D |
| ATOM | 3041 | CB | MET | D | 32 | 8.832 | −11.344 | 9.548 | 1.00 | 17.23 | D |
| ATOM | 3042 | CG | MET | D | 32 | 7.462 | −11.341 | 10.167 | 1.00 | 20.56 | D |
| ATOM | 3043 | SD | MET | D | 32 | 6.253 | −10.204 | 9.265 | 1.00 | 23.96 | D |
| ATOM | 3044 | CE | MET | D | 32 | 7.467 | −8.893 | 8.974 | 1.00 | 22.80 | D |
| ATOM | 3045 | C | MET | D | 32 | 10.182 | −10.878 | 7.641 | 1.00 | 14.86 | D |
| ATOM | 3046 | O | MET | D | 32 | 11.270 | −11.131 | 8.148 | 1.00 | 13.91 | D |
| ATOM | 3047 | N | ASN | D | 33 | 10.005 | −9.907 | 6.774 | 1.00 | 15.73 | D |
| ATOM | 3048 | CA | ASN | D | 33 | 11.160 | −9.114 | 6.296 | 1.00 | 17.19 | D |
| ATOM | 3049 | CB | ASN | D | 33 | 11.668 | −8.141 | 7.337 | 1.00 | 17.57 | D |
| ATOM | 3050 | CG | ASN | D | 33 | 10.563 | −7.224 | 7.866 | 1.00 | 18.25 | D |
| ATOM | 3051 | OD1 | ASN | D | 33 | 10.051 | −6.361 | 7.205 | 1.00 | 18.03 | D |
| ATOM | 3052 | ND2 | ASN | D | 33 | 10.208 | −7.431 | 9.087 | 1.00 | 19.11 | D |
| ATOM | 3053 | C | ASN | D | 33 | 12.295 | −10.081 | 5.965 | 1.00 | 18.30 | D |
| ATOM | 3054 | O | ASN | D | 33 | 13.437 | −9.963 | 6.511 | 1.00 | 19.30 | D |
| ATOM | 3055 | N | ASP | D | 34 | 11.935 | −11.069 | 5.121 | 1.00 | 17.78 | D |
| ATOM | 3056 | CA | ASP | D | 34 | 12.838 | −12.101 | 4.619 | 1.00 | 17.49 | D |
| ATOM | 3057 | CB | ASP | D | 34 | 13.892 | −11.475 | 3.637 | 1.00 | 20.38 | D |
| ATOM | 3058 | CG | ASP | D | 34 | 13.282 | −11.050 | 2.198 | 1.00 | 23.62 | D |
| ATOM | 3059 | OD1 | ASP | D | 34 | 12.038 | −10.779 | 1.983 | 1.00 | 26.72 | D |
| ATOM | 3060 | OD2 | ASP | D | 34 | 14.033 | −10.929 | 1.198 | 1.00 | 26.71 | D |
| ATOM | 3061 | C | ASP | D | 34 | 13.506 | −12.888 | 5.678 | 1.00 | 16.66 | D |
| ATOM | 3062 | O | ASP | D | 34 | 14.478 | −13.551 | 5.370 | 1.00 | 16.47 | D |
| ATOM | 3063 | N | MET | D | 35 | 13.049 | −12.806 | 6.922 | 1.00 | 15.98 | D |
| ATOM | 3064 | CA | MET | D | 35 | 13.697 | −13.632 | 7.930 | 1.00 | 16.12 | D |
| ATOM | 3065 | CB | MET | D | 35 | 13.915 | −12.838 | 9.248 | 1.00 | 17.65 | D |
| ATOM | 3066 | CG | MET | D | 35 | 14.956 | −11.778 | 9.140 | 1.00 | 18.47 | D |
| ATOM | 3067 | SD | MET | D | 35 | 16.568 | −12.616 | 9.066 | 1.00 | 23.67 | D |
| ATOM | 3068 | CE | MET | D | 35 | 16.870 | −12.341 | 7.112 | 1.00 | 24.72 | D |
| ATOM | 3069 | C | MET | D | 35 | 12.861 | −14.850 | 8.184 | 1.00 | 14.43 | D |
| ATOM | 3070 | O | MET | D | 35 | 11.690 | −14.730 | 8.431 | 1.00 | 14.81 | D |

TABLE 1-continued

| | | | | | | | | | |
|---|---|---|---|---|---|---|---|---|---|
| ATOM | 3071 | N | PRO | D | 36 | 13.409 | −16.047 | 8.014 | 1.00 | 14.06 | D |
| ATOM | 3072 | CD | PRO | D | 36 | 14.674 | −16.501 | 7.439 | 1.00 | 15.70 | D |
| ATOM | 3073 | CA | PRO | D | 36 | 12.517 | −17.176 | 8.334 | 1.00 | 14.90 | D |
| ATOM | 3074 | CB | PRO | D | 36 | 13.292 | −18.412 | 7.863 | 1.00 | 15.07 | D |
| ATOM | 3075 | CG | PRO | D | 36 | 14.700 | −17.981 | 7.887 | 1.00 | 16.46 | D |
| ATOM | 3076 | C | PRO | D | 36 | 12.295 | −17.194 | 9.886 | 1.00 | 12.31 | D |
| ATOM | 3077 | O | PRO | D | 36 | 13.189 | −16.903 | 10.625 | 1.00 | 10.67 | D |
| ATOM | 3078 | N | ILE | D | 37 | 11.077 | −17.465 | 10.291 | 1.00 | 11.91 | D |
| ATOM | 3079 | CA | ILE | D | 37 | 10.687 | −17.566 | 11.652 | 1.00 | 13.97 | D |
| ATOM | 3080 | CB | ILE | D | 37 | 9.611 | −16.554 | 11.935 | 1.00 | 14.61 | D |
| ATOM | 3081 | CG2 | ILE | D | 37 | 9.264 | −16.521 | 13.376 | 1.00 | 14.67 | D |
| ATOM | 3082 | CG1 | ILE | D | 37 | 10.071 | −15.172 | 11.541 | 1.00 | 16.86 | D |
| ATOM | 3083 | CD1 | ILE | D | 37 | 11.385 | −14.818 | 11.994 | 1.00 | 16.59 | D |
| ATOM | 3084 | C | ILE | D | 37 | 10.131 | −18.976 | 11.916 | 1.00 | 13.87 | D |
| ATOM | 3085 | O | ILE | D | 37 | 9.016 | −19.276 | 11.533 | 1.00 | 13.72 | D |
| ATOM | 3086 | N | TYR | D | 38 | 10.854 | −19.865 | 12.572 | 1.00 | 14.15 | D |
| ATOM | 3087 | CA | TYR | D | 38 | 10.298 | −21.185 | 12.698 | 1.00 | 15.37 | D |
| ATOM | 3088 | CB | TYR | D | 38 | 11.376 | −22.261 | 12.647 | 1.00 | 14.67 | D |
| ATOM | 3089 | CG | TYR | D | 38 | 12.017 | −22.445 | 11.284 | 1.00 | 14.83 | D |
| ATOM | 3090 | CD1 | TYR | D | 38 | 13.003 | −21.610 | 10.853 | 1.00 | 15.23 | D |
| ATOM | 3091 | CE1 | TYR | D | 38 | 13.505 | −21.714 | 9.640 | 1.00 | 17.05 | D |
| ATOM | 3092 | CD2 | TYR | D | 38 | 11.554 | −23.428 | 10.408 | 1.00 | 15.96 | D |
| ATOM | 3093 | CE2 | TYR | D | 38 | 12.019 | −23.568 | 9.210 | 1.00 | 15.39 | D |
| ATOM | 3094 | CZ | TYR | D | 38 | 12.987 | −22.743 | 8.798 | 1.00 | 17.92 | D |
| ATOM | 3095 | OH | TYR | D | 38 | 13.549 | −22.911 | 7.578 | 1.00 | 20.13 | D |
| ATOM | 3096 | C | TYR | D | 38 | 9.467 | −21.381 | 13.919 | 1.00 | 16.02 | D |
| ATOM | 3097 | O | TYR | D | 38 | 9.650 | −20.694 | 14.901 | 1.00 | 16.56 | D |
| ATOM | 3098 | N | MET | D | 39 | 8.508 | −22.313 | 13.855 | 1.00 | 16.33 | D |
| ATOM | 3099 | CA | MET | D | 39 | 7.682 | −22.625 | 15.027 | 1.00 | 17.24 | D |
| ATOM | 3100 | CB | MET | D | 39 | 6.487 | −21.709 | 15.143 | 1.00 | 16.40 | D |
| ATOM | 3101 | CG | MET | D | 39 | 5.296 | −22.131 | 14.376 | 1.00 | 16.72 | D |
| ATOM | 3102 | SD | MET | D | 39 | 4.418 | −20.557 | 14.038 | 1.00 | 20.61 | D |
| ATOM | 3103 | CE | MET | D | 39 | 2.950 | −20.997 | 12.993 | 1.00 | 22.91 | D |
| ATOM | 3104 | C | MET | D | 39 | 7.184 | −24.023 | 15.040 | 1.00 | 15.85 | D |
| ATOM | 3105 | O | MET | D | 39 | 7.157 | −24.604 | 14.035 | 1.00 | 16.63 | D |
| ATOM | 3106 | N | TYR | D | 40 | 6.859 | −24.556 | 16.185 | 1.00 | 14.80 | D |
| ATOM | 3107 | CA | TYR | D | 40 | 6.242 | −25.857 | 16.268 | 1.00 | 15.37 | D |
| ATOM | 3108 | CB | TYR | D | 40 | 6.938 | −26.748 | 17.313 | 1.00 | 15.84 | D |
| ATOM | 3109 | CG | TYR | D | 40 | 7.934 | −27.647 | 16.671 | 1.00 | 18.16 | D |
| ATOM | 3110 | CD1 | TYR | D | 40 | 9.308 | −27.414 | 16.766 | 1.00 | 18.10 | D |
| ATOM | 3111 | CE1 | TYR | D | 40 | 10.212 | −28.251 | 16.052 | 1.00 | 20.09 | D |
| ATOM | 3112 | CD2 | TYR | D | 40 | 7.497 | −28.737 | 15.882 | 1.00 | 19.24 | D |
| ATOM | 3113 | CE2 | TYR | D | 40 | 8.427 | −29.590 | 15.196 | 1.00 | 19.90 | D |
| ATOM | 3114 | CZ | TYR | D | 40 | 9.764 | −29.319 | 15.276 | 1.00 | 20.26 | D |
| ATOM | 3115 | OH | TYR | D | 40 | 10.668 | −30.032 | 14.477 | 1.00 | 23.35 | D |
| ATOM | 3116 | C | TYR | D | 40 | 4.727 | −25.603 | 16.690 | 1.00 | 14.36 | D |
| ATOM | 3117 | O | TYR | D | 40 | 4.487 | −24.863 | 17.676 | 1.00 | 13.69 | D |
| ATOM | 3118 | N | SER | D | 41 | 3.735 | −26.085 | 15.926 | 1.00 | 12.57 | D |
| ATOM | 3119 | CA | SER | D | 41 | 2.412 | −25.875 | 16.376 | 1.00 | 13.29 | D |
| ATOM | 3120 | CB | SER | D | 41 | 1.778 | −24.572 | 15.880 | 1.00 | 13.99 | D |
| ATOM | 3121 | OG | SER | D | 41 | 1.927 | −24.374 | 14.557 | 1.00 | 16.27 | D |
| ATOM | 3122 | C | SER | D | 41 | 1.456 | −26.996 | 16.217 | 1.00 | 13.90 | D |
| ATOM | 3123 | O | SER | D | 41 | 1.735 | −27.929 | 15.534 | 1.00 | 13.93 | D |
| ATOM | 3124 | N | VAL | D | 42 | 0.344 | −26.920 | 16.918 | 1.00 | 14.04 | D |
| ATOM | 3125 | CA | VAL | D | 42 | −0.674 | −27.922 | 16.819 | 1.00 | 15.42 | D |
| ATOM | 3126 | CB | VAL | D | 42 | −0.842 | −28.881 | 18.023 | 1.00 | 16.16 | D |
| ATOM | 3127 | CG1 | VAL | D | 42 | −1.304 | −30.246 | 17.531 | 1.00 | 14.91 | D |
| ATOM | 3128 | CG2 | VAL | D | 42 | 0.345 | −28.684 | 19.042 | 1.00 | 14.24 | D |
| ATOM | 3129 | C | VAL | D | 42 | −1.918 | −27.155 | 17.086 | 1.00 | 15.53 | D |
| ATOM | 3130 | O | VAL | D | 42 | −1.879 | −26.182 | 17.818 | 1.00 | 14.82 | D |
| ATOM | 3131 | N | CYS | D | 43 | −3.023 | −27.761 | 16.683 | 1.00 | 15.85 | D |
| ATOM | 3132 | CA | CYS | D | 43 | −4.341 | −27.172 | 16.866 | 1.00 | 16.96 | D |
| ATOM | 3133 | C | CYS | D | 43 | −5.450 | −28.230 | 16.646 | 1.00 | 16.91 | D |
| ATOM | 3134 | O | CYS | D | 43 | −6.345 | −27.980 | 15.931 | 1.00 | 17.08 | D |
| ATOM | 3135 | CB | CYS | D | 43 | −4.574 | −26.008 | 15.843 | 1.00 | 17.47 | D |
| ATOM | 3136 | SG | CYS | D | 43 | −5.784 | −24.716 | 16.333 | 1.00 | 18.21 | D |
| ATOM | 3137 | N | ASN | D | 44 | −5.365 | −29.407 | 17.221 | 1.00 | 16.15 | D |
| ATOM | 3138 | CA | ASN | D | 44 | −6.410 | −30.391 | 17.140 | 1.00 | 15.14 | D |
| ATOM | 3139 | CB | ASN | D | 44 | −5.796 | −31.815 | 17.270 | 1.00 | 15.90 | D |
| ATOM | 3140 | CG | ASN | D | 44 | −4.875 | −32.096 | 16.207 | 1.00 | 15.73 | D |
| ATOM | 3141 | OD1 | ASN | D | 44 | −3.998 | −32.885 | 16.326 | 1.00 | 14.28 | D |
| ATOM | 3142 | ND2 | ASN | D | 44 | −5.067 | −31.398 | 15.118 | 1.00 | 17.52 | D |
| ATOM | 3143 | C | ASN | D | 44 | −7.380 | −30.157 | 18.306 | 1.00 | 15.21 | D |
| ATOM | 3144 | O | ASN | D | 44 | −7.484 | −31.018 | 19.207 | 1.00 | 14.29 | D |
| ATOM | 3145 | N | VAL | D | 45 | −8.049 | −29.003 | 18.282 | 1.00 | 14.81 | D |
| ATOM | 3146 | CA | VAL | D | 45 | −8.961 | −28.590 | 19.325 | 1.00 | 15.44 | D |
| ATOM | 3147 | CB | VAL | D | 45 | −9.142 | −27.029 | 19.476 | 1.00 | 16.28 | D |
| ATOM | 3148 | CG1 | VAL | D | 45 | −7.874 | −26.433 | 19.876 | 1.00 | 18.01 | D |
| ATOM | 3149 | CG2 | VAL | D | 45 | −9.693 | −26.362 | 18.147 | 1.00 | 15.85 | D |
| ATOM | 3150 | C | VAL | D | 45 | −10.337 | −29.091 | 19.168 | 1.00 | 16.12 | D |

TABLE 1-continued

| | | | | | | | | | |
|---|---|---|---|---|---|---|---|---|---|
| ATOM | 3151 | O | VAL | D | 45 | −11.154 | −28.922 | 20.071 | 1.00 | 16.57 | D |
| ATOM | 3152 | N | MET | D | 46 | −10.564 | −29.806 | 18.106 | 1.00 | 16.47 | D |
| ATOM | 3153 | CA | MET | D | 46 | −11.875 | −30.225 | 17.735 | 1.00 | 16.46 | D |
| ATOM | 3154 | CB | MET | D | 46 | −12.088 | −29.758 | 16.259 | 1.00 | 19.08 | D |
| ATOM | 3155 | CG | MET | D | 46 | −13.324 | −29.004 | 15.900 | 1.00 | 21.30 | D |
| ATOM | 3156 | SD | MET | D | 46 | −13.867 | −27.607 | 17.074 | 1.00 | 26.09 | D |
| ATOM | 3157 | CE | MET | D | 46 | −13.303 | −25.962 | 15.755 | 1.00 | 24.69 | D |
| ATOM | 3158 | C | MET | D | 46 | −11.929 | −31.725 | 17.841 | 1.00 | 17.53 | D |
| ATOM | 3159 | O | MET | D | 46 | −12.845 | −32.339 | 17.330 | 1.00 | 16.49 | D |
| ATOM | 3160 | N | SER | D | 47 | −10.944 | −32.369 | 18.456 | 1.00 | 17.71 | D |
| ATOM | 3161 | CA | SER | D | 47 | −11.070 | −33.853 | 18.551 | 1.00 | 18.11 | D |
| ATOM | 3162 | CB | SER | D | 47 | −10.184 | −34.490 | 17.541 | 1.00 | 18.57 | D |
| ATOM | 3163 | OG | SER | D | 47 | −9.644 | −33.486 | 16.639 | 1.00 | 20.90 | D |
| ATOM | 3164 | C | SER | D | 47 | −10.518 | −34.076 | 19.909 | 1.00 | 20.01 | D |
| ATOM | 3165 | O | SER | D | 47 | −9.593 | −33.251 | 20.327 | 1.00 | 21.57 | D |
| ATOM | 3166 | N | GLY | D | 48 | −10.992 | −35.076 | 20.626 | 1.00 | 18.85 | D |
| ATOM | 3167 | CA | GLY | D | 48 | −10.497 | −35.182 | 21.974 | 1.00 | 17.41 | D |
| ATOM | 3168 | C | GLY | D | 48 | −9.305 | −36.075 | 22.146 | 1.00 | 17.99 | D |
| ATOM | 3169 | O | GLY | D | 48 | −8.661 | −36.431 | 21.145 | 1.00 | 17.72 | D |
| ATOM | 3170 | N | ASP | D | 49 | −8.986 | −36.422 | 23.408 | 1.00 | 18.20 | D |
| ATOM | 3171 | CA | ASP | D | 49 | −7.892 | −37.355 | 23.664 | 1.00 | 18.08 | D |
| ATOM | 3172 | CB | ASP | D | 49 | −8.322 | −38.745 | 23.165 | 1.00 | 19.81 | D |
| ATOM | 3173 | CG | ASP | D | 49 | −9.760 | −39.158 | 23.686 | 1.00 | 21.51 | D |
| ATOM | 3174 | OD1 | ASP | D | 49 | −10.639 | −39.552 | 22.889 | 1.00 | 18.09 | D |
| ATOM | 3175 | OD2 | ASP | D | 49 | −9.950 | −39.076 | 24.959 | 1.00 | 24.22 | D |
| ATOM | 3176 | C | ASP | D | 49 | −6.649 | −36.995 | 22.922 | 1.00 | 18.28 | D |
| ATOM | 3177 | O | ASP | D | 49 | −6.134 | −37.871 | 22.289 | 1.00 | 18.47 | D |
| ATOM | 3178 | N | GLN | D | 50 | −6.160 | −35.758 | 22.912 | 1.00 | 18.14 | D |
| ATOM | 3179 | CA | GLN | D | 50 | −4.923 | −35.503 | 22.166 | 1.00 | 17.18 | D |
| ATOM | 3180 | CB | GLN | D | 50 | −4.785 | −34.050 | 21.801 | 1.00 | 18.05 | D |
| ATOM | 3181 | CG | GLN | D | 50 | −5.805 | −33.562 | 20.809 | 1.00 | 18.38 | D |
| ATOM | 3182 | CD | GLN | D | 50 | −5.821 | −34.431 | 19.546 | 1.00 | 18.57 | D |
| ATOM | 3183 | OE1 | GLN | D | 50 | −4.884 | −34.408 | 18.767 | 1.00 | 18.37 | D |
| ATOM | 3184 | NE2 | GLN | D | 50 | −6.892 | −35.193 | 19.356 | 1.00 | 18.84 | D |
| ATOM | 3185 | C | GLN | D | 50 | −3.824 | −35.872 | 23.115 | 1.00 | 17.28 | D |
| ATOM | 3186 | O | GLN | D | 50 | −3.983 | −35.770 | 24.293 | 1.00 | 16.64 | D |
| ATOM | 3187 | N | ASP | D | 51 | −2.732 | −36.392 | 22.587 | 1.00 | 17.39 | D |
| ATOM | 3188 | CA | ASP | D | 51 | −1.573 | −36.738 | 23.377 | 1.00 | 16.93 | D |
| ATOM | 3189 | CB | ASP | D | 51 | −1.656 | −38.170 | 23.899 | 1.00 | 17.91 | D |
| ATOM | 3190 | CG | ASP | D | 51 | −0.582 | −38.496 | 24.980 | 1.00 | 18.72 | D |
| ATOM | 3191 | OD1 | ASP | D | 51 | −0.390 | −39.669 | 25.265 | 1.00 | 19.90 | D |
| ATOM | 3192 | OD2 | ASP | D | 51 | 0.066 | −37.609 | 25.572 | 1.00 | 18.15 | D |
| ATOM | 3193 | C | ASP | D | 51 | −0.394 | −36.588 | 22.396 | 1.00 | 17.07 | D |
| ATOM | 3194 | O | ASP | D | 51 | 0.264 | −37.549 | 22.029 | 1.00 | 16.71 | D |
| ATOM | 3195 | N | ASN | D | 52 | −0.135 | −35.374 | 21.942 | 1.00 | 15.99 | D |
| ATOM | 3196 | CA | ASN | D | 52 | 0.946 | −35.173 | 21.001 | 1.00 | 15.18 | D |
| ATOM | 3197 | CB | ASN | D | 52 | 0.531 | −34.188 | 19.930 | 1.00 | 17.08 | D |
| ATOM | 3198 | CG | ASN | D | 52 | −0.806 | −34.484 | 19.377 | 1.00 | 18.54 | D |
| ATOM | 3199 | OD1 | ASN | D | 52 | −0.925 | −35.436 | 18.598 | 1.00 | 19.73 | D |
| ATOM | 3200 | ND2 | ASN | D | 52 | −1.831 | −33.681 | 19.738 | 1.00 | 16.50 | D |
| ATOM | 3201 | C | ASN | D | 52 | 2.281 | −34.692 | 21.632 | 1.00 | 14.19 | D |
| ATOM | 3202 | O | ASN | D | 52 | 2.329 | −33.804 | 22.429 | 1.00 | 10.84 | D |
| ATOM | 3203 | N | TRP | D | 53 | 3.348 | −35.325 | 21.165 | 1.00 | 13.45 | D |
| ATOM | 3204 | CA | TRP | D | 53 | 4.606 | −35.099 | 21.725 | 1.00 | 14.05 | D |
| ATOM | 3205 | CB | TRP | D | 53 | 5.104 | −36.345 | 22.458 | 1.00 | 14.65 | D |
| ATOM | 3206 | CG | TRP | D | 53 | 4.377 | −36.737 | 23.709 | 1.00 | 14.96 | D |
| ATOM | 3207 | CD2 | TRP | D | 53 | 4.833 | −36.612 | 25.026 | 1.00 | 16.19 | D |
| ATOM | 3208 | CE2 | TRP | D | 53 | 3.839 | −37.143 | 25.849 | 1.00 | 17.40 | D |
| ATOM | 3209 | CE3 | TRP | D | 53 | 5.987 | −36.121 | 25.608 | 1.00 | 15.87 | D |
| ATOM | 3210 | CD1 | TRP | D | 53 | 3.207 | −37.277 | 23.762 | 1.00 | 14.16 | D |
| ATOM | 3211 | NE1 | TRP | D | 53 | 2.825 | −37.521 | 25.026 | 1.00 | 15.87 | D |
| ATOM | 3212 | CZ2 | TRP | D | 53 | 3.967 | −37.209 | 27.291 | 1.00 | 19.87 | D |
| ATOM | 3213 | CZ3 | TRP | D | 53 | 6.130 | −36.188 | 26.990 | 1.00 | 17.01 | D |
| ATOM | 3214 | CH2 | TRP | D | 53 | 5.121 | −36.731 | 27.821 | 1.00 | 19.17 | D |
| ATOM | 3215 | C | TRP | D | 53 | 5.667 | −34.590 | 20.841 | 1.00 | 14.61 | D |
| ATOM | 3216 | O | TRP | D | 53 | 5.806 | −34.980 | 19.771 | 1.00 | 13.50 | D |
| ATOM | 3217 | N | LEU | D | 54 | 6.451 | −33.660 | 21.379 | 1.00 | 15.67 | D |
| ATOM | 3218 | CA | LEU | D | 54 | 7.498 | −32.956 | 20.665 | 1.00 | 15.43 | D |
| ATOM | 3219 | CB | LEU | D | 54 | 7.169 | −31.456 | 20.549 | 1.00 | 15.58 | D |
| ATOM | 3220 | CG | LEU | D | 54 | 8.287 | −30.667 | 19.921 | 1.00 | 15.12 | D |
| ATOM | 3221 | CD1 | LEU | D | 54 | 8.559 | −31.248 | 18.561 | 1.00 | 14.08 | D |
| ATOM | 3222 | CD2 | LEU | D | 54 | 7.982 | −29.174 | 19.888 | 1.00 | 13.70 | D |
| ATOM | 3223 | C | LEU | D | 54 | 8.664 | −33.125 | 21.590 | 1.00 | 15.91 | D |
| ATOM | 3224 | O | LEU | D | 54 | 8.601 | −32.768 | 22.767 | 1.00 | 15.46 | D |
| ATOM | 3225 | N | ARG | D | 55 | 9.691 | −33.748 | 21.048 | 1.00 | 16.31 | D |
| ATOM | 3226 | CA | ARG | D | 55 | 10.885 | −33.974 | 21.768 | 1.00 | 16.82 | D |
| ATOM | 3227 | CB | ARG | D | 55 | 11.218 | −35.435 | 21.962 | 1.00 | 17.34 | D |
| ATOM | 3228 | CG | ARG | D | 55 | 12.498 | −35.548 | 22.830 | 1.00 | 19.18 | D |
| ATOM | 3229 | CD | ARG | D | 55 | 12.870 | −36.951 | 23.350 | 1.00 | 19.84 | D |
| ATOM | 3230 | NE | ARG | D | 55 | 13.862 | −37.737 | 22.565 | 1.00 | 21.10 | D |

TABLE 1-continued

| | | | | | | | | | | |
|---|---|---|---|---|---|---|---|---|---|---|
| ATOM | 3231 | CZ | ARG | D | 55 | 13.999 | −37.748 | 21.224 | 1.00 | 21.55 | D |
| ATOM | 3232 | NH1 | ARG | D | 55 | 13.213 | −36.954 | 20.424 | 1.00 | 24.98 | D |
| ATOM | 3233 | NH2 | ARG | D | 55 | 14.816 | −38.621 | 20.663 | 1.00 | 16.08 | D |
| ATOM | 3234 | C | ARG | D | 55 | 12.037 | −33.304 | 21.077 | 1.00 | 16.45 | D |
| ATOM | 3235 | O | ARG | D | 55 | 12.166 | −33.383 | 19.873 | 1.00 | 17.23 | D |
| ATOM | 3236 | N | THR | D | 56 | 12.828 | −32.592 | 21.857 | 1.00 | 15.45 | D |
| ATOM | 3237 | CA | THR | D | 56 | 14.011 | −31.959 | 21.397 | 1.00 | 13.60 | D |
| ATOM | 3238 | CB | THR | D | 56 | 14.664 | −31.059 | 22.580 | 1.00 | 13.89 | D |
| ATOM | 3239 | OG1 | THR | D | 56 | 15.259 | −31.914 | 23.647 | 1.00 | 9.06 | D |
| ATOM | 3240 | CG2 | THR | D | 56 | 13.632 | −30.040 | 23.101 | 1.00 | 12.40 | D |
| ATOM | 3241 | C | THR | D | 56 | 15.017 | −33.060 | 21.207 | 1.00 | 13.23 | D |
| ATOM | 3242 | O | THR | D | 56 | 14.830 | −34.221 | 21.566 | 1.00 | 11.13 | D |
| ATOM | 3243 | N | ASN | D | 57 | 16.160 | −32.660 | 20.712 | 1.00 | 14.15 | D |
| ATOM | 3244 | CA | ASN | D | 57 | 17.222 | −33.632 | 20.608 | 1.00 | 16.53 | D |
| ATOM | 3245 | CB | ASN | D | 57 | 18.075 | −33.340 | 19.468 | 1.00 | 17.83 | D |
| ATOM | 3246 | CG | ASN | D | 57 | 17.845 | −34.356 | 18.406 | 1.00 | 21.60 | D |
| ATOM | 3247 | OD1 | ASN | D | 57 | 16.764 | −34.296 | 17.696 | 1.00 | 20.48 | D |
| ATOM | 3248 | ND2 | ASN | D | 57 | 18.792 | −35.368 | 18.296 | 1.00 | 22.87 | D |
| ATOM | 3249 | C | ASN | D | 57 | 18.119 | −33.782 | 21.783 | 1.00 | 17.27 | D |
| ATOM | 3250 | O | ASN | D | 57 | 18.178 | −32.926 | 22.629 | 1.00 | 17.89 | D |
| ATOM | 3251 | N | TRP | D | 58 | 18.861 | −34.863 | 21.817 | 1.00 | 17.73 | D |
| ATOM | 3252 | CA | TRP | D | 58 | 19.779 | −35.215 | 22.891 | 1.00 | 18.44 | D |
| ATOM | 3253 | CB | TRP | D | 58 | 20.732 | −36.277 | 22.378 | 1.00 | 19.65 | D |
| ATOM | 3254 | CG | TRP | D | 58 | 21.870 | −36.804 | 23.254 | 1.00 | 20.12 | D |
| ATOM | 3255 | CD2 | TRP | D | 58 | 21.768 | −37.257 | 24.574 | 1.00 | 19.13 | D |
| ATOM | 3256 | CE2 | TRP | D | 58 | 23.037 | −37.805 | 24.945 | 1.00 | 20.24 | D |
| ATOM | 3257 | CE3 | TRP | D | 58 | 20.728 | −37.273 | 25.489 | 1.00 | 17.64 | D |
| ATOM | 3258 | CD1 | TRP | D | 58 | 23.209 | −37.083 | 22.858 | 1.00 | 22.41 | D |
| ATOM | 3259 | NE1 | TRP | D | 58 | 23.918 | −37.698 | 23.893 | 1.00 | 21.15 | D |
| ATOM | 3260 | CZ2 | TRP | D | 58 | 23.242 | −38.340 | 26.209 | 1.00 | 19.82 | D |
| ATOM | 3261 | CZ3 | TRP | D | 58 | 20.913 | −37.785 | 26.657 | 1.00 | 16.75 | D |
| ATOM | 3262 | CH2 | TRP | D | 58 | 22.164 | −38.326 | 27.041 | 1.00 | 19.77 | D |
| ATOM | 3263 | C | TRP | D | 58 | 20.541 | −33.987 | 23.285 | 1.00 | 19.15 | D |
| ATOM | 3264 | O | TRP | D | 58 | 21.017 | −33.252 | 22.379 | 1.00 | 20.09 | D |
| ATOM | 3265 | N | VAL | D | 59 | 20.627 | −33.689 | 24.581 | 1.00 | 17.10 | D |
| ATOM | 3266 | CA | VAL | D | 59 | 21.334 | −32.477 | 24.962 | 1.00 | 17.02 | D |
| ATOM | 3267 | CB | VAL | D | 59 | 20.356 | −31.311 | 25.458 | 1.00 | 15.34 | D |
| ATOM | 3268 | CG1 | VAL | D | 59 | 21.193 | −30.105 | 25.828 | 1.00 | 14.94 | D |
| ATOM | 3269 | CG2 | VAL | D | 59 | 19.340 | −30.897 | 24.437 | 1.00 | 12.10 | D |
| ATOM | 3270 | C | VAL | D | 59 | 22.341 | −32.847 | 26.076 | 1.00 | 16.27 | D |
| ATOM | 3271 | O | VAL | D | 59 | 21.967 | −33.315 | 27.151 | 1.00 | 16.45 | D |
| ATOM | 3272 | N | TYR | D | 60 | 23.610 | −32.641 | 25.780 | 1.00 | 14.78 | D |
| ATOM | 3273 | CA | TYR | D | 60 | 24.660 | −32.866 | 26.720 | 1.00 | 15.80 | D |
| ATOM | 3274 | CB | TYR | D | 60 | 26.058 | −32.592 | 26.130 | 1.00 | 16.65 | D |
| ATOM | 3275 | CG | TYR | D | 60 | 26.459 | −33.568 | 25.110 | 1.00 | 18.65 | D |
| ATOM | 3276 | CD1 | TYR | D | 60 | 26.322 | −33.280 | 23.733 | 1.00 | 19.12 | D |
| ATOM | 3277 | CE1 | TYR | D | 60 | 26.568 | −34.330 | 22.789 | 1.00 | 20.48 | D |
| ATOM | 3278 | CD2 | TYR | D | 60 | 26.857 | −34.876 | 25.515 | 1.00 | 19.52 | D |
| ATOM | 3279 | CE2 | TYR | D | 60 | 27.113 | −35.897 | 24.637 | 1.00 | 19.59 | D |
| ATOM | 3280 | CZ | TYR | D | 60 | 26.993 | −35.662 | 23.278 | 1.00 | 20.27 | D |
| ATOM | 3281 | OH | TYR | D | 60 | 27.452 | −36.678 | 22.403 | 1.00 | 21.04 | D |
| ATOM | 3282 | C | TYR | D | 60 | 24.528 | −31.902 | 27.884 | 1.00 | 14.64 | D |
| ATOM | 3283 | O | TYR | D | 60 | 24.314 | −30.703 | 27.727 | 1.00 | 12.28 | D |
| ATOM | 3284 | N | ARG | D | 61 | 24.674 | −32.494 | 29.048 | 1.00 | 14.77 | D |
| ATOM | 3285 | CA | ARG | D | 61 | 24.578 | −31.722 | 30.239 | 1.00 | 16.88 | D |
| ATOM | 3286 | CB | ARG | D | 61 | 24.307 | −32.624 | 31.466 | 1.00 | 16.82 | D |
| ATOM | 3287 | CG | ARG | D | 61 | 24.533 | −31.928 | 32.905 | 1.00 | 15.29 | D |
| ATOM | 3288 | CD | ARG | D | 61 | 24.049 | −32.889 | 34.066 | 1.00 | 15.40 | D |
| ATOM | 3289 | NE | ARG | D | 61 | 25.083 | −33.849 | 34.351 | 1.00 | 15.86 | D |
| ATOM | 3290 | CZ | ARG | D | 61 | 26.208 | −33.544 | 35.038 | 1.00 | 16.95 | D |
| ATOM | 3291 | NH1 | ARG | D | 61 | 26.400 | −32.313 | 35.542 | 1.00 | 16.24 | D |
| ATOM | 3292 | NH2 | ARG | D | 61 | 27.195 | −34.426 | 35.138 | 1.00 | 18.08 | D |
| ATOM | 3293 | C | ARG | D | 61 | 25.826 | −30.888 | 30.526 | 1.00 | 17.57 | D |
| ATOM | 3294 | O | ARG | D | 61 | 25.712 | −29.745 | 31.020 | 1.00 | 17.68 | D |
| ATOM | 3295 | N | GLY | D | 62 | 26.994 | −31.472 | 30.167 | 1.00 | 18.17 | D |
| ATOM | 3296 | CA | GLY | D | 62 | 28.306 | −30.891 | 30.452 | 1.00 | 19.04 | D |
| ATOM | 3297 | C | GLY | D | 62 | 28.538 | −30.739 | 31.967 | 1.00 | 19.64 | D |
| ATOM | 3298 | O | GLY | D | 62 | 28.498 | −31.685 | 32.764 | 1.00 | 19.02 | D |
| ATOM | 3299 | N | GLU | D | 63 | 28.716 | −29.522 | 32.393 | 1.00 | 20.35 | D |
| ATOM | 3300 | CA | GLU | D | 63 | 28.968 | −29.218 | 33.821 | 1.00 | 21.65 | D |
| ATOM | 3301 | CB | GLU | D | 63 | 30.058 | −28.070 | 33.832 | 1.00 | 22.59 | D |
| ATOM | 3302 | CG | GLU | D | 63 | 30.373 | −27.398 | 35.126 | 1.00 | 23.69 | D |
| ATOM | 3303 | CD | GLU | D | 63 | 30.948 | −28.456 | 36.070 | 1.00 | 27.34 | D |
| ATOM | 3304 | OE1 | GLU | D | 63 | 31.116 | −28.200 | 37.394 | 1.00 | 24.00 | D |
| ATOM | 3305 | OE2 | GLU | D | 63 | 31.218 | −29.586 | 35.370 | 1.00 | 30.19 | D |
| ATOM | 3306 | C | GLU | D | 63 | 27.660 | −28.736 | 34.521 | 1.00 | 21.40 | D |
| ATOM | 3307 | O | GLU | D | 63 | 27.742 | −28.617 | 35.721 | 1.00 | 22.79 | D |
| ATOM | 3308 | N | ALA | D | 64 | 26.541 | −28.408 | 33.815 | 1.00 | 19.66 | D |
| ATOM | 3309 | CA | ALA | D | 64 | 25.267 | −27.955 | 34.450 | 1.00 | 17.93 | D |
| ATOM | 3310 | CB | ALA | D | 64 | 24.147 | −27.718 | 33.375 | 1.00 | 14.92 | D |

TABLE 1-continued

| | | | | | | | | | | |
|---|---|---|---|---|---|---|---|---|---|---|
| ATOM | 3311 | C | ALA | D | 64 | 24.701 | −28.833 | 35.565 | 1.00 | 17.29 | D |
| ATOM | 3312 | O | ALA | D | 64 | 24.844 | −30.051 | 35.545 | 1.00 | 17.24 | D |
| ATOM | 3313 | N | GLU | D | 65 | 24.116 | −28.162 | 36.582 | 1.00 | 17.50 | D |
| ATOM | 3314 | CA | GLU | D | 65 | 23.369 | −28.856 | 37.691 | 1.00 | 18.23 | D |
| ATOM | 3315 | CB | GLU | D | 65 | 23.857 | −28.445 | 39.116 | 1.00 | 20.32 | D |
| ATOM | 3316 | CG | GLU | D | 65 | 25.363 | −28.417 | 39.379 | 1.00 | 24.45 | D |
| ATOM | 3317 | CD | GLU | D | 65 | 25.966 | −29.318 | 39.750 | 1.00 | 26.11 | D |
| ATOM | 3318 | OE1 | GLU | D | 65 | 25.514 | −30.424 | 40.743 | 1.00 | 26.65 | D |
| ATOM | 3319 | OE2 | GLU | D | 65 | 26.881 | −30.343 | 39.007 | 1.00 | 28.20 | D |
| ATOM | 3320 | C | GLU | D | 65 | 21.825 | −28.457 | 37.600 | 1.00 | 17.07 | D |
| ATOM | 3321 | O | GLU | D | 65 | 20.925 | −29.263 | 37.825 | 1.00 | 16.29 | D |
| ATOM | 3322 | N | ARG | D | 66 | 21.575 | −27.179 | 37.365 | 1.00 | 15.98 | D |
| ATOM | 3323 | CA | ARG | D | 66 | 20.241 | −26.667 | 37.205 | 1.00 | 15.62 | D |
| ATOM | 3324 | CB | ARG | D | 66 | 19.877 | −25.637 | 38.241 | 1.00 | 15.60 | D |
| ATOM | 3325 | CG | ARG | D | 66 | 18.454 | −25.244 | 38.275 | 1.00 | 16.25 | D |
| ATOM | 3326 | CD | ARG | D | 66 | 17.926 | −25.513 | 39.687 | 1.00 | 18.50 | D |
| ATOM | 3327 | NE | ARG | D | 66 | 16.439 | −25.348 | 39.737 | 1.00 | 20.44 | D |
| ATOM | 3328 | CZ | ARG | D | 66 | 15.526 | −26.247 | 40.125 | 1.00 | 20.77 | D |
| ATOM | 3329 | NH1 | ARG | D | 66 | 15.894 | −27.479 | 40.552 | 1.00 | 20.41 | D |
| ATOM | 3330 | NH2 | ARG | D | 66 | 14.233 | −25.895 | 40.102 | 1.00 | 20.90 | D |
| ATOM | 3331 | C | ARG | D | 66 | 20.246 | −25.943 | 35.841 | 1.00 | 16.11 | D |
| ATOM | 3332 | O | ARG | D | 66 | 21.181 | −25.223 | 35.501 | 1.00 | 16.20 | D |
| ATOM | 3333 | N | ASN | D | 67 | 19.229 | −26.161 | 35.028 | 1.00 | 15.68 | D |
| ATOM | 3334 | CA | ASN | D | 67 | 19.231 | −25.492 | 33.762 | 1.00 | 16.79 | D |
| ATOM | 3335 | CB | ASN | D | 67 | 19.298 | −26.514 | 32.599 | 1.00 | 18.54 | D |
| ATOM | 3336 | CG | ASN | D | 67 | 18.302 | −27.610 | 32.778 | 1.00 | 22.16 | D |
| ATOM | 3337 | OD1 | ASN | D | 67 | 18.292 | −28.218 | 33.888 | 1.00 | 27.48 | D |
| ATOM | 3338 | ND2 | ASN | D | 67 | 17.489 | −27.941 | 31.763 | 1.00 | 19.29 | D |
| ATOM | 3339 | C | ASN | D | 67 | 17.936 | −24.719 | 33.813 | 1.00 | 16.14 | D |
| ATOM | 3340 | O | ASN | D | 67 | 17.081 | −25.053 | 34.531 | 1.00 | 15.32 | D |
| ATOM | 3341 | N | ASN | D | 68 | 17.871 | −23.653 | 33.079 | 1.00 | 15.79 | D |
| ATOM | 3342 | CA | ASN | D | 68 | 16.743 | −22.841 | 33.040 | 1.00 | 17.53 | D |
| ATOM | 3343 | CB | ASN | D | 68 | 17.248 | −21.421 | 33.329 | 1.00 | 19.20 | D |
| ATOM | 3344 | CG | ASN | D | 68 | 17.696 | −21.252 | 34.795 | 1.00 | 22.05 | D |
| ATOM | 3345 | OD1 | ASN | D | 68 | 16.871 | −20.873 | 35.687 | 1.00 | 23.00 | D |
| ATOM | 3346 | ND2 | ASN | D | 68 | 18.976 | −21.573 | 35.093 | 1.00 | 20.89 | D |
| ATOM | 3347 | C | ASN | D | 68 | 16.133 | −22.950 | 31.584 | 1.00 | 16.88 | D |
| ATOM | 3348 | O | ASN | D | 68 | 16.927 | −23.068 | 30.571 | 1.00 | 16.43 | D |
| ATOM | 3349 | N | PHE | D | 69 | 14.786 | −22.984 | 31.471 | 1.00 | 15.36 | D |
| ATOM | 3350 | CA | PHE | D | 69 | 14.254 | −22.931 | 30.110 | 1.00 | 16.24 | D |
| ATOM | 3351 | CB | PHE | D | 69 | 13.713 | −24.207 | 29.508 | 1.00 | 17.54 | D |
| ATOM | 3352 | CG | PHE | D | 69 | 13.461 | −25.194 | 30.440 | 1.00 | 20.07 | D |
| ATOM | 3353 | CD1 | PHE | D | 69 | 12.588 | −24.926 | 31.469 | 1.00 | 22.38 | D |
| ATOM | 3354 | CD2 | PHE | D | 69 | 14.113 | −26.438 | 30.341 | 1.00 | 20.21 | D |
| ATOM | 3355 | CE1 | PHE | D | 69 | 12.350 | −25.922 | 32.448 | 1.00 | 24.68 | D |
| ATOM | 3356 | CE2 | PHE | D | 69 | 13.915 | −27.464 | 31.262 | 1.00 | 21.71 | D |
| ATOM | 3357 | CZ | PHE | D | 69 | 13.057 | −27.246 | 32.324 | 1.00 | 24.02 | D |
| ATOM | 3358 | C | PHE | D | 69 | 13.253 | −21.881 | 29.873 | 1.00 | 15.61 | D |
| ATOM | 3359 | O | PHE | D | 69 | 12.346 | −21.713 | 30.631 | 1.00 | 16.02 | D |
| ATOM | 3360 | N | GLU | D | 70 | 13.508 | −21.134 | 28.820 | 1.00 | 14.41 | D |
| ATOM | 3361 | CA | GLU | D | 70 | 12.698 | −20.073 | 28.384 | 1.00 | 14.48 | D |
| ATOM | 3362 | CB | GLU | D | 70 | 13.563 | −18.880 | 28.061 | 1.00 | 13.90 | D |
| ATOM | 3363 | CG | GLU | D | 70 | 12.780 | −17.608 | 28.136 | 1.00 | 15.09 | D |
| ATOM | 3364 | CD | GLU | D | 70 | 13.536 | −16.393 | 27.510 | 1.00 | 16.80 | D |
| ATOM | 3365 | OE1 | GLU | D | 70 | 13.518 | −15.221 | 28.089 | 1.00 | 16.75 | D |
| ATOM | 3366 | OE2 | GLU | D | 70 | 14.126 | −16.652 | 26.436 | 1.00 | 15.11 | D |
| ATOM | 3367 | C | GLU | D | 70 | 11.899 | −20.516 | 27.134 | 1.00 | 14.26 | D |
| ATOM | 3368 | O | GLU | D | 70 | 12.476 | −20.857 | 26.112 | 1.00 | 12.31 | D |
| ATOM | 3369 | N | LEU | D | 71 | 10.567 | −20.444 | 27.294 | 1.00 | 15.14 | D |
| ATOM | 3370 | CA | LEU | D | 71 | 9.511 | −20.782 | 26.310 | 1.00 | 16.19 | D |
| ATOM | 3371 | CB | LEU | D | 71 | 8.528 | −21.849 | 26.831 | 1.00 | 16.92 | D |
| ATOM | 3372 | CG | LEU | D | 71 | 9.152 | −23.156 | 27.232 | 1.00 | 16.27 | D |
| ATOM | 3373 | CD1 | LEU | D | 71 | 8.122 | −23.962 | 27.952 | 1.00 | 18.66 | D |
| ATOM | 3374 | CD2 | LEU | D | 71 | 9.628 | −23.923 | 26.133 | 1.00 | 15.92 | D |
| ATOM | 3375 | C | LEU | D | 71 | 8.698 | −19.515 | 25.913 | 1.00 | 17.85 | D |
| ATOM | 3376 | O | LEU | D | 71 | 8.204 | −18.756 | 26.791 | 1.00 | 18.28 | D |
| ATOM | 3377 | N | ASN | D | 72 | 8.568 | −19.310 | 24.582 | 1.00 | 17.64 | D |
| ATOM | 3378 | CA | ASN | D | 72 | 7.818 | −18.223 | 23.982 | 1.00 | 16.61 | D |
| ATOM | 3379 | CB | ASN | D | 72 | 8.773 | −17.373 | 23.128 | 1.00 | 18.61 | D |
| ATOM | 3380 | CG | ASN | D | 72 | 9.482 | −16.236 | 23.995 | 1.00 | 21.12 | D |
| ATOM | 3381 | OD1 | ASN | D | 72 | 10.555 | −15.568 | 23.672 | 1.00 | 18.69 | D |
| ATOM | 3382 | ND2 | ASN | D | 72 | 8.845 | −16.024 | 25.151 | 1.00 | 24.85 | D |
| ATOM | 3383 | C | ASN | D | 72 | 6.761 | −18.918 | 23.170 | 1.00 | 17.10 | D |
| ATOM | 3384 | O | ASN | D | 72 | 7.071 | −19.733 | 22.291 | 1.00 | 16.98 | D |
| ATOM | 3385 | N | PHE | D | 73 | 5.491 | −18.652 | 23.467 | 1.00 | 16.48 | D |
| ATOM | 3386 | CA | PHE | D | 73 | 4.435 | −19.306 | 22.718 | 1.00 | 16.23 | D |
| ATOM | 3387 | CB | PHE | D | 73 | 4.103 | −20.603 | 23.376 | 1.00 | 17.40 | D |
| ATOM | 3388 | CG | PHE | D | 73 | 3.731 | −20.447 | 24.816 | 1.00 | 18.25 | D |
| ATOM | 3389 | CD1 | PHE | D | 73 | 2.384 | −20.339 | 25.186 | 1.00 | 18.03 | D |
| ATOM | 3390 | CD2 | PHE | D | 73 | 4.733 | −20.284 | 25.801 | 1.00 | 17.94 | D |

TABLE 1-continued

| | | | | | | | | | | |
|---|---|---|---|---|---|---|---|---|---|---|
| ATOM | 3391 | CE1 | PHE | D | 73 | 2.050 | −20.066 | 26.489 | 1.00 | 18.65 D |
| ATOM | 3392 | CE2 | PHE | D | 73 | 4.371 | −19.998 | 27.171 | 1.00 | 19.18 D |
| ATOM | 3393 | CZ | PHE | D | 73 | 3.047 | −19.889 | 27.516 | 1.00 | 18.13 D |
| ATOM | 3394 | C | PHE | D | 73 | 3.155 | −18.526 | 22.646 | 1.00 | 16.01 D |
| ATOM | 3395 | O | PHE | D | 73 | 3.026 | −17.529 | 23.307 | 1.00 | 15.01 D |
| ATOM | 3396 | N | THR | D | 74 | 2.218 | −19.017 | 21.845 | 1.00 | 16.10 D |
| ATOM | 3397 | CA | THR | D | 74 | 0.953 | −18.382 | 21.799 | 1.00 | 18.51 D |
| ATOM | 3398 | CB | THR | D | 74 | 0.653 | −17.624 | 20.499 | 1.00 | 18.64 D |
| ATOM | 3399 | OG1 | THR | D | 74 | 0.260 | −18.528 | 19.454 | 1.00 | 19.30 D |
| ATOM | 3400 | CG2 | THR | D | 74 | 1.878 | −16.874 | 20.139 | 1.00 | 19.47 D |
| ATOM | 3401 | C | THR | D | 74 | −0.066 | −19.418 | 21.906 | 1.00 | 17.41 D |
| ATOM | 3402 | O | THR | D | 74 | 0.229 | −20.557 | 21.620 | 1.00 | 18.09 D |
| ATOM | 3403 | N | VAL | D | 75 | −1.278 | −18.991 | 22.272 | 1.00 | 17.25 D |
| ATOM | 3404 | CA | VAL | D | 75 | −2.393 | −19.903 | 22.466 | 1.00 | 16.96 D |
| ATOM | 3405 | CB | VAL | D | 75 | −2.479 | −20.335 | 23.920 | 1.00 | 1626 D |
| ATOM | 3406 | CG1 | VAL | D | 75 | −3.568 | −21.243 | 24.116 | 1.00 | 13.36 D |
| ATOM | 3407 | CG2 | VAL | D | 75 | −1.201 | −21.031 | 24.293 | 1.00 | 16.17 D |
| ATOM | 3408 | C | VAL | D | 75 | −3.715 | −19.292 | 21.991 | 1.00 | 17.35 D |
| ATOM | 3409 | O | VAL | D | 75 | −4.210 | −18.287 | 22.482 | 1.00 | 16.92 D |
| ATOM | 3410 | N | ARG | D | 76 | −4.261 | −19.922 | 20.997 | 1.00 | 17.16 D |
| ATOM | 3411 | CA | ARG | D | 76 | −5.449 | −19.402 | 20.531 | 1.00 | 17.86 D |
| ATOM | 3412 | CB | ARG | D | 76 | −5.803 | −20.006 | 19.167 | 1.00 | 18.87 D |
| ATOM | 3413 | CG | ARG | D | 76 | −7.069 | −19.460 | 18.551 | 1.00 | 18.28 D |
| ATOM | 3414 | CD | ARG | D | 76 | −7.044 | −19.606 | 17.015 | 1.00 | 19.29 D |
| ATOM | 3415 | NE | ARG | D | 76 | −8.405 | −19.484 | 16.544 | 1.00 | 17.58 D |
| ATOM | 3416 | CZ | ARG | D | 76 | −8.857 | −20.015 | 15.431 | 1.00 | 17.97 D |
| ATOM | 3417 | NH1 | ARG | D | 76 | −8.043 | −20.699 | 14.563 | 1.00 | 17.05 D |
| ATOM | 3418 | NH2 | ARG | D | 76 | −10.171 | −20.014 | 15.284 | 1.00 | 14.83 D |
| ATOM | 3419 | C | ARG | D | 76 | −6.512 | −19.697 | 21.528 | 1.00 | 18.08 D |
| ATOM | 3420 | O | ARG | D | 76 | −6.599 | −20.839 | 22.115 | 1.00 | 18.84 D |
| ATOM | 3421 | N | ASP | D | 77 | −7.341 | −18.653 | 21.715 | 1.00 | 16.95 D |
| ATOM | 3422 | CA | ASP | D | 77 | −8.507 | −18.655 | 22.616 | 1.00 | 15.75 D |
| ATOM | 3423 | CB | ASP | D | 77 | −9.160 | −17.264 | 22.511 | 1.00 | 16.64 D |
| ATOM | 3424 | CG | ASP | D | 77 | −10.469 | −17.141 | 23.265 | 1.00 | 17.76 D |
| ATOM | 3425 | OD1 | ASP | D | 77 | −10.795 | −18.045 | 24.128 | 1.00 | 18.11 D |
| ATOM | 3426 | OD2 | ASP | D | 77 | −11.138 | −16.110 | 22.944 | 1.00 | 16.43 D |
| ATOM | 3427 | C | ASP | D | 77 | −9.455 | −19.801 | 22.288 | 1.00 | 14.63 D |
| ATOM | 3428 | O | ASP | D | 77 | −9.845 | −19.962 | 21.189 | 1.00 | 12.26 D |
| ATOM | 3429 | N | CYS | D | 78 | −9.805 | −20.614 | 23.269 | 1.00 | 15.43 D |
| ATOM | 3430 | CA | CYS | D | 78 | −10.668 | −21.740 | 22.980 | 1.00 | 18.27 D |
| ATOM | 3431 | C | CYS | D | 78 | −12.060 | −21.378 | 22.549 | 1.00 | 18.14 D |
| ATOM | 3432 | O | CYS | D | 78 | −12.726 | −22.218 | 21.985 | 1.00 | 19.72 D |
| ATOM | 3433 | CB | CYS | D | 78 | −10.789 | −22.663 | 24.149 | 1.00 | 18.95 D |
| ATOM | 3434 | SG | CYS | D | 78 | −9.548 | −23.969 | 24.091 | 1.00 | 20.60 D |
| ATOM | 3435 | N | ASN | D | 79 | −12.471 | −20.148 | 22.829 | 1.00 | 17.21 D |
| ATOM | 3436 | CA | ASN | D | 79 | −13.735 | −19.696 | 22.443 | 1.00 | 16.77 D |
| ATOM | 3437 | CB | ASN | D | 79 | −14.186 | −18.625 | 23.415 | 1.00 | 16.90 D |
| ATOM | 3438 | CG | ASN | D | 79 | −14.537 | −19.162 | 24.795 | 1.00 | 17.05 D |
| ATOM | 3439 | OD1 | ASN | D | 79 | −14.511 | −18.391 | 25.702 | 1.00 | 17.05 D |
| ATOM | 3440 | ND2 | ASN | D | 79 | −14.851 | −20.425 | 24.960 | 1.00 | 17.24 D |
| ATOM | 3441 | C | ASN | D | 79 | −13.798 | −19.149 | 20.958 | 1.00 | 16.53 D |
| ATOM | 3442 | O | ASN | D | 79 | −14.871 | −18.787 | 20.404 | 1.00 | 15.73 D |
| ATOM | 3443 | N | SER | D | 80 | −12.640 | −19.035 | 20.343 | 1.00 | 15.74 D |
| ATOM | 3444 | CA | SER | D | 80 | −12.563 | −18.493 | 18.990 | 1.00 | 15.25 D |
| ATOM | 3445 | CB | SER | D | 80 | −11.191 | −17.873 | 18.749 | 1.00 | 15.76 D |
| ATOM | 3446 | OG | SER | D | 80 | −10.150 | −18.857 | 18.599 | 1.00 | 17.89 D |
| ATOM | 3447 | C | SER | D | 80 | −12.863 | −19.564 | 17.898 | 1.00 | 15.19 D |
| ATOM | 3448 | O | SER | D | 80 | −12.634 | −19.374 | 16.764 | 1.00 | 13.48 D |
| ATOM | 3449 | N | PHE | D | 81 | −13.368 | −20.702 | 18.296 | 1.00 | 16.93 D |
| ATOM | 3450 | CA | PHE | D | 81 | −13.764 | −21.698 | 17.365 | 1.00 | 17.91 D |
| ATOM | 3451 | CB | PHE | D | 81 | −13.112 | −23.008 | 17.819 | 1.00 | 19.26 D |
| ATOM | 3452 | CG | PHE | D | 81 | −11.603 | −22.994 | 17.775 | 1.00 | 19.53 D |
| ATOM | 3453 | CD1 | PHE | D | 81 | −10.869 | −22.792 | 18.947 | 1.00 | 19.84 D |
| ATOM | 3454 | CD2 | PHE | D | 81 | −10.901 | −23.160 | 16.548 | 1.00 | 18.86 D |
| ATOM | 3455 | CE1 | PHE | D | 81 | −9.432 | −22.752 | 18.914 | 1.00 | 19.84 D |
| ATOM | 3456 | CE2 | PHE | D | 81 | −9.431 | −23.117 | 16.488 | 1.00 | 18.33 D |
| ATOM | 3457 | CZ | PHE | D | 81 | −8.708 | −22.919 | 17.635 | 1.00 | 18.86 D |
| ATOM | 3458 | C | PHE | D | 81 | −15.316 | −21.720 | 17.464 | 1.00 | 17.92 D |
| ATOM | 3459 | O | PHE | D | 81 | −15.835 | −22.306 | 18.339 | 1.00 | 17.34 D |
| ATOM | 3460 | N | PRO | D | 82 | −16.038 | −21.084 | 16.520 | 1.00 | 20.82 D |
| ATOM | 3461 | CD | PRO | D | 82 | −15.424 | −20.904 | 15.185 | 1.00 | 20.79 D |
| ATOM | 3462 | CA | PRO | D | 82 | −17.509 | −20.949 | 16.401 | 1.00 | 19.73 D |
| ATOM | 3463 | CB | PRO | D | 82 | −17.732 | −20.676 | 14.926 | 1.00 | 20.80 D |
| ATOM | 3464 | CG | PRO | D | 82 | −16.503 | −20.071 | 14.438 | 1.00 | 19.96 D |
| ATOM | 3465 | C | PRO | D | 82 | −18.276 | −22.183 | 16.831 | 1.00 | 20.80 D |
| ATOM | 3466 | O | PRO | D | 82 | −17.897 | −23.286 | 16.363 | 1.00 | 21.43 D |
| ATOM | 3467 | N | GLY | D | 83 | −19.357 | −21.997 | 17.655 | 1.00 | 20.07 D |
| ATOM | 3468 | CA | GLY | D | 83 | −20.116 | −23.079 | 18.215 | 1.00 | 18.79 D |
| ATOM | 3469 | C | GLY | D | 83 | −19.206 | −23.534 | 19.368 | 1.00 | 18.59 D |
| ATOM | 3470 | O | GLY | D | 83 | −18.062 | −23.034 | 19.585 | 1.00 | 18.31 D |

TABLE 1-continued

| | | | | | | | | | |
|---|---|---|---|---|---|---|---|---|---|
| ATOM | 3471 | N | GLY | D | 84 | −19.560 | −24.466 | 20.221 | 1.00 | 17.80 | D |
| ATOM | 3472 | CA | GLY | D | 84 | −18.436 | −24.676 | 21.210 | 1.00 | 17.68 | D |
| ATOM | 3473 | C | GLY | D | 84 | −17.171 | −25.510 | 20.879 | 1.00 | 17.94 | D |
| ATOM | 3474 | O | GLY | D | 84 | −17.094 | −26.070 | 19.812 | 1.00 | 18.24 | D |
| ATOM | 3475 | N | ALA | D | 85 | −16.118 | −25.592 | 21.703 | 1.00 | 17.35 | D |
| ATOM | 3476 | CA | ALA | D | 85 | −15.054 | −26.535 | 21.301 | 1.00 | 17.01 | D |
| ATOM | 3477 | CB | ALA | D | 85 | −13.809 | −25.881 | 20.806 | 1.00 | 15.87 | D |
| ATOM | 3478 | C | ALA | D | 85 | −14.773 | −27.299 | 22.550 | 1.00 | 16.95 | D |
| ATOM | 3479 | O | ALA | D | 85 | −13.705 | −27.274 | 23.019 | 1.00 | 17.89 | D |
| ATOM | 3480 | N | SER | D | 86 | −15.739 | −28.049 | 23.051 | 1.00 | 16.46 | D |
| ATOM | 3481 | CA | SER | D | 86 | −15.563 | −28.774 | 24.280 | 1.00 | 16.14 | D |
| ATOM | 3482 | CB | SER | D | 86 | −16.689 | −29.812 | 24.451 | 1.00 | 14.71 | D |
| ATOM | 3483 | OG | SER | D | 86 | −16.641 | −30.842 | 23.557 | 1.00 | 12.44 | D |
| ATOM | 3484 | C | SER | D | 86 | −14.235 | −29.345 | 24.690 | 1.00 | 15.71 | D |
| ATOM | 3485 | O | SER | D | 86 | −13.948 | −29.211 | 25.818 | 1.00 | 16.17 | D |
| ATOM | 3486 | N | SER | D | 87 | −13.423 | −29.914 | 23.821 | 1.00 | 16.53 | D |
| ATOM | 3487 | CA | SER | D | 87 | −12.155 | −30.593 | 24.267 | 1.00 | 16.53 | D |
| ATOM | 3488 | CB | SER | D | 87 | −11.896 | −31.888 | 23.421 | 1.00 | 16.81 | D |
| ATOM | 3489 | OG | SER | D | 87 | −11.643 | −31.489 | 22.017 | 1.00 | 14.92 | D |
| ATOM | 3490 | C | SER | D | 87 | −10.942 | −29.672 | 24.101 | 1.00 | 17.20 | D |
| ATOM | 3491 | O | SER | D | 87 | −9.822 | −30.000 | 24.462 | 1.00 | 17.68 | D |
| ATOM | 3492 | N | CYS | D | 88 | −11.151 | −28.526 | 23.540 | 1.00 | 17.05 | D |
| ATOM | 3493 | CA | CYS | D | 88 | −10.082 | −27.597 | 23.304 | 1.00 | 16.09 | D |
| ATOM | 3494 | C | CYS | D | 88 | −9.582 | −27.239 | 24.646 | 1.00 | 17.58 | D |
| ATOM | 3495 | O | CYS | D | 88 | −10.362 | −27.205 | 25.576 | 1.00 | 17.80 | D |
| ATOM | 3496 | CB | CYS | D | 88 | −10.652 | −26.411 | 22.610 | 1.00 | 17.01 | D |
| ATOM | 3497 | SG | CYS | D | 88 | −9.604 | −25.039 | 22.290 | 1.00 | 19.02 | D |
| ATOM | 3498 | N | LYS | D | 89 | −8.287 | −26.933 | 24.759 | 1.00 | 17.62 | D |
| ATOM | 3499 | CA | LYS | D | 89 | −7.603 | −26.647 | 26.022 | 1.00 | 16.33 | D |
| ATOM | 3500 | CB | LYS | D | 89 | −6.597 | −27.834 | 26.350 | 1.00 | 17.51 | D |
| ATOM | 3501 | CG | LYS | D | 89 | −7.273 | −29.185 | 26.610 | 1.00 | 19.27 | D |
| ATOM | 3502 | CD | LYS | D | 89 | −8.190 | −29.138 | 27.946 | 1.00 | 18.85 | D |
| ATOM | 3503 | CE | LYS | D | 89 | −8.611 | −30.627 | 28.363 | 1.00 | 20.75 | D |
| ATOM | 3504 | NZ | LYS | D | 89 | −9.370 | −30.769 | 29.706 | 1.00 | 19.02 | D |
| ATOM | 3505 | C | LYS | D | 89 | −6.789 | −25.423 | 25.877 | 1.00 | 16.45 | D |
| ATOM | 3506 | O | LYS | D | 89 | −6.432 | −25.107 | 24.799 | 1.00 | 15.96 | D |
| ATOM | 3507 | N | GLU | D | 90 | −6.435 | −24.741 | 26.967 | 1.00 | 17.07 | D |
| ATOM | 3508 | CA | GLU | D | 90 | −5.496 | −23.647 | 26.806 | 1.00 | 17.93 | D |
| ATOM | 3509 | CB | GLU | D | 90 | −6.188 | −22.312 | 26.967 | 1.00 | 16.45 | D |
| ATOM | 3510 | CG | GLU | D | 90 | −7.409 | −22.217 | 26.142 | 1.00 | 16.16 | D |
| ATOM | 3511 | CD | GLU | D | 90 | −8.393 | −21.045 | 26.498 | 1.00 | 17.60 | D |
| ATOM | 3512 | OE1 | GLU | D | 90 | −8.856 | −20.931 | 27.628 | 1.00 | 17.89 | D |
| ATOM | 3513 | OE2 | GLU | D | 90 | −8.746 | −20.224 | 25.627 | 1.00 | 17.65 | D |
| ATOM | 3514 | C | GLU | D | 90 | −4.245 | −23.778 | 27.692 | 1.00 | 18.48 | D |
| ATOM | 3515 | O | GLU | D | 90 | −3.862 | −22.877 | 28.411 | 1.00 | 21.55 | D |
| ATOM | 3516 | N | THR | D | 91 | −3.614 | −24.935 | 27.682 | 1.00 | 18.26 | D |
| ATOM | 3517 | CA | THR | D | 91 | −2.357 | −25.089 | 28.427 | 1.00 | 16.60 | D |
| ATOM | 3518 | CB | THR | D | 91 | −2.578 | −25.460 | 29.997 | 1.00 | 14.80 | D |
| ATOM | 3519 | OG1 | THR | D | 91 | −3.294 | −26.699 | 30.125 | 1.00 | 10.95 | D |
| ATOM | 3520 | CG2 | THR | D | 91 | −3.308 | −24.369 | 30.732 | 1.00 | 12.00 | D |
| ATOM | 3521 | C | THR | D | 91 | −1.683 | −26.296 | 27.694 | 1.00 | 15.41 | D |
| ATOM | 3522 | O | THR | D | 91 | −2.302 | −26.905 | 26.838 | 1.00 | 14.59 | D |
| ATOM | 3523 | N | PHE | D | 92 | −0.421 | −26.558 | 28.023 | 1.00 | 15.32 | D |
| ATOM | 3524 | CA | PHE | D | 92 | 0.332 | −27.687 | 27.507 | 1.00 | 16.21 | D |
| ATOM | 3525 | CB | PHE | D | 92 | 1.078 | −27.348 | 26.192 | 1.00 | 16.80 | D |
| ATOM | 3526 | CG | PHE | D | 92 | 2.080 | −26.225 | 26.297 | 1.00 | 17.31 | D |
| ATOM | 3527 | CD1 | PHE | D | 92 | 3.419 | −26.487 | 26.465 | 1.00 | 15.49 | D |
| ATOM | 3528 | CD2 | PHE | D | 92 | 1.669 | −24.912 | 26.084 | 1.00 | 18.72 | D |
| ATOM | 3529 | CE1 | PHE | D | 92 | 4.314 | −25.530 | 26.395 | 1.00 | 16.65 | D |
| ATOM | 3530 | CE2 | PHE | D | 92 | 2.596 | −23.897 | 26.018 | 1.00 | 19.52 | D |
| ATOM | 3531 | CZ | PHE | D | 92 | 3.944 | −24.211 | 26.165 | 1.00 | 18.57 | D |
| ATOM | 3532 | C | PHE | D | 92 | 1.309 | −28.083 | 28.535 | 1.00 | 15.28 | D |
| ATOM | 3533 | O | PHE | D | 92 | 1.601 | −27.279 | 29.433 | 1.00 | 15.28 | D |
| ATOM | 3534 | N | ASN | D | 93 | 1.857 | −29.279 | 28.413 | 1.00 | 14.54 | D |
| ATOM | 3535 | CA | ASN | D | 93 | 2.850 | −29.753 | 29.434 | 1.00 | 15.33 | D |
| ATOM | 3536 | CB | ASN | D | 93 | 2.460 | −31.081 | 29.928 | 1.00 | 14.73 | D |
| ATOM | 3537 | CG | ASN | D | 93 | 1.130 | −31.027 | 30.584 | 1.00 | 15.73 | D |
| ATOM | 3538 | OD1 | ASN | D | 93 | 0.837 | −30.179 | 31.450 | 1.00 | 15.93 | D |
| ATOM | 3539 | ND2 | ASN | D | 93 | 0.260 | −31.893 | 30.142 | 1.00 | 16.74 | D |
| ATOM | 3540 | C | ASN | D | 93 | 4.296 | −29.788 | 29.125 | 1.00 | 15.14 | D |
| ATOM | 3541 | O | ASN | D | 93 | 4.649 | −29.966 | 27.986 | 1.00 | 16.20 | D |
| ATOM | 3542 | N | LEU | D | 94 | 5.135 | −29.555 | 30.109 | 1.00 | 15.02 | D |
| ATOM | 3543 | CA | LEU | D | 94 | 6.559 | −29.651 | 29.892 | 1.00 | 15.21 | D |
| ATOM | 3544 | CB | LEU | D | 94 | 7.194 | −28.392 | 30.310 | 1.00 | 14.73 | D |
| ATOM | 3545 | CG | LEU | D | 94 | 8.708 | −28.205 | 30.268 | 1.00 | 16.53 | D |
| ATOM | 3546 | CD1 | LEU | D | 94 | 9.234 | −28.383 | 28.858 | 1.00 | 14.89 | D |
| ATOM | 3547 | CD2 | LEU | D | 94 | 9.058 | −26.708 | 30.809 | 1.00 | 16.21 | D |
| ATOM | 3548 | C | LEU | D | 94 | 7.182 | −30.860 | 30.657 | 1.00 | 16.17 | D |
| ATOM | 3549 | O | LEU | D | 94 | 6.907 | −31.066 | 31.857 | 1.00 | 16.26 | D |
| ATOM | 3550 | N | TYR | D | 95 | 7.996 | −31.665 | 29.942 | 1.00 | 15.82 | D |

TABLE 1-continued

| | | | | | | | | | | |
|---|---|---|---|---|---|---|---|---|---|---|
| ATOM | 3551 | CA | TYR | D | 95 | 8.707 | −32.829 | 30.471 | 1.00 | 14.64 | D |
| ATOM | 3552 | CB | TYR | D | 95 | 8.130 | −34.148 | 29.932 | 1.00 | 15.76 | D |
| ATOM | 3553 | CG | TYR | D | 95 | 6.723 | −34.529 | 30.390 | 1.00 | 16.54 | D |
| ATOM | 3554 | CD1 | TYR | D | 95 | 5.572 | −33.725 | 30.056 | 1.00 | 16.70 | D |
| ATOM | 3555 | CE1 | TYR | D | 95 | 4.268 | −34.034 | 30.572 | 1.00 | 16.86 | D |
| ATOM | 3556 | CD2 | TYR | D | 95 | 6.514 | −35.647 | 31.221 | 1.00 | 16.07 | D |
| ATOM | 3557 | CE2 | TYR | D | 95 | 5.218 | −35.951 | 31.723 | 1.00 | 16.46 | D |
| ATOM | 3558 | CZ | TYR | D | 95 | 4.135 | −35.135 | 31.389 | 1.00 | 16.98 | D |
| ATOM | 3559 | OH | TYR | D | 95 | 2.938 | −35.406 | 31.914 | 1.00 | 19.26 | D |
| ATOM | 3560 | C | TYR | D | 95 | 10.225 | −32.848 | 30.121 | 1.00 | 15.26 | D |
| ATOM | 3561 | O | TYR | D | 95 | 10.791 | −32.070 | 29.313 | 1.00 | 14.09 | D |
| ATOM | 3562 | N | TYR | D | 96 | 10.913 | −33.787 | 30.751 | 1.00 | 15.14 | D |
| ATOM | 3563 | CA | TYR | D | 96 | 12.315 | −33.988 | 30.457 | 1.00 | 13.56 | D |
| ATOM | 3564 | CB | TYR | D | 96 | 13.205 | −32.955 | 31.144 | 1.00 | 16.01 | D |
| ATOM | 3565 | CG | TYR | D | 96 | 13.509 | −33.247 | 32.573 | 1.00 | 16.74 | D |
| ATOM | 3566 | CD1 | TYR | D | 96 | 14.704 | −33.880 | 32.935 | 1.00 | 18.17 | D |
| ATOM | 3567 | CE1 | TYR | D | 96 | 14.979 | −34.251 | 34.302 | 1.00 | 18.55 | D |
| ATOM | 3568 | CD2 | TYR | D | 96 | 12.575 | −32.977 | 33.562 | 1.00 | 16.69 | D |
| ATOM | 3569 | CE2 | TYR | D | 96 | 12.787 | −33.331 | 34.868 | 1.00 | 17.48 | D |
| ATOM | 3570 | CZ | TYR | D | 96 | 13.994 | −33.962 | 35.262 | 1.00 | 18.37 | D |
| ATOM | 3571 | OH | TYR | D | 96 | 14.196 | −34.286 | 36.607 | 1.00 | 17.84 | D |
| ATOM | 3572 | C | TYR | D | 96 | 12.572 | −35.347 | 30.954 | 1.00 | 13.60 | D |
| ATOM | 3573 | O | TYR | D | 96 | 11.739 | −35.950 | 31.570 | 1.00 | 11.43 | D |
| ATOM | 3574 | N | ALA | D | 97 | 13.728 | −35.850 | 30.597 | 1.00 | 14.53 | D |
| ATOM | 3575 | CA | ALA | D | 97 | 14.240 | −37.162 | 30.985 | 1.00 | 14.44 | D |
| ATOM | 3576 | CB | ALA | D | 97 | 13.651 | −38.323 | 30.085 | 1.00 | 13.27 | D |
| ATOM | 3577 | C | ALA | D | 97 | 15.773 | −37.018 | 30.828 | 1.00 | 15.30 | D |
| ATOM | 3578 | O | ALA | D | 97 | 16.304 | −36.271 | 29.926 | 1.00 | 16.06 | D |
| ATOM | 3579 | N | GLU | D | 98 | 16.479 | −37.681 | 31.751 | 1.00 | 16.31 | D |
| ATOM | 3580 | CA | GLU | D | 98 | 17.947 | −37.731 | 31.780 | 1.00 | 16.24 | D |
| ATOM | 3581 | CB | GLU | D | 98 | 18.457 | −37.594 | 33.189 | 1.00 | 16.71 | D |
| ATOM | 3582 | CG | GLU | D | 98 | 18.471 | −36.177 | 33.670 | 1.00 | 19.08 | D |
| ATOM | 3583 | CD | GLU | D | 98 | 19.048 | −36.054 | 35.126 | 1.00 | 18.93 | D |
| ATOM | 3584 | OE1 | GLU | D | 98 | 18.284 | −36.243 | 36.075 | 1.00 | 17.93 | D |
| ATOM | 3585 | OE2 | GLU | D | 98 | 20.274 | −35.836 | 35.294 | 1.00 | 19.32 | D |
| ATOM | 3586 | C | GLU | D | 98 | 18.421 | −39.057 | 31.311 | 1.00 | 15.37 | D |
| ATOM | 3587 | O | GLU | D | 98 | 17.810 | −40.024 | 31.598 | 1.00 | 14.93 | D |
| ATOM | 3588 | N | SER | D | 99 | 19.478 | −39.114 | 30.525 | 1.00 | 16.72 | D |
| ATOM | 3589 | CA | SER | D | 99 | 20.061 | −40.457 | 30.244 | 1.00 | 17.38 | D |
| ATOM | 3590 | CB | SER | D | 99 | 19.288 | −41.306 | 29.182 | 1.00 | 16.75 | D |
| ATOM | 3591 | OG | SER | D | 99 | 19.321 | −40.720 | 27.890 | 1.00 | 15.75 | D |
| ATOM | 3592 | C | SER | D | 99 | 21.492 | −40.360 | 29.915 | 1.00 | 17.91 | D |
| ATOM | 3593 | O | SER | D | 99 | 22.005 | −39.344 | 29.514 | 1.00 | 19.41 | D |
| ATOM | 3594 | N | ASP | D | 100 | 22.180 | −41.444 | 30.127 | 1.00 | 19.16 | D |
| ATOM | 3595 | CA | ASP | D | 100 | 23.596 | −41.429 | 29.817 | 1.00 | 19.48 | D |
| ATOM | 3596 | CB | ASP | D | 100 | 24.374 | −42.313 | 30.762 | 1.00 | 19.63 | D |
| ATOM | 3597 | CG | ASP | D | 100 | 24.315 | −41.803 | 32.236 | 1.00 | 21.52 | D |
| ATOM | 3598 | OD1 | ASP | D | 100 | 24.630 | −40.590 | 32.598 | 1.00 | 18.39 | D |
| ATOM | 3599 | OD2 | ASP | D | 100 | 23.918 | −42.713 | 33.067 | 1.00 | 23.94 | D |
| ATOM | 3600 | C | ASP | D | 100 | 23.902 | −41.790 | 28.408 | 1.00 | 18.32 | D |
| ATOM | 3601 | O | ASP | D | 100 | 25.060 | −41.613 | 28.048 | 1.00 | 18.89 | D |
| ATOM | 3602 | N | LEU | D | 101 | 22.896 | −42.312 | 27.677 | 1.00 | 17.62 | D |
| ATOM | 3603 | CA | LEU | D | 101 | 22.980 | −42.685 | 26.259 | 1.00 | 17.31 | D |
| ATOM | 3604 | CB | LEU | D | 101 | 22.573 | −44.142 | 25.935 | 1.00 | 18.84 | D |
| ATOM | 3605 | CG | LEU | D | 101 | 22.923 | −45.377 | 26.837 | 1.00 | 22.54 | D |
| ATOM | 3606 | CD1 | LEU | D | 101 | 22.476 | −45.092 | 28.409 | 1.00 | 24.73 | D |
| ATOM | 3607 | CD2 | LEU | D | 101 | 22.061 | −46.653 | 26.357 | 1.00 | 23.52 | D |
| ATOM | 3608 | C | LEU | D | 101 | 21.933 | −41.865 | 25.508 | 1.00 | 16.75 | D |
| ATOM | 3609 | O | LEU | D | 101 | 20.892 | −41.527 | 26.032 | 1.00 | 14.18 | D |
| ATOM | 3610 | N | ASP | D | 102 | 22.269 | −41.604 | 24.238 | 1.00 | 17.50 | D |
| ATOM | 3611 | CA | ASP | D | 102 | 21.417 | −41.002 | 23.255 | 1.00 | 19.13 | D |
| ATOM | 3612 | CB | ASP | D | 102 | 22.260 | −40.675 | 22.062 | 1.00 | 18.92 | D |
| ATOM | 3613 | CG | ASP | D | 102 | 21.563 | −39.738 | 21.150 | 1.00 | 19.98 | D |
| ATOM | 3614 | OD1 | ASP | D | 102 | 20.327 | −39.801 | 20.971 | 1.00 | 21.79 | D |
| ATOM | 3615 | OD2 | ASP | D | 102 | 22.216 | −38.864 | 20.566 | 1.00 | 20.96 | D |
| ATOM | 3616 | C | ASP | D | 102 | 20.323 | −42.106 | 22.821 | 1.00 | 20.79 | D |
| ATOM | 3617 | O | ASP | D | 102 | 20.648 | −43.183 | 22.204 | 1.00 | 21.84 | D |
| ATOM | 3618 | N | TYR | D | 103 | 19.058 | −41.870 | 23.153 | 1.00 | 21.04 | D |
| ATOM | 3619 | CA | TYR | D | 103 | 18.033 | −42.825 | 22.768 | 1.00 | 20.60 | D |
| ATOM | 3620 | CB | TYR | D | 103 | 16.664 | −42.474 | 23.435 | 1.00 | 22.48 | D |
| ATOM | 3621 | CG | TYR | D | 103 | 16.557 | −42.814 | 24.916 | 1.00 | 23.42 | D |
| ATOM | 3622 | CD1 | TYR | D | 103 | 16.933 | −44.106 | 25.410 | 1.00 | 23.40 | D |
| ATOM | 3623 | CE1 | TYR | D | 103 | 16.929 | −44.408 | 26.796 | 1.00 | 22.01 | D |
| ATOM | 3624 | CD2 | TYR | D | 103 | 16.140 | −41.792 | 25.868 | 1.00 | 25.05 | D |
| ATOM | 3625 | CE2 | TYR | D | 103 | 16.139 | −42.063 | 27.268 | 1.00 | 23.93 | D |
| ATOM | 3626 | CZ | TYR | D | 103 | 16.557 | −43.404 | 27.707 | 1.00 | 24.66 | D |
| ATOM | 3627 | OH | TYR | D | 103 | 16.627 | −43.644 | 29.156 | 1.00 | 27.59 | D |
| ATOM | 3628 | C | TYR | D | 103 | 17.816 | −42.795 | 21.268 | 1.00 | 18.98 | D |
| ATOM | 3629 | O | TYR | D | 103 | 17.120 | −43.622 | 20.726 | 1.00 | 17.79 | D |
| ATOM | 3630 | N | GLY | D | 104 | 18.361 | −41.831 | 20.604 | 1.00 | 17.98 | D |

TABLE 1-continued

| ATOM | 3631 | CA | GLY | D | 104 | 18.069 | −41.774 | 19.196 | 1.00 | 18.07 | D |
|------|------|------|-----|---|-----|--------|---------|--------|------|-------|---|
| ATOM | 3632 | C | GLY | D | 104 | 16.572 | −41.548 | 18.906 | 1.00 | 18.03 | D |
| ATOM | 3633 | O | GLY | D | 104 | 15.978 | −40.596 | 19.370 | 1.00 | 18.19 | D |
| ATOM | 3634 | N | THR | D | 105 | 15.961 | −42.466 | 18.148 | 1.00 | 18.73 | D |
| ATOM | 3635 | CA | THR | D | 105 | 14.541 | −42.369 | 17.840 | 1.00 | 19.70 | D |
| ATOM | 3636 | CB | THR | D | 105 | 14.360 | −42.928 | 16.474 | 1.00 | 19.42 | D |
| ATOM | 3637 | OG1 | THR | D | 105 | 14.703 | −41.840 | 15.590 | 1.00 | 17.63 | D |
| ATOM | 3638 | CG2 | THR | D | 105 | 12.887 | −43.426 | 16.257 | 1.00 | 20.26 | D |
| ATOM | 3639 | C | THR | D | 105 | 13.559 | −42.916 | 18.868 | 1.00 | 19.39 | D |
| ATOM | 3640 | O | THR | D | 105 | 12.389 | −42.647 | 18.781 | 1.00 | 18.30 | D |
| ATOM | 3641 | N | ASN | D | 106 | 14.089 | −43.578 | 19.883 | 1.00 | 20.32 | D |
| ATOM | 3642 | CA | ASN | D | 106 | 13.297 | −44.136 | 20.961 | 1.00 | 22.51 | D |
| ATOM | 3643 | CB | ASN | D | 106 | 14.103 | −44.933 | 21.931 | 1.00 | 24.51 | D |
| ATOM | 3644 | CG | ASN | D | 106 | 14.527 | −46.170 | 21.356 | 1.00 | 27.23 | D |
| ATOM | 3645 | OD1 | ASN | D | 106 | 15.458 | −46.852 | 21.929 | 1.00 | 29.54 | D |
| ATOM | 3646 | ND2 | ASN | D | 106 | 13.841 | −46.564 | 20.178 | 1.00 | 29.52 | D |
| ATOM | 3647 | C | ASN | D | 106 | 12.666 | −43.231 | 21.927 | 1.00 | 21.63 | D |
| ATOM | 3648 | O | ASN | D | 106 | 13.221 | −43.036 | 23.012 | 1.00 | 22.55 | D |
| ATOM | 3649 | N | PHE | D | 107 | 11.489 | −42.759 | 21.636 | 1.00 | 20.98 | D |
| ATOM | 3650 | CA | PHE | D | 107 | 10.871 | −41.941 | 22.586 | 1.00 | 19.46 | D |
| ATOM | 3651 | CB | PHE | D | 107 | 9.987 | −40.960 | 21.873 | 1.00 | 19.20 | D |
| ATOM | 3652 | CG | PHE | D | 107 | 9.221 | −40.122 | 22.831 | 1.00 | 17.97 | D |
| ATOM | 3653 | CD1 | PHE | D | 107 | 9.897 | −39.248 | 23.697 | 1.00 | 17.02 | D |
| ATOM | 3654 | CD2 | PHE | D | 107 | 7.841 | −40.141 | 22.824 | 1.00 | 16.50 | D |
| ATOM | 3655 | CE1 | PHE | D | 107 | 9.170 | −38.405 | 24.510 | 1.00 | 17.42 | D |
| ATOM | 3656 | CE2 | PHE | D | 107 | 7.162 | −39.308 | 23.626 | 1.00 | 16.48 | D |
| ATOM | 3657 | CZ | PHE | D | 107 | 7.811 | −38.444 | 24.458 | 1.00 | 16.86 | D |
| ATOM | 3658 | C | PHE | D | 107 | 10.058 | −42.827 | 23.467 | 1.00 | 17.79 | D |
| ATOM | 3659 | O | PHE | D | 107 | 9.347 | −43.647 | 22.980 | 1.00 | 17.89 | D |
| ATOM | 3660 | N | GLN | D | 108 | 10.149 | −42.635 | 24.765 | 1.00 | 17.79 | D |
| ATOM | 3661 | CA | GLN | D | 108 | 9.323 | −43.378 | 25.755 | 1.00 | 17.97 | D |
| ATOM | 3662 | CB | GLN | D | 108 | 10.199 | −44.214 | 26.653 | 1.00 | 16.17 | D |
| ATOM | 3663 | CG | GLN | D | 108 | 11.013 | −45.210 | 25.901 | 1.00 | 16.60 | D |
| ATOM | 3664 | CD | GLN | D | 108 | 10.155 | −46.331 | 25.107 | 1.00 | 17.58 | D |
| ATOM | 3665 | OE1 | GLN | D | 108 | 10.682 | −46.992 | 24.272 | 1.00 | 18.99 | D |
| ATOM | 3666 | NE2 | GLN | D | 108 | 8.874 | −46.474 | 25.372 | 1.00 | 17.06 | D |
| ATOM | 3667 | C | GLN | D | 108 | 8.686 | −42.334 | 26.624 | 1.00 | 17.83 | D |
| ATOM | 3668 | O | GLN | D | 108 | 9.404 | −41.806 | 27.447 | 1.00 | 18.84 | D |
| ATOM | 3669 | N | LYS | D | 109 | 7.402 | −42.026 | 26.430 | 1.00 | 18.01 | D |
| ATOM | 3670 | CA | LYS | D | 109 | 6.728 | −41.018 | 27.206 | 1.00 | 18.68 | D |
| ATOM | 3671 | CB | LYS | D | 109 | 5.204 | −40.950 | 26.791 | 1.00 | 20.04 | D |
| ATOM | 3672 | CG | LYS | D | 109 | 4.303 | −41.124 | 28.001 | 1.00 | 22.19 | D |
| ATOM | 3673 | CD | LYS | D | 109 | 2.783 | −41.200 | 27.657 | 1.00 | 25.55 | D |
| ATOM | 3674 | CE | LYS | D | 109 | 2.103 | −39.828 | 27.136 | 1.00 | 24.14 | D |
| ATOM | 3675 | NZ | LYS | D | 109 | 0.565 | −40.135 | 27.197 | 1.00 | 24.06 | D |
| ATOM | 3676 | C | LYS | D | 109 | 6.922 | −41.403 | 28.720 | 1.00 | 18.52 | D |
| ATOM | 3677 | O | LYS | D | 109 | 7.283 | −40.553 | 29.585 | 1.00 | 16.85 | D |
| ATOM | 3678 | N | ARG | D | 110 | 6.779 | −42.709 | 28.998 | 1.00 | 18.31 | D |
| ATOM | 3679 | CA | ARG | D | 110 | 6.843 | −43.137 | 30.369 | 1.00 | 19.11 | D |
| ATOM | 3680 | CB | ARG | D | 110 | 6.433 | −44.587 | 30.462 | 1.00 | 19.77 | D |
| ATOM | 3681 | CG | ARG | D | 110 | 4.849 | −44.532 | 30.652 | 1.00 | 23.98 | D |
| ATOM | 3682 | CD | ARG | D | 110 | 3.893 | −44.193 | 29.280 | 1.00 | 25.52 | D |
| ATOM | 3683 | NE | ARG | D | 110 | 2.446 | −43.971 | 29.651 | 1.00 | 26.82 | D |
| ATOM | 3684 | CZ | ARG | D | 110 | 2.025 | −42.857 | 30.351 | 1.00 | 27.51 | D |
| ATOM | 3685 | NH1 | ARG | D | 110 | 2.985 | −41.927 | 30.712 | 1.00 | 25.90 | D |
| ATOM | 3686 | NH2 | ARG | D | 110 | 0.689 | −42.632 | 30.641 | 1.00 | 25.29 | D |
| ATOM | 3687 | C | ARG | D | 110 | 8.133 | −42.841 | 31.128 | 1.00 | 19.88 | D |
| ATOM | 3688 | O | ARG | D | 110 | 8.145 | −42.856 | 32.385 | 1.00 | 20.52 | D |
| ATOM | 3689 | N | LEU | D | 111 | 9.184 | −42.523 | 30.357 | 1.00 | 18.67 | D |
| ATOM | 3690 | CA | LEU | D | 111 | 10.508 | −42.236 | 30.835 | 1.00 | 17.43 | D |
| ATOM | 3691 | CB | LEU | D | 111 | 11.574 | −42.631 | 29.833 | 1.00 | 16.18 | D |
| ATOM | 3692 | CG | LEU | D | 111 | 11.620 | −44.133 | 29.762 | 1.00 | 16.19 | D |
| ATOM | 3693 | CD1 | LEU | D | 111 | 12.877 | −44.441 | 29.018 | 1.00 | 18.14 | D |
| ATOM | 3694 | CD2 | LEU | D | 111 | 11.663 | −44.884 | 31.050 | 1.00 | 13.71 | D |
| ATOM | 3695 | C | LEU | D | 111 | 10.718 | −40.808 | 31.204 | 1.00 | 17.68 | D |
| ATOM | 3696 | O | LEU | D | 111 | 11.722 | −40.453 | 31.862 | 1.00 | 17.80 | D |
| ATOM | 3697 | N | PHE | D | 112 | 9.792 | −39.979 | 30.747 | 1.00 | 17.02 | D |
| ATOM | 3698 | CA | PHE | D | 112 | 9.836 | −38.549 | 31.039 | 1.00 | 16.55 | D |
| ATOM | 3699 | CB | PHE | D | 112 | 9.272 | −37.756 | 29.892 | 1.00 | 15.63 | D |
| ATOM | 3700 | CG | PHE | D | 112 | 10.183 | −37.620 | 28.785 | 1.00 | 15.09 | D |
| ATOM | 3701 | CD1 | PHE | D | 112 | 10.555 | −38.702 | 28.076 | 1.00 | 16.48 | D |
| ATOM | 3702 | CD2 | PHE | D | 112 | 10.680 | −36.370 | 28.454 | 1.00 | 14.92 | D |
| ATOM | 3703 | CE1 | PHE | D | 112 | 11.455 | −38.566 | 26.998 | 1.00 | 17.44 | D |
| ATOM | 3704 | CE2 | PHE | D | 112 | 11.541 | −36.173 | 27.459 | 1.00 | 14.66 | D |
| ATOM | 3705 | CZ | PHE | D | 112 | 11.949 | −37.264 | 26.708 | 1.00 | 18.27 | D |
| ATOM | 3706 | C | PHE | D | 112 | 9.066 | −38.125 | 32.305 | 1.00 | 16.73 | D |
| ATOM | 3707 | O | PHE | D | 112 | 7.958 | −38.616 | 32.619 | 1.00 | 16.82 | D |
| ATOM | 3708 | N | THR | D | 113 | 9.638 | −37.170 | 33.014 | 1.00 | 16.57 | D |
| ATOM | 3709 | CA | THR | D | 113 | 8.987 | −36.595 | 34.214 | 1.00 | 16.91 | D |
| ATOM | 3710 | CB | THR | D | 113 | 10.048 | −36.377 | 35.400 | 1.00 | 16.91 | D |

TABLE 1-continued

| | | | | | | | | | | |
|---|---|---|---|---|---|---|---|---|---|---|
| ATOM | 3711 | OG1 | THR | D | 113 | 10.537 | −37.644 | 35.869 | 1.00 | 18.22 | D |
| ATOM | 3712 | CG2 | THR | D | 113 | 9.468 | −35.619 | 36.485 | 1.00 | 14.61 | D |
| ATOM | 3713 | C | THR | D | 113 | 8.357 | −35.222 | 33.842 | 1.00 | 15.72 | D |
| ATOM | 3714 | O | THR | D | 113 | 8.897 | −34.433 | 33.071 | 1.00 | 15.42 | D |
| ATOM | 3715 | N | LYS | D | 114 | 7.218 | −34.936 | 34.405 | 1.00 | 15.62 | D |
| ATOM | 3716 | CA | LYS | D | 114 | 6.571 | −33.687 | 34.095 | 1.00 | 16.23 | D |
| ATOM | 3717 | CB | LYS | D | 114 | 5.032 | −33.756 | 34.419 | 1.00 | 16.53 | D |
| ATOM | 3718 | CG | LYS | D | 114 | 4.286 | −32.365 | 34.296 | 1.00 | 17.20 | D |
| ATOM | 3719 | CD | LYS | D | 114 | 2.707 | −32.431 | 34.308 | 1.00 | 17.28 | D |
| ATOM | 3720 | CE | LYS | D | 114 | 2.100 | −31.020 | 34.121 | 1.00 | 15.72 | D |
| ATOM | 3721 | NZ | LYS | D | 114 | 0.682 | −30.898 | 34.287 | 1.00 | 11.37 | D |
| ATOM | 3722 | C | LYS | D | 114 | 7.252 | −32.595 | 34.917 | 1.00 | 16.49 | D |
| ATOM | 3723 | O | LYS | D | 114 | 7.499 | −32.793 | 36.104 | 1.00 | 15.49 | D |
| ATOM | 3724 | N | ILE | D | 115 | 7.573 | −31.482 | 34.267 | 1.00 | 17.24 | D |
| ATOM | 3725 | CA | ILE | D | 115 | 8.131 | −30.369 | 34.960 | 1.00 | 17.81 | D |
| ATOM | 3726 | CB | ILE | D | 115 | 9.085 | −29.566 | 34.090 | 1.00 | 19.19 | D |
| ATOM | 3727 | CG2 | ILE | D | 115 | 9.431 | −28.193 | 34.785 | 1.00 | 18.04 | D |
| ATOM | 3728 | CG1 | ILE | D | 115 | 10.336 | −30.425 | 33.913 | 1.00 | 20.74 | D |
| ATOM | 3729 | CD1 | ILE | D | 115 | 11.330 | −30.071 | 32.768 | 1.00 | 20.99 | D |
| ATOM | 3730 | C | ILE | D | 115 | 7.071 | −29.429 | 35.520 | 1.00 | 18.88 | D |
| ATOM | 3731 | O | ILE | D | 115 | 7.149 | −29.035 | 36.702 | 1.00 | 19.12 | D |
| ATOM | 3732 | N | ASP | D | 116 | 6.075 | −29.080 | 34.693 | 1.00 | 18.58 | D |
| ATOM | 3733 | CA | ASP | D | 116 | 5.004 | −28.188 | 35.072 | 1.00 | 16.63 | D |
| ATOM | 3734 | CB | ASP | D | 116 | 5.618 | −26.813 | 35.314 | 1.00 | 16.92 | D |
| ATOM | 3735 | CG | ASP | D | 116 | 4.622 | −25.762 | 35.919 | 1.00 | 17.45 | D |
| ATOM | 3736 | OD1 | ASP | D | 116 | 4.978 | −24.575 | 35.904 | 1.00 | 17.71 | D |
| ATOM | 3737 | OD2 | ASP | D | 116 | 3.546 | −26.095 | 36.456 | 1.00 | 16.43 | D |
| ATOM | 3738 | C | ASP | D | 116 | 3.959 | −28.086 | 33.946 | 1.00 | 17.91 | D |
| ATOM | 3739 | O | ASP | D | 116 | 4.108 | −28.565 | 32.779 | 1.00 | 17.80 | D |
| ATOM | 3740 | N | THR | D | 117 | 2.856 | −27.457 | 34.291 | 1.00 | 17.06 | D |
| ATOM | 3741 | CA | THR | D | 117 | 1.883 | −27.176 | 33.278 | 1.00 | 15.84 | D |
| ATOM | 3742 | CB | THR | D | 117 | 0.487 | −27.143 | 33.950 | 1.00 | 16.17 | D |
| ATOM | 3743 | OG1 | THR | D | 117 | 0.182 | −28.454 | 34.473 | 1.00 | 17.40 | D |
| ATOM | 3744 | CG2 | THR | D | 117 | −0.623 | −26.646 | 32.971 | 1.00 | 12.20 | D |
| ATOM | 3745 | C | THR | D | 117 | 2.280 | −25.748 | 32.787 | 1.00 | 15.44 | D |
| ATOM | 3746 | O | THR | D | 117 | 2.530 | −24.906 | 33.601 | 1.00 | 13.77 | D |
| ATOM | 3747 | N | ILE | D | 118 | 2.338 | −25.506 | 31.468 | 1.00 | 15.95 | D |
| ATOM | 3748 | CA | ILE | D | 118 | 2.645 | −24.179 | 30.875 | 1.00 | 16.02 | D |
| ATOM | 3749 | CB | ILE | D | 118 | 3.584 | −24.303 | 29.552 | 1.00 | 15.86 | D |
| ATOM | 3750 | CG2 | ILE | D | 118 | 3.900 | −22.973 | 28.910 | 1.00 | 12.10 | D |
| ATOM | 3751 | CG1 | ILE | D | 118 | 4.884 | −25.048 | 29.907 | 1.00 | 15.87 | D |
| ATOM | 3752 | CD1 | ILE | D | 118 | 5.589 | −24.704 | 31.234 | 1.00 | 16.68 | D |
| ATOM | 3753 | C | ILE | D | 118 | 1.274 | −23.544 | 30.507 | 1.00 | 17.08 | D |
| ATOM | 3754 | O | ILE | D | 118 | 0.426 | −24.171 | 29.812 | 1.00 | 16.79 | D |
| ATOM | 3755 | N | ALA | D | 119 | 1.067 | −22.307 | 30.964 | 1.00 | 16.95 | D |
| ATOM | 3756 | CA | ALA | D | 119 | −0.179 | −21.637 | 30.758 | 1.00 | 17.41 | D |
| ATOM | 3757 | CB | ALA | D | 119 | −0.905 | −21.669 | 32.036 | 1.00 | 15.44 | D |
| ATOM | 3758 | C | ALA | D | 119 | 0.094 | −20.230 | 30.288 | 1.00 | 18.57 | D |
| ATOM | 3759 | O | ALA | D | 119 | 1.091 | −19.616 | 30.714 | 1.00 | 19.42 | D |
| ATOM | 3760 | N | PRO | D | 120 | −0.735 | −19.688 | 29.380 | 1.00 | 16.85 | D |
| ATOM | 3761 | CD | PRO | D | 120 | −1.798 | −20.320 | 28.601 | 1.00 | 16.90 | D |
| ATOM | 3762 | CA | PRO | D | 120 | −0.486 | −18.340 | 28.903 | 1.00 | 17.41 | D |
| ATOM | 3763 | CB | PRO | D | 120 | −1.142 | −18.343 | 27.570 | 1.00 | 17.39 | D |
| ATOM | 3764 | CG | PRO | D | 120 | −2.364 | −19.210 | 27.782 | 1.00 | 15.64 | D |
| ATOM | 3765 | C | PRO | D | 120 | −1.084 | −17.215 | 29.784 | 1.00 | 17.94 | D |
| ATOM | 3766 | O | PRO | D | 120 | −2.216 | −17.262 | 30.178 | 1.00 | 17.99 | D |
| ATOM | 3767 | N | ASP | D | 121 | −0.303 | −16.190 | 30.034 | 1.00 | 17.22 | D |
| ATOM | 3768 | CA | ASP | D | 121 | −0.765 | −15.066 | 30.783 | 1.00 | 18.49 | D |
| ATOM | 3769 | CB | ASP | D | 121 | 0.380 | −14.100 | 31.040 | 1.00 | 20.42 | D |
| ATOM | 3770 | CG | ASP | D | 121 | 1.608 | −14.820 | 31.428 | 1.00 | 23.31 | D |
| ATOM | 3771 | OD1 | ASP | D | 121 | 2.282 | −15.615 | 30.549 | 1.00 | 27.85 | D |
| ATOM | 3772 | OD2 | ASP | D | 121 | 1.898 | −14.641 | 32.607 | 1.00 | 21.86 | D |
| ATOM | 3773 | C | ASP | D | 121 | −1.753 | −14.334 | 29.899 | 1.00 | 17.73 | D |
| ATOM | 3774 | O | ASP | D | 121 | −2.548 | −13.535 | 30.419 | 1.00 | 16.59 | D |
| ATOM | 3775 | N | GLU | D | 122 | −1.660 | −14.635 | 28.596 | 1.00 | 16.93 | D |
| ATOM | 3776 | CA | GLU | D | 122 | −2.431 | −13.977 | 27.574 | 1.00 | 17.36 | D |
| ATOM | 3777 | CB | GLU | D | 122 | −1.703 | −12.740 | 27.085 | 1.00 | 17.99 | D |
| ATOM | 3778 | CG | GLU | D | 122 | −1.638 | −11.553 | 28.117 | 1.00 | 21.09 | D |
| ATOM | 3779 | CD | GLU | D | 122 | −1.389 | −10.209 | 27.377 | 1.00 | 24.18 | D |
| ATOM | 3780 | OE1 | GLU | D | 122 | −0.176 | −9.976 | 27.068 | 1.00 | 28.65 | D |
| ATOM | 3781 | OE2 | GLU | D | 122 | −2.356 | −9.400 | 27.053 | 1.00 | 24.93 | D |
| ATOM | 3782 | C | GLU | D | 122 | −2.773 | −14.839 | 26.378 | 1.00 | 17.98 | D |
| ATOM | 3783 | O | GLU | D | 122 | −1.927 | −15.123 | 25.477 | 1.00 | 17.84 | D |
| ATOM | 3784 | N | ILE | D | 123 | −4.066 | −15.157 | 26.345 | 1.00 | 17.50 | D |
| ATOM | 3785 | CA | ILE | D | 123 | −4.679 | −16.004 | 25.330 | 1.00 | 16.88 | D |
| ATOM | 3786 | CB | ILE | D | 123 | −5.952 | −16.456 | 25.887 | 1.00 | 18.94 | D |
| ATOM | 3787 | CG2 | ILE | D | 123 | −6.819 | −15.160 | 26.333 | 1.00 | 19.73 | D |
| ATOM | 3788 | CG1 | ILE | D | 123 | −6.733 | −17.177 | 24.888 | 1.00 | 19.69 | D |
| ATOM | 3789 | CD1 | ILE | D | 123 | −8.183 | −17.396 | 25.476 | 1.00 | 20.93 | D |
| ATOM | 3790 | C | ILE | D | 123 | −4.920 | −15.123 | 24.145 | 1.00 | 16.31 | D |

TABLE 1-continued

| | | | | | | | | | | |
|---|---|---|---|---|---|---|---|---|---|---|
| ATOM | 3791 | O | ILE | D | 123 | −5.227 | −13.968 | 24.305 | 1.00 | 15.09 | D |
| ATOM | 3792 | N | THR | D | 124 | −4.768 | −15.610 | 22.919 | 1.00 | 16.46 | D |
| ATOM | 3793 | CA | THR | D | 124 | −5.038 | −14.656 | 21.809 | 1.00 | 16.71 | D |
| ATOM | 3794 | CB | THR | D | 124 | −4.156 | −14.894 | 20.688 | 1.00 | 15.87 | D |
| ATOM | 3795 | OG1 | THR | D | 124 | −2.768 | −14.465 | 21.029 | 1.00 | 17.18 | D |
| ATOM | 3796 | CG2 | THR | D | 124 | −4.680 | −14.162 | 19.533 | 1.00 | 14.04 | D |
| ATOM | 3797 | C | THR | D | 124 | −6.466 | −14.749 | 21.378 | 1.00 | 17.27 | D |
| ATOM | 3798 | O | THR | D | 124 | −6.916 | −15.812 | 21.017 | 1.00 | 18.78 | D |
| ATOM | 3799 | N | VAL | D | 125 | −7.255 | −13.694 | 21.523 | 1.00 | 17.85 | D |
| ATOM | 3800 | CA | VAL | D | 125 | −8.675 | −13.846 | 21.087 | 1.00 | 18.97 | D |
| ATOM | 3801 | CB | VAL | D | 125 | −9.709 | −12.864 | 21.814 | 1.00 | 18.73 | D |
| ATOM | 3802 | CG1 | VAL | D | 125 | −9.851 | −13.253 | 23.306 | 1.00 | 19.13 | D |
| ATOM | 3803 | CG2 | VAL | D | 125 | −9.304 | −11.434 | 21.597 | 1.00 | 16.81 | D |
| ATOM | 3804 | C | VAL | D | 125 | −8.933 | −13.632 | 19.592 | 1.00 | 17.17 | D |
| ATOM | 3805 | O | VAL | D | 125 | −8.097 | −13.087 | 18.859 | 1.00 | 16.66 | D |
| ATOM | 3806 | N | SER | D | 126 | −10.133 | −13.997 | 19.210 | 1.00 | 16.76 | D |
| ATOM | 3807 | CA | SER | D | 126 | −10.527 | −13.852 | 17.834 | 1.00 | 17.39 | D |
| ATOM | 3808 | CB | SER | D | 126 | −12.013 | −14.154 | 17.653 | 1.00 | 18.04 | D |
| ATOM | 3809 | OG | SER | D | 126 | −12.465 | −13.719 | 16.387 | 1.00 | 17.70 | D |
| ATOM | 3810 | C | SER | D | 126 | −10.300 | −12.530 | 17.216 | 1.00 | 17.18 | D |
| ATOM | 3811 | O | SER | D | 126 | −9.815 | −12.427 | 16.058 | 1.00 | 16.54 | D |
| ATOM | 3812 | N | SER | D | 127 | −10.745 | −11.484 | 17.889 | 1.00 | 16.97 | D |
| ATOM | 3813 | CA | SER | D | 127 | −10.453 | −10.228 | 17.272 | 1.00 | 17.66 | D |
| ATOM | 3814 | CB | SER | D | 127 | −11.251 | −9.174 | 17.935 | 1.00 | 18.12 | D |
| ATOM | 3815 | OG | SER | D | 127 | −10.873 | −8.946 | 19.314 | 1.00 | 19.82 | D |
| ATOM | 3816 | C | SER | D | 127 | −8.956 | −9.841 | 17.275 | 1.00 | 17.71 | D |
| ATOM | 3817 | O | SER | D | 127 | −8.609 | −8.877 | 16.642 | 1.00 | 18.67 | D |
| ATOM | 3818 | N | ASP | D | 128 | −8.111 | −10.584 | 17.998 | 1.00 | 17.39 | D |
| ATOM | 3819 | CA | ASP | D | 128 | −6.683 | −10.298 | 18.093 | 1.00 | 17.49 | D |
| ATOM | 3820 | CB | ASP | D | 128 | −6.006 | −11.181 | 19.166 | 1.00 | 17.29 | D |
| ATOM | 3821 | CG | ASP | D | 128 | −6.140 | −10.614 | 20.551 | 1.00 | 17.99 | D |
| ATOM | 3822 | OD1 | ASP | D | 128 | −5.849 | −11.350 | 21.555 | 1.00 | 16.33 | D |
| ATOM | 3823 | OD2 | ASP | D | 128 | −6.555 | −9.410 | 20.584 | 1.00 | 19.07 | D |
| ATOM | 3824 | C | ASP | D | 128 | −5.980 | −10.477 | 16.769 | 1.00 | 17.26 | D |
| ATOM | 3825 | O | ASP | D | 128 | −5.076 | −9.717 | 16.400 | 1.00 | 16.55 | D |
| ATOM | 3826 | N | PHE | D | 129 | −6.337 | −11.511 | 16.038 | 1.00 | 18.26 | D |
| ATOM | 3827 | CA | PHE | D | 129 | −5.734 | −11.657 | 14.699 | 1.00 | 19.61 | D |
| ATOM | 3828 | CB | PHE | D | 129 | −6.223 | −12.961 | 14.128 | 1.00 | 18.36 | D |
| ATOM | 3829 | CG | PHE | D | 129 | −5.878 | −14.132 | 15.007 | 1.00 | 16.58 | D |
| ATOM | 3830 | CD1 | PHE | D | 129 | −6.798 | −14.681 | 15.860 | 1.00 | 14.71 | D |
| ATOM | 3831 | CD2 | PHE | D | 129 | −4.579 | −14.657 | 14.968 | 1.00 | 16.19 | D |
| ATOM | 3832 | CE1 | PHE | D | 129 | −6.437 | −15.753 | 16.650 | 1.00 | 14.45 | D |
| ATOM | 3833 | CE2 | PHE | D | 129 | −4.223 | −15.716 | 15.759 | 1.00 | 15.87 | D |
| ATOM | 3834 | CZ | PHE | D | 129 | −5.120 | −16.277 | 16.586 | 1.00 | 14.91 | D |
| ATOM | 3835 | C | PHE | D | 129 | −6.411 | −10.479 | 14.117 | 1.00 | 20.48 | D |
| ATOM | 3836 | O | PHE | D | 129 | −6.977 | −9.726 | 14.908 | 1.00 | 23.62 | D |
| ATOM | 3837 | N | GLU | D | 130 | −6.381 | −10.193 | 12.838 | 1.00 | 18.94 | D |
| ATOM | 3838 | CA | GLU | D | 130 | −7.191 | −9.002 | 12.367 | 1.00 | 17.38 | D |
| ATOM | 3839 | CB | GLU | D | 130 | −8.647 | −9.143 | 12.773 | 1.00 | 17.26 | D |
| ATOM | 3840 | CG | GLU | D | 130 | −9.646 | −9.502 | 11.697 | 1.00 | 20.32 | D |
| ATOM | 3841 | CD | GLU | D | 130 | −11.167 | −9.104 | 12.055 | 1.00 | 23.44 | D |
| ATOM | 3842 | OE1 | GLU | D | 130 | −11.911 | −8.869 | 11.041 | 1.00 | 23.75 | D |
| ATOM | 3843 | OE2 | GLU | D | 130 | −11.630 | −9.031 | 13.320 | 1.00 | 24.30 | D |
| ATOM | 3844 | C | GLU | D | 130 | −6.562 | −7.713 | 12.931 | 1.00 | 16.78 | D |
| ATOM | 3845 | O | GLU | D | 130 | −5.998 | −6.876 | 12.192 | 1.00 | 15.75 | D |
| ATOM | 3846 | N | ALA | D | 131 | −6.620 | −7.555 | 14.237 | 1.00 | 16.92 | D |
| ATOM | 3847 | CA | ALA | D | 131 | −5.906 | −6.446 | 14.841 | 1.00 | 19.08 | D |
| ATOM | 3848 | CB | ALA | D | 131 | −6.317 | −6.328 | 16.233 | 1.00 | 18.42 | D |
| ATOM | 3849 | C | ALA | D | 131 | −4.570 | −7.099 | 14.766 | 1.00 | 20.30 | D |
| ATOM | 3850 | O | ALA | D | 131 | −4.514 | −8.363 | 14.644 | 1.00 | 23.18 | D |
| ATOM | 3851 | N | ARG | D | 132 | −3.445 | −6.424 | 14.836 | 1.00 | 20.31 | D |
| ATOM | 3852 | CA | ARG | D | 132 | −2.284 | −7.364 | 14.685 | 1.00 | 19.52 | D |
| ATOM | 3853 | CB | ARG | D | 132 | −1.316 | −6.712 | 13.710 | 1.00 | 19.93 | D |
| ATOM | 3854 | CG | ARG | D | 132 | −1.385 | −7.359 | 12.263 | 1.00 | 21.23 | D |
| ATOM | 3855 | CD | ARG | D | 132 | −2.679 | −7.855 | 11.683 | 1.00 | 16.17 | D |
| ATOM | 3856 | NE | ARG | D | 132 | −2.440 | −8.262 | 10.265 | 1.00 | 15.51 | D |
| ATOM | 3857 | CZ | ARG | D | 132 | −3.114 | −9.230 | 9.604 | 1.00 | 13.45 | D |
| ATOM | 3858 | NH1 | ARG | D | 132 | −4.058 | −9.919 | 10.195 | 1.00 | 13.43 | D |
| ATOM | 3859 | NH2 | ARG | D | 132 | −2.922 | −9.450 | 8.335 | 1.00 | 11.77 | D |
| ATOM | 3860 | C | ARG | D | 132 | −1.704 | −7.572 | 16.084 | 1.00 | 18.61 | D |
| ATOM | 3861 | O | ARG | D | 132 | −0.567 | −7.369 | 16.331 | 1.00 | 17.92 | D |
| ATOM | 3862 | N | HIS | D | 133 | −2.559 | −8.010 | 16.987 | 1.00 | 18.68 | D |
| ATOM | 3863 | CA | HIS | D | 133 | −2.214 | −8.107 | 18.340 | 1.00 | 18.77 | D |
| ATOM | 3864 | CB | HIS | D | 133 | −3.239 | −7.275 | 19.188 | 1.00 | 20.10 | D |
| ATOM | 3865 | CG | HIS | D | 133 | −3.185 | −5.767 | 18.975 | 1.00 | 21.17 | D |
| ATOM | 3866 | CD2 | HIS | D | 133 | −2.571 | −4.977 | 18.024 | 1.00 | 21.68 | D |
| ATOM | 3867 | ND1 | HIS | D | 133 | −3.889 | −4.885 | 19.786 | 1.00 | 21.87 | D |
| ATOM | 3868 | CE1 | HIS | D | 133 | −3.713 | −3.627 | 19.351 | 1.00 | 20.87 | D |
| ATOM | 3869 | NE2 | HIS | D | 133 | −2.913 | −3.650 | 18.288 | 1.00 | 20.40 | D |
| ATOM | 3870 | C | HIS | D | 133 | −2.169 | −9.527 | 18.783 | 1.00 | 18.74 | D |

TABLE 1-continued

| | | | | | | | | | |
|---|---|---|---|---|---|---|---|---|---|
| ATOM | 3871 | O | HIS | D | 133 | −2.880 | −9.906 | 19.688 | 1.00 | 18.52 | D |
| ATOM | 3872 | N | VAL | D | 134 | −1.397 | −10.365 | 18.134 | 1.00 | 19.18 | D |
| ATOM | 3873 | CA | VAL | D | 134 | −1.341 | −11.726 | 18.664 | 1.00 | 19.94 | D |
| ATOM | 3874 | CB | VAL | D | 134 | −0.654 | −12.602 | 17.667 | 1.00 | 20.83 | D |
| ATOM | 3875 | CG1 | VAL | D | 134 | −0.577 | −14.032 | 18.205 | 1.00 | 20.31 | D |
| ATOM | 3876 | CG2 | VAL | D | 134 | −1.440 | −12.477 | 16.396 | 1.00 | 22.77 | D |
| ATOM | 3877 | C | VAL | D | 134 | −0.484 | −11.779 | 19.956 | 1.00 | 19.45 | D |
| ATOM | 3878 | O | VAL | D | 134 | 0.585 | −11.152 | 20.017 | 1.00 | 20.84 | D |
| ATOM | 3879 | N | LYS | D | 135 | −0.850 | −12.586 | 20.939 | 1.00 | 18.65 | D |
| ATOM | 3880 | CA | LYS | D | 135 | −0.094 | −12.530 | 22.214 | 1.00 | 15.93 | D |
| ATOM | 3881 | CB | LYS | D | 135 | −1.087 | −12.439 | 23.394 | 1.00 | 16.51 | D |
| ATOM | 3882 | CG | LYS | D | 135 | −2.344 | −11.633 | 23.157 | 1.00 | 15.27 | D |
| ATOM | 3883 | CD | LYS | D | 135 | −2.070 | −10.209 | 22.840 | 1.00 | 16.85 | D |
| ATOM | 3884 | CE | LYS | D | 135 | −3.366 | −9.325 | 23.222 | 1.00 | 19.41 | D |
| ATOM | 3885 | NZ | LYS | D | 135 | −3.198 | −7.914 | 22.807 | 1.00 | 21.66 | D |
| ATOM | 3886 | C | LYS | D | 135 | 0.934 | −13.619 | 22.469 | 1.00 | 15.29 | D |
| ATOM | 3887 | O | LYS | D | 135 | 0.703 | −14.831 | 22.540 | 1.00 | 14.56 | D |
| ATOM | 3888 | N | LEU | D | 136 | 2.124 | −13.098 | 22.553 | 1.00 | 15.44 | D |
| ATOM | 3889 | CA | LEU | D | 136 | 3.348 | −13.775 | 22.796 | 1.00 | 14.77 | D |
| ATOM | 3890 | CB | LEU | D | 136 | 4.362 | −12.994 | 22.024 | 1.00 | 14.78 | D |
| ATOM | 3891 | CG | LEU | D | 136 | 5.639 | −13.838 | 21.834 | 1.00 | 16.18 | D |
| ATOM | 3892 | CD1 | LEU | D | 136 | 6.318 | −13.986 | 23.105 | 1.00 | 17.95 | D |
| ATOM | 3893 | CD2 | LEU | D | 136 | 5.375 | −15.253 | 21.325 | 1.00 | 15.38 | D |
| ATOM | 3894 | C | LEU | D | 136 | 3.616 | −13.800 | 24.335 | 1.00 | 14.99 | D |
| ATOM | 3895 | O | LEU | D | 136 | 3.797 | −12.771 | 24.977 | 1.00 | 15.14 | D |
| ATOM | 3896 | N | ASN | D | 137 | 3.633 | −14.983 | 24.900 | 1.00 | 15.59 | D |
| ATOM | 3897 | CA | ASN | D | 137 | 3.851 | −15.261 | 26.322 | 1.00 | 16.17 | D |
| ATOM | 3898 | CB | ASN | D | 137 | 2.926 | −16.388 | 26.769 | 1.00 | 17.57 | D |
| ATOM | 3899 | CG | ASN | D | 137 | 1.476 | −15.949 | 26.770 | 1.00 | 18.81 | D |
| ATOM | 3900 | OD1 | ASN | D | 137 | 1.090 | −15.106 | 27.550 | 1.00 | 20.38 | D |
| ATOM | 3901 | ND2 | ASN | D | 137 | 0.693 | −16.516 | 25.921 | 1.00 | 18.69 | D |
| ATOM | 3902 | C | ASN | D | 137 | 5.215 | −15.728 | 26.575 | 1.00 | 15.52 | D |
| ATOM | 3903 | O | ASN | D | 137 | 5.769 | −16.298 | 25.712 | 1.00 | 15.89 | D |
| ATOM | 3904 | N | VAL | D | 138 | 5.781 | −15.502 | 27.725 | 1.00 | 15.15 | D |
| ATOM | 3905 | CA | VAL | D | 138 | 7.092 | −16.008 | 27.955 | 1.00 | 14.71 | D |
| ATOM | 3906 | CB | VAL | D | 138 | 8.172 | −14.899 | 28.136 | 1.00 | 13.21 | D |
| ATOM | 3907 | CG1 | VAL | D | 138 | 9.516 | −15.520 | 28.401 | 1.00 | 12.37 | D |
| ATOM | 3908 | CG2 | VAL | D | 138 | 8.257 | −14.019 | 26.901 | 1.00 | 12.41 | D |
| ATOM | 3909 | C | VAL | D | 138 | 6.999 | −16.808 | 29.206 | 1.00 | 16.63 | D |
| ATOM | 3910 | O | VAL | D | 138 | 6.482 | −16.375 | 30.172 | 1.00 | 18.50 | D |
| ATOM | 3911 | N | GLU | D | 139 | 7.455 | −18.003 | 29.254 | 1.00 | 16.84 | D |
| ATOM | 3912 | CA | GLU | D | 139 | 7.377 | −18.665 | 30.488 | 1.00 | 15.98 | D |
| ATOM | 3913 | CB | GLU | D | 139 | 6.260 | −19.678 | 30.406 | 1.00 | 17.05 | D |
| ATOM | 3914 | CG | GLU | D | 139 | 4.814 | −19.146 | 30.509 | 1.00 | 16.08 | D |
| ATOM | 3915 | CD | GLU | D | 139 | 4.509 | −18.487 | 31.893 | 1.00 | 16.27 | D |
| ATOM | 3916 | OE1 | GLU | D | 139 | 5.156 | −18.855 | 32.883 | 1.00 | 16.25 | D |
| ATOM | 3917 | OE2 | GLU | D | 139 | 3.613 | −17.632 | 32.002 | 1.00 | 14.20 | D |
| ATOM | 3918 | C | GLU | D | 139 | 8.697 | −19.358 | 30.721 | 1.00 | 17.18 | D |
| ATOM | 3919 | O | GLU | D | 139 | 9.239 | −20.019 | 29.813 | 1.00 | 17.52 | D |
| ATOM | 3920 | N | GLU | D | 140 | 9.259 | −19.263 | 31.922 | 1.00 | 17.31 | D |
| ATOM | 3921 | CA | GLU | D | 140 | 10.562 | −19.960 | 32.195 | 1.00 | 16.57 | D |
| ATOM | 3922 | CB | GLU | D | 140 | 11.688 | −19.014 | 32.521 | 1.00 | 18.51 | D |
| ATOM | 3923 | CG | GLU | D | 140 | 13.011 | −19.746 | 32.639 | 1.00 | 20.45 | D |
| ATOM | 3924 | CD | GLU | D | 140 | 14.213 | −18.771 | 32.449 | 1.00 | 22.96 | D |
| ATOM | 3925 | OE1 | GLU | D | 140 | 14.446 | −17.824 | 33.278 | 1.00 | 25.20 | D |
| ATOM | 3926 | OE2 | GLU | D | 140 | 14.937 | −18.851 | 31.439 | 1.00 | 23.12 | D |
| ATOM | 3927 | C | GLU | D | 140 | 10.424 | −20.879 | 33.321 | 1.00 | 15.76 | D |
| ATOM | 3928 | O | GLU | D | 140 | 9.627 | −20.610 | 34.196 | 1.00 | 15.39 | D |
| ATOM | 3929 | N | ARG | D | 141 | 11.117 | −22.016 | 33.270 | 1.00 | 14.71 | D |
| ATOM | 3930 | CA | ARG | D | 141 | 11.015 | −22.967 | 34.384 | 1.00 | 13.96 | D |
| ATOM | 3931 | CB | ARG | D | 141 | 10.067 | −24.119 | 34.145 | 1.00 | 11.96 | D |
| ATOM | 3932 | CG | ARG | D | 141 | 8.627 | −23.794 | 33.818 | 1.00 | 11.44 | D |
| ATOM | 3933 | CD | ARG | D | 141 | 7.668 | −23.883 | 34.965 | 1.00 | 11.62 | D |
| ATOM | 3934 | NE | ARG | D | 141 | 7.073 | −22.619 | 34.869 | 1.00 | 15.89 | D |
| ATOM | 3935 | CZ | ARG | D | 141 | 5.926 | −22.324 | 34.279 | 1.00 | 18.04 | D |
| ATOM | 3936 | NH1 | ARG | D | 141 | 5.154 | −23.253 | 33.735 | 1.00 | 22.44 | D |
| ATOM | 3937 | NH2 | ARG | D | 141 | 5.597 | −21.083 | 34.063 | 1.00 | 16.04 | D |
| ATOM | 3938 | C | ARG | D | 141 | 12.381 | −23.477 | 34.563 | 1.00 | 14.06 | D |
| ATOM | 3939 | O | ARG | D | 141 | 13.327 | −23.111 | 33.870 | 1.00 | 14.34 | D |
| ATOM | 3940 | N | SER | D | 142 | 12.537 | −24.353 | 35.489 | 1.00 | 14.78 | D |
| ATOM | 3941 | CA | SER | D | 142 | 13.877 | −24.857 | 35.619 | 1.00 | 16.34 | D |
| ATOM | 3942 | CB | SER | D | 142 | 14.783 | −23.877 | 36.424 | 1.00 | 15.76 | D |
| ATOM | 3943 | OG | SER | D | 142 | 14.511 | −24.085 | 37.774 | 1.00 | 17.27 | D |
| ATOM | 3944 | C | SER | D | 142 | 13.869 | −26.204 | 36.269 | 1.00 | 15.70 | D |
| ATOM | 3945 | O | SER | D | 142 | 12.947 | −26.580 | 36.973 | 1.00 | 15.90 | D |
| ATOM | 3946 | N | VAL | D | 143 | 14.931 | −26.938 | 36.083 | 1.00 | 16.29 | D |
| ATOM | 3947 | CA | VAL | D | 143 | 14.900 | −28.230 | 36.728 | 1.00 | 18.06 | D |
| ATOM | 3948 | CB | VAL | D | 143 | 14.054 | −29.272 | 35.803 | 1.00 | 17.78 | D |
| ATOM | 3949 | CG1 | VAL | D | 143 | 14.603 | −29.407 | 34.422 | 1.00 | 16.75 | D |
| ATOM | 3950 | CG2 | VAL | D | 143 | 13.990 | −30.578 | 36.469 | 1.00 | 19.37 | D |

TABLE 1-continued

| | | | | | | | | | |
|---|---|---|---|---|---|---|---|---|---|
| ATOM | 3951 | C | VAL | D | 143 | 16.315 | −28.685 | 37.095 | 1.00 | 17.29 | D |
| ATOM | 3952 | O | VAL | D | 143 | 17.309 | −28.115 | 36.614 | 1.00 | 16.48 | D |
| ATOM | 3953 | N | GLY | D | 144 | 16.405 | −29.666 | 37.986 | 1.00 | 18.13 | D |
| ATOM | 3954 | CA | GLY | D | 144 | 17.735 | −30.151 | 38.373 | 1.00 | 20.02 | D |
| ATOM | 3955 | C | GLY | D | 144 | 17.735 | −30.669 | 39.809 | 1.00 | 21.41 | D |
| ATOM | 3956 | O | GLY | D | 144 | 16.672 | −30.551 | 40.485 | 1.00 | 22.10 | D |
| ATOM | 3957 | N | PRO | D | 145 | 18.890 | −31.136 | 40.337 | 1.00 | 21.31 | D |
| ATOM | 3958 | CD | PRO | D | 145 | 19.228 | −31.309 | 41.774 | 1.00 | 20.60 | D |
| ATOM | 3959 | CA | PRO | D | 145 | 20.093 | −31.105 | 39.520 | 1.00 | 19.69 | D |
| ATOM | 3960 | CB | PRO | D | 145 | 21.225 | −31.240 | 40.515 | 1.00 | 19.27 | D |
| ATOM | 3961 | CG | PRO | D | 145 | 20.590 | −31.969 | 41.659 | 1.00 | 19.37 | D |
| ATOM | 3962 | C | PRO | D | 145 | 20.087 | −32.241 | 38.591 | 1.00 | 21.92 | D |
| ATOM | 3963 | O | PRO | D | 145 | 19.556 | −33.300 | 38.868 | 1.00 | 22.85 | D |
| ATOM | 3964 | N | LEU | D | 146 | 20.690 | −32.011 | 37.433 | 1.00 | 21.75 | D |
| ATOM | 3965 | CA | LEU | D | 146 | 20.847 | −33.048 | 36.447 | 1.00 | 20.02 | D |
| ATOM | 3966 | CB | LEU | D | 146 | 20.993 | −32.385 | 35.058 | 1.00 | 20.90 | D |
| ATOM | 3967 | CG | LEU | D | 146 | 19.671 | −32.120 | 34.308 | 1.00 | 20.22 | D |
| ATOM | 3968 | CD1 | LEU | D | 146 | 18.645 | −31.713 | 35.281 | 1.00 | 21.69 | D |
| ATOM | 3969 | CD2 | LEU | D | 146 | 19.838 | −31.002 | 33.217 | 1.00 | 20.64 | D |
| ATOM | 3970 | C | LEU | D | 146 | 22.140 | −33.725 | 36.894 | 1.00 | 20.43 | D |
| ATOM | 3971 | O | LEU | D | 146 | 22.994 | −33.167 | 37.645 | 1.00 | 19.74 | D |
| ATOM | 3972 | N | THR | D | 147 | 22.302 | −34.940 | 36.426 | 1.00 | 19.52 | D |
| ATOM | 3973 | CA | THR | D | 147 | 23.511 | −35.692 | 36.704 | 1.00 | 17.92 | D |
| ATOM | 3974 | CB | THR | D | 147 | 23.373 | −36.568 | 37.977 | 1.00 | 17.00 | D |
| ATOM | 3975 | OG1 | THR | D | 147 | 22.393 | −37.583 | 37.871 | 1.00 | 14.64 | D |
| ATOM | 3976 | CG2 | THR | D | 147 | 22.997 | −35.758 | 39.091 | 1.00 | 16.40 | D |
| ATOM | 3977 | C | THR | D | 147 | 24.058 | −36.608 | 35.521 | 1.00 | 21.08 | D |
| ATOM | 3978 | O | THR | D | 147 | 25.332 | −36.966 | 35.434 | 1.00 | 21.74 | D |
| ATOM | 3979 | N | ARG | D | 148 | 23.156 | −37.053 | 34.613 | 1.00 | 20.20 | D |
| ATOM | 3980 | CA | ARG | D | 148 | 23.633 | −37.915 | 33.524 | 1.00 | 17.96 | D |
| ATOM | 3981 | CB | ARG | D | 148 | 22.475 | −38.653 | 32.815 | 1.00 | 21.01 | D |
| ATOM | 3982 | CG | ARG | D | 148 | 21.300 | −39.094 | 33.787 | 1.00 | 22.85 | D |
| ATOM | 3983 | CD | ARG | D | 148 | 21.602 | −40.338 | 34.679 | 1.00 | 22.57 | D |
| ATOM | 3984 | NE | ARG | D | 148 | 22.490 | −40.005 | 35.818 | 1.00 | 25.29 | D |
| ATOM | 3985 | CZ | ARG | D | 148 | 23.682 | −40.644 | 36.078 | 1.00 | 27.89 | D |
| ATOM | 3986 | NH1 | ARG | D | 148 | 24.151 | −41.669 | 35.261 | 1.00 | 27.25 | D |
| ATOM | 3987 | NH2 | ARG | D | 148 | 24.469 | −40.292 | 37.150 | 1.00 | 28.22 | D |
| ATOM | 3988 | C | ARG | D | 148 | 24.397 | −37.146 | 32.474 | 1.00 | 17.52 | D |
| ATOM | 3989 | O | ARG | D | 148 | 24.563 | −35.909 | 32.546 | 1.00 | 15.31 | D |
| ATOM | 3990 | N | LYS | D | 149 | 24.786 | −37.898 | 31.439 | 1.00 | 16.63 | D |
| ATOM | 3991 | CA | LYS | D | 149 | 25.635 | −37.359 | 30.402 | 1.00 | 16.00 | D |
| ATOM | 3992 | CB | LYS | D | 149 | 26.191 | −38.560 | 29.617 | 1.00 | 17.15 | D |
| ATOM | 3993 | CG | LYS | D | 149 | 27.340 | −38.265 | 28.642 | 1.00 | 18.94 | D |
| ATOM | 3994 | CD | LYS | D | 149 | 27.806 | −39.517 | 27.930 | 1.00 | 20.32 | D |
| ATOM | 3995 | CE | LYS | D | 149 | 28.821 | −39.174 | 26.866 | 1.00 | 22.15 | D |
| ATOM | 3996 | NZ | LYS | D | 149 | 28.349 | −39.458 | 25.376 | 1.00 | 26.84 | D |
| ATOM | 3997 | C | LYS | D | 149 | 24.806 | −36.398 | 29.607 | 1.00 | 15.57 | D |
| ATOM | 3998 | O | LYS | D | 149 | 25.312 | −35.436 | 29.043 | 1.00 | 15.49 | D |
| ATOM | 3999 | N | GLY | D | 150 | 23.490 | −36.624 | 29.604 | 1.00 | 15.13 | D |
| ATOM | 4000 | CA | GLY | D | 150 | 22.618 | −35.721 | 28.830 | 1.00 | 14.07 | D |
| ATOM | 4001 | C | GLY | D | 150 | 21.140 | −35.813 | 29.167 | 1.00 | 13.01 | D |
| ATOM | 4002 | O | GLY | D | 150 | 20.715 | −36.553 | 30.077 | 1.00 | 11.84 | D |
| ATOM | 4003 | N | PHE | D | 151 | 20.375 | −35.094 | 28.370 | 1.00 | 12.47 | D |
| ATOM | 4004 | CA | PHE | D | 151 | 18.967 | −34.987 | 28.585 | 1.00 | 13.78 | D |
| ATOM | 4005 | CB | PHE | D | 151 | 18.751 | −34.002 | 29.801 | 1.00 | 14.58 | D |
| ATOM | 4006 | CG | PHE | D | 151 | 19.008 | −32.593 | 29.455 | 1.00 | 15.87 | D |
| ATOM | 4007 | CD1 | PHE | D | 151 | 17.980 | −31.783 | 28.914 | 1.00 | 15.47 | D |
| ATOM | 4008 | CD2 | PHE | D | 151 | 20.304 | −32.065 | 29.570 | 1.00 | 17.20 | D |
| ATOM | 4009 | CE1 | PHE | D | 151 | 18.244 | −30.447 | 28.476 | 1.00 | 14.64 | D |
| ATOM | 4010 | CE2 | PHE | D | 151 | 20.599 | −30.746 | 29.163 | 1.00 | 17.45 | D |
| ATOM | 4011 | CZ | PHE | D | 151 | 19.549 | −29.923 | 28.606 | 1.00 | 16.33 | D |
| ATOM | 4012 | C | PHE | D | 151 | 18.131 | −34.516 | 27.378 | 1.00 | 12.04 | D |
| ATOM | 4013 | O | PHE | D | 151 | 18.633 | −33.940 | 26.438 | 1.00 | 11.21 | D |
| ATOM | 4014 | N | TYR | D | 152 | 16.832 | −34.693 | 27.525 | 1.00 | 12.73 | D |
| ATOM | 4015 | CA | TYR | D | 152 | 15.797 | −34.359 | 26.571 | 1.00 | 13.81 | D |
| ATOM | 4016 | CB | TYR | D | 152 | 15.066 | −35.624 | 26.022 | 1.00 | 13.48 | D |
| ATOM | 4017 | CG | TYR | D | 152 | 15.889 | −36.576 | 25.230 | 1.00 | 13.74 | D |
| ATOM | 4018 | CD1 | TYR | D | 152 | 16.418 | −37.710 | 25.795 | 1.00 | 13.74 | D |
| ATOM | 4019 | CE1 | TYR | D | 152 | 17.244 | −38.545 | 25.134 | 1.00 | 16.59 | D |
| ATOM | 4020 | CD2 | TYR | D | 152 | 16.184 | −36.306 | 23.988 | 1.00 | 15.37 | D |
| ATOM | 4021 | CE2 | TYR | D | 152 | 16.988 | −37.133 | 23.278 | 1.00 | 18.02 | D |
| ATOM | 4022 | CZ | TYR | D | 152 | 17.534 | −38.257 | 23.838 | 1.00 | 18.71 | D |
| ATOM | 4023 | OH | TYR | D | 152 | 18.377 | −39.065 | 23.042 | 1.00 | 22.46 | D |
| ATOM | 4024 | C | TYR | D | 152 | 14.677 | −33.516 | 27.156 | 1.00 | 14.20 | D |
| ATOM | 4025 | O | TYR | D | 152 | 14.276 | −33.626 | 28.274 | 1.00 | 15.44 | D |
| ATOM | 4026 | N | LEU | D | 153 | 14.136 | −32.660 | 26.344 | 1.00 | 15.00 | D |
| ATOM | 4027 | CA | LEU | D | 153 | 13.024 | −31.856 | 26.697 | 1.00 | 14.56 | D |
| ATOM | 4028 | CB | LEU | D | 153 | 13.338 | −30.444 | 26.462 | 1.00 | 13.85 | D |
| ATOM | 4029 | CG | LEU | D | 153 | 13.446 | −29.635 | 27.766 | 1.00 | 15.21 | D |
| ATOM | 4030 | CD1 | LEU | D | 153 | 14.321 | −30.291 | 28.847 | 1.00 | 13.47 | D |

TABLE 1-continued

| | | | | | | | | | | |
|---|---|---|---|---|---|---|---|---|---|---|
| ATOM | 4031 | CD2 | LEU | D | 153 | 13.830 | −28.168 | 27.407 | 1.00 | 13.96 | D |
| ATOM | 4032 | C | LEU | D | 153 | 11.917 | −32.326 | 25.751 | 1.00 | 15.28 | D |
| ATOM | 4033 | O | LEU | D | 153 | 12.165 | −32.684 | 24.588 | 1.00 | 15.29 | D |
| ATOM | 4034 | N | ALA | D | 154 | 10.704 | −32.363 | 26.272 | 1.00 | 15.09 | D |
| ATOM | 4035 | CA | ALA | D | 154 | 9.620 | −32.783 | 25.515 | 1.00 | 15.28 | D |
| ATOM | 4036 | CB | ALA | D | 154 | 9.389 | −34.202 | 25.783 | 1.00 | 15.70 | D |
| ATOM | 4037 | C | ALA | D | 154 | 8.370 | −31.950 | 25.808 | 1.00 | 16.51 | D |
| ATOM | 4038 | O | ALA | D | 154 | 8.198 | −31.420 | 26.915 | 1.00 | 16.11 | D |
| ATOM | 4039 | N | PHE | D | 155 | 7.530 | −31.816 | 24.778 | 1.00 | 15.97 | D |
| ATOM | 4040 | CA | PHE | D | 155 | 6.288 | −31.117 | 24.964 | 1.00 | 16.51 | D |
| ATOM | 4041 | CB | PHE | D | 155 | 6.282 | −29.797 | 24.205 | 1.00 | 17.21 | D |
| ATOM | 4042 | CG | PHE | D | 155 | 7.503 | −29.006 | 24.436 | 1.00 | 17.44 | D |
| ATOM | 4043 | CD1 | PHE | D | 155 | 8.707 | −29.386 | 23.817 | 1.00 | 17.78 | D |
| ATOM | 4044 | CD2 | PHE | D | 155 | 7.468 | −27.862 | 25.192 | 1.00 | 15.66 | D |
| ATOM | 4045 | CE1 | PHE | D | 155 | 9.884 | −28.552 | 23.966 | 1.00 | 17.97 | D |
| ATOM | 4046 | CE2 | PHE | D | 155 | 8.603 | −27.051 | 25.320 | 1.00 | 17.24 | D |
| ATOM | 4047 | CZ | PHE | D | 155 | 9.832 | −27.387 | 24.699 | 1.00 | 16.03 | D |
| ATOM | 4048 | C | PHE | D | 155 | 5.007 | −31.897 | 24.656 | 1.00 | 17.08 | D |
| ATOM | 4049 | O | PHE | D | 155 | 4.844 | −32.510 | 23.566 | 1.00 | 15.90 | D |
| ATOM | 4050 | N | GLN | D | 156 | 4.095 | −31.868 | 25.640 | 1.00 | 16.95 | D |
| ATOM | 4051 | CA | GLN | D | 156 | 2.882 | −32.562 | 25.435 | 1.00 | 17.15 | D |
| ATOM | 4052 | CB | GLN | D | 156 | 2.651 | −33.509 | 26.570 | 1.00 | 18.41 | D |
| ATOM | 4053 | CG | GLN | D | 156 | 1.479 | −34.354 | 26.357 | 1.00 | 18.96 | D |
| ATOM | 4054 | CD | GLN | D | 156 | 0.871 | −34.864 | 27.715 | 1.00 | 19.75 | D |
| ATOM | 4055 | OE1 | GLN | D | 156 | 1.136 | −34.313 | 28.786 | 1.00 | 18.33 | D |
| ATOM | 4056 | NE2 | GLN | D | 156 | 0.037 | −35.932 | 27.628 | 1.00 | 18.57 | D |
| ATOM | 4057 | C | GLN | D | 156 | 1.663 | −31.717 | 25.189 | 1.00 | 17.47 | D |
| ATOM | 4058 | O | GLN | D | 156 | 1.168 | −30.993 | 26.039 | 1.00 | 17.33 | D |
| ATOM | 4059 | N | ASP | D | 157 | 1.192 | −31.798 | 23.951 | 1.00 | 18.17 | D |
| ATOM | 4060 | CA | ASP | D | 157 | −0.028 | −31.116 | 23.579 | 1.00 | 17.53 | D |
| ATOM | 4061 | CB | ASP | D | 157 | −0.087 | −30.808 | 22.125 | 1.00 | 16.72 | D |
| ATOM | 4062 | CG | ASP | D | 157 | −1.461 | −30.461 | 21.691 | 1.00 | 15.86 | D |
| ATOM | 4063 | OD1 | ASP | D | 157 | −1.902 | −31.159 | 20.752 | 1.00 | 14.70 | D |
| ATOM | 4064 | OD2 | ASP | D | 157 | −2.102 | −29.517 | 22.271 | 1.00 | 16.48 | D |
| ATOM | 4065 | C | ASP | D | 157 | −1.219 | −31.964 | 23.924 | 1.00 | 17.92 | D |
| ATOM | 4066 | O | ASP | D | 157 | −1.348 | −33.090 | 23.458 | 1.00 | 18.19 | D |
| ATOM | 4067 | N | ILE | D | 158 | −2.131 | −31.344 | 24.693 | 1.00 | 19.34 | D |
| ATOM | 4068 | CA | ILE | D | 158 | −3.321 | −32.008 | 25.239 | 1.00 | 18.15 | D |
| ATOM | 4069 | CB | ILE | D | 158 | −3.344 | −31.741 | 26.812 | 1.00 | 18.57 | D |
| ATOM | 4070 | CG2 | ILE | D | 158 | −4.222 | −30.630 | 27.276 | 1.00 | 16.55 | D |
| ATOM | 4071 | CG1 | ILE | D | 158 | −3.498 | −33.065 | 27.422 | 1.00 | 17.57 | D |
| ATOM | 4072 | CD1 | ILE | D | 158 | −2.133 | −33.688 | 27.404 | 1.00 | 18.15 | D |
| ATOM | 4073 | C | ILE | D | 158 | −4.571 | −31.631 | 24.571 | 1.00 | 18.22 | D |
| ATOM | 4074 | O | ILE | D | 158 | −5.604 | −31.997 | 25.054 | 1.00 | 18.15 | D |
| ATOM | 4075 | N | GLY | D | 159 | −4.470 | −30.876 | 23.474 | 1.00 | 18.06 | D |
| ATOM | 4076 | CA | GLY | D | 159 | −5.671 | −30.459 | 22.795 | 1.00 | 17.59 | D |
| ATOM | 4077 | C | GLY | D | 159 | −5.819 | −28.947 | 22.751 | 1.00 | 17.58 | D |
| ATOM | 4078 | O | GLY | D | 159 | −6.905 | −28.409 | 22.648 | 1.00 | 18.06 | D |
| ATOM | 4079 | N | ALA | D | 160 | −4.726 | −28.221 | 22.842 | 1.00 | 17.50 | D |
| ATOM | 4080 | CA | ALA | D | 160 | −4.791 | −26.781 | 22.828 | 1.00 | 17.35 | D |
| ATOM | 4081 | CB | ALA | D | 160 | −3.835 | −26.240 | 23.776 | 1.00 | 17.01 | D |
| ATOM | 4082 | C | ALA | D | 160 | −4.369 | −26.416 | 21.466 | 1.00 | 17.73 | D |
| ATOM | 4083 | O | ALA | D | 160 | −4.013 | −27.348 | 20.687 | 1.00 | 19.65 | D |
| ATOM | 4084 | N | CYS | D | 161 | −4.533 | −25.140 | 21.099 | 1.00 | 16.02 | D |
| ATOM | 4085 | CA | CYS | D | 161 | −4.071 | −24.634 | 19.824 | 1.00 | 13.50 | D |
| ATOM | 4086 | C | CYS | D | 161 | −2.861 | −23.700 | 20.197 | 1.00 | 13.37 | D |
| ATOM | 4087 | O | CYS | D | 161 | −3.001 | −22.495 | 20.529 | 1.00 | 11.69 | D |
| ATOM | 4088 | CB | CYS | D | 161 | −5.164 | −23.874 | 19.221 | 1.00 | 14.41 | D |
| ATOM | 4089 | SG | CYS | D | 161 | −4.749 | −23.293 | 17.573 | 1.00 | 16.91 | D |
| ATOM | 4090 | N | VAL | D | 162 | −1.671 | −24.289 | 20.115 | 1.00 | 13.35 | D |
| ATOM | 4091 | CA | VAL | D | 162 | −0.442 | −23.633 | 20.501 | 1.00 | 14.14 | D |
| ATOM | 4092 | CB | VAL | D | 162 | 0.360 | −24.438 | 21.475 | 1.00 | 15.06 | D |
| ATOM | 4093 | CG1 | VAL | D | 162 | 1.347 | −23.472 | 22.171 | 1.00 | 15.89 | D |
| ATOM | 4094 | CG2 | VAL | D | 162 | −0.518 | −25.227 | 22.371 | 1.00 | 13.73 | D |
| ATOM | 4095 | C | VAL | D | 162 | 0.527 | −23.418 | 19.448 | 1.00 | 14.22 | D |
| ATOM | 4096 | O | VAL | D | 162 | 0.621 | −24.202 | 18.593 | 1.00 | 13.78 | D |
| ATOM | 4097 | N | ALA | D | 163 | 1.322 | −22.380 | 19.591 | 1.00 | 14.76 | D |
| ATOM | 4098 | CA | ALA | D | 163 | 2.404 | −22.098 | 18.654 | 1.00 | 14.94 | D |
| ATOM | 4099 | CB | ALA | D | 163 | 2.093 | −20.879 | 17.844 | 1.00 | 14.64 | D |
| ATOM | 4100 | C | ALA | D | 163 | 3.709 | −21.896 | 19.469 | 1.00 | 16.16 | D |
| ATOM | 4101 | O | ALA | D | 163 | 3.981 | −20.838 | 20.031 | 1.00 | 17.24 | D |
| ATOM | 4102 | N | LEU | D | 164 | 4.569 | −22.885 | 19.519 | 1.00 | 15.46 | D |
| ATOM | 4103 | CA | LEU | D | 164 | 5.747 | −22.695 | 20.296 | 1.00 | 14.60 | D |
| ATOM | 4104 | CB | LEU | D | 164 | 6.151 | −24.020 | 20.812 | 1.00 | 14.41 | D |
| ATOM | 4105 | CG | LEU | D | 164 | 7.283 | −23.973 | 21.748 | 1.00 | 14.58 | D |
| ATOM | 4106 | CD1 | LEU | D | 164 | 7.105 | −23.110 | 22.955 | 1.00 | 13.67 | D |
| ATOM | 4107 | CD2 | LEU | D | 164 | 7.378 | −25.374 | 22.135 | 1.00 | 16.29 | D |
| ATOM | 4108 | C | LEU | D | 164 | 6.825 | −22.041 | 19.450 | 1.00 | 16.15 | D |
| ATOM | 4109 | O | LEU | D | 164 | 7.460 | −22.654 | 18.574 | 1.00 | 16.64 | D |
| ATOM | 4110 | N | LEU | D | 165 | 7.071 | −20.774 | 19.691 | 1.00 | 15.96 | D |

TABLE 1-continued

| | | | | | | | | | | |
|---|---|---|---|---|---|---|---|---|---|---|
| ATOM | 4111 | CA | LEU | D | 165 | 8.016 | −20.052 | 18.882 | 1.00 | 15.05 | D |
| ATOM | 4112 | CB | LEU | D | 165 | 7.490 | −18.634 | 18.720 | 1.00 | 17.26 | D |
| ATOM | 4113 | CG | LEU | D | 165 | 5.993 | −18.544 | 18.479 | 1.00 | 17.12 | D |
| ATOM | 4114 | CD1 | LEU | D | 165 | 5.776 | −17.180 | 18.075 | 1.00 | 17.48 | D |
| ATOM | 4115 | CD2 | LEU | D | 165 | 5.569 | −19.338 | 17.383 | 1.00 | 18.30 | D |
| ATOM | 4116 | C | LEU | D | 165 | 9.445 | −19.968 | 19.371 | 1.00 | 14.83 | D |
| ATOM | 4117 | O | LEU | D | 165 | 10.373 | −19.426 | 18.693 | 1.00 | 11.84 | D |
| ATOM | 4118 | N | SER | D | 166 | 9.686 | −20.537 | 20.530 | 1.00 | 14.57 | D |
| ATOM | 4119 | CA | SER | D | 166 | 11.046 | −20.375 | 21.005 | 1.00 | 15.28 | D |
| ATOM | 4120 | CB | SER | D | 166 | 11.305 | −18.907 | 21.431 | 1.00 | 17.01 | D |
| ATOM | 4121 | OG | SER | D | 166 | 12.641 | −18.766 | 21.853 | 1.00 | 18.16 | D |
| ATOM | 4122 | C | SER | D | 166 | 11.282 | −21.241 | 22.197 | 1.00 | 15.10 | D |
| ATOM | 4123 | O | SER | D | 166 | 10.447 | −21.271 | 23.098 | 1.00 | 13.84 | D |
| ATOM | 4124 | N | VAL | D | 167 | 12.445 | −21.879 | 22.202 | 1.00 | 14.46 | D |
| ATOM | 4125 | CA | VAL | D | 167 | 12.817 | −22.744 | 23.255 | 1.00 | 13.80 | D |
| ATOM | 4126 | CB | VAL | D | 167 | 12.703 | −24.143 | 22.830 | 1.00 | 13.46 | D |
| ATOM | 4127 | CG1 | VAL | D | 167 | 13.115 | −25.068 | 23.949 | 1.00 | 13.37 | D |
| ATOM | 4128 | CG2 | VAL | D | 167 | 11.297 | −24.413 | 22.460 | 1.00 | 12.70 | D |
| ATOM | 4129 | C | VAL | D | 167 | 14.251 | −22.432 | 23.555 | 1.00 | 15.83 | D |
| ATOM | 4130 | O | VAL | D | 167 | 15.107 | −22.682 | 22.765 | 1.00 | 15.38 | D |
| ATOM | 4131 | N | ARG | D | 168 | 14.529 | −21.800 | 24.687 | 1.00 | 16.70 | D |
| ATOM | 4132 | CA | ARG | D | 168 | 15.907 | −21.540 | 25.035 | 1.00 | 17.23 | D |
| ATOM | 4133 | CB | ARG | D | 168 | 16.184 | −20.073 | 25.273 | 1.00 | 18.88 | D |
| ATOM | 4134 | CG | ARG | D | 168 | 17.063 | −19.569 | 24.226 | 1.00 | 19.77 | D |
| ATOM | 4135 | CD | ARG | D | 168 | 18.139 | −18.563 | 24.640 | 1.00 | 20.96 | D |
| ATOM | 4136 | NE | ARG | D | 168 | 17.907 | −17.944 | 25.927 | 1.00 | 21.91 | D |
| ATOM | 4137 | CZ | ARG | D | 168 | 18.865 | −17.316 | 26.653 | 1.00 | 24.14 | D |
| ATOM | 4138 | NH1 | ARG | D | 168 | 20.186 | −17.216 | 26.248 | 1.00 | 20.99 | D |
| ATOM | 4139 | NH2 | ARG | D | 168 | 18.474 | −16.691 | 27.793 | 1.00 | 25.15 | D |
| ATOM | 4140 | C | ARG | D | 168 | 16.158 | −22.310 | 26.336 | 1.00 | 18.12 | D |
| ATOM | 4141 | O | ARG | D | 168 | 15.265 | −22.281 | 27.223 | 1.00 | 17.72 | D |
| ATOM | 4142 | N | VAL | D | 169 | 17.357 | −22.994 | 26.400 | 1.00 | 17.55 | D |
| ATOM | 4143 | CA | VAL | D | 169 | 17.820 | −23.791 | 27.555 | 1.00 | 16.91 | D |
| ATOM | 4144 | CB | VAL | D | 169 | 17.914 | −25.236 | 27.251 | 1.00 | 18.23 | D |
| ATOM | 4145 | CG1 | VAL | D | 169 | 18.393 | −26.049 | 28.523 | 1.00 | 19.32 | D |
| ATOM | 4146 | CG2 | VAL | D | 169 | 16.629 | −25.719 | 26.854 | 1.00 | 18.81 | D |
| ATOM | 4147 | C | VAL | D | 169 | 19.180 | −23.339 | 27.951 | 1.00 | 16.90 | D |
| ATOM | 4148 | O | VAL | D | 169 | 20.053 | −23.335 | 27.155 | 1.00 | 15.37 | D |
| ATOM | 4149 | N | TYR | D | 170 | 19.366 | −22.918 | 29.186 | 1.00 | 16.74 | D |
| ATOM | 4150 | CA | TYR | D | 170 | 20.696 | −22.446 | 29.553 | 1.00 | 17.49 | D |
| ATOM | 4151 | CB | TYR | D | 170 | 20.833 | −20.992 | 29.249 | 1.00 | 18.49 | D |
| ATOM | 4152 | CG | TYR | D | 170 | 19.867 | −20.200 | 30.089 | 1.00 | 19.33 | D |
| ATOM | 4153 | CD1 | TYR | D | 170 | 20.314 | −19.526 | 31.255 | 1.00 | 19.86 | D |
| ATOM | 4154 | CE1 | TYR | D | 170 | 19.471 | −18.675 | 32.000 | 1.00 | 17.87 | D |
| ATOM | 4155 | CD2 | TYR | D | 170 | 18.526 | −20.032 | 29.699 | 1.00 | 19.84 | D |
| ATOM | 4156 | CE2 | TYR | D | 170 | 17.670 | −19.197 | 30.456 | 1.00 | 18.02 | D |
| ATOM | 4157 | CZ | TYR | D | 170 | 18.174 | −18.508 | 31.594 | 1.00 | 17.47 | D |
| ATOM | 4158 | OH | TYR | D | 170 | 17.397 | −17.626 | 32.239 | 1.00 | 14.17 | D |
| ATOM | 4159 | C | TYR | D | 170 | 20.945 | −22.627 | 31.023 | 1.00 | 17.65 | D |
| ATOM | 4160 | O | TYR | D | 170 | 20.022 | −22.889 | 31.809 | 1.00 | 17.04 | D |
| ATOM | 4161 | N | TYR | D | 171 | 22.206 | −22.527 | 31.381 | 1.00 | 17.11 | D |
| ATOM | 4162 | CA | TYR | D | 171 | 22.524 | −22.671 | 32.740 | 1.00 | 18.01 | D |
| ATOM | 4163 | CB | TYR | D | 171 | 23.019 | −24.044 | 33.048 | 1.00 | 18.49 | D |
| ATOM | 4164 | CG | TYR | D | 171 | 24.393 | −24.280 | 32.603 | 1.00 | 18.53 | D |
| ATOM | 4165 | CD1 | TYR | D | 171 | 25.472 | −24.114 | 33.455 | 1.00 | 18.93 | D |
| ATOM | 4166 | CE1 | TYR | D | 171 | 26.742 | −24.439 | 33.048 | 1.00 | 19.14 | D |
| ATOM | 4167 | CD2 | TYR | D | 171 | 24.637 | −24.759 | 31.338 | 1.00 | 18.89 | D |
| ATOM | 4168 | CE2 | TYR | D | 171 | 25.874 | −25.085 | 30.917 | 1.00 | 18.87 | D |
| ATOM | 4169 | CZ | TYR | D | 171 | 26.945 | −24.947 | 31.760 | 1.00 | 20.06 | D |
| ATOM | 4170 | OH | TYR | D | 171 | 28.231 | −25.434 | 31.299 | 1.00 | 21.52 | D |
| ATOM | 4171 | C | TYR | D | 171 | 23.482 | −21.602 | 33.180 | 1.00 | 18.58 | D |
| ATOM | 4172 | O | TYR | D | 171 | 24.101 | −20.904 | 32.300 | 1.00 | 18.33 | D |
| ATOM | 4173 | N | LYS | D | 172 | 23.577 | −21.435 | 34.528 | 1.00 | 18.03 | D |
| ATOM | 4174 | CA | LYS | D | 172 | 24.408 | −20.305 | 34.987 | 1.00 | 18.52 | D |
| ATOM | 4175 | CB | LYS | D | 172 | 23.921 | −19.805 | 36.335 | 1.00 | 18.23 | D |
| ATOM | 4176 | CG | LYS | D | 172 | 23.135 | −18.520 | 36.207 | 1.00 | 19.29 | D |
| ATOM | 4177 | CD | LYS | D | 172 | 21.921 | −18.682 | 35.427 | 1.00 | 19.71 | D |
| ATOM | 4178 | CE | LYS | D | 172 | 21.022 | −17.360 | 35.417 | 1.00 | 22.20 | D |
| ATOM | 4179 | NZ | LYS | D | 172 | 19.827 | −17.388 | 36.471 | 1.00 | 24.74 | D |
| ATOM | 4180 | C | LYS | D | 172 | 25.916 | −20.415 | 34.942 | 1.00 | 18.29 | D |
| ATOM | 4181 | O | LYS | D | 172 | 26.527 | −21.247 | 35.578 | 1.00 | 17.11 | D |
| ATOM | 4182 | N | LYS | D | 173 | 26.475 | −19.498 | 34.146 | 1.00 | 19.34 | D |
| ATOM | 4183 | CA | LYS | D | 173 | 27.938 | −19.399 | 33.869 | 1.00 | 21.12 | D |
| ATOM | 4184 | CB | LYS | D | 173 | 28.452 | −17.912 | 33.848 | 1.00 | 21.63 | D |
| ATOM | 4185 | CG | LYS | D | 173 | 27.538 | −16.884 | 33.137 | 1.00 | 22.64 | D |
| ATOM | 4186 | CD | LYS | D | 173 | 26.560 | −16.208 | 34.225 | 1.00 | 23.72 | D |
| ATOM | 4187 | CE | LYS | D | 173 | 25.051 | −15.905 | 33.704 | 1.00 | 23.03 | D |
| ATOM | 4188 | NZ | LYS | D | 173 | 24.321 | −17.195 | 33.418 | 1.00 | 23.42 | D |
| ATOM | 4189 | C | LYS | D | 173 | 28.849 | −20.235 | 34.809 | 1.00 | 20.67 | D |
| ATOM | 4190 | O | LYS | D | 173 | 28.983 | −21.412 | 34.588 | 1.00 | 20.72 | D |

TABLE 1-continued

| | | | | | | | | | | |
|---|---|---|---|---|---|---|---|---|---|---|
| ATOM | 4191 | N | CYS | D | 174 | 29.472 | −19.603 | 35.813 | 1.00 | 20.52 | D |
| ATOM | 4192 | CA | CYS | D | 174 | 30.368 | −20.262 | 36.790 | 1.00 | 20.69 | D |
| ATOM | 4193 | CB | CYS | D | 174 | 29.704 | −21.531 | 37.341 | 1.00 | 24.71 | D |
| ATOM | 4194 | SG | CYS | D | 174 | 30.442 | −22.141 | 39.011 | 1.00 | 38.34 | D |
| ATOM | 4195 | C | CYS | D | 174 | 31.883 | −20.546 | 36.349 | 1.00 | 16.94 | D |
| ATOM | 4196 | O | CYS | D | 174 | 32.585 | −19.637 | 35.697 | 1.00 | 13.61 | D |
| ATOM | 4197 | OXT | CYS | D | 174 | 32.295 | −21.691 | 36.736 | 1.00 | 12.96 | D |
| ATOM | 4198 | CB | GLU | B | 1 | 7.612 | 18.581 | 18.835 | 1.00 | 19.33 | B |
| ATOM | 4199 | CG | GLU | B | 1 | 6.875 | 18.926 | 20.079 | 1.00 | 21.29 | B |
| ATOM | 4200 | CD | GLU | B | 1 | 5.396 | 18.416 | 19.996 | 1.00 | 24.09 | B |
| ATOM | 4201 | OE1 | GLU | B | 1 | 5.202 | 17.157 | 19.841 | 1.00 | 24.44 | B |
| ATOM | 4202 | OE2 | GLU | B | 1 | 4.433 | 19.251 | 20.047 | 1.00 | 24.63 | B |
| ATOM | 4203 | C | GLU | B | 1 | 9.689 | 20.099 | 18.466 | 1.00 | 18.00 | B |
| ATOM | 4204 | O | GLU | B | 1 | 10.282 | 20.737 | 19.304 | 1.00 | 18.22 | B |
| ATOM | 4205 | N | GLU | B | 1 | 9.707 | 17.977 | 19.958 | 1.00 | 18.81 | B |
| ATOM | 4206 | CA | GLU | B | 1 | 9.153 | 18.663 | 18.782 | 1.00 | 18.39 | B |
| ATOM | 4207 | N | VAL | B | 2 | 9.522 | 20.598 | 17.264 | 1.00 | 17.41 | B |
| ATOM | 4208 | CA | VAL | B | 2 | 10.070 | 21.895 | 16.917 | 1.00 | 16.39 | B |
| ATOM | 4209 | CB | VAL | B | 2 | 10.926 | 21.863 | 15.559 | 1.00 | 16.10 | B |
| ATOM | 4210 | CG1 | VAL | B | 2 | 11.341 | 23.243 | 15.099 | 1.00 | 15.92 | B |
| ATOM | 4211 | CG2 | VAL | B | 2 | 12.182 | 21.088 | 15.759 | 1.00 | 15.06 | B |
| ATOM | 4212 | C | VAL | B | 2 | 8.875 | 22.706 | 16.759 | 1.00 | 17.34 | B |
| ATOM | 4213 | O | VAL | B | 2 | 7.993 | 22.304 | 16.063 | 1.00 | 18.11 | B |
| ATOM | 4214 | N | VAL | B | 3 | 8.829 | 23.884 | 17.351 | 1.00 | 17.32 | B |
| ATOM | 4215 | CA | VAL | B | 3 | 7.631 | 24.704 | 17.308 | 1.00 | 17.02 | B |
| ATOM | 4216 | CB | VAL | B | 3 | 7.193 | 25.194 | 18.793 | 1.00 | 17.23 | B |
| ATOM | 4217 | CG1 | VAL | B | 3 | 5.841 | 25.970 | 18.755 | 1.00 | 16.84 | B |
| ATOM | 4218 | CG2 | VAL | B | 3 | 7.074 | 23.988 | 19.760 | 1.00 | 16.21 | B |
| ATOM | 4219 | C | VAL | B | 3 | 7.727 | 25.910 | 16.491 | 1.00 | 17.69 | B |
| ATOM | 4220 | O | VAL | B | 3 | 8.484 | 26.723 | 16.790 | 1.00 | 17.27 | B |
| ATOM | 4221 | N | LEU | B | 4 | 6.896 | 26.078 | 15.487 | 1.00 | 18.77 | B |
| ATOM | 4222 | CA | LEU | B | 4 | 6.970 | 27.277 | 14.629 | 1.00 | 20.01 | B |
| ATOM | 4223 | CB | LEU | B | 4 | 6.905 | 26.832 | 13.148 | 1.00 | 17.64 | B |
| ATOM | 4224 | CG | LEU | B | 4 | 7.620 | 25.484 | 12.876 | 1.00 | 16.59 | B |
| ATOM | 4225 | CD1 | LEU | B | 4 | 7.234 | 24.874 | 11.408 | 1.00 | 14.29 | B |
| ATOM | 4226 | CD2 | LEU | B | 4 | 9.075 | 25.712 | 13.008 | 1.00 | 13.20 | B |
| ATOM | 4227 | C | LEU | B | 4 | 5.691 | 27.988 | 14.918 | 1.00 | 21.19 | B |
| ATOM | 4228 | O | LEU | B | 4 | 4.692 | 27.567 | 14.356 | 1.00 | 25.23 | B |
| ATOM | 4229 | N | LEU | B | 5 | 5.563 | 29.046 | 15.642 | 1.00 | 19.13 | B |
| ATOM | 4230 | CA | LEU | B | 5 | 4.191 | 29.509 | 15.887 | 1.00 | 15.39 | B |
| ATOM | 4231 | CB | LEU | B | 5 | 3.266 | 29.480 | 14.681 | 1.00 | 15.01 | B |
| ATOM | 4232 | CG | LEU | B | 5 | 1.947 | 30.186 | 15.057 | 1.00 | 16.17 | B |
| ATOM | 4233 | CD1 | LEU | B | 5 | 2.280 | 31.480 | 15.791 | 1.00 | 15.79 | B |
| ATOM | 4234 | CD2 | LEU | B | 5 | 1.148 | 30.585 | 13.864 | 1.00 | 14.53 | B |
| ATOM | 4235 | C | LEU | B | 5 | 3.449 | 28.823 | 17.044 | 1.00 | 14.56 | B |
| ATOM | 4236 | O | LEU | B | 5 | 3.131 | 27.647 | 17.030 | 1.00 | 13.09 | B |
| ATOM | 4237 | N | ASP | B | 6 | 3.160 | 29.678 | 18.050 | 1.00 | 14.75 | B |
| ATOM | 4238 | CA | ASP | B | 6 | 2.532 | 29.333 | 19.351 | 1.00 | 14.46 | B |
| ATOM | 4239 | CB | ASP | B | 6 | 3.589 | 28.872 | 20.276 | 1.00 | 17.73 | B |
| ATOM | 4240 | CG | ASP | B | 6 | 3.046 | 28.205 | 21.405 | 1.00 | 20.84 | B |
| ATOM | 4241 | OD1 | ASP | B | 6 | 3.893 | 27.787 | 22.279 | 1.00 | 24.10 | B |
| ATOM | 4242 | OD2 | ASP | B | 6 | 1.783 | 28.070 | 21.446 | 1.00 | 23.10 | B |
| ATOM | 4243 | C | ASP | B | 6 | 1.842 | 30.510 | 19.971 | 1.00 | 14.49 | B |
| ATOM | 4244 | O | ASP | B | 6 | 2.374 | 31.328 | 20.641 | 1.00 | 14.03 | B |
| ATOM | 4245 | N | PHE | B | 7 | 0.583 | 30.539 | 19.754 | 1.00 | 15.39 | B |
| ATOM | 4246 | CA | PHE | B | 7 | −0.242 | 31.653 | 20.101 | 1.00 | 15.19 | B |
| ATOM | 4247 | CB | PHE | B | 7 | −1.660 | 31.391 | 19.591 | 1.00 | 16.89 | B |
| ATOM | 4248 | CG | PHE | B | 7 | −2.673 | 32.414 | 20.016 | 1.00 | 16.46 | B |
| ATOM | 4249 | CD1 | PHE | B | 7 | −2.750 | 33.664 | 19.371 | 1.00 | 16.28 | B |
| ATOM | 4250 | CD2 | PHE | B | 7 | −3.521 | 32.138 | 21.071 | 1.00 | 15.35 | B |
| ATOM | 4251 | CE1 | PHE | B | 7 | −3.652 | 34.612 | 19.787 | 1.00 | 16.33 | B |
| ATOM | 4252 | CE2 | PHE | B | 7 | −4.414 | 33.065 | 21.470 | 1.00 | 15.35 | B |
| ATOM | 4253 | CZ | PHE | B | 7 | −4.483 | 34.304 | 20.837 | 1.00 | 16.05 | B |
| ATOM | 4254 | C | PHE | B | 7 | −0.317 | 32.028 | 21.535 | 1.00 | 15.08 | B |
| ATOM | 4255 | O | PHE | B | 7 | −0.280 | 33.231 | 21.884 | 1.00 | 13.87 | B |
| ATOM | 4256 | N | ALA | B | 8 | −0.514 | 30.988 | 22.319 | 1.00 | 15.15 | B |
| ATOM | 4257 | CA | ALA | B | 8 | −0.628 | 31.111 | 23.736 | 1.00 | 16.00 | B |
| ATOM | 4258 | CB | ALA | B | 8 | −1.171 | 29.778 | 24.299 | 1.00 | 15.81 | B |
| ATOM | 4259 | C | ALA | B | 8 | 0.661 | 31.559 | 24.472 | 1.00 | 16.09 | B |
| ATOM | 4260 | O | ALA | B | 8 | 0.622 | 31.722 | 25.668 | 1.00 | 15.94 | B |
| ATOM | 4261 | N | ALA | B | 9 | 1.786 | 31.754 | 23.782 | 1.00 | 16.49 | B |
| ATOM | 4262 | CA | ALA | B | 9 | 3.006 | 32.168 | 24.452 | 1.00 | 17.72 | B |
| ATOM | 4263 | CB | ALA | B | 9 | 4.124 | 31.252 | 24.105 | 1.00 | 14.51 | B |
| ATOM | 4264 | C | ALA | B | 9 | 3.367 | 33.595 | 24.125 | 1.00 | 18.20 | B |
| ATOM | 4265 | O | ALA | B | 9 | 4.239 | 34.155 | 24.795 | 1.00 | 19.49 | B |
| ATOM | 4266 | N | ALA | B | 10 | 2.651 | 34.199 | 23.177 | 1.00 | 18.85 | B |
| ATOM | 4267 | CA | ALA | B | 10 | 2.996 | 35.544 | 22.608 | 1.00 | 20.20 | B |
| ATOM | 4268 | CB | ALA | B | 10 | 2.617 | 35.613 | 21.061 | 1.00 | 17.52 | B |
| ATOM | 4269 | C | ALA | B | 10 | 2.399 | 36.733 | 23.345 | 1.00 | 21.06 | B |
| ATOM | 4270 | O | ALA | B | 10 | 1.281 | 37.304 | 22.951 | 1.00 | 20.73 | B |

TABLE 1-continued

| | | | | | | | | | | |
|---|---|---|---|---|---|---|---|---|---|---|
| ATOM | 4271 | N | GLY | B | 11 | 3.160 | 37.087 | 24.420 | 1.00 | 23.08 | B |
| ATOM | 4272 | CA | GLY | B | 11 | 2.844 | 38.206 | 25.436 | 1.00 | 25.57 | B |
| ATOM | 4273 | C | GLY | B | 11 | 2.502 | 39.628 | 24.886 | 1.00 | 26.22 | B |
| ATOM | 4274 | O | GLY | B | 11 | 3.190 | 40.676 | 25.111 | 1.00 | 27.46 | B |
| ATOM | 4275 | N | GLY | B | 12 | 1.373 | 39.649 | 24.170 | 1.00 | 25.67 | B |
| ATOM | 4276 | CA | GLY | B | 12 | 0.827 | 40.803 | 23.452 | 1.00 | 24.15 | B |
| ATOM | 4277 | C | GLY | B | 12 | 0.028 | 40.087 | 22.273 | 1.00 | 23.19 | B |
| ATOM | 4278 | O | GLY | B | 12 | 0.017 | 40.552 | 21.047 | 1.00 | 22.52 | B |
| ATOM | 4279 | N | GLU | B | 13 | −0.541 | 38.904 | 22.599 | 1.00 | 22.90 | B |
| ATOM | 4280 | CA | GLU | B | 13 | −1.436 | 38.168 | 21.681 | 1.00 | 22.48 | B |
| ATOM | 4281 | CB | GLU | B | 13 | −2.690 | 39.123 | 21.414 | 1.00 | 24.88 | B |
| ATOM | 4282 | CG | GLU | B | 13 | −2.712 | 40.700 | 22.103 | 1.00 | 25.88 | B |
| ATOM | 4283 | CD | GLU | B | 13 | −4.178 | 41.467 | 22.213 | 1.00 | 25.99 | B |
| ATOM | 4284 | OE1 | GLU | B | 13 | −5.161 | 40.604 | 22.261 | 1.00 | 25.78 | B |
| ATOM | 4285 | OE2 | GLU | B | 13 | −4.308 | 42.825 | 22.290 | 1.00 | 20.93 | B |
| ATOM | 4286 | C | GLU | B | 13 | −0.741 | 37.633 | 20.334 | 1.00 | 21.79 | B |
| ATOM | 4287 | O | GLU | B | 13 | −0.421 | 36.391 | 20.229 | 1.00 | 20.36 | B |
| ATOM | 4288 | N | LEU | B | 14 | −0.451 | 38.619 | 19.417 | 1.00 | 21.93 | B |
| ATOM | 4289 | CA | LEU | B | 14 | 0.234 | 38.449 | 18.167 | 1.00 | 21.77 | B |
| ATOM | 4290 | CB | LEU | B | 14 | −0.052 | 37.055 | 17.697 | 1.00 | 22.73 | B |
| ATOM | 4291 | CG | LEU | B | 14 | 1.207 | 36.164 | 17.913 | 1.00 | 23.69 | B |
| ATOM | 4292 | CD1 | LEU | B | 14 | 0.699 | 34.811 | 18.503 | 1.00 | 20.15 | B |
| ATOM | 4293 | CD2 | LEU | B | 14 | 2.093 | 36.100 | 16.465 | 1.00 | 21.19 | B |
| ATOM | 4294 | C | LEU | B | 14 | −0.062 | 39.371 | 17.013 | 1.00 | 21.68 | B |
| ATOM | 4295 | O | LEU | B | 14 | −1.139 | 40.089 | 16.949 | 1.00 | 22.37 | B |
| ATOM | 4296 | N | GLY | B | 15 | 0.819 | 39.191 | 16.025 | 1.00 | 21.01 | B |
| ATOM | 4297 | CA | GLY | B | 15 | 0.694 | 39.937 | 14.810 | 1.00 | 20.93 | B |
| ATOM | 4298 | C | GLY | B | 15 | −0.217 | 39.142 | 13.871 | 1.00 | 21.44 | B |
| ATOM | 4299 | O | GLY | B | 15 | 0.362 | 38.443 | 12.976 | 1.00 | 23.16 | B |
| ATOM | 4300 | N | TRP | B | 16 | −1.569 | 39.125 | 14.059 | 1.00 | 20.86 | B |
| ATOM | 4301 | CA | TRP | B | 16 | −2.424 | 38.390 | 13.073 | 1.00 | 19.41 | B |
| ATOM | 4302 | CB | TRP | B | 16 | −3.280 | 37.285 | 13.733 | 1.00 | 19.25 | B |
| ATOM | 4303 | CG | TRP | B | 16 | −2.471 | 36.200 | 14.230 | 1.00 | 18.20 | B |
| ATOM | 4304 | CD2 | TRP | B | 16 | −2.837 | 34.871 | 14.494 | 1.00 | 17.00 | B |
| ATOM | 4305 | CE2 | TRP | B | 16 | −1.711 | 34.235 | 15.099 | 1.00 | 17.45 | B |
| ATOM | 4306 | CE3 | TRP | B | 16 | −3.966 | 34.138 | 14.294 | 1.00 | 15.49 | B |
| ATOM | 4307 | CD1 | TRP | B | 16 | −1.192 | 36.328 | 14.648 | 1.00 | 19.78 | B |
| ATOM | 4308 | NE1 | TRP | B | 16 | −0.709 | 35.149 | 15.176 | 1.00 | 19.12 | B |
| ATOM | 4309 | CZ2 | TRP | B | 16 | −1.712 | 32.921 | 15.509 | 1.00 | 16.27 | B |
| ATOM | 4310 | CZ3 | TRP | B | 16 | −3.965 | 32.785 | 14.714 | 1.00 | 15.94 | B |
| ATOM | 4311 | CH2 | TRP | B | 16 | −2.827 | 32.212 | 15.316 | 1.00 | 17.32 | B |
| ATOM | 4312 | C | TRP | B | 16 | −3.326 | 39.293 | 12.219 | 1.00 | 19.30 | B |
| ATOM | 4313 | O | TRP | B | 16 | −3.593 | 40.440 | 12.591 | 1.00 | 19.85 | B |
| ATOM | 4314 | N | LEU | B | 17 | −3.760 | 38.795 | 11.060 | 1.00 | 18.36 | B |
| ATOM | 4315 | CA | LEU | B | 17 | −4.653 | 39.559 | 10.131 | 1.00 | 16.56 | B |
| ATOM | 4316 | CB | LEU | B | 17 | −4.221 | 39.346 | 8.703 | 1.00 | 18.10 | B |
| ATOM | 4317 | CG | LEU | B | 17 | −5.044 | 40.121 | 7.747 | 1.00 | 19.82 | B |
| ATOM | 4318 | CD1 | LEU | B | 17 | −5.201 | 41.555 | 8.456 | 1.00 | 22.99 | B |
| ATOM | 4319 | CD2 | LEU | B | 17 | −4.322 | 40.225 | 6.367 | 1.00 | 18.76 | B |
| ATOM | 4320 | C | LEU | B | 17 | −6.085 | 39.123 | 10.303 | 1.00 | 15.21 | B |
| ATOM | 4321 | O | LEU | B | 17 | −6.387 | 37.950 | 10.538 | 1.00 | 14.49 | B |
| ATOM | 4322 | N | THR | B | 18 | −6.976 | 40.076 | 10.185 | 1.00 | 14.81 | B |
| ATOM | 4323 | CA | THR | B | 18 | −8.411 | 39.812 | 10.468 | 1.00 | 16.08 | B |
| ATOM | 4324 | CB | THR | B | 18 | −8.840 | 40.526 | 11.755 | 1.00 | 14.48 | B |
| ATOM | 4325 | OG1 | THR | B | 18 | −8.908 | 39.553 | 12.776 | 1.00 | 16.08 | B |
| ATOM | 4326 | CG2 | THR | B | 18 | −10.058 | 41.170 | 11.664 | 1.00 | 13.24 | B |
| ATOM | 4327 | C | THR | B | 18 | −9.135 | 40.317 | 9.355 | 1.00 | 17.55 | B |
| ATOM | 4328 | O | THR | B | 18 | −9.101 | 41.515 | 9.187 | 1.00 | 17.13 | B |
| ATOM | 4329 | N | HIS | B | 19 | −9.815 | 39.443 | 8.599 | 1.00 | 19.55 | B |
| ATOM | 4330 | CA | HIS | B | 19 | −10.403 | 39.997 | 7.431 | 1.00 | 21.50 | B |
| ATOM | 4331 | CB | HIS | B | 19 | −10.613 | 38.987 | 6.330 | 1.00 | 22.58 | B |
| ATOM | 4332 | CG | HIS | B | 19 | −10.873 | 39.613 | 4.955 | 1.00 | 23.08 | B |
| ATOM | 4333 | CD2 | HIS | B | 19 | −11.643 | 39.196 | 3.902 | 1.00 | 21.70 | B |
| ATOM | 4334 | ND1 | HIS | B | 19 | −10.425 | 40.880 | 4.599 | 1.00 | 23.45 | B |
| ATOM | 4335 | CE1 | HIS | B | 19 | −10.919 | 41.230 | 3.417 | 1.00 | 21.99 | B |
| ATOM | 4336 | NE2 | HIS | B | 19 | −11.665 | 40.229 | 2.973 | 1.00 | 23.35 | B |
| ATOM | 4337 | C | HIS | B | 19 | −11.610 | 40.877 | 7.688 | 1.00 | 24.72 | B |
| ATOM | 4338 | O | HIS | B | 19 | −11.571 | 41.684 | 8.714 | 1.00 | 26.75 | B |
| ATOM | 4339 | N | PRO | B | 20 | −12.770 | 40.695 | 6.961 | 1.00 | 23.56 | B |
| ATOM | 4340 | CD | PRO | B | 20 | −13.311 | 39.322 | 7.145 | 1.00 | 20.37 | B |
| ATOM | 4341 | CA | PRO | B | 20 | −13.748 | 41.778 | 7.404 | 1.00 | 20.09 | B |
| ATOM | 4342 | CB | PRO | B | 20 | −14.763 | 41.009 | 8.188 | 1.00 | 20.64 | B |
| ATOM | 4343 | CG | PRO | B | 20 | −14.814 | 39.702 | 7.330 | 1.00 | 21.42 | B |
| ATOM | 4344 | C | PRO | B | 20 | −13.006 | 42.948 | 8.233 | 1.00 | 22.82 | B |
| ATOM | 4345 | O | PRO | B | 20 | −12.596 | 44.031 | 7.672 | 1.00 | 22.68 | B |
| ATOM | 4346 | N | TYR | B | 21 | −12.749 | 42.693 | 9.542 | 1.00 | 23.57 | B |
| ATOM | 4347 | CA | TYR | B | 21 | −12.066 | 43.668 | 10.489 | 1.00 | 23.33 | B |
| ATOM | 4348 | CB | TYR | B | 21 | −10.948 | 44.539 | 9.868 | 1.00 | 24.13 | B |
| ATOM | 4349 | CG | TYR | B | 21 | −10.325 | 45.390 | 11.058 | 1.00 | 25.30 | B |
| ATOM | 4350 | CD1 | TYR | B | 21 | −9.547 | 44.744 | 12.110 | 1.00 | 24.18 | B |

TABLE 1-continued

| | | | | | | | | | |
|---|---|---|---|---|---|---|---|---|---|
| ATOM | 4351 | CE1 | TYR | B | 21 | −9.190 | 45.434 | 13.301 | 1.00 | 25.23 | B |
| ATOM | 4352 | CD2 | TYR | B | 21 | −10.696 | 46.778 | 11.251 | 1.00 | 26.09 | B |
| ATOM | 4353 | CE2 | TYR | B | 21 | −10.315 | 47.453 | 12.467 | 1.00 | 27.05 | B |
| ATOM | 4354 | CZ | TYR | B | 21 | −9.577 | 46.727 | 13.439 | 1.00 | 26.21 | B |
| ATOM | 4355 | OH | TYR | B | 21 | −9.302 | 47.352 | 14.599 | 1.00 | 30.88 | B |
| ATOM | 4356 | C | TYR | B | 21 | −13.034 | 44.677 | 11.069 | 1.00 | 24.20 | B |
| ATOM | 4357 | O | TYR | B | 21 | −13.376 | 45.669 | 10.326 | 1.00 | 24.27 | B |
| ATOM | 4358 | N | GLY | B | 22 | −13.433 | 44.469 | 12.339 | 1.00 | 25.25 | B |
| ATOM | 4359 | CA | GLY | B | 22 | −14.393 | 45.386 | 12.944 | 1.00 | 26.57 | B |
| ATOM | 4360 | C | GLY | B | 22 | −15.388 | 44.534 | 13.635 | 1.00 | 26.74 | B |
| ATOM | 4361 | O | GLY | B | 22 | −15.522 | 44.683 | 14.860 | 1.00 | 28.62 | B |
| ATOM | 4362 | N | LYS | B | 23 | −16.013 | 43.592 | 12.887 | 1.00 | 25.31 | B |
| ATOM | 4363 | CA | LYS | B | 23 | −17.121 | 42.713 | 13.439 | 1.00 | 22.94 | B |
| ATOM | 4364 | CB | LYS | B | 23 | −18.427 | 42.939 | 12.653 | 1.00 | 21.75 | B |
| ATOM | 4365 | CG | LYS | B | 23 | −19.098 | 44.333 | 12.718 | 1.00 | 21.55 | B |
| ATOM | 4366 | CD | LYS | B | 23 | −18.605 | 45.346 | 11.499 | 1.00 | 21.23 | B |
| ATOM | 4367 | CE | LYS | B | 23 | −18.946 | 46.890 | 11.762 | 1.00 | 17.99 | B |
| ATOM | 4368 | NZ | LYS | B | 23 | −20.425 | 47.011 | 11.972 | 1.00 | 19.14 | B |
| ATOM | 4369 | C | LYS | B | 23 | −16.763 | 41.185 | 13.353 | 1.00 | 22.33 | B |
| ATOM | 4370 | O | LYS | B | 23 | −17.538 | 40.327 | 13.819 | 1.00 | 22.65 | B |
| ATOM | 4371 | N | GLY | B | 24 | −15.621 | 40.868 | 12.742 | 1.00 | 20.12 | B |
| ATOM | 4372 | CA | GLY | B | 24 | −15.278 | 39.505 | 12.683 | 1.00 | 17.62 | B |
| ATOM | 4373 | C | GLY | B | 24 | −14.649 | 39.062 | 13.983 | 1.00 | 16.71 | B |
| ATOM | 4374 | O | GLY | B | 24 | −15.170 | 39.256 | 14.996 | 1.00 | 15.30 | B |
| ATOM | 4375 | N | TRP | B | 25 | −13.552 | 38.347 | 13.847 | 1.00 | 16.97 | B |
| ATOM | 4376 | CA | TRP | B | 25 | −12.696 | 37.820 | 14.834 | 1.00 | 16.53 | B |
| ATOM | 4377 | CB | TRP | B | 25 | −11.616 | 37.026 | 14.093 | 1.00 | 16.79 | B |
| ATOM | 4378 | CG | TRP | B | 25 | −11.925 | 35.706 | 13.500 | 1.00 | 15.95 | B |
| ATOM | 4379 | CD2 | TRP | B | 25 | −12.022 | 34.469 | 14.218 | 1.00 | 15.70 | B |
| ATOM | 4380 | CE2 | TRP | B | 25 | −12.252 | 33.457 | 13.257 | 1.00 | 15.64 | B |
| ATOM | 4381 | CE3 | TRP | B | 25 | −11.930 | 34.120 | 15.588 | 1.00 | 14.43 | B |
| ATOM | 4382 | CD1 | TRP | B | 25 | −12.107 | 35.380 | 12.140 | 1.00 | 16.11 | B |
| ATOM | 4383 | NE1 | TRP | B | 25 | −12.287 | 34.044 | 12.017 | 1.00 | 15.31 | B |
| ATOM | 4384 | CZ2 | TRP | B | 25 | −12.391 | 32.146 | 13.616 | 1.00 | 16.41 | B |
| ATOM | 4385 | CZ3 | TRP | B | 25 | −12.055 | 32.847 | 15.938 | 1.00 | 15.11 | B |
| ATOM | 4386 | CH2 | TRP | B | 25 | −12.287 | 31.843 | 14.969 | 1.00 | 15.11 | B |
| ATOM | 4387 | C | TRP | B | 25 | −11.991 | 39.001 | 15.587 | 1.00 | 16.75 | B |
| ATOM | 4388 | O | TRP | B | 25 | −11.402 | 39.918 | 14.972 | 1.00 | 16.41 | B |
| ATOM | 4389 | N | ASP | B | 26 | −12.046 | 38.938 | 16.923 | 1.00 | 17.33 | B |
| ATOM | 4390 | CA | ASP | B | 26 | −11.393 | 39.936 | 17.834 | 1.00 | 16.66 | B |
| ATOM | 4391 | CB | ASP | B | 26 | −12.410 | 40.805 | 18.641 | 1.00 | 21.86 | B |
| ATOM | 4392 | CG | ASP | B | 26 | −13.349 | 41.779 | 17.744 | 1.00 | 27.42 | B |
| ATOM | 4393 | OD1 | ASP | B | 26 | −13.306 | 42.078 | 16.448 | 1.00 | 28.08 | B |
| ATOM | 4394 | OD2 | ASP | B | 26 | −14.250 | 42.380 | 18.485 | 1.00 | 32.32 | B |
| ATOM | 4395 | C | ASP | B | 26 | −10.470 | 39.226 | 18.892 | 1.00 | 14.14 | B |
| ATOM | 4396 | O | ASP | B | 26 | −10.813 | 38.240 | 19.546 | 1.00 | 10.78 | B |
| ATOM | 4397 | N | LEU | B | 27 | −9.301 | 39.837 | 19.040 | 1.00 | 13.88 | B |
| ATOM | 4398 | CA | LEU | B | 27 | −8.292 | 39.460 | 19.990 | 1.00 | 13.89 | B |
| ATOM | 4399 | CB | LEU | B | 27 | −7.002 | 40.075 | 19.525 | 1.00 | 14.15 | B |
| ATOM | 4400 | CG | LEU | B | 27 | −5.789 | 39.514 | 20.281 | 1.00 | 15.05 | B |
| ATOM | 4401 | CD1 | LEU | B | 27 | −5.697 | 38.022 | 20.331 | 1.00 | 14.81 | B |
| ATOM | 4402 | CD2 | LEU | B | 27 | −4.648 | 40.231 | 19.673 | 1.00 | 12.79 | B |
| ATOM | 4403 | C | LEU | B | 27 | −8.773 | 40.009 | 21.354 | 1.00 | 14.18 | B |
| ATOM | 4404 | O | LEU | B | 27 | −9.095 | 41.098 | 21.546 | 1.00 | 14.28 | B |
| ATOM | 4405 | N | MET | B | 28 | −8.898 | 39.157 | 22.277 | 1.00 | 14.56 | B |
| ATOM | 4406 | CA | MET | B | 28 | −9.340 | 39.526 | 23.487 | 1.00 | 15.08 | B |
| ATOM | 4407 | CB | MET | B | 28 | −10.718 | 38.921 | 23.732 | 1.00 | 18.06 | B |
| ATOM | 4408 | CG | MET | B | 28 | −11.688 | 39.105 | 22.612 | 1.00 | 21.22 | B |
| ATOM | 4409 | SD | MET | B | 28 | −13.467 | 38.516 | 22.863 | 1.00 | 24.86 | B |
| ATOM | 4410 | CE | MET | B | 28 | −13.974 | 39.828 | 24.635 | 1.00 | 21.11 | B |
| ATOM | 4411 | C | MET | B | 28 | −8.362 | 39.006 | 24.568 | 1.00 | 14.66 | B |
| ATOM | 4412 | O | MET | B | 28 | −7.758 | 37.925 | 24.477 | 1.00 | 13.69 | B |
| ATOM | 4413 | N | GLN | B | 29 | −8.237 | 39.794 | 25.636 | 1.00 | 15.17 | B |
| ATOM | 4414 | CA | GLN | B | 29 | −7.400 | 39.382 | 26.737 | 1.00 | 15.92 | B |
| ATOM | 4415 | CB | GLN | B | 29 | −6.415 | 40.457 | 27.024 | 1.00 | 16.68 | B |
| ATOM | 4416 | CG | GLN | B | 29 | −5.319 | 39.848 | 27.875 | 1.00 | 18.08 | B |
| ATOM | 4417 | CD | GLN | B | 29 | −4.563 | 40.888 | 28.712 | 1.00 | 18.79 | B |
| ATOM | 4418 | OE1 | GLN | B | 29 | −3.448 | 41.224 | 28.403 | 1.00 | 19.28 | B |
| ATOM | 4419 | NE2 | GLN | B | 29 | −5.193 | 41.394 | 29.758 | 1.00 | 18.61 | B |
| ATOM | 4420 | C | GLN | B | 29 | −8.090 | 39.064 | 28.011 | 1.00 | 14.77 | B |
| ATOM | 4421 | O | GLN | B | 29 | −8.585 | 39.939 | 28.636 | 1.00 | 14.97 | B |
| ATOM | 4422 | N | ASN | B | 30 | −8.178 | 37.817 | 28.385 | 1.00 | 14.16 | B |
| ATOM | 4423 | CA | ASN | B | 30 | −8.686 | 37.536 | 29.710 | 1.00 | 13.52 | B |
| ATOM | 4424 | CB | ASN | B | 30 | −9.427 | 36.221 | 29.700 | 1.00 | 14.16 | B |
| ATOM | 4425 | CG | ASN | B | 30 | −10.836 | 36.393 | 29.181 | 1.00 | 14.84 | B |
| ATOM | 4426 | OD1 | ASN | B | 30 | −11.467 | 35.413 | 28.877 | 1.00 | 15.97 | B |
| ATOM | 4427 | ND2 | ASN | B | 30 | −11.362 | 37.643 | 29.128 | 1.00 | 12.34 | B |
| ATOM | 4428 | C | ASN | B | 30 | −7.523 | 37.493 | 30.746 | 1.00 | 11.42 | B |
| ATOM | 4429 | O | ASN | B | 30 | −6.341 | 37.556 | 30.404 | 1.00 | 6.76 | B |
| ATOM | 4430 | N | ILE | B | 31 | −7.879 | 37.407 | 32.009 | 1.00 | 12.92 | B |

TABLE 1-continued

| | | | | | | | | | | |
|---|---|---|---|---|---|---|---|---|---|---|
| ATOM | 4431 | CA | ILE | B | 31 | −6.819 | 37.317 | 32.956 | 1.00 | 16.17 | B |
| ATOM | 4432 | CB | ILE | B | 31 | −6.358 | 38.707 | 33.299 | 1.00 | 18.43 | B |
| ATOM | 4433 | CG2 | ILE | B | 31 | −7.513 | 39.522 | 33.865 | 1.00 | 22.68 | B |
| ATOM | 4434 | CG1 | ILE | B | 31 | −5.210 | 38.634 | 34.275 | 1.00 | 20.76 | B |
| ATOM | 4435 | CD1 | ILE | B | 31 | −4.862 | 40.072 | 34.704 | 1.00 | 20.25 | B |
| ATOM | 4436 | C | ILE | B | 31 | −7.154 | 36.475 | 34.101 | 1.00 | 15.67 | B |
| ATOM | 4437 | O | ILE | B | 31 | −8.201 | 36.511 | 34.572 | 1.00 | 15.55 | B |
| ATOM | 4438 | N | MET | B | 32 | −6.240 | 35.661 | 34.524 | 1.00 | 16.22 | B |
| ATOM | 4439 | CA | MET | B | 32 | −6.444 | 34.706 | 35.589 | 1.00 | 16.42 | B |
| ATOM | 4440 | CB | MET | B | 32 | −6.603 | 33.305 | 35.044 | 1.00 | 19.18 | B |
| ATOM | 4441 | CG | MET | B | 32 | −8.010 | 32.868 | 34.704 | 1.00 | 21.98 | B |
| ATOM | 4442 | SD | MET | B | 32 | −9.188 | 32.807 | 36.136 | 1.00 | 25.56 | B |
| ATOM | 4443 | CE | MET | B | 32 | −7.793 | 32.430 | 37.414 | 1.00 | 20.66 | B |
| ATOM | 4444 | C | MET | B | 32 | −5.195 | 34.641 | 36.373 | 1.00 | 15.53 | B |
| ATOM | 4445 | O | MET | B | 32 | −4.192 | 34.260 | 35.842 | 1.00 | 14.13 | B |
| ATOM | 4446 | N | ASN | B | 33 | −5.308 | 34.914 | 37.680 | 1.00 | 16.51 | B |
| ATOM | 4447 | CA | ASN | B | 33 | −4.175 | 34.945 | 38.622 | 1.00 | 16.45 | B |
| ATOM | 4448 | CB | ASN | B | 33 | −3.653 | 33.544 | 38.868 | 1.00 | 16.49 | B |
| ATOM | 4449 | CG | ASN | B | 33 | −4.672 | 32.680 | 39.494 | 1.00 | 16.71 | B |
| ATOM | 4450 | OD1 | ASN | B | 33 | −5.197 | 32.904 | 40.642 | 1.00 | 18.56 | B |
| ATOM | 4451 | ND2 | ASN | B | 33 | −5.007 | 31.692 | 38.787 | 1.00 | 16.19 | B |
| ATOM | 4452 | C | ASN | B | 33 | −3.052 | 35.793 | 38.020 | 1.00 | 17.19 | B |
| ATOM | 4453 | O | ASN | B | 33 | −1.896 | 35.386 | 37.975 | 1.00 | 18.47 | B |
| ATOM | 4454 | N | ASP | B | 34 | −3.433 | 36.920 | 37.486 | 1.00 | 17.50 | B |
| ATOM | 4455 | CA | ASP | B | 34 | −2.510 | 37.860 | 36.925 | 1.00 | 18.58 | B |
| ATOM | 4456 | CB | ASP | B | 34 | −1.478 | 38.394 | 37.988 | 1.00 | 19.45 | B |
| ATOM | 4457 | CG | ASP | B | 34 | −2.095 | 39.454 | 39.021 | 1.00 | 22.25 | B |
| ATOM | 4458 | OD1 | ASP | B | 34 | −3.328 | 39.502 | 39.425 | 1.00 | 23.92 | B |
| ATOM | 4459 | OD2 | ASP | B | 34 | −1.294 | 40.270 | 39.568 | 1.00 | 25.70 | B |
| ATOM | 4460 | C | ASP | B | 34 | −1.847 | 37.376 | 35.664 | 1.00 | 16.52 | B |
| ATOM | 4461 | O | ASP | B | 34 | −0.992 | 38.041 | 35.062 | 1.00 | 17.54 | B |
| ATOM | 4462 | N | MET | B | 35 | −2.200 | 36.215 | 35.220 | 1.00 | 15.51 | B |
| ATOM | 4463 | CA | MET | B | 35 | −1.651 | 35.888 | 33.870 | 1.00 | 14.80 | B |
| ATOM | 4464 | CB | MET | B | 35 | −1.447 | 34.404 | 33.772 | 1.00 | 15.81 | B |
| ATOM | 4465 | CG | MET | B | 35 | −0.341 | 33.964 | 34.699 | 1.00 | 17.60 | B |
| ATOM | 4466 | SD | MET | B | 35 | 1.360 | 34.661 | 34.221 | 1.00 | 18.40 | B |
| ATOM | 4467 | CE | MET | B | 35 | 1.316 | 36.284 | 35.435 | 1.00 | 18.05 | B |
| ATOM | 4468 | C | MET | B | 35 | −2.571 | 36.348 | 32.673 | 1.00 | 13.06 | B |
| ATOM | 4469 | O | MET | B | 35 | −3.733 | 36.057 | 32.646 | 1.00 | 10.06 | B |
| ATOM | 4470 | N | PRO | B | 36 | −2.048 | 37.135 | 31.731 | 1.00 | 11.97 | B |
| ATOM | 4471 | CD | PRO | B | 36 | −0.768 | 37.739 | 31.541 | 1.00 | 13.50 | B |
| ATOM | 4472 | CA | PRO | B | 36 | −2.915 | 37.491 | 30.627 | 1.00 | 13.77 | B |
| ATOM | 4473 | CB | PRO | B | 36 | −2.121 | 38.541 | 29.879 | 1.00 | 13.17 | B |
| ATOM | 4474 | CG | PRO | B | 36 | −0.888 | 38.160 | 30.088 | 1.00 | 14.36 | B |
| ATOM | 4475 | C | PRO | B | 36 | −3.184 | 36.169 | 29.779 | 1.00 | 13.15 | B |
| ATOM | 4476 | O | PRO | B | 36 | −2.315 | 35.346 | 29.586 | 1.00 | 12.74 | B |
| ATOM | 4477 | N | ILE | B | 37 | −4.433 | 35.931 | 29.430 | 1.00 | 13.54 | B |
| ATOM | 4478 | CA | ILE | B | 37 | −4.820 | 34.787 | 28.614 | 1.00 | 15.31 | B |
| ATOM | 4479 | CB | ILE | B | 37 | −5.857 | 33.984 | 29.304 | 1.00 | 15.57 | B |
| ATOM | 4480 | CG2 | ILE | B | 37 | −6.076 | 32.672 | 28.638 | 1.00 | 14.63 | B |
| ATOM | 4481 | CG1 | ILE | B | 37 | −5.405 | 33.640 | 30.705 | 1.00 | 17.71 | B |
| ATOM | 4482 | CD1 | ILE | B | 37 | −4.023 | 33.216 | 30.795 | 1.00 | 18.08 | B |
| ATOM | 4483 | C | ILE | B | 37 | −5.389 | 35.318 | 27.293 | 1.00 | 14.58 | B |
| ATOM | 4484 | O | ILE | B | 37 | −6.484 | 35.701 | 27.263 | 1.00 | 14.96 | B |
| ATOM | 4485 | N | TYR | B | 38 | −4.654 | 35.367 | 26.205 | 1.00 | 15.12 | B |
| ATOM | 4486 | CA | TYR | B | 38 | −5.283 | 35.915 | 25.008 | 1.00 | 16.20 | B |
| ATOM | 4487 | CB | TYR | B | 38 | −4.261 | 36.501 | 24.053 | 1.00 | 16.22 | B |
| ATOM | 4488 | CG | TYR | B | 38 | −3.594 | 37.757 | 24.563 | 1.00 | 15.67 | B |
| ATOM | 4489 | CD1 | TYR | B | 38 | −2.583 | 37.709 | 25.461 | 1.00 | 16.39 | B |
| ATOM | 4490 | CE1 | TYR | B | 38 | −2.122 | 38.802 | 25.950 | 1.00 | 15.95 | B |
| ATOM | 4491 | CD2 | TYR | B | 38 | −4.058 | 38.983 | 24.217 | 1.00 | 14.70 | B |
| ATOM | 4492 | CE2 | TYR | B | 38 | −3.593 | 40.037 | 24.709 | 1.00 | 14.08 | B |
| ATOM | 4493 | CZ | TYR | B | 38 | −2.634 | 39.961 | 25.570 | 1.00 | 16.32 | B |
| ATOM | 4494 | OH | TYR | B | 38 | −2.156 | 41.138 | 26.103 | 1.00 | 20.87 | B |
| ATOM | 4495 | C | TYR | B | 38 | −6.098 | 34.814 | 24.250 | 1.00 | 16.42 | B |
| ATOM | 4496 | O | TYR | B | 38 | −5.876 | 33.588 | 24.438 | 1.00 | 15.71 | B |
| ATOM | 4497 | N | MET | B | 39 | −7.011 | 35.291 | 23.388 | 1.00 | 16.19 | B |
| ATOM | 4498 | CA | MET | B | 39 | −7.862 | 34.472 | 22.585 | 1.00 | 14.97 | B |
| ATOM | 4499 | CB | MET | B | 39 | −8.990 | 33.929 | 23.393 | 1.00 | 15.17 | B |
| ATOM | 4500 | CG | MET | B | 39 | −10.195 | 34.754 | 23.436 | 1.00 | 16.34 | B |
| ATOM | 4501 | SD | MET | B | 39 | −11.118 | 34.390 | 25.002 | 1.00 | 18.85 | B |
| ATOM | 4502 | CE | MET | B | 39 | −12.532 | 35.626 | 24.930 | 1.00 | 18.74 | B |
| ATOM | 4503 | C | MET | B | 39 | −8.433 | 35.211 | 21.377 | 1.00 | 15.27 | B |
| ATOM | 4504 | O | MET | B | 39 | −8.525 | 36.417 | 21.409 | 1.00 | 14.93 | B |
| ATOM | 4505 | N | TYR | B | 40 | −8.735 | 34.487 | 20.278 | 1.00 | 14.25 | B |
| ATOM | 4506 | CA | TYR | B | 40 | −9.373 | 35.158 | 19.174 | 1.00 | 13.70 | B |
| ATOM | 4507 | CB | TYR | B | 40 | −8.620 | 34.897 | 17.892 | 1.00 | 15.06 | B |
| ATOM | 4508 | CG | TYR | B | 40 | −7.653 | 35.936 | 17.525 | 1.00 | 15.09 | B |
| ATOM | 4509 | CD1 | TYR | B | 40 | −6.272 | 35.744 | 17.670 | 1.00 | 16.16 | B |
| ATOM | 4510 | CE1 | TYR | B | 40 | −5.394 | 36.710 | 17.302 | 1.00 | 14.40 | B |

TABLE 1-continued

| ATOM | 4511 | CD2 | TYR | B | 40 | −8.079 | 37.113 | 16.991 | 1.00 | 14.86 | B |
|---|---|---|---|---|---|---|---|---|---|---|---|
| ATOM | 4512 | CE2 | TYR | B | 40 | −7.196 | 38.075 | 16.625 | 1.00 | 13.21 | B |
| ATOM | 4513 | CZ | TYR | B | 40 | −5.871 | 37.900 | 16.783 | 1.00 | 14.46 | B |
| ATOM | 4514 | OH | TYR | B | 40 | −5.043 | 38.971 | 16.471 | 1.00 | 14.12 | B |
| ATOM | 4515 | C | TYR | B | 40 | −10.830 | 34.573 | 19.194 | 1.00 | 12.92 | B |
| ATOM | 4516 | O | TYR | B | 40 | −11.057 | 33.389 | 19.406 | 1.00 | 11.67 | B |
| ATOM | 4517 | N | SER | B | 41 | −11.816 | 35.413 | 19.027 | 1.00 | 12.59 | B |
| ATOM | 4518 | CA | SER | B | 41 | −13.157 | 34.894 | 19.078 | 1.00 | 13.84 | B |
| ATOM | 4519 | CB | SER | B | 41 | −13.711 | 34.742 | 20.536 | 1.00 | 15.21 | B |
| ATOM | 4520 | OG | SER | B | 41 | −13.571 | 35.844 | 21.337 | 1.00 | 16.56 | B |
| ATOM | 4521 | C | SER | B | 41 | −14.116 | 35.670 | 18.232 | 1.00 | 14.15 | B |
| ATOM | 4522 | O | SER | B | 41 | −13.748 | 36.778 | 17.772 | 1.00 | 14.28 | B |
| ATOM | 4523 | N | VAL | B | 42 | −15.285 | 35.063 | 17.985 | 1.00 | 12.91 | B |
| ATOM | 4524 | CA | VAL | B | 42 | −16.299 | 35.688 | 17.150 | 1.00 | 14.05 | B |
| ATOM | 4525 | CB | VAL | B | 42 | −16.517 | 35.202 | 15.668 | 1.00 | 13.30 | B |
| ATOM | 4526 | CG1 | VAL | B | 42 | −16.772 | 36.407 | 14.814 | 1.00 | 13.89 | B |
| ATOM | 4527 | CG2 | VAL | B | 42 | −15.489 | 34.194 | 15.214 | 1.00 | 10.02 | B |
| ATOM | 4528 | C | VAL | B | 42 | −17.545 | 35.099 | 17.601 | 1.00 | 14.51 | B |
| ATOM | 4529 | O | VAL | B | 42 | −17.580 | 33.932 | 18.033 | 1.00 | 14.73 | B |
| ATOM | 4530 | N | CYS | B | 43 | −18.608 | 35.819 | 17.345 | 1.00 | 14.37 | B |
| ATOM | 4531 | CA | CYS | B | 43 | −19.885 | 35.291 | 17.774 | 1.00 | 18.12 | B |
| ATOM | 4532 | C | CYS | B | 43 | −21.026 | 35.978 | 16.977 | 1.00 | 16.79 | B |
| ATOM | 4533 | O | CYS | B | 43 | −22.044 | 36.257 | 17.512 | 1.00 | 18.45 | B |
| ATOM | 4534 | CB | CYS | B | 43 | −20.096 | 35.490 | 19.345 | 1.00 | 16.58 | B |
| ATOM | 4535 | SG | CYS | B | 43 | −21.487 | 34.552 | 20.121 | 1.00 | 16.93 | B |
| ATOM | 4536 | N | ASN | B | 44 | −20.866 | 36.270 | 15.723 | 1.00 | 16.51 | B |
| ATOM | 4537 | CA | ASN | B | 44 | −22.001 | 36.822 | 14.982 | 1.00 | 15.71 | B |
| ATOM | 4538 | CB | ASN | B | 44 | −21.465 | 37.499 | 13.723 | 1.00 | 15.01 | B |
| ATOM | 4539 | CG | ASN | B | 44 | −20.459 | 38.526 | 14.075 | 1.00 | 14.45 | B |
| ATOM | 4540 | OD1 | ASN | B | 44 | −19.517 | 38.810 | 13.380 | 1.00 | 11.21 | B |
| ATOM | 4541 | ND2 | ASN | B | 44 | −20.703 | 39.129 | 15.231 | 1.00 | 15.46 | B |
| ATOM | 4542 | C | ASN | B | 44 | −23.000 | 35.711 | 14.620 | 1.00 | 14.74 | B |
| ATOM | 4543 | O | ASN | B | 44 | −23.162 | 35.445 | 13.448 | 1.00 | 14.71 | B |
| ATOM | 4544 | N | VAL | B | 45 | −23.579 | 35.043 | 15.625 | 1.00 | 13.75 | B |
| ATOM | 4545 | CA | VAL | B | 45 | −24.539 | 33.970 | 15.436 | 1.00 | 14.67 | B |
| ATOM | 4546 | CB | VAL | B | 45 | −24.704 | 33.011 | 16.669 | 1.00 | 14.25 | B |
| ATOM | 4547 | CG1 | VAL | B | 45 | −23.486 | 32.393 | 16.963 | 1.00 | 17.00 | B |
| ATOM | 4548 | CG2 | VAL | B | 45 | −25.167 | 33.713 | 17.891 | 1.00 | 15.52 | B |
| ATOM | 4549 | C | VAL | B | 45 | −25.916 | 34.346 | 15.049 | 1.00 | 13.23 | B |
| ATOM | 4550 | O | VAL | B | 45 | −26.669 | 33.492 | 14.723 | 1.00 | 13.45 | B |
| ATOM | 4551 | N | MET | B | 46 | −26.174 | 35.625 | 15.009 | 1.00 | 14.82 | B |
| ATOM | 4552 | CA | MET | B | 46 | −27.503 | 36.183 | 14.807 | 1.00 | 16.63 | B |
| ATOM | 4553 | CB | MET | B | 46 | −27.800 | 37.235 | 15.902 | 1.00 | 17.75 | B |
| ATOM | 4554 | CG | MET | B | 46 | −29.002 | 37.051 | 16.744 | 1.00 | 19.21 | B |
| ATOM | 4555 | SD | MET | B | 46 | −29.425 | 35.438 | 17.494 | 1.00 | 23.11 | B |
| ATOM | 4556 | CE | MET | B | 46 | −28.880 | 35.721 | 19.629 | 1.00 | 22.04 | B |
| ATOM | 4557 | C | MET | B | 46 | −27.555 | 36.862 | 13.472 | 1.00 | 17.40 | B |
| ATOM | 4558 | O | MET | B | 46 | −28.548 | 37.505 | 13.133 | 1.00 | 17.48 | B |
| ATOM | 4559 | N | SER | B | 47 | −26.472 | 36.820 | 12.711 | 1.00 | 18.46 | B |
| ATOM | 4560 | CA | SER | B | 47 | −26.612 | 37.422 | 11.352 | 1.00 | 20.09 | B |
| ATOM | 4561 | CB | SER | B | 47 | −25.731 | 38.660 | 11.269 | 1.00 | 20.21 | B |
| ATOM | 4562 | OG | SER | B | 47 | −25.195 | 38.890 | 12.580 | 1.00 | 21.46 | B |
| ATOM | 4563 | C | SER | B | 47 | −26.206 | 36.258 | 10.384 | 1.00 | 19.53 | B |
| ATOM | 4564 | O | SER | B | 47 | −25.577 | 35.290 | 10.875 | 1.00 | 20.16 | B |
| ATOM | 4565 | N | GLY | B | 48 | −26.584 | 36.296 | 9.092 | 1.00 | 19.00 | B |
| ATOM | 4566 | CA | GLY | B | 48 | −26.240 | 35.130 | 8.299 | 1.00 | 18.74 | B |
| ATOM | 4567 | C | GLY | B | 48 | −25.132 | 35.455 | 7.371 | 1.00 | 18.48 | B |
| ATOM | 4568 | O | GLY | B | 48 | −24.690 | 36.590 | 7.377 | 1.00 | 18.70 | B |
| ATOM | 4569 | N | ASP | B | 49 | −24.655 | 34.498 | 6.600 | 1.00 | 18.26 | B |
| ATOM | 4570 | CA | ASP | B | 49 | −23.606 | 34.888 | 5.680 | 1.00 | 19.01 | B |
| ATOM | 4571 | CB | ASP | B | 49 | −24.103 | 36.057 | 4.767 | 1.00 | 18.71 | B |
| ATOM | 4572 | CG | ASP | B | 49 | −25.539 | 35.756 | 4.082 | 1.00 | 20.20 | B |
| ATOM | 4573 | OD1 | ASP | B | 49 | −26.355 | 36.707 | 3.940 | 1.00 | 18.58 | B |
| ATOM | 4574 | OD2 | ASP | B | 49 | −25.788 | 34.576 | 3.684 | 1.00 | 19.58 | B |
| ATOM | 4575 | C | ASP | B | 49 | −22.333 | 35.367 | 6.378 | 1.00 | 19.07 | B |
| ATOM | 4576 | O | ASP | B | 49 | −21.718 | 36.370 | 5.976 | 1.00 | 19.42 | B |
| ATOM | 4577 | N | GLN | B | 50 | −21.905 | 34.709 | 7.439 | 1.00 | 19.68 | B |
| ATOM | 4578 | CA | GLN | B | 50 | −20.677 | 35.216 | 8.019 | 1.00 | 19.50 | B |
| ATOM | 4579 | CB | GLN | B | 50 | −20.562 | 34.762 | 9.484 | 1.00 | 19.74 | B |
| ATOM | 4580 | CG | GLN | B | 50 | −21.590 | 35.367 | 10.404 | 1.00 | 17.55 | B |
| ATOM | 4581 | CD | GLN | B | 50 | −21.569 | 36.828 | 10.271 | 1.00 | 17.29 | B |
| ATOM | 4582 | OE1 | GLN | B | 50 | −20.565 | 37.410 | 10.500 | 1.00 | 13.85 | B |
| ATOM | 4583 | NE2 | GLN | B | 50 | −22.692 | 37.430 | 9.823 | 1.00 | 18.47 | B |
| ATOM | 4584 | C | GLN | B | 50 | −19.583 | 34.616 | 7.221 | 1.00 | 18.75 | B |
| ATOM | 4585 | O | GLN | B | 50 | −19.705 | 33.505 | 6.827 | 1.00 | 19.54 | B |
| ATOM | 4586 | N | ASP | B | 51 | −18.521 | 35.362 | 7.002 | 1.00 | 18.09 | B |
| ATOM | 4587 | CA | ASP | B | 51 | −17.352 | 34.877 | 6.277 | 1.00 | 17.00 | B |
| ATOM | 4588 | CB | ASP | B | 51 | −17.431 | 35.086 | 4.713 | 1.00 | 16.47 | B |
| ATOM | 4589 | CG | ASP | B | 51 | −16.251 | 34.308 | 3.891 | 1.00 | 17.52 | B |
| ATOM | 4590 | OD1 | ASP | B | 51 | −15.953 | 34.766 | 2.762 | 1.00 | 19.94 | B |

TABLE 1-continued

| | | | | | | | | | |
|---|---|---|---|---|---|---|---|---|---|
| ATOM | 4591 | OD2 | ASP | B | 51 | −15.611 | 33.310 | 4.328 | 1.00 | 11.67 | B |
| ATOM | 4592 | C | ASP | B | 51 | −16.191 | 35.686 | 6.886 | 1.00 | 14.22 | B |
| ATOM | 4593 | O | ASP | B | 51 | −15.622 | 36.524 | 6.290 | 1.00 | 12.63 | B |
| ATOM | 4594 | N | ASN | B | 52 | −15.885 | 35.376 | 8.105 | 1.00 | 14.01 | B |
| ATOM | 4595 | CA | ASN | B | 52 | −14.776 | 35.989 | 8.779 | 1.00 | 13.16 | B |
| ATOM | 4596 | CB | ASN | B | 52 | −15.184 | 36.357 | 10.181 | 1.00 | 15.96 | B |
| ATOM | 4597 | CG | ASN | B | 52 | −16.559 | 37.056 | 10.227 | 1.00 | 17.25 | B |
| ATOM | 4598 | OD1 | ASN | B | 52 | −16.708 | 38.179 | 9.696 | 1.00 | 15.67 | B |
| ATOM | 4599 | ND2 | ASN | B | 52 | −17.559 | 36.377 | 10.839 | 1.00 | 14.07 | B |
| ATOM | 4600 | C | ASN | B | 52 | −13.505 | 35.144 | 8.820 | 1.00 | 11.33 | B |
| ATOM | 4601 | O | ASN | B | 52 | −13.498 | 33.958 | 9.163 | 1.00 | 6.00 | B |
| ATOM | 4602 | N | TRP | B | 53 | −12.422 | 35.858 | 8.453 | 1.00 | 12.31 | B |
| ATOM | 4603 | CA | TRP | B | 53 | −11.115 | 35.307 | 8.383 | 1.00 | 13.75 | B |
| ATOM | 4604 | CB | TRP | B | 53 | −10.605 | 35.436 | 6.984 | 1.00 | 15.48 | B |
| ATOM | 4605 | CG | TRP | B | 53 | −11.375 | 34.483 | 5.967 | 1.00 | 16.61 | B |
| ATOM | 4606 | CD2 | TRP | B | 53 | −10.941 | 33.238 | 5.407 | 1.00 | 17.51 | B |
| ATOM | 4607 | CE2 | TRP | B | 53 | −11.950 | 32.821 | 4.541 | 1.00 | 18.24 | B |
| ATOM | 4608 | CE3 | TRP | B | 53 | −9.803 | 32.439 | 5.548 | 1.00 | 17.60 | B |
| ATOM | 4609 | CD1 | TRP | B | 53 | −12.586 | 34.720 | 5.442 | 1.00 | 15.74 | B |
| ATOM | 4610 | NE1 | TRP | B | 53 | −12.939 | 33.767 | 4.616 | 1.00 | 17.15 | B |
| ATOM | 4611 | CZ2 | TRP | B | 53 | −11.859 | 31.568 | 3.757 | 1.00 | 19.10 | B |
| ATOM | 4612 | CZ3 | TRP | B | 53 | −9.709 | 31.233 | 4.808 | 1.00 | 17.85 | B |
| ATOM | 4613 | CH2 | TRP | B | 53 | −10.720 | 30.808 | 3.928 | 1.00 | 18.71 | B |
| ATOM | 4614 | C | TRP | B | 53 | −10.102 | 35.798 | 9.305 | 1.00 | 14.19 | B |
| ATOM | 4615 | O | TRP | B | 53 | −10.005 | 36.976 | 9.525 | 1.00 | 13.72 | B |
| ATOM | 4616 | N | LEU | B | 54 | −9.321 | 34.834 | 9.801 | 1.00 | 15.00 | B |
| ATOM | 4617 | CA | LEU | B | 54 | −8.234 | 35.066 | 10.714 | 1.00 | 15.33 | B |
| ATOM | 4618 | CB | LEU | B | 54 | −8.464 | 34.455 | 12.121 | 1.00 | 15.24 | B |
| ATOM | 4619 | CG | LEU | B | 54 | −7.284 | 34.542 | 13.117 | 1.00 | 14.41 | B |
| ATOM | 4620 | CD1 | LEU | B | 54 | −6.989 | 35.953 | 13.347 | 1.00 | 14.23 | B |
| ATOM | 4621 | CD2 | LEU | B | 54 | −7.536 | 33.851 | 14.410 | 1.00 | 12.43 | B |
| ATOM | 4622 | C | LEU | B | 54 | −7.084 | 34.406 | 10.121 | 1.00 | 14.97 | B |
| ATOM | 4623 | O | LEU | B | 54 | −7.127 | 33.217 | 9.946 | 1.00 | 15.04 | B |
| ATOM | 4624 | N | ARG | B | 55 | −6.056 | 35.187 | 9.788 | 1.00 | 15.73 | B |
| ATOM | 4625 | CA | ARG | B | 55 | −4.795 | 34.654 | 9.279 | 1.00 | 15.37 | B |
| ATOM | 4626 | CB | ARG | B | 55 | −4.385 | 35.337 | 8.016 | 1.00 | 18.12 | B |
| ATOM | 4627 | CG | ARG | B | 55 | −3.176 | 34.572 | 7.368 | 1.00 | 20.15 | B |
| ATOM | 4628 | CD | ARG | B | 55 | −2.864 | 34.916 | 5.942 | 1.00 | 18.62 | B |
| ATOM | 4629 | NE | ARG | B | 55 | −1.799 | 35.932 | 5.752 | 1.00 | 20.30 | B |
| ATOM | 4630 | CZ | ARG | B | 55 | −1.724 | 37.078 | 6.401 | 1.00 | 19.77 | B |
| ATOM | 4631 | NH1 | ARG | B | 55 | −2.662 | 37.366 | 7.320 | 1.00 | 21.19 | B |
| ATOM | 4632 | NH2 | ARG | B | 55 | −0.756 | 37.933 | 6.105 | 1.00 | 18.44 | B |
| ATOM | 4633 | C | ARG | B | 55 | −3.635 | 34.878 | 10.257 | 1.00 | 14.55 | B |
| ATOM | 4634 | O | ARG | B | 55 | −3.488 | 35.913 | 10.841 | 1.00 | 12.29 | B |
| ATOM | 4635 | N | THR | B | 56 | −2.830 | 33.862 | 10.421 | 1.00 | 14.43 | B |
| ATOM | 4636 | CA | THR | B | 56 | −1.681 | 33.952 | 11.239 | 1.00 | 14.33 | B |
| ATOM | 4637 | CB | THR | B | 56 | −0.997 | 32.591 | 11.473 | 1.00 | 14.48 | B |
| ATOM | 4638 | OG1 | THR | B | 56 | −0.320 | 32.200 | 10.263 | 1.00 | 12.56 | B |
| ATOM | 4639 | CG2 | THR | B | 56 | −2.001 | 31.534 | 11.999 | 1.00 | 11.67 | B |
| ATOM | 4640 | C | THR | B | 56 | −0.691 | 34.711 | 10.379 | 1.00 | 16.02 | B |
| ATOM | 4641 | O | THR | B | 56 | −0.927 | 34.995 | 9.208 | 1.00 | 15.27 | B |
| ATOM | 4642 | N | ASN | B | 57 | 0.460 | 35.004 | 10.958 | 1.00 | 17.53 | B |
| ATOM | 4643 | CA | ASN | B | 57 | 1.529 | 35.615 | 10.154 | 1.00 | 19.02 | B |
| ATOM | 4644 | CB | ASN | B | 57 | 2.458 | 36.356 | 11.006 | 1.00 | 22.56 | B |
| ATOM | 4645 | CG | ASN | B | 57 | 2.351 | 37.822 | 10.755 | 1.00 | 26.43 | B |
| ATOM | 4646 | OD1 | ASN | B | 57 | 1.314 | 38.479 | 11.082 | 1.00 | 28.22 | B |
| ATOM | 4647 | ND2 | ASN | B | 57 | 3.403 | 38.381 | 10.090 | 1.00 | 28.70 | B |
| ATOM | 4648 | C | ASN | B | 57 | 2.381 | 34.636 | 9.392 | 1.00 | 18.52 | B |
| ATOM | 4649 | O | ASN | B | 57 | 2.365 | 33.386 | 9.595 | 1.00 | 18.64 | B |
| ATOM | 4650 | N | TRP | B | 58 | 3.135 | 35.206 | 8.488 | 1.00 | 17.65 | B |
| ATOM | 4651 | CA | TRP | B | 58 | 4.086 | 34.437 | 7.673 | 1.00 | 17.38 | B |
| ATOM | 4652 | CB | TRP | B | 58 | 4.990 | 35.471 | 6.953 | 1.00 | 19.06 | B |
| ATOM | 4653 | CG | TRP | B | 58 | 6.139 | 34.942 | 6.083 | 1.00 | 21.25 | B |
| ATOM | 4654 | CD2 | TRP | B | 58 | 6.014 | 34.063 | 5.013 | 1.00 | 21.12 | B |
| ATOM | 4655 | CE2 | TRP | B | 58 | 7.329 | 33.945 | 4.382 | 1.00 | 22.48 | B |
| ATOM | 4656 | CE3 | TRP | B | 58 | 4.953 | 33.364 | 4.506 | 1.00 | 19.05 | B |
| ATOM | 4657 | CD1 | TRP | B | 58 | 7.556 | 35.344 | 6.089 | 1.00 | 24.53 | B |
| ATOM | 4658 | NE1 | TRP | B | 58 | 8.251 | 34.731 | 5.049 | 1.00 | 24.44 | B |
| ATOM | 4659 | CZ2 | TRP | B | 58 | 7.526 | 33.142 | 3.270 | 1.00 | 22.22 | B |
| ATOM | 4660 | CZ3 | TRP | B | 58 | 5.157 | 32.579 | 3.423 | 1.00 | 19.92 | B |
| ATOM | 4661 | CH2 | TRP | B | 58 | 6.431 | 32.467 | 2.802 | 1.00 | 21.55 | B |
| ATOM | 4662 | C | TRP | B | 58 | 4.974 | 33.461 | 8.573 | 1.00 | 17.27 | B |
| ATOM | 4663 | O | TRP | B | 58 | 5.660 | 33.857 | 9.442 | 1.00 | 16.83 | B |
| ATOM | 4664 | N | VAL | B | 59 | 4.939 | 32.179 | 8.345 | 1.00 | 17.46 | B |
| ATOM | 4665 | CA | VAL | B | 59 | 5.734 | 31.210 | 9.094 | 1.00 | 16.60 | B |
| ATOM | 4666 | CB | VAL | B | 59 | 4.829 | 30.204 | 9.754 | 1.00 | 16.65 | B |
| ATOM | 4667 | CG1 | VAL | B | 59 | 5.656 | 29.275 | 10.571 | 1.00 | 14.38 | B |
| ATOM | 4668 | CG2 | VAL | B | 59 | 3.702 | 30.914 | 10.488 | 1.00 | 14.75 | B |
| ATOM | 4669 | C | VAL | B | 59 | 6.696 | 30.403 | 8.129 | 1.00 | 18.16 | B |
| ATOM | 4670 | O | VAL | B | 59 | 6.264 | 29.712 | 7.197 | 1.00 | 19.98 | B |

TABLE 1-continued

| | | | | | | | | | | |
|---|---|---|---|---|---|---|---|---|---|---|
| ATOM | 4671 | N | TYR | B | 60 | 7.989 | 30.499 | 8.391 | 1.00 | 16.76 | B |
| ATOM | 4672 | CA | TYR | B | 60 | 8.995 | 29.865 | 7.665 | 1.00 | 14.85 | B |
| ATOM | 4673 | CB | TYR | B | 60 | 10.356 | 30.272 | 8.166 | 1.00 | 15.39 | B |
| ATOM | 4674 | CG | TYR | B | 60 | 10.754 | 31.692 | 7.811 | 1.00 | 17.24 | B |
| ATOM | 4675 | CD1 | TYR | B | 60 | 10.755 | 32.731 | 8.768 | 1.00 | 18.55 | B |
| ATOM | 4676 | CE1 | TYR | B | 60 | 11.112 | 34.039 | 8.419 | 1.00 | 20.21 | B |
| ATOM | 4677 | CD2 | TYR | B | 60 | 11.112 | 32.022 | 6.518 | 1.00 | 18.32 | B |
| ATOM | 4678 | CE2 | TYR | B | 60 | 11.444 | 33.279 | 6.163 | 1.00 | 19.59 | B |
| ATOM | 4679 | CZ | TYR | B | 60 | 11.445 | 34.275 | 7.064 | 1.00 | 20.63 | B |
| ATOM | 4680 | OH | TYR | B | 60 | 11.677 | 35.570 | 6.568 | 1.00 | 24.76 | B |
| ATOM | 4681 | C | TYR | B | 60 | 8.827 | 28.412 | 7.843 | 1.00 | 14.53 | B |
| ATOM | 4682 | O | TYR | B | 60 | 8.542 | 27.905 | 8.912 | 1.00 | 12.59 | B |
| ATOM | 4683 | N | ARG | B | 61 | 9.034 | 27.715 | 6.754 | 1.00 | 15.46 | B |
| ATOM | 4684 | CA | ARG | B | 61 | 8.876 | 26.296 | 6.784 | 1.00 | 17.85 | B |
| ATOM | 4685 | CB | ARG | B | 61 | 8.527 | 25.775 | 5.363 | 1.00 | 18.61 | B |
| ATOM | 4686 | CG | ARG | B | 61 | 8.781 | 24.240 | 5.174 | 1.00 | 19.13 | B |
| ATOM | 4687 | CD | ARG | B | 61 | 8.344 | 23.748 | 3.698 | 1.00 | 19.41 | B |
| ATOM | 4688 | NE | ARG | B | 61 | 9.422 | 23.948 | 2.686 | 1.00 | 16.44 | B |
| ATOM | 4689 | CZ | ARG | B | 61 | 10.506 | 23.169 | 2.633 | 1.00 | 15.24 | B |
| ATOM | 4690 | NH1 | ARG | B | 61 | 10.660 | 22.154 | 3.462 | 1.00 | 12.36 | B |
| ATOM | 4691 | NH2 | ARG | B | 61 | 11.495 | 23.481 | 1.838 | 1.00 | 17.78 | B |
| ATOM | 4692 | C | ARG | B | 61 | 10.152 | 25.600 | 7.314 | 1.00 | 18.68 | B |
| ATOM | 4693 | O | ARG | B | 61 | 10.104 | 24.518 | 7.983 | 1.00 | 19.24 | B |
| ATOM | 4694 | N | GLY | B | 62 | 11.287 | 26.242 | 7.016 | 1.00 | 19.55 | B |
| ATOM | 4695 | CA | GLY | B | 62 | 12.587 | 25.641 | 7.371 | 1.00 | 19.81 | B |
| ATOM | 4696 | C | GLY | B | 62 | 12.747 | 24.250 | 6.719 | 1.00 | 20.24 | B |
| ATOM | 4697 | O | GLY | B | 62 | 12.562 | 24.058 | 5.518 | 1.00 | 19.96 | B |
| ATOM | 4698 | N | GLU | B | 63 | 13.050 | 23.268 | 7.516 | 1.00 | 20.38 | B |
| ATOM | 4699 | CA | GLU | B | 63 | 13.229 | 21.908 | 7.053 | 1.00 | 21.08 | B |
| ATOM | 4700 | CB | GLU | B | 63 | 14.338 | 21.370 | 7.949 | 1.00 | 21.50 | B |
| ATOM | 4701 | CG | GLU | B | 63 | 14.687 | 19.900 | 7.827 | 1.00 | 24.81 | B |
| ATOM | 4702 | CD | GLU | B | 63 | 15.301 | 19.717 | 6.429 | 1.00 | 28.56 | B |
| ATOM | 4703 | OE1 | GLU | B | 63 | 15.567 | 18.508 | 5.970 | 1.00 | 30.21 | B |
| ATOM | 4704 | OE2 | GLU | B | 63 | 15.484 | 20.852 | 5.783 | 1.00 | 30.22 | B |
| ATOM | 4705 | C | GLU | B | 63 | 11.899 | 21.040 | 7.172 | 1.00 | 21.62 | B |
| ATOM | 4706 | O | GLU | B | 63 | 11.862 | 19.863 | 6.838 | 1.00 | 22.66 | B |
| ATOM | 4707 | N | ALA | B | 64 | 10.792 | 21.566 | 7.697 | 1.00 | 21.48 | B |
| ATOM | 4708 | CA | ALA | B | 64 | 9.566 | 20.758 | 7.833 | 1.00 | 19.83 | B |
| ATOM | 4709 | CB | ALA | B | 64 | 8.508 | 21.563 | 8.664 | 1.00 | 18.69 | B |
| ATOM | 4710 | C | ALA | B | 64 | 8.912 | 20.275 | 6.512 | 1.00 | 18.95 | B |
| ATOM | 4711 | O | ALA | B | 64 | 8.801 | 21.039 | 5.515 | 1.00 | 19.15 | B |
| ATOM | 4712 | N | GLU | B | 65 | 8.482 | 18.995 | 6.539 | 1.00 | 18.69 | B |
| ATOM | 4713 | CA | GLU | B | 65 | 7.736 | 18.374 | 5.403 | 1.00 | 18.88 | B |
| ATOM | 4714 | CB | GLU | B | 65 | 8.111 | 16.885 | 5.082 | 1.00 | 18.68 | B |
| ATOM | 4715 | CG | GLU | B | 65 | 9.572 | 16.555 | 4.836 | 1.00 | 23.45 | B |
| ATOM | 4716 | CD | GLU | B | 65 | 10.200 | 17.093 | 3.497 | 1.00 | 25.51 | B |
| ATOM | 4717 | OE1 | GLU | B | 65 | 9.820 | 16.545 | 2.337 | 1.00 | 26.33 | B |
| ATOM | 4718 | OE2 | GLU | B | 65 | 11.039 | 18.104 | 3.630 | 1.00 | 27.68 | B |
| ATOM | 4719 | C | GLU | B | 65 | 6.283 | 18.397 | 5.785 | 1.00 | 17.56 | B |
| ATOM | 4720 | O | GLU | B | 65 | 5.441 | 18.887 | 5.011 | 1.00 | 17.97 | B |
| ATOM | 4721 | N | ARG | B | 66 | 6.021 | 17.801 | 6.944 | 1.00 | 16.42 | B |
| ATOM | 4722 | CA | ARG | B | 66 | 4.692 | 17.738 | 7.499 | 1.00 | 17.04 | B |
| ATOM | 4723 | CB | ARG | B | 66 | 4.324 | 16.314 | 7.844 | 1.00 | 15.87 | B |
| ATOM | 4724 | CG | ARG | B | 66 | 2.870 | 16.121 | 8.110 | 1.00 | 18.09 | B |
| ATOM | 4725 | CD | ARG | B | 66 | 2.276 | 15.034 | 7.128 | 1.00 | 19.99 | B |
| ATOM | 4726 | NE | ARG | B | 66 | 0.826 | 14.756 | 7.299 | 1.00 | 23.29 | B |
| ATOM | 4727 | CZ | ARG | B | 66 | −0.104 | 14.854 | 6.337 | 1.00 | 24.27 | B |
| ATOM | 4728 | NH1 | ARG | B | 66 | 0.255 | 15.216 | 5.108 | 1.00 | 24.78 | B |
| ATOM | 4729 | NH2 | ARG | B | 66 | −1.422 | 14.591 | 6.594 | 1.00 | 26.23 | B |
| ATOM | 4730 | C | ARG | B | 66 | 4.646 | 18.607 | 8.815 | 1.00 | 17.98 | B |
| ATOM | 4731 | O | ARG | B | 66 | 5.605 | 18.553 | 9.625 | 1.00 | 17.40 | B |
| ATOM | 4732 | N | ASN | B | 67 | 3.601 | 19.416 | 9.017 | 1.00 | 17.67 | B |
| ATOM | 4733 | CA | ASN | B | 67 | 3.554 | 20.122 | 10.275 | 1.00 | 19.03 | B |
| ATOM | 4734 | CB | ASN | B | 67 | 3.591 | 21.604 | 10.118 | 1.00 | 21.52 | B |
| ATOM | 4735 | CG | ASN | B | 67 | 2.609 | 22.029 | 9.077 | 1.00 | 25.37 | B |
| ATOM | 4736 | OD1 | ASN | B | 67 | 2.527 | 21.293 | 8.015 | 1.00 | 30.51 | B |
| ATOM | 4737 | ND2 | ASN | B | 67 | 1.903 | 23.177 | 9.258 | 1.00 | 20.88 | B |
| ATOM | 4738 | C | ASN | B | 67 | 2.258 | 19.729 | 10.893 | 1.00 | 19.15 | B |
| ATOM | 4739 | O | ASN | B | 67 | 1.356 | 19.456 | 10.213 | 1.00 | 18.38 | B |
| ATOM | 4740 | N | ASN | B | 68 | 2.234 | 19.636 | 12.220 | 1.00 | 18.54 | B |
| ATOM | 4741 | CA | ASN | B | 68 | 1.090 | 19.283 | 12.984 | 1.00 | 17.80 | B |
| ATOM | 4742 | CB | ASN | B | 68 | 1.578 | 18.262 | 14.045 | 1.00 | 19.39 | B |
| ATOM | 4743 | CG | ASN | B | 68 | 1.992 | 16.858 | 13.384 | 1.00 | 21.86 | B |
| ATOM | 4744 | OD1 | ASN | B | 68 | 1.161 | 15.885 | 13.214 | 1.00 | 19.99 | B |
| ATOM | 4745 | ND2 | ASN | B | 68 | 3.265 | 16.768 | 12.947 | 1.00 | 22.31 | B |
| ATOM | 4746 | C | ASN | B | 68 | 0.583 | 20.650 | 13.618 | 1.00 | 18.31 | B |
| ATOM | 4747 | O | ASN | B | 68 | 1.373 | 21.613 | 13.916 | 1.00 | 16.58 | B |
| ATOM | 4748 | N | PHE | B | 69 | −0.731 | 20.798 | 13.695 | 1.00 | 18.18 | B |
| ATOM | 4749 | CA | PHE | B | 69 | −1.242 | 21.928 | 14.439 | 1.00 | 17.82 | B |
| ATOM | 4750 | CB | PHE | B | 69 | −1.689 | 23.119 | 13.641 | 1.00 | 19.88 | B |

TABLE 1-continued

| | | | | | | | | | | |
|---|---|---|---|---|---|---|---|---|---|---|
| ATOM | 4751 | CG | PHE | B | 69 | −2.050 | 22.820 | 12.318 | 1.00 | 21.14 | B |
| ATOM | 4752 | CD1 | PHE | B | 69 | −2.999 | 21.825 | 12.064 | 1.00 | 22.59 | B |
| ATOM | 4753 | CD2 | PHE | B | 69 | −1.429 | 23.513 | 11.309 | 1.00 | 19.84 | B |
| ATOM | 4754 | CE1 | PHE | B | 69 | −3.322 | 21.515 | 10.708 | 1.00 | 25.59 | B |
| ATOM | 4755 | CE2 | PHE | B | 69 | −1.698 | 23.244 | 10.000 | 1.00 | 21.61 | B |
| ATOM | 4756 | CZ | PHE | B | 69 | −2.623 | 22.262 | 9.658 | 1.00 | 23.46 | B |
| ATOM | 4757 | C | PHE | B | 69 | −2.360 | 21.578 | 15.410 | 1.00 | 18.17 | B |
| ATOM | 4758 | O | PHE | B | 69 | −3.344 | 20.870 | 15.092 | 1.00 | 17.32 | B |
| ATOM | 4759 | N | GLU | B | 70 | −2.092 | 22.079 | 16.641 | 1.00 | 18.13 | B |
| ATOM | 4760 | CA | GLU | B | 70 | −2.901 | 21.876 | 17.788 | 1.00 | 16.07 | B |
| ATOM | 4761 | CB | GLU | B | 70 | −1.993 | 21.505 | 18.927 | 1.00 | 17.62 | B |
| ATOM | 4762 | CG | GLU | B | 70 | −2.743 | 20.687 | 19.970 | 1.00 | 17.75 | B |
| ATOM | 4763 | CD | GLU | B | 70 | −2.022 | 20.710 | 21.327 | 1.00 | 16.94 | B |
| ATOM | 4764 | OE1 | GLU | B | 70 | −1.969 | 19.707 | 22.062 | 1.00 | 16.49 | B |
| ATOM | 4765 | OE2 | GLU | B | 70 | −1.516 | 21.759 | 21.616 | 1.00 | 16.63 | B |
| ATOM | 4766 | C | GLU | B | 70 | −3.689 | 23.112 | 18.020 | 1.00 | 15.01 | B |
| ATOM | 4767 | O | GLU | B | 70 | −3.129 | 24.189 | 18.109 | 1.00 | 12.35 | B |
| ATOM | 4768 | N | LEU | B | 71 | −5.010 | 22.912 | 18.041 | 1.00 | 15.98 | B |
| ATOM | 4769 | CA | LEU | B | 71 | −6.052 | 23.954 | 18.253 | 1.00 | 16.76 | B |
| ATOM | 4770 | CB | LEU | B | 71 | −7.022 | 23.998 | 17.087 | 1.00 | 16.88 | B |
| ATOM | 4771 | CG | LEU | B | 71 | −6.443 | 24.472 | 15.770 | 1.00 | 17.52 | B |
| ATOM | 4772 | CD1 | LEU | B | 71 | −7.444 | 24.296 | 14.702 | 1.00 | 19.23 | B |
| ATOM | 4773 | CD2 | LEU | B | 71 | −6.083 | 25.922 | 15.820 | 1.00 | 15.65 | B |
| ATOM | 4774 | C | LEU | B | 71 | −6.851 | 23.654 | 19.542 | 1.00 | 16.95 | B |
| ATOM | 4775 | O | LEU | B | 71 | −7.248 | 22.542 | 19.764 | 1.00 | 17.98 | B |
| ATOM | 4776 | N | ASN | B | 72 | −6.990 | 24.678 | 20.402 | 1.00 | 16.90 | B |
| ATOM | 4777 | CA | ASN | B | 72 | −7.726 | 24.676 | 21.663 | 1.00 | 16.38 | B |
| ATOM | 4778 | CB | ASN | B | 72 | −6.750 | 24.973 | 22.819 | 1.00 | 17.11 | B |
| ATOM | 4779 | CG | ASN | B | 72 | −6.159 | 23.749 | 23.387 | 1.00 | 17.46 | B |
| ATOM | 4780 | OD1 | ASN | B | 72 | −5.132 | 23.742 | 24.131 | 1.00 | 16.01 | B |
| ATOM | 4781 | ND2 | ASN | B | 72 | −6.806 | 22.636 | 23.034 | 1.00 | 21.17 | B |
| ATOM | 4782 | C | ASN | B | 72 | −8.807 | 25.789 | 21.529 | 1.00 | 15.99 | B |
| ATOM | 4783 | O | ASN | B | 72 | −8.500 | 27.019 | 21.332 | 1.00 | 15.09 | B |
| ATOM | 4784 | N | PHE | B | 73 | −10.079 | 25.343 | 21.635 | 1.00 | 15.40 | B |
| ATOM | 4785 | CA | PHE | B | 73 | −11.181 | 26.258 | 21.450 | 1.00 | 15.38 | B |
| ATOM | 4786 | CB | PHE | B | 73 | −11.526 | 26.368 | 19.932 | 1.00 | 17.03 | B |
| ATOM | 4787 | CG | PHE | B | 73 | −11.876 | 25.033 | 19.296 | 1.00 | 18.18 | B |
| ATOM | 4788 | CD1 | PHE | B | 73 | −13.193 | 24.625 | 19.204 | 1.00 | 18.81 | B |
| ATOM | 4789 | CD2 | PHE | B | 73 | −10.896 | 24.091 | 18.962 | 1.00 | 17.52 | B |
| ATOM | 4790 | CE1 | PHE | B | 73 | −13.497 | 23.313 | 18.817 | 1.00 | 18.20 | B |
| ATOM | 4791 | CE2 | PHE | B | 73 | −11.221 | 22.801 | 18.588 | 1.00 | 17.47 | B |
| ATOM | 4792 | CZ | PHE | B | 73 | −12.501 | 22.417 | 18.517 | 1.00 | 17.20 | B |
| ATOM | 4793 | C | PHE | B | 73 | −12.395 | 25.838 | 22.165 | 1.00 | 14.62 | B |
| ATOM | 4794 | O | PHE | B | 73 | −12.471 | 24.710 | 22.645 | 1.00 | 13.80 | B |
| ATOM | 4795 | N | THR | B | 74 | −13.366 | 26.741 | 22.189 | 1.00 | 13.55 | B |
| ATOM | 4796 | CA | THR | B | 74 | −14.603 | 26.430 | 22.832 | 1.00 | 14.60 | B |
| ATOM | 4797 | CB | THR | B | 74 | −14.870 | 27.159 | 24.170 | 1.00 | 13.98 | B |
| ATOM | 4798 | OG1 | THR | B | 74 | −15.063 | 28.564 | 23.937 | 1.00 | 11.90 | B |
| ATOM | 4799 | CG2 | THR | B | 74 | −13.790 | 26.992 | 25.017 | 1.00 | 13.65 | B |
| ATOM | 4800 | C | THR | B | 74 | −15.613 | 26.944 | 21.884 | 1.00 | 13.40 | B |
| ATOM | 4801 | O | THR | B | 74 | −15.294 | 27.818 | 21.084 | 1.00 | 12.90 | B |
| ATOM | 4802 | N | VAL | B | 75 | −16.832 | 26.443 | 22.104 | 1.00 | 13.81 | B |
| ATOM | 4803 | CA | VAL | B | 75 | −17.943 | 26.721 | 21.243 | 1.00 | 15.93 | B |
| ATOM | 4804 | CB | VAL | B | 75 | −18.056 | 25.607 | 20.120 | 1.00 | 16.07 | B |
| ATOM | 4805 | CG1 | VAL | B | 75 | −19.101 | 25.979 | 19.057 | 1.00 | 16.19 | B |
| ATOM | 4806 | CG2 | VAL | B | 75 | −16.749 | 25.468 | 19.471 | 1.00 | 15.94 | B |
| ATOM | 4807 | C | VAL | B | 75 | −19.262 | 26.842 | 21.986 | 1.00 | 14.37 | B |
| ATOM | 4808 | O | VAL | B | 75 | −19.764 | 25.908 | 22.577 | 1.00 | 13.41 | B |
| ATOM | 4809 | N | ARG | B | 76 | −19.799 | 28.039 | 21.934 | 1.00 | 14.06 | B |
| ATOM | 4810 | CA | ARG | B | 76 | −20.997 | 28.233 | 22.605 | 1.00 | 15.21 | B |
| ATOM | 4811 | CB | ARG | B | 76 | −21.305 | 29.692 | 22.755 | 1.00 | 14.50 | B |
| ATOM | 4812 | CG | ARG | B | 76 | −22.594 | 29.933 | 23.498 | 1.00 | 13.14 | B |
| ATOM | 4813 | CD | ARG | B | 76 | −22.541 | 31.245 | 24.105 | 1.00 | 13.87 | B |
| ATOM | 4814 | NE | ARG | B | 76 | −23.862 | 31.587 | 24.506 | 1.00 | 16.23 | B |
| ATOM | 4815 | CZ | ARG | B | 76 | −24.359 | 32.822 | 24.703 | 1.00 | 17.19 | B |
| ATOM | 4816 | NH1 | ARG | B | 76 | −23.609 | 33.955 | 24.572 | 1.00 | 17.54 | B |
| ATOM | 4817 | NH2 | ARG | B | 76 | −25.667 | 32.899 | 24.908 | 1.00 | 14.81 | B |
| ATOM | 4818 | C | ARG | B | 76 | −22.110 | 27.544 | 21.858 | 1.00 | 15.93 | B |
| ATOM | 4819 | O | ARG | B | 76 | −22.258 | 27.741 | 20.665 | 1.00 | 17.51 | B |
| ATOM | 4820 | N | ASP | B | 77 | −22.849 | 26.714 | 22.590 | 1.00 | 16.16 | B |
| ATOM | 4821 | CA | ASP | B | 77 | −24.000 | 25.962 | 22.152 | 1.00 | 16.50 | B |
| ATOM | 4822 | CB | ASP | B | 77 | −24.627 | 25.297 | 23.388 | 1.00 | 17.55 | B |
| ATOM | 4823 | CG | ASP | B | 77 | −25.975 | 24.754 | 23.111 | 1.00 | 19.97 | B |
| ATOM | 4824 | OD1 | ASP | B | 77 | −26.355 | 24.883 | 21.899 | 1.00 | 24.40 | B |
| ATOM | 4825 | OD2 | ASP | B | 77 | −26.660 | 24.251 | 24.030 | 1.00 | 17.39 | B |
| ATOM | 4826 | C | ASP | B | 77 | −24.948 | 26.832 | 21.407 | 1.00 | 14.82 | B |
| ATOM | 4827 | O | ASP | B | 77 | −25.299 | 27.821 | 21.897 | 1.00 | 14.45 | B |
| ATOM | 4828 | N | CYS | B | 78 | −25.356 | 26.466 | 20.203 | 1.00 | 14.62 | B |
| ATOM | 4829 | CA | CYS | B | 78 | −26.276 | 27.368 | 19.451 | 1.00 | 16.17 | B |
| ATOM | 4830 | C | CYS | B | 78 | −27.669 | 27.522 | 20.014 | 1.00 | 15.90 | B |

TABLE 1-continued

| | | | | | | | | | | |
|---|---|---|---|---|---|---|---|---|---|---|
| ATOM | 4831 | O | CYS | B | 78 | −28.354 | 28.483 | 19.726 | 1.00 | 16.87 | B |
| ATOM | 4832 | CB | CYS | B | 78 | −26.436 | 26.962 | 18.018 | 1.00 | 14.89 | B |
| ATOM | 4833 | SG | CYS | B | 78 | −25.153 | 27.504 | 16.883 | 1.00 | 15.70 | B |
| ATOM | 4834 | N | ASN | B | 79 | −28.093 | 26.556 | 20.817 | 1.00 | 16.65 | B |
| ATOM | 4835 | CA | ASN | B | 79 | −29.386 | 26.696 | 21.435 | 1.00 | 16.39 | B |
| ATOM | 4836 | CB | ASN | B | 79 | −29.884 | 25.328 | 21.789 | 1.00 | 16.64 | B |
| ATOM | 4837 | CG | ASN | B | 79 | −30.230 | 24.501 | 20.580 | 1.00 | 16.72 | B |
| ATOM | 4838 | OD1 | ASN | B | 79 | −30.277 | 23.238 | 20.621 | 1.00 | 16.35 | B |
| ATOM | 4839 | ND2 | ASN | B | 79 | −30.487 | 25.180 | 19.494 | 1.00 | 16.89 | B |
| ATOM | 4840 | C | ASN | B | 79 | −29.397 | 27.622 | 22.693 | 1.00 | 16.39 | B |
| ATOM | 4841 | O | ASN | B | 79 | −30.369 | 27.793 | 23.342 | 1.00 | 16.12 | B |
| ATOM | 4842 | N | SER | B | 80 | −28.239 | 28.154 | 23.060 | 1.00 | 16.95 | B |
| ATOM | 4843 | CA | SER | B | 80 | −28.138 | 29.013 | 24.199 | 1.00 | 16.32 | B |
| ATOM | 4844 | CB | SER | B | 80 | −26.732 | 28.934 | 24.796 | 1.00 | 17.02 | B |
| ATOM | 4845 | OG | SER | B | 80 | −25.827 | 29.531 | 23.911 | 1.00 | 18.22 | B |
| ATOM | 4846 | C | SER | B | 80 | −28.429 | 30.433 | 23.735 | 1.00 | 15.84 | B |
| ATOM | 4847 | O | SER | B | 80 | −28.095 | 31.324 | 24.419 | 1.00 | 15.06 | B |
| ATOM | 4848 | N | PHE | B | 81 | −28.963 | 30.656 | 22.551 | 1.00 | 16.04 | B |
| ATOM | 4849 | CA | PHE | B | 81 | −29.294 | 32.014 | 22.202 | 1.00 | 17.04 | B |
| ATOM | 4850 | CB | PHE | B | 81 | −28.664 | 32.391 | 20.870 | 1.00 | 16.65 | B |
| ATOM | 4851 | CG | PHE | B | 81 | −27.161 | 32.440 | 20.901 | 1.00 | 17.19 | B |
| ATOM | 4852 | CD1 | PHE | B | 81 | −26.412 | 31.295 | 20.579 | 1.00 | 17.94 | B |
| ATOM | 4853 | CD2 | PHE | B | 81 | −26.464 | 33.590 | 21.342 | 1.00 | 15.89 | B |
| ATOM | 4854 | CE1 | PHE | B | 81 | −25.005 | 31.282 | 20.708 | 1.00 | 18.01 | B |
| ATOM | 4855 | CE2 | PHE | B | 81 | −25.078 | 33.575 | 21.458 | 1.00 | 15.67 | B |
| ATOM | 4856 | CZ | PHE | B | 81 | −24.314 | 32.444 | 21.155 | 1.00 | 15.32 | B |
| ATOM | 4857 | C | PHE | B | 81 | −30.862 | 32.032 | 22.218 | 1.00 | 18.38 | B |
| ATOM | 4858 | O | PHE | B | 81 | −31.462 | 31.499 | 21.307 | 1.00 | 18.60 | B |
| ATOM | 4859 | N | PRO | B | 82 | −31.537 | 32.685 | 23.239 | 1.00 | 18.08 | B |
| ATOM | 4860 | CD | PRO | B | 82 | −31.017 | 33.858 | 23.951 | 1.00 | 18.52 | B |
| ATOM | 4861 | CA | PRO | B | 82 | −33.014 | 32.696 | 23.349 | 1.00 | 17.37 | B |
| ATOM | 4862 | CB | PRO | B | 82 | −33.327 | 33.728 | 24.453 | 1.00 | 18.46 | B |
| ATOM | 4863 | CG | PRO | B | 82 | −32.029 | 33.971 | 25.128 | 1.00 | 18.61 | B |
| ATOM | 4864 | C | PRO | B | 82 | −33.786 | 32.998 | 22.118 | 1.00 | 18.85 | B |
| ATOM | 4865 | O | PRO | B | 82 | −33.535 | 34.053 | 21.440 | 1.00 | 16.11 | B |
| ATOM | 4866 | N | GLY | B | 83 | −34.765 | 32.078 | 21.857 | 1.00 | 19.90 | B |
| ATOM | 4867 | CA | GLY | B | 83 | −35.667 | 32.195 | 20.695 | 1.00 | 22.16 | B |
| ATOM | 4868 | C | GLY | B | 83 | −34.778 | 31.487 | 19.685 | 1.00 | 22.85 | B |
| ATOM | 4869 | O | GLY | B | 83 | −33.587 | 31.287 | 20.089 | 1.00 | 24.74 | B |
| ATOM | 4870 | N | GLY | B | 84 | −35.153 | 31.085 | 18.453 | 1.00 | 21.78 | B |
| ATOM | 4871 | CA | GLY | B | 84 | −34.072 | 30.345 | 17.732 | 1.00 | 19.79 | B |
| ATOM | 4872 | C | GLY | B | 84 | −32.874 | 31.159 | 17.203 | 1.00 | 19.52 | B |
| ATOM | 4873 | O | GLY | B | 84 | −32.898 | 32.381 | 17.284 | 1.00 | 19.55 | B |
| ATOM | 4874 | N | ALA | B | 85 | −31.785 | 30.558 | 16.694 | 1.00 | 19.18 | B |
| ATOM | 4875 | CA | ALA | B | 85 | −30.631 | 31.365 | 16.108 | 1.00 | 17.34 | B |
| ATOM | 4876 | CB | ALA | B | 85 | −29.401 | 31.425 | 17.029 | 1.00 | 17.97 | B |
| ATOM | 4877 | C | ALA | B | 85 | −30.279 | 30.631 | 14.872 | 1.00 | 16.55 | B |
| ATOM | 4878 | O | ALA | B | 85 | −29.171 | 30.219 | 14.741 | 1.00 | 16.67 | B |
| ATOM | 4879 | N | SER | B | 86 | −31.278 | 30.414 | 14.003 | 1.00 | 15.82 | B |
| ATOM | 4880 | CA | SER | B | 86 | −31.163 | 29.702 | 12.706 | 1.00 | 12.31 | B |
| ATOM | 4881 | CB | SER | B | 86 | −32.308 | 30.119 | 11.787 | 1.00 | 11.37 | B |
| ATOM | 4882 | OG | SER | B | 86 | −32.335 | 31.397 | 11.284 | 1.00 | 7.32 | B |
| ATOM | 4883 | C | SER | B | 86 | −29.835 | 29.776 | 11.981 | 1.00 | 12.90 | B |
| ATOM | 4884 | O | SER | B | 86 | −29.438 | 28.776 | 11.507 | 1.00 | 12.88 | B |
| ATOM | 4885 | N | SER | B | 87 | −29.134 | 30.931 | 11.901 | 1.00 | 14.30 | B |
| ATOM | 4886 | CA | SER | B | 87 | −27.842 | 30.991 | 11.195 | 1.00 | 15.27 | B |
| ATOM | 4887 | CB | SER | B | 87 | −27.647 | 32.298 | 10.466 | 1.00 | 15.62 | B |
| ATOM | 4888 | OG | SER | B | 87 | −27.550 | 33.299 | 11.409 | 1.00 | 17.54 | B |
| ATOM | 4889 | C | SER | B | 87 | −26.571 | 30.646 | 12.033 | 1.00 | 14.59 | B |
| ATOM | 4890 | O | SER | B | 87 | −25.490 | 30.499 | 11.529 | 1.00 | 14.90 | B |
| ATOM | 4891 | N | CYS | B | 88 | −26.780 | 30.328 | 13.266 | 1.00 | 14.58 | B |
| ATOM | 4892 | CA | CYS | B | 88 | −25.708 | 30.047 | 14.093 | 1.00 | 15.79 | B |
| ATOM | 4893 | C | CYS | B | 88 | −25.142 | 28.733 | 13.693 | 1.00 | 15.92 | B |
| ATOM | 4894 | O | CYS | B | 88 | −25.865 | 27.918 | 13.325 | 1.00 | 17.64 | B |
| ATOM | 4895 | CB | CYS | B | 88 | −26.212 | 30.017 | 15.556 | 1.00 | 13.94 | B |
| ATOM | 4896 | SG | CYS | B | 88 | −25.038 | 29.493 | 16.816 | 1.00 | 13.45 | B |
| ATOM | 4897 | N | LYS | B | 89 | −23.845 | 28.517 | 13.825 | 1.00 | 16.51 | B |
| ATOM | 4898 | CA | LYS | B | 89 | −23.206 | 27.244 | 13.493 | 1.00 | 17.72 | B |
| ATOM | 4899 | CB | LYS | B | 89 | −22.214 | 27.448 | 12.295 | 1.00 | 17.56 | B |
| ATOM | 4900 | CG | LYS | B | 89 | −22.956 | 28.048 | 11.093 | 1.00 | 20.56 | B |
| ATOM | 4901 | CD | LYS | B | 89 | −23.853 | 26.936 | 10.430 | 1.00 | 18.27 | B |
| ATOM | 4902 | CE | LYS | B | 89 | −24.268 | 27.379 | 8.992 | 1.00 | 21.22 | B |
| ATOM | 4903 | NZ | LYS | B | 89 | −24.997 | 26.311 | 8.043 | 1.00 | 21.37 | B |
| ATOM | 4904 | C | LYS | B | 89 | −22.379 | 26.786 | 14.650 | 1.00 | 16.60 | B |
| ATOM | 4905 | O | LYS | B | 89 | −21.970 | 27.586 | 15.427 | 1.00 | 16.83 | B |
| ATOM | 4906 | N | GLU | B | 90 | −22.048 | 25.522 | 14.697 | 1.00 | 15.98 | B |
| ATOM | 4907 | CA | GLU | B | 90 | −21.140 | 25.069 | 15.702 | 1.00 | 17.08 | B |
| ATOM | 4908 | CB | GLU | B | 90 | −21.840 | 24.133 | 16.633 | 1.00 | 15.98 | B |
| ATOM | 4909 | CG | GLU | B | 90 | −23.057 | 24.782 | 17.171 | 1.00 | 17.62 | B |
| ATOM | 4910 | CD | GLU | B | 90 | −23.888 | 23.879 | 18.120 | 1.00 | 19.92 | B |

TABLE 1-continued

| | | | | | | | | | |
|---|---|---|---|---|---|---|---|---|---|
| ATOM | 4911 | OE1 | GLU | B | 90 | −24.118 | 22.668 | 17.787 | 1.00 | 19.73 | B |
| ATOM | 4912 | OE2 | GLU | B | 90 | −24.337 | 24.402 | 19.189 | 1.00 | 20.64 | B |
| ATOM | 4913 | C | GLU | B | 90 | −19.844 | 24.451 | 15.135 | 1.00 | 17.10 | B |
| ATOM | 4914 | O | GLU | B | 90 | −19.359 | 23.453 | 15.677 | 1.00 | 19.22 | B |
| ATOM | 4915 | N | THR | B | 91 | −19.301 | 25.000 | 14.046 | 1.00 | 15.57 | B |
| ATOM | 4916 | CA | THR | B | 91 | −18.040 | 24.474 | 13.552 | 1.00 | 14.25 | B |
| ATOM | 4917 | CB | THR | B | 91 | −18.188 | 23.273 | 12.460 | 1.00 | 12.39 | B |
| ATOM | 4918 | OG1 | THR | B | 91 | −18.775 | 23.819 | 11.293 | 1.00 | 12.21 | B |
| ATOM | 4919 | CG2 | THR | B | 91 | −18.952 | 22.060 | 12.984 | 1.00 | 7.39 | B |
| ATOM | 4920 | C | THR | B | 91 | −17.352 | 25.663 | 12.892 | 1.00 | 14.09 | B |
| ATOM | 4921 | O | THR | B | 91 | −17.941 | 26.764 | 12.704 | 1.00 | 13.26 | B |
| ATOM | 4922 | N | PHE | B | 92 | −16.077 | 25.462 | 12.578 | 1.00 | 14.00 | B |
| ATOM | 4923 | CA | PHE | B | 92 | −15.336 | 26.481 | 11.810 | 1.00 | 15.15 | B |
| ATOM | 4924 | CB | PHE | B | 92 | −14.591 | 27.510 | 12.733 | 1.00 | 16.53 | B |
| ATOM | 4925 | CG | PHE | B | 92 | −13.526 | 26.881 | 13.648 | 1.00 | 16.90 | B |
| ATOM | 4926 | CD1 | PHE | B | 92 | −12.217 | 26.895 | 13.332 | 1.00 | 16.23 | B |
| ATOM | 4927 | CD2 | PHE | B | 92 | −13.888 | 26.377 | 14.859 | 1.00 | 18.25 | B |
| ATOM | 4928 | CE1 | PHE | B | 92 | −11.247 | 26.432 | 14.217 | 1.00 | 17.76 | B |
| ATOM | 4929 | CE2 | PHE | B | 92 | −12.950 | 25.888 | 15.797 | 1.00 | 19.08 | B |
| ATOM | 4930 | CZ | PHE | B | 92 | −11.611 | 25.919 | 15.474 | 1.00 | 18.57 | B |
| ATOM | 4931 | C | PHE | B | 92 | −14.312 | 25.766 | 10.937 | 1.00 | 13.55 | B |
| ATOM | 4932 | O | PHE | B | 92 | −13.924 | 24.648 | 11.205 | 1.00 | 12.04 | B |
| ATOM | 4933 | N | ASN | B | 93 | −13.787 | 26.489 | 9.973 | 1.00 | 13.21 | B |
| ATOM | 4934 | CA | ASN | B | 93 | −12.810 | 25.932 | 9.045 | 1.00 | 13.96 | B |
| ATOM | 4935 | CB | ASN | B | 93 | −13.257 | 26.241 | 7.682 | 1.00 | 14.49 | B |
| ATOM | 4936 | CG | ASN | B | 93 | −14.538 | 25.619 | 7.422 | 1.00 | 15.18 | B |
| ATOM | 4937 | OD1 | ASN | B | 93 | −14.701 | 24.426 | 7.747 | 1.00 | 16.48 | B |
| ATOM | 4938 | ND2 | ASN | B | 93 | −15.471 | 26.351 | 6.855 | 1.00 | 13.61 | B |
| ATOM | 4939 | C | ASN | B | 93 | −11.388 | 26.272 | 9.133 | 1.00 | 13.69 | B |
| ATOM | 4940 | O | ASN | B | 93 | −11.046 | 27.383 | 9.510 | 1.00 | 13.40 | B |
| ATOM | 4941 | N | LEU | B | 94 | −10.565 | 25.294 | 8.780 | 1.00 | 14.37 | B |
| ATOM | 4942 | CA | LEU | B | 94 | −9.136 | 25.455 | 8.786 | 1.00 | 15.67 | B |
| ATOM | 4943 | CB | LEU | B | 94 | −8.514 | 24.348 | 9.602 | 1.00 | 14.69 | B |
| ATOM | 4944 | CG | LEU | B | 94 | −6.992 | 24.433 | 9.820 | 1.00 | 15.06 | B |
| ATOM | 4945 | CD1 | LEU | B | 94 | −6.570 | 25.804 | 10.344 | 1.00 | 12.51 | B |
| ATOM | 4946 | CD2 | LEU | B | 94 | −6.574 | 23.224 | 10.713 | 1.00 | 13.48 | B |
| ATOM | 4947 | C | LEU | B | 94 | −8.543 | 25.467 | 7.382 | 1.00 | 16.08 | B |
| ATOM | 4948 | O | LEU | B | 94 | −8.806 | 24.555 | 6.615 | 1.00 | 16.41 | B |
| ATOM | 4949 | N | TYR | B | 95 | −7.748 | 26.500 | 7.065 | 1.00 | 16.73 | B |
| ATOM | 4950 | CA | TYR | B | 95 | −7.039 | 26.650 | 5.787 | 1.00 | 18.07 | B |
| ATOM | 4951 | CB | TYR | B | 95 | −7.606 | 27.767 | 4.942 | 1.00 | 17.89 | B |
| ATOM | 4952 | CG | TYR | B | 95 | −9.007 | 27.502 | 4.435 | 1.00 | 18.90 | B |
| ATOM | 4953 | CD1 | TYR | B | 95 | −10.119 | 27.456 | 5.280 | 1.00 | 18.68 | B |
| ATOM | 4954 | CE1 | TYR | B | 95 | −11.412 | 27.222 | 4.746 | 1.00 | 18.73 | B |
| ATOM | 4955 | CD2 | TYR | B | 95 | −9.245 | 27.320 | 3.054 | 1.00 | 20.07 | B |
| ATOM | 4956 | CE2 | TYR | B | 95 | −10.553 | 27.101 | 2.515 | 1.00 | 18.99 | B |
| ATOM | 4957 | CZ | TYR | B | 95 | −11.598 | 27.043 | 3.356 | 1.00 | 18.31 | B |
| ATOM | 4958 | OH | TYR | B | 95 | −12.833 | 26.746 | 2.859 | 1.00 | 17.65 | B |
| ATOM | 4959 | C | TYR | B | 95 | −5.551 | 26.971 | 5.887 | 1.00 | 17.03 | B |
| ATOM | 4960 | O | TYR | B | 95 | −5.042 | 27.378 | 6.915 | 1.00 | 18.16 | B |
| ATOM | 4961 | N | TYR | B | 96 | −4.845 | 26.779 | 4.791 | 1.00 | 16.05 | B |
| ATOM | 4962 | CA | TYR | B | 96 | −3.456 | 27.156 | 4.755 | 1.00 | 15.76 | B |
| ATOM | 4963 | CB | TYR | B | 96 | −2.585 | 26.093 | 5.284 | 1.00 | 15.67 | B |
| ATOM | 4964 | CG | TYR | B | 96 | −2.291 | 25.091 | 4.283 | 1.00 | 16.34 | B |
| ATOM | 4965 | CD1 | TYR | B | 96 | −1.113 | 25.128 | 3.550 | 1.00 | 17.94 | B |
| ATOM | 4966 | CE1 | TYR | B | 96 | −0.844 | 24.171 | 2.536 | 1.00 | 19.00 | B |
| ATOM | 4967 | CD2 | TYR | B | 96 | −3.191 | 24.119 | 4.013 | 1.00 | 16.93 | B |
| ATOM | 4968 | CE2 | TYR | B | 96 | −2.973 | 23.168 | 3.020 | 1.00 | 18.11 | B |
| ATOM | 4969 | CZ | TYR | B | 96 | −1.812 | 23.187 | 2.294 | 1.00 | 18.96 | B |
| ATOM | 4970 | OH | TYR | B | 96 | −1.558 | 22.195 | 1.393 | 1.00 | 20.65 | B |
| ATOM | 4971 | C | TYR | B | 96 | −3.135 | 27.482 | 3.294 | 1.00 | 14.11 | B |
| ATOM | 4972 | O | TYR | B | 96 | −3.946 | 27.291 | 2.459 | 1.00 | 11.99 | B |
| ATOM | 4973 | N | ALA | B | 97 | −2.009 | 28.107 | 3.071 | 1.00 | 13.70 | B |
| ATOM | 4974 | CA | ALA | B | 97 | −1.503 | 28.486 | 1.781 | 1.00 | 14.91 | B |
| ATOM | 4975 | CB | ALA | B | 97 | −2.051 | 29.855 | 1.278 | 1.00 | 13.86 | B |
| ATOM | 4976 | C | ALA | B | 97 | 0.042 | 28.533 | 1.998 | 1.00 | 16.54 | B |
| ATOM | 4977 | O | ALA | B | 97 | 0.546 | 28.810 | 3.148 | 1.00 | 15.55 | B |
| ATOM | 4978 | N | GLU | B | 98 | 0.762 | 28.171 | 0.916 | 1.00 | 16.47 | B |
| ATOM | 4979 | CA | GLU | B | 98 | 2.209 | 28.122 | 0.885 | 1.00 | 16.24 | B |
| ATOM | 4980 | CB | GLU | B | 98 | 2.689 | 26.818 | 0.259 | 1.00 | 15.85 | B |
| ATOM | 4981 | CG | GLU | B | 98 | 2.781 | 25.688 | 1.217 | 1.00 | 15.93 | B |
| ATOM | 4982 | CD | GLU | B | 98 | 3.312 | 24.448 | 0.617 | 1.00 | 15.89 | B |
| ATOM | 4983 | OE1 | GLU | B | 98 | 2.515 | 23.739 | −0.022 | 1.00 | 17.23 | B |
| ATOM | 4984 | OE2 | GLU | B | 98 | 4.525 | 24.177 | 0.782 | 1.00 | 14.77 | B |
| ATOM | 4985 | C | GLU | B | 98 | 2.671 | 29.232 | 0.012 | 1.00 | 18.17 | B |
| ATOM | 4986 | O | GLU | B | 98 | 1.991 | 29.526 | −0.931 | 1.00 | 18.17 | B |
| ATOM | 4987 | N | SER | B | 99 | 3.733 | 29.953 | 0.360 | 1.00 | 18.45 | B |
| ATOM | 4988 | CA | SER | B | 99 | 4.301 | 30.860 | −0.655 | 1.00 | 18.26 | B |
| ATOM | 4989 | CB | SER | B | 99 | 3.558 | 32.182 | −0.838 | 1.00 | 20.24 | B |
| ATOM | 4990 | OG | SER | B | 99 | 3.593 | 32.873 | 0.391 | 1.00 | 25.26 | B |

TABLE 1-continued

| ATOM | 4991 | C | SER | B | 99 | 5.800 | 31.050 | −0.401 | 1.00 | 17.99 | B |
|---|---|---|---|---|---|---|---|---|---|---|---|
| ATOM | 4992 | O | SER | B | 99 | 6.339 | 30.640 | 0.612 | 1.00 | 16.48 | B |
| ATOM | 4993 | N | ASP | B | 100 | 6.479 | 31.561 | −1.409 | 1.00 | 18.22 | B |
| ATOM | 4994 | CA | ASP | B | 100 | 7.881 | 31.714 | −1.298 | 1.00 | 19.45 | B |
| ATOM | 4995 | CB | ASP | B | 100 | 8.575 | 31.391 | −2.592 | 1.00 | 19.22 | B |
| ATOM | 4996 | CG | ASP | B | 100 | 8.608 | 29.914 | −2.850 | 1.00 | 21.25 | B |
| ATOM | 4997 | OD1 | ASP | B | 100 | 8.845 | 29.050 | −1.896 | 1.00 | 17.83 | B |
| ATOM | 4998 | OD2 | ASP | B | 100 | 8.400 | 29.582 | −4.102 | 1.00 | 24.79 | B |
| ATOM | 4999 | C | ASP | B | 100 | 8.247 | 33.076 | −0.835 | 1.00 | 20.29 | B |
| ATOM | 5000 | O | ASP | B | 100 | 9.386 | 33.219 | −0.369 | 1.00 | 21.38 | B |
| ATOM | 5001 | N | LEU | B | 101 | 7.287 | 34.005 | −0.959 | 1.00 | 20.64 | B |
| ATOM | 5002 | CA | LEU | B | 101 | 7.318 | 35.415 | −0.557 | 1.00 | 20.18 | B |
| ATOM | 5003 | CB | LEU | B | 101 | 6.880 | 36.383 | −1.662 | 1.00 | 20.56 | B |
| ATOM | 5004 | CG | LEU | B | 101 | 7.203 | 36.279 | −3.154 | 1.00 | 21.43 | B |
| ATOM | 5005 | CD1 | LEU | B | 101 | 6.609 | 34.820 | −3.597 | 1.00 | 24.14 | B |
| ATOM | 5006 | CD2 | LEU | B | 101 | 6.292 | 37.385 | −3.971 | 1.00 | 20.67 | B |
| ATOM | 5007 | C | LEU | B | 101 | 6.210 | 35.596 | 0.542 | 1.00 | 21.16 | B |
| ATOM | 5008 | O | LEU | B | 101 | 5.194 | 34.833 | 0.576 | 1.00 | 21.49 | B |
| ATOM | 5009 | N | ASP | B | 102 | 6.456 | 36.607 | 1.399 | 1.00 | 20.45 | B |
| ATOM | 5010 | CA | ASP | B | 102 | 5.623 | 37.105 | 2.440 | 1.00 | 20.12 | B |
| ATOM | 5011 | CB | ASP | B | 102 | 6.453 | 38.001 | 3.339 | 1.00 | 20.39 | B |
| ATOM | 5012 | CG | ASP | B | 102 | 5.755 | 38.269 | 4.626 | 1.00 | 21.26 | B |
| ATOM | 5013 | OD1 | ASP | B | 102 | 4.476 | 38.372 | 4.607 | 1.00 | 19.97 | B |
| ATOM | 5014 | OD2 | ASP | B | 102 | 6.486 | 38.356 | 5.666 | 1.00 | 22.53 | B |
| ATOM | 5015 | C | ASP | B | 102 | 4.514 | 38.030 | 1.824 | 1.00 | 20.29 | B |
| ATOM | 5016 | O | ASP | B | 102 | 4.777 | 39.140 | 1.456 | 1.00 | 20.40 | B |
| ATOM | 5017 | N | TYR | B | 103 | 3.280 | 37.596 | 1.775 | 1.00 | 20.58 | B |
| ATOM | 5018 | CA | TYR | B | 103 | 2.248 | 38.435 | 1.222 | 1.00 | 20.35 | B |
| ATOM | 5019 | CB | TYR | B | 103 | 0.904 | 37.722 | 1.195 | 1.00 | 21.94 | B |
| ATOM | 5020 | CG | TYR | B | 103 | 0.830 | 36.670 | 0.131 | 1.00 | 23.57 | B |
| ATOM | 5021 | CD1 | TYR | B | 103 | 1.122 | 36.960 | −1.239 | 1.00 | 24.55 | B |
| ATOM | 5022 | CE1 | TYR | B | 103 | 1.119 | 35.894 | −2.303 | 1.00 | 23.64 | B |
| ATOM | 5023 | CD2 | TYR | B | 103 | 0.495 | 35.356 | 0.477 | 1.00 | 25.26 | B |
| ATOM | 5024 | CE2 | TYR | B | 103 | 0.464 | 34.301 | −0.527 | 1.00 | 24.92 | B |
| ATOM | 5025 | CZ | TYR | B | 103 | 0.804 | 34.572 | −1.911 | 1.00 | 25.39 | B |
| ATOM | 5026 | OH | TYR | B | 103 | 0.938 | 33.437 | −2.826 | 1.00 | 26.04 | B |
| ATOM | 5027 | C | TYR | B | 103 | 2.016 | 39.735 | 1.956 | 1.00 | 19.61 | B |
| ATOM | 5028 | O | TYR | B | 103 | 1.329 | 40.649 | 1.440 | 1.00 | 19.62 | B |
| ATOM | 5029 | N | GLY | B | 104 | 2.599 | 39.889 | 3.128 | 1.00 | 19.20 | B |
| ATOM | 5030 | CA | GLY | B | 104 | 2.266 | 41.112 | 3.885 | 1.00 | 18.21 | B |
| ATOM | 5031 | C | GLY | B | 104 | 0.739 | 41.213 | 4.260 | 1.00 | 18.08 | B |
| ATOM | 5032 | O | GLY | B | 104 | 0.157 | 40.346 | 4.878 | 1.00 | 17.24 | B |
| ATOM | 5033 | N | THR | B | 105 | 0.086 | 42.266 | 3.827 | 1.00 | 18.34 | B |
| ATOM | 5034 | CA | THR | B | 105 | −1.274 | 42.461 | 4.130 | 1.00 | 18.03 | B |
| ATOM | 5035 | CB | THR | B | 105 | −1.417 | 43.864 | 4.378 | 1.00 | 18.87 | B |
| ATOM | 5036 | OG1 | THR | B | 105 | −1.057 | 44.037 | 5.760 | 1.00 | 20.45 | B |
| ATOM | 5037 | CG2 | THR | B | 105 | −2.846 | 44.359 | 4.071 | 1.00 | 20.37 | B |
| ATOM | 5038 | C | THR | B | 105 | −2.340 | 41.936 | 3.198 | 1.00 | 18.41 | B |
| ATOM | 5039 | O | THR | B | 105 | −3.530 | 41.924 | 3.494 | 1.00 | 17.77 | B |
| ATOM | 5040 | N | ASN | B | 106 | −1.850 | 41.411 | 2.084 | 1.00 | 19.83 | B |
| ATOM | 5041 | CA | ASN | B | 106 | −2.591 | 40.752 | 0.989 | 1.00 | 20.60 | B |
| ATOM | 5042 | CB | ASN | B | 106 | −1.677 | 40.408 | −0.153 | 1.00 | 22.84 | B |
| ATOM | 5043 | CG | ASN | B | 106 | −1.291 | 41.599 | −0.828 | 1.00 | 25.27 | B |
| ATOM | 5044 | OD1 | ASN | B | 106 | −0.415 | 41.603 | −1.755 | 1.00 | 29.95 | B |
| ATOM | 5045 | ND2 | ASN | B | 106 | −1.956 | 42.716 | −0.429 | 1.00 | 26.57 | B |
| ATOM | 5046 | C | ASN | B | 106 | −3.186 | 39.519 | 1.308 | 1.00 | 19.37 | B |
| ATOM | 5047 | O | ASN | B | 106 | −2.591 | 38.472 | 1.015 | 1.00 | 20.06 | B |
| ATOM | 5048 | N | PHE | B | 107 | −4.361 | 39.588 | 1.860 | 1.00 | 18.63 | B |
| ATOM | 5049 | CA | PHE | B | 107 | −4.939 | 38.302 | 2.073 | 1.00 | 19.14 | B |
| ATOM | 5050 | CB | PHE | B | 107 | −5.722 | 38.268 | 3.370 | 1.00 | 16.66 | B |
| ATOM | 5051 | CG | PHE | B | 107 | −6.459 | 37.004 | 3.569 | 1.00 | 15.24 | B |
| ATOM | 5052 | CD1 | PHE | B | 107 | −5.789 | 35.850 | 3.878 | 1.00 | 16.36 | B |
| ATOM | 5053 | CD2 | PHE | B | 107 | −7.818 | 36.987 | 3.495 | 1.00 | 14.04 | B |
| ATOM | 5054 | CE1 | PHE | B | 107 | −6.482 | 34.699 | 4.136 | 1.00 | 17.20 | B |
| ATOM | 5055 | CE2 | PHE | B | 107 | −8.498 | 35.901 | 3.732 | 1.00 | 14.67 | B |
| ATOM | 5056 | CZ | PHE | B | 107 | −7.841 | 34.727 | 4.068 | 1.00 | 17.22 | B |
| ATOM | 5057 | C | PHE | B | 107 | −5.812 | 37.931 | 0.827 | 1.00 | 17.52 | B |
| ATOM | 5058 | O | PHE | B | 107 | −6.674 | 38.703 | 0.363 | 1.00 | 18.26 | B |
| ATOM | 5059 | N | GLN | B | 108 | −5.555 | 36.759 | 0.303 | 1.00 | 17.47 | B |
| ATOM | 5060 | CA | GLN | B | 108 | −6.404 | 36.231 | −0.752 | 1.00 | 19.69 | B |
| ATOM | 5061 | CB | GLN | B | 108 | −5.566 | 35.884 | −1.980 | 1.00 | 18.56 | B |
| ATOM | 5062 | CG | GLN | B | 108 | −4.773 | 37.046 | −2.468 | 1.00 | 18.77 | B |
| ATOM | 5063 | CD | GLN | B | 108 | −5.606 | 38.172 | −3.091 | 1.00 | 19.09 | B |
| ATOM | 5064 | OE1 | GLN | B | 108 | −5.160 | 39.296 | −3.150 | 1.00 | 19.82 | B |
| ATOM | 5065 | NE2 | GLN | B | 108 | −6.798 | 37.878 | −3.563 | 1.00 | 18.38 | B |
| ATOM | 5066 | C | GLN | B | 108 | −7.082 | 34.927 | −0.333 | 1.00 | 18.56 | B |
| ATOM | 5067 | O | GLN | B | 108 | −6.378 | 33.930 | −0.421 | 1.00 | 19.40 | B |
| ATOM | 5068 | N | LYS | B | 109 | −8.362 | 34.907 | 0.042 | 1.00 | 17.49 | B |
| ATOM | 5069 | CA | LYS | B | 109 | −8.996 | 33.667 | 0.501 | 1.00 | 16.85 | B |
| ATOM | 5070 | CB | LYS | B | 109 | −10.477 | 34.012 | 0.856 | 1.00 | 19.46 | B |

TABLE 1-continued

| | | | | | | | | | | |
|---|---|---|---|---|---|---|---|---|---|---|
| ATOM | 5071 | CG | LYS | B | 109 | −11.475 | 33.372 | −0.072 | 1.00 | 21.61 | B |
| ATOM | 5072 | CD | LYS | B | 109 | −13.031 | 33.763 | 0.169 | 1.00 | 23.95 | B |
| ATOM | 5073 | CE | LYS | B | 109 | −13.721 | 33.105 | 1.476 | 1.00 | 24.08 | B |
| ATOM | 5074 | NZ | LYS | B | 109 | −15.170 | 33.196 | 1.264 | 1.00 | 21.40 | B |
| ATOM | 5075 | C | LYS | B | 109 | −8.854 | 32.571 | −0.669 | 1.00 | 15.89 | B |
| ATOM | 5076 | O | LYS | B | 109 | −8.617 | 31.299 | −0.494 | 1.00 | 12.35 | B |
| ATOM | 5077 | N | ARG | B | 110 | −8.880 | 33.097 | −1.891 | 1.00 | 14.60 | B |
| ATOM | 5078 | CA | ARG | B | 110 | −8.815 | 32.177 | −2.990 | 1.00 | 15.89 | B |
| ATOM | 5079 | CB | ARG | B | 110 | −9.346 | 32.799 | −4.238 | 1.00 | 16.83 | B |
| ATOM | 5080 | CG | ARG | B | 110 | −10.980 | 32.521 | −4.137 | 1.00 | 21.24 | B |
| ATOM | 5081 | CD | ARG | B | 110 | −11.879 | 33.539 | −3.202 | 1.00 | 21.02 | B |
| ATOM | 5082 | NE | ARG | B | 110 | −13.312 | 33.170 | −3.113 | 1.00 | 23.25 | B |
| ATOM | 5083 | CZ | ARG | B | 110 | −13.784 | 32.069 | −2.476 | 1.00 | 24.79 | B |
| ATOM | 5084 | NH1 | ARG | B | 110 | −12.865 | 31.223 | −1.885 | 1.00 | 25.25 | B |
| ATOM | 5085 | NH2 | ARG | B | 110 | −15.143 | 31.803 | −2.399 | 1.00 | 23.68 | B |
| ATOM | 5086 | C | ARG | B | 110 | −7.557 | 31.368 | −3.194 | 1.00 | 17.11 | B |
| ATOM | 5087 | O | ARG | B | 110 | −7.591 | 30.318 | −3.873 | 1.00 | 16.11 | B |
| ATOM | 5088 | N | LEU | B | 111 | −6.519 | 31.758 | −2.445 | 1.00 | 17.17 | B |
| ATOM | 5089 | CA | LEU | B | 111 | −5.169 | 31.137 | −2.476 | 1.00 | 17.26 | B |
| ATOM | 5090 | CB | LEU | B | 111 | −4.036 | 32.167 | −2.342 | 1.00 | 18.20 | B |
| ATOM | 5091 | CG | LEU | B | 111 | −4.060 | 33.214 | −3.474 | 1.00 | 19.41 | B |
| ATOM | 5092 | CD1 | LEU | B | 111 | −2.899 | 34.138 | −3.310 | 1.00 | 17.58 | B |
| ATOM | 5093 | CD2 | LEU | B | 111 | −3.994 | 32.545 | −4.902 | 1.00 | 17.72 | B |
| ATOM | 5094 | C | LEU | B | 111 | −4.982 | 30.128 | −1.408 | 1.00 | 18.04 | B |
| ATOM | 5095 | O | LEU | B | 111 | −3.982 | 29.404 | −1.374 | 1.00 | 17.35 | B |
| ATOM | 5096 | N | PHE | B | 112 | −5.943 | 30.109 | −0.478 | 1.00 | 17.83 | B |
| ATOM | 5097 | CA | PHE | B | 112 | −5.926 | 29.104 | 0.636 | 1.00 | 16.42 | B |
| ATOM | 5098 | CB | PHE | B | 112 | −6.470 | 29.684 | 1.927 | 1.00 | 17.10 | B |
| ATOM | 5099 | CG | PHE | B | 112 | −5.533 | 30.601 | 2.582 | 1.00 | 16.68 | B |
| ATOM | 5100 | CD1 | PHE | B | 112 | −5.257 | 31.854 | 2.041 | 1.00 | 16.52 | B |
| ATOM | 5101 | CD2 | PHE | B | 112 | −4.898 | 30.170 | 3.763 | 1.00 | 16.97 | B |
| ATOM | 5102 | CE1 | PHE | B | 112 | −4.361 | 32.661 | 2.678 | 1.00 | 16.57 | B |
| ATOM | 5103 | CE2 | PHE | B | 112 | −4.002 | 30.918 | 4.418 | 1.00 | 15.70 | B |
| ATOM | 5104 | CZ | PHE | B | 112 | −3.725 | 32.196 | 3.871 | 1.00 | 17.79 | B |
| ATOM | 5105 | C | PHE | B | 112 | −6.747 | 27.838 | 0.338 | 1.00 | 17.05 | B |
| ATOM | 5106 | O | PHE | B | 112 | −7.789 | 27.846 | −0.320 | 1.00 | 15.97 | B |
| ATOM | 5107 | N | THR | B | 113 | −6.246 | 26.745 | 0.853 | 1.00 | 17.20 | B |
| ATOM | 5108 | CA | THR | B | 113 | −6.832 | 25.447 | 0.690 | 1.00 | 16.84 | B |
| ATOM | 5109 | CB | THR | B | 113 | −5.730 | 24.379 | 0.338 | 1.00 | 17.57 | B |
| ATOM | 5110 | OG1 | THR | B | 113 | −5.171 | 24.614 | −0.933 | 1.00 | 19.95 | B |
| ATOM | 5111 | CG2 | THR | B | 113 | −6.232 | 23.039 | 0.358 | 1.00 | 15.25 | B |
| ATOM | 5112 | C | THR | B | 113 | −7.414 | 25.029 | 2.038 | 1.00 | 17.62 | B |
| ATOM | 5113 | O | THR | B | 113 | −6.805 | 25.140 | 3.131 | 1.00 | 18.46 | B |
| ATOM | 5114 | N | LYS | B | 114 | −8.571 | 24.439 | 1.970 | 1.00 | 17.70 | B |
| ATOM | 5115 | CA | LYS | B | 114 | −9.197 | 24.006 | 3.206 | 1.00 | 17.47 | B |
| ATOM | 5116 | CB | LYS | B | 114 | −10.742 | 23.752 | 3.006 | 1.00 | 16.74 | B |
| ATOM | 5117 | CG | LYS | B | 114 | −11.429 | 23.132 | 4.219 | 1.00 | 16.56 | B |
| ATOM | 5118 | CD | LYS | B | 114 | −12.959 | 23.310 | 4.316 | 1.00 | 16.18 | B |
| ATOM | 5119 | CE | LYS | B | 114 | −13.512 | 22.429 | 5.474 | 1.00 | 15.87 | B |
| ATOM | 5120 | NZ | LYS | B | 114 | −15.013 | 22.221 | 5.628 | 1.00 | 13.84 | B |
| ATOM | 5121 | C | LYS | B | 114 | −8.474 | 22.801 | 3.712 | 1.00 | 16.93 | B |
| ATOM | 5122 | O | LYS | B | 114 | −8.117 | 21.927 | 2.911 | 1.00 | 17.05 | B |
| ATOM | 5123 | N | ILE | B | 115 | −8.176 | 22.786 | 5.013 | 1.00 | 16.93 | B |
| ATOM | 5124 | CA | ILE | B | 115 | −7.564 | 21.598 | 5.584 | 1.00 | 16.66 | B |
| ATOM | 5125 | CB | ILE | B | 115 | −6.564 | 21.876 | 6.713 | 1.00 | 16.31 | B |
| ATOM | 5126 | CG2 | ILE | B | 115 | −6.257 | 20.522 | 7.445 | 1.00 | 13.14 | B |
| ATOM | 5127 | CG1 | ILE | B | 115 | −5.379 | 22.621 | 6.055 | 1.00 | 16.88 | B |
| ATOM | 5128 | CD1 | ILE | B | 115 | −4.255 | 23.104 | 6.829 | 1.00 | 15.62 | B |
| ATOM | 5129 | C | ILE | B | 115 | −8.665 | 20.620 | 6.087 | 1.00 | 17.02 | B |
| ATOM | 5130 | O | ILE | B | 115 | −8.644 | 19.366 | 5.714 | 1.00 | 16.82 | B |
| ATOM | 5131 | N | ASP | B | 116 | −9.622 | 21.174 | 6.866 | 1.00 | 16.05 | B |
| ATOM | 5132 | CA | ASP | B | 116 | −10.658 | 20.382 | 7.443 | 1.00 | 14.70 | B |
| ATOM | 5133 | CB | ASP | B | 116 | −10.054 | 19.448 | 8.531 | 1.00 | 13.68 | B |
| ATOM | 5134 | CG | ASP | B | 116 | −11.029 | 18.293 | 8.978 | 1.00 | 12.42 | B |
| ATOM | 5135 | OD1 | ASP | B | 116 | −10.764 | 17.458 | 9.872 | 1.00 | 11.35 | B |
| ATOM | 5136 | OD2 | ASP | B | 116 | −12.081 | 18.225 | 8.399 | 1.00 | 9.98 | B |
| ATOM | 5137 | C | ASP | B | 116 | −11.673 | 21.260 | 8.092 | 1.00 | 16.52 | B |
| ATOM | 5138 | O | ASP | B | 116 | −11.486 | 22.455 | 8.233 | 1.00 | 16.01 | B |
| ATOM | 5139 | N | THR | B | 117 | −12.796 | 20.659 | 8.485 | 1.00 | 16.77 | B |
| ATOM | 5140 | CA | THR | B | 117 | −13.804 | 21.353 | 9.261 | 1.00 | 15.35 | B |
| ATOM | 5141 | CB | THR | B | 117 | −15.182 | 20.745 | 8.943 | 1.00 | 17.06 | B |
| ATOM | 5142 | OG1 | THR | B | 117 | −15.518 | 21.037 | 7.562 | 1.00 | 19.25 | B |
| ATOM | 5143 | CG2 | THR | B | 117 | −16.260 | 21.228 | 9.920 | 1.00 | 13.11 | B |
| ATOM | 5144 | C | THR | B | 117 | −13.418 | 20.987 | 10.736 | 1.00 | 16.54 | B |
| ATOM | 5145 | O | THR | B | 117 | −13.202 | 19.763 | 11.088 | 1.00 | 14.72 | B |
| ATOM | 5146 | N | ILE | B | 118 | −13.293 | 22.042 | 11.601 | 1.00 | 17.37 | B |
| ATOM | 5147 | CA | ILE | B | 118 | −13.006 | 21.852 | 13.055 | 1.00 | 16.98 | B |
| ATOM | 5148 | CB | ILE | B | 118 | −12.085 | 22.942 | 13.548 | 1.00 | 17.48 | B |
| ATOM | 5149 | CG2 | ILE | B | 118 | −11.748 | 22.697 | 15.050 | 1.00 | 15.79 | B |
| ATOM | 5150 | CG1 | ILE | B | 118 | −10.887 | 23.032 | 12.582 | 1.00 | 17.41 | B |

TABLE 1-continued

| | | | | | | | | | |
|---|---|---|---|---|---|---|---|---|---|
| ATOM | 5151 | CD1 | ILE | B | 118 | −10.165 | 21.768 | 12.321 | 1.00 | 15.94 | B |
| ATOM | 5152 | C | ILE | B | 118 | −14.368 | 21.806 | 13.825 | 1.00 | 16.93 | B |
| ATOM | 5153 | O | ILE | B | 118 | −15.206 | 22.668 | 13.674 | 1.00 | 17.25 | B |
| ATOM | 5154 | N | ALA | B | 119 | −14.554 | 20.773 | 14.614 | 1.00 | 16.02 | B |
| ATOM | 5155 | CA | ALA | B | 119 | −15.778 | 20.566 | 15.307 | 1.00 | 15.24 | B |
| ATOM | 5156 | CB | ALA | B | 119 | −16.511 | 19.450 | 14.673 | 1.00 | 12.04 | B |
| ATOM | 5157 | C | ALA | B | 119 | −15.485 | 20.212 | 16.794 | 1.00 | 16.10 | B |
| ATOM | 5158 | O | ALA | B | 119 | −14.612 | 19.371 | 17.105 | 1.00 | 15.69 | B |
| ATOM | 5159 | N | PRO | B | 120 | −16.245 | 20.805 | 17.737 | 1.00 | 16.19 | B |
| ATOM | 5160 | CD | PRO | B | 120 | −17.319 | 21.806 | 17.579 | 1.00 | 16.59 | B |
| ATOM | 5161 | CA | PRO | B | 120 | −16.016 | 20.507 | 19.168 | 1.00 | 17.05 | B |
| ATOM | 5162 | CB | PRO | B | 120 | −16.719 | 21.646 | 19.876 | 1.00 | 17.65 | B |
| ATOM | 5163 | CG | PRO | B | 120 | −17.964 | 21.829 | 18.969 | 1.00 | 17.14 | B |
| ATOM | 5164 | C | PRO | B | 120 | −16.648 | 19.203 | 19.603 | 1.00 | 18.92 | B |
| ATOM | 5165 | O | PRO | B | 120 | −17.813 | 18.942 | 19.301 | 1.00 | 19.34 | B |
| ATOM | 5166 | N | ASP | B | 121 | −15.920 | 18.405 | 20.349 | 1.00 | 18.94 | B |
| ATOM | 5167 | CA | ASP | B | 121 | −16.454 | 17.189 | 20.855 | 1.00 | 18.21 | B |
| ATOM | 5168 | CB | ASP | B | 121 | −15.337 | 16.414 | 21.476 | 1.00 | 20.64 | B |
| ATOM | 5169 | CG | ASP | B | 121 | −13.999 | 16.565 | 20.669 | 1.00 | 23.80 | B |
| ATOM | 5170 | OD1 | ASP | B | 121 | −13.406 | 17.852 | 20.492 | 1.00 | 25.52 | B |
| ATOM | 5171 | OD2 | ASP | B | 121 | −13.607 | 15.401 | 20.250 | 1.00 | 21.30 | B |
| ATOM | 5172 | C | ASP | B | 121 | −17.430 | 17.573 | 21.957 | 1.00 | 18.43 | B |
| ATOM | 5173 | O | ASP | B | 121 | −18.282 | 16.788 | 22.357 | 1.00 | 18.55 | B |
| ATOM | 5174 | N | GLU | B | 122 | −17.254 | 18.772 | 22.499 | 1.00 | 18.17 | B |
| ATOM | 5175 | CA | GLU | B | 122 | −18.056 | 19.330 | 23.588 | 1.00 | 16.27 | B |
| ATOM | 5176 | CB | GLU | B | 122 | −17.347 | 19.159 | 24.919 | 1.00 | 16.98 | B |
| ATOM | 5177 | CG | GLU | B | 122 | −17.260 | 17.720 | 25.391 | 1.00 | 18.67 | B |
| ATOM | 5178 | CD | GLU | B | 122 | −16.819 | 17.567 | 26.832 | 1.00 | 19.76 | B |
| ATOM | 5179 | OE1 | GLU | B | 122 | −15.562 | 17.684 | 27.091 | 1.00 | 19.83 | B |
| ATOM | 5180 | OE2 | GLU | B | 122 | −17.747 | 17.311 | 27.675 | 1.00 | 20.93 | B |
| ATOM | 5181 | C | GLU | B | 122 | −18.387 | 20.797 | 23.398 | 1.00 | 15.94 | B |
| ATOM | 5182 | O | GLU | B | 122 | −17.581 | 21.745 | 23.468 | 1.00 | 15.41 | B |
| ATOM | 5183 | N | ILE | B | 123 | −19.677 | 20.943 | 23.223 | 1.00 | 16.20 | B |
| ATOM | 5184 | CA | ILE | B | 123 | −20.284 | 22.227 | 23.011 | 1.00 | 16.27 | B |
| ATOM | 5185 | CB | ILE | B | 123 | −21.568 | 21.950 | 22.337 | 1.00 | 17.11 | B |
| ATOM | 5186 | CG2 | ILE | B | 123 | −22.382 | 21.029 | 23.212 | 1.00 | 15.78 | B |
| ATOM | 5187 | CG1 | ILE | B | 123 | −22.371 | 23.189 | 22.208 | 1.00 | 18.61 | B |
| ATOM | 5188 | CD1 | ILE | B | 123 | −23.754 | 22.842 | 21.672 | 1.00 | 21.90 | B |
| ATOM | 5189 | C | ILE | B | 123 | −20.493 | 22.789 | 24.431 | 1.00 | 15.78 | B |
| ATOM | 5190 | O | ILE | B | 123 | −20.795 | 22.044 | 25.350 | 1.00 | 15.60 | B |
| ATOM | 5191 | N | THR | B | 124 | −20.389 | 24.079 | 24.611 | 1.00 | 15.21 | B |
| ATOM | 5192 | CA | THR | B | 124 | −20.562 | 24.535 | 25.973 | 1.00 | 16.43 | B |
| ATOM | 5193 | CB | THR | B | 124 | −19.636 | 25.781 | 26.256 | 1.00 | 15.84 | B |
| ATOM | 5194 | OG1 | THR | B | 124 | −18.249 | 25.385 | 26.278 | 1.00 | 13.22 | B |
| ATOM | 5195 | CG2 | THR | B | 124 | −20.067 | 26.477 | 27.609 | 1.00 | 17.27 | B |
| ATOM | 5196 | C | THR | B | 124 | −21.998 | 24.924 | 26.098 | 1.00 | 15.83 | B |
| ATOM | 5197 | O | THR | B | 124 | −22.413 | 25.812 | 25.352 | 1.00 | 15.69 | B |
| ATOM | 5198 | N | VAL | B | 125 | −22.771 | 24.285 | 26.989 | 1.00 | 15.33 | B |
| ATOM | 5199 | CA | VAL | B | 125 | −24.191 | 24.721 | 27.122 | 1.00 | 16.47 | B |
| ATOM | 5200 | CB | VAL | B | 125 | −25.183 | 23.595 | 27.521 | 1.00 | 17.07 | B |
| ATOM | 5201 | CG1 | VAL | B | 125 | −25.343 | 22.564 | 26.354 | 1.00 | 16.08 | B |
| ATOM | 5202 | CG2 | VAL | B | 125 | −24.769 | 22.966 | 28.790 | 1.00 | 17.79 | B |
| ATOM | 5203 | C | VAL | B | 125 | −24.483 | 25.931 | 28.037 | 1.00 | 16.44 | B |
| ATOM | 5204 | O | VAL | B | 125 | −23.595 | 26.402 | 28.773 | 1.00 | 16.07 | B |
| ATOM | 5205 | N | SER | B | 126 | −25.669 | 26.480 | 27.925 | 1.00 | 15.05 | B |
| ATOM | 5206 | CA | SER | B | 126 | −25.974 | 27.654 | 28.746 | 1.00 | 15.14 | B |
| ATOM | 5207 | CB | SER | B | 126 | −27.406 | 28.131 | 28.517 | 1.00 | 14.60 | B |
| ATOM | 5208 | OG | SER | B | 126 | −28.068 | 28.307 | 29.741 | 1.00 | 15.76 | B |
| ATOM | 5209 | C | SER | B | 126 | −25.767 | 27.476 | 30.245 | 1.00 | 15.82 | B |
| ATOM | 5210 | O | SER | B | 126 | −25.308 | 28.385 | 30.921 | 1.00 | 15.53 | B |
| ATOM | 5211 | N | SER | B | 127 | −26.067 | 26.316 | 30.794 | 1.00 | 16.06 | B |
| ATOM | 5212 | CA | SER | B | 127 | −25.877 | 26.261 | 32.182 | 1.00 | 17.17 | B |
| ATOM | 5213 | CB | SER | B | 127 | −26.720 | 25.195 | 32.774 | 1.00 | 16.50 | B |
| ATOM | 5214 | OG | SER | B | 127 | −26.134 | 23.961 | 32.465 | 1.00 | 17.74 | B |
| ATOM | 5215 | C | SER | B | 127 | −24.417 | 26.001 | 32.530 | 1.00 | 18.97 | B |
| ATOM | 5216 | O | SER | B | 127 | −24.054 | 26.038 | 33.728 | 1.00 | 20.17 | B |
| ATOM | 5217 | N | ASP | B | 128 | −23.608 | 25.637 | 31.515 | 1.00 | 19.12 | B |
| ATOM | 5218 | CA | ASP | B | 128 | −22.169 | 25.428 | 31.681 | 1.00 | 18.68 | B |
| ATOM | 5219 | CB | ASP | B | 128 | −21.512 | 24.958 | 30.361 | 1.00 | 18.14 | B |
| ATOM | 5220 | CG | ASP | B | 128 | −21.573 | 23.509 | 30.175 | 1.00 | 17.31 | B |
| ATOM | 5221 | OD1 | ASP | B | 128 | −21.305 | 23.105 | 28.956 | 1.00 | 17.10 | B |
| ATOM | 5222 | OD2 | ASP | B | 128 | −21.896 | 22.830 | 31.223 | 1.00 | 14.81 | B |
| ATOM | 5223 | C | ASP | B | 128 | −21.447 | 26.716 | 32.153 | 1.00 | 18.03 | B |
| ATOM | 5224 | O | ASP | B | 128 | −20.466 | 26.608 | 32.930 | 1.00 | 17.44 | B |
| ATOM | 5225 | N | PHE | B | 129 | −21.836 | 27.892 | 31.646 | 1.00 | 18.38 | B |
| ATOM | 5226 | CA | PHE | B | 129 | −21.200 | 29.123 | 32.187 | 1.00 | 20.97 | B |
| ATOM | 5227 | CB | PHE | B | 129 | −21.712 | 30.304 | 31.432 | 1.00 | 19.70 | B |
| ATOM | 5228 | CG | PHE | B | 129 | −21.386 | 30.221 | 30.022 | 1.00 | 19.92 | B |
| ATOM | 5229 | CD1 | PHE | B | 129 | −22.267 | 29.580 | 29.123 | 1.00 | 19.64 | B |
| ATOM | 5230 | CD2 | PHE | B | 129 | −20.105 | 30.631 | 29.584 | 1.00 | 20.27 | B |

TABLE 1-continued

| | | | | | | | | | | |
|---|---|---|---|---|---|---|---|---|---|---|
| ATOM | 5231 | CE1 | PHE | B | 129 | −21.858 | 29.320 | 27.742 | 1.00 | 19.36 | B |
| ATOM | 5232 | CE2 | PHE | B | 129 | −19.667 | 30.389 | 28.248 | 1.00 | 19.46 | B |
| ATOM | 5233 | CZ | PHE | B | 129 | −20.542 | 29.723 | 27.316 | 1.00 | 19.73 | B |
| ATOM | 5234 | C | PHE | B | 129 | −21.805 | 29.037 | 33.576 | 1.00 | 20.89 | B |
| ATOM | 5235 | O | PHE | B | 129 | −22.275 | 27.979 | 33.856 | 1.00 | 24.07 | B |
| ATOM | 5236 | N | GLU | B | 130 | −21.819 | 30.009 | 34.455 | 1.00 | 20.17 | B |
| ATOM | 5237 | CA | GLU | B | 130 | −22.545 | 29.815 | 35.759 | 1.00 | 18.11 | B |
| ATOM | 5238 | CB | GLU | B | 130 | −24.027 | 29.554 | 35.519 | 1.00 | 17.97 | B |
| ATOM | 5239 | CG | GLU | B | 130 | −25.041 | 30.667 | 35.618 | 1.00 | 18.72 | B |
| ATOM | 5240 | CD | GLU | B | 130 | −26.427 | 30.089 | 35.921 | 1.00 | 20.80 | B |
| ATOM | 5241 | OE1 | GLU | B | 130 | −27.194 | 30.956 | 36.438 | 1.00 | 21.32 | B |
| ATOM | 5242 | OE2 | GLU | B | 130 | −26.753 | 28.806 | 35.654 | 1.00 | 20.07 | B |
| ATOM | 5243 | C | GLU | B | 130 | −21.927 | 28.646 | 36.513 | 1.00 | 17.80 | B |
| ATOM | 5244 | O | GLU | B | 130 | −21.408 | 28.813 | 37.578 | 1.00 | 17.90 | B |
| ATOM | 5245 | N | ALA | B | 131 | −22.020 | 27.437 | 36.021 | 1.00 | 16.81 | B |
| ATOM | 5246 | CA | ALA | B | 131 | −21.298 | 26.346 | 36.607 | 1.00 | 17.21 | B |
| ATOM | 5247 | CB | ALA | B | 131 | −21.688 | 25.115 | 35.926 | 1.00 | 15.26 | B |
| ATOM | 5248 | C | ALA | B | 131 | −19.899 | 26.825 | 36.077 | 1.00 | 18.68 | B |
| ATOM | 5249 | O | ALA | B | 131 | −19.794 | 27.814 | 35.185 | 1.00 | 20.46 | B |
| ATOM | 5250 | N | ARG | B | 132 | −18.800 | 26.244 | 36.490 | 1.00 | 18.41 | B |
| ATOM | 5251 | CA | ARG | B | 132 | −17.663 | 26.886 | 35.839 | 1.00 | 18.56 | B |
| ATOM | 5252 | CB | ARG | B | 132 | −16.627 | 27.432 | 36.873 | 1.00 | 19.13 | B |
| ATOM | 5253 | CG | ARG | B | 132 | −16.605 | 29.079 | 37.036 | 1.00 | 20.34 | B |
| ATOM | 5254 | CD | ARG | B | 132 | −17.874 | 29.822 | 37.020 | 1.00 | 16.61 | B |
| ATOM | 5255 | NE | ARG | B | 132 | −17.717 | 31.200 | 37.359 | 1.00 | 14.34 | B |
| ATOM | 5256 | CZ | ARG | B | 132 | −18.437 | 32.217 | 36.852 | 1.00 | 13.69 | B |
| ATOM | 5257 | NH1 | ARG | B | 132 | −19.375 | 31.975 | 35.889 | 1.00 | 11.05 | B |
| ATOM | 5258 | NH2 | ARG | B | 132 | −18.290 | 33.467 | 37.376 | 1.00 | 10.66 | B |
| ATOM | 5259 | C | ARG | B | 132 | −17.125 | 25.765 | 35.016 | 1.00 | 19.07 | B |
| ATOM | 5260 | O | ARG | B | 132 | −15.979 | 25.346 | 35.156 | 1.00 | 17.92 | B |
| ATOM | 5261 | N | HIS | B | 133 | −17.992 | 25.282 | 34.130 | 1.00 | 18.80 | B |
| ATOM | 5262 | CA | HIS | B | 133 | −17.644 | 24.146 | 33.351 | 1.00 | 19.87 | B |
| ATOM | 5263 | CB | HIS | B | 133 | −18.696 | 23.073 | 33.598 | 1.00 | 21.82 | B |
| ATOM | 5264 | CG | HIS | B | 133 | −18.665 | 22.467 | 34.977 | 1.00 | 23.90 | B |
| ATOM | 5265 | CD2 | HIS | B | 133 | −18.081 | 22.871 | 36.153 | 1.00 | 24.98 | B |
| ATOM | 5266 | ND1 | HIS | B | 133 | −19.289 | 21.266 | 35.265 | 1.00 | 24.94 | B |
| ATOM | 5267 | CE1 | HIS | B | 133 | −19.093 | 20.953 | 36.556 | 1.00 | 25.41 | B |
| ATOM | 5268 | NE2 | HIS | B | 133 | −18.363 | 21.909 | 37.122 | 1.00 | 24.84 | B |
| ATOM | 5269 | C | HIS | B | 133 | −17.562 | 24.444 | 31.864 | 1.00 | 21.12 | B |
| ATOM | 5270 | O | HIS | B | 133 | −18.173 | 23.755 | 31.049 | 1.00 | 20.74 | B |
| ATOM | 5271 | N | VAL | B | 134 | −16.832 | 25.463 | 31.454 | 1.00 | 21.26 | B |
| ATOM | 5272 | CA | VAL | B | 134 | −16.809 | 25.755 | 30.012 | 1.00 | 19.73 | B |
| ATOM | 5273 | CB | VAL | B | 134 | −16.172 | 27.078 | 29.773 | 1.00 | 20.41 | B |
| ATOM | 5274 | CG1 | VAL | B | 134 | −16.186 | 27.387 | 28.305 | 1.00 | 19.64 | B |
| ATOM | 5275 | CG2 | VAL | B | 134 | −16.959 | 28.111 | 30.535 | 1.00 | 18.82 | B |
| ATOM | 5276 | C | VAL | B | 134 | −15.963 | 24.627 | 29.403 | 1.00 | 21.59 | B |
| ATOM | 5277 | O | VAL | B | 134 | −14.970 | 24.164 | 30.028 | 1.00 | 22.11 | B |
| ATOM | 5278 | N | LYS | B | 135 | −16.342 | 24.152 | 28.224 | 1.00 | 20.69 | B |
| ATOM | 5279 | CA | LYS | B | 135 | −15.643 | 23.033 | 27.600 | 1.00 | 18.10 | B |
| ATOM | 5280 | CB | LYS | B | 135 | −16.654 | 22.079 | 27.001 | 1.00 | 18.62 | B |
| ATOM | 5281 | CG | LYS | B | 135 | −17.918 | 21.871 | 27.780 | 1.00 | 17.47 | B |
| ATOM | 5282 | CD | LYS | B | 135 | −17.588 | 21.210 | 29.099 | 1.00 | 20.44 | B |
| ATOM | 5283 | CE | LYS | B | 135 | −18.874 | 20.600 | 29.715 | 1.00 | 20.62 | B |
| ATOM | 5284 | NZ | LYS | B | 135 | −18.599 | 20.214 | 31.116 | 1.00 | 23.73 | B |
| ATOM | 5285 | C | LYS | B | 135 | −14.667 | 23.433 | 26.544 | 1.00 | 17.97 | B |
| ATOM | 5286 | O | LYS | B | 135 | −15.010 | 24.089 | 25.508 | 1.00 | 18.77 | B |
| ATOM | 5287 | N | LEU | B | 136 | −13.422 | 23.059 | 26.858 | 1.00 | 17.35 | B |
| ATOM | 5288 | CA | LEU | B | 136 | −12.201 | 23.317 | 26.076 | 1.00 | 15.80 | B |
| ATOM | 5289 | CB | LEU | B | 136 | −11.107 | 23.694 | 27.066 | 1.00 | 15.35 | B |
| ATOM | 5290 | CG | LEU | B | 136 | −9.845 | 24.233 | 26.446 | 1.00 | 14.92 | B |
| ATOM | 5291 | CD1 | LEU | B | 136 | −9.199 | 23.060 | 25.743 | 1.00 | 17.73 | B |
| ATOM | 5292 | CD2 | LEU | B | 136 | −10.104 | 25.343 | 25.510 | 1.00 | 11.48 | B |
| ATOM | 5293 | C | LEU | B | 136 | −11.859 | 22.074 | 25.221 | 1.00 | 15.41 | B |
| ATOM | 5294 | O | LEU | B | 136 | −11.508 | 21.087 | 25.724 | 1.00 | 15.64 | B |
| ATOM | 5295 | N | ASN | B | 137 | −11.948 | 22.184 | 23.927 | 1.00 | 15.88 | B |
| ATOM | 5296 | CA | ASN | B | 137 | −11.723 | 21.133 | 23.001 | 1.00 | 16.42 | B |
| ATOM | 5297 | CB | ASN | B | 137 | −12.661 | 21.297 | 21.883 | 1.00 | 16.31 | B |
| ATOM | 5298 | CG | ASN | B | 137 | −14.076 | 21.109 | 22.321 | 1.00 | 17.79 | B |
| ATOM | 5299 | OD1 | ASN | B | 137 | −14.538 | 19.946 | 22.598 | 1.00 | 17.36 | B |
| ATOM | 5300 | ND2 | ASN | B | 137 | −14.798 | 22.241 | 22.411 | 1.00 | 16.17 | B |
| ATOM | 5301 | C | ASN | B | 137 | −10.356 | 21.204 | 22.441 | 1.00 | 16.76 | B |
| ATOM | 5302 | O | ASN | B | 137 | −9.830 | 22.301 | 22.311 | 1.00 | 18.09 | B |
| ATOM | 5303 | N | VAL | B | 138 | −9.748 | 20.070 | 22.119 | 1.00 | 16.82 | B |
| ATOM | 5304 | CA | VAL | B | 138 | −8.411 | 20.131 | 21.536 | 1.00 | 16.47 | B |
| ATOM | 5305 | CB | VAL | B | 138 | −7.350 | 19.349 | 22.378 | 1.00 | 15.77 | B |
| ATOM | 5306 | CG1 | VAL | B | 138 | −6.054 | 19.460 | 21.672 | 1.00 | 15.93 | B |
| ATOM | 5307 | CG2 | VAL | B | 138 | −7.215 | 19.909 | 23.774 | 1.00 | 14.29 | B |
| ATOM | 5308 | C | VAL | B | 138 | −8.496 | 19.463 | 20.167 | 1.00 | 17.25 | B |
| ATOM | 5309 | O | VAL | B | 138 | −8.932 | 18.373 | 20.030 | 1.00 | 18.38 | B |
| ATOM | 5310 | N | GLU | B | 139 | −8.104 | 20.083 | 19.110 | 1.00 | 17.36 | B |

TABLE 1-continued

| | | | | | | | | | | |
|---|---|---|---|---|---|---|---|---|---|---|
| ATOM | 5311 | CA | GLU | B | 139 | −8.183 | 19.335 | 17.883 | 1.00 | 16.66 | B |
| ATOM | 5312 | CB | GLU | B | 139 | −9.327 | 19.873 | 17.018 | 1.00 | 16.47 | B |
| ATOM | 5313 | CG | GLU | B | 139 | −10.777 | 19.462 | 17.320 | 1.00 | 15.21 | B |
| ATOM | 5314 | CD | GLU | B | 139 | −10.978 | 18.005 | 17.296 | 1.00 | 14.25 | B |
| ATOM | 5315 | OE1 | GLU | B | 139 | −10.204 | 17.302 | 16.754 | 1.00 | 15.84 | B |
| ATOM | 5316 | OE2 | GLU | B | 139 | −11.905 | 17.479 | 17.831 | 1.00 | 15.49 | B |
| ATOM | 5317 | C | GLU | B | 139 | −6.858 | 19.504 | 17.156 | 1.00 | 16.69 | B |
| ATOM | 5318 | O | GLU | B | 139 | −6.329 | 20.622 | 16.980 | 1.00 | 16.31 | B |
| ATOM | 5319 | N | GLU | B | 140 | −6.265 | 18.393 | 16.794 | 1.00 | 16.98 | B |
| ATOM | 5320 | CA | GLU | B | 140 | −5.067 | 18.499 | 15.978 | 1.00 | 17.36 | B |
| ATOM | 5321 | CB | GLU | B | 140 | −3.961 | 17.694 | 16.586 | 1.00 | 19.21 | B |
| ATOM | 5322 | CG | GLU | B | 140 | −2.604 | 18.039 | 15.925 | 1.00 | 21.45 | B |
| ATOM | 5323 | CD | GLU | B | 140 | −1.329 | 17.695 | 16.850 | 1.00 | 24.11 | B |
| ATOM | 5324 | OE1 | GLU | B | 140 | −1.083 | 16.439 | 17.162 | 1.00 | 24.27 | B |
| ATOM | 5325 | OE2 | GLU | B | 140 | −0.565 | 18.702 | 17.248 | 1.00 | 24.40 | B |
| ATOM | 5326 | C | GLU | B | 140 | −5.258 | 18.054 | 14.490 | 1.00 | 16.73 | B |
| ATOM | 5327 | O | GLU | B | 140 | −6.002 | 17.124 | 14.180 | 1.00 | 15.95 | B |
| ATOM | 5328 | N | ARG | B | 141 | −4.634 | 18.773 | 13.563 | 1.00 | 16.19 | B |
| ATOM | 5329 | CA | ARG | B | 141 | −4.697 | 18.328 | 12.157 | 1.00 | 16.28 | B |
| ATOM | 5330 | CB | ARG | B | 141 | −5.593 | 19.186 | 11.300 | 1.00 | 15.03 | B |
| ATOM | 5331 | CG | ARG | B | 141 | −7.094 | 19.307 | 11.716 | 1.00 | 13.64 | B |
| ATOM | 5332 | CD | ARG | B | 141 | −7.997 | 18.224 | 11.214 | 1.00 | 13.47 | B |
| ATOM | 5333 | NE | ARG | B | 141 | −8.603 | 17.627 | 12.393 | 1.00 | 14.13 | B |
| ATOM | 5334 | CZ | ARG | B | 141 | −9.776 | 17.988 | 12.877 | 1.00 | 15.37 | B |
| ATOM | 5335 | NH1 | ARG | B | 141 | −10.562 | 18.914 | 12.348 | 1.00 | 19.59 | B |
| ATOM | 5336 | NH2 | ARG | B | 141 | −10.149 | 17.508 | 13.950 | 1.00 | 15.27 | B |
| ATOM | 5337 | C | ARG | B | 141 | −3.298 | 18.456 | 11.624 | 1.00 | 16.92 | B |
| ATOM | 5338 | O | ARG | B | 141 | −2.420 | 18.979 | 12.262 | 1.00 | 17.24 | B |
| ATOM | 5339 | N | SER | B | 142 | −3.063 | 17.993 | 10.445 | 1.00 | 17.90 | B |
| ATOM | 5340 | CA | SER | B | 142 | −1.735 | 18.135 | 9.951 | 1.00 | 19.10 | B |
| ATOM | 5341 | CB | SER | B | 142 | −0.892 | 16.941 | 10.367 | 1.00 | 17.92 | B |
| ATOM | 5342 | OG | SER | B | 142 | −1.132 | 15.972 | 9.398 | 1.00 | 20.94 | B |
| ATOM | 5343 | C | SER | B | 142 | −1.802 | 18.284 | 8.434 | 1.00 | 18.88 | B |
| ATOM | 5344 | O | SER | B | 142 | −2.835 | 17.945 | 7.807 | 1.00 | 20.40 | B |
| ATOM | 5345 | N | VAL | B | 143 | −0.744 | 18.808 | 7.836 | 1.00 | 18.94 | B |
| ATOM | 5346 | CA | VAL | B | 143 | −0.763 | 18.978 | 6.414 | 1.00 | 20.12 | B |
| ATOM | 5347 | CB | VAL | B | 143 | −1.569 | 20.349 | 6.013 | 1.00 | 19.94 | B |
| ATOM | 5348 | CG1 | VAL | B | 143 | −0.930 | 21.571 | 6.565 | 1.00 | 20.30 | B |
| ATOM | 5349 | CG2 | VAL | B | 143 | −1.670 | 20.487 | 4.574 | 1.00 | 20.41 | B |
| ATOM | 5350 | C | VAL | B | 143 | 0.612 | 18.878 | 5.864 | 1.00 | 18.60 | B |
| ATOM | 5351 | O | VAL | B | 143 | 1.553 | 18.922 | 6.615 | 1.00 | 17.93 | B |
| ATOM | 5352 | N | GLY | B | 144 | 0.697 | 18.653 | 4.562 | 1.00 | 19.10 | B |
| ATOM | 5353 | CA | GLY | B | 144 | 1.980 | 18.510 | 3.891 | 1.00 | 19.68 | B |
| ATOM | 5354 | C | GLY | B | 144 | 1.977 | 17.485 | 2.764 | 1.00 | 19.29 | B |
| ATOM | 5355 | O | GLY | B | 144 | 0.922 | 16.866 | 2.542 | 1.00 | 20.60 | B |
| ATOM | 5356 | N | PRO | B | 145 | 3.136 | 17.243 | 2.073 | 1.00 | 21.01 | B |
| ATOM | 5357 | CD | PRO | B | 145 | 3.430 | 16.086 | 1.163 | 1.00 | 18.66 | B |
| ATOM | 5358 | CA | PRO | B | 145 | 4.373 | 17.959 | 2.417 | 1.00 | 17.49 | B |
| ATOM | 5359 | CB | PRO | B | 145 | 5.478 | 17.155 | 1.712 | 1.00 | 17.98 | B |
| ATOM | 5360 | CG | PRO | B | 145 | 4.870 | 16.476 | 0.630 | 1.00 | 17.35 | B |
| ATOM | 5361 | C | PRO | B | 145 | 4.377 | 19.341 | 2.011 | 1.00 | 17.21 | B |
| ATOM | 5362 | O | PRO | B | 145 | 3.834 | 19.657 | 1.023 | 1.00 | 17.81 | B |
| ATOM | 5363 | N | LEU | B | 146 | 4.993 | 20.187 | 2.846 | 1.00 | 18.84 | B |
| ATOM | 5364 | CA | LEU | B | 146 | 5.129 | 21.616 | 2.502 | 1.00 | 18.78 | B |
| ATOM | 5365 | CB | LEU | B | 146 | 5.272 | 22.454 | 3.791 | 1.00 | 19.59 | B |
| ATOM | 5366 | CG | LEU | B | 146 | 3.933 | 22.973 | 4.380 | 1.00 | 19.90 | B |
| ATOM | 5367 | CD1 | LEU | B | 146 | 2.956 | 21.888 | 4.372 | 1.00 | 19.96 | B |
| ATOM | 5368 | CD2 | LEU | B | 146 | 4.148 | 23.502 | 5.909 | 1.00 | 20.53 | B |
| ATOM | 5369 | C | LEU | B | 146 | 6.408 | 21.621 | 1.687 | 1.00 | 17.77 | B |
| ATOM | 5370 | O | LEU | B | 146 | 7.291 | 20.713 | 1.816 | 1.00 | 17.80 | B |
| ATOM | 5371 | N | THR | B | 147 | 6.524 | 22.662 | 0.875 | 1.00 | 17.34 | B |
| ATOM | 5372 | CA | THR | B | 147 | 7.752 | 22.838 | 0.062 | 1.00 | 17.24 | B |
| ATOM | 5373 | CB | THR | B | 147 | 7.588 | 22.231 | −1.397 | 1.00 | 15.58 | B |
| ATOM | 5374 | OG1 | THR | B | 147 | 6.690 | 23.044 | −2.167 | 1.00 | 12.89 | B |
| ATOM | 5375 | CG2 | THR | B | 147 | 7.159 | 20.825 | −1.344 | 1.00 | 14.21 | B |
| ATOM | 5376 | C | THR | B | 147 | 8.305 | 24.258 | −0.193 | 1.00 | 17.33 | B |
| ATOM | 5377 | O | THR | B | 147 | 9.442 | 24.377 | −0.710 | 1.00 | 18.43 | B |
| ATOM | 5378 | N | ARG | B | 148 | 7.488 | 25.281 | 0.001 | 1.00 | 17.27 | B |
| ATOM | 5379 | CA | ARG | B | 148 | 7.918 | 26.664 | −0.242 | 1.00 | 17.86 | B |
| ATOM | 5380 | CB | ARO | B | 148 | 6.754 | 27.594 | −0.611 | 1.00 | 18.33 | B |
| ATOM | 5381 | CG | ARG | B | 148 | 5.554 | 26.989 | −1.296 | 1.00 | 19.06 | B |
| ATOM | 5382 | CD | ARG | B | 148 | 5.801 | 26.875 | −2.750 | 1.00 | 22.60 | B |
| ATOM | 5383 | NE | ARG | B | 148 | 6.728 | 25.771 | −3.111 | 1.00 | 24.69 | B |
| ATOM | 5384 | CZ | ARG | B | 148 | 7.819 | 25.948 | −3.930 | 1.00 | 26.31 | B |
| ATOM | 5385 | NH1 | ARG | B | 148 | 8.099 | 27.163 | −4.494 | 1.00 | 21.81 | B |
| ATOM | 5386 | NH2 | ARG | B | 148 | 8.733 | 24.935 | −4.080 | 1.00 | 26.44 | B |
| ATOM | 5387 | C | ARG | B | 148 | 8.616 | 27.292 | 1.008 | 1.00 | 17.51 | B |
| ATOM | 5388 | O | ARG | B | 148 | 8.639 | 26.716 | 2.106 | 1.00 | 18.60 | B |
| ATOM | 5389 | N | LYS | B | 149 | 9.207 | 28.452 | 0.822 | 1.00 | 17.08 | B |
| ATOM | 5390 | CA | LYS | B | 149 | 9.944 | 29.189 | 1.878 | 1.00 | 17.17 | B |

TABLE 1-continued

| ATOM | 5391 | CB  | LYS | B | 149 | 10.339  | 30.546 | 1.332  | 1.00 | 16.42 | B |
|------|------|-----|-----|---|-----|---------|--------|--------|------|-------|---|
| ATOM | 5392 | CG  | LYS | B | 149 | 11.695  | 30.995 | 1.744  | 1.00 | 17.93 | B |
| ATOM | 5393 | CD  | LYS | B | 149 | 11.975  | 32.460 | 1.275  | 1.00 | 19.98 | B |
| ATOM | 5394 | CE  | LYS | B | 149 | 13.057  | 33.185 | 2.117  | 1.00 | 19.89 | B |
| ATOM | 5395 | NZ  | LYS | B | 149 | 12.645  | 34.592 | 2.753  | 1.00 | 22.50 | B |
| ATOM | 5396 | C   | LYS | B | 149 | 9.081   | 29.333 | 3.120  | 1.00 | 17.33 | B |
| ATOM | 5397 | O   | LYS | B | 149 | 9.510   | 29.093 | 4.199  | 1.00 | 17.30 | B |
| ATOM | 5398 | N   | GLY | B | 150 | 7.813   | 29.637 | 2.914  | 1.00 | 18.69 | B |
| ATOM | 5399 | CA  | GLY | B | 150 | 6.893   | 29.804 | 4.021  | 1.00 | 18.90 | B |
| ATOM | 5400 | C   | GLY | B | 150 | 5.399   | 29.428 | 3.824  | 1.00 | 18.31 | B |
| ATOM | 5401 | O   | GLY | B | 150 | 4.938   | 28.890 | 2.751  | 1.00 | 18.68 | B |
| ATOM | 5402 | N   | PHE | B | 151 | 4.627   | 29.760 | 4.877  | 1.00 | 18.11 | B |
| ATOM | 5403 | CA  | PHE | B | 151 | 3.231   | 29.413 | 4.935  | 1.00 | 16.78 | B |
| ATOM | 5404 | CB  | PHE | B | 151 | 3.088   | 27.904 | 5.163  | 1.00 | 17.44 | B |
| ATOM | 5405 | CG  | PHE | B | 151 | 3.382   | 27.482 | 6.567  | 1.00 | 17.11 | B |
| ATOM | 5406 | CD1 | PHE | B | 151 | 2.379   | 27.426 | 7.534  | 1.00 | 16.68 | B |
| ATOM | 5407 | CD2 | PHE | B | 151 | 4.665   | 27.100 | 6.953  | 1.00 | 17.64 | B |
| ATOM | 5408 | CE1 | PHE | B | 151 | 2.654   | 27.000 | 8.808  | 1.00 | 14.19 | B |
| ATOM | 5409 | CE2 | PHE | B | 151 | 4.918   | 26.652 | 8.295  | 1.00 | 13.97 | B |
| ATOM | 5410 | CZ  | PHE | B | 151 | 3.933   | 26.608 | 9.164  | 1.00 | 12.62 | B |
| ATOM | 5411 | C   | PHE | B | 151 | 2.423   | 30.135 | 5.945  | 1.00 | 15.60 | B |
| ATOM | 5412 | O   | PHE | B | 151 | 2.903   | 30.526 | 6.914  | 1.00 | 15.64 | B |
| ATOM | 5413 | N   | TYR | B | 152 | 1.168   | 30.282 | 5.627  | 1.00 | 15.57 | B |
| ATOM | 5414 | CA  | TYR | B | 152 | 0.163   | 30.858 | 6.438  | 1.00 | 15.81 | B |
| ATOM | 5415 | CB  | TYR | B | 152 | −0.565  | 31.926 | 5.686  | 1.00 | 15.32 | B |
| ATOM | 5416 | CG  | TYR | B | 152 | 0.224   | 33.046 | 5.302  | 1.00 | 16.12 | B |
| ATOM | 5417 | CD1 | TYR | B | 152 | 0.831   | 33.092 | 4.072  | 1.00 | 15.82 | B |
| ATOM | 5418 | CE1 | TYR | B | 152 | 1.587   | 34.221 | 3.674  | 1.00 | 17.14 | B |
| ATOM | 5419 | CD2 | TYR | B | 152 | 0.356   | 34.137 | 6.167  | 1.00 | 16.49 | B |
| ATOM | 5420 | CE2 | TYR | B | 152 | 1.067   | 35.247 | 5.807  | 1.00 | 16.67 | B |
| ATOM | 5421 | CZ  | TYR | B | 152 | 1.706   | 35.310 | 4.563  | 1.00 | 17.34 | B |
| ATOM | 5422 | OH  | TYR | B | 152 | 2.492   | 36.458 | 4.294  | 1.00 | 18.36 | B |
| ATOM | 5423 | C   | TYR | B | 152 | −0.933  | 29.816 | 6.876  | 1.00 | 15.64 | B |
| ATOM | 5424 | O   | TYR | B | 152 | −1.247  | 28.826 | 6.186  | 1.00 | 16.19 | B |
| ATOM | 5425 | N   | LEU | B | 153 | −1.544  | 30.111 | 8.032  | 1.00 | 15.05 | B |
| ATOM | 5426 | CA  | LEU | B | 153 | −2.660  | 29.347 | 8.556  | 1.00 | 14.67 | B |
| ATOM | 5427 | CB  | LEU | B | 153 | −2.332  | 28.764 | 9.874  | 1.00 | 13.90 | B |
| ATOM | 5428 | CG  | LEU | B | 153 | −2.191  | 27.269 | 9.922  | 1.00 | 13.61 | B |
| ATOM | 5429 | CD1 | LEU | B | 153 | −1.370  | 26.740 | 8.897  | 1.00 | 13.27 | B |
| ATOM | 5430 | CD2 | LEU | B | 153 | −1.719  | 26.902 | 11.246 | 1.00 | 14.00 | B |
| ATOM | 5431 | C   | LEU | B | 153 | −3.789  | 30.354 | 8.671  | 1.00 | 14.95 | B |
| ATOM | 5432 | O   | LEU | B | 153 | −3.583  | 31.576 | 8.903  | 1.00 | 14.79 | B |
| ATOM | 5433 | N   | ALA | B | 154 | −4.985  | 29.876 | 8.398  | 1.00 | 14.73 | B |
| ATOM | 5434 | CA  | ALA | B | 154 | −6.083  | 30.774 | 8.489  | 1.00 | 15.28 | B |
| ATOM | 5435 | CB  | ALA | B | 154 | −6.282  | 31.529 | 7.166  | 1.00 | 14.40 | B |
| ATOM | 5436 | C   | ALA | B | 154 | −7.382  | 30.106 | 8.953  | 1.00 | 15.82 | B |
| ATOM | 5437 | O   | ALA | B | 154 | −7.632  | 28.972 | 8.640  | 1.00 | 16.05 | B |
| ATOM | 5438 | N   | PHE | B | 155 | −8.215  | 30.876 | 9.668  | 1.00 | 16.13 | B |
| ATOM | 5439 | CA  | PHE | B | 155 | −9.468  | 30.391 | 10.200 | 1.00 | 15.47 | B |
| ATOM | 5440 | CB  | PHE | B | 155 | −9.451  | 30.381 | 11.698 | 1.00 | 15.41 | B |
| ATOM | 5441 | CG  | PHE | B | 155 | −8.182  | 29.835 | 12.296 | 1.00 | 14.85 | B |
| ATOM | 5442 | CD1 | PHE | B | 155 | −6.972  | 30.589 | 12.260 | 1.00 | 15.26 | B |
| ATOM | 5443 | CD2 | PHE | B | 155 | −8.177  | 28.569 | 12.859 | 1.00 | 13.36 | B |
| ATOM | 5444 | CE1 | PHE | B | 155 | −5.843  | 30.049 | 12.760 | 1.00 | 15.00 | B |
| ATOM | 5445 | CE2 | PHE | B | 155 | −7.029  | 28.012 | 13.364 | 1.00 | 14.50 | B |
| ATOM | 5446 | CZ  | PHE | B | 155 | −5.861  | 28.709 | 13.326 | 1.00 | 14.69 | B |
| ATOM | 5447 | C   | PHE | B | 155 | −10.730 | 31.108 | 9.742  | 1.00 | 16.14 | B |
| ATOM | 5448 | O   | PHE | B | 155 | −10.925 | 32.340 | 9.911  | 1.00 | 15.30 | B |
| ATOM | 5449 | N   | GLN | B | 156 | −11.603 | 30.282 | 9.133  | 1.00 | 15.86 | B |
| ATOM | 5450 | CA  | GLN | B | 156 | −12.800 | 30.816 | 8.669  | 1.00 | 15.64 | B |
| ATOM | 5451 | CB  | GLN | B | 156 | −12.990 | 30.381 | 7.292  | 1.00 | 16.47 | B |
| ATOM | 5452 | CG  | GLN | B | 156 | −14.127 | 31.041 | 6.646  | 1.00 | 17.66 | B |
| ATOM | 5453 | CD  | GLN | B | 156 | −14.806 | 30.040 | 5.674  | 1.00 | 19.35 | B |
| ATOM | 5454 | OE1 | GLN | B | 156 | −14.556 | 28.805 | 5.755  | 1.00 | 21.53 | B |
| ATOM | 5455 | NE2 | GLN | B | 156 | −15.673 | 30.533 | 4.811  | 1.00 | 18.19 | B |
| ATOM | 5456 | C   | GLN | B | 156 | −14.023 | 30.556 | 9.561  | 1.00 | 15.50 | B |
| ATOM | 5457 | O   | GLN | B | 156 | −14.419 | 29.422 | 9.900  | 1.00 | 15.53 | B |
| ATOM | 5458 | N   | ASP | B | 157 | −14.573 | 31.652 | 10.033 | 1.00 | 14.39 | B |
| ATOM | 5459 | CA  | ASP | B | 157 | −15.705 | 31.515 | 10.871 | 1.00 | 13.40 | B |
| ATOM | 5460 | CB  | ASP | B | 157 | −15.714 | 32.526 | 12.020 | 1.00 | 13.18 | B |
| ATOM | 5461 | CG  | ASP | B | 157 | −17.097 | 32.740 | 12.546 | 1.00 | 12.78 | B |
| ATOM | 5462 | OD1 | ASP | B | 157 | −17.648 | 33.815 | 12.379 | 1.00 | 15.04 | B |
| ATOM | 5463 | OD2 | ASP | B | 157 | −17.694 | 31.840 | 13.061 | 1.00 | 9.81  | B |
| ATOM | 5464 | C   | ASP | B | 157 | −16.910 | 31.702 | 9.965  | 1.00 | 13.07 | B |
| ATOM | 5465 | O   | ASP | B | 157 | −17.033 | 32.648 | 9.196  | 1.00 | 8.80  | B |
| ATOM | 5466 | N   | ILE | B | 158 | −17.836 | 30.782 | 10.209 | 1.00 | 15.42 | B |
| ATOM | 5467 | CA  | ILE | B | 158 | −19.009 | 30.664 | 9.400  | 1.00 | 18.87 | B |
| ATOM | 5468 | CB  | ILE | B | 158 | −18.976 | 29.214 | 8.836  | 1.00 | 20.10 | B |
| ATOM | 5469 | CG2 | ILE | B | 158 | −19.961 | 28.291 | 9.293  | 1.00 | 19.47 | B |
| ATOM | 5470 | CG1 | ILE | B | 158 | −19.107 | 29.401 | 7.409  | 1.00 | 21.36 | B |

TABLE 1-continued

| | | | | | | | | | | |
|---|---|---|---|---|---|---|---|---|---|---|
| ATOM | 5471 | CD1 | ILE | B | 158 | −17.696 | 29.886 | 6.837 | 1.00 | 21.75 | B |
| ATOM | 5472 | C | ILE | B | 158 | −20.275 | 31.074 | 10.026 | 1.00 | 19.64 | B |
| ATOM | 5473 | O | ILE | B | 158 | −21.341 | 30.856 | 9.484 | 1.00 | 21.18 | B |
| ATOM | 5474 | N | GLY | B | 159 | −20.165 | 31.767 | 11.163 | 1.00 | 19.33 | B |
| ATOM | 5475 | CA | GLY | B | 159 | −21.380 | 32.117 | 11.915 | 1.00 | 17.08 | B |
| ATOM | 5476 | C | GLY | B | 159 | −21.523 | 31.333 | 13.242 | 1.00 | 15.47 | B |
| ATOM | 5477 | O | GLY | B | 159 | −22.647 | 31.153 | 13.773 | 1.00 | 14.48 | B |
| ATOM | 5478 | N | ALA | B | 160 | −20.401 | 30.815 | 13.740 | 1.00 | 14.27 | B |
| ATOM | 5479 | CA | ALA | B | 160 | −20.401 | 30.119 | 15.020 | 1.00 | 14.67 | B |
| ATOM | 5480 | CB | ALA | B | 160 | −19.522 | 28.943 | 14.956 | 1.00 | 12.28 | B |
| ATOM | 5481 | C | ALA | B | 160 | −19.956 | 31.160 | 16.173 | 1.00 | 14.43 | B |
| ATOM | 5482 | O | ALA | B | 160 | −19.756 | 32.392 | 15.944 | 1.00 | 16.31 | B |
| ATOM | 5483 | N | CYS | B | 161 | −20.027 | 30.717 | 17.411 | 1.00 | 14.52 | B |
| ATOM | 5484 | CA | CYS | B | 161 | −19.581 | 31.490 | 18.622 | 1.00 | 13.42 | B |
| ATOM | 5485 | C | CYS | B | 161 | −18.414 | 30.661 | 19.150 | 1.00 | 12.18 | B |
| ATOM | 5486 | O | CYS | B | 161 | −18.548 | 29.745 | 19.930 | 1.00 | 10.07 | B |
| ATOM | 5487 | CB | CYS | B | 161 | −20.638 | 31.534 | 19.719 | 1.00 | 15.19 | B |
| ATOM | 5488 | SG | CYS | B | 161 | −20.475 | 32.886 | 21.059 | 1.00 | 18.03 | B |
| ATOM | 5489 | N | VAL | B | 162 | −17.243 | 31.009 | 18.666 | 1.00 | 12.41 | B |
| ATOM | 5490 | CA | VAL | B | 162 | −16.057 | 30.307 | 18.998 | 1.00 | 12.71 | B |
| ATOM | 5491 | CB | VAL | B | 162 | −15.264 | 29.877 | 17.757 | 1.00 | 15.52 | B |
| ATOM | 5492 | CG1 | VAL | B | 162 | −14.353 | 28.785 | 18.073 | 1.00 | 17.01 | B |
| ATOM | 5493 | CG2 | VAL | B | 162 | −16.140 | 29.600 | 16.546 | 1.00 | 16.89 | B |
| ATOM | 5494 | C | VAL | B | 162 | −15.099 | 31.214 | 19.669 | 1.00 | 12.25 | B |
| ATOM | 5495 | O | VAL | B | 162 | −15.045 | 32.427 | 19.391 | 1.00 | 9.22 | B |
| ATOM | 5496 | N | ALA | B | 163 | −14.304 | 30.533 | 20.472 | 1.00 | 12.60 | B |
| ATOM | 5497 | CA | ALA | B | 163 | −13.214 | 31.140 | 21.120 | 1.00 | 14.23 | B |
| ATOM | 5498 | CB | ALA | B | 163 | −13.464 | 31.287 | 22.548 | 1.00 | 14.60 | B |
| ATOM | 5499 | C | ALA | B | 163 | −11.971 | 30.310 | 20.873 | 1.00 | 14.42 | B |
| ATOM | 5500 | O | ALA | B | 163 | −11.774 | 29.253 | 21.429 | 1.00 | 15.48 | B |
| ATOM | 5501 | N | LEU | B | 164 | −11.111 | 30.824 | 20.040 | 1.00 | 14.36 | B |
| ATOM | 5502 | CA | LEU | B | 164 | −9.885 | 30.130 | 19.796 | 1.00 | 14.34 | B |
| ATOM | 5503 | CB | LEU | B | 164 | −9.485 | 30.418 | 18.350 | 1.00 | 15.10 | B |
| ATOM | 5504 | CG | LEU | B | 164 | −8.353 | 29.538 | 17.966 | 1.00 | 15.85 | B |
| ATOM | 5505 | CD1 | LEU | B | 164 | −8.630 | 28.067 | 18.092 | 1.00 | 16.13 | B |
| ATOM | 5506 | CD2 | LEU | B | 164 | −8.136 | 29.885 | 16.547 | 1.00 | 17.53 | B |
| ATOM | 5507 | C | LEU | B | 164 | −8.817 | 30.606 | 20.830 | 1.00 | 14.80 | B |
| ATOM | 5508 | O | LEU | B | 164 | −8.305 | 31.741 | 20.825 | 1.00 | 12.64 | B |
| ATOM | 5509 | N | LEU | B | 165 | −8.487 | 29.688 | 21.712 | 1.00 | 16.26 | B |
| ATOM | 5510 | CA | LEU | B | 165 | −7.551 | 29.984 | 22.749 | 1.00 | 17.14 | B |
| ATOM | 5511 | CB | LEU | B | 165 | −8.037 | 29.376 | 24.044 | 1.00 | 19.43 | B |
| ATOM | 5512 | CG | LEU | B | 165 | −9.530 | 29.559 | 24.316 | 1.00 | 19.79 | B |
| ATOM | 5513 | CD1 | LEU | B | 165 | −9.754 | 29.075 | 25.719 | 1.00 | 20.37 | B |
| ATOM | 5514 | CD2 | LEU | B | 165 | −9.902 | 30.972 | 24.204 | 1.00 | 18.03 | B |
| ATOM | 5515 | C | LEU | B | 165 | −6.144 | 29.538 | 22.582 | 1.00 | 18.15 | B |
| ATOM | 5516 | O | LEU | B | 165 | −5.307 | 29.840 | 23.442 | 1.00 | 17.75 | B |
| ATOM | 5517 | N | SER | B | 166 | −5.825 | 28.855 | 21.505 | 1.00 | 17.73 | B |
| ATOM | 5518 | CA | SER | B | 166 | −4.474 | 28.394 | 21.397 | 1.00 | 16.17 | B |
| ATOM | 5519 | CB | SER | B | 166 | −4.219 | 27.309 | 22.426 | 1.00 | 14.98 | B |
| ATOM | 5520 | OG | SER | B | 166 | −3.027 | 26.736 | 22.078 | 1.00 | 15.42 | B |
| ATOM | 5521 | C | SER | B | 166 | −4.304 | 27.827 | 20.011 | 1.00 | 16.84 | B |
| ATOM | 5522 | O | SER | B | 166 | −5.247 | 27.173 | 19.395 | 1.00 | 17.31 | B |
| ATOM | 5523 | N | VAL | B | 167 | −3.091 | 28.021 | 19.525 | 1.00 | 16.01 | B |
| ATOM | 5524 | CA | VAL | B | 167 | −2.796 | 27.557 | 18.183 | 1.00 | 14.75 | B |
| ATOM | 5525 | CB | VAL | B | 167 | −2.927 | 28.686 | 17.122 | 1.00 | 15.41 | B |
| ATOM | 5526 | CG1 | VAL | B | 167 | −2.492 | 28.139 | 15.801 | 1.00 | 15.39 | B |
| ATOM | 5527 | CG2 | VAL | B | 167 | −4.323 | 29.203 | 17.021 | 1.00 | 12.61 | B |
| ATOM | 5528 | C | VAL | B | 167 | −1.351 | 27.216 | 18.231 | 1.00 | 14.00 | B |
| ATOM | 5529 | O | VAL | B | 167 | −0.546 | 28.117 | 18.252 | 1.00 | 11.09 | B |
| ATOM | 5530 | N | ARG | B | 168 | −1.073 | 25.918 | 18.309 | 1.00 | 14.19 | B |
| ATOM | 5531 | CA | ARG | B | 168 | 0.283 | 25.437 | 18.254 | 1.00 | 15.80 | B |
| ATOM | 5532 | CB | ARG | B | 168 | 0.649 | 24.444 | 19.341 | 1.00 | 16.65 | B |
| ATOM | 5533 | CG | ARG | B | 168 | 1.576 | 25.138 | 20.315 | 1.00 | 18.51 | B |
| ATOM | 5534 | CD | ARG | B | 168 | 2.588 | 24.256 | 21.110 | 1.00 | 18.84 | B |
| ATOM | 5535 | NE | ARG | B | 168 | 2.387 | 22.845 | 20.873 | 1.00 | 19.58 | B |
| ATOM | 5536 | CZ | ARG | B | 168 | 3.349 | 21.933 | 20.924 | 1.00 | 20.14 | B |
| ATOM | 5537 | NH1 | ARG | B | 168 | 4.593 | 22.262 | 21.184 | 1.00 | 17.87 | B |
| ATOM | 5538 | NH2 | ARG | B | 168 | 3.035 | 20.646 | 20.804 | 1.00 | 22.21 | B |
| ATOM | 5539 | C | ARG | B | 168 | 0.504 | 24.765 | 16.897 | 1.00 | 16.72 | B |
| ATOM | 5540 | O | ARG | B | 168 | −0.448 | 24.080 | 16.423 | 1.00 | 16.12 | B |
| ATOM | 5541 | N | VAL | B | 169 | 1.718 | 25.013 | 16.299 | 1.00 | 16.99 | B |
| ATOM | 5542 | CA | VAL | B | 169 | 2.184 | 24.461 | 15.045 | 1.00 | 16.45 | B |
| ATOM | 5543 | CB | VAL | B | 169 | 2.234 | 25.477 | 13.911 | 1.00 | 17.41 | B |
| ATOM | 5544 | CG1 | VAL | B | 169 | 2.693 | 24.749 | 12.534 | 1.00 | 16.86 | B |
| ATOM | 5545 | CG2 | VAL | B | 169 | 0.873 | 26.148 | 13.741 | 1.00 | 16.77 | B |
| ATOM | 5546 | C | VAL | B | 169 | 3.556 | 24.004 | 15.237 | 1.00 | 17.13 | B |
| ATOM | 5547 | O | VAL | B | 169 | 4.390 | 24.783 | 15.608 | 1.00 | 15.77 | B |
| ATOM | 5548 | N | TYR | B | 170 | 3.821 | 22.749 | 14.918 | 1.00 | 17.98 | B |
| ATOM | 5549 | CA | TYR | B | 170 | 5.156 | 22.193 | 15.137 | 1.00 | 18.35 | B |
| ATOM | 5550 | CB | TYR | B | 170 | 5.250 | 21.640 | 16.525 | 1.00 | 17.90 | B |

TABLE 1-continued

| ATOM | 5551 | CG | TYR | B | 170 | 4.304 | 20.502 | 16.832 | 1.00 | 17.70 | B |
|---|---|---|---|---|---|---|---|---|---|---|---|
| ATOM | 5552 | CD1 | TYR | B | 170 | 4.759 | 19.194 | 16.837 | 1.00 | 17.50 | B |
| ATOM | 5553 | CE1 | TYR | B | 170 | 3.887 | 18.098 | 17.112 | 1.00 | 17.97 | B |
| ATOM | 5554 | CD2 | TYR | B | 170 | 2.931 | 20.741 | 17.103 | 1.00 | 17.53 | B |
| ATOM | 5555 | CE2 | TYR | B | 170 | 2.032 | 19.651 | 17.352 | 1.00 | 17.98 | B |
| ATOM | 5556 | CZ | TYR | B | 170 | 2.549 | 18.315 | 17.363 | 1.00 | 17.69 | B |
| ATOM | 5557 | OH | TYR | B | 170 | 1.728 | 17.256 | 17.668 | 1.00 | 17.02 | B |
| ATOM | 5558 | C | TYR | B | 170 | 5.393 | 21.063 | 14.189 | 1.00 | 20.07 | B |
| ATOM | 5559 | O | TYR | B | 170 | 4.432 | 20.661 | 13.493 | 1.00 | 21.18 | B |
| ATOM | 5560 | N | TYR | B | 171 | 6.657 | 20.570 | 14.106 | 1.00 | 20.52 | B |
| ATOM | 5561 | CA | TYR | B | 171 | 6.923 | 19.425 | 13.229 | 1.00 | 19.29 | B |
| ATOM | 5562 | CB | TYR | B | 171 | 7.378 | 19.841 | 11.905 | 1.00 | 20.20 | B |
| ATOM | 5563 | CG | TYR | B | 171 | 8.734 | 20.411 | 11.881 | 1.00 | 19.99 | B |
| ATOM | 5564 | CD1 | TYR | B | 171 | 9.838 | 19.585 | 11.637 | 1.00 | 19.32 | B |
| ATOM | 5565 | CE1 | TYR | B | 171 | 11.143 | 20.109 | 11.624 | 1.00 | 19.13 | B |
| ATOM | 5566 | CD2 | TYR | B | 171 | 8.946 | 21.796 | 12.090 | 1.00 | 19.46 | B |
| ATOM | 5567 | CE2 | TYR | B | 171 | 10.240 | 22.308 | 12.044 | 1.00 | 19.43 | B |
| ATOM | 5568 | CZ | TYR | B | 171 | 11.341 | 21.434 | 11.815 | 1.00 | 18.80 | B |
| ATOM | 5569 | OH | TYR | B | 171 | 12.618 | 21.865 | 11.685 | 1.00 | 18.79 | B |
| ATOM | 5570 | C | TYR | B | 171 | 7.870 | 18.507 | 13.892 | 1.00 | 20.15 | B |
| ATOM | 5571 | O | TYR | B | 171 | 8.436 | 18.914 | 14.935 | 1.00 | 19.24 | B |
| ATOM | 5572 | N | LYS | B | 172 | 8.006 | 17.258 | 13.369 | 1.00 | 20.37 | B |
| ATOM | 5573 | CA | LYS | B | 172 | 8.815 | 16.274 | 14.110 | 1.00 | 20.52 | B |
| ATOM | 5574 | CB | LYS | B | 172 | 8.426 | 14.837 | 13.861 | 1.00 | 20.27 | B |
| ATOM | 5575 | CG | LYS | B | 172 | 7.546 | 14.308 | 15.023 | 1.00 | 22.25 | B |
| ATOM | 5576 | CD | LYS | B | 172 | 6.364 | 15.276 | 15.341 | 1.00 | 22.36 | B |
| ATOM | 5577 | CE | LYS | B | 172 | 5.366 | 14.538 | 16.301 | 1.00 | 25.31 | B |
| ATOM | 5578 | NZ | LYS | B | 172 | 4.130 | 13.686 | 15.515 | 1.00 | 24.77 | B |
| ATOM | 5579 | C | LYS | B | 172 | 10.257 | 16.425 | 14.002 | 1.00 | 21.56 | B |
| ATOM | 5580 | O | LYS | B | 172 | 10.806 | 16.487 | 12.949 | 1.00 | 22.58 | B |
| ATOM | 5581 | N | LYS | B | 173 | 10.861 | 16.559 | 15.159 | 1.00 | 22.45 | B |
| ATOM | 5582 | CA | LYS | B | 173 | 12.273 | 16.767 | 15.371 | 1.00 | 21.91 | B |
| ATOM | 5583 | CB | LYS | B | 173 | 12.746 | 15.958 | 16.589 | 1.00 | 23.05 | B |
| ATOM | 5584 | CG | LYS | B | 173 | 11.858 | 16.199 | 17.845 | 1.00 | 23.33 | B |
| ATOM | 5585 | CD | LYS | B | 173 | 10.958 | 14.964 | 17.974 | 1.00 | 23.51 | B |
| ATOM | 5586 | CE | LYS | B | 173 | 9.492 | 15.287 | 18.483 | 1.00 | 22.79 | B |
| ATOM | 5587 | NZ | LYS | B | 173 | 8.844 | 16.223 | 17.430 | 1.00 | 22.82 | B |
| ATOM | 5588 | C | LYS | B | 173 | 13.215 | 16.543 | 14.303 | 1.00 | 21.24 | B |
| ATOM | 5589 | O | LYS | B | 173 | 13.193 | 17.281 | 13.362 | 1.00 | 20.74 | B |
| ATOM | 5590 | N | CYS | B | 174 | 14.157 | 15.656 | 14.573 | 1.00 | 21.13 | B |
| ATOM | 5591 | CA | CYS | B | 174 | 15.245 | 15.298 | 13.651 | 1.00 | 23.17 | B |
| ATOM | 5592 | CB | CYS | B | 174 | 14.860 | 15.616 | 12.163 | 1.00 | 25.74 | B |
| ATOM | 5593 | SG | CYS | B | 174 | 13.859 | 14.160 | 11.367 | 1.00 | 35.68 | B |
| ATOM | 5594 | C | CYS | B | 174 | 16.669 | 15.784 | 13.927 | 1.00 | 21.06 | B |
| ATOM | 5595 | O | CYS | B | 174 | 17.439 | 14.813 | 14.061 | 1.00 | 20.42 | B |
| ATOM | 5596 | OXT | CYS | B | 174 | 16.994 | 17.056 | 13.968 | 1.00 | 21.98 | B |
| ATOM | 5597 | CB | GLU | E | 1 | −40.500 | −14.824 | 45.862 | 1.00 | 17.54 | E |
| ATOM | 5598 | CG | GLU | E | 1 | −39.798 | −13.752 | 46.644 | 1.00 | 18.18 | E |
| ATOM | 5599 | CD | GLU | E | 1 | −38.300 | −13.513 | 46.180 | 1.00 | 19.81 | E |
| ATOM | 5600 | OE1 | GLU | E | 1 | −38.043 | −12.903 | 45.100 | 1.00 | 18.92 | E |
| ATOM | 5601 | OE2 | GLU | E | 1 | −37.344 | −13.944 | 46.882 | 1.00 | 19.29 | E |
| ATOM | 5602 | C | GLU | E | 1 | −42.565 | −15.542 | 47.249 | 1.00 | 18.49 | E |
| ATOM | 5603 | O | GLU | E | 1 | −43.079 | −14.826 | 48.077 | 1.00 | 19.61 | E |
| ATOM | 5604 | N | GLU | E | 1 | −42.604 | −13.559 | 45.628 | 1.00 | 16.63 | E |
| ATOM | 5605 | CA | GLU | E | 1 | −42.046 | −14.887 | 45.940 | 1.00 | 17.50 | E |
| ATOM | 5606 | N | VAL | E | 2 | −42.485 | −16.868 | 47.419 | 1.00 | 17.50 | E |
| ATOM | 5607 | CA | VAL | E | 2 | −42.997 | −17.499 | 48.610 | 1.00 | 15.10 | E |
| ATOM | 5608 | CB | VAL | E | 2 | −43.906 | −18.701 | 48.257 | 1.00 | 17.13 | E |
| ATOM | 5609 | CG1 | VAL | E | 2 | −44.173 | −19.546 | 49.391 | 1.00 | 16.22 | E |
| ATOM | 5610 | CG2 | VAL | E | 2 | −45.175 | −18.211 | 47.626 | 1.00 | 17.04 | E |
| ATOM | 5611 | C | VAL | E | 2 | −41.754 | −17.889 | 49.347 | 1.00 | 14.54 | E |
| ATOM | 5612 | O | VAL | E | 2 | −40.746 | −18.219 | 48.784 | 1.00 | 12.59 | E |
| ATOM | 5613 | N | VAL | E | 3 | −41.791 | −17.727 | 50.663 | 1.00 | 13.91 | E |
| ATOM | 5614 | CA | VAL | E | 3 | −40.605 | −18.009 | 51.463 | 1.00 | 13.41 | E |
| ATOM | 5615 | CB | VAL | E | 3 | −40.202 | −16.750 | 52.299 | 1.00 | 14.35 | E |
| ATOM | 5616 | CG1 | VAL | E | 3 | −38.890 | −17.047 | 53.011 | 1.00 | 15.74 | E |
| ATOM | 5617 | CG2 | VAL | E | 3 | −40.109 | −15.530 | 51.406 | 1.00 | 13.57 | E |
| ATOM | 5618 | C | VAL | E | 3 | −40.748 | −19.190 | 52.373 | 1.00 | 13.45 | E |
| ATOM | 5619 | O | VAL | E | 3 | −41.613 | −19.262 | 53.200 | 1.00 | 12.20 | E |
| ATOM | 5620 | N | LEU | E | 4 | −39.842 | −20.104 | 52.238 | 1.00 | 14.58 | E |
| ATOM | 5621 | CA | LEU | E | 4 | −39.850 | −21.301 | 53.045 | 1.00 | 17.59 | E |
| ATOM | 5622 | CB | LEU | E | 4 | −39.672 | −22.528 | 52.117 | 1.00 | 16.38 | E |
| ATOM | 5623 | CG | LEU | E | 4 | −40.414 | −22.490 | 50.797 | 1.00 | 16.05 | E |
| ATOM | 5624 | CD1 | LEU | E | 4 | −40.221 | −23.868 | 50.024 | 1.00 | 16.28 | E |
| ATOM | 5625 | CD2 | LEU | E | 4 | −41.853 | −22.204 | 51.090 | 1.00 | 15.40 | E |
| ATOM | 5626 | C | LEU | E | 4 | −38.620 | −21.142 | 53.762 | 1.00 | 17.49 | E |
| ATOM | 5627 | O | LEU | E | 4 | −37.672 | −21.207 | 53.125 | 1.00 | 21.18 | E |
| ATOM | 5628 | N | LEU | E | 5 | −38.494 | −21.012 | 55.023 | 1.00 | 16.67 | E |
| ATOM | 5629 | CA | LEU | E | 5 | −37.097 | −20.720 | 55.451 | 1.00 | 16.17 | E |
| ATOM | 5630 | CB | LEU | E | 5 | −36.085 | −21.782 | 55.078 | 1.00 | 14.47 | E |

TABLE 1-continued

| ATOM | 5631 | CG | LEU | E | 5 | −34.730 | −21.530 | 55.767 | 1.00 | 14.74 | E |
| ATOM | 5632 | CD1 | LEU | E | 5 | −35.041 | −21.139 | 57.195 | 1.00 | 17.46 | E |
| ATOM | 5633 | CD2 | LEU | E | 5 | −33.892 | −22.831 | 55.861 | 1.00 | 13.64 | E |
| ATOM | 5634 | C | LEU | E | 5 | −36.414 | −19.369 | 55.139 | 1.00 | 14.29 | E |
| ATOM | 5635 | O | LEU | E | 5 | −36.073 | −19.062 | 54.010 | 1.00 | 14.40 | E |
| ATOM | 5636 | N | ASP | E | 6 | −36.192 | −18.626 | 56.229 | 1.00 | 14.04 | E |
| ATOM | 5637 | CA | ASP | E | 6 | −35.520 | −17.319 | 56.248 | 1.00 | 15.78 | E |
| ATOM | 5638 | CB | ASP | E | 6 | −36.569 | −16.239 | 56.128 | 1.00 | 14.96 | E |
| ATOM | 5639 | CG | ASP | E | 6 | −35.983 | −14.969 | 55.851 | 1.00 | 15.94 | E |
| ATOM | 5640 | OD1 | ASP | E | 6 | −36.769 | −13.997 | 55.829 | 1.00 | 15.54 | E |
| ATOM | 5641 | OD2 | ASP | E | 6 | −34.733 | −14.947 | 55.617 | 1.00 | 16.51 | E |
| ATOM | 5642 | C | ASP | E | 6 | −34.712 | −17.094 | 57.540 | 1.00 | 13.60 | E |
| ATOM | 5643 | O | ASP | E | 6 | −35.239 | −16.630 | 58.544 | 1.00 | 12.68 | E |
| ATOM | 5644 | N | PHE | E | 7 | −33.443 | −17.407 | 57.450 | 1.00 | 13.80 | E |
| ATOM | 5645 | CA | PHE | E | 7 | −32.537 | −17.344 | 58.582 | 1.00 | 16.27 | E |
| ATOM | 5646 | CB | PHE | E | 7 | −31.089 | −17.747 | 58.178 | 1.00 | 16.28 | E |
| ATOM | 5647 | CG | PHE | E | 7 | −30.116 | −17.627 | 59.323 | 1.00 | 16.15 | E |
| ATOM | 5648 | CD1 | PHE | E | 7 | −30.099 | −18.560 | 60.356 | 1.00 | 16.21 | E |
| ATOM | 5649 | CD2 | PHE | E | 7 | −29.299 | −16.506 | 59.409 | 1.00 | 16.20 | E |
| ATOM | 5650 | CE1 | PHE | E | 7 | −29.249 | −18.350 | 61.473 | 1.00 | 17.54 | E |
| ATOM | 5651 | CE2 | PHE | E | 7 | −28.454 | −16.273 | 60.502 | 1.00 | 16.19 | E |
| ATOM | 5652 | CZ | PHE | E | 7 | −28.422 | −17.189 | 61.528 | 1.00 | 17.41 | E |
| ATOM | 5653 | C | PHE | E | 7 | −32.514 | −15.993 | 59.381 | 1.00 | 14.91 | E |
| ATOM | 5654 | O | PHE | E | 7 | −32.831 | −16.038 | 60.529 | 1.00 | 13.55 | E |
| ATOM | 5655 | N | ALA | E | 8 | −32.170 | −14.881 | 58.732 | 1.00 | 14.66 | E |
| ATOM | 5656 | CA | ALA | E | 8 | −32.149 | −13.567 | 59.391 | 1.00 | 15.47 | E |
| ATOM | 5657 | CB | ALA | E | 8 | −31.613 | −12.481 | 58.425 | 1.00 | 14.39 | E |
| ATOM | 5658 | C | ALA | E | 8 | −33.494 | −13.084 | 60.011 | 1.00 | 16.54 | E |
| ATOM | 5659 | O | ALA | E | 8 | −33.498 | −12.020 | 60.588 | 1.00 | 16.72 | E |
| ATOM | 5660 | N | ALA | E | 9 | −34.643 | −13.812 | 59.862 | 1.00 | 16.28 | E |
| ATOM | 5661 | CA | ALA | E | 9 | −35.886 | −13.363 | 60.464 | 1.00 | 16.12 | E |
| ATOM | 5662 | CB | ALA | E | 9 | −36.924 | −13.354 | 59.514 | 1.00 | 11.82 | E |
| ATOM | 5663 | C | ALA | E | 9 | −36.281 | −14.104 | 61.682 | 1.00 | 17.75 | E |
| ATOM | 5664 | O | ALA | E | 9 | −37.206 | −13.671 | 62.367 | 1.00 | 19.74 | E |
| ATOM | 5665 | N | ALA | E | 10 | −35.593 | −15.217 | 62.006 | 1.00 | 19.23 | E |
| ATOM | 5666 | CA | ALA | E | 10 | −35.894 | −16.051 | 63.239 | 1.00 | 20.03 | E |
| ATOM | 5667 | CB | ALA | E | 10 | −35.552 | −17.478 | 62.942 | 1.00 | 16.54 | E |
| ATOM | 5668 | C | ALA | E | 10 | −35.185 | −15.507 | 64.554 | 1.00 | 21.95 | E |
| ATOM | 5669 | O | ALA | E | 10 | −33.902 | −15.785 | 64.946 | 1.00 | 23.19 | E |
| ATOM | 5670 | N | GLY | E | 11 | −35.987 | −14.662 | 65.233 | 1.00 | 23.44 | E |
| ATOM | 5671 | CA | GLY | E | 11 | −35.614 | −13.986 | 66.559 | 1.00 | 23.93 | E |
| ATOM | 5672 | C | GLY | E | 11 | −35.226 | −14.881 | 67.817 | 1.00 | 23.95 | E |
| ATOM | 5673 | O | GLY | E | 11 | −35.879 | −14.913 | 68.900 | 1.00 | 23.53 | E |
| ATOM | 5674 | N | GLY | E | 12 | −34.154 | −15.672 | 67.574 | 1.00 | 22.90 | E |
| ATOM | 5675 | CA | GLY | E | 12 | −33.560 | −16.587 | 68.525 | 1.00 | 22.04 | E |
| ATOM | 5676 | C | GLY | E | 12 | −32.646 | −17.465 | 67.626 | 1.00 | 21.91 | E |
| ATOM | 5677 | O | GLY | E | 12 | −32.429 | −18.724 | 68.021 | 1.00 | 20.96 | E |
| ATOM | 5678 | N | GLU | E | 13 | −32.194 | −16.883 | 66.461 | 1.00 | 21.33 | E |
| ATOM | 5679 | CA | GLU | E | 13 | −31.283 | −17.622 | 65.514 | 1.00 | 23.11 | E |
| ATOM | 5680 | CB | GLU | E | 13 | −30.039 | −18.184 | 66.300 | 1.00 | 24.43 | E |
| ATOM | 5681 | CG | GLU | E | 13 | −29.989 | −18.022 | 68.018 | 1.00 | 28.30 | E |
| ATOM | 5682 | CD | GLU | E | 13 | −28.443 | −18.128 | 68.722 | 1.00 | 30.09 | E |
| ATOM | 5683 | OE1 | GLU | E | 13 | −27.472 | −17.924 | 67.876 | 1.00 | 32.18 | E |
| ATOM | 5684 | OE2 | GLU | E | 13 | −28.194 | −18.363 | 70.040 | 1.00 | 27.22 | E |
| ATOM | 5685 | C | GLU | E | 13 | −32.020 | −18.868 | 64.683 | 1.00 | 23.49 | E |
| ATOM | 5686 | O | GLU | E | 13 | −32.315 | −18.717 | 63.466 | 1.00 | 22.95 | E |
| ATOM | 5687 | N | LEU | E | 14 | −32.346 | −20.010 | 65.395 | 1.00 | 22.62 | E |
| ATOM | 5688 | CA | LEU | E | 14 | −33.008 | −21.138 | 64.772 | 1.00 | 23.06 | E |
| ATOM | 5689 | CB | LEU | E | 14 | −32.736 | −21.159 | 63.254 | 1.00 | 23.18 | E |
| ATOM | 5690 | CG | LEU | E | 14 | −33.972 | −20.635 | 62.512 | 1.00 | 23.29 | E |
| ATOM | 5691 | CD1 | LEU | E | 14 | −33.518 | −19.598 | 61.376 | 1.00 | 20.99 | E |
| ATOM | 5692 | CD2 | LEU | E | 14 | −34.839 | −21.857 | 61.967 | 1.00 | 22.45 | E |
| ATOM | 5693 | C | LEU | E | 14 | −32.666 | −22.566 | 65.258 | 1.00 | 23.87 | E |
| ATOM | 5694 | O | LEU | E | 14 | −31.551 | −22.891 | 65.900 | 1.00 | 24.06 | E |
| ATOM | 5695 | N | GLY | E | 15 | −33.585 | −23.439 | 64.828 | 1.00 | 21.87 | E |
| ATOM | 5696 | CA | GLY | E | 15 | −33.472 | −24.817 | 65.181 | 1.00 | 20.86 | E |
| ATOM | 5697 | C | GLY | E | 15 | −32.546 | −25.509 | 64.117 | 1.00 | 21.39 | E |
| ATOM | 5698 | O | GLY | E | 15 | −33.145 | −26.246 | 63.265 | 1.00 | 21.68 | E |
| ATOM | 5699 | N | TRP | E | 16 | −31.165 | −25.311 | 64.112 | 1.00 | 20.01 | E |
| ATOM | 5700 | CA | TRP | E | 16 | −30.314 | −25.971 | 63.086 | 1.00 | 17.82 | E |
| ATOM | 5701 | CB | TRP | E | 16 | −29.463 | −25.003 | 62.248 | 1.00 | 18.50 | E |
| ATOM | 5702 | CG | TRP | E | 16 | −30.275 | −24.111 | 61.422 | 1.00 | 18.62 | E |
| ATOM | 5703 | CD2 | TRP | E | 16 | −29.952 | −23.451 | 60.183 | 1.00 | 17.92 | E |
| ATOM | 5704 | CE2 | TRP | E | 16 | −31.013 | −22.578 | 59.870 | 1.00 | 17.33 | E |
| ATOM | 5705 | CE3 | TRP | E | 16 | −28.899 | −23.516 | 59.296 | 1.00 | 18.87 | E |
| ATOM | 5706 | CD1 | TRP | E | 16 | −31.483 | −23.628 | 61.776 | 1.00 | 18.88 | E |
| ATOM | 5707 | NE1 | TRP | E | 16 | −31.933 | −22.704 | 60.867 | 1.00 | 18.19 | E |
| ATOM | 5708 | CZ2 | TRP | E | 16 | −31.041 | −21.748 | 58.684 | 1.00 | 15.18 | E |
| ATOM | 5709 | CZ3 | TRP | E | 16 | −28.950 | −22.632 | 58.064 | 1.00 | 18.80 | E |
| ATOM | 5710 | CH2 | TRP | E | 16 | −30.032 | −21.784 | 57.817 | 1.00 | 14.99 | E |

TABLE 1-continued

| ATOM | 5711 | C | TRP | E | 16 | −29.414 | −26.981 | 63.742 | 1.00 | 17.93 | E |
|---|---|---|---|---|---|---|---|---|---|---|---|
| ATOM | 5712 | O | TRP | E | 16 | −29.262 | −26.946 | 64.907 | 1.00 | 18.57 | E |
| ATOM | 5713 | N | LEU | E | 17 | −28.932 | −27.930 | 62.981 | 1.00 | 16.32 | E |
| ATOM | 5714 | CA | LEU | E | 17 | −28.071 | −28.994 | 63.412 | 1.00 | 15.21 | E |
| ATOM | 5715 | CB | LEU | E | 17 | −28.536 | −30.308 | 62.782 | 1.00 | 16.25 | E |
| ATOM | 5716 | CG | LEU | E | 17 | −27.665 | −31.451 | 63.206 | 1.00 | 18.64 | E |
| ATOM | 5717 | CD1 | LEU | E | 17 | −27.566 | −31.413 | 64.766 | 1.00 | 19.94 | E |
| ATOM | 5718 | CD2 | LEU | E | 17 | −28.294 | −32.796 | 62.751 | 1.00 | 20.55 | E |
| ATOM | 5719 | C | LEU | E | 17 | −26.605 | −28.623 | 63.014 | 1.00 | 13.68 | E |
| ATOM | 5720 | O | LEU | E | 17 | −26.330 | −27.973 | 61.982 | 1.00 | 12.88 | E |
| ATOM | 5721 | N | THR | E | 18 | −25.693 | −29.023 | 63.871 | 1.00 | 13.55 | E |
| ATOM | 5722 | CA | THR | E | 18 | −24.291 | −28.681 | 63.752 | 1.00 | 14.74 | E |
| ATOM | 5723 | CB | THR | E | 18 | −24.018 | −27.573 | 64.744 | 1.00 | 14.30 | E |
| ATOM | 5724 | OG1 | THR | E | 18 | −24.107 | −26.349 | 63.988 | 1.00 | 14.02 | E |
| ATOM | 5725 | CG2 | THR | E | 18 | −22.791 | −27.774 | 65.450 | 1.00 | 13.43 | E |
| ATOM | 5726 | C | THR | E | 18 | −23.477 | −29.885 | 63.967 | 1.00 | 15.28 | E |
| ATOM | 5727 | O | THR | E | 18 | −23.401 | −30.353 | 65.072 | 1.00 | 13.96 | E |
| ATOM | 5728 | N | HIS | E | 19 | −22.815 | −30.370 | 62.910 | 1.00 | 17.68 | E |
| ATOM | 5729 | CA | HIS | E | 19 | −22.208 | −31.652 | 63.109 | 1.00 | 19.76 | E |
| ATOM | 5730 | CB | HIS | E | 19 | −22.121 | −32.424 | 61.850 | 1.00 | 20.70 | E |
| ATOM | 5731 | CG | HIS | E | 19 | −21.826 | −33.883 | 62.077 | 1.00 | 20.93 | E |
| ATOM | 5732 | CD2 | HIS | E | 19 | −21.168 | −34.800 | 61.307 | 1.00 | 19.15 | E |
| ATOM | 5733 | ND1 | HIS | E | 19 | −22.002 | −34.471 | 63.320 | 1.00 | 21.74 | E |
| ATOM | 5734 | CE1 | HIS | E | 19 | −21.452 | −35.678 | 63.299 | 1.00 | 20.25 | E |
| ATOM | 5735 | NE2 | HIS | E | 19 | −20.939 | −35.898 | 62.090 | 1.00 | 19.63 | E |
| ATOM | 5736 | C | HIS | E | 19 | −20.951 | −31.618 | 63.928 | 1.00 | 20.13 | E |
| ATOM | 5737 | O | HIS | E | 19 | −20.824 | −30.701 | 64.799 | 1.00 | 22.46 | E |
| ATOM | 5738 | N | PRO | E | 20 | −19.900 | −32.292 | 63.541 | 1.00 | 18.49 | E |
| ATOM | 5739 | CD | PRO | E | 20 | −19.381 | −31.767 | 62.283 | 1.00 | 16.99 | E |
| ATOM | 5740 | CA | PRO | E | 20 | −18.882 | −32.141 | 64.641 | 1.00 | 19.63 | E |
| ATOM | 5741 | CB | PRO | E | 20 | −17.796 | −31.279 | 64.041 | 1.00 | 17.90 | E |
| ATOM | 5742 | CG | PRO | E | 20 | −17.855 | −31.716 | 62.657 | 1.00 | 17.15 | E |
| ATOM | 5743 | C | PRO | E | 20 | −19.540 | −31.663 | 66.032 | 1.00 | 18.52 | E |
| ATOM | 5744 | O | PRO | E | 20 | −19.851 | −32.491 | 66.946 | 1.00 | 20.06 | E |
| ATOM | 5745 | N | TYR | E | 21 | −19.856 | −30.376 | 66.146 | 1.00 | 17.81 | E |
| ATOM | 5746 | CA | TYR | E | 21 | −20.479 | −29.748 | 67.381 | 1.00 | 17.96 | E |
| ATOM | 5747 | CB | TYR | E | 21 | −21.661 | −30.504 | 68.048 | 1.00 | 17.89 | E |
| ATOM | 5748 | CG | TYR | E | 21 | −22.219 | −29.594 | 69.152 | 1.00 | 18.42 | E |
| ATOM | 5749 | CD1 | TYR | E | 21 | −22.912 | −28.429 | 68.824 | 1.00 | 17.73 | E |
| ATOM | 5750 | CE1 | TYR | E | 21 | −23.212 | −27.482 | 69.809 | 1.00 | 15.75 | E |
| ATOM | 5751 | CD2 | TYR | E | 21 | −21.838 | −29.767 | 70.578 | 1.00 | 18.97 | E |
| ATOM | 5752 | CE2 | TYR | E | 21 | −22.120 | −28.806 | 71.524 | 1.00 | 15.43 | E |
| ATOM | 5753 | CZ | TYR | E | 21 | −22.802 | −27.688 | 71.129 | 1.00 | 15.38 | E |
| ATOM | 5754 | OH | TYR | E | 21 | −23.137 | −26.703 | 71.983 | 1.00 | 14.78 | E |
| ATOM | 5755 | C | TYR | E | 21 | −19.446 | −29.508 | 68.463 | 1.00 | 15.14 | E |
| ATOM | 5756 | O | TYR | E | 21 | −19.024 | −30.413 | 69.142 | 1.00 | 13.47 | E |
| ATOM | 5757 | N | GLY | E | 22 | −19.146 | −28.263 | 68.663 | 1.00 | 15.36 | E |
| ATOM | 5758 | CA | GLY | E | 22 | −18.160 | −27.923 | 69.667 | 1.00 | 16.75 | E |
| ATOM | 5759 | C | GLY | E | 22 | −17.061 | −26.999 | 69.146 | 1.00 | 16.87 | E |
| ATOM | 5760 | O | GLY | E | 22 | −16.768 | −26.026 | 69.814 | 1.00 | 18.12 | E |
| ATOM | 5761 | N | LYS | E | 23 | −16.572 | −27.290 | 67.938 | 1.00 | 16.06 | E |
| ATOM | 5762 | CA | LYS | E | 23 | −15.539 | −26.581 | 67.305 | 1.00 | 14.99 | E |
| ATOM | 5763 | CB | LYS | E | 23 | −14.285 | −27.454 | 67.272 | 1.00 | 16.08 | E |
| ATOM | 5764 | CG | LYS | E | 23 | −13.631 | −27.744 | 68.573 | 1.00 | 17.84 | E |
| ATOM | 5765 | CD | LYS | E | 23 | −14.083 | −29.042 | 69.254 | 1.00 | 20.21 | E |
| ATOM | 5766 | CE | LYS | E | 23 | −13.550 | −29.339 | 70.677 | 1.00 | 18.57 | E |
| ATOM | 5767 | NZ | LYS | E | 23 | −12.133 | −29.605 | 70.755 | 1.00 | 19.07 | E |
| ATOM | 5768 | C | LYS | E | 23 | −15.847 | −26.158 | 65.900 | 1.00 | 13.36 | E |
| ATOM | 5769 | O | LYS | E | 23 | −15.056 | −25.486 | 65.312 | 1.00 | 10.77 | E |
| ATOM | 5770 | N | GLY | E | 24 | −16.962 | −26.625 | 65.335 | 1.00 | 13.52 | E |
| ATOM | 5771 | CA | GLY | E | 24 | −17.251 | −26.320 | 63.938 | 1.00 | 14.07 | E |
| ATOM | 5772 | C | GLY | E | 24 | −18.091 | −25.056 | 63.874 | 1.00 | 14.52 | E |
| ATOM | 5773 | O | GLY | E | 24 | −17.796 | −24.077 | 64.557 | 1.00 | 12.98 | E |
| ATOM | 5774 | N | TRP | E | 25 | −19.137 | −25.100 | 63.044 | 1.00 | 15.04 | E |
| ATOM | 5775 | CA | TRP | E | 25 | −20.070 | −24.059 | 62.899 | 1.00 | 14.96 | E |
| ATOM | 5776 | CB | TRP | E | 25 | −21.109 | −24.547 | 61.977 | 1.00 | 14.57 | E |
| ATOM | 5777 | CG | TRP | E | 25 | −20.779 | −24.701 | 60.586 | 1.00 | 13.79 | E |
| ATOM | 5778 | CD2 | TRP | E | 25 | −20.759 | −23.685 | 59.635 | 1.00 | 14.35 | E |
| ATOM | 5779 | CE2 | TRP | E | 25 | −20.532 | −24.302 | 58.398 | 1.00 | 13.82 | E |
| ATOM | 5780 | CE3 | TRP | E | 25 | −20.900 | −22.278 | 59.703 | 1.00 | 15.59 | E |
| ATOM | 5781 | CD1 | TRP | E | 25 | −20.563 | −25.844 | 59.923 | 1.00 | 12.59 | E |
| ATOM | 5782 | NE1 | TRP | E | 25 | −20.411 | −25.625 | 58.641 | 1.00 | 11.10 | E |
| ATOM | 5783 | CZ2 | TRP | E | 25 | −20.454 | −23.586 | 57.194 | 1.00 | 15.85 | E |
| ATOM | 5784 | CZ3 | TRP | E | 25 | −20.815 | −21.557 | 58.553 | 1.00 | 18.05 | E |
| ATOM | 5785 | CH2 | TRP | E | 25 | −20.595 | −22.217 | 57.273 | 1.00 | 16.95 | E |
| ATOM | 5786 | C | TRP | E | 25 | −20.732 | −23.723 | 64.269 | 1.00 | 15.40 | E |
| ATOM | 5787 | O | TRP | E | 25 | −21.207 | −24.673 | 64.929 | 1.00 | 14.34 | E |
| ATOM | 5788 | N | ASP | E | 26 | −20.694 | −22.413 | 64.667 | 1.00 | 15.60 | E |
| ATOM | 5789 | CA | ASP | E | 26 | −21.345 | −21.845 | 65.886 | 1.00 | 16.44 | E |
| ATOM | 5790 | CB | ASP | E | 26 | −20.404 | −21.248 | 66.985 | 1.00 | 19.52 | E |

TABLE 1-continued

| ATOM | 5791 | CG | ASP | E | 26 | −19.460 | −22.253 | 67.711 | 1.00 | 24.25 | E |
|---|---|---|---|---|---|---|---|---|---|---|---|
| ATOM | 5792 | OD1 | ASP | E | 26 | −19.226 | −23.587 | 67.457 | 1.00 | 21.39 | E |
| ATOM | 5793 | OD2 | ASP | E | 26 | −18.858 | −21.525 | 68.691 | 1.00 | 28.89 | E |
| ATOM | 5794 | C | ASP | E | 26 | −22.294 | −20.640 | 65.562 | 1.00 | 15.01 | E |
| ATOM | 5795 | O | ASP | E | 26 | −21.956 | −19.648 | 64.835 | 1.00 | 12.18 | E |
| ATOM | 5796 | N | LEU | E | 27 | −23.483 | −20.735 | 66.161 | 1.00 | 14.51 | E |
| ATOM | 5797 | CA | LEU | E | 27 | −24.447 | −19.636 | 66.105 | 1.00 | 15.72 | E |
| ATOM | 5798 | CB | LEU | E | 27 | −25.732 | −20.153 | 66.656 | 1.00 | 16.61 | E |
| ATOM | 5799 | CG | LEU | E | 27 | −26.932 | −19.276 | 66.250 | 1.00 | 17.73 | E |
| ATOM | 5800 | CD1 | LEU | E | 27 | −27.044 | −18.900 | 64.742 | 1.00 | 15.98 | E |
| ATOM | 5801 | CD2 | LEU | E | 27 | −28.051 | −20.060 | 66.847 | 1.00 | 16.11 | E |
| ATOM | 5802 | C | LEU | E | 27 | −23.886 | −18.446 | 67.020 | 1.00 | 15.05 | E |
| ATOM | 5803 | O | LEU | E | 27 | −23.451 | −18.624 | 68.088 | 1.00 | 13.59 | E |
| ATOM | 5804 | N | MET | E | 28 | −23.903 | −17.274 | 66.489 | 1.00 | 15.13 | E |
| ATOM | 5805 | CA | MET | E | 28 | −23.357 | −16.196 | 67.135 | 1.00 | 17.09 | E |
| ATOM | 5806 | CB | MET | E | 28 | −21.965 | −15.846 | 66.552 | 1.00 | 19.52 | E |
| ATOM | 5807 | CG | MET | E | 28 | −20.966 | −16.978 | 66.587 | 1.00 | 22.38 | E |
| ATOM | 5808 | SD | MET | E | 28 | −19.171 | −16.558 | 66.266 | 1.00 | 26.05 | E |
| ATOM | 5809 | CE | MET | E | 28 | −18.792 | −15.296 | 67.763 | 1.00 | 22.95 | E |
| ATOM | 5810 | C | MET | E | 28 | −24.272 | −15.007 | 66.941 | 1.00 | 17.06 | E |
| ATOM | 5811 | O | MET | E | 28 | −24.839 | −14.805 | 65.817 | 1.00 | 16.55 | E |
| ATOM | 5812 | N | GLN | E | 29 | −24.367 | −14.197 | 68.009 | 1.00 | 16.75 | E |
| ATOM | 5813 | CA | GLN | E | 29 | −25.230 | −13.060 | 67.976 | 1.00 | 17.76 | E |
| ATOM | 5814 | CB | GLN | E | 29 | −26.292 | −13.229 | 69.066 | 1.00 | 17.99 | E |
| ATOM | 5815 | CG | GLN | E | 29 | −27.430 | −12.249 | 68.833 | 1.00 | 19.97 | E |
| ATOM | 5816 | CD | GLN | E | 29 | −28.060 | −11.758 | 70.130 | 1.00 | 20.58 | E |
| ATOM | 5817 | OE1 | GLN | E | 29 | −29.075 | −12.290 | 70.552 | 1.00 | 21.59 | E |
| ATOM | 5818 | NE2 | GLN | E | 29 | −27.461 | −10.749 | 70.756 | 1.00 | 19.62 | E |
| ATOM | 5819 | C | GLN | E | 29 | −24.560 | −11.669 | 68.133 | 1.00 | 18.79 | E |
| ATOM | 5820 | O | GLN | E | 29 | −24.124 | −11.291 | 69.233 | 1.00 | 18.82 | E |
| ATOM | 5821 | N | ASN | E | 30 | −24.559 | −10.880 | 67.061 | 1.00 | 18.71 | E |
| ATOM | 5822 | CA | ASN | E | 30 | −24.073 | −9.545 | 67.143 | 1.00 | 17.17 | E |
| ATOM | 5823 | CB | ASN | E | 30 | −23.344 | −9.130 | 65.918 | 1.00 | 16.68 | E |
| ATOM | 5824 | CG | ASN | E | 30 | −22.026 | −9.802 | 65.789 | 1.00 | 15.39 | E |
| ATOM | 5825 | OD1 | ASN | E | 30 | −21.550 | −9.981 | 64.657 | 1.00 | 16.10 | E |
| ATOM | 5826 | ND2 | ASN | E | 30 | −21.427 | −10.184 | 66.891 | 1.00 | 11.59 | E |
| ATOM | 5827 | C | ASN | E | 30 | −25.236 | −8.610 | 67.343 | 1.00 | 18.15 | E |
| ATOM | 5828 | O | ASN | E | 30 | −26.384 | −8.916 | 67.221 | 1.00 | 18.49 | E |
| ATOM | 5829 | N | ILE | E | 31 | −24.925 | −7.397 | 67.637 | 1.00 | 18.36 | E |
| ATOM | 5830 | CA | ILE | E | 31 | −26.001 | −6.532 | 67.812 | 1.00 | 17.29 | E |
| ATOM | 5831 | CB | ILE | E | 31 | −26.363 | −6.585 | 69.270 | 1.00 | 19.25 | E |
| ATOM | 5832 | CG2 | ILE | E | 31 | −25.198 | −6.130 | 70.057 | 1.00 | 19.58 | E |
| ATOM | 5833 | CG1 | ILE | E | 31 | −27.476 | −5.562 | 69.533 | 1.00 | 21.12 | E |
| ATOM | 5834 | CD1 | ILE | E | 31 | −28.002 | −5.736 | 70.901 | 1.00 | 22.51 | E |
| ATOM | 5835 | C | ILE | E | 31 | −25.622 | −5.140 | 67.336 | 1.00 | 16.35 | E |
| ATOM | 5836 | O | ILE | E | 31 | −24.620 | −4.673 | 67.607 | 1.00 | 14.86 | E |
| ATOM | 5837 | N | MET | E | 32 | −26.497 | −4.534 | 66.594 | 1.00 | 16.48 | E |
| ATOM | 5838 | CA | MET | E | 32 | −26.358 | −3.238 | 66.026 | 1.00 | 17.13 | E |
| ATOM | 5839 | CB | MET | E | 32 | −26.364 | −3.306 | 64.499 | 1.00 | 19.28 | E |
| ATOM | 5840 | CG | MET | E | 32 | −25.004 | −3.419 | 63.854 | 1.00 | 21.71 | E |
| ATOM | 5841 | SD | MET | E | 32 | −23.830 | −2.155 | 64.401 | 1.00 | 22.92 | E |
| ATOM | 5842 | CE | MET | E | 32 | −24.954 | −0.731 | 64.372 | 1.00 | 16.97 | E |
| ATOM | 5843 | C | MET | E | 32 | −27.634 | −2.527 | 66.318 | 1.00 | 17.04 | E |
| ATOM | 5844 | O | MET | E | 32 | −28.738 | −3.047 | 65.913 | 1.00 | 17.01 | E |
| ATOM | 5845 | N | ASN | E | 33 | −27.496 | −1.317 | 66.884 | 1.00 | 15.90 | E |
| ATOM | 5846 | CA | ASN | E | 33 | −28.623 | −0.421 | 67.215 | 1.00 | 15.39 | E |
| ATOM | 5847 | CB | ASN | E | 33 | −29.218 | 0.236 | 66.016 | 1.00 | 15.11 | E |
| ATOM | 5848 | CG | ASN | E | 33 | −28.229 | 1.024 | 65.257 | 1.00 | 16.41 | E |
| ATOM | 5849 | OD1 | ASN | E | 33 | −27.722 | 2.023 | 65.717 | 1.00 | 19.30 | E |
| ATOM | 5850 | ND2 | ASN | E | 33 | −27.952 | 0.612 | 64.060 | 1.00 | 15.69 | E |
| ATOM | 5851 | C | ASN | E | 33 | −29.705 | −1.225 | 67.847 | 1.00 | 16.58 | E |
| ATOM | 5852 | O | ASN | E | 33 | −30.867 | −1.120 | 67.418 | 1.00 | 16.52 | E |
| ATOM | 5853 | N | ASP | E | 34 | −29.312 | −2.040 | 68.816 | 1.00 | 15.97 | E |
| ATOM | 5854 | CA | ASP | E | 34 | −30.229 | −2.860 | 69.497 | 1.00 | 17.21 | E |
| ATOM | 5855 | CB | ASP | E | 34 | −31.286 | −1.973 | 70.230 | 1.00 | 17.98 | E |
| ATOM | 5856 | CG | ASP | E | 34 | −30.725 | −1.315 | 71.610 | 1.00 | 20.73 | E |
| ATOM | 5857 | OD1 | ASP | E | 34 | −29.505 | −0.884 | 71.756 | 1.00 | 20.64 | E |
| ATOM | 5858 | OD2 | ASP | E | 34 | −31.558 | −1.206 | 72.526 | 1.00 | 22.46 | E |
| ATOM | 5859 | C | ASP | E | 34 | −30.877 | −3.973 | 68.628 | 1.00 | 18.02 | E |
| ATOM | 5860 | O | ASP | E | 34 | −31.743 | −4.745 | 69.068 | 1.00 | 18.99 | E |
| ATOM | 5861 | N | MET | E | 35 | −30.507 | −4.110 | 67.388 | 1.00 | 16.56 | E |
| ATOM | 5862 | CA | MET | E | 35 | −31.123 | −5.256 | 66.742 | 1.00 | 15.52 | E |
| ATOM | 5863 | CB | MET | E | 35 | −31.361 | −4.912 | 65.256 | 1.00 | 15.76 | E |
| ATOM | 5864 | CG | MET | E | 35 | −32.481 | −3.858 | 65.058 | 1.00 | 15.64 | E |
| ATOM | 5865 | SD | MET | E | 35 | −34.138 | −4.470 | 65.755 | 1.00 | 18.42 | E |
| ATOM | 5866 | CE | MET | E | 35 | −34.066 | −3.713 | 67.487 | 1.00 | 18.66 | E |
| ATOM | 5867 | C | MET | E | 35 | −30.184 | −6.495 | 66.886 | 1.00 | 15.94 | E |
| ATOM | 5868 | O | MET | E | 35 | −28.963 | −6.362 | 66.744 | 1.00 | 14.48 | E |
| ATOM | 5869 | N | PRO | E | 36 | −30.707 | −7.661 | 67.305 | 1.00 | 14.21 | E |
| ATOM | 5870 | CD | PRO | E | 36 | −32.016 | −7.948 | 67.882 | 1.00 | 14.01 | E |

TABLE 1-continued

| | | | | | | | | | | |
|---|---|---|---|---|---|---|---|---|---|---|
| ATOM | 5871 | CA | PRO | E | 36 | −29.782 | −8.819 | 67.365 | 1.00 | 14.00 | E |
| ATOM | 5872 | CB | PRO | E | 36 | −30.496 | −9.825 | 68.208 | 1.00 | 14.34 | E |
| ATOM | 5873 | CG | PRO | E | 36 | −31.957 | −9.378 | 68.013 | 1.00 | 14.93 | E |
| ATOM | 5874 | C | PRO | E | 36 | −29.569 | −9.319 | 65.857 | 1.00 | 15.54 | E |
| ATOM | 5875 | O | PRO | E | 36 | −30.496 | −9.350 | 65.066 | 1.00 | 15.01 | E |
| ATOM | 5876 | N | ILE | E | 37 | −28.325 | −9.604 | 65.461 | 1.00 | 15.54 | E |
| ATOM | 5877 | CA | ILE | E | 37 | −27.975 | −10.056 | 64.104 | 1.00 | 14.11 | E |
| ATOM | 5878 | CB | ILE | E | 37 | −26.964 | −9.114 | 63.537 | 1.00 | 16.41 | E |
| ATOM | 5879 | CG2 | ILE | E | 37 | −26.731 | −9.324 | 62.110 | 1.00 | 11.52 | E |
| ATOM | 5880 | CG1 | ILE | E | 37 | −27.423 | −7.657 | 63.790 | 1.00 | 19.05 | E |
| ATOM | 5881 | CD1 | ILE | E | 37 | −28.756 | −7.427 | 63.345 | 1.00 | 21.44 | E |
| ATOM | 5882 | C | ILE | E | 37 | −27.370 | −11.438 | 64.314 | 1.00 | 14.61 | E |
| ATOM | 5883 | O | ILE | E | 37 | −26.295 | −11.566 | 64.785 | 1.00 | 13.92 | E |
| ATOM | 5884 | N | TYR | E | 38 | −28.089 | −12.510 | 64.023 | 1.00 | 14.65 | E |
| ATOM | 5885 | CA | TYR | E | 38 | −27.514 | −13.820 | 64.198 | 1.00 | 12.84 | E |
| ATOM | 5886 | CB | TYR | E | 38 | −28.551 | −14.819 | 64.445 | 1.00 | 13.47 | E |
| ATOM | 5887 | CG | TYR | E | 38 | −29.193 | −14.669 | 65.726 | 1.00 | 13.81 | E |
| ATOM | 5888 | CD1 | TYR | E | 38 | −30.242 | −13.747 | 65.926 | 1.00 | 13.74 | E |
| ATOM | 5889 | CE1 | TYR | E | 38 | −30.747 | −13.611 | 67.171 | 1.00 | 14.37 | E |
| ATOM | 5890 | CD2 | TYR | E | 38 | −28.734 | −15.407 | 66.803 | 1.00 | 12.72 | E |
| ATOM | 5891 | CE2 | TYR | E | 38 | −29.251 | −15.274 | 67.973 | 1.00 | 13.34 | E |
| ATOM | 5892 | CZ | TYR | E | 38 | −30.236 | −14.407 | 68.185 | 1.00 | 14.68 | E |
| ATOM | 5893 | OH | TYR | E | 38 | −30.746 | −14.426 | 69.445 | 1.00 | 18.73 | E |
| ATOM | 5894 | C | TYR | E | 38 | −26.769 | −14.243 | 62.963 | 1.00 | 13.57 | E |
| ATOM | 5895 | O | TYR | E | 38 | −27.008 | −13.725 | 61.867 | 1.00 | 12.74 | E |
| ATOM | 5896 | N | MET | E | 39 | −25.846 | −15.195 | 63.152 | 1.00 | 14.30 | E |
| ATOM | 5897 | CA | MET | E | 39 | −25.018 | −15.696 | 62.069 | 1.00 | 13.13 | E |
| ATOM | 5898 | CB | MET | E | 39 | −23.897 | −14.706 | 61.752 | 1.00 | 13.36 | E |
| ATOM | 5899 | CG | MET | E | 39 | −22.647 | −14.802 | 62.659 | 1.00 | 13.27 | E |
| ATOM | 5900 | SD | MET | E | 39 | −21.677 | −13.379 | 62.498 | 1.00 | 16.34 | E |
| ATOM | 5901 | CE | MET | E | 39 | −20.266 | −13.645 | 63.797 | 1.00 | 17.50 | E |
| ATOM | 5902 | C | MET | E | 39 | −24.431 | −17.017 | 62.421 | 1.00 | 13.77 | E |
| ATOM | 5903 | O | MET | E | 39 | −24.268 | −17.335 | 63.569 | 1.00 | 13.98 | E |
| ATOM | 5904 | N | TYR | E | 40 | −24.112 | −17.811 | 61.427 | 1.00 | 14.35 | E |
| ATOM | 5905 | CA | TYR | E | 40 | −23.447 | −19.063 | 61.681 | 1.00 | 14.12 | E |
| ATOM | 5906 | CB | TYR | E | 40 | −24.220 | −20.165 | 60.990 | 1.00 | 15.10 | E |
| ATOM | 5907 | CG | TYR | E | 40 | −25.184 | −20.927 | 61.932 | 1.00 | 17.57 | E |
| ATOM | 5908 | CD1 | TYR | E | 40 | −26.574 | −20.692 | 61.912 | 1.00 | 18.28 | E |
| ATOM | 5909 | CE1 | TYR | E | 40 | −27.386 | −21.272 | 62.805 | 1.00 | 18.00 | E |
| ATOM | 5910 | CD2 | TYR | E | 40 | −24.707 | −21.818 | 62.908 | 1.00 | 17.98 | E |
| ATOM | 5911 | CE2 | TYR | E | 40 | −25.552 | −22.407 | 63.792 | 1.00 | 18.04 | E |
| ATOM | 5912 | CZ | TYR | E | 40 | −26.867 | −22.127 | 63.736 | 1.00 | 18.27 | E |
| ATOM | 5913 | OH | TYR | E | 40 | −27.632 | −22.747 | 64.669 | 1.00 | 19.86 | E |
| ATOM | 5914 | C | TYR | E | 40 | −21.954 | −18.945 | 61.170 | 1.00 | 14.12 | E |
| ATOM | 5915 | O | TYR | E | 40 | −21.635 | −18.605 | 60.009 | 1.00 | 14.37 | E |
| ATOM | 5916 | N | SER | E | 41 | −21.008 | −19.182 | 62.027 | 1.00 | 15.04 | E |
| ATOM | 5917 | CA | SER | E | 41 | −19.617 | −19.062 | 61.576 | 1.00 | 14.94 | E |
| ATOM | 5918 | CB | SER | E | 41 | −19.061 | −17.678 | 61.905 | 1.00 | 17.47 | E |
| ATOM | 5919 | OG | SER | E | 41 | −19.170 | −17.393 | 63.258 | 1.00 | 17.12 | E |
| ATOM | 5920 | C | SER | E | 41 | −18.631 | −20.110 | 62.051 | 1.00 | 13.51 | E |
| ATOM | 5921 | O | SER | E | 41 | −18.896 | −20.803 | 63.007 | 1.00 | 12.21 | E |
| ATOM | 5922 | N | VAL | E | 42 | −17.534 | −20.245 | 61.309 | 1.00 | 14.01 | E |
| ATOM | 5923 | CA | VAL | E | 42 | −16.479 | −21.210 | 61.626 | 1.00 | 14.68 | E |
| ATOM | 5924 | CB | VAL | E | 42 | −16.298 | −22.494 | 60.687 | 1.00 | 15.07 | E |
| ATOM | 5925 | CG1 | VAL | E | 42 | −16.034 | −23.748 | 61.536 | 1.00 | 13.46 | E |
| ATOM | 5926 | CG2 | VAL | E | 42 | −17.404 | −22.583 | 59.579 | 1.00 | 13.20 | E |
| ATOM | 5927 | C | VAL | E | 42 | −15.338 | −20.506 | 61.156 | 1.00 | 14.82 | E |
| ATOM | 5928 | O | VAL | E | 42 | −15.487 | −19.687 | 60.269 | 1.00 | 14.86 | E |
| ATOM | 5929 | N | CYS | E | 43 | −14.189 | −20.932 | 61.648 | 1.00 | 14.99 | E |
| ATOM | 5930 | CA | CYS | E | 43 | −12.894 | −20.349 | 61.288 | 1.00 | 14.83 | E |
| ATOM | 5931 | C | CYS | E | 43 | −11.772 | −21.274 | 61.714 | 1.00 | 16.17 | E |
| ATOM | 5932 | O | CYS | E | 43 | −10.801 | −20.726 | 62.229 | 1.00 | 18.57 | E |
| ATOM | 5933 | CB | CYS | E | 43 | −12.661 | −18.964 | 61.976 | 1.00 | 12.22 | E |
| ATOM | 5934 | SG | CYS | E | 43 | −11.473 | −17.828 | 61.237 | 1.00 | 9.84 | E |
| ATOM | 5935 | N | ASN | E | 44 | −11.893 | −22.609 | 61.541 | 1.00 | 14.86 | E |
| ATOM | 5936 | CA | ASN | E | 44 | −10.797 | −23.518 | 61.806 | 1.00 | 12.39 | E |
| ATOM | 5937 | CB | ASN | E | 44 | −11.321 | −24.892 | 62.195 | 1.00 | 14.16 | E |
| ATOM | 5938 | CG | ASN | E | 44 | −12.166 | −24.846 | 63.378 | 1.00 | 15.67 | E |
| ATOM | 5939 | OD1 | ASN | E | 44 | −13.100 | −25.573 | 63.468 | 1.00 | 18.08 | E |
| ATOM | 5940 | ND2 | ASN | E | 44 | −11.864 | −23.967 | 64.322 | 1.00 | 17.65 | E |
| ATOM | 5941 | C | ASN | E | 44 | −9.792 | −23.639 | 60.636 | 1.00 | 10.64 | E |
| ATOM | 5942 | O | ASN | E | 44 | −9.530 | −24.683 | 60.117 | 1.00 | 8.56 | E |
| ATOM | 5943 | N | VAL | E | 45 | −9.213 | −22.511 | 60.278 | 1.00 | 11.44 | E |
| ATOM | 5944 | CA | VAL | E | 45 | −8.229 | −22.324 | 59.221 | 1.00 | 14.14 | E |
| ATOM | 5945 | CB | VAL | E | 45 | −8.092 | −20.889 | 58.766 | 1.00 | 14.24 | E |
| ATOM | 5946 | CG1 | VAL | E | 45 | −9.360 | −20.474 | 58.209 | 1.00 | 15.73 | E |
| ATOM | 5947 | CG2 | VAL | E | 45 | −7.643 | −19.929 | 59.958 | 1.00 | 15.14 | E |
| ATOM | 5948 | C | VAL | E | 45 | −6.849 | −22.771 | 59.578 | 1.00 | 13.90 | E |
| ATOM | 5949 | O | VAL | E | 45 | −6.031 | −22.904 | 58.696 | 1.00 | 15.60 | E |
| ATOM | 5950 | N | MET | E | 46 | −6.623 | −23.091 | 60.826 | 1.00 | 14.87 | E |

TABLE 1-continued

| | | | | | | | | | | |
|---|---|---|---|---|---|---|---|---|---|---|
| ATOM | 5951 | CA | MET | E | 46 | −5.311 | −23.442 | 61.294 | 1.00 | 17.11 | E |
| ATOM | 5952 | CB | MET | E | 46 | −5.095 | −22.675 | 62.626 | 1.00 | 18.14 | E |
| ATOM | 5953 | CG | MET | E | 46 | −3.816 | −21.754 | 62.749 | 1.00 | 20.11 | E |
| ATOM | 5954 | SD | MET | E | 46 | −3.301 | −20.497 | 61.489 | 1.00 | 23.45 | E |
| ATOM | 5955 | CE | MET | E | 46 | −3.996 | −18.896 | 62.261 | 1.00 | 20.43 | E |
| ATOM | 5956 | C | MET | E | 46 | −5.144 | −24.945 | 61.488 | 1.00 | 16.99 | E |
| ATOM | 5957 | O | MET | E | 46 | −4.113 | −25.401 | 61.986 | 1.00 | 16.29 | E |
| ATOM | 5958 | N | SER | E | 47 | −6.182 | −25.717 | 61.178 | 1.00 | 17.58 | E |
| ATOM | 5959 | CA | SER | E | 47 | −6.051 | −27.173 | 61.337 | 1.00 | 19.69 | E |
| ATOM | 5960 | CB | SER | E | 47 | −6.878 | −27.703 | 62.453 | 1.00 | 18.09 | E |
| ATOM | 5961 | OG | SER | E | 47 | −7.296 | −26.542 | 63.170 | 1.00 | 26.32 | E |
| ATOM | 5962 | C | SER | E | 47 | −6.549 | −27.744 | 60.014 | 1.00 | 20.59 | E |
| ATOM | 5963 | O | SER | E | 47 | −7.342 | −27.120 | 59.271 | 1.00 | 22.35 | E |
| ATOM | 5964 | N | GLY | E | 48 | −6.109 | −28.923 | 59.670 | 1.00 | 20.61 | E |
| ATOM | 5965 | CA | GLY | E | 48 | −6.564 | −29.375 | 58.409 | 1.00 | 19.90 | E |
| ATOM | 5966 | C | GLY | E | 48 | −7.683 | −30.341 | 58.520 | 1.00 | 19.69 | E |
| ATOM | 5967 | O | GLY | E | 48 | −8.174 | −30.607 | 59.629 | 1.00 | 19.11 | E |
| ATOM | 5968 | N | ASP | E | 49 | −8.095 | −30.832 | 57.349 | 1.00 | 19.65 | E |
| ATOM | 5969 | CA | ASP | E | 49 | −9.110 | −31.844 | 57.337 | 1.00 | 20.07 | E |
| ATOM | 5970 | CB | ASP | E | 49 | −8.640 | −33.018 | 58.220 | 1.00 | 20.56 | E |
| ATOM | 5971 | CG | ASP | E | 49 | −7.290 | −33.608 | 57.790 | 1.00 | 22.27 | E |
| ATOM | 5972 | OD1 | ASP | E | 49 | −6.364 | −33.840 | 58.719 | 1.00 | 20.74 | E |
| ATOM | 5973 | OD2 | ASP | E | 49 | −7.217 | −33.852 | 56.538 | 1.00 | 20.58 | E |
| ATOM | 5974 | C | ASP | E | 49 | −10.457 | −31.320 | 57.942 | 1.00 | 19.87 | E |
| ATOM | 5975 | O | ASP | E | 49 | −11.171 | −32.094 | 58.567 | 1.00 | 19.81 | E |
| ATOM | 5976 | N | GLN | E | 50 | −10.830 | −30.067 | 57.807 | 1.00 | 18.83 | E |
| ATOM | 5977 | CA | GLN | E | 50 | −12.097 | −29.712 | 58.400 | 1.00 | 17.49 | E |
| ATOM | 5978 | CB | GLN | E | 50 | −12.257 | −28.189 | 58.416 | 1.00 | 17.76 | E |
| ATOM | 5979 | CG | GLN | E | 50 | −11.228 | −27.449 | 59.312 | 1.00 | 14.96 | E |
| ATOM | 5980 | CD | GLN | E | 50 | −11.217 | −28.037 | 60.799 | 1.00 | 14.65 | E |
| ATOM | 5981 | OE1 | GLN | E | 50 | −12.187 | −27.926 | 61.487 | 1.00 | 11.71 | E |
| ATOM | 5982 | NE2 | GLN | E | 50 | −10.107 | −28.646 | 61.238 | 1.00 | 13.70 | E |
| ATOM | 5983 | C | GLN | E | 50 | −13.186 | −30.333 | 57.553 | 1.00 | 17.28 | E |
| ATOM | 5984 | O | GLN | E | 50 | −13.048 | −30.398 | 56.353 | 1.00 | 17.32 | E |
| ATOM | 5985 | N | ASP | E | 51 | −14.238 | −30.828 | 58.217 | 1.00 | 15.92 | E |
| ATOM | 5986 | CA | ASP | E | 51 | −15.448 | −31.391 | 57.602 | 1.00 | 13.69 | E |
| ATOM | 5987 | CB | ASP | E | 51 | −15.380 | −32.903 | 57.463 | 1.00 | 13.32 | E |
| ATOM | 5988 | CG | ASP | E | 51 | −16.500 | −33.466 | 56.555 | 1.00 | 14.48 | E |
| ATOM | 5989 | OD1 | ASP | E | 51 | −16.748 | −34.687 | 56.615 | 1.00 | 15.60 | E |
| ATOM | 5990 | OD2 | ASP | E | 51 | −17.168 | −32.721 | 55.801 | 1.00 | 12.38 | E |
| ATOM | 5991 | C | ASP | E | 51 | −16.613 | −30.985 | 58.525 | 1.00 | 11.84 | E |
| ATOM | 5992 | O | ASP | E | 51 | −17.261 | −31.764 | 59.171 | 1.00 | 9.71 | E |
| ATOM | 5993 | N | ASN | E | 52 | −16.875 | −29.721 | 58.568 | 1.00 | 12.37 | E |
| ATOM | 5994 | CA | ASN | E | 52 | −17.958 | −29.250 | 59.440 | 1.00 | 15.07 | E |
| ATOM | 5995 | CB | ASN | E | 52 | −17.491 | −27.968 | 60.169 | 1.00 | 14.14 | E |
| ATOM | 5996 | CG | ASN | E | 52 | −16.213 | −28.166 | 60.761 | 1.00 | 13.78 | E |
| ATOM | 5997 | OD1 | ASN | E | 52 | −16.098 | −29.046 | 61.629 | 1.00 | 15.37 | E |
| ATOM | 5998 | ND2 | ASN | E | 52 | −15.192 | −27.419 | 60.298 | 1.00 | 11.95 | E |
| ATOM | 5999 | C | ASN | E | 52 | −19.278 | −28.985 | 58.722 | 1.00 | 13.95 | E |
| ATOM | 6000 | O | ASN | E | 52 | −19.312 | −28.323 | 57.714 | 1.00 | 14.08 | E |
| ATOM | 6001 | N | TRP | E | 53 | −20.349 | −29.425 | 59.326 | 1.00 | 14.78 | E |
| ATOM | 6002 | CA | TRP | E | 53 | −21.630 | −29.321 | 58.711 | 1.00 | 16.85 | E |
| ATOM | 6003 | CB | TRP | E | 53 | −22.166 | −30.757 | 58.350 | 1.00 | 15.38 | E |
| ATOM | 6004 | CG | TRP | E | 53 | −21.429 | −31.463 | 57.272 | 1.00 | 14.26 | E |
| ATOM | 6005 | CD2 | TRP | E | 53 | −21.829 | −31.594 | 55.924 | 1.00 | 15.05 | E |
| ATOM | 6006 | CE2 | TRP | E | 53 | −20.817 | −32.309 | 55.278 | 1.00 | 15.74 | E |
| ATOM | 6007 | CE3 | TRP | E | 53 | −22.947 | −31.205 | 55.201 | 1.00 | 15.77 | E |
| ATOM | 6008 | CD1 | TRP | E | 53 | −20.238 | −32.071 | 57.377 | 1.00 | 13.30 | E |
| ATOM | 6009 | NE1 | TRP | E | 53 | −19.837 | −32.571 | 56.198 | 1.00 | 14.03 | E |
| ATOM | 6010 | CZ2 | TRP | E | 53 | −20.915 | −32.625 | 53.915 | 1.00 | 16.65 | E |
| ATOM | 6011 | CZ3 | TRP | E | 53 | −23.028 | −31.533 | 53.857 | 1.00 | 15.77 | E |
| ATOM | 6012 | CH2 | TRP | E | 53 | −22.040 | −32.227 | 53.238 | 1.00 | 17.16 | E |
| ATOM | 6013 | C | TRP | E | 53 | −22.668 | −28.582 | 59.525 | 1.00 | 16.97 | E |
| ATOM | 6014 | O | TRP | E | 53 | −22.757 | −28.718 | 60.775 | 1.00 | 17.52 | E |
| ATOM | 6015 | N | LEU | E | 54 | −23.425 | −27.790 | 58.762 | 1.00 | 15.79 | E |
| ATOM | 6016 | CA | LEU | E | 54 | −24.532 | −27.064 | 59.258 | 1.00 | 14.14 | E |
| ATOM | 6017 | CB | LEU | E | 54 | −24.342 | −25.581 | 59.014 | 1.00 | 14.07 | E |
| ATOM | 6018 | CG | LEU | E | 54 | −25.539 | −24.734 | 59.468 | 1.00 | 12.73 | E |
| ATOM | 6019 | CD1 | LEU | E | 54 | −25.721 | −24.831 | 60.979 | 1.00 | 8.56 | E |
| ATOM | 6020 | CD2 | LEU | E | 54 | −25.323 | −23.339 | 59.035 | 1.00 | 11.88 | E |
| ATOM | 6021 | C | LEU | E | 54 | −25.747 | −27.549 | 58.437 | 1.00 | 14.50 | E |
| ATOM | 6022 | O | LEU | E | 54 | −25.755 | −27.524 | 57.172 | 1.00 | 12.15 | E |
| ATOM | 6023 | N | ARG | E | 55 | −26.771 | −28.004 | 59.169 | 1.00 | 13.75 | E |
| ATOM | 6024 | CA | ARG | E | 55 | −27.985 | −28.409 | 58.542 | 1.00 | 13.63 | E |
| ATOM | 6025 | CB | ARG | E | 55 | −28.313 | −29.875 | 58.751 | 1.00 | 16.67 | E |
| ATOM | 6026 | CG | ARG | E | 55 | −29.633 | −30.231 | 58.023 | 1.00 | 18.39 | E |
| ATOM | 6027 | CD | ARG | E | 55 | −29.835 | −31.688 | 57.901 | 1.00 | 19.82 | E |
| ATOM | 6028 | NE | ARG | E | 55 | −30.804 | −32.309 | 58.818 | 1.00 | 19.78 | E |
| ATOM | 6029 | CZ | ARG | E | 55 | −30.888 | −32.045 | 60.074 | 1.00 | 17.91 | E |
| ATOM | 6030 | NH1 | ARG | E | 55 | −30.073 | −31.162 | 60.543 | 1.00 | 19.61 | E |

TABLE 1-continued

| | | | | | | | | | |
|---|---|---|---|---|---|---|---|---|---|
| ATOM | 6031 | NH2 | ARG | E | 55 | −31.735 | −32.706 | 60.813 | 1.00 | 15.91 | E |
| ATOM | 6032 | C | ARG | E | 55 | −29.157 | −27.618 | 58.970 | 1.00 | 13.96 | E |
| ATOM | 6033 | O | ARG | E | 55 | −29.403 | −27.433 | 60.115 | 1.00 | 12.33 | E |
| ATOM | 6034 | N | THR | E | 56 | −29.917 | −27.146 | 57.990 | 1.00 | 14.93 | E |
| ATOM | 6035 | CA | THR | E | 56 | −31.120 | −26.413 | 58.350 | 1.00 | 15.15 | E |
| ATOM | 6036 | CB | THR | E | 56 | −31.817 | −25.778 | 57.147 | 1.00 | 16.31 | E |
| ATOM | 6037 | OG1 | THR | E | 56 | −32.375 | −26.829 | 56.370 | 1.00 | 16.16 | E |
| ATOM | 6038 | CG2 | THR | E | 56 | −30.924 | −24.988 | 56.303 | 1.00 | 13.90 | E |
| ATOM | 6039 | C | THR | E | 56 | −32.101 | −27.510 | 58.878 | 1.00 | 15.78 | E |
| ATOM | 6040 | O | THR | E | 56 | −31.839 | −28.750 | 58.907 | 1.00 | 15.27 | E |
| ATOM | 6041 | N | ASN | E | 57 | −33.268 | −27.029 | 59.252 | 1.00 | 16.68 | E |
| ATOM | 6042 | CA | ASN | E | 57 | −34.271 | −27.946 | 59.679 | 1.00 | 16.58 | E |
| ATOM | 6043 | CB | ASN | E | 57 | −35.163 | −27.337 | 60.751 | 1.00 | 19.69 | E |
| ATOM | 6044 | CG | ASN | E | 57 | −35.055 | −28.107 | 62.075 | 1.00 | 23.08 | E |
| ATOM | 6045 | OD1 | ASN | E | 57 | −34.077 | −27.896 | 62.856 | 1.00 | 22.94 | E |
| ATOM | 6046 | ND2 | ASN | E | 57 | −36.035 | −29.074 | 62.311 | 1.00 | 22.21 | E |
| ATOM | 6047 | C | ASN | E | 57 | −35.100 | −28.328 | 58.552 | 1.00 | 14.30 | E |
| ATOM | 6048 | O | ASN | E | 57 | −35.004 | −27.744 | 57.516 | 1.00 | 12.02 | E |
| ATOM | 6049 | N | TRP | E | 58 | −35.924 | −29.330 | 58.829 | 1.00 | 14.50 | E |
| ATOM | 6050 | CA | TRP | E | 58 | −36.908 | −29.960 | 57.906 | 1.00 | 14.67 | E |
| ATOM | 6051 | CB | TRP | E | 58 | −37.772 | −30.901 | 58.719 | 1.00 | 16.80 | E |
| ATOM | 6052 | CG | TRP | E | 58 | −38.855 | −31.635 | 58.026 | 1.00 | 20.49 | E |
| ATOM | 6053 | CD2 | TRP | E | 58 | −38.736 | −32.429 | 56.891 | 1.00 | 21.32 | E |
| ATOM | 6054 | CE2 | TRP | E | 58 | −40.018 | −33.041 | 56.653 | 1.00 | 22.89 | E |
| ATOM | 6055 | CE3 | TRP | E | 58 | −37.692 | −32.700 | 56.034 | 1.00 | 21.09 | E |
| ATOM | 6056 | CD1 | TRP | E | 58 | −40.177 | −31.760 | 58.446 | 1.00 | 24.00 | E |
| ATOM | 6057 | NE1 | TRP | E | 58 | −40.884 | −32.609 | 57.622 | 1.00 | 24.86 | E |
| ATOM | 6058 | CZ2 | TRP | E | 58 | −40.253 | −33.924 | 55.568 | 1.00 | 23.20 | E |
| ATOM | 6059 | CZ3 | TRP | E | 58 | −37.927 | −33.586 | 54.951 | 1.00 | 21.85 | E |
| ATOM | 6060 | CH2 | TRP | E | 58 | −39.192 | −34.181 | 54.739 | 1.00 | 23.10 | E |
| ATOM | 6061 | C | TRP | E | 58 | −37.742 | −28.884 | 57.224 | 1.00 | 14.39 | E |
| ATOM | 6062 | O | TRP | E | 58 | −38.357 | −28.091 | 57.838 | 1.00 | 13.90 | E |
| ATOM | 6063 | N | VAL | E | 59 | −37.748 | −28.845 | 55.911 | 1.00 | 16.03 | E |
| ATOM | 6064 | CA | VAL | E | 59 | −38.491 | −27.784 | 55.247 | 1.00 | 16.25 | E |
| ATOM | 6065 | CB | VAL | E | 59 | −37.495 | −26.765 | 54.464 | 1.00 | 16.30 | E |
| ATOM | 6066 | CG1 | VAL | E | 59 | −38.263 | −25.743 | 53.635 | 1.00 | 14.52 | E |
| ATOM | 6067 | CG2 | VAL | E | 59 | −36.534 | −26.072 | 55.464 | 1.00 | 11.90 | E |
| ATOM | 6068 | C | VAL | E | 59 | −39.419 | −28.504 | 54.283 | 1.00 | 16.84 | E |
| ATOM | 6069 | O | VAL | E | 59 | −38.973 | −29.270 | 53.458 | 1.00 | 18.24 | E |
| ATOM | 6070 | N | TYR | E | 60 | −40.707 | −28.182 | 54.397 | 1.00 | 17.02 | E |
| ATOM | 6071 | CA | TYR | E | 60 | −41.768 | −28.723 | 53.615 | 1.00 | 14.98 | E |
| ATOM | 6072 | CB | TYR | E | 60 | −43.129 | −28.336 | 54.158 | 1.00 | 14.59 | E |
| ATOM | 6073 | CG | TYR | E | 60 | −43.611 | −29.095 | 55.351 | 1.00 | 15.80 | E |
| ATOM | 6074 | CD1 | TYR | E | 60 | −43.637 | −28.499 | 56.622 | 1.00 | 15.68 | E |
| ATOM | 6075 | CE1 | TYR | E | 60 | −43.922 | −29.242 | 57.751 | 1.00 | 15.80 | E |
| ATOM | 6076 | CD2 | TYR | E | 60 | −43.897 | −30.444 | 55.277 | 1.00 | 15.96 | E |
| ATOM | 6077 | CE2 | TYR | E | 60 | −44.189 | −31.166 | 56.441 | 1.00 | 16.82 | E |
| ATOM | 6078 | CZ | TYR | E | 60 | −44.195 | −30.531 | 57.660 | 1.00 | 15.99 | E |
| ATOM | 6079 | OH | TYR | E | 60 | −44.528 | −31.262 | 58.779 | 1.00 | 18.24 | E |
| ATOM | 6080 | C | TYR | E | 60 | −41.651 | −28.148 | 52.248 | 1.00 | 15.23 | E |
| ATOM | 6081 | O | TYR | E | 60 | −41.393 | −26.968 | 52.099 | 1.00 | 15.08 | E |
| ATOM | 6082 | N | ARG | E | 61 | −41.842 | −28.984 | 51.222 | 1.00 | 15.41 | E |
| ATOM | 6083 | CA | ARG | E | 61 | −41.782 | −28.483 | 49.873 | 1.00 | 15.24 | E |
| ATOM | 6084 | CB | ARG | E | 61 | −41.580 | −29.651 | 48.948 | 1.00 | 16.41 | E |
| ATOM | 6085 | CG | ARG | E | 61 | −41.865 | −29.377 | 47.389 | 1.00 | 16.00 | E |
| ATOM | 6086 | CD | ARG | E | 61 | −41.389 | −30.574 | 46.567 | 1.00 | 16.59 | E |
| ATOM | 6087 | NE | ARG | E | 61 | −42.411 | −31.648 | 46.589 | 1.00 | 14.77 | E |
| ATOM | 6088 | CZ | ARG | E | 61 | −43.534 | −31.596 | 45.859 | 1.00 | 12.78 | E |
| ATOM | 6089 | NH1 | ARG | E | 61 | −43.774 | −30.579 | 45.066 | 1.00 | 13.11 | E |
| ATOM | 6090 | NH2 | ARG | E | 61 | −44.450 | −32.495 | 45.982 | 1.00 | 11.46 | E |
| ATOM | 6091 | C | ARG | E | 61 | −43.053 | −27.761 | 49.433 | 1.00 | 15.89 | E |
| ATOM | 6092 | O | ARG | E | 61 | −43.083 | −26.832 | 48.623 | 1.00 | 15.16 | E |
| ATOM | 6093 | N | GLY | E | 62 | −44.142 | −28.232 | 49.964 | 1.00 | 17.47 | E |
| ATOM | 6094 | CA | GLY | E | 62 | −45.448 | −27.758 | 49.507 | 1.00 | 18.94 | E |
| ATOM | 6095 | C | GLY | E | 62 | −45.549 | −27.969 | 47.960 | 1.00 | 20.23 | E |
| ATOM | 6096 | O | GLY | E | 62 | −45.263 | −29.046 | 47.402 | 1.00 | 20.50 | E |
| ATOM | 6097 | N | GLU | E | 63 | −45.857 | −26.899 | 47.251 | 1.00 | 21.20 | E |
| ATOM | 6098 | CA | GLU | E | 63 | −46.056 | −26.938 | 45.804 | 1.00 | 20.96 | E |
| ATOM | 6099 | CB | GLU | E | 63 | −47.237 | −25.961 | 45.542 | 1.00 | 20.90 | E |
| ATOM | 6100 | CG | GLU | E | 63 | −47.547 | −25.661 | 44.165 | 1.00 | 22.47 | E |
| ATOM | 6101 | CD | GLU | E | 63 | −48.359 | −26.798 | 43.581 | 1.00 | 26.60 | E |
| ATOM | 6102 | OE1 | GLU | E | 63 | −48.673 | −26.771 | 42.304 | 1.00 | 24.49 | E |
| ATOM | 6103 | OE2 | GLU | E | 63 | −48.679 | −27.728 | 44.499 | 1.00 | 30.49 | E |
| ATOM | 6104 | C | GLU | E | 63 | −44.752 | −26.552 | 45.064 | 1.00 | 21.80 | E |
| ATOM | 6105 | O | GLU | E | 63 | −44.712 | −26.519 | 43.875 | 1.00 | 23.85 | E |
| ATOM | 6106 | N | ALA | E | 64 | −43.634 | −26.293 | 45.714 | 1.00 | 21.22 | E |
| ATOM | 6107 | CA | ALA | E | 64 | −42.449 | −25.876 | 44.961 | 1.00 | 19.40 | E |
| ATOM | 6108 | CB | ALA | E | 64 | −41.409 | −25.422 | 45.948 | 1.00 | 14.31 | E |
| ATOM | 6109 | C | ALA | E | 64 | −41.875 | −27.019 | 44.066 | 1.00 | 19.72 | E |
| ATOM | 6110 | O | ALA | E | 64 | −41.899 | −28.200 | 44.480 | 1.00 | 21.85 | E |

TABLE 1-continued

| | | | | | | | | | |
|---|---|---|---|---|---|---|---|---|---|
| ATOM | 6111 | N | GLU | E | 65 | −41.361 | −26.686 | 42.860 | 1.00 | 19.85 | E |
| ATOM | 6112 | CA | GLU | E | 65 | −40.656 | −27.656 | 41.960 | 1.00 | 19.09 | E |
| ATOM | 6113 | CB | GLU | E | 65 | −41.137 | −27.553 | 40.527 | 1.00 | 20.89 | E |
| ATOM | 6114 | CG | GLU | E | 65 | −42.735 | −27.667 | 40.331 | 1.00 | 24.27 | E |
| ATOM | 6115 | CD | GLU | E | 65 | −43.218 | −29.161 | 40.123 | 1.00 | 25.72 | E |
| ATOM | 6116 | OE1 | GLU | E | 65 | −42.675 | −29.849 | 39.161 | 1.00 | 23.25 | E |
| ATOM | 6117 | OE2 | GLU | E | 65 | −44.099 | −29.630 | 40.961 | 1.00 | 28.03 | E |
| ATOM | 6118 | C | GLU | E | 65 | −39.165 | −27.290 | 41.972 | 1.00 | 17.26 | E |
| ATOM | 6119 | O | GLU | E | 65 | −38.290 | −28.138 | 42.085 | 1.00 | 15.65 | E |
| ATOM | 6120 | N | ARG | E | 66 | −38.895 | −26.018 | 41.792 | 1.00 | 16.68 | E |
| ATOM | 6121 | CA | ARG | E | 66 | −37.526 | −25.455 | 41.850 | 1.00 | 17.26 | E |
| ATOM | 6122 | CB | ARG | E | 66 | −37.182 | −24.732 | 40.588 | 1.00 | 15.97 | E |
| ATOM | 6123 | CG | ARG | E | 66 | −35.732 | −24.523 | 40.525 | 1.00 | 18.16 | E |
| ATOM | 6124 | CD | ARG | E | 66 | −35.197 | −24.574 | 39.036 | 1.00 | 20.10 | E |
| ATOM | 6125 | NE | ARG | E | 66 | −33.736 | −24.528 | 38.792 | 1.00 | 20.79 | E |
| ATOM | 6126 | CZ | ARG | E | 66 | −32.859 | −25.553 | 38.690 | 1.00 | 20.84 | E |
| ATOM | 6127 | NH1 | ARG | E | 66 | −33.232 | −26.857 | 38.818 | 1.00 | 21.34 | E |
| ATOM | 6128 | NH2 | ARG | E | 66 | −31.581 | −25.253 | 38.409 | 1.00 | 19.26 | E |
| ATOM | 6129 | C | ARG | E | 66 | −37.563 | −24.420 | 43.001 | 1.00 | 17.96 | E |
| ATOM | 6130 | O | ARG | E | 66 | −38.556 | −23.701 | 43.157 | 1.00 | 18.70 | E |
| ATOM | 6131 | N | ASN | E | 67 | −36.532 | −24.362 | 43.833 | 1.00 | 18.78 | E |
| ATOM | 6132 | CA | ASN | E | 67 | −36.530 | −23.337 | 44.901 | 1.00 | 18.75 | E |
| ATOM | 6133 | CB | ASN | E | 67 | −36.535 | −23.994 | 46.286 | 1.00 | 19.72 | E |
| ATOM | 6134 | CG | ASN | E | 67 | −35.572 | −25.128 | 46.336 | 1.00 | 22.12 | E |
| ATOM | 6135 | OD1 | ASN | E | 67 | −35.401 | −25.751 | 45.252 | 1.00 | 27.94 | E |
| ATOM | 6136 | ND2 | ASN | E | 67 | −34.959 | −25.472 | 47.488 | 1.00 | 16.83 | E |
| ATOM | 6137 | C | ASN | E | 67 | −35.253 | −22.584 | 44.632 | 1.00 | 19.17 | E |
| ATOM | 6138 | O | ASN | E | 67 | −34.345 | −23.135 | 44.053 | 1.00 | 19.21 | E |
| ATOM | 6139 | N | ASN | E | 68 | −35.202 | −21.310 | 44.983 | 1.00 | 18.78 | E |
| ATOM | 6140 | CA | ASN | E | 68 | −34.014 | −20.478 | 44.816 | 1.00 | 18.14 | E |
| ATOM | 6141 | CB | ASN | E | 68 | −34.433 | −19.155 | 44.207 | 1.00 | 19.80 | E |
| ATOM | 6142 | CG | ASN | E | 68 | −34.941 | −19.321 | 42.781 | 1.00 | 22.23 | E |
| ATOM | 6143 | OD1 | ASN | E | 68 | −34.142 | −19.298 | 41.804 | 1.00 | 22.35 | E |
| ATOM | 6144 | ND2 | ASN | E | 68 | −36.282 | −19.553 | 42.616 | 1.00 | 22.95 | E |
| ATOM | 6145 | C | ASN | E | 68 | −33.467 | −20.221 | 46.237 | 1.00 | 18.36 | E |
| ATOM | 6146 | O | ASN | E | 68 | −34.300 | −20.110 | 47.234 | 1.00 | 18.17 | E |
| ATOM | 6147 | N | PHE | E | 69 | −32.128 | −20.227 | 46.395 | 1.00 | 17.31 | E |
| ATOM | 6148 | CA | PHE | E | 69 | −31.577 | −19.848 | 47.707 | 1.00 | 17.41 | E |
| ATOM | 6149 | CB | PHE | E | 69 | −31.071 | −20.952 | 48.583 | 1.00 | 18.43 | E |
| ATOM | 6150 | CG | PHE | E | 69 | −30.881 | −22.162 | 47.891 | 1.00 | 20.34 | E |
| ATOM | 6151 | CD1 | PHE | E | 69 | −30.088 | −22.173 | 46.783 | 1.00 | 22.64 | E |
| ATOM | 6152 | CD2 | PHE | E | 69 | −31.406 | −23.328 | 48.366 | 1.00 | 19.77 | E |
| ATOM | 6153 | CE1 | PHE | E | 69 | −29.782 | −23.391 | 46.109 | 1.00 | 24.52 | E |
| ATOM | 6154 | CE2 | PHE | E | 69 | −31.133 | −24.503 | 47.750 | 1.00 | 20.70 | E |
| ATOM | 6155 | CZ | PHE | E | 69 | −30.312 | −24.562 | 46.607 | 1.00 | 21.88 | E |
| ATOM | 6156 | C | PHE | E | 69 | −30.538 | −18.779 | 47.711 | 1.00 | 16.19 | E |
| ATOM | 6157 | O | PHE | E | 69 | −29.564 | −18.786 | 47.000 | 1.00 | 16.60 | E |
| ATOM | 6158 | N | GLU | E | 70 | −30.811 | −17.804 | 48.542 | 1.00 | 15.29 | E |
| ATOM | 6159 | CA | GLU | E | 70 | −29.941 | −16.652 | 48.626 | 1.00 | 15.38 | E |
| ATOM | 6160 | CB | GLU | E | 70 | −30.809 | −15.391 | 48.612 | 1.00 | 15.60 | E |
| ATOM | 6161 | CG | GLU | E | 70 | −30.153 | −14.188 | 48.177 | 1.00 | 16.93 | E |
| ATOM | 6162 | CD | GLU | E | 70 | −30.922 | −12.873 | 48.635 | 1.00 | 19.44 | E |
| ATOM | 6163 | OE1 | GLU | E | 70 | −31.036 | −11.898 | 47.766 | 1.00 | 19.19 | E |
| ATOM | 6164 | OE2 | GLU | E | 70 | −31.384 | −12.790 | 49.854 | 1.00 | 17.96 | E |
| ATOM | 6165 | C | GLU | E | 70 | −29.125 | −16.816 | 49.907 | 1.00 | 13.25 | E |
| ATOM | 6166 | O | GLU | E | 70 | −29.677 | −17.056 | 50.942 | 1.00 | 11.55 | E |
| ATOM | 6167 | N | LEU | E | 71 | −27.812 | −16.804 | 49.727 | 1.00 | 13.10 | E |
| ATOM | 6168 | CA | LEU | E | 71 | −26.806 | −16.855 | 50.807 | 1.00 | 14.19 | E |
| ATOM | 6169 | CB | LEU | E | 71 | −25.794 | −17.950 | 50.540 | 1.00 | 14.82 | E |
| ATOM | 6170 | CG | LEU | E | 71 | −26.395 | −19.292 | 50.450 | 1.00 | 15.47 | E |
| ATOM | 6171 | CD1 | LEU | E | 71 | −25.465 | −20.221 | 49.900 | 1.00 | 16.88 | E |
| ATOM | 6172 | CD2 | LEU | E | 71 | −26.809 | −19.710 | 51.824 | 1.00 | 17.13 | E |
| ATOM | 6173 | C | LEU | E | 71 | −26.077 | −15.529 | 50.869 | 1.00 | 13.51 | E |
| ATOM | 6174 | O | LEU | E | 71 | −25.719 | −15.019 | 49.827 | 1.00 | 13.35 | E |
| ATOM | 6175 | N | ASN | E | 72 | −25.904 | −14.984 | 52.070 | 1.00 | 13.53 | E |
| ATOM | 6176 | CA | ASN | E | 72 | −25.221 | −13.699 | 52.413 | 1.00 | 13.41 | E |
| ATOM | 6177 | CB | ASN | E | 72 | −26.262 | −12.747 | 53.004 | 1.00 | 13.76 | E |
| ATOM | 6178 | CG | ASN | E | 72 | −26.854 | −11.816 | 51.949 | 1.00 | 15.72 | E |
| ATOM | 6179 | OD1 | ASN | E | 72 | −27.948 | −11.162 | 52.030 | 1.00 | 14.06 | E |
| ATOM | 6180 | ND2 | ASN | E | 72 | −26.081 | −11.721 | 50.899 | 1.00 | 19.82 | E |
| ATOM | 6181 | C | ASN | E | 72 | −24.157 | −14.199 | 53.466 | 1.00 | 14.48 | E |
| ATOM | 6182 | O | ASN | E | 72 | −24.476 | −14.823 | 54.494 | 1.00 | 14.71 | E |
| ATOM | 6183 | N | PHE | E | 73 | −22.884 | −13.978 | 53.155 | 1.00 | 14.52 | E |
| ATOM | 6184 | CA | PHE | E | 73 | −21.795 | −14.388 | 53.965 | 1.00 | 14.06 | E |
| ATOM | 6185 | CB | PHE | E | 73 | −21.488 | −15.794 | 53.599 | 1.00 | 15.94 | E |
| ATOM | 6186 | CG | PHE | E | 73 | −21.114 | −15.963 | 52.098 | 1.00 | 17.14 | E |
| ATOM | 6187 | CD1 | PHE | E | 73 | −19.800 | −15.893 | 51.678 | 1.00 | 16.19 | E |
| ATOM | 6188 | CD2 | PHE | E | 73 | −22.135 | −16.158 | 51.101 | 1.00 | 18.13 | E |
| ATOM | 6189 | CE1 | PHE | E | 73 | −19.470 | −16.002 | 50.317 | 1.00 | 18.48 | E |
| ATOM | 6190 | CE2 | PHE | E | 73 | −21.795 | −16.265 | 49.718 | 1.00 | 19.69 | E |

TABLE 1-continued

| | | | | | | | | | | |
|---|---|---|---|---|---|---|---|---|---|---|
| ATOM | 6191 | CZ | PHE | E | 73 | −20.432 | −16.182 | 49.320 | 1.00 | 18.38 | E |
| ATOM | 6192 | C | PHE | E | 73 | −20.565 | −13.530 | 53.719 | 1.00 | 13.10 | E |
| ATOM | 6193 | O | PHE | E | 73 | −20.555 | −12.661 | 52.841 | 1.00 | 11.99 | E |
| ATOM | 6194 | N | THR | E | 74 | −19.518 | −13.810 | 54.477 | 1.00 | 12.48 | E |
| ATOM | 6195 | CA | THR | E | 74 | −18.253 | −13.070 | 54.291 | 1.00 | 14.51 | E |
| ATOM | 6196 | CB | THR | E | 74 | −17.872 | −11.995 | 55.398 | 1.00 | 12.83 | E |
| ATOM | 6197 | OG1 | THR | E | 74 | −17.494 | −12.721 | 56.591 | 1.00 | 13.04 | E |
| ATOM | 6198 | CG2 | THR | E | 74 | −18.973 | −11.147 | 55.701 | 1.00 | 11.29 | E |
| ATOM | 6199 | C | THR | E | 74 | −17.258 | −14.111 | 54.509 | 1.00 | 14.04 | E |
| ATOM | 6200 | O | THR | E | 74 | −17.507 | −15.090 | 55.210 | 1.00 | 15.22 | E |
| ATOM | 6201 | N | VAL | E | 75 | −16.093 | −13.820 | 53.962 | 1.00 | 15.40 | E |
| ATOM | 6202 | CA | VAL | E | 75 | −14.959 | −14.741 | 54.055 | 1.00 | 16.62 | E |
| ATOM | 6203 | CB | VAL | E | 75 | −14.848 | −15.457 | 52.750 | 1.00 | 15.81 | E |
| ATOM | 6204 | CG1 | VAL | E | 75 | −13.743 | −16.442 | 52.752 | 1.00 | 12.67 | E |
| ATOM | 6205 | CG2 | VAL | E | 75 | −16.206 | −16.060 | 52.488 | 1.00 | 14.62 | E |
| ATOM | 6206 | C | VAL | E | 75 | −13.674 | −14.030 | 54.441 | 1.00 | 15.35 | E |
| ATOM | 6207 | O | VAL | E | 75 | −13.290 | −13.079 | 53.774 | 1.00 | 14.97 | E |
| ATOM | 6208 | N | ARG | E | 76 | −13.075 | −14.462 | 55.558 | 1.00 | 15.15 | E |
| ATOM | 6209 | CA | ARG | E | 76 | −11.852 | −13.814 | 55.942 | 1.00 | 15.96 | E |
| ATOM | 6210 | CB | ARG | E | 76 | −11.464 | −14.109 | 57.368 | 1.00 | 16.60 | E |
| ATOM | 6211 | CG | ARG | E | 76 | −10.273 | −13.385 | 57.776 | 1.00 | 15.83 | E |
| ATOM | 6212 | CD | ARG | E | 76 | −10.324 | −13.175 | 59.274 | 1.00 | 18.02 | E |
| ATOM | 6213 | NE | ARG | E | 76 | −8.934 | −12.927 | 59.682 | 1.00 | 18.59 | E |
| ATOM | 6214 | CZ | ARG | E | 76 | −8.403 | −13.055 | 60.893 | 1.00 | 18.47 | E |
| ATOM | 6215 | NH1 | ARG | E | 76 | −9.125 | −13.392 | 61.991 | 1.00 | 18.14 | E |
| ATOM | 6216 | NH2 | ARG | E | 76 | −7.085 | −13.048 | 60.935 | 1.00 | 15.37 | E |
| ATOM | 6217 | C | ARG | E | 76 | −10.794 | −14.308 | 55.013 | 1.00 | 15.68 | E |
| ATOM | 6218 | O | ARG | E | 76 | −10.772 | −15.482 | 54.720 | 1.00 | 15.43 | E |
| ATOM | 6219 | N | ASP | E | 77 | −9.971 | −13.371 | 54.527 | 1.00 | 16.75 | E |
| ATOM | 6220 | CA | ASP | E | 77 | −8.818 | −13.585 | 53.629 | 1.00 | 16.19 | E |
| ATOM | 6221 | CB | ASP | E | 77 | −8.206 | −12.240 | 53.314 | 1.00 | 17.88 | E |
| ATOM | 6222 | CG | ASP | E | 77 | −6.775 | −12.310 | 52.629 | 1.00 | 19.17 | E |
| ATOM | 6223 | OD1 | ASP | E | 77 | −6.324 | −13.383 | 52.191 | 1.00 | 20.98 | E |
| ATOM | 6224 | OD2 | ASP | E | 77 | −6.073 | −11.265 | 52.527 | 1.00 | 18.67 | E |
| ATOM | 6225 | C | ASP | E | 77 | −7.850 | −14.531 | 54.325 | 1.00 | 17.22 | E |
| ATOM | 6226 | O | ASP | E | 77 | −7.530 | −14.431 | 55.524 | 1.00 | 16.25 | E |
| ATOM | 6227 | N | CYS | E | 78 | −7.445 | −15.534 | 53.575 | 1.00 | 17.78 | E |
| ATOM | 6228 | CA | CYS | E | 78 | −6.565 | −16.553 | 54.082 | 1.00 | 17.63 | E |
| ATOM | 6229 | C | CYS | E | 78 | −5.167 | −16.083 | 54.393 | 1.00 | 18.33 | E |
| ATOM | 6230 | O | CYS | E | 78 | −4.454 | −16.736 | 55.186 | 1.00 | 18.96 | E |
| ATOM | 6231 | CB | CYS | E | 78 | −6.479 | −17.735 | 53.139 | 1.00 | 17.54 | E |
| ATOM | 6232 | SG | CYS | E | 78 | −7.731 | −19.076 | 53.534 | 1.00 | 17.45 | E |
| ATOM | 6233 | N | ASN | E | 79 | −4.807 | −14.939 | 53.814 | 1.00 | 17.70 | E |
| ATOM | 6234 | CA | ASN | E | 79 | −3.497 | −14.372 | 54.062 | 1.00 | 16.39 | E |
| ATOM | 6235 | CB | ASN | E | 79 | −2.990 | −13.636 | 52.824 | 1.00 | 17.34 | E |
| ATOM | 6236 | CG | ASN | E | 79 | −2.604 | −14.575 | 51.648 | 1.00 | 16.94 | E |
| ATOM | 6237 | OD1 | ASN | E | 79 | −2.458 | −14.126 | 50.569 | 1.00 | 18.11 | E |
| ATOM | 6238 | ND2 | ASN | E | 79 | −2.457 | −15.849 | 51.871 | 1.00 | 19.57 | E |
| ATOM | 6239 | C | ASN | E | 79 | −3.464 | −13.427 | 55.290 | 1.00 | 15.90 | E |
| ATOM | 6240 | O | ASN | E | 79 | −2.412 | −12.907 | 55.653 | 1.00 | 14.33 | E |
| ATOM | 6241 | N | SER | E | 80 | −4.638 | −13.232 | 55.894 | 1.00 | 16.17 | E |
| ATOM | 6242 | CA | SER | E | 80 | −4.816 | −12.393 | 57.054 | 1.00 | 16.30 | E |
| ATOM | 6243 | CB | SER | E | 80 | −6.209 | −11.902 | 57.094 | 1.00 | 16.42 | E |
| ATOM | 6244 | OG | SER | E | 80 | −7.079 | −12.953 | 57.496 | 1.00 | 17.09 | E |
| ATOM | 6245 | C | SER | E | 80 | −4.522 | −13.227 | 58.328 | 1.00 | 16.75 | E |
| ATOM | 6246 | O | SER | E | 80 | −4.810 | −12.789 | 59.394 | 1.00 | 16.99 | E |
| ATOM | 6247 | N | PHE | E | 81 | −4.016 | −14.448 | 58.227 | 1.00 | 16.78 | E |
| ATOM | 6248 | CA | PHE | E | 81 | −3.617 | −15.132 | 59.462 | 1.00 | 16.00 | E |
| ATOM | 6249 | CB | PHE | E | 81 | −4.207 | −16.533 | 59.493 | 1.00 | 16.43 | E |
| ATOM | 6250 | CG | PHE | E | 81 | −5.726 | −16.600 | 59.493 | 1.00 | 15.74 | E |
| ATOM | 6251 | CD1 | PHE | E | 81 | −6.451 | −16.671 | 58.324 | 1.00 | 16.05 | E |
| ATOM | 6252 | CD2 | PHE | E | 81 | −6.436 | −16.480 | 60.673 | 1.00 | 14.91 | E |
| ATOM | 6253 | CE1 | PHE | E | 81 | −7.855 | −16.598 | 58.343 | 1.00 | 15.28 | E |
| ATOM | 6254 | CE2 | PHE | E | 81 | −7.820 | −16.408 | 60.683 | 1.00 | 13.54 | E |
| ATOM | 6255 | CZ | PHE | E | 81 | −8.522 | −16.460 | 59.526 | 1.00 | 13.66 | E |
| ATOM | 6256 | C | PHE | E | 81 | −2.024 | −15.161 | 59.395 | 1.00 | 15.94 | E |
| ATOM | 6257 | O | PHE | E | 81 | −1.458 | −15.909 | 58.602 | 1.00 | 15.49 | E |
| ATOM | 6258 | N | PRO | E | 82 | −1.309 | −14.349 | 60.252 | 1.00 | 17.28 | E |
| ATOM | 6259 | CD | PRO | E | 82 | −1.876 | −13.871 | 61.555 | 1.00 | 17.72 | E |
| ATOM | 6260 | CA | PRO | E | 82 | 0.181 | −14.229 | 60.316 | 1.00 | 16.68 | E |
| ATOM | 6261 | CB | PRO | E | 82 | 0.429 | −13.529 | 61.681 | 1.00 | 18.21 | E |
| ATOM | 6262 | CG | PRO | E | 82 | −0.909 | −12.819 | 62.026 | 1.00 | 17.84 | E |
| ATOM | 6263 | C | PRO | E | 82 | 0.968 | −15.482 | 60.256 | 1.00 | 14.82 | E |
| ATOM | 6264 | O | PRO | E | 82 | 0.768 | −16.383 | 61.068 | 1.00 | 12.06 | E |
| ATOM | 6265 | N | GLY | E | 83 | 1.933 | −15.478 | 59.378 | 1.00 | 15.96 | E |
| ATOM | 6266 | CA | GLY | E | 83 | 2.726 | −16.680 | 59.171 | 1.00 | 17.76 | E |
| ATOM | 6267 | C | GLY | E | 83 | 1.826 | −17.401 | 58.104 | 1.00 | 18.64 | E |
| ATOM | 6268 | O | GLY | E | 83 | 0.666 | −16.983 | 57.741 | 1.00 | 19.46 | E |
| ATOM | 6269 | N | GLY | E | 84 | 2.240 | −18.477 | 57.497 | 1.00 | 19.44 | E |
| ATOM | 6270 | CA | GLY | E | 84 | 1.187 | −18.903 | 56.526 | 1.00 | 19.59 | E |

TABLE 1-continued

| | | | | | | | | | |
|---|---|---|---|---|---|---|---|---|---|
| ATOM | 6271 | C | GLY | E | 84 | −0.014 | −19.618 | 57.123 | 1.00 | 19.37 | E |
| ATOM | 6272 | O | GLY | E | 84 | −0.063 | −19.776 | 58.307 | 1.00 | 19.69 | E |
| ATOM | 6273 | N | ALA | E | 85 | −1.068 | −19.976 | 56.380 | 1.00 | 19.96 | E |
| ATOM | 6274 | CA | ALA | E | 85 | −2.199 | −20.799 | 56.993 | 1.00 | 19.30 | E |
| ATOM | 6275 | CB | ALA | E | 85 | −3.463 | −19.923 | 57.369 | 1.00 | 18.79 | E |
| ATOM | 6276 | C | ALA | E | 85 | −2.494 | −21.775 | 55.875 | 1.00 | 18.29 | E |
| ATOM | 6277 | O | ALA | E | 85 | −3.501 | −21.699 | 55.215 | 1.00 | 19.66 | E |
| ATOM | 6278 | N | SER | E | 86 | −1.551 | −22.641 | 55.623 | 1.00 | 17.08 | E |
| ATOM | 6279 | CA | SER | E | 86 | −1.660 | −23.605 | 54.554 | 1.00 | 15.47 | E |
| ATOM | 6280 | CB | SER | E | 86 | −0.547 | −24.661 | 54.686 | 1.00 | 13.48 | E |
| ATOM | 6281 | OG | SER | E | 86 | −0.563 | −25.451 | 55.823 | 1.00 | 7.69 | E |
| ATOM | 6282 | C | SER | E | 86 | −2.984 | −24.307 | 54.312 | 1.00 | 15.71 | E |
| ATOM | 6283 | O | SER | E | 86 | −3.321 | −24.372 | 53.225 | 1.00 | 16.72 | E |
| ATOM | 6284 | N | SER | E | 87 | −3.710 | −24.833 | 55.294 | 1.00 | 14.82 | E |
| ATOM | 6285 | CA | SER | E | 87 | −4.983 | −25.535 | 55.105 | 1.00 | 13.49 | E |
| ATOM | 6286 | CB | SER | E | 87 | −5.203 | −26.588 | 56.230 | 1.00 | 12.95 | E |
| ATOM | 6287 | OG | SER | E | 87 | −5.582 | −25.988 | 57.528 | 1.00 | 12.88 | E |
| ATOM | 6288 | C | SER | E | 87 | −6.213 | −24.616 | 55.040 | 1.00 | 13.31 | E |
| ATOM | 6289 | O | SER | E | 87 | −7.299 | −25.079 | 54.962 | 1.00 | 12.98 | E |
| ATOM | 6290 | N | CYS | E | 88 | −6.000 | −23.316 | 55.080 | 1.00 | 13.59 | E |
| ATOM | 6291 | CA | CYS | E | 88 | −7.066 | −22.336 | 55.071 | 1.00 | 14.64 | E |
| ATOM | 6292 | C | CYS | E | 88 | −7.651 | −22.392 | 53.669 | 1.00 | 14.44 | E |
| ATOM | 6293 | O | CYS | E | 88 | −6.968 | −22.687 | 52.762 | 1.00 | 14.06 | E |
| ATOM | 6294 | CB | CYS | E | 88 | −6.496 | −20.944 | 55.374 | 1.00 | 14.18 | E |
| ATOM | 6295 | SG | CYS | E | 88 | −7.662 | −19.563 | 55.471 | 1.00 | 14.76 | E |
| ATOM | 6296 | N | LYS | E | 89 | −8.929 | −22.119 | 53.559 | 1.00 | 15.70 | E |
| ATOM | 6297 | CA | LYS | E | 89 | −9.665 | −22.196 | 52.323 | 1.00 | 17.40 | E |
| ATOM | 6298 | CB | LYS | E | 89 | −10.669 | −23.348 | 52.402 | 1.00 | 17.23 | E |
| ATOM | 6299 | CG | LYS | E | 89 | −9.961 | −24.681 | 52.491 | 1.00 | 20.05 | E |
| ATOM | 6300 | CD | LYS | E | 89 | −9.193 | −25.021 | 51.083 | 1.00 | 20.00 | E |
| ATOM | 6301 | CE | LYS | E | 89 | −8.532 | −26.410 | 51.119 | 1.00 | 23.12 | E |
| ATOM | 6302 | NZ | LYS | E | 89 | −7.897 | −26.803 | 49.830 | 1.00 | 26.04 | E |
| ATOM | 6303 | C | LYS | E | 89 | −10.485 | −20.939 | 52.204 | 1.00 | 18.57 | E |
| ATOM | 6304 | O | LYS | E | 89 | −10.697 | −20.307 | 53.225 | 1.00 | 19.95 | E |
| ATOM | 6305 | N | GLU | E | 90 | −11.001 | −20.605 | 51.004 | 1.00 | 17.71 | E |
| ATOM | 6306 | CA | GLU | E | 90 | −11.830 | −19.463 | 50.861 | 1.00 | 16.42 | E |
| ATOM | 6307 | CB | GLU | E | 90 | −11.066 | −18.290 | 50.253 | 1.00 | 16.22 | E |
| ATOM | 6308 | CG | GLU | E | 90 | −9.826 | −17.865 | 51.085 | 1.00 | 16.01 | E |
| ATOM | 6309 | CD | GLU | E | 90 | −9.039 | −16.687 | 50.474 | 1.00 | 15.59 | E |
| ATOM | 6310 | OE1 | GLU | E | 90 | −8.772 | −16.722 | 49.283 | 1.00 | 17.47 | E |
| ATOM | 6311 | OE2 | GLU | E | 90 | −8.670 | −15.742 | 51.126 | 1.00 | 12.32 | E |
| ATOM | 6312 | C | GLU | E | 90 | −13.101 | −19.791 | 50.100 | 1.00 | 16.80 | E |
| ATOM | 6313 | O | GLU | E | 90 | −13.587 | −19.010 | 49.259 | 1.00 | 17.69 | E |
| ATOM | 6314 | N | THR | E | 91 | −13.690 | −20.926 | 50.413 | 1.00 | 15.11 | E |
| ATOM | 6315 | CA | THR | E | 91 | −14.945 | −21.295 | 49.748 | 1.00 | 13.04 | E |
| ATOM | 6316 | CB | THR | E | 91 | −14.763 | −22.034 | 48.314 | 1.00 | 12.30 | E |
| ATOM | 6317 | OG1 | THR | E | 91 | −14.057 | −23.242 | 48.468 | 1.00 | 10.81 | E |
| ATOM | 6318 | CG2 | THR | E | 91 | −14.084 | −21.166 | 47.304 | 1.00 | 10.91 | E |
| ATOM | 6319 | C | THR | E | 91 | −15.521 | −22.273 | 50.694 | 1.00 | 13.17 | E |
| ATOM | 6320 | O | THR | E | 91 | −14.785 | −22.740 | 51.609 | 1.00 | 12.32 | E |
| ATOM | 6321 | N | PHE | E | 92 | −16.819 | −22.552 | 50.498 | 1.00 | 13.58 | E |
| ATOM | 6322 | CA | PHE | E | 92 | −17.586 | −23.547 | 51.267 | 1.00 | 15.03 | E |
| ATOM | 6323 | CB | PHE | E | 92 | −18.282 | −22.969 | 52.502 | 1.00 | 15.29 | E |
| ATOM | 6324 | CG | PHE | E | 92 | −19.311 | −21.955 | 52.200 | 1.00 | 16.38 | E |
| ATOM | 6325 | CD1 | PHE | E | 92 | −20.599 | −22.282 | 52.117 | 1.00 | 17.33 | E |
| ATOM | 6326 | CD2 | PHE | E | 92 | −18.972 | −20.645 | 52.065 | 1.00 | 16.21 | E |
| ATOM | 6327 | CE1 | PHE | E | 92 | −21.529 | −21.305 | 51.917 | 1.00 | 19.03 | E |
| ATOM | 6328 | CE2 | PHE | E | 92 | −19.874 | −19.678 | 51.849 | 1.00 | 16.57 | E |
| ATOM | 6329 | CZ | PHE | E | 92 | −21.143 | −19.979 | 51.783 | 1.00 | 18.33 | E |
| ATOM | 6330 | C | PHE | E | 92 | −18.606 | −24.196 | 50.434 | 1.00 | 15.15 | E |
| ATOM | 6331 | O | PHE | E | 92 | −19.003 | −23.654 | 49.443 | 1.00 | 16.22 | E |
| ATOM | 6332 | N | ASN | E | 93 | −19.107 | −25.337 | 50.888 | 1.00 | 15.62 | E |
| ATOM | 6333 | CA | ASN | E | 93 | −20.085 | −26.150 | 50.098 | 1.00 | 15.17 | E |
| ATOM | 6334 | CB | ASN | E | 93 | −19.608 | −27.545 | 50.031 | 1.00 | 13.93 | E |
| ATOM | 6335 | CG | ASN | E | 93 | −18.381 | −27.630 | 49.246 | 1.00 | 13.21 | E |
| ATOM | 6336 | OD1 | ASN | E | 93 | −18.272 | −27.032 | 48.180 | 1.00 | 14.04 | E |
| ATOM | 6337 | ND2 | ASN | E | 93 | −17.431 | −28.332 | 49.758 | 1.00 | 10.33 | E |
| ATOM | 6338 | C | ASN | E | 93 | −21.552 | −26.220 | 50.388 | 1.00 | 15.92 | E |
| ATOM | 6339 | O | ASN | E | 93 | −21.951 | −26.322 | 51.494 | 1.00 | 16.30 | E |
| ATOM | 6340 | N | LEU | E | 94 | −22.367 | −26.149 | 49.351 | 1.00 | 16.65 | E |
| ATOM | 6341 | CA | LEU | E | 94 | −23.745 | −26.211 | 49.551 | 1.00 | 16.33 | E |
| ATOM | 6342 | CB | LEU | E | 94 | −24.385 | −25.088 | 48.770 | 1.00 | 16.88 | E |
| ATOM | 6343 | CG | LEU | E | 94 | −25.939 | −24.974 | 48.781 | 1.00 | 17.95 | E |
| ATOM | 6344 | CD1 | LEU | E | 94 | −26.449 | −24.793 | 50.277 | 1.00 | 16.58 | E |
| ATOM | 6345 | CD2 | LEU | E | 94 | −26.323 | −23.776 | 47.878 | 1.00 | 15.22 | E |
| ATOM | 6346 | C | LEU | E | 94 | −24.270 | −27.579 | 49.089 | 1.00 | 16.93 | E |
| ATOM | 6347 | O | LEU | E | 94 | −23.914 | −28.040 | 48.031 | 1.00 | 15.67 | E |
| ATOM | 6348 | N | TYR | E | 95 | −25.106 | −28.195 | 49.947 | 1.00 | 17.18 | E |
| ATOM | 6349 | CA | TYR | E | 95 | −25.852 | −29.434 | 49.705 | 1.00 | 16.91 | E |
| ATOM | 6350 | CB | TYR | E | 95 | −25.259 | −30.557 | 50.514 | 1.00 | 19.26 | E |

TABLE 1-continued

| | | | | | | | | | | |
|---|---|---|---|---|---|---|---|---|---|---|
| ATOM | 6351 | CG | TYR | E | 95 | −23.869 | −30.984 | 50.135 | 1.00 | 19.91 | E |
| ATOM | 6352 | CD1 | TYR | E | 95 | −22.727 | −30.109 | 50.298 | 1.00 | 19.04 | E |
| ATOM | 6353 | CE1 | TYR | E | 95 | −21.442 | −30.578 | 49.963 | 1.00 | 18.87 | E |
| ATOM | 6354 | CD2 | TYR | E | 95 | −23.661 | −32.301 | 49.641 | 1.00 | 19.19 | E |
| ATOM | 6355 | CE2 | TYR | E | 95 | −22.361 | −32.724 | 49.328 | 1.00 | 19.91 | E |
| ATOM | 6356 | CZ | TYR | E | 95 | −21.314 | −31.869 | 49.501 | 1.00 | 19.01 | E |
| ATOM | 6357 | OH | TYR | E | 95 | −20.164 | −32.429 | 49.241 | 1.00 | 22.56 | E |
| ATOM | 6358 | C | TYR | E | 95 | −27.342 | −29.385 | 50.135 | 1.00 | 16.09 | E |
| ATOM | 6359 | O | TYR | E | 95 | −27.829 | −28.519 | 50.935 | 1.00 | 14.36 | E |
| ATOM | 6360 | N | TYR | E | 96 | −28.022 | −30.430 | 49.710 | 1.00 | 14.99 | E |
| ATOM | 6361 | CA | TYR | E | 96 | −29.405 | −30.586 | 50.129 | 1.00 | 14.75 | E |
| ATOM | 6362 | CB | TYR | E | 96 | −30.360 | −29.811 | 49.250 | 1.00 | 15.33 | E |
| ATOM | 6363 | CG | TYR | E | 96 | −30.653 | −30.506 | 47.948 | 1.00 | 16.05 | E |
| ATOM | 6364 | CD1 | TYR | E | 96 | −31.846 | −31.182 | 47.733 | 1.00 | 17.53 | E |
| ATOM | 6365 | CE1 | TYR | E | 96 | −32.099 | −31.893 | 46.508 | 1.00 | 17.27 | E |
| ATOM | 6366 | CD2 | TYR | E | 96 | −29.705 | −30.542 | 46.947 | 1.00 | 16.61 | E |
| ATOM | 6367 | CE2 | TYR | E | 96 | −29.913 | −31.236 | 45.778 | 1.00 | 16.73 | E |
| ATOM | 6368 | CZ | TYR | E | 96 | −31.108 | −31.894 | 45.562 | 1.00 | 17.15 | E |
| ATOM | 6369 | OH | TYR | E | 96 | −31.258 | −32.459 | 44.366 | 1.00 | 16.74 | E |
| ATOM | 6370 | C | TYR | E | 96 | −29.716 | −32.099 | 50.037 | 1.00 | 13.64 | E |
| ATOM | 6371 | O | TYR | E | 96 | −28.927 | −32.853 | 49.572 | 1.00 | 11.59 | E |
| ATOM | 6372 | N | ALA | E | 97 | −30.854 | −32.485 | 50.599 | 1.00 | 13.95 | E |
| ATOM | 6373 | CA | ALA | E | 97 | −31.366 | −33.828 | 50.570 | 1.00 | 15.10 | E |
| ATOM | 6374 | CB | ALA | E | 97 | −30.856 | −34.760 | 51.782 | 1.00 | 13.81 | E |
| ATOM | 6375 | C | ALA | E | 97 | −32.851 | −33.631 | 50.603 | 1.00 | 14.09 | E |
| ATOM | 6376 | O | ALA | E | 97 | −33.353 | −32.606 | 51.073 | 1.00 | 13.80 | E |
| ATOM | 6377 | N | GLU | E | 98 | −33.517 | −34.611 | 49.996 | 1.00 | 15.05 | E |
| ATOM | 6378 | CA | GLU | E | 98 | −35.008 | −34.707 | 49.902 | 1.00 | 15.83 | E |
| ATOM | 6379 | CB | GLU | E | 98 | −35.428 | −34.923 | 48.473 | 1.00 | 14.87 | E |
| ATOM | 6380 | CG | GLU | E | 98 | −35.615 | −33.623 | 47.705 | 1.00 | 15.57 | E |
| ATOM | 6381 | CD | GLU | E | 98 | −36.085 | −33.881 | 46.218 | 1.00 | 15.31 | E |
| ATOM | 6382 | OE1 | GLU | E | 98 | −35.316 | −34.324 | 45.361 | 1.00 | 13.39 | E |
| ATOM | 6383 | OE2 | GLU | E | 98 | −37.247 | −33.646 | 45.961 | 1.00 | 16.49 | E |
| ATOM | 6384 | C | GLU | E | 98 | −35.493 | −35.873 | 50.753 | 1.00 | 14.85 | E |
| ATOM | 6385 | O | GLU | E | 98 | −34.792 | −36.884 | 50.896 | 1.00 | 16.25 | E |
| ATOM | 6386 | N | SER | E | 99 | −36.591 | −35.713 | 51.448 | 1.00 | 14.03 | E |
| ATOM | 6387 | CA | SER | E | 99 | −37.144 | −36.906 | 52.059 | 1.00 | 14.68 | E |
| ATOM | 6388 | CB | SER | E | 99 | −36.371 | −37.501 | 53.244 | 1.00 | 11.64 | E |
| ATOM | 6389 | OG | SER | E | 99 | −36.464 | −36.657 | 54.248 | 1.00 | 12.92 | E |
| ATOM | 6390 | C | SER | E | 99 | −38.632 | −36.746 | 52.354 | 1.00 | 14.77 | E |
| ATOM | 6391 | O | SER | E | 99 | −39.162 | −35.679 | 52.362 | 1.00 | 15.41 | E |
| ATOM | 6392 | N | ASP | E | 100 | −39.319 | −37.838 | 52.564 | 1.00 | 15.55 | E |
| ATOM | 6393 | CA | ASP | E | 100 | −40.704 | −37.740 | 52.846 | 1.00 | 16.63 | E |
| ATOM | 6394 | CB | ASP | E | 100 | −41.504 | −38.899 | 52.193 | 1.00 | 17.49 | E |
| ATOM | 6395 | CG | ASP | E | 100 | −41.602 | −38.795 | 50.644 | 1.00 | 18.85 | E |
| ATOM | 6396 | OD1 | ASP | E | 100 | −41.892 | −37.656 | 50.151 | 1.00 | 17.20 | E |
| ATOM | 6397 | OD2 | ASP | E | 100 | −41.345 | −39.884 | 49.949 | 1.00 | 19.56 | E |
| ATOM | 6398 | C | ASP | E | 100 | −40.938 | −37.719 | 54.287 | 1.00 | 16.71 | E |
| ATOM | 6399 | O | ASP | E | 100 | −42.013 | −37.382 | 54.688 | 1.00 | 16.40 | E |
| ATOM | 6400 | N | LEU | E | 101 | −39.941 | −38.146 | 55.054 | 1.00 | 17.37 | E |
| ATOM | 6401 | CA | LEU | E | 101 | −39.931 | −38.213 | 56.527 | 1.00 | 17.39 | E |
| ATOM | 6402 | CB | LEU | E | 101 | −39.378 | −39.503 | 57.102 | 1.00 | 17.46 | E |
| ATOM | 6403 | CG | LEU | E | 101 | −39.594 | −40.865 | 56.569 | 1.00 | 19.04 | E |
| ATOM | 6404 | CD1 | LEU | E | 101 | −39.205 | −40.840 | 55.139 | 1.00 | 16.93 | E |
| ATOM | 6405 | CD2 | LEU | E | 101 | −38.767 | −41.875 | 57.403 | 1.00 | 17.43 | E |
| ATOM | 6406 | C | LEU | E | 101 | −38.919 | −37.137 | 57.069 | 1.00 | 18.40 | E |
| ATOM | 6407 | O | LEU | E | 101 | −37.964 | −36.765 | 56.364 | 1.00 | 18.46 | E |
| ATOM | 6408 | N | ASP | E | 102 | −39.146 | −36.703 | 58.333 | 1.00 | 18.50 | E |
| ATOM | 6409 | CA | ASP | E | 102 | −38.316 | −35.754 | 59.060 | 1.00 | 17.72 | E |
| ATOM | 6410 | CB | ASP | E | 102 | −39.145 | −35.128 | 60.121 | 1.00 | 18.22 | E |
| ATOM | 6411 | CG | ASP | E | 102 | −38.426 | −34.012 | 60.887 | 1.00 | 19.07 | E |
| ATOM | 6412 | OD1 | ASP | E | 102 | −37.125 | −34.029 | 60.991 | 1.00 | 17.53 | E |
| ATOM | 6413 | OD2 | ASP | E | 102 | −39.221 | −33.149 | 61.384 | 1.00 | 17.99 | E |
| ATOM | 6414 | C | ASP | E | 102 | −37.258 | −36.631 | 59.741 | 1.00 | 18.07 | E |
| ATOM | 6415 | O | ASP | E | 102 | −37.589 | −37.424 | 60.604 | 1.00 | 17.74 | E |
| ATOM | 6416 | N | TYR | E | 103 | −35.999 | −36.486 | 59.359 | 1.00 | 17.24 | E |
| ATOM | 6417 | CA | TYR | E | 103 | −34.931 | −37.277 | 59.923 | 1.00 | 15.91 | E |
| ATOM | 6418 | CB | TYR | E | 103 | −33.572 | −37.037 | 59.180 | 1.00 | 18.59 | E |
| ATOM | 6419 | CG | TYR | E | 103 | −33.393 | −37.736 | 57.853 | 1.00 | 21.01 | E |
| ATOM | 6420 | CD1 | TYR | E | 103 | −33.710 | −39.118 | 57.706 | 1.00 | 22.98 | E |
| ATOM | 6421 | CE1 | TYR | E | 103 | −33.583 | −39.806 | 56.432 | 1.00 | 23.16 | E |
| ATOM | 6422 | CD2 | TYR | E | 103 | −32.971 | −37.052 | 56.768 | 1.00 | 20.65 | E |
| ATOM | 6423 | CE2 | TYR | E | 103 | −32.864 | −37.686 | 55.549 | 1.00 | 22.35 | E |
| ATOM | 6424 | CZ | TYR | E | 103 | −33.150 | −39.056 | 55.362 | 1.00 | 23.18 | E |
| ATOM | 6425 | OH | TYR | E | 103 | −32.970 | −39.562 | 54.073 | 1.00 | 22.50 | E |
| ATOM | 6426 | C | TYR | E | 103 | −34.637 | −36.954 | 61.367 | 1.00 | 15.32 | E |
| ATOM | 6427 | O | TYR | E | 103 | −33.785 | −37.655 | 62.007 | 1.00 | 12.42 | E |
| ATOM | 6428 | N | GLY | E | 104 | −35.278 | −35.879 | 61.862 | 1.00 | 14.82 | E |
| ATOM | 6429 | CA | GLY | E | 104 | −34.980 | −35.431 | 63.208 | 1.00 | 15.74 | E |
| ATOM | 6430 | C | GLY | E | 104 | −33.455 | −35.150 | 63.379 | 1.00 | 16.88 | E |

TABLE 1-continued

| ATOM | 6431 | O | GLY | E | 104 | −32.822 | −34.379 | 62.648 | 1.00 | 16.81 | E |
| ATOM | 6432 | N | THR | E | 105 | −32.806 | −35.853 | 64.303 | 1.00 | 18.13 | E |
| ATOM | 6433 | CA | THR | E | 105 | −31.396 | −35.611 | 64.490 | 1.00 | 18.61 | E |
| ATOM | 6434 | CB | THR | E | 105 | −31.174 | −35.692 | 65.992 | 1.00 | 19.97 | E |
| ATOM | 6435 | OG1 | THR | E | 105 | −31.410 | −34.345 | 66.507 | 1.00 | 20.30 | E |
| ATOM | 6436 | CG2 | THR | E | 105 | −29.836 | −36.162 | 66.350 | 1.00 | 18.82 | E |
| ATOM | 6437 | C | THR | E | 105 | −30.328 | −36.332 | 63.641 | 1.00 | 18.61 | E |
| ATOM | 6438 | O | THR | E | 105 | −29.162 | −35.971 | 63.614 | 1.00 | 18.06 | E |
| ATOM | 6439 | N | ASN | E | 106 | −30.788 | −37.310 | 62.879 | 1.00 | 19.59 | E |
| ATOM | 6440 | CA | ASN | E | 106 | −30.006 | −38.155 | 62.005 | 1.00 | 19.02 | E |
| ATOM | 6441 | CB | ASN | E | 106 | −30.890 | −39.160 | 61.321 | 1.00 | 21.25 | E |
| ATOM | 6442 | CG | ASN | E | 106 | −31.167 | −40.332 | 62.139 | 1.00 | 23.24 | E |
| ATOM | 6443 | OD1 | ASN | E | 106 | −31.919 | −41.211 | 61.698 | 1.00 | 25.09 | E |
| ATOM | 6444 | ND2 | ASN | E | 106 | −30.545 | −40.421 | 63.332 | 1.00 | 24.78 | E |
| ATOM | 6445 | C | ASN | E | 106 | −29.446 | −37.396 | 60.891 | 1.00 | 19.65 | E |
| ATOM | 6446 | O | ASN | E | 106 | −30.075 | −37.230 | 59.900 | 1.00 | 19.66 | E |
| ATOM | 6447 | N | PHE | E | 107 | −28.252 | −36.914 | 60.993 | 1.00 | 19.97 | E |
| ATOM | 6448 | CA | PHE | E | 107 | −27.720 | −36.255 | 59.812 | 1.00 | 18.63 | E |
| ATOM | 6449 | CB | PHE | E | 107 | −26.951 | −35.018 | 60.228 | 1.00 | 19.17 | E |
| ATOM | 6450 | CG | PHE | E | 107 | −26.181 | −34.398 | 59.083 | 1.00 | 17.37 | E |
| ATOM | 6451 | CD1 | PHE | E | 107 | −26.882 | −33.740 | 58.031 | 1.00 | 17.32 | E |
| ATOM | 6452 | CD2 | PHE | E | 107 | −24.821 | −34.546 | 59.017 | 1.00 | 14.92 | E |
| ATOM | 6453 | CE1 | PHE | E | 107 | −26.241 | −33.266 | 56.957 | 1.00 | 17.07 | E |
| ATOM | 6454 | CE2 | PHE | E | 107 | −24.140 | −34.100 | 57.976 | 1.00 | 14.54 | E |
| ATOM | 6455 | CZ | PHE | E | 107 | −24.844 | −33.446 | 56.910 | 1.00 | 17.52 | E |
| ATOM | 6456 | C | PHE | E | 107 | −26.749 | −37.297 | 59.140 | 1.00 | 19.38 | E |
| ATOM | 6457 | O | PHE | E | 107 | −25.982 | −38.019 | 59.804 | 1.00 | 18.61 | E |
| ATOM | 6458 | N | GLN | E | 108 | −26.763 | −37.381 | 57.830 | 1.00 | 19.64 | E |
| ATOM | 6459 | CA | GLN | E | 108 | −25.899 | −38.420 | 57.151 | 1.00 | 18.89 | E |
| ATOM | 6460 | CB | GLN | E | 108 | −26.747 | −39.598 | 56.585 | 1.00 | 21.12 | E |
| ATOM | 6461 | CG | GLN | E | 108 | −27.830 | −40.233 | 57.558 | 1.00 | 21.41 | E |
| ATOM | 6462 | CD | GLN | E | 108 | −27.154 | −41.316 | 58.272 | 1.00 | 21.53 | E |
| ATOM | 6463 | OE1 | GLN | E | 108 | −27.783 | −42.003 | 59.099 | 1.00 | 23.21 | E |
| ATOM | 6464 | NE2 | GLN | E | 108 | −25.836 | −41.506 | 57.982 | 1.00 | 18.21 | E |
| ATOM | 6465 | C | GLN | E | 108 | −25.374 | −37.729 | 55.966 | 1.00 | 18.44 | E |
| ATOM | 6466 | O | GLN | E | 108 | −26.048 | −37.626 | 54.959 | 1.00 | 18.73 | E |
| ATOM | 6467 | N | LYS | E | 109 | −24.172 | −37.252 | 56.034 | 1.00 | 17.82 | E |
| ATOM | 6468 | CA | LYS | E | 109 | −23.663 | −36.495 | 54.891 | 1.00 | 17.27 | E |
| ATOM | 6469 | CB | LYS | E | 109 | −22.196 | −36.076 | 55.172 | 1.00 | 17.50 | E |
| ATOM | 6470 | CG | LYS | E | 109 | −21.225 | −36.831 | 54.295 | 1.00 | 19.07 | E |
| ATOM | 6471 | CD | LYS | E | 109 | −19.754 | −36.876 | 54.774 | 1.00 | 19.43 | E |
| ATOM | 6472 | CE | LYS | E | 109 | −19.099 | −35.553 | 54.600 | 1.00 | 21.33 | E |
| ATOM | 6473 | NZ | LYS | E | 109 | −17.626 | −35.824 | 54.497 | 1.00 | 21.30 | E |
| ATOM | 6474 | C | LYS | E | 109 | −23.776 | −37.224 | 53.569 | 1.00 | 15.93 | E |
| ATOM | 6475 | O | LYS | E | 109 | −23.958 | −36.634 | 52.527 | 1.00 | 16.56 | E |
| ATOM | 6476 | N | ARG | E | 110 | −23.699 | −38.525 | 53.630 | 1.00 | 16.29 | E |
| ATOM | 6477 | CA | ARG | E | 110 | −23.718 | −39.327 | 52.458 | 1.00 | 16.42 | E |
| ATOM | 6478 | CB | ARG | E | 110 | −23.203 | −40.719 | 52.814 | 1.00 | 17.44 | E |
| ATOM | 6479 | CG | ARG | E | 110 | −21.743 | −40.670 | 52.485 | 1.00 | 19.56 | E |
| ATOM | 6480 | CD | ARG | E | 110 | −20.868 | −40.022 | 53.663 | 1.00 | 21.63 | E |
| ATOM | 6481 | NE | ARG | E | 110 | −19.425 | −39.884 | 53.254 | 1.00 | 22.79 | E |
| ATOM | 6482 | CZ | ARG | E | 110 | −18.999 | −38.938 | 52.383 | 1.00 | 24.03 | E |
| ATOM | 6483 | NH1 | ARG | E | 110 | −19.873 | −38.022 | 51.831 | 1.00 | 22.73 | E |
| ATOM | 6484 | NH2 | ARG | E | 110 | −17.713 | −38.895 | 52.028 | 1.00 | 24.55 | E |
| ATOM | 6485 | C | ARG | E | 110 | −24.985 | −39.370 | 51.737 | 1.00 | 15.11 | E |
| ATOM | 6486 | O | ARG | E | 110 | −24.981 | −39.771 | 50.641 | 1.00 | 14.00 | E |
| ATOM | 6487 | N | LEU | E | 111 | −26.031 | −38.867 | 52.363 | 1.00 | 16.11 | E |
| ATOM | 6488 | CA | LEU | E | 111 | −27.362 | −38.779 | 51.858 | 1.00 | 17.20 | E |
| ATOM | 6489 | CB | LEU | E | 111 | −28.313 | −38.923 | 53.015 | 1.00 | 16.82 | E |
| ATOM | 6490 | CG | LEU | E | 111 | −28.243 | −40.300 | 53.625 | 1.00 | 17.62 | E |
| ATOM | 6491 | CD1 | LEU | E | 111 | −29.447 | −40.341 | 54.638 | 1.00 | 20.07 | E |
| ATOM | 6492 | CD2 | LEU | E | 111 | −28.379 | −41.499 | 52.584 | 1.00 | 16.54 | E |
| ATOM | 6493 | C | LEU | E | 111 | −27.586 | −37.503 | 51.110 | 1.00 | 17.24 | E |
| ATOM | 6494 | O | LEU | E | 111 | −28.554 | −37.374 | 50.293 | 1.00 | 19.81 | E |
| ATOM | 6495 | N | PHE | E | 112 | −26.719 | −36.536 | 51.354 | 1.00 | 16.22 | E |
| ATOM | 6496 | CA | PHE | E | 112 | −26.799 | −35.207 | 50.676 | 1.00 | 14.57 | E |
| ATOM | 6497 | CB | PHE | E | 112 | −26.235 | −34.093 | 51.617 | 1.00 | 13.54 | E |
| ATOM | 6498 | CG | PHE | E | 112 | −27.162 | −33.691 | 52.683 | 1.00 | 12.97 | E |
| ATOM | 6499 | CD1 | PHE | E | 112 | −27.542 | −34.616 | 53.657 | 1.00 | 14.63 | E |
| ATOM | 6500 | CD2 | PHE | E | 112 | −27.687 | −32.386 | 52.674 | 1.00 | 13.17 | E |
| ATOM | 6501 | CE1 | PHE | E | 112 | −28.508 | −34.252 | 54.686 | 1.00 | 15.88 | E |
| ATOM | 6502 | CE2 | PHE | E | 112 | −28.612 | −31.944 | 53.619 | 1.00 | 14.40 | E |
| ATOM | 6503 | CZ | PHE | E | 112 | −29.060 | −32.900 | 54.672 | 1.00 | 17.13 | E |
| ATOM | 6504 | C | PHE | E | 112 | −26.123 | −35.132 | 49.333 | 1.00 | 12.88 | E |
| ATOM | 6505 | O | PHE | E | 112 | −25.232 | −35.885 | 49.002 | 1.00 | 12.05 | E |
| ATOM | 6506 | N | THR | E | 113 | −26.585 | −34.200 | 48.541 | 1.00 | 13.03 | E |
| ATOM | 6507 | CA | THR | E | 113 | −26.069 | −34.000 | 47.227 | 1.00 | 14.32 | E |
| ATOM | 6508 | CB | THR | E | 113 | −27.179 | −34.093 | 46.176 | 1.00 | 13.31 | E |
| ATOM | 6509 | OG1 | THR | E | 113 | −27.695 | −35.363 | 46.236 | 1.00 | 10.62 | E |
| ATOM | 6510 | CG2 | THR | E | 113 | −26.722 | −33.787 | 44.805 | 1.00 | 10.98 | E |

TABLE 1-continued

| | | | | | | | | | |
|---|---|---|---|---|---|---|---|---|---|
| ATOM | 6511 | C | THR | E | 113 | −25.532 | −32.602 | 47.196 | 1.00 | 15.03 | E |
| ATOM | 6512 | O | THR | E | 113 | −26.193 | −31.654 | 47.643 | 1.00 | 15.83 | E |
| ATOM | 6513 | N | LYS | E | 114 | −24.357 | −32.458 | 46.588 | 1.00 | 15.80 | E |
| ATOM | 6514 | CA | LYS | E | 114 | −23.749 | −31.133 | 46.519 | 1.00 | 15.94 | E |
| ATOM | 6515 | CB | LYS | E | 114 | −22.219 | −31.216 | 46.207 | 1.00 | 15.87 | E |
| ATOM | 6516 | CG | LYS | E | 114 | −21.482 | −29.897 | 45.896 | 1.00 | 15.71 | E |
| ATOM | 6517 | CD | LYS | E | 114 | −19.940 | −29.891 | 46.035 | 1.00 | 15.07 | E |
| ATOM | 6518 | CE | LYS | E | 114 | −19.432 | −28.458 | 45.728 | 1.00 | 14.75 | E |
| ATOM | 6519 | NZ | LYS | E | 114 | −17.951 | −28.224 | 45.588 | 1.00 | 12.28 | E |
| ATOM | 6520 | C | LYS | E | 114 | −24.499 | −30.361 | 45.497 | 1.00 | 16.48 | E |
| ATOM | 6521 | O | LYS | E | 114 | −24.899 | −30.923 | 44.484 | 1.00 | 16.39 | E |
| ATOM | 6522 | N | ILE | E | 115 | −24.725 | −29.082 | 45.793 | 1.00 | 16.61 | E |
| ATOM | 6523 | CA | ILE | E | 115 | −25.367 | −28.213 | 44.850 | 1.00 | 16.39 | E |
| ATOM | 6524 | CB | ILE | E | 115 | −26.386 | −27.227 | 45.462 | 1.00 | 14.84 | E |
| ATOM | 6525 | CG2 | ILE | E | 115 | −26.741 | −26.202 | 44.437 | 1.00 | 11.81 | E |
| ATOM | 6526 | CG1 | ILE | E | 115 | −27.653 | −28.035 | 45.895 | 1.00 | 14.66 | E |
| ATOM | 6527 | CD1 | ILE | E | 115 | −28.615 | −27.527 | 46.817 | 1.00 | 9.75 | E |
| ATOM | 6528 | C | ILE | E | 115 | −24.307 | −27.405 | 44.086 | 1.00 | 17.37 | E |
| ATOM | 6529 | O | ILE | E | 115 | −24.395 | −27.260 | 42.855 | 1.00 | 18.34 | E |
| ATOM | 6530 | N | ASP | E | 116 | −23.308 | −26.926 | 44.784 | 1.00 | 17.29 | E |
| ATOM | 6531 | CA | ASP | E | 116 | −22.321 | −26.076 | 44.190 | 1.00 | 16.48 | E |
| ATOM | 6532 | CB | ASP | E | 116 | −22.956 | −24.771 | 43.645 | 1.00 | 15.51 | E |
| ATOM | 6533 | CG | ASP | E | 116 | −21.982 | −23.940 | 42.695 | 1.00 | 15.30 | E |
| ATOM | 6534 | OD1 | ASP | E | 116 | −22.377 | −22.873 | 42.087 | 1.00 | 14.48 | E |
| ATOM | 6535 | OD2 | ASP | E | 116 | −20.844 | −24.374 | 42.530 | 1.00 | 12.31 | E |
| ATOM | 6536 | C | ASP | E | 116 | −21.353 | −25.642 | 45.254 | 1.00 | 16.48 | E |
| ATOM | 6537 | O | ASP | E | 116 | −21.630 | −25.701 | 46.459 | 1.00 | 15.57 | E |
| ATOM | 6538 | N | THR | E | 117 | −20.205 | −25.157 | 44.771 | 1.00 | 16.45 | E |
| ATOM | 6539 | CA | THR | E | 117 | −19.198 | −24.570 | 45.642 | 1.00 | 16.37 | E |
| ATOM | 6540 | CB | THR | E | 117 | −17.855 | −24.690 | 44.989 | 1.00 | 15.90 | E |
| ATOM | 6541 | OG1 | THR | E | 117 | −17.589 | −26.098 | 44.866 | 1.00 | 15.41 | E |
| ATOM | 6542 | CG2 | THR | E | 117 | −16.804 | −23.935 | 45.775 | 1.00 | 12.86 | E |
| ATOM | 6543 | C | THR | E | 117 | −19.602 | −23.074 | 45.776 | 1.00 | 18.17 | E |
| ATOM | 6544 | O | THR | E | 117 | −19.869 | −22.440 | 44.773 | 1.00 | 18.65 | E |
| ATOM | 6545 | N | ILE | E | 118 | −19.700 | −22.540 | 46.993 | 1.00 | 18.37 | E |
| ATOM | 6546 | CA | ILE | E | 118 | −19.948 | −21.136 | 47.199 | 1.00 | 17.75 | E |
| ATOM | 6547 | CB | ILE | E | 118 | −20.829 | −20.968 | 48.414 | 1.00 | 17.69 | E |
| ATOM | 6548 | CG2 | ILE | E | 118 | −21.264 | −19.529 | 48.561 | 1.00 | 15.50 | E |
| ATOM | 6549 | CG1 | ILE | E | 118 | −22.019 | −21.909 | 48.313 | 1.00 | 17.52 | E |
| ATOM | 6550 | CD1 | ILE | E | 118 | −23.006 | −21.639 | 47.101 | 1.00 | 16.32 | E |
| ATOM | 6551 | C | ILE | E | 118 | −18.611 | −20.339 | 47.383 | 1.00 | 18.29 | E |
| ATOM | 6552 | O | ILE | E | 118 | −17.805 | −20.561 | 48.307 | 1.00 | 18.52 | E |
| ATOM | 6553 | N | ALA | E | 119 | −18.374 | −19.384 | 46.494 | 1.00 | 18.76 | E |
| ATOM | 6554 | CA | ALA | E | 119 | −17.113 | −18.573 | 46.540 | 1.00 | 18.15 | E |
| ATOM | 6555 | CB | ALA | E | 119 | −16.327 | −18.864 | 45.274 | 1.00 | 18.06 | E |
| ATOM | 6556 | C | ALA | E | 119 | −17.424 | −17.076 | 46.611 | 1.00 | 17.29 | E |
| ATOM | 6557 | O | ALA | E | 119 | −18.222 | −16.588 | 45.859 | 1.00 | 17.72 | E |
| ATOM | 6558 | N | PRO | E | 120 | −16.711 | −16.339 | 47.447 | 1.00 | 16.44 | E |
| ATOM | 6559 | CD | PRO | E | 120 | −15.536 | −16.733 | 48.220 | 1.00 | 16.16 | E |
| ATOM | 6560 | CA | PRO | E | 120 | −16.939 | −14.931 | 47.574 | 1.00 | 16.14 | E |
| ATOM | 6561 | CB | PRO | E | 120 | −16.229 | −14.612 | 48.854 | 1.00 | 16.22 | E |
| ATOM | 6562 | CG | PRO | E | 120 | −15.044 | −15.411 | 48.702 | 1.00 | 15.92 | E |
| ATOM | 6563 | C | PRO | E | 120 | −16.404 | −14.040 | 46.432 | 1.00 | 16.56 | E |
| ATOM | 6564 | O | PRO | E | 120 | −15.267 | −14.150 | 45.974 | 1.00 | 15.51 | E |
| ATOM | 6565 | N | ASP | E | 121 | −17.223 | −13.114 | 45.977 | 1.00 | 16.58 | E |
| ATOM | 6566 | CA | ASP | E | 121 | −16.705 | −12.190 | 44.975 | 1.00 | 17.95 | E |
| ATOM | 6567 | CB | ASP | E | 121 | −17.838 | −11.352 | 44.474 | 1.00 | 20.01 | E |
| ATOM | 6568 | CG | ASP | E | 121 | −19.063 | −12.183 | 44.347 | 1.00 | 23.40 | E |
| ATOM | 6569 | OD1 | ASP | E | 121 | −19.613 | −12.703 | 45.500 | 1.00 | 24.39 | E |
| ATOM | 6570 | OD2 | ASP | E | 121 | −19.441 | −12.365 | 43.109 | 1.00 | 23.51 | E |
| ATOM | 6571 | C | ASP | E | 121 | −15.704 | −11.268 | 45.666 | 1.00 | 18.36 | E |
| ATOM | 6572 | O | ASP | E | 121 | −14.877 | −10.644 | 44.994 | 1.00 | 19.20 | E |
| ATOM | 6573 | N | GLU | E | 122 | −15.845 | −11.125 | 47.004 | 1.00 | 16.89 | E |
| ATOM | 6574 | CA | GLU | E | 122 | −15.024 | −10.232 | 47.786 | 1.00 | 15.29 | E |
| ATOM | 6575 | CB | GLU | E | 122 | −15.720 | −8.930 | 47.947 | 1.00 | 15.71 | E |
| ATOM | 6576 | CG | GLU | E | 122 | −15.822 | −8.082 | 46.707 | 1.00 | 18.69 | E |
| ATOM | 6577 | CD | GLU | E | 122 | −16.290 | −6.625 | 47.045 | 1.00 | 21.92 | E |
| ATOM | 6578 | OE1 | GLU | E | 122 | −17.491 | −6.434 | 47.423 | 1.00 | 20.67 | E |
| ATOM | 6579 | OE2 | GLU | E | 122 | −15.427 | −5.654 | 46.945 | 1.00 | 25.39 | E |
| ATOM | 6580 | C | GLU | E | 122 | −14.588 | −10.765 | 49.121 | 1.00 | 14.92 | E |
| ATOM | 6581 | O | GLU | E | 122 | −15.348 | −10.958 | 50.082 | 1.00 | 14.19 | E |
| ATOM | 6582 | N | ILE | E | 123 | −13.318 | −11.037 | 49.176 | 1.00 | 14.88 | E |
| ATOM | 6583 | CA | ILE | E | 123 | −12.735 | −11.590 | 50.375 | 1.00 | 16.40 | E |
| ATOM | 6584 | CB | ILE | E | 123 | −11.484 | −12.301 | 49.944 | 1.00 | 18.48 | E |
| ATOM | 6585 | CG2 | ILE | E | 123 | −10.498 | −11.259 | 49.179 | 1.00 | 20.37 | E |
| ATOM | 6586 | CG1 | ILE | E | 123 | −10.764 | −12.819 | 51.116 | 1.00 | 20.55 | E |
| ATOM | 6587 | CD1 | ILE | E | 123 | −9.366 | −13.265 | 50.561 | 1.00 | 26.57 | E |
| ATOM | 6588 | C | ILE | E | 123 | −12.440 | −10.403 | 51.344 | 1.00 | 14.59 | E |
| ATOM | 6589 | O | ILE | E | 123 | −12.123 | −9.365 | 50.939 | 1.00 | 13.75 | E |
| ATOM | 6590 | N | THR | E | 124 | −12.586 | −10.543 | 52.625 | 1.00 | 14.63 | E |

TABLE 1-continued

| ATOM | 6591 | CA | THR | E | 124 | −12.379 | −9.359 | 53.479 | 1.00 | 16.51 | E |
| --- | --- | --- | --- | --- | --- | --- | --- | --- | --- | --- | --- |
| ATOM | 6592 | CB | THR | E | 124 | −13.251 | −9.427 | 54.690 | 1.00 | 16.26 | E |
| ATOM | 6593 | OG1 | THR | E | 124 | −14.610 | −9.206 | 54.296 | 1.00 | 16.59 | E |
| ATOM | 6594 | CG2 | THR | E | 124 | −12.813 | −8.419 | 55.667 | 1.00 | 16.04 | E |
| ATOM | 6595 | C | THR | E | 124 | −10.963 | −9.355 | 53.928 | 1.00 | 15.70 | E |
| ATOM | 6596 | O | THR | E | 124 | −10.580 | −10.325 | 54.620 | 1.00 | 16.38 | E |
| ATOM | 6597 | N | VAL | E | 125 | −10.171 | −8.361 | 53.528 | 1.00 | 14.98 | E |
| ATOM | 6598 | CA | VAL | E | 125 | −8.752 | −8.436 | 53.918 | 1.00 | 14.90 | E |
| ATOM | 6599 | CB | VAL | E | 125 | −7.728 | −7.733 | 52.932 | 1.00 | 15.04 | E |
| ATOM | 6600 | CG1 | VAL | E | 125 | −7.631 | −8.524 | 51.564 | 1.00 | 14.54 | E |
| ATOM | 6601 | CG2 | VAL | E | 125 | −8.081 | −6.261 | 52.723 | 1.00 | 14.04 | E |
| ATOM | 6602 | C | VAL | E | 125 | −8.470 | −7.864 | 55.294 | 1.00 | 14.94 | E |
| ATOM | 6603 | O | VAL | E | 125 | −9.325 | −7.158 | 55.880 | 1.00 | 14.74 | E |
| ATOM | 6604 | N | SER | E | 126 | −7.300 | −8.221 | 55.831 | 1.00 | 14.54 | E |
| ATOM | 6605 | CA | SER | E | 126 | −6.901 | −7.697 | 57.131 | 1.00 | 14.49 | E |
| ATOM | 6606 | CB | SER | E | 126 | −5.457 | −7.978 | 57.354 | 1.00 | 15.66 | E |
| ATOM | 6607 | OG | SER | E | 126 | −4.853 | −6.884 | 57.999 | 1.00 | 18.70 | E |
| ATOM | 6608 | C | SER | E | 126 | −7.158 | −6.171 | 57.333 | 1.00 | 13.59 | E |
| ATOM | 6609 | O | SER | E | 126 | −7.667 | −5.766 | 58.334 | 1.00 | 11.77 | E |
| ATOM | 6610 | N | SER | E | 127 | −6.833 | −5.333 | 56.400 | 1.00 | 14.09 | E |
| ATOM | 6611 | CA | SER | E | 127 | −7.085 | −3.979 | 56.723 | 1.00 | 15.57 | E |
| ATOM | 6612 | CB | SER | E | 127 | −6.277 | −3.093 | 55.857 | 1.00 | 17.12 | E |
| ATOM | 6613 | OG | SER | E | 127 | −6.906 | −3.089 | 54.601 | 1.00 | 20.60 | E |
| ATOM | 6614 | C | SER | E | 127 | −8.527 | −3.552 | 56.641 | 1.00 | 16.74 | E |
| ATOM | 6615 | O | SER | E | 127 | −8.823 | −2.435 | 57.091 | 1.00 | 16.95 | E |
| ATOM | 6616 | N | ASP | E | 128 | −9.408 | −4.415 | 56.063 | 1.00 | 16.20 | E |
| ATOM | 6617 | CA | ASP | E | 128 | −10.873 | −4.216 | 55.930 | 1.00 | 14.45 | E |
| ATOM | 6618 | CB | ASP | E | 128 | −11.482 | −5.347 | 55.138 | 1.00 | 17.24 | E |
| ATOM | 6619 | CG | ASP | E | 128 | −11.352 | −5.150 | 53.556 | 1.00 | 19.18 | E |
| ATOM | 6620 | OD1 | ASP | E | 128 | −11.596 | −6.143 | 52.812 | 1.00 | 20.26 | E |
| ATOM | 6621 | OD2 | ASP | E | 128 | −11.019 | −4.015 | 53.052 | 1.00 | 20.41 | E |
| ATOM | 6622 | C | ASP | E | 128 | −11.557 | −4.135 | 57.309 | 1.00 | 15.83 | E |
| ATOM | 6623 | O | ASP | E | 128 | −12.517 | −3.377 | 57.488 | 1.00 | 13.37 | E |
| ATOM | 6624 | N | PHE | E | 129 | −11.136 | −4.943 | 58.292 | 1.00 | 16.40 | E |
| ATOM | 6625 | CA | PHE | E | 129 | −11.701 | −4.792 | 59.597 | 1.00 | 17.76 | E |
| ATOM | 6626 | CB | PHE | E | 129 | −11.180 | −5.866 | 60.472 | 1.00 | 18.43 | E |
| ATOM | 6627 | CG | PHE | E | 129 | −11.520 | −7.207 | 59.990 | 1.00 | 17.90 | E |
| ATOM | 6628 | CD1 | PHE | E | 129 | −10.627 | −7.933 | 59.177 | 1.00 | 16.58 | E |
| ATOM | 6629 | CD2 | PHE | E | 129 | −12.791 | −7.731 | 60.228 | 1.00 | 17.36 | E |
| ATOM | 6630 | CE1 | PHE | E | 129 | −11.018 | −9.145 | 58.613 | 1.00 | 14.21 | E |
| ATOM | 6631 | CE2 | PHE | E | 129 | −13.192 | −8.994 | 59.646 | 1.00 | 15.67 | E |
| ATOM | 6632 | CZ | PHE | E | 129 | −12.309 | −9.673 | 58.854 | 1.00 | 13.85 | E |
| ATOM | 6633 | C | PHE | E | 129 | −11.004 | −3.529 | 59.898 | 1.00 | 20.00 | E |
| ATOM | 6634 | O | PHE | E | 129 | −10.281 | −3.052 | 59.018 | 1.00 | 22.54 | E |
| ATOM | 6635 | N | GLU | E | 130 | −11.125 | −2.900 | 61.044 | 1.00 | 19.43 | E |
| ATOM | 6636 | CA | GLU | E | 130 | −10.295 | −1.618 | 61.206 | 1.00 | 18.56 | E |
| ATOM | 6637 | CB | GLU | E | 130 | −8.818 | −1.822 | 60.789 | 1.00 | 19.67 | E |
| ATOM | 6638 | CG | GLU | E | 130 | −7.807 | −1.831 | 61.927 | 1.00 | 22.90 | E |
| ATOM | 6639 | CD | GLU | E | 130 | −6.312 | −1.389 | 61.511 | 1.00 | 25.42 | E |
| ATOM | 6640 | OE1 | GLU | E | 130 | −5.623 | −1.004 | 62.519 | 1.00 | 25.22 | E |
| ATOM | 6641 | OE2 | GLU | E | 130 | −5.827 | −1.453 | 60.250 | 1.00 | 25.30 | E |
| ATOM | 6642 | C | GLU | E | 130 | −10.914 | −0.522 | 60.314 | 1.00 | 16.75 | E |
| ATOM | 6643 | O | GLU | E | 130 | −11.357 | 0.466 | 60.845 | 1.00 | 15.63 | E |
| ATOM | 6644 | N | ALA | E | 131 | −10.913 | −0.703 | 58.982 | 1.00 | 15.59 | E |
| ATOM | 6645 | CA | ALA | E | 131 | −11.633 | 0.209 | 58.135 | 1.00 | 16.51 | E |
| ATOM | 6646 | CB | ALA | E | 131 | −11.287 | 0.018 | 56.793 | 1.00 | 15.31 | E |
| ATOM | 6647 | C | ALA | E | 131 | −12.986 | −0.436 | 58.445 | 1.00 | 17.12 | E |
| ATOM | 6648 | O | ALA | E | 131 | −13.070 | −1.562 | 59.061 | 1.00 | 19.07 | E |
| ATOM | 6649 | N | ARG | E | 132 | −14.094 | 0.161 | 58.142 | 1.00 | 16.64 | E |
| ATOM | 6650 | CA | ARG | E | 132 | −15.163 | −0.703 | 58.592 | 1.00 | 16.72 | E |
| ATOM | 6651 | CB | ARG | E | 132 | −16.143 | 0.092 | 59.429 | 1.00 | 18.51 | E |
| ATOM | 6652 | CG | ARG | E | 132 | −16.226 | −0.358 | 60.934 | 1.00 | 20.17 | E |
| ATOM | 6653 | CD | ARG | E | 132 | −14.946 | −0.373 | 61.698 | 1.00 | 17.38 | E |
| ATOM | 6654 | NE | ARG | E | 132 | −15.203 | −0.532 | 63.133 | 1.00 | 13.68 | E |
| ATOM | 6655 | CZ | ARG | E | 132 | −14.507 | −1.326 | 63.939 | 1.00 | 12.56 | E |
| ATOM | 6656 | NH1 | ARG | E | 132 | −13.516 | −2.098 | 63.494 | 1.00 | 8.35 | E |
| ATOM | 6657 | NH2 | ARG | E | 132 | −14.678 | −1.198 | 65.253 | 1.00 | 13.51 | E |
| ATOM | 6658 | C | ARG | E | 132 | −15.802 | −1.169 | 57.341 | 1.00 | 15.59 | E |
| ATOM | 6659 | O | ARG | E | 132 | −16.973 | −0.944 | 57.152 | 1.00 | 13.78 | E |
| ATOM | 6660 | N | HIS | E | 133 | −14.969 | −1.755 | 56.508 | 1.00 | 15.20 | E |
| ATOM | 6661 | CA | HIS | E | 133 | −15.336 | −2.233 | 55.231 | 1.00 | 18.08 | E |
| ATOM | 6662 | CB | HIS | E | 133 | −14.378 | −1.678 | 54.171 | 1.00 | 19.39 | E |
| ATOM | 6663 | CG | HIS | E | 133 | −14.400 | −0.188 | 54.047 | 1.00 | 21.57 | E |
| ATOM | 6664 | CD2 | HIS | E | 133 | −14.926 | 0.796 | 54.842 | 1.00 | 22.32 | E |
| ATOM | 6665 | ND1 | HIS | E | 133 | −13.798 | 0.455 | 52.988 | 1.00 | 23.50 | E |
| ATOM | 6666 | CE1 | HIS | E | 133 | −13.954 | 1.775 | 53.136 | 1.00 | 23.19 | E |
| ATOM | 6667 | NE2 | HIS | E | 133 | −14.636 | 2.012 | 54.253 | 1.00 | 20.89 | E |
| ATOM | 6668 | C | HIS | E | 133 | −15.344 | −3.744 | 55.124 | 1.00 | 18.16 | E |
| ATOM | 6669 | O | HIS | E | 133 | −14.589 | −4.268 | 54.353 | 1.00 | 17.56 | E |
| ATOM | 6670 | N | VAL | E | 134 | −16.156 | −4.427 | 55.928 | 1.00 | 19.28 | E |

TABLE 1-continued

| | | | | | | | | | | |
|---|---|---|---|---|---|---|---|---|---|---|
| ATOM | 6671 | CA | VAL | E | 134 | −16.201 | −5.846 | 55.814 | 1.00 | 19.85 | E |
| ATOM | 6672 | CB | VAL | E | 134 | −16.767 | −6.451 | 57.030 | 1.00 | 21.00 | E |
| ATOM | 6673 | CG1 | VAL | E | 134 | −16.636 | −8.013 | 56.918 | 1.00 | 22.46 | E |
| ATOM | 6674 | CG2 | VAL | E | 134 | −15.921 | −6.024 | 58.189 | 1.00 | 18.74 | E |
| ATOM | 6675 | C | VAL | E | 134 | −17.022 | −6.195 | 54.543 | 1.00 | 19.81 | E |
| ATOM | 6676 | O | VAL | E | 134 | −18.020 | −5.518 | 54.220 | 1.00 | 20.32 | E |
| ATOM | 6677 | N | LYS | E | 135 | −16.576 | −7.214 | 53.787 | 1.00 | 19.28 | E |
| ATOM | 6678 | CA | LYS | E | 135 | −17.279 | −7.550 | 52.524 | 1.00 | 17.66 | E |
| ATOM | 6679 | CB | LYS | E | 135 | −16.238 | −7.903 | 51.448 | 1.00 | 18.76 | E |
| ATOM | 6680 | CG | LYS | E | 135 | −15.059 | −6.976 | 51.367 | 1.00 | 18.77 | E |
| ATOM | 6681 | CD | LYS | E | 135 | −15.521 | −5.531 | 51.174 | 1.00 | 19.68 | E |
| ATOM | 6682 | CE | LYS | E | 135 | −14.348 | −4.724 | 50.622 | 1.00 | 20.70 | E |
| ATOM | 6683 | NZ | LYS | E | 135 | −14.684 | −3.267 | 50.708 | 1.00 | 22.03 | E |
| ATOM | 6684 | C | LYS | E | 135 | −18.338 | −8.629 | 52.649 | 1.00 | 16.06 | E |
| ATOM | 6685 | O | LYS | E | 135 | −18.087 | −9.798 | 53.019 | 1.00 | 15.14 | E |
| ATOM | 6686 | N | LEU | E | 136 | −19.542 | −8.162 | 52.352 | 1.00 | 15.57 | E |
| ATOM | 6687 | CA | LEU | E | 136 | −20.758 | −8.970 | 52.410 | 1.00 | 16.54 | E |
| ATOM | 6688 | CB | LEU | E | 136 | −21.853 | −8.099 | 53.012 | 1.00 | 15.87 | E |
| ATOM | 6689 | CG | LEU | E | 136 | −23.090 | −8.908 | 53.358 | 1.00 | 17.20 | E |
| ATOM | 6690 | CD1 | LEU | E | 136 | −23.807 | −9.239 | 52.057 | 1.00 | 20.95 | E |
| ATOM | 6691 | CD2 | LEU | E | 136 | −22.811 | −10.207 | 54.060 | 1.00 | 16.42 | E |
| ATOM | 6692 | C | LEU | E | 136 | −21.115 | −9.508 | 50.977 | 1.00 | 16.11 | E |
| ATOM | 6693 | O | LEU | E | 136 | −21.463 | −8.745 | 50.093 | 1.00 | 16.33 | E |
| ATOM | 6694 | N | ASN | E | 137 | −20.997 | −10.810 | 50.773 | 1.00 | 15.86 | E |
| ATOM | 6695 | CA | ASN | E | 137 | −21.251 | −11.398 | 49.473 | 1.00 | 16.10 | E |
| ATOM | 6696 | CB | ASN | E | 137 | −20.287 | −12.499 | 49.254 | 1.00 | 14.53 | E |
| ATOM | 6697 | CG | ASN | E | 137 | −18.877 | −12.020 | 49.150 | 1.00 | 13.48 | E |
| ATOM | 6698 | OD1 | ASN | E | 137 | −18.436 | −11.406 | 48.169 | 1.00 | 9.06 | E |
| ATOM | 6699 | ND2 | ASN | E | 137 | −18.148 | −12.355 | 50.151 | 1.00 | 11.57 | E |
| ATOM | 6700 | C | ASN | E | 137 | −22.653 | −11.981 | 49.311 | 1.00 | 16.65 | E |
| ATOM | 6701 | O | ASN | E | 137 | −23.290 | −12.515 | 50.267 | 1.00 | 17.37 | E |
| ATOM | 6702 | N | VAL | E | 138 | −23.235 | −11.824 | 48.133 | 1.00 | 16.09 | E |
| ATOM | 6703 | CA | VAL | E | 138 | −24.528 | −12.445 | 47.990 | 1.00 | 16.12 | E |
| ATOM | 6704 | CB | VAL | E | 138 | −25.621 | −11.457 | 47.586 | 1.00 | 16.05 | E |
| ATOM | 6705 | CG1 | VAL | E | 138 | −26.960 | −12.160 | 47.618 | 1.00 | 16.04 | E |
| ATOM | 6706 | CG2 | VAL | E | 138 | −25.692 | −10.373 | 48.474 | 1.00 | 16.32 | E |
| ATOM | 6707 | C | VAL | E | 138 | −24.418 | −13.548 | 46.924 | 1.00 | 15.29 | E |
| ATOM | 6708 | O | VAL | E | 138 | −23.984 | −13.280 | 45.799 | 1.00 | 14.63 | E |
| ATOM | 6709 | N | GLU | E | 139 | −24.772 | −14.767 | 47.296 | 1.00 | 14.90 | E |
| ATOM | 6710 | CA | GLU | E | 139 | −24.780 | −15.823 | 46.290 | 1.00 | 17.15 | E |
| ATOM | 6711 | CB | GLU | E | 139 | −23.698 | −16.900 | 46.557 | 1.00 | 16.12 | E |
| ATOM | 6712 | CG | GLU | E | 139 | −22.204 | −16.449 | 46.245 | 1.00 | 15.13 | E |
| ATOM | 6713 | CD | GLU | E | 139 | −21.966 | −16.068 | 44.833 | 1.00 | 14.55 | E |
| ATOM | 6714 | OE1 | GLU | E | 139 | −22.753 | −16.468 | 43.958 | 1.00 | 16.56 | E |
| ATOM | 6715 | OE2 | GLU | E | 139 | −20.970 | −15.411 | 44.557 | 1.00 | 13.89 | E |
| ATOM | 6716 | C | GLU | E | 139 | −26.090 | −16.488 | 46.163 | 1.00 | 16.86 | E |
| ATOM | 6717 | O | GLU | E | 139 | −26.717 | −16.868 | 47.173 | 1.00 | 19.05 | E |
| ATOM | 6718 | N | GLU | E | 140 | −26.592 | −16.600 | 44.960 | 1.00 | 16.56 | E |
| ATOM | 6719 | CA | GLU | E | 140 | −27.865 | −17.386 | 44.820 | 1.00 | 16.69 | E |
| ATOM | 6720 | CB | GLU | E | 140 | −28.977 | −16.536 | 44.243 | 1.00 | 17.39 | E |
| ATOM | 6721 | CG | GLU | E | 140 | −30.304 | −17.307 | 44.286 | 1.00 | 18.53 | E |
| ATOM | 6722 | CD | GLU | E | 140 | −31.524 | −16.399 | 44.354 | 1.00 | 19.91 | E |
| ATOM | 6723 | OE1 | GLU | E | 140 | −31.933 | −15.842 | 43.278 | 1.00 | 17.40 | E |
| ATOM | 6724 | OE2 | GLU | E | 140 | −31.985 | −16.296 | 45.539 | 1.00 | 19.84 | E |
| ATOM | 6725 | C | GLU | E | 140 | −27.725 | −18.706 | 43.983 | 1.00 | 15.31 | E |
| ATOM | 6726 | O | GLU | E | 140 | −27.063 | −18.757 | 43.002 | 1.00 | 14.18 | E |
| ATOM | 6727 | N | ARG | E | 141 | −28.302 | −19.791 | 44.422 | 1.00 | 15.10 | E |
| ATOM | 6728 | CA | ARG | E | 141 | −28.249 | −20.992 | 43.645 | 1.00 | 15.24 | E |
| ATOM | 6729 | CB | ARG | E | 141 | −27.366 | −22.057 | 44.258 | 1.00 | 14.64 | E |
| ATOM | 6730 | CG | ARG | E | 141 | −25.875 | −21.724 | 44.438 | 1.00 | 13.54 | E |
| ATOM | 6731 | CD | ARG | E | 141 | −24.954 | −21.901 | 43.279 | 1.00 | 12.12 | E |
| ATOM | 6732 | NE | ARG | E | 141 | −24.374 | −20.578 | 43.062 | 1.00 | 13.29 | E |
| ATOM | 6733 | CZ | ARG | E | 141 | −23.152 | −20.155 | 43.463 | 1.00 | 13.00 | E |
| ATOM | 6734 | NH1 | ARG | E | 141 | −22.242 | −20.851 | 44.090 | 1.00 | 11.44 | E |
| ATOM | 6735 | NH2 | ARG | E | 141 | −22.884 | −18.917 | 43.369 | 1.00 | 13.49 | E |
| ATOM | 6736 | C | ARG | E | 141 | −29.653 | −21.539 | 43.577 | 1.00 | 15.27 | E |
| ATOM | 6737 | O | ARG | E | 141 | −30.564 | −21.072 | 44.211 | 1.00 | 15.16 | E |
| ATOM | 6738 | N | SER | E | 142 | −29.826 | −22.568 | 42.798 | 1.00 | 16.25 | E |
| ATOM | 6739 | CA | SER | E | 142 | −31.144 | −23.114 | 42.679 | 1.00 | 17.12 | E |
| ATOM | 6740 | CB | SER | E | 142 | −31.901 | −22.334 | 41.635 | 1.00 | 16.28 | E |
| ATOM | 6741 | OG | SER | E | 142 | −31.817 | −23.130 | 40.551 | 1.00 | 16.66 | E |
| ATOM | 6742 | C | SER | E | 142 | −31.110 | −24.621 | 42.406 | 1.00 | 16.25 | E |
| ATOM | 6743 | O | SER | E | 142 | −30.151 | −25.169 | 41.961 | 1.00 | 16.95 | E |
| ATOM | 6744 | N | VAL | E | 143 | −32.148 | −25.309 | 42.785 | 1.00 | 17.72 | E |
| ATOM | 6745 | CA | VAL | E | 143 | −32.116 | −26.748 | 42.606 | 1.00 | 18.33 | E |
| ATOM | 6746 | CB | VAL | E | 143 | −31.273 | −27.467 | 43.821 | 1.00 | 18.69 | E |
| ATOM | 6747 | CG1 | VAL | E | 143 | −32.050 | −27.485 | 45.164 | 1.00 | 18.76 | E |
| ATOM | 6748 | CG2 | VAL | E | 143 | −31.047 | −28.839 | 43.538 | 1.00 | 19.46 | E |
| ATOM | 6749 | C | VAL | E | 143 | −33.529 | −27.273 | 42.431 | 1.00 | 17.44 | E |
| ATOM | 6750 | O | VAL | E | 143 | −34.536 | −26.637 | 42.783 | 1.00 | 17.56 | E |

TABLE 1-continued

| ATOM | 6751 | N | GLY | E | 144 | −33.607 | −28.425 | 41.794 | 1.00 | 18.15 | E |
|---|---|---|---|---|---|---|---|---|---|---|---|
| ATOM | 6752 | CA | GLY | E | 144 | −34.923 | −29.007 | 41.505 | 1.00 | 18.55 | E |
| ATOM | 6753 | C | GLY | E | 144 | −34.919 | −29.899 | 40.274 | 1.00 | 18.23 | E |
| ATOM | 6754 | O | GLY | E | 144 | −33.858 | −30.113 | 39.688 | 1.00 | 18.41 | E |
| ATOM | 6755 | N | PRO | E | 145 | −36.070 | −30.503 | 39.917 | 1.00 | 17.96 | E |
| ATOM | 6756 | CD | PRO | E | 145 | −36.395 | −31.115 | 38.598 | 1.00 | 18.72 | E |
| ATOM | 6757 | CA | PRO | E | 145 | −37.297 | −30.312 | 40.699 | 1.00 | 18.34 | E |
| ATOM | 6758 | CB | PRO | E | 145 | −38.419 | −30.718 | 39.713 | 1.00 | 17.66 | E |
| ATOM | 6759 | CG | PRO | E | 145 | −37.799 | −31.754 | 38.841 | 1.00 | 17.11 | E |
| ATOM | 6760 | C | PRO | E | 145 | −37.362 | −31.107 | 41.994 | 1.00 | 17.46 | E |
| ATOM | 6761 | O | PRO | E | 145 | −36.929 | −32.237 | 42.092 | 1.00 | 17.87 | E |
| ATOM | 6762 | N | LEU | E | 146 | −37.892 | −30.488 | 43.012 | 1.00 | 17.07 | E |
| ATOM | 6763 | CA | LEU | E | 146 | −38.018 | −31.205 | 44.229 | 1.00 | 17.15 | E |
| ATOM | 6764 | CB | LEU | E | 146 | −38.131 | −30.181 | 45.353 | 1.00 | 16.92 | E |
| ATOM | 6765 | CG | LEU | E | 146 | −36.787 | −29.828 | 46.017 | 1.00 | 17.41 | E |
| ATOM | 6766 | CD1 | LEU | E | 146 | −35.752 | −29.684 | 45.052 | 1.00 | 16.28 | E |
| ATOM | 6767 | CD2 | LEU | E | 146 | −36.892 | −28.589 | 46.855 | 1.00 | 16.20 | E |
| ATOM | 6768 | C | LEU | E | 146 | −39.301 | −31.984 | 44.027 | 1.00 | 16.38 | E |
| ATOM | 6769 | O | LEU | E | 146 | −40.159 | −31.589 | 43.252 | 1.00 | 16.87 | E |
| ATOM | 6770 | N | THR | E | 147 | −39.440 | −33.083 | 44.745 | 1.00 | 16.07 | E |
| ATOM | 6771 | CA | THR | E | 147 | −40.647 | −33.944 | 44.653 | 1.00 | 15.53 | E |
| ATOM | 6772 | CB | THR | E | 147 | −40.469 | −35.098 | 43.630 | 1.00 | 14.60 | E |
| ATOM | 6773 | OG1 | THR | E | 147 | −39.513 | −36.016 | 44.149 | 1.00 | 16.34 | E |
| ATOM | 6774 | CG2 | THR | E | 147 | −40.047 | −34.619 | 42.322 | 1.00 | 11.13 | E |
| ATOM | 6775 | C | THR | E | 147 | −41.126 | −34.587 | 45.960 | 1.00 | 13.99 | E |
| ATOM | 6776 | O | THR | E | 147 | −42.252 | −35.000 | 46.024 | 1.00 | 15.17 | E |
| ATOM | 6777 | N | ARG | E | 148 | −40.290 | −34.672 | 46.995 | 1.00 | 13.67 | E |
| ATOM | 6778 | CA | ARG | E | 148 | −40.692 | −35.293 | 48.271 | 1.00 | 12.84 | E |
| ATOM | 6779 | CB | ARG | E | 148 | −39.472 | −35.791 | 49.024 | 1.00 | 14.22 | E |
| ATOM | 6780 | CG | ARG | E | 148 | −38.394 | −36.400 | 48.200 | 1.00 | 15.41 | E |
| ATOM | 6781 | CD | ARG | E | 148 | −38.711 | −37.781 | 47.742 | 1.00 | 17.75 | E |
| ATOM | 6782 | NE | ARG | E | 148 | −39.645 | −37.799 | 46.607 | 1.00 | 19.67 | E |
| ATOM | 6783 | CZ | ARG | E | 148 | −40.774 | −38.552 | 46.551 | 1.00 | 21.23 | E |
| ATOM | 6784 | NH1 | ARG | E | 148 | −41.159 | −39.363 | 47.541 | 1.00 | 17.03 | E |
| ATOM | 6785 | NH2 | ARG | E | 148 | −41.514 | −38.503 | 45.441 | 1.00 | 22.58 | E |
| ATOM | 6786 | C | ARG | E | 148 | −41.507 | −34.343 | 49.153 | 1.00 | 10.99 | E |
| ATOM | 6787 | O | ARG | E | 148 | −41.798 | −33.249 | 48.778 | 1.00 | 7.88 | E |
| ATOM | 6788 | N | LYS | E | 149 | −41.872 | −34.797 | 50.316 | 1.00 | 12.39 | E |
| ATOM | 6789 | CA | LYS | E | 149 | −42.693 | −33.981 | 51.201 | 1.00 | 15.90 | E |
| ATOM | 6790 | CB | LYS | E | 149 | −43.165 | −34.810 | 52.367 | 1.00 | 17.39 | E |
| ATOM | 6791 | CG | LYS | E | 149 | −44.362 | −34.337 | 53.172 | 1.00 | 18.52 | E |
| ATOM | 6792 | CD | LYS | E | 149 | −44.741 | −35.432 | 54.249 | 1.00 | 20.56 | E |
| ATOM | 6793 | CE | LYS | E | 149 | −45.699 | −34.835 | 55.268 | 1.00 | 21.51 | E |
| ATOM | 6794 | NZ | LYS | E | 149 | −45.173 | −34.855 | 56.743 | 1.00 | 24.22 | E |
| ATOM | 6795 | C | LYS | E | 149 | −41.871 | −32.836 | 51.727 | 1.00 | 16.88 | E |
| ATOM | 6796 | O | LYS | E | 149 | −42.283 | −31.668 | 51.822 | 1.00 | 17.46 | E |
| ATOM | 6797 | N | GLY | E | 150 | −40.617 | −33.162 | 51.990 | 1.00 | 17.48 | E |
| ATOM | 6798 | CA | GLY | E | 150 | −39.695 | −32.137 | 52.461 | 1.00 | 17.49 | E |
| ATOM | 6799 | C | GLY | E | 150 | −38.249 | −32.250 | 52.018 | 1.00 | 16.99 | E |
| ATOM | 6800 | O | GLY | E | 150 | −37.890 | −33.157 | 51.190 | 1.00 | 16.65 | E |
| ATOM | 6801 | N | PHE | E | 151 | −37.460 | −31.331 | 52.559 | 1.00 | 15.38 | E |
| ATOM | 6802 | CA | PHE | E | 151 | −36.080 | −31.202 | 52.242 | 1.00 | 14.94 | E |
| ATOM | 6803 | CB | PHE | E | 151 | −35.978 | −30.503 | 50.869 | 1.00 | 14.76 | E |
| ATOM | 6804 | CG | PHE | E | 151 | −36.252 | −29.009 | 50.924 | 1.00 | 15.55 | E |
| ATOM | 6805 | CD1 | PHE | E | 151 | −35.249 | −28.094 | 51.188 | 1.00 | 15.30 | E |
| ATOM | 6806 | CD2 | PHE | E | 151 | −37.489 | −28.505 | 50.626 | 1.00 | 16.02 | E |
| ATOM | 6807 | CE1 | PHE | E | 151 | −35.543 | −26.789 | 51.105 | 1.00 | 14.72 | E |
| ATOM | 6808 | CE2 | PHE | E | 151 | −37.726 | −27.176 | 50.554 | 1.00 | 14.01 | E |
| ATOM | 6809 | CZ | PHE | E | 151 | −36.788 | −26.343 | 50.777 | 1.00 | 13.57 | E |
| ATOM | 6810 | C | PHE | E | 151 | −35.232 | −30.401 | 53.302 | 1.00 | 15.20 | E |
| ATOM | 6811 | O | PHE | E | 151 | −35.750 | −29.547 | 54.103 | 1.00 | 13.46 | E |
| ATOM | 6812 | N | TYR | E | 152 | −33.927 | −30.654 | 53.199 | 1.00 | 14.21 | E |
| ATOM | 6813 | CA | TYR | E | 152 | −32.928 | −30.079 | 54.033 | 1.00 | 14.08 | E |
| ATOM | 6814 | CB | TYR | E | 152 | −32.188 | −31.163 | 54.801 | 1.00 | 15.02 | E |
| ATOM | 6815 | CG | TYR | E | 152 | −32.962 | −31.879 | 55.847 | 1.00 | 14.78 | E |
| ATOM | 6816 | CD1 | TYR | E | 152 | −33.545 | −33.099 | 55.548 | 1.00 | 13.35 | E |
| ATOM | 6817 | CE1 | TYR | E | 152 | −34.320 | −33.784 | 56.470 | 1.00 | 16.00 | E |
| ATOM | 6818 | CD2 | TYR | E | 152 | −33.153 | −31.298 | 57.134 | 1.00 | 14.94 | E |
| ATOM | 6819 | CE2 | TYR | E | 152 | −33.946 | −31.934 | 58.097 | 1.00 | 16.09 | E |
| ATOM | 6820 | CZ | TYR | E | 152 | −34.558 | −33.203 | 57.802 | 1.00 | 16.72 | E |
| ATOM | 6821 | OH | TYR | E | 152 | −35.331 | −33.890 | 58.770 | 1.00 | 16.01 | E |
| ATOM | 6822 | C | TYR | E | 152 | −31.927 | −29.410 | 53.175 | 1.00 | 15.21 | E |
| ATOM | 6823 | O | TYR | E | 152 | −31.650 | −29.851 | 52.050 | 1.00 | 13.99 | E |
| ATOM | 6824 | N | LEU | E | 153 | −31.361 | −28.359 | 53.741 | 1.00 | 14.80 | E |
| ATOM | 6825 | CA | LEU | E | 153 | −30.256 | −27.667 | 53.146 | 1.00 | 15.38 | E |
| ATOM | 6826 | CB | LEU | E | 153 | −30.635 | −26.252 | 53.033 | 1.00 | 15.54 | E |
| ATOM | 6827 | CG | LEU | E | 153 | −30.698 | −25.694 | 51.667 | 1.00 | 16.01 | E |
| ATOM | 6828 | CD1 | LEU | E | 153 | −31.519 | −26.439 | 50.739 | 1.00 | 15.43 | E |
| ATOM | 6829 | CD2 | LEU | E | 153 | −31.188 | −24.280 | 51.840 | 1.00 | 17.03 | E |
| ATOM | 6830 | C | LEU | E | 153 | −29.081 | −27.865 | 54.124 | 1.00 | 16.34 | E |

TABLE 1-continued

| | | | | | | | | | |
|---|---|---|---|---|---|---|---|---|---|
| ATOM | 6831 | O | LEU | E | 153 | −29.274 | −27.998 | 55.381 | 1.00 | 17.54 | E |
| ATOM | 6832 | N | ALA | E | 154 | −27.867 | −27.900 | 53.602 | 1.00 | 16.56 | E |
| ATOM | 6833 | CA | ALA | E | 154 | −26.700 | −28.089 | 54.474 | 1.00 | 15.48 | E |
| ATOM | 6834 | CB | ALA | E | 154 | −26.459 | −29.571 | 54.734 | 1.00 | 14.70 | E |
| ATOM | 6835 | C | ALA | E | 154 | −25.443 | −27.373 | 53.952 | 1.00 | 16.09 | E |
| ATOM | 6836 | O | ALA | E | 154 | −25.288 | −27.075 | 52.820 | 1.00 | 15.33 | E |
| ATOM | 6837 | N | PHE | E | 155 | −24.558 | −27.082 | 54.861 | 1.00 | 16.55 | E |
| ATOM | 6838 | CA | PHE | E | 155 | −23.383 | −26.376 | 54.531 | 1.00 | 16.26 | E |
| ATOM | 6839 | CB | PHE | E | 155 | −23.486 | −24.933 | 55.032 | 1.00 | 16.84 | E |
| ATOM | 6840 | CG | PHE | E | 155 | −24.774 | −24.203 | 54.656 | 1.00 | 15.32 | E |
| ATOM | 6841 | CD1 | PHE | E | 155 | −25.897 | −24.349 | 55.408 | 1.00 | 15.36 | E |
| ATOM | 6842 | CD2 | PHE | E | 155 | −24.802 | −23.354 | 53.604 | 1.00 | 13.95 | E |
| ATOM | 6843 | CE1 | PHE | E | 155 | −26.967 | −23.662 | 55.094 | 1.00 | 14.40 | E |
| ATOM | 6844 | CE2 | PHE | E | 155 | −25.871 | −22.666 | 53.289 | 1.00 | 12.91 | E |
| ATOM | 6845 | CZ | PHE | E | 155 | −26.924 | −22.803 | 53.998 | 1.00 | 14.82 | E |
| ATOM | 6846 | C | PHE | E | 155 | −22.116 | −27.023 | 55.125 | 1.00 | 17.92 | E |
| ATOM | 6847 | O | PHE | E | 155 | −22.009 | −27.260 | 56.366 | 1.00 | 17.38 | E |
| ATOM | 6848 | N | GLN | E | 156 | −21.146 | −27.218 | 54.251 | 1.00 | 16.88 | E |
| ATOM | 6849 | CA | GLN | E | 156 | −19.991 | −27.894 | 54.605 | 1.00 | 15.83 | E |
| ATOM | 6850 | CB | GLN | E | 156 | −19.758 | −28.993 | 53.627 | 1.00 | 17.44 | E |
| ATOM | 6851 | CG | GLN | E | 156 | −18.758 | −29.978 | 54.121 | 1.00 | 18.26 | E |
| ATOM | 6852 | CD | GLN | E | 156 | −18.054 | −30.675 | 52.940 | 1.00 | 18.17 | E |
| ATOM | 6853 | OE1 | GLN | E | 156 | −18.218 | −30.310 | 51.785 | 1.00 | 19.45 | E |
| ATOM | 6854 | NE2 | GLN | E | 156 | −17.234 | −31.629 | 53.250 | 1.00 | 16.43 | E |
| ATOM | 6855 | C | GLN | E | 156 | −18.858 | −26.949 | 54.558 | 1.00 | 17.03 | E |
| ATOM | 6856 | O | GLN | E | 156 | −18.599 | −26.288 | 53.469 | 1.00 | 15.74 | E |
| ATOM | 6857 | N | ASP | E | 157 | −18.237 | −26.802 | 55.764 | 1.00 | 14.94 | E |
| ATOM | 6858 | CA | ASP | E | 157 | −17.142 | −25.945 | 55.882 | 1.00 | 14.03 | E |
| ATOM | 6859 | CB | ASP | E | 157 | −17.090 | −25.246 | 57.250 | 1.00 | 13.56 | E |
| ATOM | 6860 | CG | ASP | E | 157 | −15.722 | −24.696 | 57.568 | 1.00 | 11.59 | E |
| ATOM | 6861 | OD1 | ASP | E | 157 | −15.237 | −25.078 | 58.580 | 1.00 | 13.09 | E |
| ATOM | 6862 | OD2 | ASP | E | 157 | −15.144 | −23.972 | 56.807 | 1.00 | 8.80 | E |
| ATOM | 6863 | C | ASP | E | 157 | −15.986 | −26.792 | 55.700 | 1.00 | 14.87 | E |
| ATOM | 6864 | O | ASP | E | 157 | −15.890 | −27.811 | 56.344 | 1.00 | 14.30 | E |
| ATOM | 6865 | N | ILE | E | 158 | −15.106 | −26.345 | 54.822 | 1.00 | 15.17 | E |
| ATOM | 6866 | CA | ILE | E | 158 | −13.889 | −27.044 | 54.485 | 1.00 | 16.94 | E |
| ATOM | 6867 | CB | ILE | E | 158 | −13.843 | −27.228 | 52.876 | 1.00 | 16.81 | E |
| ATOM | 6868 | CG2 | ILE | E | 158 | −12.850 | −26.361 | 52.215 | 1.00 | 16.58 | E |
| ATOM | 6869 | CG1 | ILE | E | 158 | −13.691 | −28.673 | 52.583 | 1.00 | 16.22 | E |
| ATOM | 6870 | CD1 | ILE | E | 158 | −14.878 | −29.334 | 52.981 | 1.00 | 18.00 | E |
| ATOM | 6871 | C | ILE | E | 158 | −12.604 | −26.472 | 55.019 | 1.00 | 16.70 | E |
| ATOM | 6872 | O | ILE | E | 158 | −11.543 | −26.842 | 54.553 | 1.00 | 17.08 | E |
| ATOM | 6873 | N | GLY | E | 159 | −12.692 | −25.620 | 56.039 | 1.00 | 16.29 | E |
| ATOM | 6874 | CA | GLY | E | 159 | −11.480 | −25.060 | 56.561 | 1.00 | 15.73 | E |
| ATOM | 6875 | C | GLY | E | 159 | −11.297 | −23.587 | 56.216 | 1.00 | 15.89 | E |
| ATOM | 6876 | O | GLY | E | 159 | −10.186 | −23.106 | 56.173 | 1.00 | 15.42 | E |
| ATOM | 6877 | N | ALA | E | 160 | −12.406 | −22.896 | 55.915 | 1.00 | 16.10 | E |
| ATOM | 6878 | CA | ALA | E | 160 | −12.452 | −21.493 | 55.582 | 1.00 | 15.12 | E |
| ATOM | 6879 | CB | ALA | E | 160 | −13.405 | −21.226 | 54.598 | 1.00 | 14.72 | E |
| ATOM | 6880 | C | ALA | E | 160 | −12.883 | −20.831 | 56.823 | 1.00 | 14.54 | E |
| ATOM | 6881 | O | ALA | E | 160 | −13.103 | −21.524 | 57.808 | 1.00 | 16.07 | E |
| ATOM | 6882 | N | CYS | E | 161 | −12.872 | −19.484 | 56.794 | 1.00 | 13.79 | E |
| ATOM | 6883 | CA | CYS | E | 161 | −13.245 | −18.562 | 57.876 | 1.00 | 11.75 | E |
| ATOM | 6884 | C | CYS | E | 161 | −14.390 | −17.776 | 57.302 | 1.00 | 10.91 | E |
| ATOM | 6885 | O | CYS | E | 161 | −14.280 | −16.664 | 56.715 | 1.00 | 10.17 | E |
| ATOM | 6886 | CB | CYS | E | 161 | −12.126 | −17.582 | 58.280 | 1.00 | 8.68 | E |
| ATOM | 6887 | SG | CYS | E | 161 | −12.525 | −16.697 | 59.806 | 1.00 | 8.53 | E |
| ATOM | 6888 | N | VAL | E | 162 | −15.529 | −18.394 | 57.550 | 1.00 | 12.28 | E |
| ATOM | 6889 | CA | VAL | E | 162 | −16.792 | −17.846 | 57.079 | 1.00 | 15.17 | E |
| ATOM | 6890 | CB | VAL | E | 162 | −17.623 | −18.900 | 56.282 | 1.00 | 16.84 | E |
| ATOM | 6891 | CG1 | VAL | E | 162 | −18.644 | −18.183 | 55.326 | 1.00 | 17.21 | E |
| ATOM | 6892 | CG2 | VAL | E | 162 | −16.686 | −19.851 | 55.574 | 1.00 | 17.79 | E |
| ATOM | 6893 | C | VAL | E | 162 | −17.726 | −17.374 | 58.157 | 1.00 | 12.14 | E |
| ATOM | 6894 | O | VAL | E | 162 | −17.750 | −17.899 | 59.225 | 1.00 | 8.37 | E |
| ATOM | 6895 | N | ALA | E | 163 | −18.477 | −16.392 | 57.749 | 1.00 | 11.78 | E |
| ATOM | 6896 | CA | ALA | E | 163 | −19.504 | −15.901 | 58.490 | 1.00 | 13.52 | E |
| ATOM | 6897 | CB | ALA | E | 163 | −19.166 | −14.637 | 58.753 | 1.00 | 15.31 | E |
| ATOM | 6898 | C | ALA | E | 163 | −20.831 | −15.965 | 57.610 | 1.00 | 14.75 | E |
| ATOM | 6899 | O | ALA | E | 163 | −20.983 | −15.156 | 56.653 | 1.00 | 15.36 | E |
| ATOM | 6900 | N | LEU | E | 164 | −21.765 | −16.898 | 57.895 | 1.00 | 13.40 | E |
| ATOM | 6901 | CA | LEU | E | 164 | −22.959 | −16.984 | 57.104 | 1.00 | 13.40 | E |
| ATOM | 6902 | CB | LEU | E | 164 | −23.319 | −18.449 | 56.939 | 1.00 | 14.16 | E |
| ATOM | 6903 | CG | LEU | E | 164 | −24.573 | −18.600 | 56.049 | 1.00 | 15.22 | E |
| ATOM | 6904 | CD1 | LEU | E | 164 | −24.492 | −17.916 | 54.711 | 1.00 | 14.03 | E |
| ATOM | 6905 | CD2 | LEU | E | 164 | −24.839 | −20.150 | 55.988 | 1.00 | 15.62 | E |
| ATOM | 6906 | C | LEU | E | 164 | −24.045 | −16.190 | 57.734 | 1.00 | 13.76 | E |
| ATOM | 6907 | O | LEU | E | 164 | −24.615 | −16.523 | 58.752 | 1.00 | 13.05 | E |
| ATOM | 6908 | N | LEU | E | 165 | −24.346 | −15.088 | 57.126 | 1.00 | 14.53 | E |
| ATOM | 6909 | CA | LEU | E | 165 | −25.318 | −14.202 | 57.736 | 1.00 | 16.67 | E |
| ATOM | 6910 | CB | LEU | E | 165 | −24.882 | −12.740 | 57.542 | 1.00 | 18.92 | E |

TABLE 1-continued

| | | | | | | | | | | |
|---|---|---|---|---|---|---|---|---|---|---|
| ATOM | 6911 | CG | LEU | E | 165 | −23.420 | −12.539 | 57.773 | 1.00 | 20.53 | E |
| ATOM | 6912 | CD1 | LEU | E | 165 | −23.233 | −11.029 | 57.681 | 1.00 | 22.40 | E |
| ATOM | 6913 | CD2 | LEU | E | 165 | −22.953 | −13.071 | 59.157 | 1.00 | 20.79 | E |
| ATOM | 6914 | C | LEU | E | 165 | −26.779 | −14.268 | 57.323 | 1.00 | 16.84 | E |
| ATOM | 6915 | O | LEU | E | 165 | −27.711 | −13.642 | 57.994 | 1.00 | 15.77 | E |
| ATOM | 6916 | N | SER | E | 166 | −27.029 | −14.968 | 56.215 | 1.00 | 15.15 | E |
| ATOM | 6917 | CA | SER | E | 166 | −28.444 | −15.019 | 55.793 | 1.00 | 14.02 | E |
| ATOM | 6918 | CB | SER | E | 166 | −28.849 | −13.693 | 55.111 | 1.00 | 15.14 | E |
| ATOM | 6919 | OG | SER | E | 166 | −30.176 | −13.770 | 54.650 | 1.00 | 15.62 | E |
| ATOM | 6920 | C | SER | E | 166 | −28.667 | −16.166 | 54.830 | 1.00 | 13.29 | E |
| ATOM | 6921 | O | SER | E | 166 | −27.843 | −16.504 | 53.997 | 1.00 | 11.41 | E |
| ATOM | 6922 | N | VAL | E | 167 | −29.823 | −16.720 | 54.946 | 1.00 | 13.06 | E |
| ATOM | 6923 | CA | VAL | E | 167 | −30.168 | −17.869 | 54.209 | 1.00 | 12.96 | E |
| ATOM | 6924 | CB | VAL | E | 167 | −29.941 | −19.198 | 54.999 | 1.00 | 14.14 | E |
| ATOM | 6925 | CG1 | VAL | E | 167 | −30.273 | −20.447 | 54.104 | 1.00 | 15.94 | E |
| ATOM | 6926 | CG2 | VAL | E | 167 | −28.513 | −19.300 | 55.457 | 1.00 | 13.60 | E |
| ATOM | 6927 | C | VAL | E | 167 | −31.600 | −17.790 | 53.931 | 1.00 | 12.87 | E |
| ATOM | 6928 | O | VAL | E | 167 | −32.404 | −18.054 | 54.752 | 1.00 | 10.53 | E |
| ATOM | 6929 | N | ARG | E | 168 | −31.912 | −17.304 | 52.750 | 1.00 | 15.13 | E |
| ATOM | 6930 | CA | ARG | E | 168 | −33.309 | −17.238 | 52.248 | 1.00 | 17.08 | E |
| ATOM | 6931 | CB | ARG | E | 168 | −33.691 | −15.913 | 51.593 | 1.00 | 18.29 | E |
| ATOM | 6932 | CG | ARG | E | 168 | −34.477 | −15.118 | 52.534 | 1.00 | 18.73 | E |
| ATOM | 6933 | CD | ARG | E | 168 | −35.480 | −14.206 | 51.924 | 1.00 | 17.51 | E |
| ATOM | 6934 | NE | ARG | E | 168 | −35.244 | −14.016 | 50.535 | 1.00 | 19.70 | E |
| ATOM | 6935 | CZ | ARG | E | 168 | −36.183 | −13.534 | 49.679 | 1.00 | 22.27 | E |
| ATOM | 6936 | NH1 | ARG | E | 168 | −37.464 | −13.211 | 50.057 | 1.00 | 21.88 | E |
| ATOM | 6937 | NH2 | ARG | E | 168 | −35.835 | −13.257 | 48.430 | 1.00 | 23.33 | E |
| ATOM | 6938 | C | ARG | E | 168 | −33.519 | −18.322 | 51.158 | 1.00 | 17.23 | E |
| ATOM | 6939 | O | ARG | E | 168 | −32.607 | −18.562 | 50.321 | 1.00 | 16.85 | E |
| ATOM | 6940 | N | VAL | E | 169 | −34.706 | −18.947 | 51.277 | 1.00 | 17.01 | E |
| ATOM | 6941 | CA | VAL | E | 169 | −35.168 | −20.019 | 50.451 | 1.00 | 16.62 | E |
| ATOM | 6942 | CB | VAL | E | 169 | −35.212 | −21.386 | 51.120 | 1.00 | 16.68 | E |
| ATOM | 6943 | CG1 | VAL | E | 169 | −35.620 | −22.493 | 49.989 | 1.00 | 17.87 | E |
| ATOM | 6944 | CG2 | VAL | E | 169 | −33.855 | −21.708 | 51.705 | 1.00 | 17.09 | E |
| ATOM | 6945 | C | VAL | E | 169 | −36.551 | −19.716 | 50.100 | 1.00 | 15.40 | E |
| ATOM | 6946 | O | VAL | E | 169 | −37.404 | −19.674 | 50.906 | 1.00 | 14.21 | E |
| ATOM | 6947 | N | TYR | E | 170 | −36.750 | −19.491 | 48.831 | 1.00 | 16.12 | E |
| ATOM | 6948 | CA | TYR | E | 170 | −38.052 | −19.221 | 48.319 | 1.00 | 17.12 | E |
| ATOM | 6949 | CB | TYR | E | 170 | −38.181 | −17.740 | 48.225 | 1.00 | 17.05 | E |
| ATOM | 6950 | CG | TYR | E | 170 | −37.260 | −17.236 | 47.188 | 1.00 | 18.08 | E |
| ATOM | 6951 | CD1 | TYR | E | 170 | −37.723 | −17.049 | 45.854 | 1.00 | 18.79 | E |
| ATOM | 6952 | CE1 | TYR | E | 170 | −36.847 | −16.516 | 44.805 | 1.00 | 18.94 | E |
| ATOM | 6953 | CD2 | TYR | E | 170 | −35.924 | −16.912 | 47.514 | 1.00 | 18.80 | E |
| ATOM | 6954 | CE2 | TYR | E | 170 | −35.017 | −16.373 | 46.539 | 1.00 | 18.69 | E |
| ATOM | 6955 | CZ | TYR | E | 170 | −35.480 | −16.162 | 45.165 | 1.00 | 19.13 | E |
| ATOM | 6956 | OH | TYR | E | 170 | −34.663 | −15.576 | 44.204 | 1.00 | 16.63 | E |
| ATOM | 6957 | C | TYR | E | 170 | −38.286 | −19.883 | 46.910 | 1.00 | 16.79 | E |
| ATOM | 6958 | O | TYR | E | 170 | −37.371 | −20.403 | 46.286 | 1.00 | 16.44 | E |
| ATOM | 6959 | N | TYR | E | 171 | −39.534 | −19.852 | 46.460 | 1.00 | 17.66 | E |
| ATOM | 6960 | CA | TYR | E | 171 | −39.847 | −20.339 | 45.160 | 1.00 | 19.26 | E |
| ATOM | 6961 | CB | TYR | E | 171 | −40.314 | −21.788 | 45.232 | 1.00 | 19.10 | E |
| ATOM | 6962 | CG | TYR | E | 171 | −41.643 | −21.999 | 45.758 | 1.00 | 19.55 | E |
| ATOM | 6963 | CD1 | TYR | E | 171 | −42.745 | −22.073 | 44.867 | 1.00 | 20.16 | E |
| ATOM | 6964 | CE1 | TYR | E | 171 | −44.074 | −22.258 | 45.349 | 1.00 | 20.50 | E |
| ATOM | 6965 | CD2 | TYR | E | 171 | −41.867 | −22.118 | 47.152 | 1.00 | 18.51 | E |
| ATOM | 6966 | CE2 | TYR | E | 171 | −43.175 | −22.308 | 47.625 | 1.00 | 18.75 | E |
| ATOM | 6967 | CZ | TYR | E | 171 | −44.317 | −22.385 | 46.714 | 1.00 | 19.47 | E |
| ATOM | 6968 | OH | TYR | E | 171 | −45.692 | −22.688 | 47.052 | 1.00 | 18.56 | E |
| ATOM | 6969 | C | TYR | E | 171 | −40.825 | −19.371 | 44.466 | 1.00 | 19.55 | E |
| ATOM | 6970 | O | TYR | E | 171 | −41.454 | −18.480 | 45.144 | 1.00 | 20.82 | E |
| ATOM | 6971 | N | LYS | E | 172 | −40.906 | −19.458 | 43.132 | 1.00 | 19.23 | E |
| ATOM | 6972 | CA | LYS | E | 172 | −41.812 | −18.533 | 42.416 | 1.00 | 18.37 | E |
| ATOM | 6973 | CB | LYS | E | 172 | −41.405 | −18.328 | 41.040 | 1.00 | 16.63 | E |
| ATOM | 6974 | CG | LYS | E | 172 | −40.651 | −17.136 | 40.922 | 1.00 | 16.92 | E |
| ATOM | 6975 | CD | LYS | E | 172 | −39.289 | −17.314 | 41.460 | 1.00 | 17.09 | E |
| ATOM | 6976 | CE | LYS | E | 172 | −38.533 | −16.041 | 41.271 | 1.00 | 20.27 | E |
| ATOM | 6977 | NZ | LYS | E | 172 | −37.327 | −16.266 | 40.453 | 1.00 | 23.79 | E |
| ATOM | 6978 | C | LYS | E | 172 | −43.280 | −18.798 | 42.469 | 1.00 | 18.57 | E |
| ATOM | 6979 | O | LYS | E | 172 | −43.823 | −19.861 | 42.126 | 1.00 | 17.82 | E |
| ATOM | 6980 | N | LYS | E | 173 | −43.883 | −17.721 | 42.967 | 1.00 | 20.37 | E |
| ATOM | 6981 | CA | LYS | E | 173 | −45.299 | −17.585 | 43.271 | 1.00 | 21.55 | E |
| ATOM | 6982 | CB | LYS | E | 173 | −45.744 | −16.170 | 43.027 | 1.00 | 22.19 | E |
| ATOM | 6983 | CG | LYS | E | 173 | −44.778 | −15.208 | 43.609 | 1.00 | 22.22 | E |
| ATOM | 6984 | CD | LYS | E | 173 | −43.889 | −14.730 | 42.367 | 1.00 | 23.81 | E |
| ATOM | 6985 | CE | LYS | E | 173 | −42.448 | −14.216 | 42.674 | 1.00 | 21.21 | E |
| ATOM | 6986 | NZ | LYS | E | 173 | −41.779 | −15.463 | 43.080 | 1.00 | 21.67 | E |
| ATOM | 6987 | C | LYS | E | 173 | −46.141 | −18.486 | 42.518 | 1.00 | 21.83 | E |
| ATOM | 6988 | O | LYS | E | 173 | −46.498 | −19.537 | 42.989 | 1.00 | 21.67 | E |
| ATOM | 6989 | N | CYS | E | 174 | −46.431 | −17.978 | 41.333 | 1.00 | 23.48 | E |
| ATOM | 6990 | CA | CYS | E | 174 | −47.292 | −18.624 | 40.295 | 1.00 | 26.07 | E |

TABLE 1-continued

| | | | | | | | | | | |
|---|---|---|---|---|---|---|---|---|---|---|
| ATOM | 6991 | CB | CYS | E | 174 | −46.898 | −20.118 | 40.064 | 1.00 | 28.33 | E |
| ATOM | 6992 | SG | CYS | E | 174 | −47.547 | −21.311 | 41.242 | 1.00 | 37.24 | E |
| ATOM | 6993 | C | CYS | E | 174 | −48.839 | −18.439 | 40.429 | 1.00 | 24.49 | E |
| ATOM | 6994 | O | CYS | E | 174 | −49.380 | −17.418 | 39.759 | 1.00 | 23.93 | E |
| ATOM | 6995 | OXT | CYS | E | 174 | −49.404 | −19.288 | 41.210 | 1.00 | 24.43 | E |
| ATOM | 6996 | CB | GLU | F | 1 | −2.728 | 11.997 | 57.914 | 1.00 | 20.39 | F |
| ATOM | 6997 | CG | GLU | F | 1 | −3.528 | 10.624 | 57.681 | 1.00 | 20.38 | F |
| ATOM | 6998 | CD | GLU | F | 1 | −5.005 | 10.820 | 57.167 | 1.00 | 21.53 | F |
| ATOM | 6999 | OE1 | GLU | F | 1 | −5.252 | 11.468 | 56.108 | 1.00 | 20.45 | F |
| ATOM | 7000 | OE2 | GLU | F | 1 | −5.934 | 10.324 | 57.851 | 1.00 | 20.95 | F |
| ATOM | 7001 | C | GLU | F | 1 | −0.640 | 11.397 | 59.324 | 1.00 | 18.86 | F |
| ATOM | 7002 | O | GLU | F | 1 | −0.128 | 10.256 | 59.410 | 1.00 | 18.79 | F |
| ATOM | 7003 | N | GLU | F | 1 | −0.600 | 11.207 | 56.812 | 1.00 | 19.68 | F |
| ATOM | 7004 | CA | GLU | F | 1 | −1.140 | 11.968 | 57.995 | 1.00 | 19.54 | F |
| ATOM | 7005 | N | VAL | F | 2 | −0.774 | 12.174 | 60.383 | 1.00 | 18.86 | F |
| ATOM | 7006 | CA | VAL | F | 2 | −0.271 | 11.690 | 61.703 | 1.00 | 19.81 | F |
| ATOM | 7007 | CB | VAL | F | 2 | 0.585 | 12.889 | 62.400 | 1.00 | 19.82 | F |
| ATOM | 7008 | CG1 | VAL | F | 2 | 0.795 | 12.626 | 63.926 | 1.00 | 19.52 | F |
| ATOM | 7009 | CG2 | VAL | F | 2 | 1.943 | 13.026 | 61.654 | 1.00 | 19.23 | F |
| ATOM | 7010 | C | VAL | F | 2 | −1.507 | 11.280 | 62.514 | 1.00 | 18.72 | F |
| ATOM | 7011 | O | VAL | F | 2 | −2.511 | 12.038 | 62.483 | 1.00 | 19.42 | F |
| ATOM | 7012 | N | VAL | F | 3 | −1.452 | 10.157 | 63.227 | 1.00 | 17.02 | F |
| ATOM | 7013 | CA | VAL | F | 3 | −2.622 | 9.721 | 63.945 | 1.00 | 16.74 | F |
| ATOM | 7014 | CB | VAL | F | 3 | −3.031 | 8.228 | 63.577 | 1.00 | 16.06 | F |
| ATOM | 7015 | CG1 | VAL | F | 3 | −4.280 | 7.826 | 64.340 | 1.00 | 15.77 | F |
| ATOM | 7016 | CG2 | VAL | F | 3 | −3.210 | 8.082 | 62.076 | 1.00 | 16.38 | F |
| ATOM | 7017 | C | VAL | F | 3 | −2.523 | 9.740 | 65.427 | 1.00 | 16.20 | F |
| ATOM | 7018 | O | VAL | F | 3 | −1.719 | 9.074 | 65.960 | 1.00 | 15.73 | F |
| ATOM | 7019 | N | LEU | F | 4 | −3.431 | 10.424 | 66.093 | 1.00 | 15.43 | F |
| ATOM | 7020 | CA | LEU | F | 4 | −3.446 | 10.572 | 67.560 | 1.00 | 16.79 | F |
| ATOM | 7021 | CB | LEU | F | 4 | −3.547 | 12.101 | 67.933 | 1.00 | 16.42 | F |
| ATOM | 7022 | CG | LEU | F | 4 | −2.769 | 13.085 | 67.063 | 1.00 | 16.97 | F |
| ATOM | 7023 | CD1 | LEU | F | 4 | −2.972 | 14.527 | 67.486 | 1.00 | 17.37 | F |
| ATOM | 7024 | CD2 | LEU | F | 4 | −1.288 | 12.616 | 67.125 | 1.00 | 16.95 | F |
| ATOM | 7025 | C | LEU | F | 4 | −4.750 | 9.944 | 67.898 | 1.00 | 17.54 | F |
| ATOM | 7026 | O | LEU | F | 4 | −5.775 | 10.513 | 67.580 | 1.00 | 19.30 | F |
| ATOM | 7027 | N | LEU | F | 5 | −4.844 | 8.839 | 68.558 | 1.00 | 17.14 | F |
| ATOM | 7028 | CA | LEU | F | 5 | −6.204 | 8.343 | 68.650 | 1.00 | 16.97 | F |
| ATOM | 7029 | CB | LEU | F | 5 | −7.165 | 9.344 | 69.279 | 1.00 | 17.54 | F |
| ATOM | 7030 | CG | LEU | F | 5 | −8.493 | 8.603 | 69.466 | 1.00 | 17.74 | F |
| ATOM | 7031 | CD1 | LEU | F | 5 | −8.131 | 7.328 | 70.168 | 1.00 | 18.18 | F |
| ATOM | 7032 | CD2 | LEU | F | 5 | −9.331 | 9.382 | 70.427 | 1.00 | 19.76 | F |
| ATOM | 7033 | C | LEU | F | 5 | −6.944 | 7.769 | 67.371 | 1.00 | 17.10 | F |
| ATOM | 7034 | O | LEU | F | 5 | −7.307 | 8.463 | 66.331 | 1.00 | 16.49 | F |
| ATOM | 7035 | N | ASP | F | 6 | −7.266 | 6.497 | 67.590 | 1.00 | 17.53 | F |
| ATOM | 7036 | CA | ASP | F | 6 | −7.845 | 5.595 | 66.584 | 1.00 | 17.36 | F |
| ATOM | 7037 | CB | ASP | F | 6 | −6.759 | 4.974 | 65.729 | 1.00 | 19.57 | F |
| ATOM | 7038 | CG | ASP | F | 6 | −7.277 | 4.529 | 64.426 | 1.00 | 20.55 | F |
| ATOM | 7039 | OD1 | ASP | F | 6 | −6.596 | 3.859 | 63.692 | 1.00 | 22.17 | F |
| ATOM | 7040 | OD2 | ASP | F | 6 | −8.405 | 4.864 | 64.104 | 1.00 | 23.58 | F |
| ATOM | 7041 | C | ASP | F | 6 | −8.521 | 4.465 | 67.275 | 1.00 | 16.65 | F |
| ATOM | 7042 | O | ASP | F | 6 | −7.930 | 3.444 | 67.589 | 1.00 | 15.42 | F |
| ATOM | 7043 | N | PHE | F | 7 | −9.830 | 4.682 | 67.411 | 1.00 | 16.95 | F |
| ATOM | 7044 | CA | PHE | F | 7 | −10.667 | 3.755 | 68.098 | 1.00 | 18.07 | F |
| ATOM | 7045 | CB | PHE | F | 7 | −12.118 | 4.294 | 68.074 | 1.00 | 18.22 | F |
| ATOM | 7046 | CG | PHE | F | 7 | −13.069 | 3.403 | 68.732 | 1.00 | 17.78 | F |
| ATOM | 7047 | CD1 | PHE | F | 7 | −13.074 | 3.231 | 70.114 | 1.00 | 17.61 | F |
| ATOM | 7048 | CD2 | PHE | F | 7 | −13.889 | 2.666 | 67.984 | 1.00 | 17.91 | F |
| ATOM | 7049 | CE1 | PHE | F | 7 | −13.965 | 2.241 | 70.775 | 1.00 | 18.04 | F |
| ATOM | 7050 | CE2 | PHE | F | 7 | −14.779 | 1.665 | 68.607 | 1.00 | 19.61 | F |
| ATOM | 7051 | CZ | PHE | F | 7 | −14.804 | 1.467 | 70.001 | 1.00 | 18.12 | F |
| ATOM | 7052 | C | PHE | F | 7 | −10.604 | 2.316 | 67.606 | 1.00 | 16.56 | F |
| ATOM | 7053 | O | PHE | F | 7 | −10.411 | 1.408 | 68.334 | 1.00 | 16.37 | F |
| ATOM | 7054 | N | ALA | F | 8 | −10.800 | 2.172 | 66.335 | 1.00 | 16.70 | F |
| ATOM | 7055 | CA | ALA | F | 8 | −10.879 | 0.858 | 65.756 | 1.00 | 17.11 | F |
| ATOM | 7056 | CB | ALA | F | 8 | −11.469 | 0.918 | 64.313 | 1.00 | 16.64 | F |
| ATOM | 7057 | C | ALA | F | 8 | −9.611 | 0.050 | 65.795 | 1.00 | 16.36 | F |
| ATOM | 7058 | O | ALA | F | 8 | −9.658 | −1.141 | 65.492 | 1.00 | 16.80 | F |
| ATOM | 7059 | N | ALA | F | 9 | −8.478 | 0.615 | 66.216 | 1.00 | 15.07 | F |
| ATOM | 7060 | CA | ALA | F | 9 | −7.297 | −0.243 | 66.297 | 1.00 | 14.93 | F |
| ATOM | 7061 | CB | ALA | F | 9 | −6.154 | 0.472 | 65.832 | 1.00 | 10.27 | F |
| ATOM | 7062 | C | ALA | F | 9 | −7.064 | −0.854 | 67.684 | 1.00 | 16.28 | F |
| ATOM | 7063 | O | ALA | F | 9 | −6.419 | −1.892 | 67.841 | 1.00 | 16.88 | F |
| ATOM | 7064 | N | ALA | F | 10 | −7.639 | −0.239 | 68.711 | 1.00 | 18.01 | F |
| ATOM | 7065 | CA | ALA | F | 10 | −7.323 | −0.561 | 70.150 | 1.00 | 19.18 | F |
| ATOM | 7066 | CB | ALA | F | 10 | −7.657 | 0.698 | 70.992 | 1.00 | 16.66 | F |
| ATOM | 7067 | C | ALA | F | 10 | −7.901 | −1.884 | 70.766 | 1.00 | 21.98 | F |
| ATOM | 7068 | O | ALA | F | 10 | −9.079 | −1.984 | 71.337 | 1.00 | 22.74 | F |
| ATOM | 7069 | N | GLY | F | 11 | −7.070 | −2.937 | 70.570 | 1.00 | 23.93 | F |
| ATOM | 7070 | CA | GLY | F | 11 | −7.327 | −4.364 | 70.943 | 1.00 | 25.28 | F |

TABLE 1-continued

| | | | | | | | | | | |
|---|---|---|---|---|---|---|---|---|---|---|
| ATOM | 7071 | C | GLY | F | 11 | −7.831 | −4.707 | 72.372 | 1.00 | 26.08 | F |
| ATOM | 7072 | O | GLY | F | 11 | −7.342 | −5.599 | 73.165 | 1.00 | 26.04 | F |
| ATOM | 7073 | N | GLY | F | 12 | −8.880 | −3.978 | 72.719 | 1.00 | 25.96 | F |
| ATOM | 7074 | CA | GLY | F | 12 | −9.470 | −4.103 | 74.040 | 1.00 | 25.51 | F |
| ATOM | 7075 | C | GLY | F | 12 | −10.373 | −2.832 | 74.087 | 1.00 | 25.24 | F |
| ATOM | 7076 | O | GLY | F | 12 | −10.494 | −2.250 | 75.250 | 1.00 | 25.74 | F |
| ATOM | 7077 | N | GLU | F | 13 | −10.895 | −2.361 | 72.913 | 1.00 | 23.76 | F |
| ATOM | 7078 | CA | GLU | F | 13 | −11.867 | −1.238 | 72.844 | 1.00 | 22.92 | F |
| ATOM | 7079 | CB | GLU | F | 13 | −13.121 | −1.566 | 73.736 | 1.00 | 23.20 | F |
| ATOM | 7080 | CG | GLU | F | 13 | −13.150 | −3.007 | 74.742 | 1.00 | 24.68 | F |
| ATOM | 7081 | CD | GLU | F | 13 | −14.616 | −3.355 | 75.395 | 1.00 | 26.25 | F |
| ATOM | 7082 | OE1 | GLU | F | 13 | −15.617 | −3.066 | 74.585 | 1.00 | 28.23 | F |
| ATOM | 7083 | OE2 | GLU | F | 13 | −14.768 | −3.935 | 76.622 | 1.00 | 22.68 | F |
| ATOM | 7084 | C | GLU | F | 13 | −11.247 | 0.166 | 73.202 | 1.00 | 23.12 | F |
| ATOM | 7085 | O | GLU | F | 13 | −11.100 | 1.026 | 72.244 | 1.00 | 22.67 | F |
| ATOM | 7086 | N | LEU | F | 14 | −10.860 | 0.355 | 74.500 | 1.00 | 22.47 | F |
| ATOM | 7087 | CA | LEU | F | 14 | −10.140 | 1.514 | 74.964 | 1.00 | 22.89 | F |
| ATOM | 7088 | CB | LEU | F | 14 | −10.402 | 2.614 | 73.980 | 1.00 | 23.15 | F |
| ATOM | 7089 | CG | LEU | F | 14 | −9.076 | 2.905 | 73.167 | 1.00 | 23.81 | F |
| ATOM | 7090 | CD1 | LEU | F | 14 | −9.493 | 3.111 | 71.611 | 1.00 | 22.72 | F |
| ATOM | 7091 | CD2 | LEU | F | 14 | −8.229 | 4.247 | 73.862 | 1.00 | 18.84 | F |
| ATOM | 7092 | C | LEU | F | 14 | −10.378 | 2.086 | 76.367 | 1.00 | 23.06 | F |
| ATOM | 7093 | O | LEU | F | 14 | −11.453 | 1.821 | 77.061 | 1.00 | 23.98 | F |
| ATOM | 7094 | N | GLY | F | 15 | −9.502 | 3.033 | 76.696 | 1.00 | 21.94 | F |
| ATOM | 7095 | CA | GLY | F | 15 | −9.730 | 3.626 | 78.002 | 1.00 | 21.59 | F |
| ATOM | 7096 | C | GLY | F | 15 | −10.647 | 4.851 | 77.834 | 1.00 | 21.82 | F |
| ATOM | 7097 | O | GLY | F | 15 | −10.098 | 5.914 | 77.675 | 1.00 | 22.99 | F |
| ATOM | 7098 | N | TRP | F | 16 | −11.974 | 4.760 | 77.832 | 1.00 | 21.20 | F |
| ATOM | 7099 | CA | TRP | F | 16 | −12.814 | 6.000 | 77.694 | 1.00 | 20.62 | F |
| ATOM | 7100 | CB | TRP | F | 16 | −13.699 | 6.024 | 76.408 | 1.00 | 20.02 | F |
| ATOM | 7101 | CG | TRP | F | 16 | −12.876 | 6.041 | 75.100 | 1.00 | 19.11 | F |
| ATOM | 7102 | CD2 | TRP | F | 16 | −13.222 | 6.584 | 73.813 | 1.00 | 18.32 | F |
| ATOM | 7103 | CE2 | TRP | F | 16 | −12.177 | 6.270 | 72.950 | 1.00 | 18.49 | F |
| ATOM | 7104 | CE3 | TRP | F | 16 | −14.286 | 7.277 | 73.324 | 1.00 | 16.95 | F |
| ATOM | 7105 | CD1 | TRP | F | 16 | −11.631 | 5.429 | 74.920 | 1.00 | 19.65 | F |
| ATOM | 7106 | NE1 | TRP | F | 16 | −11.228 | 5.576 | 73.666 | 1.00 | 18.28 | F |
| ATOM | 7107 | CZ2 | TRP | F | 16 | −12.173 | 6.642 | 71.560 | 1.00 | 18.58 | F |
| ATOM | 7108 | CZ3 | TRP | F | 16 | −14.288 | 7.658 | 71.972 | 1.00 | 18.07 | F |
| ATOM | 7109 | CH2 | TRP | F | 16 | −13.229 | 7.338 | 71.091 | 1.00 | 18.40 | F |
| ATOM | 7110 | C | TRP | F | 16 | −13.750 | 6.238 | 78.907 | 1.00 | 20.08 | F |
| ATOM | 7111 | O | TRP | F | 16 | −13.980 | 5.354 | 79.771 | 1.00 | 20.86 | F |
| ATOM | 7112 | N | LEU | F | 17 | −14.284 | 7.423 | 78.972 | 1.00 | 17.51 | F |
| ATOM | 7113 | CA | LEU | F | 17 | −15.116 | 7.708 | 80.102 | 1.00 | 16.91 | F |
| ATOM | 7114 | CB | LEU | F | 17 | −14.634 | 9.018 | 80.774 | 1.00 | 17.51 | F |
| ATOM | 7115 | CG | LEU | F | 17 | −15.424 | 9.421 | 81.970 | 1.00 | 19.85 | F |
| ATOM | 7116 | CD1 | LEU | F | 17 | −15.693 | 8.134 | 82.888 | 1.00 | 22.42 | F |
| ATOM | 7117 | CD2 | LEU | F | 17 | −14.699 | 10.553 | 82.842 | 1.00 | 22.16 | F |
| ATOM | 7118 | C | LEU | F | 17 | −16.580 | 7.803 | 79.665 | 1.00 | 15.67 | F |
| ATOM | 7119 | O | LEU | F | 17 | −16.938 | 8.370 | 78.592 | 1.00 | 14.78 | F |
| ATOM | 7120 | N | THR | F | 18 | −17.429 | 7.324 | 80.542 | 1.00 | 14.69 | F |
| ATOM | 7121 | CA | THR | F | 18 | −18.810 | 7.279 | 80.264 | 1.00 | 16.12 | F |
| ATOM | 7122 | CB | THR | F | 18 | −19.246 | 5.832 | 80.109 | 1.00 | 14.46 | F |
| ATOM | 7123 | OG1 | THR | F | 18 | −19.164 | 5.529 | 78.741 | 1.00 | 13.32 | F |
| ATOM | 7124 | CG2 | THR | F | 18 | −20.536 | 5.598 | 80.584 | 1.00 | 14.57 | F |
| ATOM | 7125 | C | THR | F | 18 | −19.533 | 7.953 | 81.350 | 1.00 | 17.16 | F |
| ATOM | 7126 | O | THR | F | 18 | −19.548 | 7.467 | 82.506 | 1.00 | 16.71 | F |
| ATOM | 7127 | N | HIS | F | 19 | −20.172 | 9.060 | 80.999 | 1.00 | 18.66 | F |
| ATOM | 7128 | CA | HIS | F | 19 | −20.877 | 9.702 | 82.021 | 1.00 | 22.00 | F |
| ATOM | 7129 | CB | HIS | F | 19 | −21.078 | 11.190 | 81.760 | 1.00 | 22.36 | F |
| ATOM | 7130 | CG | HIS | F | 19 | −21.421 | 11.959 | 83.026 | 1.00 | 23.66 | F |
| ATOM | 7131 | CD2 | HIS | F | 19 | −22.139 | 13.095 | 83.222 | 1.00 | 22.61 | F |
| ATOM | 7132 | ND1 | HIS | F | 19 | −20.977 | 11.565 | 84.290 | 1.00 | 24.95 | F |
| ATOM | 7133 | CE1 | HIS | F | 19 | −21.398 | 12.447 | 85.195 | 1.00 | 24.37 | F |
| ATOM | 7134 | NE2 | HIS | F | 19 | −22.100 | 13.378 | 84.567 | 1.00 | 23.51 | F |
| ATOM | 7135 | C | HIS | F | 19 | −22.125 | 8.945 | 82.551 | 1.00 | 22.68 | F |
| ATOM | 7136 | O | HIS | F | 19 | −22.112 | 7.680 | 82.513 | 1.00 | 24.14 | F |
| ATOM | 7137 | N | PRO | F | 20 | −23.242 | 9.599 | 82.825 | 1.00 | 21.34 | F |
| ATOM | 7138 | CD | PRO | F | 20 | −23.726 | 10.082 | 81.505 | 1.00 | 20.46 | F |
| ATOM | 7139 | CA | PRO | F | 20 | −24.236 | 8.651 | 83.405 | 1.00 | 23.47 | F |
| ATOM | 7140 | CB | PRO | F | 20 | −25.249 | 8.467 | 82.256 | 1.00 | 22.31 | F |
| ATOM | 7141 | CG | PRO | F | 20 | −25.218 | 9.925 | 81.677 | 1.00 | 21.85 | F |
| ATOM | 7142 | C | PRO | F | 20 | −23.561 | 7.298 | 83.895 | 1.00 | 24.89 | F |
| ATOM | 7143 | O | PRO | F | 20 | −23.215 | 7.125 | 85.077 | 1.00 | 25.33 | F |
| ATOM | 7144 | N | TYR | F | 21 | −23.259 | 6.368 | 82.978 | 1.00 | 24.71 | F |
| ATOM | 7145 | CA | TYR | F | 21 | −22.568 | 5.088 | 83.341 | 1.00 | 24.45 | F |
| ATOM | 7146 | CB | TYR | F | 21 | −21.438 | 5.168 | 84.400 | 1.00 | 24.55 | F |
| ATOM | 7147 | CG | TYR | F | 21 | −20.799 | 3.736 | 84.529 | 1.00 | 24.68 | F |
| ATOM | 7148 | CD1 | TYR | F | 21 | −19.914 | 3.217 | 83.487 | 1.00 | 24.10 | F |
| ATOM | 7149 | CE1 | TYR | F | 21 | −19.507 | 1.834 | 83.445 | 1.00 | 23.86 | F |
| ATOM | 7150 | CD2 | TYR | F | 21 | −21.238 | 2.819 | 85.560 | 1.00 | 26.49 | F |

TABLE 1-continued

| ATOM | 7151 | CE2 | TYR | F | 21 | −20.832 | 1.366 | 85.559 | 1.00 | 25.94 | F |
| ATOM | 7152 | CZ | TYR | F | 21 | −20.000 | 0.906 | 84.486 | 1.00 | 26.22 | F |
| ATOM | 7153 | OH | TYR | F | 21 | −19.850 | −0.555 | 84.390 | 1.00 | 28.19 | F |
| ATOM | 7154 | C | TYR | F | 21 | −23.598 | 4.148 | 83.907 | 1.00 | 25.68 | F |
| ATOM | 7155 | O | TYR | F | 21 | −24.101 | 4.396 | 85.062 | 1.00 | 25.63 | F |
| ATOM | 7156 | N | GLY | F | 22 | −23.942 | 3.120 | 83.080 | 1.00 | 25.31 | F |
| ATOM | 7157 | CA | GLY | F | 22 | −24.927 | 2.136 | 83.507 | 1.00 | 25.58 | F |
| ATOM | 7158 | C | GLY | F | 22 | −26.001 | 2.009 | 82.471 | 1.00 | 25.87 | F |
| ATOM | 7159 | O | GLY | F | 22 | −26.439 | 0.841 | 82.133 | 1.00 | 27.06 | F |
| ATOM | 7160 | N | LYS | F | 23 | −26.423 | 3.161 | 81.951 | 1.00 | 24.38 | F |
| ATOM | 7161 | CA | LYS | F | 23 | −27.532 | 3.238 | 81.023 | 1.00 | 22.36 | F |
| ATOM | 7162 | CB | LYS | F | 23 | −28.799 | 3.831 | 81.680 | 1.00 | 21.27 | F |
| ATOM | 7163 | CG | LYS | F | 23 | −29.532 | 2.942 | 82.797 | 1.00 | 22.18 | F |
| ATOM | 7164 | CD | LYS | F | 23 | −29.069 | 3.401 | 84.282 | 1.00 | 21.61 | F |
| ATOM | 7165 | CE | LYS | F | 23 | −29.428 | 2.378 | 85.395 | 1.00 | 20.42 | F |
| ATOM | 7166 | NZ | LYS | F | 23 | −30.929 | 2.142 | 85.730 | 1.00 | 23.65 | F |
| ATOM | 7167 | C | LYS | F | 23 | −27.244 | 4.081 | 79.814 | 1.00 | 22.42 | F |
| ATOM | 7168 | O | LYS | F | 23 | −28.089 | 4.047 | 78.892 | 1.00 | 23.18 | F |
| ATOM | 7169 | N | GLY | F | 24 | −26.136 | 4.854 | 79.788 | 1.00 | 20.83 | F |
| ATOM | 7170 | CA | GLY | F | 24 | −25.854 | 5.677 | 78.601 | 1.00 | 18.98 | F |
| ATOM | 7171 | C | GLY | F | 24 | −25.028 | 4.828 | 77.602 | 1.00 | 18.79 | F |
| ATOM | 7172 | O | GLY | F | 24 | −25.414 | 3.650 | 77.239 | 1.00 | 17.53 | F |
| ATOM | 7173 | N | TRP | F | 25 | −23.932 | 5.455 | 77.136 | 1.00 | 18.17 | F |
| ATOM | 7174 | CA | TRP | F | 25 | −22.991 | 4.861 | 76.230 | 1.00 | 18.48 | F |
| ATOM | 7175 | CB | TRP | F | 25 | −21.968 | 5.876 | 75.908 | 1.00 | 17.21 | F |
| ATOM | 7176 | CG | TRP | F | 25 | −22.399 | 7.020 | 75.134 | 1.00 | 17.11 | F |
| ATOM | 7177 | CD2 | TRP | F | 25 | −22.415 | 7.119 | 73.693 | 1.00 | 17.35 | F |
| ATOM | 7178 | CE2 | TRP | F | 25 | −22.581 | 8.483 | 73.364 | 1.00 | 18.05 | F |
| ATOM | 7179 | CE3 | TRP | F | 25 | −22.303 | 6.169 | 72.650 | 1.00 | 16.76 | F |
| ATOM | 7180 | CD1 | TRP | F | 25 | −22.580 | 8.319 | 75.582 | 1.00 | 17.87 | F |
| ATOM | 7181 | NE1 | TRP | F | 25 | −22.661 | 9.198 | 74.523 | 1.00 | 17.86 | F |
| ATOM | 7182 | CZ2 | TRP | F | 25 | −22.631 | 8.905 | 72.063 | 1.00 | 19.01 | F |
| ATOM | 7183 | CZ3 | TRP | F | 25 | −22.351 | 6.584 | 71.386 | 1.00 | 16.85 | F |
| ATOM | 7184 | CH2 | TRP | F | 25 | −22.514 | 7.910 | 71.074 | 1.00 | 18.20 | F |
| ATOM | 7185 | C | TRP | F | 25 | −22.300 | 3.539 | 76.804 | 1.00 | 19.51 | F |
| ATOM | 7186 | O | TRP | F | 25 | −21.840 | 3.532 | 77.999 | 1.00 | 19.97 | F |
| ATOM | 7187 | N | ASP | F | 26 | −22.325 | 2.428 | 75.983 | 1.00 | 19.72 | F |
| ATOM | 7188 | CA | ASP | F | 26 | −21.767 | 1.036 | 76.318 | 1.00 | 19.12 | F |
| ATOM | 7189 | CB | ASP | F | 26 | −22.826 | −0.071 | 76.617 | 1.00 | 22.63 | F |
| ATOM | 7190 | CG | ASP | F | 26 | −23.646 | 0.134 | 77.986 | 1.00 | 27.22 | F |
| ATOM | 7191 | OD1 | ASP | F | 26 | −23.657 | 1.258 | 78.745 | 1.00 | 27.40 | F |
| ATOM | 7192 | OD2 | ASP | F | 26 | −24.398 | −0.916 | 78.337 | 1.00 | 31.20 | F |
| ATOM | 7193 | C | ASP | F | 26 | −20.886 | 0.516 | 75.162 | 1.00 | 18.06 | F |
| ATOM | 7194 | O | ASP | F | 26 | −21.190 | 0.624 | 73.980 | 1.00 | 16.36 | F |
| ATOM | 7195 | N | LEU | F | 27 | −19.745 | 0.034 | 75.566 | 1.00 | 17.18 | F |
| ATOM | 7196 | CA | LEU | F | 27 | −18.739 | −0.485 | 74.711 | 1.00 | 16.47 | F |
| ATOM | 7197 | CB | LEU | F | 27 | −17.433 | −0.431 | 75.474 | 1.00 | 16.18 | F |
| ATOM | 7198 | CG | LEU | F | 27 | −16.178 | −0.736 | 74.665 | 1.00 | 16.69 | F |
| ATOM | 7199 | CD1 | LEU | F | 27 | −16.011 | 0.122 | 73.446 | 1.00 | 15.26 | F |
| ATOM | 7200 | CD2 | LEU | F | 27 | −15.060 | −0.692 | 75.615 | 1.00 | 15.20 | F |
| ATOM | 7201 | C | LEU | F | 27 | −19.161 | −1.921 | 74.458 | 1.00 | 16.49 | F |
| ATOM | 7202 | O | LEU | F | 27 | −19.316 | −2.674 | 75.363 | 1.00 | 16.40 | F |
| ATOM | 7203 | N | MET | F | 28 | −19.346 | −2.286 | 73.221 | 1.00 | 16.24 | F |
| ATOM | 7204 | CA | MET | F | 28 | −19.792 | −3.613 | 72.935 | 1.00 | 17.30 | F |
| ATOM | 7205 | CB | MET | F | 28 | −21.262 | −3.636 | 72.393 | 1.00 | 19.90 | F |
| ATOM | 7206 | CG | MET | F | 28 | −22.075 | −2.331 | 72.522 | 1.00 | 23.66 | F |
| ATOM | 7207 | SD | MET | F | 28 | −24.006 | −2.414 | 72.661 | 1.00 | 27.35 | F |
| ATOM | 7208 | CE | MET | F | 28 | −24.264 | −4.482 | 72.733 | 1.00 | 21.38 | F |
| ATOM | 7209 | C | MET | F | 28 | −18.840 | −4.177 | 71.856 | 1.00 | 16.40 | F |
| ATOM | 7210 | O | MET | F | 28 | −18.379 | −3.447 | 70.971 | 1.00 | 16.32 | F |
| ATOM | 7211 | N | GLN | F | 29 | −18.551 | −5.447 | 71.963 | 1.00 | 15.08 | F |
| ATOM | 7212 | CA | GLN | F | 29 | −17.698 | −6.110 | 71.044 | 1.00 | 15.65 | F |
| ATOM | 7213 | CB | GLN | F | 29 | −16.719 | −6.943 | 71.829 | 1.00 | 15.26 | F |
| ATOM | 7214 | CG | GLN | F | 29 | −15.605 | −7.321 | 71.007 | 1.00 | 18.11 | F |
| ATOM | 7215 | CD | GLN | F | 29 | −14.874 | −8.641 | 71.431 | 1.00 | 20.31 | F |
| ATOM | 7216 | OE1 | GLN | F | 29 | −13.875 | −8.576 | 72.079 | 1.00 | 21.94 | F |
| ATOM | 7217 | NE2 | GLN | F | 29 | −15.351 | −9.825 | 70.995 | 1.00 | 21.20 | F |
| ATOM | 7218 | C | GLN | F | 29 | −18.387 | −7.081 | 70.069 | 1.00 | 15.96 | F |
| ATOM | 7219 | O | GLN | F | 29 | −18.822 | −8.184 | 70.478 | 1.00 | 15.78 | F |
| ATOM | 7220 | N | ASN | F | 30 | −18.456 | −6.723 | 68.793 | 1.00 | 15.49 | F |
| ATOM | 7221 | CA | ASN | F | 30 | −19.019 | −7.687 | 67.851 | 1.00 | 15.99 | F |
| ATOM | 7222 | CB | ASN | F | 30 | −19.775 | −6.978 | 66.713 | 1.00 | 15.62 | F |
| ATOM | 7223 | CG | ASN | F | 30 | −21.101 | −6.465 | 67.184 | 1.00 | 14.94 | F |
| ATOM | 7224 | OD1 | ASN | F | 30 | −21.578 | −5.542 | 66.652 | 1.00 | 15.76 | F |
| ATOM | 7225 | ND2 | ASN | F | 30 | −21.704 | −7.083 | 68.185 | 1.00 | 14.68 | F |
| ATOM | 7226 | C | ASN | F | 30 | −17.863 | −8.490 | 67.310 | 1.00 | 16.10 | F |
| ATOM | 7227 | O | ASN | F | 30 | −16.668 | −8.193 | 67.566 | 1.00 | 14.78 | F |
| ATOM | 7228 | N | ILE | F | 31 | −18.200 | −9.548 | 66.615 | 1.00 | 16.26 | F |
| ATOM | 7229 | CA | ILE | F | 31 | −17.139 | −10.250 | 66.005 | 1.00 | 16.19 | F |
| ATOM | 7230 | CB | ILE | F | 31 | −16.744 | −11.257 | 66.953 | 1.00 | 17.20 | F |

TABLE 1-continued

| ATOM | 7231 | CG2 | ILE | F | 31 | −17.859 | −12.139 | 67.180 | 1.00 | 18.41 | F |
|---|---|---|---|---|---|---|---|---|---|---|---|
| ATOM | 7232 | CG1 | ILE | F | 31 | −15.587 | −12.007 | 66.455 | 1.00 | 17.93 | F |
| ATOM | 7233 | CD1 | ILE | F | 31 | −15.281 | −13.180 | 67.345 | 1.00 | 17.42 | F |
| ATOM | 7234 | C | ILE | F | 31 | −17.530 | −10.787 | 64.602 | 1.00 | 17.27 | F |
| ATOM | 7235 | O | ILE | F | 31 | −18.608 | −11.332 | 64.342 | 1.00 | 17.19 | F |
| ATOM | 7236 | N | MET | F | 32 | −16.617 | −10.609 | 63.679 | 1.00 | 16.62 | F |
| ATOM | 7237 | CA | MET | F | 32 | −16.752 | −10.973 | 62.317 | 1.00 | 15.80 | F |
| ATOM | 7238 | CB | MET | F | 32 | −16.748 | −9.747 | 61.385 | 1.00 | 18.12 | F |
| ATOM | 7239 | CG | MET | F | 32 | −18.155 | −9.209 | 61.079 | 1.00 | 21.41 | F |
| ATOM | 7240 | SD | MET | F | 32 | −19.276 | −10.545 | 60.761 | 1.00 | 23.72 | F |
| ATOM | 7241 | CE | MET | F | 32 | −17.980 | −11.479 | 59.603 | 1.00 | 19.76 | F |
| ATOM | 7242 | C | MET | F | 32 | −15.544 | −11.697 | 61.974 | 1.00 | 15.88 | F |
| ATOM | 7243 | O | MET | F | 32 | −14.503 | −11.099 | 62.019 | 1.00 | 14.27 | F |
| ATOM | 7244 | N | ASN | F | 33 | −15.708 | −12.954 | 61.500 | 1.00 | 16.32 | F |
| ATOM | 7245 | CA | ASN | F | 33 | −14.584 | −13.759 | 61.045 | 1.00 | 16.40 | F |
| ATOM | 7246 | CB | ASN | F | 33 | −14.065 | −13.278 | 59.720 | 1.00 | 17.40 | F |
| ATOM | 7247 | CG | ASN | F | 33 | −15.067 | −13.352 | 58.672 | 1.00 | 17.52 | F |
| ATOM | 7248 | OD1 | ASN | F | 33 | −15.472 | −14.439 | 58.252 | 1.00 | 17.85 | F |
| ATOM | 7249 | ND2 | ASN | F | 33 | −15.473 | −12.201 | 58.214 | 1.00 | 17.46 | F |
| ATOM | 7250 | C | ASN | F | 33 | −13.447 | −13.699 | 62.036 | 1.00 | 15.93 | F |
| ATOM | 7251 | O | ASN | F | 33 | −12.309 | −13.467 | 61.689 | 1.00 | 16.40 | F |
| ATOM | 7252 | N | ASP | F | 34 | −13.808 | −13.937 | 63.280 | 1.00 | 16.34 | F |
| ATOM | 7253 | CA | ASP | F | 34 | −12.909 | −13.967 | 64.388 | 1.00 | 16.68 | F |
| ATOM | 7254 | CB | ASP | F | 34 | −11.912 | −15.120 | 64.157 | 1.00 | 17.06 | F |
| ATOM | 7255 | CG | ASP | F | 34 | −12.536 | −16.511 | 64.486 | 1.00 | 20.25 | F |
| ATOM | 7256 | OD1 | ASP | F | 34 | −13.831 | −16.768 | 64.269 | 1.00 | 21.53 | F |
| ATOM | 7257 | OD2 | ASP | F | 34 | −11.787 | −17.485 | 64.965 | 1.00 | 22.23 | F |
| ATOM | 7258 | C | ASP | F | 34 | −12.243 | −12.581 | 64.634 | 1.00 | 16.65 | F |
| ATOM | 7259 | O | ASP | F | 34 | −11.312 | −12.470 | 65.425 | 1.00 | 17.32 | F |
| ATOM | 7260 | N | MET | F | 35 | −12.664 | −11.524 | 63.950 | 1.00 | 16.51 | F |
| ATOM | 7261 | CA | MET | F | 35 | −12.067 | −10.246 | 64.245 | 1.00 | 15.64 | F |
| ATOM | 7262 | CB | MET | F | 35 | −11.864 | −9.452 | 62.955 | 1.00 | 17.61 | F |
| ATOM | 7263 | CG | MET | F | 35 | −10.729 | −9.931 | 62.126 | 1.00 | 17.09 | F |
| ATOM | 7264 | SD | MET | F | 35 | −9.145 | −9.928 | 63.022 | 1.00 | 21.41 | F |
| ATOM | 7265 | CE | MET | F | 35 | −9.110 | −11.665 | 63.710 | 1.00 | 19.69 | F |
| ATOM | 7266 | C | MET | F | 35 | −12.958 | −9.451 | 65.233 | 1.00 | 14.08 | F |
| ATOM | 7267 | O | MET | F | 35 | −14.095 | −9.291 | 65.003 | 1.00 | 12.74 | F |
| ATOM | 7268 | N | PRO | F | 36 | −12.436 | −9.057 | 66.416 | 1.00 | 14.60 | F |
| ATOM | 7269 | CD | PRO | F | 36 | −11.196 | −9.422 | 67.106 | 1.00 | 15.37 | F |
| ATOM | 7270 | CA | PRO | F | 36 | −13.301 | −8.275 | 67.328 | 1.00 | 13.87 | F |
| ATOM | 7271 | CB | PRO | F | 36 | −12.518 | −8.228 | 68.646 | 1.00 | 14.00 | F |
| ATOM | 7272 | CG | PRO | F | 36 | −11.213 | −8.401 | 68.267 | 1.00 | 15.42 | F |
| ATOM | 7273 | C | PRO | F | 36 | −13.562 | −6.890 | 66.758 | 1.00 | 12.90 | F |
| ATOM | 7274 | O | PRO | F | 36 | −12.665 | −6.197 | 66.395 | 1.00 | 12.46 | F |
| ATOM | 7275 | N | ILE | F | 37 | −14.798 | −6.521 | 66.602 | 1.00 | 13.00 | F |
| ATOM | 7276 | CA | ILE | F | 37 | −15.108 | −5.191 | 66.099 | 1.00 | 14.29 | F |
| ATOM | 7277 | CB | ILE | F | 37 | −16.137 | −5.327 | 65.062 | 1.00 | 15.11 | F |
| ATOM | 7278 | CG2 | ILE | F | 37 | −16.455 | −3.988 | 64.392 | 1.00 | 15.50 | F |
| ATOM | 7279 | CG1 | ILE | F | 37 | −15.708 | −6.417 | 64.087 | 1.00 | 17.19 | F |
| ATOM | 7280 | CD1 | ILE | F | 37 | −14.368 | −6.238 | 63.639 | 1.00 | 17.22 | F |
| ATOM | 7281 | C | ILE | F | 37 | −15.695 | −4.336 | 67.329 | 1.00 | 15.35 | F |
| ATOM | 7282 | O | ILE | F | 37 | −16.840 | −4.524 | 67.712 | 1.00 | 15.59 | F |
| ATOM | 7283 | N | TYR | F | 38 | −14.974 | −3.438 | 67.975 | 1.00 | 14.97 | F |
| ATOM | 7284 | CA | TYR | F | 38 | −15.635 | −2.802 | 69.051 | 1.00 | 15.15 | F |
| ATOM | 7285 | CB | TYR | F | 38 | −14.623 | −2.306 | 70.095 | 1.00 | 15.34 | F |
| ATOM | 7286 | CG | TYR | F | 38 | −13.975 | −3.397 | 70.857 | 1.00 | 15.22 | F |
| ATOM | 7287 | CD1 | TYR | F | 38 | −12.914 | −4.057 | 70.369 | 1.00 | 15.04 | F |
| ATOM | 7288 | CE1 | TYR | F | 38 | −12.429 | −5.055 | 71.078 | 1.00 | 14.46 | F |
| ATOM | 7289 | CD2 | TYR | F | 38 | −14.502 | −3.826 | 72.076 | 1.00 | 13.92 | F |
| ATOM | 7290 | CE2 | TYR | F | 38 | −13.989 | −4.836 | 72.729 | 1.00 | 12.69 | F |
| ATOM | 7291 | CZ | TYR | F | 38 | −12.959 | −5.423 | 72.238 | 1.00 | 13.79 | F |
| ATOM | 7292 | OH | TYR | F | 38 | −12.349 | −6.369 | 72.977 | 1.00 | 16.17 | F |
| ATOM | 7293 | C | TYR | F | 38 | −16.458 | −1.619 | 68.592 | 1.00 | 15.82 | F |
| ATOM | 7294 | O | TYR | F | 38 | −16.152 | −1.054 | 67.565 | 1.00 | 16.55 | F |
| ATOM | 7295 | N | MET | F | 39 | −17.513 | −1.262 | 69.354 | 1.00 | 15.99 | F |
| ATOM | 7296 | CA | MET | F | 39 | −18.264 | −0.028 | 69.102 | 1.00 | 16.15 | F |
| ATOM | 7297 | CB | MET | F | 39 | −19.391 | −0.278 | 68.162 | 1.00 | 14.36 | F |
| ATOM | 7298 | CG | MET | F | 39 | −20.598 | −0.756 | 68.799 | 1.00 | 14.60 | F |
| ATOM | 7299 | SD | MET | F | 39 | −21.447 | −2.038 | 67.652 | 1.00 | 16.18 | F |
| ATOM | 7300 | CE | MET | F | 39 | −22.997 | −2.556 | 68.622 | 1.00 | 11.50 | F |
| ATOM | 7301 | C | MET | F | 39 | −18.804 | 0.629 | 70.399 | 1.00 | 15.29 | F |
| ATOM | 7302 | O | MET | F | 39 | −18.981 | −0.044 | 71.378 | 1.00 | 16.10 | F |
| ATOM | 7303 | N | TYR | F | 40 | −19.004 | 1.930 | 70.398 | 1.00 | 15.22 | F |
| ATOM | 7304 | CA | TYR | F | 40 | −19.701 | 2.576 | 71.517 | 1.00 | 16.06 | F |
| ATOM | 7305 | CB | TYR | F | 40 | −18.971 | 3.880 | 71.947 | 1.00 | 16.47 | F |
| ATOM | 7306 | CG | TYR | F | 40 | −17.991 | 3.680 | 73.074 | 1.00 | 17.74 | F |
| ATOM | 7307 | CD1 | TYR | F | 40 | −16.658 | 3.743 | 72.873 | 1.00 | 17.70 | F |
| ATOM | 7308 | CE1 | TYR | F | 40 | −15.757 | 3.457 | 73.872 | 1.00 | 19.15 | F |
| ATOM | 7309 | CD2 | TYR | F | 40 | −18.445 | 3.330 | 74.364 | 1.00 | 19.42 | F |
| ATOM | 7310 | CE2 | TYR | F | 40 | −17.551 | 3.037 | 75.417 | 1.00 | 20.62 | F |

TABLE 1-continued

| ATOM | 7311 | CZ | TYR | F | 40 | −16.197 | 3.103 | 75.119 | 1.00 | 21.41 | F |
| --- | --- | --- | --- | --- | --- | --- | --- | --- | --- | --- | --- |
| ATOM | 7312 | OH | TYR | F | 40 | −15.259 | 2.749 | 76.067 | 1.00 | 25.97 | F |
| ATOM | 7313 | C | TYR | F | 40 | −21.185 | 2.907 | 71.075 | 1.00 | 15.67 | F |
| ATOM | 7314 | O | TYR | F | 40 | −21.434 | 3.597 | 70.003 | 1.00 | 14.18 | F |
| ATOM | 7315 | N | SER | F | 41 | −22.169 | 2.437 | 71.838 | 1.00 | 15.42 | F |
| ATOM | 7316 | CA | SER | F | 41 | −23.547 | 2.731 | 71.399 | 1.00 | 15.93 | F |
| ATOM | 7317 | CB | SER | F | 41 | −24.099 | 1.571 | 70.504 | 1.00 | 16.40 | F |
| ATOM | 7318 | OG | SER | F | 41 | −23.882 | 0.277 | 71.029 | 1.00 | 13.61 | F |
| ATOM | 7319 | C | SER | F | 41 | −24.519 | 2.997 | 72.529 | 1.00 | 17.88 | F |
| ATOM | 7320 | O | SER | F | 41 | −24.264 | 2.638 | 73.728 | 1.00 | 17.79 | F |
| ATOM | 7321 | N | VAL | F | 42 | −25.650 | 3.607 | 72.154 | 1.00 | 17.67 | F |
| ATOM | 7322 | CA | VAL | F | 42 | −26.671 | 3.919 | 73.146 | 1.00 | 16.84 | F |
| ATOM | 7323 | CB | VAL | F | 42 | −26.893 | 5.520 | 73.504 | 1.00 | 17.23 | F |
| ATOM | 7324 | CG1 | VAL | F | 42 | −27.216 | 5.725 | 74.948 | 1.00 | 15.09 | F |
| ATOM | 7325 | CG2 | VAL | F | 42 | −25.835 | 6.408 | 72.904 | 1.00 | 14.70 | F |
| ATOM | 7326 | C | VAL | F | 42 | −27.862 | 3.806 | 72.313 | 1.00 | 18.29 | F |
| ATOM | 7327 | O | VAL | F | 42 | −27.811 | 4.181 | 71.156 | 1.00 | 17.36 | F |
| ATOM | 7328 | N | CYS | F | 43 | −28.980 | 3.527 | 72.970 | 1.00 | 19.19 | F |
| ATOM | 7329 | CA | CYS | F | 43 | −30.289 | 3.517 | 72.283 | 1.00 | 19.70 | F |
| ATOM | 7330 | C | CYS | F | 43 | −31.423 | 3.802 | 73.317 | 1.00 | 20.13 | F |
| ATOM | 7331 | O | CYS | F | 43 | −32.335 | 2.999 | 73.444 | 1.00 | 19.43 | F |
| ATOM | 7332 | CB | CYS | F | 43 | −30.475 | 2.131 | 71.674 | 1.00 | 21.56 | F |
| ATOM | 7333 | SG | CYS | F | 43 | −31.671 | 2.079 | 70.263 | 1.00 | 21.13 | F |
| ATOM | 7334 | N | ASN | F | 44 | −31.323 | 4.892 | 74.075 | 1.00 | 19.79 | F |
| ATOM | 7335 | CA | ASN | F | 44 | −32.353 | 5.259 | 75.040 | 1.00 | 19.21 | F |
| ATOM | 7336 | CB | ASN | F | 44 | −31.727 | 5.939 | 76.256 | 1.00 | 18.46 | F |
| ATOM | 7337 | CG | ASN | F | 44 | −30.921 | 4.992 | 77.031 | 1.00 | 18.16 | F |
| ATOM | 7338 | OD1 | ASN | F | 44 | −30.092 | 5.411 | 77.794 | 1.00 | 19.18 | F |
| ATOM | 7339 | ND2 | ASN | F | 44 | −31.142 | 3.670 | 76.826 | 1.00 | 16.22 | F |
| ATOM | 7340 | C | ASN | F | 44 | −33.341 | 6.191 | 74.332 | 1.00 | 19.99 | F |
| ATOM | 7341 | O | ASN | F | 44 | −33.449 | 7.388 | 74.687 | 1.00 | 21.01 | F |
| ATOM | 7342 | N | VAL | F | 45 | −34.020 | 5.654 | 73.291 | 1.00 | 19.37 | F |
| ATOM | 7343 | CA | VAL | F | 45 | −34.975 | 6.424 | 72.443 | 1.00 | 17.16 | F |
| ATOM | 7344 | CB | VAL | F | 45 | −35.115 | 5.837 | 70.982 | 1.00 | 17.72 | F |
| ATOM | 7345 | CG1 | VAL | F | 45 | −33.883 | 5.921 | 70.352 | 1.00 | 18.04 | F |
| ATOM | 7346 | CG2 | VAL | F | 45 | −35.601 | 4.318 | 70.929 | 1.00 | 16.72 | F |
| ATOM | 7347 | C | VAL | F | 45 | −36.374 | 6.487 | 73.035 | 1.00 | 18.31 | F |
| ATOM | 7348 | O | VAL | F | 45 | −37.167 | 7.286 | 72.595 | 1.00 | 17.62 | F |
| ATOM | 7349 | N | MET | F | 46 | −36.645 | 5.654 | 74.027 | 1.00 | 18.43 | F |
| ATOM | 7350 | CA | MET | F | 46 | −37.951 | 5.568 | 74.611 | 1.00 | 18.48 | F |
| ATOM | 7351 | CB | MET | F | 46 | −38.195 | 4.074 | 74.867 | 1.00 | 20.14 | F |
| ATOM | 7352 | CG | MET | F | 46 | −39.437 | 3.356 | 74.388 | 1.00 | 20.78 | F |
| ATOM | 7353 | SD | MET | F | 46 | −40.168 | 3.552 | 72.626 | 1.00 | 25.07 | F |
| ATOM | 7354 | CE | MET | F | 46 | −39.284 | 1.884 | 71.769 | 1.00 | 20.73 | F |
| ATOM | 7355 | C | MET | F | 46 | −37.991 | 6.354 | 76.032 | 1.00 | 20.36 | F |
| ATOM | 7356 | O | MET | F | 46 | −38.887 | 6.103 | 76.884 | 1.00 | 20.30 | F |
| ATOM | 7357 | N | SER | F | 47 | −37.014 | 7.230 | 76.321 | 1.00 | 20.61 | F |
| ATOM | 7358 | CA | SER | F | 47 | −37.029 | 7.956 | 77.597 | 1.00 | 20.41 | F |
| ATOM | 7359 | CB | SER | F | 47 | −36.082 | 7.308 | 78.634 | 1.00 | 21.22 | F |
| ATOM | 7360 | OG | SER | F | 47 | −35.616 | 6.032 | 78.207 | 1.00 | 21.71 | F |
| ATOM | 7361 | C | SER | F | 47 | −36.585 | 9.348 | 77.183 | 1.00 | 20.03 | F |
| ATOM | 7362 | O | SER | F | 47 | −35.855 | 9.499 | 76.155 | 1.00 | 20.01 | F |
| ATOM | 7363 | N | GLY | F | 48 | −37.029 | 10.368 | 77.917 | 1.00 | 19.74 | F |
| ATOM | 7364 | CA | GLY | F | 48 | −36.670 | 11.671 | 77.422 | 1.00 | 19.20 | F |
| ATOM | 7365 | C | GLY | F | 48 | −35.536 | 12.244 | 78.129 | 1.00 | 18.38 | F |
| ATOM | 7366 | O | GLY | F | 48 | −34.999 | 11.568 | 78.994 | 1.00 | 18.14 | F |
| ATOM | 7367 | N | ASP | F | 49 | −35.116 | 13.437 | 77.702 | 1.00 | 18.94 | F |
| ATOM | 7368 | CA | ASP | F | 49 | −34.039 | 14.058 | 78.477 | 1.00 | 20.39 | F |
| ATOM | 7369 | CB | ASP | F | 49 | −34.513 | 14.208 | 79.944 | 1.00 | 20.22 | F |
| ATOM | 7370 | CG | ASP | F | 49 | −35.877 | 14.932 | 80.046 | 1.00 | 22.03 | F |
| ATOM | 7371 | OD1 | ASP | F | 49 | −36.746 | 14.493 | 80.886 | 1.00 | 22.35 | F |
| ATOM | 7372 | OD2 | ASP | F | 49 | −36.010 | 15.945 | 79.299 | 1.00 | 19.76 | F |
| ATOM | 7373 | C | ASP | F | 49 | −32.789 | 13.203 | 78.555 | 1.00 | 18.83 | F |
| ATOM | 7374 | O | ASP | F | 49 | −32.257 | 12.992 | 79.643 | 1.00 | 19.67 | F |
| ATOM | 7375 | N | GLN | F | 50 | −32.341 | 12.651 | 77.473 | 1.00 | 18.22 | F |
| ATOM | 7376 | CA | GLN | F | 50 | −31.113 | 11.912 | 77.603 | 1.00 | 17.72 | F |
| ATOM | 7377 | CB | GLN | F | 50 | −30.946 | 10.924 | 76.434 | 1.00 | 17.65 | F |
| ATOM | 7378 | CG | GLN | F | 50 | −31.944 | 9.801 | 76.477 | 1.00 | 16.45 | F |
| ATOM | 7379 | CD | GLN | F | 50 | −31.923 | 9.141 | 77.830 | 1.00 | 17.91 | F |
| ATOM | 7380 | OE1 | GLN | F | 50 | −30.959 | 8.416 | 78.211 | 1.00 | 15.56 | F |
| ATOM | 7381 | NE2 | GLN | F | 50 | −32.982 | 9.437 | 78.631 | 1.00 | 19.35 | F |
| ATOM | 7382 | C | GLN | F | 50 | −30.060 | 12.952 | 77.552 | 1.00 | 17.11 | F |
| ATOM | 7383 | O | GLN | F | 50 | −30.265 | 14.008 | 76.932 | 1.00 | 16.82 | F |
| ATOM | 7384 | N | ASP | F | 51 | −28.927 | 12.692 | 78.214 | 1.00 | 17.64 | F |
| ATOM | 7385 | CA | ASP | F | 51 | −27.711 | 13.628 | 78.196 | 1.00 | 17.98 | F |
| ATOM | 7386 | CB | ASP | F | 51 | −27.816 | 14.713 | 79.303 | 1.00 | 19.40 | F |
| ATOM | 7387 | CG | ASP | F | 51 | −26.734 | 15.767 | 79.169 | 1.00 | 22.27 | F |
| ATOM | 7388 | OD1 | ASP | F | 51 | −26.433 | 16.554 | 80.218 | 1.00 | 22.06 | F |
| ATOM | 7389 | OD2 | ASP | F | 51 | −26.172 | 15.821 | 77.962 | 1.00 | 23.40 | F |
| ATOM | 7390 | C | ASP | F | 51 | −26.542 | 12.686 | 78.516 | 1.00 | 17.64 | F |

TABLE 1-continued

| | | | | | | | | | | |
|---|---|---|---|---|---|---|---|---|---|---|
| ATOM | 7391 | O | ASP | F | 51 | −25.940 | 12.783 | 79.554 | 1.00 | 17.33 | F |
| ATOM | 7392 | N | ASN | F | 52 | −26.275 | 11.720 | 77.629 | 1.00 | 18.03 | F |
| ATOM | 7393 | CA | ASN | F | 52 | −25.214 | 10.732 | 77.831 | 1.00 | 16.66 | F |
| ATOM | 7394 | CB | ASN | F | 52 | −25.674 | 9.460 | 77.316 | 1.00 | 16.91 | F |
| ATOM | 7395 | CG | ASN | F | 52 | −26.933 | 9.099 | 77.931 | 1.00 | 16.34 | F |
| ATOM | 7396 | OD1 | ASN | F | 52 | −27.000 | 8.846 | 79.131 | 1.00 | 16.67 | F |
| ATOM | 7397 | ND2 | ASN | F | 52 | −27.975 | 9.130 | 77.153 | 1.00 | 14.26 | F |
| ATOM | 7398 | C | ASN | F | 52 | −23.948 | 11.137 | 77.202 | 1.00 | 16.78 | F |
| ATOM | 7399 | O | ASN | F | 52 | −23.947 | 11.619 | 76.076 | 1.00 | 16.13 | F |
| ATOM | 7400 | N | TRP | F | 53 | −22.863 | 11.062 | 77.975 | 1.00 | 17.70 | F |
| ATOM | 7401 | CA | TRP | F | 53 | −21.571 | 11.490 | 77.430 | 1.00 | 17.73 | F |
| ATOM | 7402 | CB | TRP | F | 53 | −21.000 | 12.673 | 78.225 | 1.00 | 18.12 | F |
| ATOM | 7403 | CG | TRP | F | 53 | −21.761 | 13.942 | 78.057 | 1.00 | 17.61 | F |
| ATOM | 7404 | CD2 | TRP | F | 53 | −21.353 | 15.101 | 77.330 | 1.00 | 17.68 | F |
| ATOM | 7405 | CE2 | TRP | F | 53 | −22.361 | 16.073 | 77.479 | 1.00 | 18.04 | F |
| ATOM | 7406 | CE3 | TRP | F | 53 | −20.210 | 15.416 | 76.568 | 1.00 | 18.53 | F |
| ATOM | 7407 | CD1 | TRP | F | 53 | −22.974 | 14.237 | 78.585 | 1.00 | 17.16 | F |
| ATOM | 7408 | NE1 | TRP | F | 53 | −23.354 | 15.519 | 78.210 | 1.00 | 17.28 | F |
| ATOM | 7409 | CZ2 | TRP | F | 53 | −22.271 | 17.332 | 76.926 | 1.00 | 18.17 | F |
| ATOM | 7410 | CZ3 | TRP | F | 53 | −20.102 | 16.664 | 75.999 | 1.00 | 18.75 | F |
| ATOM | 7411 | CH2 | TRP | F | 53 | −21.132 | 17.630 | 76.180 | 1.00 | 20.22 | F |
| ATOM | 7412 | C | TRP | F | 53 | −20.554 | 10.419 | 77.384 | 1.00 | 16.97 | F |
| ATOM | 7413 | O | TRP | F | 53 | −20.457 | 9.628 | 78.314 | 1.00 | 16.55 | F |
| ATOM | 7414 | N | LEU | F | 54 | −19.794 | 10.449 | 76.281 | 1.00 | 16.85 | F |
| ATOM | 7415 | CA | LEU | F | 54 | −18.664 | 9.546 | 76.086 | 1.00 | 15.36 | F |
| ATOM | 7416 | CB | LEU | F | 54 | −18.822 | 8.712 | 74.829 | 1.00 | 17.24 | F |
| ATOM | 7417 | CG | LEU | F | 54 | −17.615 | 7.845 | 74.370 | 1.00 | 18.00 | F |
| ATOM | 7418 | CD1 | LEU | F | 54 | −17.312 | 6.768 | 75.417 | 1.00 | 16.06 | F |
| ATOM | 7419 | CD2 | LEU | F | 54 | −17.947 | 7.133 | 73.024 | 1.00 | 16.92 | F |
| ATOM | 7420 | C | LEU | F | 54 | −17.536 | 10.480 | 75.877 | 1.00 | 14.02 | F |
| ATOM | 7421 | O | LEU | F | 54 | −17.648 | 11.428 | 75.104 | 1.00 | 10.88 | F |
| ATOM | 7422 | N | ARG | F | 55 | −16.457 | 10.195 | 76.611 | 1.00 | 14.52 | F |
| ATOM | 7423 | CA | ARG | F | 55 | −15.264 | 10.993 | 76.482 | 1.00 | 16.62 | F |
| ATOM | 7424 | CB | ARG | F | 55 | −14.911 | 11.753 | 77.825 | 1.00 | 17.62 | F |
| ATOM | 7425 | CG | ARG | F | 55 | −13.629 | 12.620 | 77.592 | 1.00 | 19.50 | F |
| ATOM | 7426 | CD | ARG | F | 55 | −13.241 | 13.659 | 78.640 | 1.00 | 20.08 | F |
| ATOM | 7427 | NE | ARG | F | 55 | −12.162 | 13.283 | 79.578 | 1.00 | 21.04 | F |
| ATOM | 7428 | CZ | ARG | F | 55 | −12.065 | 12.089 | 80.162 | 1.00 | 21.38 | F |
| ATOM | 7429 | NH1 | ARG | F | 55 | −12.933 | 11.115 | 79.899 | 1.00 | 24.29 | F |
| ATOM | 7430 | NH2 | ARG | F | 55 | −11.189 | 11.881 | 81.106 | 1.00 | 21.54 | F |
| ATOM | 7431 | C | ARG | F | 55 | −14.089 | 10.125 | 76.109 | 1.00 | 17.07 | F |
| ATOM | 7432 | O | ARG | F | 55 | −13.866 | 9.069 | 76.672 | 1.00 | 16.85 | F |
| ATOM | 7433 | N | THR | F | 56 | −13.307 | 10.570 | 75.180 | 1.00 | 17.81 | F |
| ATOM | 7434 | CA | THR | F | 56 | −12.094 | 9.828 | 74.878 | 1.00 | 17.94 | F |
| ATOM | 7435 | CB | THR | F | 56 | −11.345 | 10.481 | 73.623 | 1.00 | 17.92 | F |
| ATOM | 7436 | OG1 | THR | F | 56 | −10.701 | 11.792 | 73.963 | 1.00 | 14.27 | F |
| ATOM | 7437 | CG2 | THR | F | 56 | −12.340 | 10.591 | 72.498 | 1.00 | 15.52 | F |
| ATOM | 7438 | C | THR | F | 56 | −11.092 | 10.125 | 76.002 | 1.00 | 20.02 | F |
| ATOM | 7439 | O | THR | F | 56 | −11.285 | 11.024 | 76.899 | 1.00 | 20.01 | F |
| ATOM | 7440 | N | ASN | F | 57 | −9.948 | 9.468 | 75.906 | 1.00 | 19.77 | F |
| ATOM | 7441 | CA | ASN | F | 57 | −8.952 | 9.800 | 76.891 | 1.00 | 19.46 | F |
| ATOM | 7442 | CB | ASN | F | 57 | −8.077 | 8.669 | 77.159 | 1.00 | 22.49 | F |
| ATOM | 7443 | CG | ASN | F | 57 | −8.233 | 8.276 | 78.586 | 1.00 | 26.37 | F |
| ATOM | 7444 | OD1 | ASN | F | 57 | −9.336 | 7.764 | 78.944 | 1.00 | 29.26 | F |
| ATOM | 7445 | ND2 | ASN | F | 57 | −7.199 | 8.550 | 79.482 | 1.00 | 27.00 | F |
| ATOM | 7446 | C | ASN | F | 57 | −8.142 | 10.920 | 76.451 | 1.00 | 18.91 | F |
| ATOM | 7447 | O | ASN | F | 57 | −8.290 | 11.378 | 75.285 | 1.00 | 17.90 | F |
| ATOM | 7448 | N | TRP | F | 58 | −7.294 | 11.366 | 77.388 | 1.00 | 18.09 | F |
| ATOM | 7449 | CA | TRP | F | 58 | −6.340 | 12.506 | 77.236 | 1.00 | 17.83 | F |
| ATOM | 7450 | CB | TRP | F | 58 | −5.432 | 12.575 | 78.531 | 1.00 | 20.23 | F |
| ATOM | 7451 | CG | TRP | F | 58 | −4.291 | 13.579 | 78.599 | 1.00 | 22.73 | F |
| ATOM | 7452 | CD2 | TRP | F | 58 | −4.412 | 14.985 | 78.474 | 1.00 | 23.37 | F |
| ATOM | 7453 | CE2 | TRP | F | 58 | −3.141 | 15.585 | 78.847 | 1.00 | 24.20 | F |
| ATOM | 7454 | CE3 | TRP | F | 58 | −5.471 | 15.814 | 78.116 | 1.00 | 22.39 | F |
| ATOM | 7455 | CD1 | TRP | F | 58 | −3.006 | 13.337 | 79.018 | 1.00 | 25.60 | F |
| ATOM | 7456 | NE1 | TRP | F | 58 | −2.282 | 14.572 | 79.183 | 1.00 | 26.30 | F |
| ATOM | 7457 | CZ2 | TRP | F | 58 | −2.920 | 16.969 | 78.833 | 1.00 | 23.62 | F |
| ATOM | 7458 | CZ3 | TRP | F | 58 | −5.262 | 17.210 | 78.101 | 1.00 | 23.49 | F |
| ATOM | 7459 | CH2 | TRP | F | 58 | −3.991 | 17.772 | 78.456 | 1.00 | 24.17 | F |
| ATOM | 7460 | C | TRP | F | 58 | −5.462 | 12.331 | 76.024 | 1.00 | 17.18 | F |
| ATOM | 7461 | O | TRP | F | 58 | −4.776 | 11.352 | 75.916 | 1.00 | 16.02 | F |
| ATOM | 7462 | N | VAL | F | 59 | −5.446 | 13.304 | 75.156 | 1.00 | 17.28 | F |
| ATOM | 7463 | CA | VAL | F | 59 | −4.686 | 13.165 | 73.961 | 1.00 | 17.07 | F |
| ATOM | 7464 | CB | VAL | F | 59 | −5.634 | 13.116 | 72.669 | 1.00 | 17.89 | F |
| ATOM | 7465 | CG1 | VAL | F | 59 | −4.809 | 12.992 | 71.428 | 1.00 | 16.99 | F |
| ATOM | 7466 | CG2 | VAL | F | 59 | −6.650 | 11.921 | 72.763 | 1.00 | 17.27 | F |
| ATOM | 7467 | C | VAL | F | 59 | −3.798 | 14.355 | 73.815 | 1.00 | 17.62 | F |
| ATOM | 7468 | O | VAL | F | 59 | −4.310 | 15.489 | 73.778 | 1.00 | 18.42 | F |
| ATOM | 7469 | N | TYR | F | 60 | −2.480 | 14.096 | 73.721 | 1.00 | 17.57 | F |
| ATOM | 7470 | CA | TYR | F | 60 | −1.438 | 15.105 | 73.563 | 1.00 | 16.69 | F |

TABLE 1-continued

| | | | | | | | | | | |
|---|---|---|---|---|---|---|---|---|---|---|
| ATOM | 7471 | CB | TYR | F | 60 | −0.033 | 14.475 | 73.609 | 1.00 | 17.15 | F |
| ATOM | 7472 | CG | TYR | F | 60 | 0.413 | 13.962 | 74.934 | 1.00 | 18.84 | F |
| ATOM | 7473 | CD1 | TYR | F | 60 | 0.370 | 12.617 | 75.253 | 1.00 | 20.11 | F |
| ATOM | 7474 | CE1 | TYR | F | 60 | 0.730 | 12.120 | 76.563 | 1.00 | 21.41 | F |
| ATOM | 7475 | CD2 | TYR | F | 60 | 0.812 | 14.830 | 75.889 | 1.00 | 19.79 | F |
| ATOM | 7476 | CE2 | TYR | F | 60 | 1.151 | 14.425 | 77.166 | 1.00 | 21.31 | F |
| ATOM | 7477 | CZ | TYR | F | 60 | 1.110 | 13.048 | 77.524 | 1.00 | 22.37 | F |
| ATOM | 7478 | OH | TYR | F | 60 | 1.396 | 12.599 | 78.875 | 1.00 | 23.95 | F |
| ATOM | 7479 | C | TYR | F | 60 | −1.594 | 15.775 | 72.232 | 1.00 | 16.70 | F |
| ATOM | 7480 | O | TYR | F | 60 | −1.828 | 15.163 | 71.217 | 1.00 | 17.86 | F |
| ATOM | 7481 | N | ARG | F | 61 | −1.440 | 17.055 | 72.210 | 1.00 | 16.75 | F |
| ATOM | 7482 | CA | ARG | F | 61 | −1.527 | 17.793 | 70.984 | 1.00 | 16.90 | F |
| ATOM | 7483 | CB | ARG | F | 61 | −1.671 | 19.290 | 71.320 | 1.00 | 17.05 | F |
| ATOM | 7484 | CG | ARG | F | 61 | −1.633 | 20.231 | 70.121 | 1.00 | 18.46 | F |
| ATOM | 7485 | CD | ARG | F | 61 | −2.109 | 21.730 | 70.517 | 1.00 | 21.19 | F |
| ATOM | 7486 | NE | ARG | F | 61 | −1.017 | 22.403 | 71.288 | 1.00 | 20.67 | F |
| ATOM | 7487 | CZ | ARG | F | 61 | 0.115 | 22.817 | 70.706 | 1.00 | 20.66 | F |
| ATOM | 7488 | NH1 | ARG | F | 61 | 0.293 | 22.690 | 69.360 | 1.00 | 17.43 | F |
| ATOM | 7489 | NH2 | ARG | F | 61 | 1.145 | 23.204 | 71.499 | 1.00 | 22.20 | F |
| ATOM | 7490 | C | ARG | F | 61 | −0.314 | 17.622 | 70.129 | 1.00 | 16.98 | F |
| ATOM | 7491 | O | ARG | F | 61 | −0.445 | 17.546 | 68.878 | 1.00 | 16.61 | F |
| ATOM | 7492 | N | GLY | F | 62 | 0.843 | 17.562 | 70.842 | 1.00 | 17.87 | F |
| ATOM | 7493 | CA | GLY | F | 62 | 2.168 | 17.519 | 70.250 | 1.00 | 19.78 | F |
| ATOM | 7494 | C | GLY | F | 62 | 2.344 | 18.758 | 69.366 | 1.00 | 21.03 | F |
| ATOM | 7495 | O | GLY | F | 62 | 2.167 | 19.898 | 69.849 | 1.00 | 21.82 | F |
| ATOM | 7496 | N | GLU | F | 63 | 2.661 | 18.594 | 68.058 | 1.00 | 21.36 | F |
| ATOM | 7497 | CA | GLU | F | 63 | 2.884 | 19.775 | 67.182 | 1.00 | 21.47 | F |
| ATOM | 7498 | CB | GLU | F | 63 | 4.039 | 19.394 | 66.252 | 1.00 | 21.39 | F |
| ATOM | 7499 | CG | GLU | F | 63 | 4.270 | 20.359 | 65.117 | 1.00 | 21.92 | F |
| ATOM | 7500 | CD | GLU | F | 63 | 4.968 | 21.643 | 65.547 | 1.00 | 24.82 | F |
| ATOM | 7501 | OE1 | GLU | F | 63 | 5.058 | 22.632 | 64.665 | 1.00 | 23.24 | F |
| ATOM | 7502 | OE2 | GLU | F | 63 | 5.397 | 21.663 | 66.805 | 1.00 | 26.86 | F |
| ATOM | 7503 | C | GLU | F | 63 | 1.612 | 20.180 | 66.398 | 1.00 | 22.01 | F |
| ATOM | 7504 | O | GLU | F | 63 | 1.694 | 21.082 | 65.530 | 1.00 | 22.97 | F |
| ATOM | 7505 | N | ALA | F | 64 | 0.458 | 19.563 | 66.693 | 1.00 | 21.93 | F |
| ATOM | 7506 | CA | ALA | F | 64 | −0.777 | 19.842 | 65.908 | 1.00 | 21.90 | F |
| ATOM | 7507 | CB | ALA | F | 64 | −1.845 | 18.752 | 66.263 | 1.00 | 20.63 | F |
| ATOM | 7508 | C | ALA | F | 64 | −1.400 | 21.201 | 66.095 | 1.00 | 21.51 | F |
| ATOM | 7509 | O | ALA | F | 64 | −1.445 | 21.624 | 67.216 | 1.00 | 22.67 | F |
| ATOM | 7510 | N | GLU | F | 65 | −1.891 | 21.869 | 65.049 | 1.00 | 21.61 | F |
| ATOM | 7511 | CA | GLU | F | 65 | −2.598 | 23.206 | 65.192 | 1.00 | 20.92 | F |
| ATOM | 7512 | CB | GLU | F | 65 | −2.243 | 24.276 | 64.083 | 1.00 | 20.39 | F |
| ATOM | 7513 | CG | GLU | F | 65 | −0.716 | 24.636 | 63.865 | 1.00 | 23.79 | F |
| ATOM | 7514 | CD | GLU | F | 65 | −0.090 | 25.495 | 65.089 | 1.00 | 25.42 | F |
| ATOM | 7515 | OE1 | GLU | F | 65 | −0.552 | 26.737 | 65.250 | 1.00 | 26.06 | F |
| ATOM | 7516 | OE2 | GLU | F | 65 | 0.781 | 24.869 | 65.830 | 1.00 | 25.01 | F |
| ATOM | 7517 | C | GLU | F | 65 | −4.066 | 22.834 | 64.970 | 1.00 | 20.61 | F |
| ATOM | 7518 | O | GLU | F | 65 | −4.912 | 23.123 | 65.836 | 1.00 | 21.41 | F |
| ATOM | 7519 | N | ARG | F | 66 | −4.358 | 22.237 | 63.796 | 1.00 | 20.32 | F |
| ATOM | 7520 | CA | ARG | F | 66 | −5.738 | 21.796 | 63.392 | 1.00 | 20.02 | F |
| ATOM | 7521 | CB | ARG | F | 66 | −6.135 | 22.272 | 61.993 | 1.00 | 19.21 | F |
| ATOM | 7522 | CG | ARG | F | 66 | −7.680 | 22.212 | 61.757 | 1.00 | 20.29 | F |
| ATOM | 7523 | CD | ARG | F | 66 | −8.098 | 23.527 | 61.039 | 1.00 | 21.87 | F |
| ATOM | 7524 | NE | ARG | F | 66 | −9.549 | 23.672 | 60.742 | 1.00 | 23.92 | F |
| ATOM | 7525 | CZ | ARG | F | 66 | −10.446 | 24.206 | 61.585 | 1.00 | 24.36 | F |
| ATOM | 7526 | NH1 | ARG | F | 66 | −10.018 | 24.628 | 62.792 | 1.00 | 25.98 | F |
| ATOM | 7527 | NH2 | ARG | F | 66 | −11.718 | 24.369 | 61.233 | 1.00 | 22.79 | F |
| ATOM | 7528 | C | ARG | F | 66 | −5.747 | 20.312 | 63.300 | 1.00 | 20.03 | F |
| ATOM | 7529 | O | ARG | F | 66 | −4.900 | 19.774 | 62.605 | 1.00 | 20.79 | F |
| ATOM | 7530 | N | ASN | F | 67 | −6.627 | 19.642 | 64.014 | 1.00 | 20.76 | F |
| ATOM | 7531 | CA | ASN | F | 67 | −6.711 | 18.179 | 63.902 | 1.00 | 21.01 | F |
| ATOM | 7532 | CB | ASN | F | 67 | −6.794 | 17.561 | 65.265 | 1.00 | 20.04 | F |
| ATOM | 7533 | CG | ASN | F | 67 | −7.800 | 18.279 | 66.145 | 1.00 | 20.79 | F |
| ATOM | 7534 | OD1 | ASN | F | 67 | −8.118 | 19.460 | 65.889 | 1.00 | 22.65 | F |
| ATOM | 7535 | ND2 | ASN | F | 67 | −8.311 | 17.610 | 67.180 | 1.00 | 17.93 | F |
| ATOM | 7536 | C | ASN | F | 67 | −7.995 | 17.866 | 63.118 | 1.00 | 21.01 | F |
| ATOM | 7537 | O | ASN | F | 67 | −8.892 | 18.708 | 63.085 | 1.00 | 22.23 | F |
| ATOM | 7538 | N | ASN | F | 68 | −8.063 | 16.686 | 62.460 | 1.00 | 21.46 | F |
| ATOM | 7539 | CA | ASN | F | 68 | −9.242 | 16.278 | 61.658 | 1.00 | 20.89 | F |
| ATOM | 7540 | CB | ASN | F | 68 | −8.777 | 15.958 | 60.250 | 1.00 | 20.26 | F |
| ATOM | 7541 | CG | ASN | F | 68 | −8.313 | 17.199 | 59.556 | 1.00 | 20.49 | F |
| ATOM | 7542 | OD1 | ASN | F | 68 | −9.147 | 17.956 | 58.942 | 1.00 | 21.33 | F |
| ATOM | 7543 | ND2 | ASN | F | 68 | −7.011 | 17.506 | 59.690 | 1.00 | 18.05 | F |
| ATOM | 7544 | C | ASN | F | 68 | −9.762 | 15.093 | 62.356 | 1.00 | 20.02 | F |
| ATOM | 7545 | O | ASN | F | 68 | −8.914 | 14.323 | 62.912 | 1.00 | 20.51 | F |
| ATOM | 7546 | N | PHE | F | 69 | −11.099 | 14.972 | 62.435 | 1.00 | 20.39 | F |
| ATOM | 7547 | CA | PHE | F | 69 | −11.634 | 13.702 | 63.024 | 1.00 | 20.50 | F |
| ATOM | 7548 | CB | PHE | F | 69 | −12.089 | 13.775 | 64.444 | 1.00 | 19.76 | F |
| ATOM | 7549 | CG | PHE | F | 69 | −12.324 | 15.085 | 64.874 | 1.00 | 19.51 | F |
| ATOM | 7550 | CD1 | PHE | F | 69 | −13.246 | 15.867 | 64.176 | 1.00 | 19.84 | F |

TABLE 1-continued

| | | | | | | | | | | |
|---|---|---|---|---|---|---|---|---|---|---|
| ATOM | 7551 | CD2 | PHE | F | 69 | −11.696 | 15.561 | 66.072 | 1.00 | 17.91 | F |
| ATOM | 7552 | CE1 | PHE | F | 69 | −13.561 | 17.135 | 64.692 | 1.00 | 21.02 | F |
| ATOM | 7553 | CE2 | PHE | F | 69 | −11.987 | 16.782 | 66.580 | 1.00 | 17.20 | F |
| ATOM | 7554 | CZ | PHE | F | 69 | −12.912 | 17.598 | 65.930 | 1.00 | 18.63 | F |
| ATOM | 7555 | C | PHE | F | 69 | −12.734 | 13.076 | 62.215 | 1.00 | 19.34 | F |
| ATOM | 7556 | O | PHE | F | 69 | −13.661 | 13.721 | 61.757 | 1.00 | 19.78 | F |
| ATOM | 7557 | N | GLU | F | 70 | −12.497 | 11.793 | 62.002 | 1.00 | 18.40 | F |
| ATOM | 7558 | CA | GLU | F | 70 | −13.310 | 10.990 | 61.176 | 1.00 | 16.81 | F |
| ATOM | 7559 | CB | GLU | F | 70 | −12.390 | 10.210 | 60.232 | 1.00 | 18.46 | F |
| ATOM | 7560 | CG | GLU | F | 70 | −13.045 | 9.693 | 59.004 | 1.00 | 19.74 | F |
| ATOM | 7561 | CD | GLU | F | 70 | −12.271 | 8.608 | 58.358 | 1.00 | 20.63 | F |
| ATOM | 7562 | OE1 | GLU | F | 70 | −12.114 | 8.633 | 57.084 | 1.00 | 22.80 | F |
| ATOM | 7563 | OE2 | GLU | F | 70 | −11.837 | 7.724 | 59.136 | 1.00 | 20.41 | F |
| ATOM | 7564 | C | GLU | F | 70 | −14.041 | 10.089 | 62.129 | 1.00 | 15.73 | F |
| ATOM | 7565 | O | GLU | F | 70 | −13.415 | 9.400 | 62.986 | 1.00 | 11.85 | F |
| ATOM | 7566 | N | LEU | F | 71 | −15.371 | 10.161 | 61.919 | 1.00 | 15.25 | F |
| ATOM | 7567 | CA | LEU | F | 71 | −16.380 | 9.434 | 62.630 | 1.00 | 16.54 | F |
| ATOM | 7568 | CB | LEU | F | 71 | −17.346 | 10.454 | 63.234 | 1.00 | 17.54 | F |
| ATOM | 7569 | CG | LEU | F | 71 | −16.801 | 11.270 | 64.389 | 1.00 | 17.29 | F |
| ATOM | 7570 | CD1 | LEU | F | 71 | −17.892 | 12.261 | 64.735 | 1.00 | 19.31 | F |
| ATOM | 7571 | CD2 | LEU | F | 71 | −16.389 | 10.395 | 65.565 | 1.00 | 14.19 | F |
| ATOM | 7572 | C | LEU | F | 71 | −17.169 | 8.469 | 61.743 | 1.00 | 17.34 | F |
| ATOM | 7573 | O | LEU | F | 71 | −17.587 | 8.884 | 60.649 | 1.00 | 16.94 | F |
| ATOM | 7574 | N | ASN | F | 72 | −17.352 | 7.214 | 62.207 | 1.00 | 16.00 | F |
| ATOM | 7575 | CA | ASN | F | 72 | −18.100 | 6.132 | 61.499 | 1.00 | 15.09 | F |
| ATOM | 7576 | CB | ASN | F | 72 | −17.162 | 5.020 | 61.064 | 1.00 | 14.95 | F |
| ATOM | 7577 | CG | ASN | F | 72 | −16.475 | 5.330 | 59.758 | 1.00 | 15.55 | F |
| ATOM | 7578 | OD1 | ASN | F | 72 | −15.506 | 4.671 | 59.344 | 1.00 | 14.82 | F |
| ATOM | 7579 | ND2 | ASN | F | 72 | −16.994 | 6.324 | 59.069 | 1.00 | 17.95 | F |
| ATOM | 7580 | C | ASN | F | 72 | −19.187 | 5.578 | 62.492 | 1.00 | 16.52 | F |
| ATOM | 7581 | O | ASN | F | 72 | −18.943 | 4.998 | 63.676 | 1.00 | 16.09 | F |
| ATOM | 7582 | N | PHE | F | 73 | −20.433 | 5.751 | 62.062 | 1.00 | 14.46 | F |
| ATOM | 7583 | CA | PHE | F | 73 | −21.496 | 5.345 | 62.927 | 1.00 | 13.74 | F |
| ATOM | 7584 | CB | PHE | F | 73 | −21.819 | 6.555 | 63.815 | 1.00 | 13.32 | F |
| ATOM | 7585 | CG | PHE | F | 73 | −22.186 | 7.811 | 63.027 | 1.00 | 14.30 | F |
| ATOM | 7586 | CD1 | PHE | F | 73 | −23.526 | 8.148 | 62.787 | 1.00 | 15.01 | F |
| ATOM | 7587 | CD2 | PHE | F | 73 | −21.242 | 8.565 | 62.428 | 1.00 | 14.39 | F |
| ATOM | 7588 | CE1 | PHE | F | 73 | −23.865 | 9.203 | 61.940 | 1.00 | 16.63 | F |
| ATOM | 7589 | CE2 | PHE | F | 73 | −21.576 | 9.603 | 61.598 | 1.00 | 17.49 | F |
| ATOM | 7590 | CZ | PHE | F | 73 | −22.895 | 9.929 | 61.341 | 1.00 | 17.14 | F |
| ATOM | 7591 | C | PHE | F | 73 | −22.795 | 4.940 | 62.090 | 1.00 | 15.69 | F |
| ATOM | 7592 | O | PHE | F | 73 | −22.897 | 5.138 | 60.864 | 1.00 | 13.68 | F |
| ATOM | 7593 | N | THR | F | 74 | −23.795 | 4.486 | 62.799 | 1.00 | 15.42 | F |
| ATOM | 7594 | CA | THR | F | 74 | −24.990 | 4.219 | 62.192 | 1.00 | 16.86 | F |
| ATOM | 7595 | CB | THR | F | 74 | −25.313 | 2.697 | 62.182 | 1.00 | 19.48 | F |
| ATOM | 7596 | OG1 | THR | F | 74 | −25.657 | 2.153 | 63.497 | 1.00 | 18.95 | F |
| ATOM | 7597 | CG2 | THR | F | 74 | −24.074 | 1.993 | 61.785 | 1.00 | 23.35 | F |
| ATOM | 7598 | C | THR | F | 74 | −25.974 | 4.757 | 63.110 | 1.00 | 18.58 | F |
| ATOM | 7599 | O | THR | F | 74 | −25.788 | 4.766 | 64.362 | 1.00 | 18.85 | F |
| ATOM | 7600 | N | VAL | F | 75 | −27.120 | 5.011 | 62.538 | 1.00 | 16.99 | F |
| ATOM | 7601 | CA | VAL | F | 75 | −28.232 | 5.477 | 63.369 | 1.00 | 16.13 | F |
| ATOM | 7602 | CB | VAL | F | 75 | −28.301 | 7.017 | 63.125 | 1.00 | 15.97 | F |
| ATOM | 7603 | CG1 | VAL | F | 75 | −29.413 | 7.672 | 63.942 | 1.00 | 14.56 | F |
| ATOM | 7604 | CG2 | VAL | F | 75 | −26.995 | 7.577 | 63.394 | 1.00 | 14.36 | F |
| ATOM | 7605 | C | VAL | F | 75 | −29.579 | 4.686 | 63.080 | 1.00 | 14.70 | F |
| ATOM | 7606 | O | VAL | F | 75 | −30.040 | 4.630 | 61.952 | 1.00 | 13.71 | F |
| ATOM | 7607 | N | ARG | F | 76 | −30.124 | 4.035 | 64.084 | 1.00 | 14.06 | F |
| ATOM | 7608 | CA | ARG | F | 76 | −31.343 | 3.370 | 63.845 | 1.00 | 14.70 | F |
| ATOM | 7609 | CB | ARG | F | 76 | −31.711 | 2.487 | 64.966 | 1.00 | 13.28 | F |
| ATOM | 7610 | CG | ARG | F | 76 | −32.958 | 1.821 | 64.836 | 1.00 | 10.50 | F |
| ATOM | 7611 | CD | ARG | F | 76 | −32.890 | 0.529 | 65.546 | 1.00 | 9.53 | F |
| ATOM | 7612 | NE | ARG | F | 76 | −34.251 | 0.090 | 65.687 | 1.00 | 11.10 | F |
| ATOM | 7613 | CZ | ARG | F | 76 | −34.732 | −0.803 | 66.589 | 1.00 | 13.58 | F |
| ATOM | 7614 | NH1 | ARG | F | 76 | −33.918 | −1.405 | 67.460 | 1.00 | 12.11 | F |
| ATOM | 7615 | NH2 | ARG | F | 76 | −36.072 | −1.022 | 66.693 | 1.00 | 11.13 | F |
| ATOM | 7616 | C | ARG | F | 76 | −32.434 | 4.398 | 63.593 | 1.00 | 16.37 | F |
| ATOM | 7617 | O | ARG | F | 76 | −32.446 | 5.461 | 64.161 | 1.00 | 17.13 | F |
| ATOM | 7618 | N | ASP | F | 77 | −33.308 | 4.103 | 62.622 | 1.00 | 17.74 | F |
| ATOM | 7619 | CA | ASP | F | 77 | −34.412 | 4.962 | 62.184 | 1.00 | 17.52 | F |
| ATOM | 7620 | CB | ASP | F | 77 | −35.074 | 4.321 | 60.997 | 1.00 | 20.14 | F |
| ATOM | 7621 | CG | ASP | F | 77 | −36.406 | 4.977 | 60.634 | 1.00 | 22.18 | F |
| ATOM | 7622 | OD1 | ASP | F | 77 | −36.806 | 6.040 | 61.274 | 1.00 | 21.73 | F |
| ATOM | 7623 | OD2 | ASP | F | 77 | −37.041 | 4.425 | 59.678 | 1.00 | 22.82 | F |
| ATOM | 7624 | C | ASP | F | 77 | −35.348 | 5.027 | 63.336 | 1.00 | 18.99 | F |
| ATOM | 7625 | O | ASP | F | 77 | −35.673 | 3.930 | 63.957 | 1.00 | 16.85 | F |
| ATOM | 7626 | N | CYS | F | 78 | −35.744 | 6.292 | 63.669 | 1.00 | 19.28 | F |
| ATOM | 7627 | CA | CYS | F | 78 | −36.680 | 6.576 | 64.858 | 1.00 | 19.49 | F |
| ATOM | 7628 | C | CYS | F | 78 | −38.102 | 6.038 | 64.713 | 1.00 | 20.54 | F |
| ATOM | 7629 | O | CYS | F | 78 | −38.841 | 5.817 | 65.748 | 1.00 | 21.74 | F |
| ATOM | 7630 | CB | CYS | F | 78 | −36.820 | 8.101 | 65.246 | 1.00 | 18.84 | F |

TABLE 1-continued

| ATOM | 7631 | SG  | CYS | F | 78 | −35.467 | 8.818  | 66.334 | 1.00 | 16.80 | F |
| ---- | ---- | --- | --- | - | -- | ------- | ------ | ------ | ---- | ----- | - |
| ATOM | 7632 | N   | ASN | F | 79 | −38.471 | 5.803  | 63.444 | 1.00 | 19.80 | F |
| ATOM | 7633 | CA  | ASN | F | 79 | −39.762 | 5.215  | 63.144 | 1.00 | 17.95 | F |
| ATOM | 7634 | CB  | ASN | F | 79 | −40.217 | 5.653  | 61.726 | 1.00 | 17.14 | F |
| ATOM | 7635 | CG  | ASN | F | 79 | −40.618 | 7.122  | 61.688 | 1.00 | 16.04 | F |
| ATOM | 7636 | OD1 | ASN | F | 79 | −40.631 | 7.795  | 60.678 | 1.00 | 13.51 | F |
| ATOM | 7637 | ND2 | ASN | F | 79 | −40.968 | 7.615  | 62.843 | 1.00 | 19.12 | F |
| ATOM | 7638 | C   | ASN | F | 79 | −39.719 | 3.692  | 63.298 | 1.00 | 17.07 | F |
| ATOM | 7639 | O   | ASN | F | 79 | −40.739 | 3.119  | 63.315 | 1.00 | 16.31 | F |
| ATOM | 7640 | N   | SER | F | 80 | −38.551 | 3.096  | 63.464 | 1.00 | 16.20 | F |
| ATOM | 7641 | CA  | SER | F | 80 | −38.468 | 1.703  | 63.564 | 1.00 | 16.28 | F |
| ATOM | 7642 | CB  | SER | F | 80 | −37.065 | 1.230  | 63.232 | 1.00 | 16.73 | F |
| ATOM | 7643 | OG  | SER | F | 80 | −36.062 | 1.808  | 64.119 | 1.00 | 19.07 | F |
| ATOM | 7644 | C   | SER | F | 80 | −38.808 | 1.252  | 64.922 | 1.00 | 16.23 | F |
| ATOM | 7645 | O   | SER | F | 80 | −38.445 | 0.153  | 65.250 | 1.00 | 15.44 | F |
| ATOM | 7646 | N   | PHE | F | 81 | −39.401 | 2.101  | 65.768 | 1.00 | 16.71 | F |
| ATOM | 7647 | CA  | PHE | F | 81 | −39.718 | 1.614  | 67.146 | 1.00 | 17.47 | F |
| ATOM | 7648 | CB  | PHE | F | 81 | −39.046 | 2.545  | 68.193 | 1.00 | 17.52 | F |
| ATOM | 7649 | CG  | PHE | F | 81 | −37.510 | 2.527  | 68.175 | 1.00 | 15.80 | F |
| ATOM | 7650 | CD1 | PHE | F | 81 | −36.790 | 3.426  | 67.427 | 1.00 | 12.99 | F |
| ATOM | 7651 | CD2 | PHE | F | 81 | −36.800 | 1.580  | 68.920 | 1.00 | 14.82 | F |
| ATOM | 7652 | CE1 | PHE | F | 81 | −35.417 | 3.363  | 67.438 | 1.00 | 12.15 | F |
| ATOM | 7653 | CE2 | PHE | F | 81 | −35.399 | 1.550  | 68.904 | 1.00 | 12.98 | F |
| ATOM | 7654 | CZ  | PHE | F | 81 | −34.718 | 2.423  | 68.176 | 1.00 | 10.08 | F |
| ATOM | 7655 | C   | PHE | F | 81 | −41.301 | 1.615  | 67.177 | 1.00 | 19.38 | F |
| ATOM | 7656 | O   | PHE | F | 81 | −41.903 | 2.636  | 67.327 | 1.00 | 17.40 | F |
| ATOM | 7657 | N   | PRO | F | 82 | −41.965 | 0.420  | 67.059 | 1.00 | 20.84 | F |
| ATOM | 7658 | CD  | PRO | F | 82 | −41.357 | −0.816 | 67.634 | 1.00 | 21.23 | F |
| ATOM | 7659 | CA  | PRO | F | 82 | −43.433 | 0.290  | 67.005 | 1.00 | 20.58 | F |
| ATOM | 7660 | CB  | PRO | F | 82 | −43.733 | −1.171 | 67.406 | 1.00 | 22.42 | F |
| ATOM | 7661 | CG  | PRO | F | 82 | −42.352 | −1.928 | 67.245 | 1.00 | 21.93 | F |
| ATOM | 7662 | C   | PRO | F | 82 | −44.127 | 1.160  | 67.919 | 1.00 | 22.52 | F |
| ATOM | 7663 | O   | PRO | F | 82 | −43.750 | 1.178  | 69.113 | 1.00 | 22.62 | F |
| ATOM | 7664 | N   | GLY | F | 83 | −45.177 | 1.828  | 67.431 | 1.00 | 22.64 | F |
| ATOM | 7665 | CA  | GLY | F | 83 | −45.949 | 2.760  | 68.274 | 1.00 | 22.27 | F |
| ATOM | 7666 | C   | GLY | F | 83 | −45.141 | 4.045  | 68.099 | 1.00 | 21.94 | F |
| ATOM | 7667 | O   | GLY | F | 83 | −44.026 | 3.941  | 67.493 | 1.00 | 22.58 | F |
| ATOM | 7668 | N   | GLY | F | 84 | −45.557 | 5.252  | 68.518 | 1.00 | 21.58 | F |
| ATOM | 7669 | CA  | GLY | F | 84 | −44.551 | 6.336  | 68.239 | 1.00 | 20.94 | F |
| ATOM | 7670 | C   | GLY | F | 84 | −43.291 | 6.386  | 69.163 | 1.00 | 21.14 | F |
| ATOM | 7671 | O   | GLY | F | 84 | −43.306 | 5.671  | 70.195 | 1.00 | 20.77 | F |
| ATOM | 7672 | N   | ALA | F | 85 | −42.188 | 7.106  | 68.837 | 1.00 | 20.59 | F |
| ATOM | 7673 | CA  | ALA | F | 85 | −41.052 | 7.198  | 69.836 | 1.00 | 20.44 | F |
| ATOM | 7674 | CB  | ALA | F | 85 | −39.751 | 6.403  | 69.414 | 1.00 | 18.39 | F |
| ATOM | 7675 | C   | ALA | F | 85 | −40.728 | 8.672  | 69.899 | 1.00 | 20.58 | F |
| ATOM | 7676 | O   | ALA | F | 85 | −39.665 | 9.034  | 69.531 | 1.00 | 21.80 | F |
| ATOM | 7677 | N   | SER | F | 86 | −41.688 | 9.511  | 70.310 | 1.00 | 19.75 | F |
| ATOM | 7678 | CA  | SER | F | 86 | −41.564 | 10.983 | 70.433 | 1.00 | 17.42 | F |
| ATOM | 7679 | CB  | SER | F | 86 | −42.684 | 11.586 | 71.310 | 1.00 | 16.21 | F |
| ATOM | 7680 | OG  | SER | F | 86 | −42.744 | 11.017 | 72.616 | 1.00 | 14.75 | F |
| ATOM | 7681 | C   | SER | F | 86 | −40.256 | 11.567 | 70.914 | 1.00 | 17.11 | F |
| ATOM | 7682 | O   | SER | F | 86 | −39.829 | 12.629 | 70.421 | 1.00 | 17.13 | F |
| ATOM | 7683 | N   | SER | F | 87 | −39.586 | 10.946 | 71.867 | 1.00 | 16.91 | F |
| ATOM | 7684 | CA  | SER | F | 87 | −38.301 | 11.580 | 72.300 | 1.00 | 16.12 | F |
| ATOM | 7685 | CB  | SER | F | 87 | −38.157 | 11.436 | 73.842 | 1.00 | 15.06 | F |
| ATOM | 7686 | OG  | SER | F | 87 | −37.918 | 10.096 | 74.284 | 1.00 | 13.73 | F |
| ATOM | 7687 | C   | SER | F | 87 | −37.048 | 11.072 | 71.549 | 1.00 | 15.21 | F |
| ATOM | 7688 | O   | SER | F | 87 | −35.999 | 11.520 | 71.804 | 1.00 | 15.82 | F |
| ATOM | 7689 | N   | CYS | F | 88 | −37.186 | 10.097 | 70.667 | 1.00 | 15.28 | F |
| ATOM | 7690 | CA  | CYS | F | 88 | −36.066 | 9.554  | 69.905 | 1.00 | 13.74 | F |
| ATOM | 7691 | C   | CYS | F | 88 | −35.595 | 10.623 | 68.981 | 1.00 | 14.39 | F |
| ATOM | 7692 | O   | CYS | F | 88 | −36.346 | 11.479 | 68.542 | 1.00 | 14.18 | F |
| ATOM | 7693 | CB  | CYS | F | 88 | −36.519 | 8.343  | 69.148 | 1.00 | 13.08 | F |
| ATOM | 7694 | SG  | CYS | F | 88 | −35.466 | 7.528  | 67.910 | 1.00 | 13.76 | F |
| ATOM | 7695 | N   | LYS | F | 89 | −34.302 | 10.610 | 68.761 | 1.00 | 15.83 | F |
| ATOM | 7696 | CA  | LYS | F | 89 | −33.594 | 11.591 | 67.913 | 1.00 | 17.51 | F |
| ATOM | 7697 | CB  | LYS | F | 89 | −32.637 | 12.432 | 68.825 | 1.00 | 18.79 | F |
| ATOM | 7698 | CG  | LYS | F | 89 | −33.406 | 13.153 | 70.007 | 1.00 | 20.71 | F |
| ATOM | 7699 | CD  | LYS | F | 89 | −34.188 | 14.326 | 69.375 | 1.00 | 19.47 | F |
| ATOM | 7700 | CE  | LYS | F | 89 | −34.926 | 15.144 | 70.373 | 1.00 | 20.57 | F |
| ATOM | 7701 | NZ  | LYS | F | 89 | −35.464 | 16.526 | 69.809 | 1.00 | 21.34 | F |
| ATOM | 7702 | C   | LYS | F | 89 | −32.721 | 10.875 | 66.866 | 1.00 | 16.88 | F |
| ATOM | 7703 | O   | LYS | F | 89 | −32.368 | 9.729  | 67.027 | 1.00 | 16.59 | F |
| ATOM | 7704 | N   | GLU | F | 90 | −32.317 | 11.571 | 65.843 | 1.00 | 17.11 | F |
| ATOM | 7705 | CA  | GLU | F | 90 | −31.433 | 10.974 | 64.847 | 1.00 | 19.09 | F |
| ATOM | 7706 | CB  | GLU | F | 90 | −32.170 | 10.720 | 63.521 | 1.00 | 17.54 | F |
| ATOM | 7707 | CG  | GLU | F | 90 | −33.348 | 9.790  | 63.795 | 1.00 | 18.53 | F |
| ATOM | 7708 | CD  | GLU | F | 90 | −34.336 | 9.609  | 62.624 | 1.00 | 19.25 | F |
| ATOM | 7709 | OE1 | GLU | F | 90 | −34.583 | 10.668 | 61.941 | 1.00 | 17.26 | F |
| ATOM | 7710 | OE2 | GLU | F | 90 | −34.854 | 8.418  | 62.437 | 1.00 | 18.46 | F |

TABLE 1-continued

| | | | | | | | | | | |
|---|---|---|---|---|---|---|---|---|---|---|
| ATOM | 7711 | C | GLU | F | 90 | −30.147 | 11.795 | 64.582 | 1.00 | 19.97 | F |
| ATOM | 7712 | O | GLU | F | 90 | −29.729 | 11.981 | 63.421 | 1.00 | 21.73 | F |
| ATOM | 7713 | N | THR | F | 91 | −29.562 | 12.337 | 65.640 | 1.00 | 20.08 | F |
| ATOM | 7714 | CA | THR | F | 91 | −28.328 | 13.075 | 65.514 | 1.00 | 18.48 | F |
| ATOM | 7715 | CB | THR | F | 91 | −28.544 | 14.572 | 65.195 | 1.00 | 18.45 | F |
| ATOM | 7716 | OG1 | THR | F | 91 | −29.372 | 15.175 | 66.205 | 1.00 | 17.11 | F |
| ATOM | 7717 | CG2 | THR | F | 91 | −29.196 | 14.734 | 63.893 | 1.00 | 16.88 | F |
| ATOM | 7718 | C | THR | F | 91 | −27.778 | 12.977 | 66.916 | 1.00 | 19.39 | F |
| ATOM | 7719 | O | THR | F | 91 | −28.468 | 12.432 | 67.845 | 1.00 | 18.72 | F |
| ATOM | 7720 | N | PHE | F | 92 | −26.522 | 13.426 | 67.018 | 1.00 | 18.82 | F |
| ATOM | 7721 | CA | PHE | F | 92 | −25.743 | 13.472 | 68.252 | 1.00 | 17.54 | F |
| ATOM | 7722 | CB | PHE | F | 92 | −25.076 | 12.106 | 68.548 | 1.00 | 18.30 | F |
| ATOM | 7723 | CG | PHE | F | 92 | −24.036 | 11.669 | 67.534 | 1.00 | 18.24 | F |
| ATOM | 7724 | CD1 | PHE | F | 92 | −22.698 | 11.996 | 67.707 | 1.00 | 17.06 | F |
| ATOM | 7725 | CD2 | PHE | F | 92 | −24.434 | 10.843 | 66.448 | 1.00 | 17.44 | F |
| ATOM | 7726 | CE1 | PHE | F | 92 | −21.718 | 11.509 | 66.831 | 1.00 | 19.53 | F |
| ATOM | 7727 | CE2 | PHE | F | 92 | −23.482 | 10.326 | 65.529 | 1.00 | 18.36 | F |
| ATOM | 7728 | CZ | PHE | F | 92 | −22.105 | 10.626 | 65.681 | 1.00 | 19.37 | F |
| ATOM | 7729 | C | PHE | F | 92 | −24.684 | 14.567 | 68.155 | 1.00 | 17.98 | F |
| ATOM | 7730 | O | PHE | F | 92 | −24.345 | 15.064 | 67.061 | 1.00 | 15.98 | F |
| ATOM | 7731 | N | ASN | F | 93 | −24.111 | 14.909 | 69.321 | 1.00 | 18.04 | F |
| ATOM | 7732 | CA | ASN | F | 93 | −23.161 | 15.988 | 69.357 | 1.00 | 17.17 | F |
| ATOM | 7733 | CB | ASN | F | 93 | −23.625 | 16.935 | 70.388 | 1.00 | 19.16 | F |
| ATOM | 7734 | CG | ASN | F | 93 | −24.868 | 17.592 | 69.949 | 1.00 | 20.34 | F |
| ATOM | 7735 | OD1 | ASN | F | 93 | −24.861 | 18.108 | 68.788 | 1.00 | 20.41 | F |
| ATOM | 7736 | ND2 | ASN | F | 93 | −25.953 | 17.565 | 70.790 | 1.00 | 16.00 | F |
| ATOM | 7737 | C | ASN | F | 93 | −21.752 | 15.721 | 69.594 | 1.00 | 17.39 | F |
| ATOM | 7738 | O | ASN | F | 93 | −21.413 | 14.847 | 70.405 | 1.00 | 15.99 | F |
| ATOM | 7739 | N | LEU | F | 94 | −20.927 | 16.542 | 68.908 | 1.00 | 17.16 | F |
| ATOM | 7740 | CA | LEU | F | 94 | −19.477 | 16.429 | 69.045 | 1.00 | 16.62 | F |
| ATOM | 7741 | CB | LEU | F | 94 | −18.820 | 16.329 | 67.682 | 1.00 | 15.88 | F |
| ATOM | 7742 | CG | LEU | F | 94 | −17.306 | 16.222 | 67.610 | 1.00 | 15.26 | F |
| ATOM | 7743 | CD1 | LEU | F | 94 | −16.759 | 15.049 | 68.372 | 1.00 | 12.98 | F |
| ATOM | 7744 | CD2 | LEU | F | 94 | −16.966 | 16.188 | 66.153 | 1.00 | 14.95 | F |
| ATOM | 7745 | C | LEU | F | 94 | −18.848 | 17.597 | 69.803 | 1.00 | 18.23 | F |
| ATOM | 7746 | O | LEU | F | 94 | −19.068 | 18.732 | 69.457 | 1.00 | 17.33 | F |
| ATOM | 7747 | N | TYR | F | 95 | −18.029 | 17.277 | 70.822 | 1.00 | 19.17 | F |
| ATOM | 7748 | CA | TYR | F | 95 | −17.403 | 18.321 | 71.655 | 1.00 | 19.53 | F |
| ATOM | 7749 | CB | TYR | F | 95 | −18.041 | 18.404 | 73.037 | 1.00 | 20.25 | F |
| ATOM | 7750 | CG | TYR | F | 95 | −19.466 | 18.976 | 73.210 | 1.00 | 20.51 | F |
| ATOM | 7751 | CD1 | TYR | F | 95 | −20.609 | 18.274 | 72.806 | 1.00 | 18.75 | F |
| ATOM | 7752 | CE1 | TYR | F | 95 | −21.858 | 18.839 | 72.943 | 1.00 | 18.77 | F |
| ATOM | 7753 | CD2 | TYR | F | 95 | −19.650 | 20.288 | 73.776 | 1.00 | 20.41 | F |
| ATOM | 7754 | CE2 | TYR | F | 95 | −20.897 | 20.829 | 73.893 | 1.00 | 20.20 | F |
| ATOM | 7755 | CZ | TYR | F | 95 | −21.988 | 20.112 | 73.484 | 1.00 | 18.71 | F |
| ATOM | 7756 | OH | TYR | F | 95 | −23.146 | 20.789 | 73.646 | 1.00 | 19.94 | F |
| ATOM | 7757 | C | TYR | F | 95 | −15.931 | 17.922 | 71.963 | 1.00 | 21.16 | F |
| ATOM | 7758 | O | TYR | F | 95 | −15.497 | 16.660 | 71.993 | 1.00 | 20.40 | F |
| ATOM | 7759 | N | TYR | F | 96 | −15.178 | 18.984 | 72.257 | 1.00 | 20.41 | F |
| ATOM | 7760 | CA | TYR | F | 96 | −13.804 | 18.781 | 72.696 | 1.00 | 19.39 | F |
| ATOM | 7761 | CB | TYR | F | 96 | −12.858 | 19.081 | 71.534 | 1.00 | 19.27 | F |
| ATOM | 7762 | CG | TYR | F | 96 | −12.635 | 20.543 | 71.298 | 1.00 | 17.40 | F |
| ATOM | 7763 | CD1 | TYR | F | 96 | −11.475 | 21.179 | 71.733 | 1.00 | 16.51 | F |
| ATOM | 7764 | CE1 | TYR | F | 96 | −11.233 | 22.522 | 71.458 | 1.00 | 15.00 | F |
| ATOM | 7765 | CD2 | TYR | F | 96 | −13.554 | 21.291 | 70.607 | 1.00 | 16.75 | F |
| ATOM | 7766 | CE2 | TYR | F | 96 | −13.314 | 22.637 | 70.320 | 1.00 | 15.23 | F |
| ATOM | 7767 | CZ | TYR | F | 96 | −12.161 | 23.248 | 70.738 | 1.00 | 14.71 | F |
| ATOM | 7768 | OH | TYR | F | 96 | −11.913 | 24.566 | 70.402 | 1.00 | 12.37 | F |
| ATOM | 7769 | C | TYR | F | 96 | −13.582 | 19.761 | 73.905 | 1.00 | 20.35 | F |
| ATOM | 7770 | O | TYR | F | 96 | −14.561 | 20.424 | 74.350 | 1.00 | 18.90 | F |
| ATOM | 7771 | N | ALA | F | 97 | −12.333 | 19.842 | 74.397 | 1.00 | 19.69 | F |
| ATOM | 7772 | CA | ALA | F | 97 | −11.898 | 20.745 | 75.523 | 1.00 | 19.37 | F |
| ATOM | 7773 | CB | ALA | F | 97 | −12.492 | 20.332 | 76.945 | 1.00 | 16.02 | F |
| ATOM | 7774 | C | ALA | F | 97 | −10.390 | 20.544 | 75.495 | 1.00 | 20.97 | F |
| ATOM | 7775 | O | ALA | F | 97 | −9.860 | 19.415 | 75.189 | 1.00 | 22.19 | F |
| ATOM | 7776 | N | GLU | F | 98 | −9.661 | 21.653 | 75.714 | 1.00 | 21.67 | F |
| ATOM | 7777 | CA | GLU | F | 98 | −8.177 | 21.636 | 75.697 | 1.00 | 19.70 | F |
| ATOM | 7778 | CB | GLU | F | 98 | −7.662 | 22.880 | 74.946 | 1.00 | 19.11 | F |
| ATOM | 7779 | CG | GLU | F | 98 | −7.529 | 22.686 | 73.470 | 1.00 | 18.15 | F |
| ATOM | 7780 | CD | GLU | F | 98 | −7.125 | 23.890 | 72.778 | 1.00 | 17.02 | F |
| ATOM | 7781 | OE1 | GLU | F | 98 | −8.032 | 24.728 | 72.601 | 1.00 | 16.72 | F |
| ATOM | 7782 | OE2 | GLU | F | 98 | −5.912 | 23.976 | 72.411 | 1.00 | 16.61 | F |
| ATOM | 7783 | C | GLU | F | 98 | −7.852 | 21.768 | 77.151 | 1.00 | 20.71 | F |
| ATOM | 7784 | O | GLU | F | 98 | −8.661 | 22.315 | 77.914 | 1.00 | 20.46 | F |
| ATOM | 7785 | N | SER | F | 99 | −6.766 | 21.156 | 77.588 | 1.00 | 21.75 | F |
| ATOM | 7786 | CA | SER | F | 99 | −6.221 | 21.501 | 78.972 | 1.00 | 21.94 | F |
| ATOM | 7787 | CB | SER | F | 99 | −6.950 | 20.841 | 80.143 | 1.00 | 22.46 | F |
| ATOM | 7788 | OG | SER | F | 99 | −6.785 | 19.415 | 80.153 | 1.00 | 24.05 | F |
| ATOM | 7789 | C | SER | F | 99 | −4.758 | 21.131 | 79.035 | 1.00 | 22.13 | F |
| ATOM | 7790 | O | SER | F | 99 | −4.312 | 20.246 | 78.314 | 1.00 | 22.69 | F |

TABLE 1-continued

| ATOM | 7791 | N | ASP | F | 100 | −3.988 | 21.825 | 79.830 | 1.00 | 21.95 | F |
|---|---|---|---|---|---|---|---|---|---|---|---|
| ATOM | 7792 | CA | ASP | F | 100 | −2.561 | 21.545 | 79.843 | 1.00 | 21.70 | F |
| ATOM | 7793 | CB | ASP | F | 100 | −1.761 | 22.743 | 80.269 | 1.00 | 20.70 | F |
| ATOM | 7794 | CG | ASP | F | 100 | −1.643 | 23.838 | 79.196 | 1.00 | 21.98 | F |
| ATOM | 7795 | OD1 | ASP | F | 100 | −1.208 | 23.583 | 78.017 | 1.00 | 21.84 | F |
| ATOM | 7796 | OD2 | ASP | F | 100 | −1.910 | 25.059 | 79.536 | 1.00 | 23.79 | F |
| ATOM | 7797 | C | ASP | F | 100 | −2.295 | 20.422 | 80.822 | 1.00 | 22.54 | F |
| ATOM | 7798 | O | ASP | F | 100 | −1.146 | 19.964 | 80.874 | 1.00 | 23.44 | F |
| ATOM | 7799 | N | LEU | F | 101 | −3.322 | 19.996 | 81.565 | 1.00 | 21.78 | F |
| ATOM | 7800 | CA | LEU | F | 101 | −3.230 | 18.928 | 82.531 | 1.00 | 21.06 | F |
| ATOM | 7801 | CB | LEU | F | 101 | −3.627 | 19.371 | 83.957 | 1.00 | 22.57 | F |
| ATOM | 7802 | CG | LEU | F | 101 | −3.225 | 20.715 | 84.606 | 1.00 | 24.63 | F |
| ATOM | 7803 | CD1 | LEU | F | 101 | −3.742 | 21.851 | 83.601 | 1.00 | 24.86 | F |
| ATOM | 7804 | CD2 | LEU | F | 101 | −3.937 | 20.945 | 86.019 | 1.00 | 25.84 | F |
| ATOM | 7805 | C | LEU | F | 101 | −4.285 | 17.845 | 82.159 | 1.00 | 21.36 | F |
| ATOM | 7806 | O | LEU | F | 101 | −5.372 | 18.093 | 81.548 | 1.00 | 20.77 | F |
| ATOM | 7807 | N | ASP | F | 102 | −4.016 | 16.671 | 82.707 | 1.00 | 21.76 | F |
| ATOM | 7808 | CA | ASP | F | 102 | −4.829 | 15.520 | 82.463 | 1.00 | 22.41 | F |
| ATOM | 7809 | CB | ASP | F | 102 | −3.943 | 14.285 | 82.681 | 1.00 | 24.13 | F |
| ATOM | 7810 | CG | ASP | F | 102 | −4.655 | 12.969 | 82.281 | 1.00 | 26.68 | F |
| ATOM | 7811 | OD1 | ASP | F | 102 | −5.947 | 12.969 | 82.385 | 1.00 | 26.81 | F |
| ATOM | 7812 | OD2 | ASP | F | 102 | −3.897 | 11.968 | 81.860 | 1.00 | 27.35 | F |
| ATOM | 7813 | C | ASP | F | 102 | −5.975 | 15.526 | 83.412 | 1.00 | 21.70 | F |
| ATOM | 7814 | O | ASP | F | 102 | −5.765 | 15.201 | 84.584 | 1.00 | 22.52 | F |
| ATOM | 7815 | N | TYR | F | 103 | −7.192 | 15.885 | 82.999 | 1.00 | 21.58 | F |
| ATOM | 7816 | CA | TYR | F | 103 | −8.250 | 15.802 | 84.086 | 1.00 | 21.32 | F |
| ATOM | 7817 | CB | TYR | F | 103 | −9.709 | 16.172 | 83.659 | 1.00 | 21.33 | F |
| ATOM | 7818 | CG | TYR | F | 103 | −9.895 | 17.609 | 83.284 | 1.00 | 23.03 | F |
| ATOM | 7819 | CD1 | TYR | F | 103 | −9.444 | 18.665 | 84.210 | 1.00 | 23.51 | F |
| ATOM | 7820 | CE1 | TYR | F | 103 | −9.457 | 20.049 | 83.828 | 1.00 | 23.14 | F |
| ATOM | 7821 | CD2 | TYR | F | 103 | −10.415 | 17.987 | 81.919 | 1.00 | 24.52 | F |
| ATOM | 7822 | CE2 | TYR | F | 103 | −10.444 | 19.417 | 81.479 | 1.00 | 24.53 | F |
| ATOM | 7823 | CZ | TYR | F | 103 | −9.927 | 20.460 | 82.486 | 1.00 | 25.14 | F |
| ATOM | 7824 | OH | TYR | F | 103 | −9.833 | 21.830 | 82.017 | 1.00 | 24.24 | F |
| ATOM | 7825 | C | TYR | F | 103 | −8.402 | 14.474 | 84.744 | 1.00 | 20.20 | F |
| ATOM | 7826 | O | TYR | F | 103 | −9.134 | 14.422 | 85.657 | 1.00 | 20.37 | F |
| ATOM | 7827 | N | GLY | F | 104 | −7.776 | 13.396 | 84.303 | 1.00 | 20.66 | F |
| ATOM | 7828 | CA | GLY | F | 104 | −8.074 | 12.099 | 84.957 | 1.00 | 21.48 | F |
| ATOM | 7829 | C | GLY | F | 104 | −9.593 | 11.759 | 84.763 | 1.00 | 22.31 | F |
| ATOM | 7830 | O | GLY | F | 104 | −10.150 | 11.877 | 83.624 | 1.00 | 23.34 | F |
| ATOM | 7831 | N | THR | F | 105 | −10.295 | 11.386 | 85.837 | 1.00 | 22.68 | F |
| ATOM | 7832 | CA | THR | F | 105 | −11.749 | 11.075 | 85.786 | 1.00 | 22.14 | F |
| ATOM | 7833 | CB | THR | F | 105 | −12.008 | 10.074 | 86.851 | 1.00 | 23.31 | F |
| ATOM | 7834 | OG1 | THR | F | 105 | −11.624 | 8.789 | 86.303 | 1.00 | 24.26 | F |
| ATOM | 7835 | CG2 | THR | F | 105 | −13.517 | 10.144 | 87.340 | 1.00 | 23.48 | F |
| ATOM | 7836 | C | THR | F | 105 | −12.768 | 12.258 | 85.918 | 1.00 | 21.24 | F |
| ATOM | 7837 | O | THR | F | 105 | −13.974 | 12.124 | 85.979 | 1.00 | 19.90 | F |
| ATOM | 7838 | N | ASN | F | 106 | −12.211 | 13.434 | 85.837 | 1.00 | 21.10 | F |
| ATOM | 7839 | CA | ASN | F | 106 | −12.964 | 14.629 | 86.016 | 1.00 | 23.05 | F |
| ATOM | 7840 | CB | ASN | F | 106 | −12.126 | 15.843 | 86.442 | 1.00 | 22.76 | F |
| ATOM | 7841 | CG | ASN | F | 106 | −11.800 | 15.841 | 87.892 | 1.00 | 23.72 | F |
| ATOM | 7842 | OD1 | ASN | F | 106 | −11.018 | 16.823 | 88.446 | 1.00 | 26.89 | F |
| ATOM | 7843 | ND2 | ASN | F | 106 | −12.386 | 14.834 | 88.604 | 1.00 | 23.43 | F |
| ATOM | 7844 | C | ASN | F | 106 | −13.655 | 15.068 | 84.846 | 1.00 | 22.70 | F |
| ATOM | 7845 | O | ASN | F | 106 | −13.197 | 16.063 | 84.193 | 1.00 | 23.91 | F |
| ATOM | 7846 | N | PHE | F | 107 | −14.810 | 14.500 | 84.641 | 1.00 | 22.13 | F |
| ATOM | 7847 | CA | PHE | F | 107 | −15.448 | 15.035 | 83.496 | 1.00 | 22.36 | F |
| ATOM | 7848 | CB | PHE | F | 107 | −16.300 | 13.932 | 82.867 | 1.00 | 21.74 | F |
| ATOM | 7849 | CG | PHE | F | 107 | −16.972 | 14.371 | 81.640 | 1.00 | 20.73 | F |
| ATOM | 7850 | CD1 | PHE | F | 107 | −16.256 | 14.882 | 80.576 | 1.00 | 20.44 | F |
| ATOM | 7851 | CD2 | PHE | F | 107 | −18.324 | 14.381 | 81.615 | 1.00 | 19.88 | F |
| ATOM | 7852 | CE1 | PHE | F | 107 | −16.933 | 15.456 | 79.449 | 1.00 | 21.78 | F |
| ATOM | 7853 | CE2 | PHE | F | 107 | −19.032 | 14.933 | 80.495 | 1.00 | 21.12 | F |
| ATOM | 7854 | CZ | PHE | F | 107 | −18.332 | 15.473 | 79.431 | 1.00 | 21.14 | F |
| ATOM | 7855 | C | PHE | F | 107 | −16.337 | 16.242 | 83.844 | 1.00 | 21.07 | F |
| ATOM | 7856 | O | PHE | F | 107 | −17.204 | 16.121 | 84.759 | 1.00 | 20.66 | F |
| ATOM | 7857 | N | GLN | F | 108 | −16.168 | 17.327 | 83.060 | 1.00 | 20.57 | F |
| ATOM | 7858 | CA | GLN | F | 108 | −17.007 | 18.540 | 83.207 | 1.00 | 21.03 | F |
| ATOM | 7859 | CB | GLN | F | 108 | −16.208 | 19.807 | 83.613 | 1.00 | 22.68 | F |
| ATOM | 7860 | CG | GLN | F | 108 | −15.229 | 19.563 | 84.625 | 1.00 | 25.02 | F |
| ATOM | 7861 | CD | GLN | F | 108 | −15.896 | 19.503 | 85.976 | 1.00 | 27.43 | F |
| ATOM | 7862 | OE1 | GLN | F | 108 | −15.128 | 19.361 | 87.033 | 1.00 | 30.47 | F |
| ATOM | 7863 | NE2 | GLN | F | 108 | −17.305 | 19.670 | 86.011 | 1.00 | 26.35 | F |
| ATOM | 7864 | C | GLN | F | 108 | −17.597 | 18.920 | 81.916 | 1.00 | 19.49 | F |
| ATOM | 7865 | O | GLN | F | 108 | −16.925 | 19.596 | 81.117 | 1.00 | 19.28 | F |
| ATOM | 7866 | N | LYS | F | 109 | −18.868 | 18.559 | 81.735 | 1.00 | 19.62 | F |
| ATOM | 7867 | CA | LYS | F | 109 | −19.537 | 18.886 | 80.485 | 1.00 | 18.79 | F |
| ATOM | 7868 | CB | LYS | F | 109 | −21.022 | 18.456 | 80.621 | 1.00 | 19.39 | F |
| ATOM | 7869 | CG | LYS | F | 109 | −21.937 | 19.609 | 80.287 | 1.00 | 21.43 | F |
| ATOM | 7870 | CD | LYS | F | 109 | −23.371 | 19.345 | 80.650 | 1.00 | 24.07 | F |

TABLE 1-continued

| | | | | | | | | | | |
|---|---|---|---|---|---|---|---|---|---|---|
| ATOM | 7871 | CE | LYS | F | 109 | −24.118 | 18.620 | 79.439 | 1.00 | 27.28 | F |
| ATOM | 7872 | NZ | LYS | F | 109 | −25.707 | 18.622 | 79.557 | 1.00 | 26.49 | F |
| ATOM | 7873 | C | LYS | F | 109 | −19.306 | 20.398 | 80.205 | 1.00 | 17.99 | F |
| ATOM | 7874 | O | LYS | F | 109 | −18.845 | 20.811 | 79.109 | 1.00 | 18.54 | F |
| ATOM | 7875 | N | ARG | F | 110 | −19.528 | 21.216 | 81.220 | 1.00 | 18.45 | F |
| ATOM | 7876 | CA | ARG | F | 110 | −19.446 | 22.649 | 80.952 | 1.00 | 18.56 | F |
| ATOM | 7877 | CB | ARG | F | 110 | −19.953 | 23.459 | 82.133 | 1.00 | 19.81 | F |
| ATOM | 7878 | CG | ARG | F | 110 | −21.458 | 23.667 | 82.029 | 1.00 | 22.73 | F |
| ATOM | 7879 | CD | ARG | F | 110 | −22.303 | 22.276 | 82.312 | 1.00 | 25.99 | F |
| ATOM | 7880 | NE | ARG | F | 110 | −23.740 | 22.464 | 81.981 | 1.00 | 26.09 | F |
| ATOM | 7881 | CZ | ARG | F | 110 | −24.217 | 22.471 | 80.737 | 1.00 | 26.48 | F |
| ATOM | 7882 | NH1 | ARG | F | 110 | −23.359 | 22.279 | 79.699 | 1.00 | 22.86 | F |
| ATOM | 7883 | NH2 | ARG | F | 110 | −25.566 | 22.672 | 80.564 | 1.00 | 27.18 | F |
| ATOM | 7884 | C | ARG | F | 110 | −18.151 | 23.154 | 80.488 | 1.00 | 17.73 | F |
| ATOM | 7885 | O | ARG | F | 110 | −18.096 | 24.256 | 80.024 | 1.00 | 17.45 | F |
| ATOM | 7886 | N | LEU | F | 111 | −17.120 | 22.311 | 80.549 | 1.00 | 18.54 | F |
| ATOM | 7887 | CA | LEU | F | 111 | −15.734 | 22.671 | 80.095 | 1.00 | 19.81 | F |
| ATOM | 7888 | CB | LEU | F | 111 | −14.666 | 21.912 | 80.895 | 1.00 | 18.84 | F |
| ATOM | 7889 | CG | LEU | F | 111 | −14.670 | 22.440 | 82.397 | 1.00 | 18.97 | F |
| ATOM | 7890 | CD1 | LEU | F | 111 | −13.473 | 21.809 | 83.084 | 1.00 | 17.73 | F |
| ATOM | 7891 | CD2 | LEU | F | 111 | −14.600 | 24.097 | 82.561 | 1.00 | 18.05 | F |
| ATOM | 7892 | C | LEU | F | 111 | −15.485 | 22.437 | 78.643 | 1.00 | 20.38 | F |
| ATOM | 7893 | O | LEU | F | 111 | −14.504 | 22.924 | 78.078 | 1.00 | 21.82 | F |
| ATOM | 7894 | N | PHE | F | 112 | −16.376 | 21.611 | 78.057 | 1.00 | 20.35 | F |
| ATOM | 7895 | CA | PHE | F | 112 | −16.353 | 21.279 | 76.621 | 1.00 | 18.43 | F |
| ATOM | 7896 | CB | PHE | F | 112 | −16.935 | 19.923 | 76.437 | 1.00 | 18.45 | F |
| ATOM | 7897 | CG | PHE | F | 112 | −16.029 | 18.859 | 76.791 | 1.00 | 17.93 | F |
| ATOM | 7898 | CD1 | PHE | F | 112 | −15.771 | 18.586 | 78.149 | 1.00 | 18.28 | F |
| ATOM | 7899 | CD2 | PHE | F | 112 | −15.417 | 18.061 | 75.746 | 1.00 | 17.55 | F |
| ATOM | 7900 | CE1 | PHE | F | 112 | −14.914 | 17.518 | 78.499 | 1.00 | 18.45 | F |
| ATOM | 7901 | CE2 | PHE | F | 112 | −14.564 | 16.995 | 76.038 | 1.00 | 16.01 | F |
| ATOM | 7902 | CZ | PHE | F | 112 | −14.283 | 16.683 | 77.402 | 1.00 | 18.65 | F |
| ATOM | 7903 | C | PHE | F | 112 | −17.145 | 22.232 | 75.769 | 1.00 | 18.67 | F |
| ATOM | 7904 | O | PHE | F | 112 | −18.187 | 22.747 | 76.240 | 1.00 | 17.68 | F |
| ATOM | 7905 | N | THR | F | 113 | −16.640 | 22.435 | 74.549 | 1.00 | 18.68 | F |
| ATOM | 7906 | CA | THR | F | 113 | −17.213 | 23.261 | 73.494 | 1.00 | 17.39 | F |
| ATOM | 7907 | CB | THR | F | 113 | −16.179 | 24.106 | 72.880 | 1.00 | 18.17 | F |
| ATOM | 7908 | OG1 | THR | F | 113 | −15.659 | 24.897 | 73.897 | 1.00 | 19.67 | F |
| ATOM | 7909 | CG2 | THR | F | 113 | −16.719 | 25.027 | 71.742 | 1.00 | 17.26 | F |
| ATOM | 7910 | C | THR | F | 113 | −17.760 | 22.323 | 72.384 | 1.00 | 18.96 | F |
| ATOM | 7911 | O | THR | F | 113 | −17.215 | 21.245 | 72.007 | 1.00 | 19.02 | F |
| ATOM | 7912 | N | LYS | F | 114 | −18.901 | 22.737 | 71.871 | 1.00 | 19.40 | F |
| ATOM | 7913 | CA | LYS | F | 114 | −19.525 | 21.974 | 70.861 | 1.00 | 18.20 | F |
| ATOM | 7914 | CB | LYS | F | 114 | −21.081 | 22.327 | 70.797 | 1.00 | 18.71 | F |
| ATOM | 7915 | CG | LYS | F | 114 | −21.859 | 21.541 | 69.715 | 1.00 | 18.59 | F |
| ATOM | 7916 | CD | LYS | F | 114 | −23.333 | 21.629 | 69.683 | 1.00 | 17.51 | F |
| ATOM | 7917 | CE | LYS | F | 114 | −23.852 | 20.980 | 68.308 | 1.00 | 18.89 | F |
| ATOM | 7918 | NZ | LYS | F | 114 | −25.464 | 20.928 | 68.081 | 1.00 | 19.46 | F |
| ATOM | 7919 | C | LYS | F | 114 | −18.735 | 22.257 | 69.569 | 1.00 | 18.49 | F |
| ATOM | 7920 | O | LYS | F | 114 | −18.394 | 23.374 | 69.290 | 1.00 | 18.66 | F |
| ATOM | 7921 | N | ILE | F | 115 | −18.352 | 21.212 | 68.851 | 1.00 | 18.86 | F |
| ATOM | 7922 | CA | ILE | F | 115 | −17.752 | 21.360 | 67.563 | 1.00 | 17.76 | F |
| ATOM | 7923 | CB | ILE | F | 115 | −16.890 | 20.228 | 67.233 | 1.00 | 16.34 | F |
| ATOM | 7924 | CG2 | ILE | F | 115 | −16.578 | 20.337 | 65.776 | 1.00 | 14.37 | F |
| ATOM | 7925 | CG1 | ILE | F | 115 | −15.693 | 20.293 | 68.174 | 1.00 | 16.12 | F |
| ATOM | 7926 | CD1 | ILE | F | 115 | −14.725 | 19.228 | 68.328 | 1.00 | 12.42 | F |
| ATOM | 7927 | C | ILE | F | 115 | −18.878 | 21.421 | 66.509 | 1.00 | 18.07 | F |
| ATOM | 7928 | O | ILE | F | 115 | −18.840 | 22.323 | 65.665 | 1.00 | 18.75 | F |
| ATOM | 7929 | N | ASP | F | 116 | −19.863 | 20.491 | 66.577 | 1.00 | 18.12 | F |
| ATOM | 7930 | CA | ASP | F | 116 | −20.960 | 20.389 | 65.588 | 1.00 | 17.75 | F |
| ATOM | 7931 | CB | ASP | F | 116 | −20.350 | 20.039 | 64.192 | 1.00 | 17.80 | F |
| ATOM | 7932 | CG | ASP | F | 116 | −21.278 | 20.352 | 63.027 | 1.00 | 18.06 | F |
| ATOM | 7933 | OD1 | ASP | F | 116 | −20.931 | 19.980 | 61.858 | 1.00 | 17.33 | F |
| ATOM | 7934 | OD2 | ASP | F | 116 | −22.337 | 20.974 | 63.287 | 1.00 | 18.33 | F |
| ATOM | 7935 | C | ASP | F | 116 | −21.950 | 19.287 | 65.954 | 1.00 | 16.91 | F |
| ATOM | 7936 | O | ASP | F | 116 | −21.635 | 18.394 | 66.765 | 1.00 | 15.63 | F |
| ATOM | 7937 | N | THR | F | 117 | −23.138 | 19.379 | 65.324 | 1.00 | 16.63 | F |
| ATOM | 7938 | CA | THR | F | 117 | −24.163 | 18.349 | 65.392 | 1.00 | 16.66 | F |
| ATOM | 7939 | CB | THR | F | 117 | −25.504 | 18.920 | 64.987 | 1.00 | 17.21 | F |
| ATOM | 7940 | OG1 | THR | F | 117 | −25.887 | 19.832 | 65.964 | 1.00 | 18.24 | F |
| ATOM | 7941 | CG2 | THR | F | 117 | −26.599 | 17.846 | 65.011 | 1.00 | 16.97 | F |
| ATOM | 7942 | C | THR | F | 117 | −23.730 | 17.285 | 64.304 | 1.00 | 17.10 | F |
| ATOM | 7943 | O | THR | F | 117 | −23.411 | 17.643 | 63.155 | 1.00 | 15.77 | F |
| ATOM | 7944 | N | ILE | F | 118 | −23.678 | 16.008 | 64.675 | 1.00 | 17.28 | F |
| ATOM | 7945 | CA | ILE | F | 118 | −23.345 | 14.956 | 63.719 | 1.00 | 18.12 | F |
| ATOM | 7946 | CB | ILE | F | 118 | −22.408 | 13.888 | 64.367 | 1.00 | 17.69 | F |
| ATOM | 7947 | CG2 | ILE | F | 118 | −22.016 | 12.707 | 63.333 | 1.00 | 15.57 | F |
| ATOM | 7948 | CG1 | ILE | F | 118 | −21.205 | 14.633 | 64.971 | 1.00 | 16.42 | F |
| ATOM | 7949 | CD1 | ILE | F | 118 | −20.459 | 15.464 | 64.046 | 1.00 | 13.64 | F |
| ATOM | 7950 | C | ILE | F | 118 | −24.723 | 14.281 | 63.266 | 1.00 | 19.40 | F |

TABLE 1-continued

| | | | | | | | | | | |
|---|---|---|---|---|---|---|---|---|---|---|
| ATOM | 7951 | O | ILE | F | 118 | −25.547 | 13.780 | 64.110 | 1.00 | 19.85 | F |
| ATOM | 7952 | N | ALA | F | 119 | −24.941 | 14.289 | 61.938 | 1.00 | 18.86 | F |
| ATOM | 7953 | CA | ALA | F | 119 | −26.162 | 13.753 | 61.366 | 1.00 | 18.17 | F |
| ATOM | 7954 | CB | ALA | F | 119 | −26.960 | 14.925 | 60.799 | 1.00 | 15.15 | F |
| ATOM | 7955 | C | ALA | F | 119 | −25.861 | 12.701 | 60.281 | 1.00 | 17.74 | F |
| ATOM | 7956 | O | ALA | F | 119 | −25.026 | 12.897 | 59.421 | 1.00 | 18.40 | F |
| ATOM | 7957 | N | PRO | F | 120 | −26.563 | 11.575 | 60.318 | 1.00 | 18.72 | F |
| ATOM | 7958 | CD | PRO | F | 120 | −27.731 | 11.234 | 61.180 | 1.00 | 18.40 | F |
| ATOM | 7959 | CA | PRO | F | 120 | −26.331 | 10.527 | 59.291 | 1.00 | 18.72 | F |
| ATOM | 7960 | CB | PRO | F | 120 | −27.059 | 9.289 | 59.879 | 1.00 | 18.18 | F |
| ATOM | 7961 | CG | PRO | F | 120 | −28.315 | 9.921 | 60.428 | 1.00 | 18.12 | F |
| ATOM | 7962 | C | PRO | F | 120 | −26.954 | 10.903 | 57.886 | 1.00 | 18.31 | F |
| ATOM | 7963 | O | PRO | F | 120 | −28.038 | 11.404 | 57.796 | 1.00 | 18.14 | F |
| ATOM | 7964 | N | ASP | F | 121 | −26.232 | 10.647 | 56.815 | 1.00 | 19.05 | F |
| ATOM | 7965 | CA | ASP | F | 121 | −26.718 | 10.875 | 55.489 | 1.00 | 19.83 | F |
| ATOM | 7966 | CB | ASP | F | 121 | −25.569 | 10.748 | 54.511 | 1.00 | 21.55 | F |
| ATOM | 7967 | CG | ASP | F | 121 | −24.310 | 11.330 | 55.062 | 1.00 | 23.79 | F |
| ATOM | 7968 | OD1 | ASP | F | 121 | −23.626 | 10.731 | 56.063 | 1.00 | 24.38 | F |
| ATOM | 7969 | OD2 | ASP | F | 121 | −24.039 | 12.436 | 54.477 | 1.00 | 23.34 | F |
| ATOM | 7970 | C | ASP | F | 121 | −27.676 | 9.694 | 55.218 | 1.00 | 18.94 | F |
| ATOM | 7971 | O | ASP | F | 121 | −28.516 | 9.777 | 54.362 | 1.00 | 18.08 | F |
| ATOM | 7972 | N | GLU | F | 122 | −27.493 | 8.611 | 55.955 | 1.00 | 18.57 | F |
| ATOM | 7973 | CA | GLU | F | 122 | −28.314 | 7.458 | 55.806 | 1.00 | 18.47 | F |
| ATOM | 7974 | CB | GLU | F | 122 | −27.606 | 6.439 | 54.942 | 1.00 | 19.00 | F |
| ATOM | 7975 | CG | GLU | F | 122 | −27.443 | 6.825 | 53.547 | 1.00 | 21.62 | F |
| ATOM | 7976 | CD | GLU | F | 122 | −27.095 | 5.574 | 52.634 | 1.00 | 24.99 | F |
| ATOM | 7977 | OE1 | GLU | F | 122 | −25.930 | 4.973 | 52.682 | 1.00 | 25.45 | F |
| ATOM | 7978 | OE2 | GLU | F | 122 | −28.019 | 5.162 | 51.856 | 1.00 | 26.81 | F |
| ATOM | 7979 | C | GLU | F | 122 | −28.741 | 6.757 | 57.125 | 1.00 | 18.03 | F |
| ATOM | 7980 | O | GLU | F | 122 | −27.969 | 6.049 | 57.850 | 1.00 | 17.76 | F |
| ATOM | 7981 | N | ILE | F | 123 | −30.017 | 6.902 | 57.386 | 1.00 | 17.32 | F |
| ATOM | 7982 | CA | ILE | F | 123 | −30.549 | 6.329 | 58.570 | 1.00 | 17.23 | F |
| ATOM | 7983 | CB | ILE | F | 123 | −31.805 | 6.981 | 58.739 | 1.00 | 18.05 | F |
| ATOM | 7984 | CG2 | ILE | F | 123 | −32.556 | 6.898 | 57.372 | 1.00 | 17.42 | F |
| ATOM | 7985 | CG1 | ILE | F | 123 | −32.593 | 6.313 | 59.834 | 1.00 | 18.47 | F |
| ATOM | 7986 | CD1 | ILE | F | 123 | −33.986 | 6.950 | 59.829 | 1.00 | 22.94 | F |
| ATOM | 7987 | C | ILE | F | 123 | −30.745 | 4.846 | 58.227 | 1.00 | 16.61 | F |
| ATOM | 7988 | O | ILE | F | 123 | −30.966 | 4.567 | 57.133 | 1.00 | 16.45 | F |
| ATOM | 7989 | N | THR | F | 124 | −30.711 | 3.925 | 59.161 | 1.00 | 15.83 | F |
| ATOM | 7990 | CA | THR | F | 124 | −30.904 | 2.550 | 58.835 | 1.00 | 15.31 | F |
| ATOM | 7991 | CB | THR | F | 124 | −30.018 | 1.644 | 59.750 | 1.00 | 13.78 | F |
| ATOM | 7992 | OG1 | THR | F | 124 | −28.729 | 1.667 | 59.257 | 1.00 | 13.94 | F |
| ATOM | 7993 | CG2 | THR | F | 124 | −30.415 | 0.326 | 59.825 | 1.00 | 11.84 | F |
| ATOM | 7994 | C | THR | F | 124 | −32.311 | 2.301 | 59.162 | 1.00 | 15.76 | F |
| ATOM | 7995 | O | THR | F | 124 | −32.688 | 2.490 | 60.360 | 1.00 | 17.16 | F |
| ATOM | 7996 | N | VAL | F | 125 | −33.104 | 1.885 | 58.193 | 1.00 | 16.17 | F |
| ATOM | 7997 | CA | VAL | F | 125 | −34.527 | 1.559 | 58.526 | 1.00 | 18.24 | F |
| ATOM | 7998 | CB | VAL | F | 125 | −35.571 | 1.788 | 57.325 | 1.00 | 16.53 | F |
| ATOM | 7999 | CG1 | VAL | F | 125 | −35.688 | 3.249 | 57.056 | 1.00 | 16.59 | F |
| ATOM | 8000 | CG2 | VAL | F | 125 | −35.174 | 0.993 | 56.100 | 1.00 | 14.89 | F |
| ATOM | 8001 | C | VAL | F | 125 | −34.770 | 0.153 | 59.032 | 1.00 | 17.00 | F |
| ATOM | 8002 | O | VAL | F | 125 | −33.901 | −0.659 | 59.037 | 1.00 | 17.82 | F |
| ATOM | 8003 | N | SER | F | 126 | −35.957 | −0.076 | 59.532 | 1.00 | 17.88 | F |
| ATOM | 8004 | CA | SER | F | 126 | −36.347 | −1.417 | 59.982 | 1.00 | 18.69 | F |
| ATOM | 8005 | CB | SER | F | 126 | −37.845 | −1.364 | 60.332 | 1.00 | 17.96 | F |
| ATOM | 8006 | OG | SER | F | 126 | −38.386 | −2.662 | 60.338 | 1.00 | 20.87 | F |
| ATOM | 8007 | C | SER | F | 126 | −36.086 | −2.651 | 58.965 | 1.00 | 18.30 | F |
| ATOM | 8008 | O | SER | F | 126 | −35.642 | −3.750 | 59.317 | 1.00 | 18.89 | F |
| ATOM | 8009 | N | SER | F | 127 | −36.372 | −2.506 | 57.690 | 1.00 | 18.33 | F |
| ATOM | 8010 | CA | SER | F | 127 | −36.149 | −3.674 | 56.889 | 1.00 | 18.60 | F |
| ATOM | 8011 | CB | SER | F | 127 | −37.012 | −3.648 | 55.653 | 1.00 | 17.02 | F |
| ATOM | 8012 | OG | SER | F | 127 | −36.576 | −2.576 | 54.874 | 1.00 | 18.52 | F |
| ATOM | 8013 | C | SER | F | 127 | −34.632 | −3.754 | 56.520 | 1.00 | 18.68 | F |
| ATOM | 8014 | O | SER | F | 127 | −34.225 | −4.750 | 55.944 | 1.00 | 20.86 | F |
| ATOM | 8015 | N | ASP | F | 128 | −33.822 | −2.728 | 56.825 | 1.00 | 17.30 | F |
| ATOM | 8016 | CA | ASP | F | 128 | −32.366 | −2.739 | 56.572 | 1.00 | 15.89 | F |
| ATOM | 8017 | CB | ASP | F | 128 | −31.714 | −1.367 | 56.907 | 1.00 | 17.17 | F |
| ATOM | 8018 | CG | ASP | F | 128 | −31.868 | −0.418 | 55.824 | 1.00 | 18.76 | F |
| ATOM | 8019 | OD1 | ASP | F | 128 | −31.739 | 0.845 | 56.035 | 1.00 | 18.67 | F |
| ATOM | 8020 | OD2 | ASP | F | 128 | −32.132 | −0.958 | 54.684 | 1.00 | 21.51 | F |
| ATOM | 8021 | C | ASP | F | 128 | −31.649 | −3.841 | 57.389 | 1.00 | 14.40 | F |
| ATOM | 8022 | O | ASP | F | 128 | −30.626 | −4.441 | 56.946 | 1.00 | 11.88 | F |
| ATOM | 8023 | N | PHE | F | 129 | −32.086 | −4.061 | 58.616 | 1.00 | 14.15 | F |
| ATOM | 8024 | CA | PHE | F | 129 | −31.509 | −5.182 | 59.344 | 1.00 | 17.47 | F |
| ATOM | 8025 | CB | PHE | F | 129 | −31.986 | −5.163 | 60.779 | 1.00 | 17.76 | F |
| ATOM | 8026 | CG | PHE | F | 129 | −31.668 | −3.883 | 61.479 | 1.00 | 19.38 | F |
| ATOM | 8027 | CD1 | PHE | F | 129 | −32.524 | −2.775 | 61.400 | 1.00 | 18.95 | F |
| ATOM | 8028 | CD2 | PHE | F | 129 | −30.419 | −3.721 | 62.065 | 1.00 | 20.28 | F |
| ATOM | 8029 | CE1 | PHE | F | 129 | −32.106 | −1.512 | 61.884 | 1.00 | 19.29 | F |
| ATOM | 8030 | CE2 | PHE | F | 129 | −29.971 | −2.457 | 62.563 | 1.00 | 20.74 | F |

TABLE 1-continued

| | | | | | | | | | | |
|---|---|---|---|---|---|---|---|---|---|---|
| ATOM | 8031 | CZ | PHE | F | 129 | −30.829 | −1.344 | 62.461 | 1.00 | 19.66 | F |
| ATOM | 8032 | C | PHE | F | 129 | −32.162 | −6.313 | 58.568 | 1.00 | 18.25 | F |
| ATOM | 8033 | O | PHE | F | 129 | −32.775 | −6.036 | 57.522 | 1.00 | 20.74 | F |
| ATOM | 8034 | N | GLU | F | 130 | −32.103 | −7.564 | 58.932 | 1.00 | 16.99 | F |
| ATOM | 8035 | CA | GLU | F | 130 | −32.908 | −8.537 | 58.044 | 1.00 | 17.50 | F |
| ATOM | 8036 | CB | GLU | F | 130 | −34.406 | −8.124 | 57.890 | 1.00 | 17.40 | F |
| ATOM | 8037 | CG | GLU | F | 130 | −35.397 | −8.859 | 58.772 | 1.00 | 19.70 | F |
| ATOM | 8038 | CD | GLU | F | 130 | −36.826 | −8.685 | 58.265 | 1.00 | 22.19 | F |
| ATOM | 8039 | OE1 | GLU | F | 130 | −37.534 | −9.657 | 58.624 | 1.00 | 25.58 | F |
| ATOM | 8040 | OE2 | GLU | F | 130 | −37.266 | −7.684 | 57.557 | 1.00 | 20.54 | F |
| ATOM | 8041 | C | GLU | F | 130 | −32.259 | −8.588 | 56.652 | 1.00 | 16.31 | F |
| ATOM | 8042 | O | GLU | F | 130 | −31.748 | −9.636 | 56.326 | 1.00 | 15.71 | F |
| ATOM | 8043 | N | ALA | F | 131 | −32.306 | −7.486 | 55.889 | 1.00 | 15.36 | F |
| ATOM | 8044 | CA | ALA | F | 131 | −31.573 | −7.379 | 54.691 | 1.00 | 16.88 | F |
| ATOM | 8045 | CB | ALA | F | 131 | −31.913 | −6.190 | 54.072 | 1.00 | 14.70 | F |
| ATOM | 8046 | C | ALA | F | 131 | −30.284 | −7.212 | 55.358 | 1.00 | 18.22 | F |
| ATOM | 8047 | O | ALA | F | 131 | −30.190 | −6.991 | 56.646 | 1.00 | 21.12 | F |
| ATOM | 8048 | N | ARG | F | 132 | −29.174 | −7.239 | 54.671 | 1.00 | 18.79 | F |
| ATOM | 8049 | CA | ARG | F | 132 | −27.994 | −7.009 | 55.623 | 1.00 | 17.03 | F |
| ATOM | 8050 | CB | ARG | F | 132 | −27.048 | −8.171 | 55.550 | 1.00 | 17.70 | F |
| ATOM | 8051 | CG | ARG | F | 132 | −27.024 | −9.058 | 56.786 | 1.00 | 17.34 | F |
| ATOM | 8052 | CD | ARG | F | 132 | −28.304 | −9.520 | 57.379 | 1.00 | 15.30 | F |
| ATOM | 8053 | NE | ARG | F | 132 | −28.045 | −10.505 | 58.502 | 1.00 | 12.58 | F |
| ATOM | 8054 | CZ | ARG | F | 132 | −28.788 | −10.681 | 59.633 | 1.00 | 10.96 | F |
| ATOM | 8055 | NH1 | ARG | F | 132 | −29.846 | −9.947 | 59.913 | 1.00 | 7.09 | F |
| ATOM | 8056 | NH2 | ARG | F | 132 | −28.575 | −11.693 | 60.434 | 1.00 | 8.17 | F |
| ATOM | 8057 | C | ARG | F | 132 | −27.376 | −5.776 | 55.142 | 1.00 | 16.53 | F |
| ATOM | 8058 | O | ARG | F | 132 | −26.195 | −5.747 | 54.785 | 1.00 | 15.75 | F |
| ATOM | 8059 | N | HIS | F | 133 | −28.244 | −4.769 | 55.101 | 1.00 | 17.21 | F |
| ATOM | 8060 | CA | HIS | F | 133 | −27.900 | −3.499 | 54.592 | 1.00 | 18.39 | F |
| ATOM | 8061 | CB | HIS | F | 133 | −28.892 | −3.060 | 53.536 | 1.00 | 20.15 | F |
| ATOM | 8062 | CG | HIS | F | 133 | −28.907 | −3.889 | 52.279 | 1.00 | 22.69 | F |
| ATOM | 8063 | CD2 | HIS | F | 133 | −28.359 | −5.107 | 51.978 | 1.00 | 23.95 | F |
| ATOM | 8064 | ND1 | HIS | F | 133 | −29.548 | −3.453 | 51.123 | 1.00 | 23.97 | F |
| ATOM | 8065 | CE1 | HIS | F | 133 | −29.373 | −4.371 | 50.166 | 1.00 | 25.13 | F |
| ATOM | 8066 | NE2 | HIS | F | 133 | −28.658 | −5.385 | 50.651 | 1.00 | 23.81 | F |
| ATOM | 8067 | C | HIS | F | 133 | −27.833 | −2.467 | 55.657 | 1.00 | 17.80 | F |
| ATOM | 8068 | O | HIS | F | 133 | −28.509 | −1.440 | 55.538 | 1.00 | 18.07 | F |
| ATOM | 8069 | N | VAL | F | 134 | −27.039 | −2.727 | 56.710 | 1.00 | 18.00 | F |
| ATOM | 8070 | CA | VAL | F | 134 | −26.926 | −1.665 | 57.705 | 1.00 | 19.48 | F |
| ATOM | 8071 | CB | VAL | F | 134 | −26.349 | −2.190 | 58.931 | 1.00 | 19.24 | F |
| ATOM | 8072 | CG1 | VAL | F | 134 | −26.444 | −1.084 | 60.071 | 1.00 | 19.78 | F |
| ATOM | 8073 | CG2 | VAL | F | 134 | −27.212 | −3.354 | 59.312 | 1.00 | 20.08 | F |
| ATOM | 8074 | C | VAL | F | 134 | −26.127 | −0.396 | 57.131 | 1.00 | 17.18 | F |
| ATOM | 8075 | O | VAL | F | 134 | −25.172 | −0.568 | 56.426 | 1.00 | 16.53 | F |
| ATOM | 8076 | N | LYS | F | 135 | −26.576 | 0.834 | 57.392 | 1.00 | 17.06 | F |
| ATOM | 8077 | CA | LYS | F | 135 | −25.953 | 2.052 | 56.829 | 1.00 | 17.62 | F |
| ATOM | 8078 | CB | LYS | F | 135 | −26.979 | 3.128 | 56.429 | 1.00 | 17.34 | F |
| ATOM | 8079 | CG | LYS | F | 135 | −28.168 | 2.567 | 55.672 | 1.00 | 18.08 | F |
| ATOM | 8080 | CD | LYS | F | 135 | −27.748 | 1.670 | 54.425 | 1.00 | 19.74 | F |
| ATOM | 8081 | CE | LYS | F | 135 | −28.973 | 1.624 | 53.441 | 1.00 | 21.68 | F |
| ATOM | 8082 | NZ | LYS | F | 135 | −28.836 | 0.505 | 52.466 | 1.00 | 23.72 | F |
| ATOM | 8083 | C | LYS | F | 135 | −24.923 | 2.720 | 57.682 | 1.00 | 18.24 | F |
| ATOM | 8084 | O | LYS | F | 135 | −25.232 | 3.291 | 58.730 | 1.00 | 18.78 | F |
| ATOM | 8085 | N | LEU | F | 136 | −23.695 | 2.678 | 57.150 | 1.00 | 17.95 | F |
| ATOM | 8086 | CA | LEU | F | 136 | −22.513 | 3.177 | 57.768 | 1.00 | 17.68 | F |
| ATOM | 8087 | CB | LEU | F | 136 | −21.430 | 2.188 | 57.488 | 1.00 | 17.40 | F |
| ATOM | 8088 | CG | LEU | F | 136 | −20.237 | 2.409 | 58.387 | 1.00 | 17.70 | F |
| ATOM | 8089 | CD1 | LEU | F | 136 | −19.676 | 3.566 | 57.792 | 1.00 | 20.44 | F |
| ATOM | 8090 | CD2 | LEU | F | 136 | −20.504 | 2.638 | 59.858 | 1.00 | 15.34 | F |
| ATOM | 8091 | C | LEU | F | 136 | −22.184 | 4.520 | 57.256 | 1.00 | 18.24 | F |
| ATOM | 8092 | O | LEU | F | 136 | −21.797 | 4.649 | 56.159 | 1.00 | 18.63 | F |
| ATOM | 8093 | N | ASN | F | 137 | −22.313 | 5.549 | 58.060 | 1.00 | 18.35 | F |
| ATOM | 8094 | CA | ASN | F | 137 | −22.051 | 6.920 | 57.634 | 1.00 | 17.21 | F |
| ATOM | 8095 | CB | ASN | F | 137 | −23.000 | 7.765 | 58.370 | 1.00 | 16.60 | F |
| ATOM | 8096 | CG | ASN | F | 137 | −24.453 | 7.473 | 57.968 | 1.00 | 15.91 | F |
| ATOM | 8097 | OD1 | ASN | F | 137 | −24.920 | 7.873 | 56.845 | 1.00 | 14.32 | F |
| ATOM | 8098 | ND2 | ASN | F | 137 | −25.183 | 6.836 | 58.860 | 1.00 | 11.24 | F |
| ATOM | 8099 | C | ASN | F | 137 | −20.635 | 7.318 | 58.007 | 1.00 | 17.68 | F |
| ATOM | 8100 | O | ASN | F | 137 | −20.032 | 6.778 | 58.968 | 1.00 | 18.29 | F |
| ATOM | 8101 | N | VAL | F | 138 | −20.061 | 8.207 | 57.227 | 1.00 | 16.72 | F |
| ATOM | 8102 | CA | VAL | F | 138 | −18.747 | 8.679 | 57.553 | 1.00 | 15.09 | F |
| ATOM | 8103 | CB | VAL | F | 138 | −17.699 | 8.345 | 56.499 | 1.00 | 14.14 | F |
| ATOM | 8104 | CG1 | VAL | F | 138 | −16.376 | 8.898 | 56.926 | 1.00 | 13.76 | F |
| ATOM | 8105 | CG2 | VAL | F | 138 | −17.579 | 6.922 | 56.326 | 1.00 | 11.12 | F |
| ATOM | 8106 | C | VAL | F | 138 | −18.857 | 10.189 | 57.694 | 1.00 | 16.81 | F |
| ATOM | 8107 | O | VAL | F | 138 | −19.299 | 10.876 | 56.772 | 1.00 | 16.76 | F |
| ATOM | 8108 | N | GLU | F | 139 | −18.516 | 10.719 | 58.871 | 1.00 | 17.99 | F |
| ATOM | 8109 | CA | GLU | F | 139 | −18.568 | 12.157 | 59.069 | 1.00 | 18.23 | F |
| ATOM | 8110 | CB | GLU | F | 139 | −19.673 | 12.544 | 60.016 | 1.00 | 18.48 | F |

TABLE 1-continued

| | | | | | | | | | | |
|---|---|---|---|---|---|---|---|---|---|---|
| ATOM | 8111 | CG | GLU | F | 139 | −21.110 | 12.523 | 59.463 | 1.00 | 18.05 | F |
| ATOM | 8112 | CD | GLU | F | 139 | −21.325 | 13.415 | 58.210 | 1.00 | 18.41 | F |
| ATOM | 8113 | OE1 | GLU | F | 139 | −20.618 | 14.460 | 57.952 | 1.00 | 17.12 | F |
| ATOM | 8114 | OE2 | GLU | F | 139 | −22.232 | 13.044 | 57.424 | 1.00 | 19.58 | F |
| ATOM | 8115 | C | GLU | F | 139 | −17.239 | 12.638 | 59.604 | 1.00 | 20.08 | F |
| ATOM | 8116 | O | GLU | F | 139 | −16.667 | 12.050 | 60.600 | 1.00 | 20.67 | F |
| ATOM | 8117 | N | GLU | F | 140 | −16.701 | 13.650 | 58.903 | 1.00 | 20.71 | F |
| ATOM | 8118 | CA | GLU | F | 140 | −15.460 | 14.276 | 59.367 | 1.00 | 20.09 | F |
| ATOM | 8119 | CB | GLU | F | 140 | −14.349 | 14.245 | 58.315 | 1.00 | 21.57 | F |
| ATOM | 8120 | CG | GLU | F | 140 | −12.974 | 14.692 | 59.013 | 1.00 | 22.16 | F |
| ATOM | 8121 | CD | GLU | F | 140 | −11.716 | 14.122 | 58.324 | 1.00 | 23.68 | F |
| ATOM | 8122 | OE1 | GLU | F | 140 | −11.362 | 14.754 | 57.260 | 1.00 | 23.94 | F |
| ATOM | 8123 | OE2 | GLU | F | 140 | −11.137 | 13.071 | 58.879 | 1.00 | 22.35 | F |
| ATOM | 8124 | C | GLU | F | 140 | −15.667 | 15.723 | 59.752 | 1.00 | 19.99 | F |
| ATOM | 8125 | O | GLU | F | 140 | −16.518 | 16.451 | 59.165 | 1.00 | 19.97 | F |
| ATOM | 8126 | N | ARG | F | 141 | −14.908 | 16.157 | 60.743 | 1.00 | 19.34 | F |
| ATOM | 8127 | CA | ARG | F | 141 | −14.987 | 17.583 | 61.156 | 1.00 | 18.20 | F |
| ATOM | 8128 | CB | ARG | F | 141 | −15.926 | 17.850 | 62.349 | 1.00 | 18.40 | F |
| ATOM | 8129 | CG | ARG | F | 141 | −17.402 | 17.364 | 62.251 | 1.00 | 18.91 | F |
| ATOM | 8130 | CD | ARG | F | 141 | −18.300 | 18.445 | 61.718 | 1.00 | 19.72 | F |
| ATOM | 8131 | NE | ARG | F | 141 | −18.970 | 17.871 | 60.587 | 1.00 | 23.18 | F |
| ATOM | 8132 | CZ | ARG | F | 141 | −20.087 | 17.171 | 60.676 | 1.00 | 23.79 | F |
| ATOM | 8133 | NH1 | ARG | F | 141 | −20.683 | 17.009 | 61.822 | 1.00 | 26.82 | F |
| ATOM | 8134 | NH2 | ARG | F | 141 | −20.499 | 16.483 | 59.678 | 1.00 | 23.26 | F |
| ATOM | 8135 | C | ARG | F | 141 | −13.571 | 17.917 | 61.589 | 1.00 | 17.25 | F |
| ATOM | 8136 | O | ARG | F | 141 | −12.666 | 17.031 | 61.747 | 1.00 | 15.49 | F |
| ATOM | 8137 | N | SER | F | 142 | −13.395 | 19.206 | 61.817 | 1.00 | 16.54 | F |
| ATOM | 8138 | CA | SER | F | 142 | −12.091 | 19.642 | 62.232 | 1.00 | 16.57 | F |
| ATOM | 8139 | CB | SER | F | 142 | −11.254 | 19.984 | 60.980 | 1.00 | 16.75 | F |
| ATOM | 8140 | OG | SER | F | 142 | −11.510 | 21.285 | 60.589 | 1.00 | 14.53 | F |
| ATOM | 8141 | C | SER | F | 142 | −12.186 | 20.811 | 63.193 | 1.00 | 17.21 | F |
| ATOM | 8142 | O | SER | F | 142 | −13.183 | 21.618 | 63.197 | 1.00 | 14.95 | F |
| ATOM | 8143 | N | VAL | F | 143 | −11.190 | 20.855 | 64.052 | 1.00 | 17.92 | F |
| ATOM | 8144 | CA | VAL | F | 143 | −11.172 | 21.975 | 64.972 | 1.00 | 19.41 | F |
| ATOM | 8145 | CB | VAL | F | 143 | −11.956 | 21.606 | 66.293 | 1.00 | 19.62 | F |
| ATOM | 8146 | CG1 | VAL | F | 143 | −11.292 | 20.496 | 67.055 | 1.00 | 19.44 | F |
| ATOM | 8147 | CG2 | VAL | F | 143 | −12.100 | 22.812 | 67.168 | 1.00 | 18.93 | F |
| ATOM | 8148 | C | VAL | F | 143 | −9.729 | 22.542 | 65.208 | 1.00 | 21.44 | F |
| ATOM | 8149 | O | VAL | F | 143 | −8.662 | 21.854 | 64.906 | 1.00 | 21.69 | F |
| ATOM | 8150 | N | GLY | F | 144 | −9.660 | 23.832 | 65.635 | 1.00 | 21.35 | F |
| ATOM | 8151 | CA | GLY | F | 144 | −8.338 | 24.501 | 65.918 | 1.00 | 22.07 | F |
| ATOM | 8152 | C | GLY | F | 144 | −8.396 | 26.053 | 65.860 | 1.00 | 22.20 | F |
| ATOM | 8153 | O | GLY | F | 144 | −9.492 | 26.630 | 65.459 | 1.00 | 21.80 | F |
| ATOM | 8154 | N | PRO | F | 145 | −7.280 | 26.749 | 66.151 | 1.00 | 18.78 | F |
| ATOM | 8155 | CD | PRO | F | 145 | −6.911 | 28.027 | 65.549 | 1.00 | 19.69 | F |
| ATOM | 8156 | CA | PRO | F | 145 | −6.090 | 25.983 | 66.493 | 1.00 | 21.93 | F |
| ATOM | 8157 | CB | PRO | F | 145 | −4.925 | 26.935 | 66.203 | 1.00 | 19.62 | F |
| ATOM | 8158 | CG | PRO | F | 145 | −5.544 | 28.272 | 66.088 | 1.00 | 18.86 | F |
| ATOM | 8159 | C | PRO | F | 145 | −6.023 | 25.435 | 67.892 | 1.00 | 22.11 | F |
| ATOM | 8160 | O | PRO | F | 145 | −6.545 | 26.024 | 68.841 | 1.00 | 22.14 | F |
| ATOM | 8161 | N | LEU | F | 146 | −5.479 | 24.248 | 68.048 | 1.00 | 20.74 | F |
| ATOM | 8162 | CA | LEU | F | 146 | −5.351 | 23.819 | 69.417 | 1.00 | 20.84 | F |
| ATOM | 8163 | CB | LEU | F | 146 | −5.201 | 22.312 | 69.452 | 1.00 | 20.19 | F |
| ATOM | 8164 | CG | LEU | F | 146 | −6.503 | 21.543 | 69.593 | 1.00 | 20.22 | F |
| ATOM | 8165 | CD1 | LEU | F | 146 | −7.681 | 22.228 | 68.912 | 1.00 | 20.95 | F |
| ATOM | 8166 | CD2 | LEU | F | 146 | −6.281 | 20.138 | 69.026 | 1.00 | 19.02 | F |
| ATOM | 8167 | C | LEU | F | 146 | −4.064 | 24.499 | 69.894 | 1.00 | 21.36 | F |
| ATOM | 8168 | O | LEU | F | 146 | −3.162 | 24.898 | 69.089 | 1.00 | 20.63 | F |
| ATOM | 8169 | N | THR | F | 147 | −3.928 | 24.612 | 71.220 | 1.00 | 21.08 | F |
| ATOM | 8170 | CA | THR | F | 147 | −2.663 | 25.273 | 71.722 | 1.00 | 20.61 | F |
| ATOM | 8171 | CB | THR | F | 147 | −2.820 | 26.720 | 72.016 | 1.00 | 19.97 | F |
| ATOM | 8172 | OG1 | THR | F | 147 | −3.910 | 26.847 | 72.933 | 1.00 | 17.13 | F |
| ATOM | 8173 | CG2 | THR | F | 147 | −3.075 | 27.537 | 70.770 | 1.00 | 17.92 | F |
| ATOM | 8174 | C | THR | F | 147 | −2.098 | 24.659 | 72.990 | 1.00 | 22.40 | F |
| ATOM | 8175 | O | THR | F | 147 | −0.864 | 24.792 | 73.200 | 1.00 | 24.60 | F |
| ATOM | 8176 | N | ARG | F | 148 | −2.944 | 24.007 | 73.818 | 1.00 | 21.03 | F |
| ATOM | 8177 | CA | ARG | F | 148 | −2.501 | 23.386 | 75.070 | 1.00 | 18.24 | F |
| ATOM | 8178 | CB | ARG | F | 148 | −3.673 | 23.075 | 75.991 | 1.00 | 18.70 | F |
| ATOM | 8179 | CG | ARG | F | 148 | −4.852 | 24.122 | 75.969 | 1.00 | 20.02 | F |
| ATOM | 8180 | CD | ARG | F | 148 | −4.482 | 25.364 | 76.689 | 1.00 | 21.40 | F |
| ATOM | 8181 | NE | ARG | F | 148 | −3.536 | 26.237 | 75.916 | 1.00 | 23.21 | F |
| ATOM | 8182 | CZ | ARG | F | 148 | −2.404 | 26.750 | 76.460 | 1.00 | 24.44 | F |
| ATOM | 8183 | NH1 | ARG | F | 148 | −2.089 | 26.472 | 77.739 | 1.00 | 22.25 | F |
| ATOM | 8184 | NH2 | ARG | F | 148 | −1.595 | 27.554 | 75.750 | 1.00 | 24.04 | F |
| ATOM | 8185 | C | ARG | F | 148 | −1.731 | 22.130 | 74.866 | 1.00 | 17.86 | F |
| ATOM | 8186 | O | ARG | F | 148 | −1.543 | 21.639 | 73.750 | 1.00 | 16.53 | F |
| ATOM | 8187 | N | LYS | F | 149 | −1.279 | 21.599 | 75.978 | 1.00 | 18.10 | F |
| ATOM | 8188 | CA | LYS | F | 149 | −0.456 | 20.425 | 75.972 | 1.00 | 19.89 | F |
| ATOM | 8189 | CB | LYS | F | 149 | 0.012 | 20.132 | 77.408 | 1.00 | 19.06 | F |
| ATOM | 8190 | CG | LYS | F | 149 | 1.166 | 19.160 | 77.579 | 1.00 | 19.13 | F |

TABLE 1-continued

| ATOM | 8191 | CD  | LYS | F | 149 | 1.461   | 18.847 | 79.082 | 1.00 | 19.48 | F |
|------|------|-----|-----|---|-----|---------|--------|--------|------|-------|---|
| ATOM | 8192 | CE  | LYS | F | 149 | 2.553   | 17.751 | 79.201 | 1.00 | 20.51 | F |
| ATOM | 8193 | NZ  | LYS | F | 149 | 2.377   | 16.710 | 80.365 | 1.00 | 20.23 | F |
| ATOM | 8194 | C   | LYS | F | 149 | −1.336  | 19.231 | 75.448 | 1.00 | 21.71 | F |
| ATOM | 8195 | O   | LYS | F | 149 | −0.824  | 18.299 | 74.812 | 1.00 | 22.77 | F |
| ATOM | 8196 | N   | GLY | F | 150 | −2.632  | 19.264 | 75.772 | 1.00 | 22.76 | F |
| ATOM | 8197 | CA  | GLY | F | 150 | −3.517  | 18.170 | 75.376 | 1.00 | 22.30 | F |
| ATOM | 8198 | C   | GLY | F | 150 | −4.950  | 18.571 | 75.054 | 1.00 | 21.92 | F |
| ATOM | 8199 | O   | GLY | F | 150 | −5.260  | 19.802 | 74.997 | 1.00 | 21.48 | F |
| ATOM | 8200 | N   | PHE | F | 151 | −5.781  | 17.524 | 74.835 | 1.00 | 21.12 | F |
| ATOM | 8201 | CA  | PHE | F | 151 | −7.205  | 17.644 | 74.529 | 1.00 | 19.12 | F |
| ATOM | 8202 | CB  | PHE | F | 151 | −7.355  | 18.223 | 73.160 | 1.00 | 19.47 | F |
| ATOM | 8203 | CG  | PHE | F | 151 | −7.021  | 17.286 | 72.041 | 1.00 | 19.87 | F |
| ATOM | 8204 | CD1 | PHE | F | 151 | −8.039  | 16.522 | 71.423 | 1.00 | 20.03 | F |
| ATOM | 8205 | CD2 | PHE | F | 151 | −5.744  | 17.168 | 71.541 | 1.00 | 20.02 | F |
| ATOM | 8206 | CE1 | PHE | F | 151 | −7.747  | 15.719 | 70.371 | 1.00 | 18.56 | F |
| ATOM | 8207 | CE2 | PHE | F | 151 | −5.486  | 16.336 | 70.496 | 1.00 | 19.11 | F |
| ATOM | 8208 | CZ  | PHE | F | 151 | −6.498  | 15.615 | 69.914 | 1.00 | 18.60 | F |
| ATOM | 8209 | C   | PHE | F | 151 | −8.008  | 16.348 | 74.655 | 1.00 | 19.90 | F |
| ATOM | 8210 | O   | PHE | F | 151 | −7.466  | 15.181 | 74.612 | 1.00 | 19.44 | F |
| ATOM | 8211 | N   | TYR | F | 152 | −9.309  | 16.568 | 74.837 | 1.00 | 19.06 | F |
| ATOM | 8212 | CA  | TYR | F | 152 | −10.315 | 15.504 | 74.924 | 1.00 | 18.17 | F |
| ATOM | 8213 | CB  | TYR | F | 152 | −11.076 | 15.551 | 76.229 | 1.00 | 19.27 | F |
| ATOM | 8214 | CG  | TYR | F | 152 | −10.257 | 15.264 | 77.441 | 1.00 | 20.80 | F |
| ATOM | 8215 | CD1 | TYR | F | 152 | −9.596  | 16.301 | 78.144 | 1.00 | 20.93 | F |
| ATOM | 8216 | CE1 | TYR | F | 152 | −8.771  | 16.022 | 79.288 | 1.00 | 22.33 | F |
| ATOM | 8217 | CD2 | TYR | F | 152 | −10.093 | 13.947 | 77.878 | 1.00 | 20.90 | F |
| ATOM | 8218 | CE2 | TYR | F | 152 | −9.297  | 13.642 | 79.007 | 1.00 | 22.21 | F |
| ATOM | 8219 | CZ  | TYR | F | 152 | −8.613  | 14.702 | 79.754 | 1.00 | 22.99 | F |
| ATOM | 8220 | OH  | TYR | F | 152 | −7.942  | 14.406 | 81.009 | 1.00 | 22.87 | F |
| ATOM | 8221 | C   | TYR | F | 152 | −11.398 | 15.659 | 73.848 | 1.00 | 17.95 | F |
| ATOM | 8222 | O   | TYR | F | 152 | −11.637 | 16.722 | 73.309 | 1.00 | 18.56 | F |
| ATOM | 8223 | N   | LEU | F | 153 | −12.070 | 14.581 | 73.558 | 1.00 | 15.59 | F |
| ATOM | 8224 | CA  | LEU | F | 153 | −13.093 | 14.652 | 72.610 | 1.00 | 14.44 | F |
| ATOM | 8225 | CB  | LEU | F | 153 | −12.744 | 13.830 | 71.389 | 1.00 | 15.02 | F |
| ATOM | 8226 | CG  | LEU | F | 153 | −12.628 | 14.545 | 70.054 | 1.00 | 15.97 | F |
| ATOM | 8227 | CD1 | LEU | F | 153 | −11.663 | 15.637 | 70.051 | 1.00 | 16.81 | F |
| ATOM | 8228 | CD2 | LEU | F | 153 | −12.199 | 13.547 | 69.065 | 1.00 | 17.36 | F |
| ATOM | 8229 | C   | LEU | F | 153 | −14.261 | 14.049 | 73.322 | 1.00 | 13.60 | F |
| ATOM | 8230 | O   | LEU | F | 153 | −14.146 | 13.111 | 74.190 | 1.00 | 12.89 | F |
| ATOM | 8231 | N   | ALA | F | 154 | −15.418 | 14.584 | 73.027 | 1.00 | 12.95 | F |
| ATOM | 8232 | CA  | ALA | F | 154 | −16.501 | 13.934 | 73.676 | 1.00 | 14.62 | F |
| ATOM | 8233 | CB  | ALA | F | 154 | −16.793 | 14.655 | 75.055 | 1.00 | 16.24 | F |
| ATOM | 8234 | C   | ALA | F | 154 | −17.771 | 13.854 | 72.806 | 1.00 | 14.87 | F |
| ATOM | 8235 | O   | ALA | F | 154 | −17.991 | 14.619 | 71.878 | 1.00 | 13.87 | F |
| ATOM | 8236 | N   | PHE | F | 155 | −18.621 | 12.962 | 73.215 | 1.00 | 14.88 | F |
| ATOM | 8237 | CA  | PHE | F | 155 | −19.817 | 12.749 | 72.510 | 1.00 | 16.44 | F |
| ATOM | 8238 | CB  | PHE | F | 155 | −19.767 | 11.428 | 71.708 | 1.00 | 17.75 | F |
| ATOM | 8239 | CG  | PHE | F | 155 | −18.568 | 11.253 | 70.916 | 1.00 | 18.05 | F |
| ATOM | 8240 | CD1 | PHE | F | 155 | −17.393 | 10.730 | 71.529 | 1.00 | 19.66 | F |
| ATOM | 8241 | CD2 | PHE | F | 155 | −18.570 | 11.558 | 69.589 | 1.00 | 16.49 | F |
| ATOM | 8242 | CE1 | PHE | F | 155 | −16.265 | 10.525 | 70.762 | 1.00 | 19.11 | F |
| ATOM | 8243 | CE2 | PHE | F | 155 | −17.442 | 11.359 | 68.799 | 1.00 | 16.58 | F |
| ATOM | 8244 | CZ  | PHE | F | 155 | −16.298 | 10.843 | 69.374 | 1.00 | 18.23 | F |
| ATOM | 8245 | C   | PHE | F | 155 | −21.083 | 12.712 | 73.343 | 1.00 | 16.10 | F |
| ATOM | 8246 | O   | PHE | F | 155 | −21.303 | 11.820 | 74.276 | 1.00 | 14.87 | F |
| ATOM | 8247 | N   | GLN | F | 156 | −21.923 | 13.642 | 72.946 | 1.00 | 14.96 | F |
| ATOM | 8248 | CA  | GLN | F | 156 | −23.134 | 13.739 | 73.600 | 1.00 | 15.70 | F |
| ATOM | 8249 | CB  | GLN | F | 156 | −23.387 | 15.201 | 73.835 | 1.00 | 16.50 | F |
| ATOM | 8250 | CG  | GLN | F | 156 | −24.481 | 15.375 | 74.803 | 1.00 | 18.27 | F |
| ATOM | 8251 | CD  | GLN | F | 156 | −25.189 | 16.716 | 74.660 | 1.00 | 18.95 | F |
| ATOM | 8252 | OE1 | GLN | F | 156 | −25.047 | 17.385 | 73.619 | 1.00 | 20.75 | F |
| ATOM | 8253 | NE2 | GLN | F | 156 | −25.983 | 17.104 | 75.692 | 1.00 | 16.11 | F |
| ATOM | 8254 | C   | GLN | F | 156 | −24.367 | 13.088 | 72.949 | 1.00 | 15.52 | F |
| ATOM | 8255 | O   | GLN | F | 156 | −24.845 | 13.495 | 71.850 | 1.00 | 14.56 | F |
| ATOM | 8256 | N   | ASP | F | 157 | −24.878 | 12.078 | 73.622 | 1.00 | 14.30 | F |
| ATOM | 8257 | CA  | ASP | F | 157 | −26.040 | 11.510 | 73.141 | 1.00 | 15.01 | F |
| ATOM | 8258 | CB  | ASP | F | 157 | −26.150 | 10.021 | 73.443 | 1.00 | 13.64 | F |
| ATOM | 8259 | CG  | ASP | F | 157 | −27.547 | 9.478  | 73.132 | 1.00 | 12.51 | F |
| ATOM | 8260 | OD1 | ASP | F | 157 | −28.107 | 8.876  | 74.055 | 1.00 | 11.68 | F |
| ATOM | 8261 | OD2 | ASP | F | 157 | −28.029 | 9.666  | 71.976 | 1.00 | 9.63  | F |
| ATOM | 8262 | C   | ASP | F | 157 | −27.275 | 12.232 | 73.690 | 1.00 | 16.75 | F |
| ATOM | 8263 | O   | ASP | F | 157 | −27.478 | 12.330 | 74.879 | 1.00 | 16.06 | F |
| ATOM | 8264 | N   | ILE | F | 158 | −28.133 | 12.652 | 72.777 | 1.00 | 17.72 | F |
| ATOM | 8265 | CA  | ILE | F | 158 | −29.354 | 13.299 | 73.125 | 1.00 | 18.64 | F |
| ATOM | 8266 | CB  | ILE | F | 158 | −29.418 | 14.513 | 72.181 | 1.00 | 19.36 | F |
| ATOM | 8267 | CG2 | ILE | F | 158 | −30.429 | 14.442 | 71.049 | 1.00 | 17.18 | F |
| ATOM | 8268 | CG1 | ILE | F | 158 | −29.476 | 15.695 | 73.088 | 1.00 | 19.60 | F |
| ATOM | 8269 | CD1 | ILE | F | 158 | −28.180 | 15.987 | 73.581 | 1.00 | 19.72 | F |
| ATOM | 8270 | C   | ILE | F | 158 | −30.656 | 12.429 | 73.111 | 1.00 | 19.62 | F |

TABLE 1-continued

| ATOM | 8271 | O | ILE | F | 158 | −31.758 | 12.962 | 73.165 | 1.00 | 18.47 | F |
|---|---|---|---|---|---|---|---|---|---|---|---|
| ATOM | 8272 | N | GLY | F | 159 | −30.510 | 11.098 | 73.122 | 1.00 | 19.68 | F |
| ATOM | 8273 | CA | GLY | F | 159 | −31.663 | 10.216 | 72.969 | 1.00 | 20.40 | F |
| ATOM | 8274 | C | GLY | F | 159 | −31.843 | 9.591 | 71.511 | 1.00 | 20.77 | F |
| ATOM | 8275 | O | GLY | F | 159 | −32.978 | 9.389 | 71.016 | 1.00 | 21.19 | F |
| ATOM | 8276 | N | ALA | F | 160 | −30.728 | 9.325 | 70.823 | 1.00 | 19.60 | F |
| ATOM | 8277 | CA | ALA | F | 160 | −30.736 | 8.745 | 69.519 | 1.00 | 20.03 | F |
| ATOM | 8278 | CB | ALA | F | 160 | −29.757 | 9.456 | 68.566 | 1.00 | 17.83 | F |
| ATOM | 8279 | C | ALA | F | 160 | −30.287 | 7.334 | 69.791 | 1.00 | 19.57 | F |
| ATOM | 8280 | O | ALA | F | 160 | −29.918 | 7.037 | 70.949 | 1.00 | 21.17 | F |
| ATOM | 8281 | N | CYS | F | 161 | −30.422 | 6.485 | 68.778 | 1.00 | 18.38 | F |
| ATOM | 8282 | CA | CYS | F | 161 | −30.024 | 5.089 | 68.776 | 1.00 | 18.34 | F |
| ATOM | 8283 | C | CYS | F | 161 | −28.866 | 5.074 | 67.754 | 1.00 | 17.68 | F |
| ATOM | 8284 | O | CYS | F | 161 | −29.107 | 4.840 | 66.541 | 1.00 | 17.74 | F |
| ATOM | 8285 | CB | CYS | F | 161 | −31.078 | 4.208 | 68.156 | 1.00 | 17.28 | F |
| ATOM | 8286 | SG | CYS | F | 161 | −30.660 | 2.538 | 68.455 | 1.00 | 18.13 | F |
| ATOM | 8287 | N | VAL | F | 162 | −27.640 | 5.289 | 68.269 | 1.00 | 16.61 | F |
| ATOM | 8288 | CA | VAL | F | 162 | −26.391 | 5.329 | 67.516 | 1.00 | 15.78 | F |
| ATOM | 8289 | CB | VAL | F | 162 | −25.557 | 6.603 | 67.853 | 1.00 | 16.61 | F |
| ATOM | 8290 | CG1 | VAL | F | 162 | −24.654 | 6.992 | 66.710 | 1.00 | 15.97 | F |
| ATOM | 8291 | CG2 | VAL | F | 162 | −26.394 | 7.684 | 68.276 | 1.00 | 15.20 | F |
| ATOM | 8292 | C | VAL | F | 162 | −25.464 | 4.204 | 67.834 | 1.00 | 15.06 | F |
| ATOM | 8293 | O | VAL | F | 162 | −25.512 | 3.574 | 68.917 | 1.00 | 13.20 | F |
| ATOM | 8294 | N | ALA | F | 163 | −24.647 | 3.943 | 66.843 | 1.00 | 15.41 | F |
| ATOM | 8295 | CA | ALA | F | 163 | −23.578 | 2.996 | 67.050 | 1.00 | 17.33 | F |
| ATOM | 8296 | CB | ALA | F | 163 | −23.866 | 1.713 | 66.427 | 1.00 | 16.50 | F |
| ATOM | 8297 | C | ALA | F | 163 | −22.269 | 3.658 | 66.495 | 1.00 | 17.96 | F |
| ATOM | 8298 | O | ALA | F | 163 | −22.006 | 3.753 | 65.319 | 1.00 | 20.30 | F |
| ATOM | 8299 | N | LEU | F | 164 | −21.426 | 4.177 | 67.380 | 1.00 | 18.56 | F |
| ATOM | 8300 | CA | LEU | F | 164 | −20.219 | 4.809 | 66.898 | 1.00 | 16.94 | F |
| ATOM | 8301 | CB | LEU | F | 164 | −19.896 | 5.882 | 67.896 | 1.00 | 17.95 | F |
| ATOM | 8302 | CG | LEU | F | 164 | −18.733 | 6.589 | 67.400 | 1.00 | 17.89 | F |
| ATOM | 8303 | CD1 | LEU | F | 164 | −18.995 | 7.282 | 66.124 | 1.00 | 15.47 | F |
| ATOM | 8304 | CD2 | LEU | F | 164 | −18.381 | 7.448 | 68.493 | 1.00 | 20.54 | F |
| ATOM | 8305 | C | LEU | F | 164 | −19.161 | 3.739 | 66.769 | 1.00 | 16.01 | F |
| ATOM | 8306 | O | LEU | F | 164 | −18.660 | 3.138 | 67.768 | 1.00 | 13.62 | F |
| ATOM | 8307 | N | LEU | F | 165 | −18.864 | 3.473 | 65.502 | 1.00 | 16.80 | F |
| ATOM | 8308 | CA | LEU | F | 165 | −17.904 | 2.361 | 65.260 | 1.00 | 17.88 | F |
| ATOM | 8309 | CB | LEU | F | 165 | −18.377 | 1.450 | 64.143 | 1.00 | 19.70 | F |
| ATOM | 8310 | CG | LEU | F | 165 | −19.865 | 1.154 | 64.115 | 1.00 | 20.22 | F |
| ATOM | 8311 | CD1 | LEU | F | 165 | −20.006 | 0.091 | 63.073 | 1.00 | 22.42 | F |
| ATOM | 8312 | CD2 | LEU | F | 165 | −20.383 | 0.571 | 65.317 | 1.00 | 20.24 | F |
| ATOM | 8313 | C | LEU | F | 165 | −16.455 | 2.751 | 64.945 | 1.00 | 17.28 | F |
| ATOM | 8314 | O | LEU | F | 165 | −15.576 | 1.899 | 64.820 | 1.00 | 16.77 | F |
| ATOM | 8315 | N | SER | F | 166 | −16.191 | 4.047 | 64.838 | 1.00 | 16.42 | F |
| ATOM | 8316 | CA | SER | F | 166 | −14.857 | 4.362 | 64.615 | 1.00 | 14.94 | F |
| ATOM | 8317 | CB | SER | F | 166 | −14.486 | 4.023 | 63.190 | 1.00 | 16.92 | F |
| ATOM | 8318 | OG | SER | F | 166 | −13.342 | 4.771 | 62.741 | 1.00 | 17.83 | F |
| ATOM | 8319 | C | SER | F | 166 | −14.714 | 5.803 | 64.881 | 1.00 | 13.50 | F |
| ATOM | 8320 | O | SER | F | 166 | −15.612 | 6.553 | 64.597 | 1.00 | 10.37 | F |
| ATOM | 8321 | N | VAL | F | 167 | −13.526 | 6.136 | 65.366 | 1.00 | 13.03 | F |
| ATOM | 8322 | CA | VAL | F | 167 | −13.225 | 7.443 | 65.680 | 1.00 | 14.10 | F |
| ATOM | 8323 | CB | VAL | F | 167 | −13.414 | 7.684 | 67.170 | 1.00 | 14.20 | F |
| ATOM | 8324 | CG1 | VAL | F | 167 | −12.915 | 9.039 | 67.498 | 1.00 | 18.13 | F |
| ATOM | 8325 | CG2 | VAL | F | 167 | −14.806 | 7.616 | 67.561 | 1.00 | 12.07 | F |
| ATOM | 8326 | C | VAL | F | 167 | −11.803 | 7.635 | 65.348 | 1.00 | 14.46 | F |
| ATOM | 8327 | O | VAL | F | 167 | −10.934 | 7.137 | 66.057 | 1.00 | 15.15 | F |
| ATOM | 8328 | N | ARG | F | 168 | −11.540 | 8.293 | 64.247 | 1.00 | 15.11 | F |
| ATOM | 8329 | CA | ARG | F | 168 | −10.146 | 8.565 | 63.932 | 1.00 | 17.77 | F |
| ATOM | 8330 | CB | ARG | F | 168 | −9.778 | 8.130 | 62.505 | 1.00 | 17.66 | F |
| ATOM | 8331 | CG | ARG | F | 168 | −8.876 | 6.956 | 62.610 | 1.00 | 19.47 | F |
| ATOM | 8332 | CD | ARG | F | 168 | −7.898 | 6.768 | 61.396 | 1.00 | 21.26 | F |
| ATOM | 8333 | NE | ARG | F | 168 | −8.028 | 7.792 | 60.327 | 1.00 | 21.00 | F |
| ATOM | 8334 | CZ | ARG | F | 168 | −7.041 | 8.177 | 59.477 | 1.00 | 20.85 | F |
| ATOM | 8335 | NH1 | ARG | F | 168 | −5.786 | 7.667 | 59.460 | 1.00 | 17.36 | F |
| ATOM | 8336 | NH2 | ARG | F | 168 | −7.327 | 9.138 | 58.638 | 1.00 | 21.21 | F |
| ATOM | 8337 | C | ARG | F | 168 | −9.844 | 10.106 | 64.134 | 1.00 | 16.88 | F |
| ATOM | 8338 | O | ARG | F | 168 | −10.717 | 10.949 | 63.807 | 1.00 | 16.38 | F |
| ATOM | 8339 | N | VAL | F | 169 | −8.632 | 10.411 | 64.663 | 1.00 | 16.86 | F |
| ATOM | 8340 | CA | VAL | F | 169 | −8.172 | 11.809 | 64.934 | 1.00 | 17.91 | F |
| ATOM | 8341 | CB | VAL | F | 169 | −8.100 | 12.158 | 66.441 | 1.00 | 18.20 | F |
| ATOM | 8342 | CG1 | VAL | F | 169 | −7.660 | 13.596 | 66.573 | 1.00 | 20.51 | F |
| ATOM | 8343 | CG2 | VAL | F | 169 | −9.456 | 12.014 | 67.146 | 1.00 | 16.17 | F |
| ATOM | 8344 | C | VAL | F | 169 | −6.736 | 12.029 | 64.423 | 1.00 | 19.08 | F |
| ATOM | 8345 | O | VAL | F | 169 | −5.725 | 11.400 | 64.899 | 1.00 | 17.96 | F |
| ATOM | 8346 | N | TYR | F | 170 | −6.574 | 12.943 | 63.484 | 1.00 | 18.49 | F |
| ATOM | 8347 | CA | TYR | F | 170 | −5.240 | 13.047 | 62.988 | 1.00 | 18.41 | F |
| ATOM | 8348 | CB | TYR | F | 170 | −5.114 | 12.139 | 61.760 | 1.00 | 18.99 | F |
| ATOM | 8349 | CG | TYR | F | 170 | −6.045 | 12.616 | 60.651 | 1.00 | 19.19 | F |
| ATOM | 8350 | CD1 | TYR | F | 170 | −5.590 | 13.483 | 59.652 | 1.00 | 18.68 | F |

TABLE 1-continued

| | | | | | | | | | | |
|---|---|---|---|---|---|---|---|---|---|---|
| ATOM | 8351 | CE1 | TYR | F | 170 | −6.453 | 13.874 | 58.623 | 1.00 | 19.39 | F |
| ATOM | 8352 | CD2 | TYR | F | 170 | −7.416 | 12.143 | 60.609 | 1.00 | 19.74 | F |
| ATOM | 8353 | CE2 | TYR | F | 170 | −8.261 | 12.513 | 59.616 | 1.00 | 19.19 | F |
| ATOM | 8354 | CZ | TYR | F | 170 | −7.792 | 13.378 | 58.609 | 1.00 | 19.84 | F |
| ATOM | 8355 | OH | TYR | F | 170 | −8.675 | 13.731 | 57.536 | 1.00 | 21.13 | F |
| ATOM | 8356 | C | TYR | F | 170 | −5.037 | 14.423 | 62.525 | 1.00 | 19.59 | F |
| ATOM | 8357 | O | TYR | F | 170 | −6.007 | 15.144 | 62.391 | 1.00 | 19.70 | F |
| ATOM | 8358 | N | TYR | F | 171 | −3.786 | 14.759 | 62.203 | 1.00 | 19.49 | F |
| ATOM | 8359 | CA | TYR | F | 171 | −3.493 | 16.033 | 61.590 | 1.00 | 19.13 | F |
| ATOM | 8360 | CB | TYR | F | 171 | −2.938 | 16.974 | 62.637 | 1.00 | 19.53 | F |
| ATOM | 8361 | CG | TYR | F | 171 | −1.582 | 16.675 | 63.187 | 1.00 | 19.26 | F |
| ATOM | 8362 | CD1 | TYR | F | 171 | −0.480 | 17.351 | 62.687 | 1.00 | 20.08 | F |
| ATOM | 8363 | CE1 | TYR | F | 171 | 0.836 | 17.098 | 63.233 | 1.00 | 21.47 | F |
| ATOM | 8364 | CD2 | TYR | F | 171 | −1.400 | 15.726 | 64.243 | 1.00 | 19.19 | F |
| ATOM | 8365 | CE2 | TYR | F | 171 | −0.154 | 15.446 | 64.763 | 1.00 | 20.64 | F |
| ATOM | 8366 | CZ | TYR | F | 171 | 0.973 | 16.111 | 64.275 | 1.00 | 22.12 | F |
| ATOM | 8367 | OH | TYR | F | 171 | 2.244 | 15.764 | 64.815 | 1.00 | 24.13 | F |
| ATOM | 8368 | C | TYR | F | 171 | −2.519 | 15.938 | 60.386 | 1.00 | 20.61 | F |
| ATOM | 8369 | O | TYR | F | 171 | −1.791 | 14.978 | 60.191 | 1.00 | 20.69 | F |
| ATOM | 8370 | N | LYS | F | 172 | −2.462 | 16.980 | 59.585 | 1.00 | 21.78 | F |
| ATOM | 8371 | CA | LYS | F | 172 | −1.608 | 16.943 | 58.432 | 1.00 | 22.09 | F |
| ATOM | 8372 | CB | LYS | F | 172 | −1.987 | 17.963 | 57.489 | 1.00 | 21.09 | F |
| ATOM | 8373 | CG | LYS | F | 172 | −2.767 | 17.366 | 56.466 | 1.00 | 22.57 | F |
| ATOM | 8374 | CD | LYS | F | 172 | −3.985 | 16.657 | 57.014 | 1.00 | 22.13 | F |
| ATOM | 8375 | CE | LYS | F | 172 | −4.879 | 16.193 | 55.811 | 1.00 | 23.79 | F |
| ATOM | 8376 | NZ | LYS | F | 172 | −6.168 | 17.147 | 55.581 | 1.00 | 22.42 | F |
| ATOM | 8377 | C | LYS | F | 172 | −0.113 | 17.022 | 58.624 | 1.00 | 24.94 | F |
| ATOM | 8378 | O | LYS | F | 172 | 0.525 | 18.018 | 59.227 | 1.00 | 25.56 | F |
| ATOM | 8379 | N | LYS | F | 173 | 0.463 | 15.944 | 58.076 | 1.00 | 24.70 | F |
| ATOM | 8380 | CA | LYS | F | 173 | 1.863 | 15.699 | 58.215 | 1.00 | 23.81 | F |
| ATOM | 8381 | CB | LYS | F | 173 | 2.436 | 15.059 | 56.958 | 1.00 | 24.31 | F |
| ATOM | 8382 | CG | LYS | F | 173 | 1.527 | 13.942 | 56.539 | 1.00 | 24.27 | F |
| ATOM | 8383 | CD | LYS | F | 173 | 0.602 | 14.561 | 55.473 | 1.00 | 23.72 | F |
| ATOM | 8384 | CE | LYS | F | 173 | −0.839 | 13.906 | 55.453 | 1.00 | 24.62 | F |
| ATOM | 8385 | NZ | LYS | F | 173 | −1.838 | 14.334 | 56.572 | 1.00 | 24.16 | F |
| ATOM | 8386 | C | LYS | F | 173 | 2.727 | 16.784 | 58.583 | 1.00 | 24.88 | F |
| ATOM | 8387 | O | LYS | F | 173 | 3.145 | 16.774 | 59.779 | 1.00 | 23.67 | F |
| ATOM | 8388 | N | CYS | F | 174 | 2.782 | 17.755 | 57.607 | 1.00 | 24.69 | F |
| ATOM | 8389 | CA | CYS | F | 174 | 3.896 | 18.815 | 57.497 | 1.00 | 25.67 | F |
| ATOM | 8390 | CB | CYS | F | 174 | 3.791 | 19.978 | 58.516 | 1.00 | 26.56 | F |
| ATOM | 8391 | SG | CYS | F | 174 | 5.375 | 21.125 | 58.129 | 1.00 | 34.09 | F |
| ATOM | 8392 | C | CYS | F | 174 | 5.441 | 18.125 | 57.645 | 1.00 | 24.67 | F |
| ATOM | 8393 | O | CYS | F | 174 | 6.471 | 18.857 | 57.943 | 1.00 | 24.74 | F |
| ATOM | 8394 | OXT | CYS | F | 174 | 5.617 | 16.797 | 57.555 | 1.00 | 24.80 | F |
| END | | | | | | | | | | | |

---

Having described the invention, the following is claimed:

1. A method of treating cancer in an individual, comprising administering to the individual a therapeutically effective amount of doxazosin, wherein the cancer is selected from the group consisting of skin cancer, lung cancer, pancreatic cancer and melanomas.

2. A method of treating cancer in an individual, comprising administering to the individual a therapeutically effective amount of an agonist of EphA receptor protein, the agonist inhibiting proliferation of cancer cells, the EphA receptor protein comprising at least one of EphA1, EphA2, or EphA3, the agonist having the general formula:

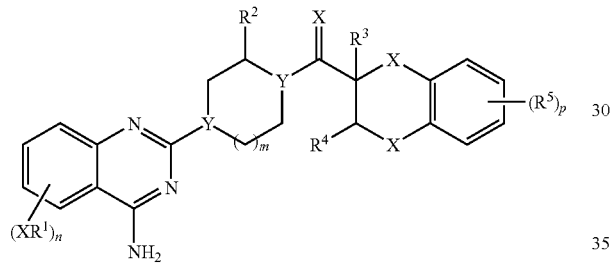

wherein
$R^1$ is selected from H, $C_{1-6}$alkyl, $C_{1-6}$aralkyl, $C_{1-6}$alkanoyl, aryl, heterocyclyl, $C_{1-6}$heterocyclylalkyl, $C_{1-6}$carbocyclylalkyl, and carbocyclyl, or two occurrences of $R^1$ together are $C_{1-6}$alkyl, thereby forming a ring;
$R^2$, $R^3$, and $R^4$ are independently selected from H, $C_{1-6}$alkyl, $C_{1-6}$aralkyl, $C_{1-6}$heterocyclylalkyl, and $C_{1-6}$carbocyclylalkyl;
$R^5$ is selected from $C_{1-6}$alkyl, $C_{1-6}$alkoxy, halogen, $C_{1-6}$alkanoyl, $C_{1-6}$alkoxycarbonyl, $C(O)N(R^6)(R^7)$, and $SO_2N(R^6)(R^7)$;
$R^6$ and $R^7$ are independently selected from H and $C_{1-6}$alkyl;
X is selected from $CH_2$, NH, and O;
each Y is independently selected from CH and N;
m is an integer from 1 to 2;
n is an integer from 1 to 3; and
p is an integer from 0 to 3,
wherein the cancer is selected from the group consisting of skin cancer, lung cancer, pancreatic cancer, and melanomas.

* * * * *